US007935804B2

(12) United States Patent
Dubensky, Jr. et al.

(10) Patent No.: US 7,935,804 B2
(45) Date of Patent: May 3, 2011

(54) **ENGINEERED *LISTERIA* AND METHODS OF USE THEREOF**

(75) Inventors: Thomas W. Dubensky, Jr., Piedmont, CA (US); Justin Skoble, Berkeley, CA (US); Peter M. Lauer, Berkeley, CA (US); David N. Cook, Lafayette, CA (US)

(73) Assignee: Aduro BioTech, Berkeley, CA (US)

( * ) Notice: Subject to any disclaimer, the term of this patent is extended or adjusted under 35 U.S.C. 154(b) by 446 days.

(21) Appl. No.: 11/395,197

(22) Filed: Mar. 30, 2006

(65) Prior Publication Data

US 2007/0207170 A1 Sep. 6, 2007

Related U.S. Application Data

(60) Provisional application No. 60/784,576, filed on Mar. 21, 2006, provisional application No. 60/778,471, filed on Mar. 1, 2006.

(51) Int. Cl.
*C07H 21/02* (2006.01)
*C07H 21/04* (2006.01)
*A61K 39/02* (2006.01)

(52) U.S. Cl. ............ 536/23.7; 536/23.1; 536/24.3; 536/24.32; 530/300; 530/350; 424/9.2; 424/93.2; 424/190.1; 424/234.1

(58) Field of Classification Search ............ 536/23.1, 536/23.7, 24.3, 24.32; 530/300, 350; 424/9.2, 424/190.1, 93.2, 234.1
See application file for complete search history.

(56) References Cited

U.S. PATENT DOCUMENTS

| | | | |
|---|---|---|---|
| 5,723,318 A | 3/1998 | Yamaguchi et al. |
| 5,757,063 A | 5/1998 | Tomita et al. |
| 5,830,702 A | 11/1998 | Portnoy et al. |
| 5,888,530 A | 3/1999 | Netti et al. |
| 6,051,237 A | 4/2000 | Paterson |
| 6,153,430 A | 11/2000 | Pastan et al. |
| 6,379,943 B1 | 4/2002 | Graham et al. |
| 6,565,852 B1 | 5/2003 | Paterson |
| 6,767,542 B2 | 7/2004 | Paterson et al. |
| 6,809,184 B1 | 10/2004 | Pastan et al. |
| 6,855,320 B2 | 2/2005 | Paterson |
| 7,135,188 B2 | 11/2006 | Paterson |
| 2003/0203472 A1 | 10/2003 | Portnoy et al. |
| 2004/0013690 A1 | 1/2004 | Portnoy et al. |
| 2004/0197343 A1 | 10/2004 | Dubensky, Jr. et al. |
| 2004/0228877 A1 | 11/2004 | Dubensky, Jr. et al. |
| 2005/0048081 A1 | 3/2005 | Frankel et al. |
| 2005/0118184 A1 | 6/2005 | Paterson et al. |
| 2005/0129715 A1 | 6/2005 | Paterson et al. |
| 2005/0147621 A1 | 7/2005 | Higgins et al. |
| 2005/0175625 A1 | 8/2005 | Jaffee et al. |
| 2005/0214304 A1 | 9/2005 | Pastan et al. |
| 2005/0249748 A1 | 11/2005 | Dubensky, Jr. et al. |
| 2005/0281783 A1 | 12/2005 | Kinch et al. |
| 2006/0093582 A1 | 5/2006 | Paterson et al. |
| 2006/0204516 A1 | 9/2006 | Paterson et al. |
| 2006/0205067 A1 | 9/2006 | Paterson et al. |
| 2006/0210540 A1 | 9/2006 | Paterson et al. |
| 2006/0233835 A1 | 10/2006 | Paterson et al. |
| 2007/0031457 A1 | 2/2007 | Dubensky, Jr. et al. |
| 2007/0190029 A1 | 8/2007 | Pardoll et al. |
| 2007/0190063 A1 | 8/2007 | Bahjat et al. |
| 2007/0207171 A1 | 9/2007 | Dubensky et al. |

FOREIGN PATENT DOCUMENTS

| | | |
|---|---|---|
| FR | 2 686 896 A1 | 8/1993 |
| WO | WO-93/15212 A1 | 8/1993 |
| WO | WO-94/17192 A2 | 8/1994 |
| WO | WO-94/17192 A3 | 8/1994 |
| WO | WO-96/14087 A1 | 5/1996 |
| WO | WO-01/27295 A1 | 4/2001 |
| WO | WO-01/72329 A1 | 10/2001 |
| WO | WO-01/95942 A2 | 12/2001 |
| WO | WO-01/95942 A3 | 12/2001 |
| WO | WO-02/33109 A2 | 4/2002 |
| WO | WO-02/33109 A3 | 4/2002 |
| WO | WO-03/083056 A2 | 10/2003 |
| WO | WO-03/083056 A3 | 10/2003 |
| WO | WO-03/092600 A2 | 11/2003 |
| WO | WO-03/092600 A3 | 11/2003 |
| WO | WO-2004/006837 A2 | 1/2004 |
| WO | WO-2004/006837 A3 | 1/2004 |
| WO | WO-2004/062597 A2 | 7/2004 |
| WO | WO-2004/062597 A3 | 7/2004 |
| WO | WO-2004/084936 A2 | 10/2004 |
| WO | WO-2004/084936 A3 | 10/2004 |
| WO | WO-2004/110481 A2 | 12/2004 |
| WO | WO-2004/110481 A3 | 12/2004 |
| WO | WO-2005/009463 A2 | 2/2005 |
| WO | WO-2005/009463 A3 | 2/2005 |
| WO | WO-2005/037233 A2 | 4/2005 |
| WO | WO-2005/037233 A3 | 4/2005 |
| WO | WO-2005/067460 A2 | 7/2005 |
| WO | WO-2005/071088 A2 | 8/2005 |
| WO | WO-2005/071088 A3 | 8/2005 |
| WO | WO-2005/092372 A2 | 10/2005 |
| WO | WO-2005/092372 A3 | 10/2005 |
| WO | WO-2006/036550 A2 | 4/2006 |
| WO | WO-2006/036550 A3 | 4/2006 |
| WO | WO-2007/022511 A2 | 2/2007 |
| WO | WO-2007/022511 A3 | 2/2007 |
| WO | WO-2007/022520 A2 | 2/2007 |

(Continued)

OTHER PUBLICATIONS

Adams, D.E. et al. (1992). "Cre-*lox* Recombination in *Escherichia coli* Cells Mechanistic Differences from the in Vitro Reaction," *J. Mol. Biol.* 226:661-673.

(Continued)

*Primary Examiner* — Rodney P. Swartz
(74) *Attorney, Agent, or Firm* — Michael A. Whittaker; BioTechnology Law Group

(57) ABSTRACT

The invention provides a bacterium containing a polynucleotide comprising a nucleic acid encoding a heterologous antigen, as well as fusion protein partners. Also provided are vectors for mediating site-specific recombination and vectors comprising removable antibiotic resistance genes.

84 Claims, 45 Drawing Sheets

FOREIGN PATENT DOCUMENTS

| | | |
|---|---|---|
| WO | WO-2007/022520 A3 | 2/2007 |
| WO | WO-2007/103225 A2 | 9/2007 |
| WO | WO-2007/103261 A2 | 9/2007 |
| WO | WO-2007/117371 A2 | 10/2007 |

OTHER PUBLICATIONS

Angelakopoulos, H. et al. (Jul. 2002). "Safety and Shedding of an Attenuated Strain of *Listeria monocytogenes* with a Deletion of *actA/plcB* in Adult Volunteers: A Dose Escalation Study of Oral Inoculation," *Infection and Immunity* 70(7):3592-3601.

Brockstedt, D.G. et al. (Apr. 2005). "Recombinant *Listeria monocytogenes*-based Immunotherapy Targeting Mesothelin for the Treatment of Pancreatic and Ovarian Cancer," *Proceedings of the American Association for Cancer Research Annual Meeting* 46:1418.

Brockstedt, D.G. et al. (Apr. 2005). "Recombinant *Listeria monocytogenes*-based Immunotherapy Targeting Mesothelin for the Treatment of Pancreatic and Ovarian Cancer," *96th Annual Meeting of the American Association for Cancer Research* Anaheim, CA, Apr. 16-20, 2005, Abstract No. 6028, one page.

Darji, A. et al. (2003). "Induction of Immune Responses by Attenuated Isogenic Mutant Strains of *Listeria monocytogenes*," *Vaccine* 21:S2/102-S2/109.

Dramsi, S. et al. (1995). "Entry of *Listeria monocytogenes* into Hepatocytes Requires Expression of InIB, A Surface Protein of the Internalin Multigene Family," *Molecular Microbiology* 16(2):251-261.

Galen, J.E. et al. (Aug. 2001). "Can a 'Flawless' Live Vector Vaccine Strain be Engineered?" *Trends in Microbiology* 9(8):372-376.

Gregory, S.H. et al. (Dec. 1997). "Internalin B Promotes the Replication of *Listeria monocytogenes* in Mouse Hepatocytes," *Infection and Immunity* 65(12):5137-5141.

Rule 99 Third Party Submission submitted Nov. 5, 2007, for U.S. Appl. No. 11/395,197, filed Mar. 30, 2006, five pages.

Rule 99 Third Party Submission submitted Nov. 5, 2007, for U.S. Appl. No. 11/396,216, filed Mar. 30, 2006, five pages.

Sewell, D.A. et al. (Jan. 2004). "Regression of HPV-Positive Tumors Treated With a New *Listeria monocytogenes* Vaccine," *Arch. Otolaryngol. Head Neck Surg.* 130:92-97.

Abachin, E. et al. (Jan. 2002). "Formation of D-alanyl-lipoteichoic Acid is Required for Adhesion and Virulence of *Listeria monocytogenes*," *Molecular Microbiology* 43(1):1-14.

Ahlenstiel, G. et al. (Mar. 2005). "Hepatitis C Virus and the Threshold of Natural Killer Cell Inhibition," *Hepatology* 41(3):675-677.

Ahmad, A. et al. (Oct. 2004). "Role of NK and NKT Cells in the Immunopathogenesis of HCV-Induced Hepatitis," *Journal of Leukocyte Biology* 76(4):743-759.

Alexander, D.C. et al. (Sep. 2003). "Development of the *Micromonospora carbonacea* var. *africana* ATCC 39149 Bacteriophage pMLP1 Integrase for Site-Specific Integration in *Micromonospora* spp.," *Microbiology* 149(9):2443-2453.

Andersson, A. et al. (1998). "Early IFN-γ Production and Innate Immunity During *Listeria monocytogenes* Infection in the Absence of NK Cells," *The Journal of Immunology* 161:5600-5606.

Anonymous. (Mar. 2005). "Recombinant *Listeria monocytogenes*-Based Immunotherapy Targeting the Receptor Tyrosine Kinase EphA2," presented at *American Association for Cancer Research (AACR), 95th Annual Meeting*, Mar. 27-31, 2004, as posted on <http://www.cerus.com/index.cfm/abstracts/2004/RecombinantListeriamonocytogenesBasedImmunotherapyTarg...>, last visited on Apr. 28, 2006, one page.

Araki, K. et al. (2002). "Site-Directed Integration of the *cre* Gene Mediated by Cre Recombinase Using a Combination of Mutant *lox* Sites," *Nucleic Acids Research* 30(19-e103):1-18.

Argani, P. et al. (Jun. 1, 2001) "Discovery of New Markers of Cancer Through Serial Analysis of Gene Expression: Prostate Stem Cell Antigen Is Overexpressed in Pancreatic Adenocarcinoma," *Cancer Research* 61(11):4320-4324.

Argani, P. et al. (Dec. 2001). "Mesothelin Is Overexpressed in the Vast Majority of Ductal Adenocarcinomas of the Pancreas: Identification of a New Pancreatic Cancer Marker by Serial Analysis of Gene Expression (SAGE)," *Clinical Cancer Research* 7:3862-3868.

Auerbuch, V. et al. (Sep. 2001). "Development of a Competitive Index Assay To Evaluate the Virulence of *Listeria monocytogenes actA* Mutants During Primary and Secondary Infection of Mice," *Infection and Immunity* 69(9):5953-5957.

Baer, A. et al. (Feb. 2001). "Coping with Kinetic and Thermodynamic Barriers: RMCE, an Efficient Strategy for the Targeted Integration of Transgenes," *Current Opinion in Biotechnology* 12(1):473-479.

Behari, J. et al. (Dec. 1998). "A Homolog of CcpA Mediates Catabolite Control in *Listeria monocytogenes* but Not Carbon Source Regulation of Virulence Genes," *Journal of Bacteriology* 180(23):6316-6324.

Bierne, H. et al. (2000). "InIB, a Surface Protein of *Listeria monocytogenes* that Behaves as an Invasin and a Growth Factor," *Journal of Cell Science* 115(17):3357-3367.

Bierne, H. et al, (2002). "Inactivation of the *srtA* Gene in *Listeria monocytogenes* Inhibits Anchoring of Surface Proteins and Affects Virulence," *Molecular Microbiology* 43(4):869-881.

Bierne, H. et al. (Apr. 2004). "Sortase B, a New Class of Sortase in *Listeria monocytogenes,*" *Journal of Bacteriology* 186(7):1972-1982.

Bishop, D.K. et al. (Sep. 15, 1987). "Adoptive Transfer of Immunity to *Listeria moncytogenes*: The Influence of In Vitro Stimulation on Lymphocyte Subset Requirements," *The Journal of Immunology* 139(6):2005-2009.

Biswas, I. et al. (Jun. 1993). "High-Efficiency Gene Inactivation and Replacement System for Gram-Positive Bacteria," *Journal of Bacteriology* 175(11):3628-3635.

Bode, J. et al. (Sep./Oct. 2000). "The Transgeneticist's Toolbox: Novel Methods for the Targeted Modification of Eukaryotic Genomes," *Biological Chemistry* 381(9/10):801-813.

Bodmer, H.C. et al. (Jan. 29, 1988). "Enhanced Recognition of a Modified Peptide Antigen by Cytotoxic T Cells Specific for Influenza Nucleoprotein," *Cell* 52(2):253-258.

Borezee, E. et al. (2001). "SvpA, a Novel Surface Virulence-Associated Protein Required for Intracellular Survival of *Listeria monocytogenes,*" *Microbiology* 147:2931-2923.

Boujemaa-Paterski, R. et al. (Sep. 25, 2001, e-pub. Aug. 30, 2001). "Listeria Protein ActA Mimics WASP Family Proteins: It Activates Filament Barbed End Branching by Arp2/3 Complex," *Biochemistry* 40(38):11390-11404.

Bouwer, H.G.A. et al. (Apr. 14, 2003). "Recombinant *L. monocytogenes* as a Vaccine For Stimulation of Anti-Tumor Responses," Abstract *presented at The American Association of Immunologists 90th Anniversary Meeting*, Denver, CO, May 6-10, 2003, *FASEB Journal*, 17(7):C330-331, Abstract 162.17.

Bouwer, H.G.A. et al. (May 6, 2003). "Recombinant *L. monocytogenes* as a Vaccine For Stimulation of Anti-Tumor Responses," Poster, *presented at The American Association of Immunologists 90th Anniversary Meeting*, Denver, CO, May 6-10, 2003, one page.

Bowers, P.M. et al. (2004). "Prolinks: A Database of Protein Functional Linkages Derived From Coevolution," *Genome Biology* 5(5):R35.1-R35.13.

Brieher, W.M. et al. (Apr. 26, 2004). "Fascin-Mediated Propulsion of *Listeria monocytogenes* Independent of Frequent Nucleation by the Arp2/3 Complex," *The Journal of Cell Biology* 165(2):233-242.

Brockstedt, D. et al. (Feb. 19, 2003). "Recombinant Attenuated *Listeria monocytogenes* Elicits Striking Antigen-Specific CD8+ T-Cell Responses that Correlate with Prolonged Survival in a Murine Transplant Model of Melanoma," *presented at Keystone Symposia Meeting*, Keystone, CO, Feb. 17-23, 2003, one page.

Brockstedt, D. et al. (Mar. 2003). "Recombinant Attenuated *Listeria monocytogenes* Elicits Robust Cellular Immune Response to Tumor-Associated Antigen in *Listeria* Immune Mice," *Proceedings of the American Association for Cancer Research, 94th Annual Meeting*, Apr. 5-9, 2003, Toronto, Ontario, CA, 44:194, Abstract No. 851, one page.

Brockstedt, D. et al. (Jul. 2003). "Recombinant Attenuated *Listeria monocytogenes* Elicits Robust Cellular Immune Response to Tumor-Associated Antigen in *Listeria* Immune Mice," (Abstract for the 94th Annual Meeting of the American Association for Cancer Research, Washington DC, USA, Jul. 11-14, 2003) *Proceedings of the American Association For Cancer Research Annual Meeting* 44(2):168, Abstract No. 851.

Brockstedt, D. et al. (Oct. 3, 2003). "Novel Strategies to Develop *Listeria monocytogenes* Vaccine Strains for Cancer Immunotherapy Applications," Poster, presented at *Cancer Vaccines 2003*, Oct. 1-3, 2003, one page.

Brockstedt, D. et al. (Mar. 2004). "The Living Dead: Psoralen-killed Metabolically Active *Listeria* DNA Repair Mutant-based Vaccines Induce Therapeutic Anti-tumor Efficacy Targeted Against an Endogenous Antigen," abstract *presented at the American Association for Cancer Research (AACR)*, Mar. 27-31, 2004, as posted on <http://www.cerus.com/pages/solution/abs156.html>, last visited on Aug. 26, 2004, two pages.

Brockstedt, D. et al. (Jul. 2004). "The Living Dead: Psoralen-killed Metabolically Active *Listeria* DNA Repair Mutant-based Vaccines Induce Therapeutic Anti-tumor Efficacy Targeted Against an Endogenous Antigen," abstract *presented at the Gordon Research Conference on Microbial Toxins and Pathogenicity*, Jul. 18-23, 2004, Andover, NH, as posted on <http://www.cerus.com/pages/solution/04_GordonResearchConf_Brockstedt.html>, last visited on Aug. 26, 2004, two pages.

Brockstedt, D.G. (Date Unknown). "*Listeria*—CEA Vaccine-Infected DC for Cancer Therapy," Abstract for Grant No. 1R43CA108026-01 located at <http://crisp.cit.nih.gov/crisp/CRISP_LIB.getdoc?testkey=6787426&p_grant_num=1R43C...>, last visited Jun. 27, 2004, two pages.

Brockstedt, D.G. (Date Unknown). "*Listeria*—CEA Vaccine-Infected DC for Cancer Therapy," Abstract for Grant No. 1R43CA108026-01 located at <http://crisp.cit.nih.gov/crisp/CRISP_LIB.getdoc?testkey=6787426&p_grant_num=1R43C...>, last visited Apr. 28, 2006, two pages.

Brockstedt, D.G. et al. (Sep. 21, 2004). "*Listeria*-based Cancer Vaccines That Segregate Immunogenicity From Toxicity," *Proc. Natl. Acad. Sci. USA* 101(38):13832-13837.

Brockstedt, D.G. et al. (Nov. 16, 2004). "Killed but Metabolically Active Recombinant *Listeria monocytogenes* as an Antigen Delivery and Activation Platform for Human Dendritic Cell-Based Cancer Immunotherapy," Poster Board No./Session No. 717-III, Abstract No. 3447, *46th Annual Meeting Program and Abstracts presented at the American Society of Hematology*, Dec. 4-7, 2004, San Diego, CA, *Blood* 104(11-pt. 1):939A.

Brockstedt, D.G. et al. (Nov. 16, 2004). "Killed but Metabolically Active Recombinant *Listeria monocytogenes* as an Antigen Delivery and Activation Platform for Human Dendritic Cell-Based Cancer Immunotherapy," Poster, *presented at the 46th Annual Meeting of the American Society of Hematology (ASH)*, Dec. 4-7, 2004, San Diego, CA, *Blood* 104(11-pt. 1):939A.

Brockstedt, D.G. et al. (Dec. 2004). "Killed but Metabolically Active Recombinant *Listeria monocytogenes* as an Antigen Delivery and Activation Platform for Human Dendritic Cell-Based Cancer Immunotherapy," Abstract presented at *American Society of Hematology(ASH)*, *46th Annual Meeting* Dec. 4-7, 2004, located at <http://www.cerus.com/index.cfm/abstracts/2004/KilledbutMetabolicallyActiveRecombina...>, last visited on Apr. 28, 2006, one page.

Brockstedt, D.G. et al. (Dec. 6, 2004). "Killed but Metabolically Active Recombinant *Listeria monocytogenes* as an Antigen Delivery and Activation Platform for Human Dendritic Cell-Based Cancer Immunotherapy," Abstract No. 3447, *46th Annual Meeting of the American Society of Hematology*, San Diego, CA, Dec. 4-7, 2004, located at <http://www.abstracts2view.com/hem_sandiego2004/view.php?nu=HEM4L1_5352>, last visited on Apr. 28, 2006, one page.

Brockstedt, D.G. et al. (Feb. 2005). "Killed but Metabolically Active Recombinant *Listeria monocytogenes* as an Antigen Delivery and Activation Platform for Human Dendritic Cell-Based Cancer Immunotherapy," Abstract presented at *Keystone Symposium—Dendritic Cells at the Center of Innate and Adaptive Immunity: Eradication of Pathogens and Cancer and Control of Immunopathology*, Feb. 1-7, 2005, located at <http://www.cerus.com/index.cfm/abstracts/2005/KilledbutMetabolicallyActiveRecombina...>, last visited on Apr. 28, 2006, one page.

Brockstedt, D.G. et al. (Feb. 2005). "Killed but Metabolically Active Recombinant *Listeria monocytogenes* as an Antigen Delivery and Activation Platform for Human Dendritic Cell-Based Cancer Immunotherapy," Poster presented at *Keystone Symnposia—Dendritic Cells at the Center of Innate and Adaptive Immunity: Eradication of Pathogens and Cancer and Control of Immunopathology(B2)*, Vancouver, British Columbia, Feb. 1-7, 2005, one page.

Brockstedt, D.G. et al. (Jul. 24, 2005) "Killed but Metabolically Active Microbes: A New Vaccine Paradigm For Eliciting Effector T-Cell Responses and Protective Immunity," *Nature Medicine—Advance Online Publication* pp. 1-8.

Brockstedt, D.G. et al. (Aug. 2005) "Killed but Metabolically Active Microbes: A New Vaccine Paradigm For Eliciting Effector T-Cell Responses and Protective Immunity," *Nature Medicine* 11(8):853-860.

Brockstedt, D.G. et al. (Nov./Dec. 2005). "Characterization of Mesothelin-Specific T cell Responses in Healthy Individuals," *Journal of Immunotherapy* 28(6):631, Abstract.

Brown, D.P. et al. (May 1988). "Site-Specific Integration in *Saccharopolyspora erythraea* and Multisite Integration in *Streptomyces lividans* of Actinomycete Plasmid pSE101," *Journal of Bacteriology* 170(5):2287-2295.

Brundage, R.A. et al. (Dec. 15, 1993). "Expression and Phosphorylation of the *Listeria monocytogenes* ActA Protein in Mammalian Cells," *Proc. Natl. Acad. Sci. USA* 90(24):11890-11894.

Brzoza, K.L. et al. (2004). "Cytoplasmic entry of *Listeria monocytogenes* Enhances Dendritic Cell Maturation and T Cell Differentiation and Function," *The Journal of Immunology* 173:2641-2651.

Bubert, A. et al. (Aug. 1992). "The Homologous and Heterologous Regions within the *iap* Gene Allow Genus- and Species-Specific Identification of *Listeria* spp. by Polymerase Chain Reaction," *Applied and Environmental Microbiology* .58(8):2625-2632.

Bubert, A. et al. (Dec. 1992). "Structural and Functional Properties of the p60 Proteins From Different *Listeria* Species," *Journal of Bacteriology* 174(24):8166-8171.

Buchrieser, C. et al. (2003). "Comparison of the Genome Sequences of *Listeria monocytogenes* and *Listeria innocua*: Clues for Evolution and Pathogenicity," *FEMS Immunology and Medical Microbiology* 35:207-213.

Bullock, T.N.J. et al. (Mar. 1, 2000). "The Density of Peptides Displayed by Dendritic Cells Affects Immune Responses to Human Tyrosinase and gp100 in HLA-A2 Transgenic Mice," *Journal of Immunology* 164(5):2354-2361.

Cabanes, D. et al. (Mar. 2004). "Auto, A Surface Associated Autolysin of *Listeria monocytogenes* Required for Entry into Eukaryotic Cells and Virulence," *Molecular Microbiology* 51(6):1601-1614.

Calorini, L. et al. (2002). "IFNγ and TNFα Account for a Pro-Clonogenic Activity Secreted by Activated Murine Peritoneal Macrophages," *Clin. Exp. Metastasis* 19(3):259-264.

Cameron, L.A. et al. (Apr. 1999). "Motility of ActA Protein-Coated Microspheres Driven by Actin Polymerization," *Proc. Natl. Acad. Sci. USA* 96:4908-4913.

Camilli, A. et al. (1993). "Dual Roles of *plcA* in *Listeria monocytogenes* Pathogenesis," *Molecular Microbiology* 8(1):143-157.

Campbell, A. (1994). "Comparative Molecular Biology of Lambdoid Phages," *Annu. Rev. Microbiol.* 48:193-222.

Chakraborty, T. et al. (2000). "Genome Organization and the Evolution of the Virulence Gene Locus in *Listeria* species," *Int. J. Med. Microbiol.* 290:167-174.

Chan, C.W. et al. (e-pub. Jan. 29, 2006). "Interferon-Producing Killer Dendritic Cells Provide a Link Between Innate and Adaptive Immunity," *Nature Medicine* pp. 1-7.

Chang, K. et al. (Jan. 9, 1996). "Molecular Cloning of Mesothelin, a Differentiation Antigen Present on Mesothelium, Mesotheliomas, and Ovarian Cancers," *Proc. Natl. Acad. Sci. USA* 93(1):136-140.

Chen, Y. et al. (Jan. 2005). "Activation and Function of Hepatic NK Cells in Hepatitis B Infection: An Underinvestigated Innate Immune Response," *Journal of Viral Hepatitis* 12(1):38-45.

Chowdhury, P.S. et al. (Jan. 1998). "Isolation of a High-Affinity Stable Single-Chain Fv Specific for Mesothelin from DNA-Immunized Mice by Phage Display and Construction of a Recombinant Immunotoxin with Anti-Tumor Activity," *Proc. Natl. Acad. Sci. USA* 95:669-674.

Christiansen, J.J. et al. (Apr. 1, 2003). "Polarity of Prostate Specific Membrane Antigen, Prostate Stem Cell Antigen, and Prostate Specific Antigen in Prostate Tissue and in a Cultured Epithelial Cell Line," *Prostate* 55(1):9-19.

Cicchetti, G. et al.(Nov. 19, 1999). "Actin and Phosphoinositide Binding by the ActA Protein of the Bacterial Pathogen *Listeria monocytogenes*," *The Journal of Biological Chemistry* 274(47):33616-33626.

Clemens, D.L. et al. (Oct. 2002). "The *Mycobacterium tuberculosis* Phagosome in Human Macrophages Is Isolated from the Host Cell Cytoplasm," *Infection and Immunity* 70(10):5800-5807.

Cleveland, M.G. et al. (Jun. 1996). "Lipoteichoic Acid Preparations of Gram-Positive Bacteria Induce Interleukin-12 Through a CD14-Dependent Pathway," *Infection and Immunity* 64(6):1906-1912.

Collin, L. et al. (Jul. 2004). "Epstein-Barr Virus (EBV)-Induced Liver Failure in the Absence of Extensive Liver-Cell Necrosis: A Case for Cytokine-Induced Liver Dysfunction?" *Journal of Hepatology* 41(1):174-175.

Cook, G.C. (Dec. 1997). "Liver Involvement in Systemic Infection," *Eur. J. Gasteroenterol. Hepatol.* 9(12):1239-1247.

Cossart, P. (2002). "Molecular and Cellular Basis of the Infection by *Listeria monocytogenes*: An Overview," *Int. J. Med. Microbiol.* 291:401-409.

Darji, A. et al. (Sep. 1, 1998). "The Role of the Bacterial Membrane Protein ActA in Immunity and Protection Against *Listeria monocytogenes*," *The Journal of Immunology* 161(5):2414-2420.

Darwin, K.H. et al. (Aug. 2005). "Role for Nucleotide Excision Repair in Virulence of *Mycobacterium tuberculosis*," *Infection and Immunity* 73(8):4581-4587.

Datsenko, K.A. et al. (Jun. 6, 2000). "One-Step Inactivation of Chromosomal Genes in *Escherichia coli* K-12 Using PCR Products," *Proc. Natl. Acad. Sci. USA* 97(12):6640-6645.

Domann, E. et al. (Jan. 1997). "Indentification and Characterization of a Novel PrfA-Regulated Gene in *Listeria monocytogenes* Whose Product, IrpA, Is Highly Homologous to Internalin Proteins, Which Contain Leucine-Rich Repeats," *Infection and Immunity* 65(1):101-109.

Doumith, M. et al. (Feb. 2004). "New Aspects Regarding Evolution and Virulence of *Listeria monocytogenes* Revealed by Comparative Genomics and DNA Arrays," *Infection and Immunity* 72(2):1072-1083.

Dramsi, S. et al. (May 1997). "Identification of Four New Members of the Internalin Multigene Family of *Listeria monocytogenes* EGD," *Infection and Immunity* 65(5):1615-1625.

Dramsi, S. et al. (Mar. 18, 2002). "Listeriolysin O: A Genuine Cytolysin Optimized for an Intracellular Parasite," *J. Cell Biol.* 156(6):943-946.

Dramsi, S. et al. (Jul. 2004). "FbpA, a Novel Multifunctional *Listeria monocytogenes* Virulence Factor," *Molecular Microbiology* 53(2):639-649.

Dubail, I. et al. (2001). "Functional Assembly of Two Membrane-Binding Domains in Listeriolysin O, the Cytolysin of *Listeria monocytogenes*," *Microbiology* 147:2679-2688.

Dubensky, T. (Feb. 22, 2003). "Cancer Vaccines Derived from Selected Attenuated Strains of *Listeria Monocytogenes*," presented at *Keystone Symposia Meeting*, Keystone, CO, Feb. 17-23, 2003, 22 pages.

Dubensky, T. (Mar. 14, 2003). "Cancer Vaccines Derived From Selected Attenuated Strains of *Listeria monocytogenes*," presented at *Days of Molecular Medicine—Immunotherapy*, 24 pages.

Dubensky, T. (Dec. 4, 2003). "*Listeria*-Based Therapeutic Vaccines of Infectious Disease and Cancer: Vaccines Disguised as an Invading Pathogen," presented at *Johns Hopkins University*, 57 pages.

Dubensky, T.W. (Date Unknown). "Development of *Listera*-Based Clinical Consensus HCV Vaccine Candidates," Abstract for Grant No. 1U01AI070834-01 (project dates: Aug. 1, 2006-Jul. 31, 2009) located at <http://crisp.cit.nih.gov/crisp/CRISP_LIB.getdoc?textkey=7136591&p_grant_num=1U01AI07083...>, last visited Dec. 6, 2006, two pages.

Dubensky, T.W. (Date Unknown). "*Listeria* Immunotherapy for Pancreatic and Ovarian Cancer," Abstract for Grant No. 2R44CA101421-02 located at <http://crisp.cit.nih.gov/crisp/CRISP_LIB.getdoc?testkey=6992210&p_grant_num=2R44C...>, last visited Dec. 7, 2005, two pages.

Dubensky, T.W. (Date Unknown). "*Listeria* Immunotherapy for Pancreatic and Ovarian Cancer," Abstract for Grant No. 2R44CA101421-02 located at <http://crisp.cit.nih.gov/crisp/CRISP_LIB.getdoc?testkey=6992210&p_grant_num=2R44C...>, last visited Apr. 28, 206, two pages.

Dubensky, T.W. (Date Unknown). "*Listeria* Immunotherapy for Pancreatic and Ovarian Cancer," Abstract for Grant No. 2R44CA101421-02 (project dates: Apr. 1, 2003-Aug. 31, 2007) located at <http://crisp.cit.nih.gov/crisp/CRISP_LIB.getdoc?textkey=6992210&p_grant_num=2R44CA10142...>, last visited Dec. 6, 2006, two pages.

Dubensky, T.W. (Date Unknown). "*Listeria* Immunotherapy for Pancreatic and Ovarian Cancer," Abstract for Grant No. 5R44CA101421-03 (project dates: Apr. 1, 2003-Aug. 31, 2007) located at <http://crisp.cit.nih.gov/crisp/CRISP_LIB.getdoc?textkey=7118681&p_grant_num=5R44CA10142...>, last visited Dec. 6, 2006, two pages.

Dubensky, T.W. (Date Unknown). "*Listeria*-Based Vaccines for Ovarian Cancer Therapy," Abstract for Grant No. 1R43CA101421-01 located at <http://crisp.cit.nih.gov/crisp/CRISP_LIB.getdoc?testkey=6645288&p_grant_num=1R43CA...>, last visited Nov. 3, 2004, two pages.

Dubensky, T.W. (Date Unknown). "*Listeria*-Based Vaccines for Ovarian Cancer Therapy," Abstract for Grant No. 1R43CA101421-01 located at <http://crisp.cit.nih.gov/crisp/CRISP_LIB.getdoc?testkey=6645288&p_grant_num=1R43CA...>, last visited Apr. 28, 2006, two pages.

Dubensky, T.W. (Date Unknown). "*Listeria*-Based Vaccines for Ovarian Cancer Therapy," Abstract for Grant No. 1R43CA101421-01 (project dates: Apr. 1, 2003-Oct. 1, 2003) located at <http://crisp.cit.nih.gov/crisp/CRISP_LIB.getdoc?textkey=6645288&p_grant_num=1R43CA10142...>, last visited Dec. 6, 2006, two pages.

Dubensky, T.W. (Date Unknown). "Psoralen-Killed, Metabolically-Active Anthrax Vaccine," Abstract for Grant No. 1U01AI061199-01 (project dates: Jul. 1, 2004-Jun. 30, 2007) located at <http://crisp.cit.nih.gov/crisp/CRISP_LIB.getdoc?textkey=6818020&p_grant_num=1U01AI06119...>, last visited Dec. 6, 2006, two pages.

Dubensky, T.W. (Date Unknown). "Psoralen-Killed, Metabolically-Active Anthrax Vaccine," Abstract for Grant No. 5U01AI061199-02 (project dates: Jul. 1, 2004-Jun. 30, 2007) located at <http://crisp.cit.nih.gov/crisp/CRISP_LIB.getdoc?textkey=6916362&p_grant_num=5U01AI06119...>, last visited Dec. 6, 2006, two pages.

Dubensky, T.W. (Date Unknown). "Psoralen-Killed, Metabolically-Active Anthrax Vaccine," Abstract for Grant No. 5U01AI061199-03 (project dates: Jul. 1, 2004-Jun. 30, 2007) located at <http://crisp.cit.nih.gov/crisp/CRISP_LIB.getdoc?textkey=7110322&p_grant_num=5U01AI06119...>, last visited Dec. 6, 2006, two pages.

Dussurget, O. et al. (Aug. 2002). "*Listeria monocytogenes* Bile Salt Hydrolase is a PrfA-Regulated Virulence Factor Involved in the Intestinal and Hepatic Phases of Listeriosis," *Molecular Microbiology* 45(4):1095-1106.

Dussurget, O. et al. (2004). "Molecular Determinants of *Listeria monocytogenes* Virulence," *Ann. Rev. Microbiology* 58:587-610.

Dustoor, M. et al. (Mar. 1977). "Bateriological and Histopathological Evaluation of Guinea Pigs After Infection with *Listeria monocytogenes*," *Infection and Immunity* 15(3):916-924.

Emoto, Y. et al. (Dec. 1997). "Transient Control of Interleukin-4-Producing Natural Killer T Cells in the Livers of *Listeria monocytogenes*-Infected Mice by Interleukin-12," *Infection and Immunity* 65(12):5003-5009.

Esplugues, E. et al. (Jun. 1, 2005). "Induction of Tumor NK-Cell Immunity by Anti-CD69 Antibody Therapy," *Blood* 105(11):4399-4406.

Esposito, D. et al. (1997). "The Integrase Family of Tyrosine Recombinases: Evolution of a Conserved Active Site Domain," *Nucleic Acids Research* 25(18):3605-3614.

Fjaer, R.B. et al. (Feb. 2005). "Extrahepatic Bile Duct Atresia and Viral Involvement," *Pediatr. Transplant.* 9(1):68-73.

Flo, T.H. et al. (2000). "Human Toll-Like Receptor 2 Mediates Monocyte Activation by *Listeria monocytogenes*, But Not by Group B Streptococci or Lipopolysaccharide," *The Journal of Immunology* 164:2064-2069.

Fradelizi, J. et al. (Aug. 2001). "ActA and Human Zyxin Harbour Arp2/3-Independent Actin-Polymerization Activity," *Nature Cell Biology* 3(8):699-707.

Frankel, F.R. et al. (1995). "Induction of Cell-Mediated Immune Responses to Human Immunodeficiency Virus Type 1 Gag Protein by Using *Listeria monocytogenes* as a Live Vaccine Vector," *The Journal of Immunology* 155:4775-4782.

Friederich, E. et al. (1995). "Targeting of *Listeria monocytogenes* ActA Protein to the Plasma Membrane as a Tool to Dissect Both Actin-Based Cell Morphogenesis and ActA Function," *The EMBO Journal* 14(12):2731-2744.

Friedman, R.S. et al. (Nov. 2000). "Induction of Human Immunodeficiency Virus (HIV)-Specific CD8 T-Cell Responses by *Listeria monocytogenes* and a Hyperattenuated *Listeria* Strain Engineered to Express HIV Antigens," *Journal of Virology* 74(21):9987-9993.

Fuessel, S. et al. (Jul. 2003). "Multiple Tumor Marker Analyses (PSA, hK2, PSCA, trp-p8) in Primary Prostate Cancers Using Quantitative RT-PCR," *Int. J. Oncol.* 23(1):221-228.

Gaillard, J.-L. et al. (Jun. 28, 1991). "Entry of *L. monocytogenes* Into Cells Is Mediated by Internalin, a Repeat Protein Reminiscent of Surface Antigens from Gram-Positive Cocci," *Cell* 65:1127-1141.

Gedde, M.M. et al. (Feb. 2000). "Role of Listeriolysin O in Cell-to-Cell Spread of *Listeria monocytogenes*," *Infection and Immunity* 68(2):999-1003.

Geginat, G. et al. (Feb. 1, 2001). "A Novel Approach of Direct Ex Vivo Epitope Mapping Identifies Dominant and Subdominant CD4 and CD8 T Cell Epitopes from *Listeria monocytogenes*," *The Journal of Immunology* 166(3):1877-1884.

GenBank Accession No. AE017262 updated on Dec. 7, 1995, located at <http://www.ncbi.nlm.nih.gov/entrez/viewer.fcgi?val=83316099&itemID=5797&view=gbw...>, last visited on Jan. 16, 2006, 2 pages.

GenBank Accession No. AE017323 updated on Apr. 30, 2004, located at <http://www.ncbi.nlm.nih.gov/entrez/viewer.fcgi?db=nuccore&id=46879761>, last visited Oct. 5, 2007, 165 pages.

GenBank Accession No. AF043498 updated on Feb. 24, 1998, located at <http://www.ncbi.nlm.nih.gov/entrez/viewer.fcgi?db=nuccore&id=2909843>, last visited Oct. 5, 2007, two pages.

GenBank Accession No. AF143506 updated on Aug. 16, 1999, located at <http://www.ncbi.nlm.nih.gov/entrez/viewer.fcgi?db=nuccore&id=5733483>, last visited Oct. 5, 2007, two pages.

GenBank Accession No. AF174588 updated on Feb. 4, 2000, located at <http://www.ncbi.nlm.nih.gov/entrez/viewer.fcgi?db=nuccore&id=5929907>, last visited on Oct. 5, 2007, two pages.

GenBank Accession No. AF497169 updated on Sep. 10, 2002, located at <http://www.ncbi.nlm.nih.gov/entrez/viewer.fcgi?db=nuccore&id=22770473>, last visited Oct. 5, 2007, 2 pages.

GenBank Accession No. AF497170 updated Sep. 10, 2002, located at <http://www.ncbi.nlm.gov/entrez/viewer.fcgi?db=nuccore&id=2270475>, last visited Oct. 5, 2007, 2 pages.

GenBank Accession No. AF497171 updated Sep. 10, 2002, located at <http://www.ncbi.nlm.gov/entrez/viewer.fcgi?db=nuccore&id=22770477>, last visited Oct. 5, 2007, 2 pages.

GenBank Accession No. AF497172 updated Sep. 10, 2002, located at <http://www.ncbi.nlm.gov/entrez/viewer.fcgi?db=nuccore&id=22770479>, last visited Oct. 5, 2007, 2 pages.

GenBank Accession No. AF497173 updated Sep. 10, 2002, located at <http://www.ncbi.nlm.gov/entrez/viewer.fcgi?db=nuccore&id=22770481>, last visited Oct. 5, 2007, 2 pages.

GenBank Accession No. AF497174 updated Sep. 10, 2002, located at <http://www.ncbi.nlm.gov/entrez/viewer.fcgi?db=nuccore&id=22770483>, last visited Oct. 5, 2007, 2 pages.

GenBank Accession No. AF497175 updated Sep. 10, 2002, located at <http://www.ncbi.nlm.gov/entrez/viewer.fcgi?db=nuccore&id=22770485>, last visited Oct. 5, 2007, 2 pages.

GenBank Accession No. AF497176 updated Sep. 10, 2002, located at <http://www.ncbi.nlm.gov/entrez/viewer.fcgi?db=nuccore&id=22770487>, last visited Oct. 5, 2007, 2 pages.

GenBank Accession No. AF497177 updated Sep. 10, 2002, located at <http://www.ncbi.nlm.gov/entrez/viewer.fcgi?db=nuccore&id=22770489>, last visited Oct. 5, 2007, 2 pages.

GenBank Accession No. AF497178 updated Sep. 10, 2002, located at <http://www.ncbi.nlm.gov/entrez/viewer.fcgi?db=nuccore&id=22770491>, last visited Oct. 5, 2007, 2 pages.

GenBank Accession No. AF497179 updated Sep. 10, 2002, located at <http://www.ncbi.nlm.gov/entrez/viewer.fcgi?db=nuccore&id=22770493>, last visited Oct. 5, 2007, 2 pages.

GenBank Accession No. AF497180 updated Sep. 10, 2002, located at <http://www.ncbi.nlm.gov/entrez/viewer.fcgi?db=nuccore&id=22770495>, last visited Oct. 5, 2007, 2 pages.

GenBank Accession No. AF497181 updated Sep. 10, 2002, located at <http://www.ncbi.nlm.gov/entrez/viewer.fcgi?db=nuccore&id=22770497>, last visited Oct. 5, 2007, 2 pages.

GenBank Accession No. AF497182 updated Sep. 10, 2002, located at <http://www.ncbi.nlm.gov/entrez/viewer.fcgi?db=nuccore&id=22770499>, last visited Oct. 8, 2007, 2 pages.

GenBank Accession No. AF497183 updated Sep. 10, 2002, located at <http://www.ncbi.nlm.gov/entrez/viewer.fcgi?db=nuccore&id=22770501>, last visited Oct. 5, 2007, 2 pages.

GenBank Accession No. AJ006589 updated on Nov. 14, 2006, located at <http://www.ncbi.nlm.nih.gov/entrez/viewer.fcgi?db=nuccore&id=40313242>, last visited Oct. 7, 2007, 27 pages.

GenBank Accession No. AJ242593 updated Apr. 15, 2005, located at <http://www.ncbi.nlm.nih.gov/entrez/viewer.fcgi?db=nuccore&id=5823598>, last visited Oct. 5, 2007, 29 pages.

GenBank Accession No. AJ401047 updated Jun. 16, 2000, located at <http://www.ncbi.nlm.nih.gov/entrez/viewer.fcgi?db=nuccore&id=8346631>, last visited Oct. 5, 2007, five pages.

GenBank Accession No. AJ414670 updated Nov. 14, 2006, located at <http://www.ncbi.nlm.nih.gov/entrez/viewer.fcgi?db=nuccore&id=17974209>, last visited Oct. 5, 2007, four pages.

GenBank Accession No. AJ417449 updated Aug. 23, 2005, located at <http://www.ncbi.nlm.nih.gov/entrez/viewer.fcgi?db=nuccore&id=73745527>, last visited Oct. 5, 2007, five pages.

GenBank Accession No. AJ417488 updated Oct. 5, 2005, located at <http://www.ncbi.nlm.nih.gov/entrez/viewer.fcgi?db=nuccore&id=77157549>, last visited Oct. 5, 2007, five pages.

GenBank Accession No. AJ417499 updated Oct. 29, 2001, located at <http://www.ncbi.nlm.nih.gov/entrez/viewer.fcgi?db=nuccore&id=16549054>, last visited Oct. 5, 2007, two pages.

GenBank Accession No. AL591824 updated Mar. 24, 2007, located at <http://www.ncbi.nlm.nih.gov/entrez/viewer.fcgi?db=nuccore&id=30407125>, last visited Oct. 5, 2007, two pages GenBank Accession No. AL591974, Regions 5581..5818, updated Apr. 16, 2005, located at <http://www/ncbi.nlm.nih.gov/entrez/viewer.fcgi?db=nuccore&qty=1&c_start=1&list_uids...>, last visited on Sep. 22, 2007, two pages.

GenBank Accession No. AL591974, Regions 9456..11389, updated Apr. 16, 2005, located at <http://www/ncbi.nlm.nih.gov/entrez/viewer.fcgi?db=nuccore&qty=1&c_start=1&list_uids...>, last visited on Sep. 22, 2007, two pages.

GenBank Accession No. AL591975 updated Jan. 16, 2006, located at <http://www.ncbi.nlm.nih.gov/entrez/viewer.fcgi?db=nuccore&id=16409709>, last visited Oct. 8, 2007, 176 pages.

GenBank Accession No. AL591977 updated on Apr. 16, 2005, located at <http://www.ncbi.nlm.nih.gov/entrez/viewer.fcgi?val=16410252&itemID=247&view=gbwi...>, last visited on Jan. 16, 2006, 2 pages.

GenBank Accession No. AL591978 updated on Apr. 16, 2005, located at <http://www.ncbi.nlm.nih.gov/entrez/viewer.fcgi?val=16410540&itemID=153&view=gbwi...>, last visited on Jan. 16, 2006, 2 pages.

GenBank Accession No. AL591981 updated on Apr. 16, 2005, located at <http://www.ncbi.nlm.nih.gov/entrez/viewer.fcgi?val=16411141&itemID=267&view=gbwi...>, last visited on Jan. 16, 2006, 2 pages.
GenBank Accession No. AL591983 updated on Apr. 16, 2005, located at <http://www.ncbi.nlm.nih.gov/entrez/viewer.fcgi?val=16411809&itemID=12&vie=gbwit...>, last visited on Jan. 16, 2006, 2 pages.
GenBank Accession No. AL592022 updated Mar. 24, 2007, located at <http://www.ncbi.nlm.nih.gov/entrez/viewer.fcgi?db=nuccore&id=30407126>, last visited Oct. 7, 2007, two pages.
GenBank Accession No. AL596163 updated on Apr. 16, 2005, located at <http://www.ncbi.nlm.nih.gov/entrez/viewer.fcgi?val=16412421&itemID=70&view=gbwit...>, last visited on Jan. 16, 2006, 2 pages.
GenBank Accession No. AL596168 updated on Apr. 16, 2005, located at <http://www.ncbi.nlm.nih.gov/entrez/viewer.fcgi?val=16413677&itemID=112&view=gbwi...>, last visited on Jan. 16, 2006, 2 pages.
GenBank Accession No. AL596169 updated on Apr. 16, 2005, located at <http://www.ncbi.nlm.nih.gov/entrez/viewer.fcgi?db=nuccore&id=16414035>, last visited Oct. 5, 2007, 153 pages.
GenBank Accession No. AL596173 updated on Apr. 16, 2005, located at <http://www.ncbi.nlm.nih.gov/entrez/viewer.fcgi?val=16415123&itemID=24&view=gbwit...>, last visited on Jan. 16, 2006, 2 pages.
GenBank Accession No. AR026974 updated Sep. 29, 1999, located at <http://www.ncbi.nlm.nih.gov/entrez/viewer.fcgi?db=nuccore&id=5937814>, last visited Oct. 5, 2007, one page.
GenBank Accession No. AR302232 updated Jun. 12, 2003, located at <http://www.ncbi.nlm.nih.gov/entrez/viewer.fcgi?db=nuccore&id=31690451>, last visited Oct. 5, 2007, two pages.
GenBank Accession No. AY093430 updated Nov. 25, 2003, located at <http://www.ncbi.nlm.nih.gov/entrez/viewer.fcgi?db=nuccore&id=22651575>, last visited Oct. 5, 2007, four pages.
GenBank Accession No. AY423864 updated May 6, 2004, located at <http://www.ncbi.nlm.nih.gov/entrez/viewer.fcgi?db=nuccore&id=40456274>, last visited Oct. 5, 2007, four pages.
GenBank Accession No. AY510073 updated on May 5, 1995, located at <http://www.ncbi.nlm.nih.gov/entrez/viewer.fcgi?db=nucleotide&val=40889000>, last visited on Jan. 19, 2006, 7 pages.
GenBank Accession No. AY512476 updated May 10, 2005, located at <http://www.ncbi.nlm.nih.gov/entrez/viewer.fcgi?db=nuccore&id=46252284>, last visited Oct. 5, 2007, six pages.
GenBank Accession No. AY562545 updated Apr. 5, 2004, located at <http://www.ncbi.nlm.nih.gov/entrez/viewer.fcgi?db=nuccore&id=45862386>, last visited Oct. 5, 2007, five pages.
GenBank Accession No. AY597272 updated May 25, 2005, located at <http://www.ncbi.nlm.nih.gov/entrez/viewer.fcgi?db=nuccore&id=47027951>, last visited Oct. 5, 2007, three pages.
GenBank Accession No. BAB63910 updated Aug. 9, 2007, located at <http://www.ncbi.nlm.nih.gov/entrez/viewer.fcgi?db=nuccore&id=15375402>, last visited Oct. 7, 2007, two pages.
GenBank Accession No. BC003512 updated Jul. 15, 2006, located at <http://www.ncbi.nlm.nih.gov/entrez/viewer.fcgi?db=nuccore&id=13097581>, last visited Oct. 7, 2007, four pages.
GenBank Accession No. NC_002973 updated on Dec. 3, 1995, located at <http://www.ncbi.nlm.nih.gov/entrez/viewer.fcgi?val=46906224&itemID=5796&view=gbw...>, last visited on Jan. 16, 2006, 2 pages.
GenBank Accession No. NC_003291 updated Sep. 26, 2007, located at <http://www.ncbi.nlm.nih.gov/entrez/viewer.fcgi?db=nuccore&id=29789895>, last visited Oct. 7, 2007, 31 pages.
GenBank Accession No. NM_005823 updated Sep. 17, 2007, located at <http://www.ncbi.nlm.nih.gov/entrez/viewer.fcgi?db=nuccore&id=68303642>, last visited Oct. 7, 2007, six pages.
GenBank Accession No. NM_013404 updated Sep. 25, 2007, located at <http://www.ncbi.nlm.nih.gov/entrez/viewer.fcgi?db=nuccore&id=68303653>, last visited Oct. 7, 2007, six pages.
GenBank Accession No. U40434 updated Jan. 19, 1996, located at <http://www.ncbi.nlm.nih.gov/entrez/viewer.fcgi?db=nuccore&id=1145723>, last visited Oct. 7, 2007, three pages.
GenBank Accession No. U51223 updated Apr. 25, 1996, located at <http://www.ncbi.nlm.nih.gov/entrez/viewer.fcgi?db=nuccore&id=1277147>, last visited Oct. 7, 2007, three pages.
GenBank Accession No. X57036 updated Jun. 30, 1993, located at <http://www.ncbi.nlm.nih.gov/entrez/viewer.fcgi?db=nuccore&id=14810>, last visited Oct. 7, 2007, three pages.
GenBank Accession No. X59723 updated Apr. 18, 2005, located at <http://www.ncbi.nlm.nih.gov/entrez/viewer.fcgi?db=nuccore&id=44091>, last visited Oct. 7, 2007, three pages.
GenBank Accession No. X60952 updated Jun. 30, 1993, located at <http://www.ncbi.nlm.nih.gov/entrez/viewer.fcgi?db=nuccore&id=48953>, last visited Oct. 7, 2007, two pages.
GenBank Accession No. X81135 updated on Aug. 8, 1995, located at <http://www.ncbi.nlm.nih.gov/entrez/viewer.fcgi?db=nucleotide&val=563492>, last visited on Jan. 19, 2006, 3 pages.
Gerstel, B. et al. (Jun. 1996). "The ActA Polypeptides of *Listeria ivanovii* and *Listeria monocytogenes* Harbor Related Binding Sites for Host Microfilament Proteins," *Infection and Immunity* 64(6):1929-1936.
Giedlin, M. et al. (Date Unknown). "The Living Dead: Vaccines Against Microbial Pathogens Based on Psoralen-Killed Metabolically Active DNA Repair Mutants," Abstract 189 (H) located at <http://www.asmbiodefense.org/2004tueabs.asp>, last visited Nov. 5, 2004, one page.
Giedlin, M. et al. (Mar. 2004). "The Living Dead: Vaccines Against Microbial Pathogens Based on Psoralen-Killed Metabolically Active DNA Repair Mutants," abstract *presented at the American Society for Microbiology (ASM) Biodefense Research Meeting*, Mar. 7-10, 2004, as posted on <http://www.cerus.com/pages/solution/abs158.html>, last visited Jul. 18, 2004, two pages.
Giedlin, M. et al. (Mar. 9, 2004). "The Living Dead: Vaccines Against Microbial Pathogens Based on Psoralen-Killed Metabolically Active DNA Repair Mutants," Poster, *presented at American Society for Microbiology Biodefense Research Meeting(ASMBRM)*, Mar. 7-10, 2004, Baltimore, MD, two pages.
Giedlin, M. et al. (Apr. 2005). "Recombinant *Listeria monocytogenes*-Based Immunotherapy Targeting Mesothelin for the Treatment of Pancreatic and Ovarian Cancer," Poster, *presented at the 96th American Society for Cancer Research (AACR) Annual Meeting*, Anaheim, CA, Apr. 16-20, 2005, one page.
Giedlin, M.A. (Date Unknown). "*Listeria*-Based Ovarian Cancer Polyepitope Vaccines," Abstract for Grant No. 1R43CA109868-01A1 located at <http://crisp.cit.nih.gov/crisp/CRISP_LIB.getdoc/testkey=6932934&p_grant_num=1R43C...>, last visited Dec. 7, 2005, two pages.
Giedlin, M.A. (Date Unknown). "Use of *Listeria* as Colon Cancer Vaccine Adjuvants," Abstract for Grant No. 1R43CA101378-01 located at <http://crisp.cit.nih.gov/crisp/CRISP_LIB.getdoc?testkey=6645212&p_grant_num=1R43CA...>, last visited Nov. 3, 2004, two pages.
Giedlin, M.A. et al. (Mar. 2003). "Therapeutic Immunization with Attenuated Recombinant *Listeria monocytogenes* Prolongs Survival in a Murine Transplant Model of Melanoma," *Proceedings of the American Association for Cancer Research, 94th Annual Meeting*, Apr. 5-9, 2003,Toronto, Ontario, CA, 44:194, Abstract No. 850, one page.
Giedlin, M.A. et al. (Jul. 2003). "Therapeutic Immunization with Attenuated Recombinant *Listeria monocytogenes* Prolongs Survival in a Murine Transplant Model of Melanoma," (Abstract for the 94th Annual Meeting of the American Association for Cancer Research, Washington DC, USA, Jul. 11-14, 2003) *Proceedings of the American Association for Cancer Research Annual Meeting* 44(2):167-168, Abstract No. 850.
Gilbreth, S.E. et al. (Aug. 2004). "Catabolite Repression and Virulence Gene Expression in *Listeria monocytogenes*," *Current Microbiology* 49(2):95-98.
Gilliam, A.D. et al. (Jun. 2004). "A Phase II Study of G17DT in Gastric Carcinoma," *Eur. J. Surg. Oncol.* 30(5):536-543.
Glaser, P. et al. (Oct. 26, 2001). "Comparative Genomics of *Listeria* Species," *Science* 294:849-852.

Glomski, I.J. et al. (Mar. 18, 2002). "The *Listeria monocytogenes* Hemolysin has an Acidic pH Optimum to Compartmentalize Activity and Prevent Damage to Infected Host Cells," *The Journal of Cell Biology* 156(6):1029-1038.

Glomski, I.J. et al. (Dec. 2003). "*Listeria monocytogenes* Mutants That Fail to Compartmentalize Listerolysin O Activity are Cytotoxic, Avirulent, and Unable to Evade Host Extracellular Defenses," *Infection and Immunity* 71(12):6754-6765.

Goebel, W. et al. (Apr. 1993). "*Listeria monocytogenes*—a Model System for Studying the Pathomechanisms of an Intracellular Microorganism," *Zbl. Bakt.* 278(2-3):334-347.

Gouin, E. et al. (2005). "Actin-Based Motility of Intracellular Pathogens," *Current Opinion Microbiology* 8:35-45.

Grenningloh, R et al. (Sep. 1997). "Lysteriolysin and IrpA are Major Protein Targets of the Human Humoral Response Against *Listeria monocytogenes*," *Infection and Immunity* 65(9):3976-3980.

Grindley, N.D.F. (Oct. 1, 1997). "Site-Specific Recombination: Synapsis and Strand Exchange Revealed," *Current Biology* 7(10):R608-R612.

Grossman, L. (1994). "Damage Recognition by UvrABC: A Study of Vectorial Movement," *Ann. NY Acad. Sci.* 726:252-265.

Groth, A.C. et al. (May 23, 2000). "A Phage Integrase Directs Efficient Site-Specific Integration in Human Cells," *Proc. Natl. Acad. Sci. USA* 97(11):5995-6000.

Groth, A.C. et al. (2004). "Phage Integrases: Biology and Applications," *J. Mol. Biol.* 335:667-678.

Gunn, G.R. et al. (2001). "Two *Listeria monocytogenes* Vaccine Vectors That Express Different Molecular Forms of Human Papilloma Virus-16 (HPV-16) E7 Induce Qualitatively Different T Cell Immunity That Correlates with Their Ability to Induce Regression of Established Tumors Immortalized by HPV-16," *The Journal of Immunology* 167:6471-6479.

Gunn, G.R. et al. (2002). "Recombinant Intra-Cellular Bacteria as Carriers for Tumor Antigens" Chapter 14 *in Vaccine Delivery Strategies*, Dietrich, G. et al. eds., Horizon Scientific Press: UK., pp. 315-348.

Guo, F. et al. (Sep. 4, 1997). "Structure of Cre Recombinase Complexed with DNA in a Site-Specific Recombination Synapse," *Nature* 389(6646):40-46.

Guzmán, C.A. et al. (Jun. 1998). "Attenuated *Listeria monocytogenes* Carrier Strains can Deliver an HIV-1 gp120 T Helper Epitope to MHC Class II-Restricted Human CD4+ T Cells," *Eur. J. Immunol.* 28:1807-1814.

Hallett, B. et al. (Sep. 1997). "Transposition and Site-Specific Recombination: Adapting DNA Cut-and-Paste Mechanisms to a Variety of Genetic Rearrangements," *FEMS Microbiology Reviews* 21(2):157-178.

Hassan, R. et al. (Jun. 15, 2004). "Mesothelin: A New Target for Immunotherapy," *Clinical Cancer Research* 10(12, part 1):3937-3942.

He, W. et al. (Sep. 1997). "Construction of the Temperature-Sensitive Vectors pLUCH80 and pLUCH88 for Delivery of Tn917::NotI/SmaI and Use of These Vectors To Derive a Circular Map of *Listeria monocytogenes* Scott A, a Serotype 4b Isolate," *Applied and Environmental Microbiology* 63(9):3480-3487.

Hess, J. et al. (2000). "Exploiting the Immune System: Toward New Vaccines Against Intracellular Bacteria," *in Advances in Immunology*, Dixon, F.J. et al. eds., Academic Press, Inc.: San Diego, CA, 75:1-88.

Hodgson, D.A. (2000). "Generalized Transduction of Serotype 1/2 and Serotype 4b Strains of *Listeria monocytogenes*," *Molecular Microbiology* 35(2):312-323.

Hoess, R.H. et al. (Nov. 1978). "Structure of the λ *att* Sites Generated by *int*-Dependent Deletions," *Proc. Natl. Acad. Sci. USA* 75(11):5437-5441.

Hoess, R.H. et al. (1986). "The Role of the *loxP* Spacer Region in P1 Site-Specific Recombination," *Nucleic Acids Research* 14(5):2287-2300.

Hof, H. et al. (Apr. 1997). "Management of Listeriosis," *Clinical Microbiology Reviews* 10(2):345-357.

Howard, P.J. et al. (Feb. 1992). "Differentiation of *Listeria monocytogenes, Listeria innocua, Listeria ivanovii*, and *Listeria seeligeri* by Pulsed-Field Gel Electrophoresis," *Applied and Environmental Microbiology* 58(2):709-712.

Huang. A.Y.C. et al. (May 13, 1994). "Role of Bone Marrow-Derived Cells in Presenting MHC Class I-Restricted Tumor Antigens," *Science* 264:961-965.

Iacobuzio-Donahue, C.A. et al. (Dec. 15, 2003). "Highly Expressed Genes in Pancreatic Ductal Adenocarcinomas: A Comprehensive Characterization and Comparison of the Transcription Profiles Obtained from Three Major Technologies," *Cancer Research* 63:8614-8622.

Ikonomidis, G. et al. (Dec. 1994). "Delivery of a Viral Antigen to the Class I Processing and Presentation Pathway by *Listeria monocytogenes*," *J. Exp. Med.* 180:2209-2218.

Ikonomidis, G. et al. (1994). "Delivery of a Viral Antigen to the Class I Pathway by *Listeria monocytogenes*: A Potential Vaccine Vector," *Abstracts of the 94th General Meeting of the American Society For Microbiology*, May 23-27, 1994, Las Vegas Convention Center: Las Vegas, NV, p. 159, Abstract No. E-90.

Jaradat, Z.W. et al. (May 2003). "A *Listeria* adhesion Protein-Deficient *Listeria monocytogenes* Strain Shows Reduced Adhesion Primarily to Intestinal Cell Lines," *Med. Microbiol. Immunol.* 192(2):85-91.

Jensen, E.R. et al. (Nov. 1997). "Recombinant *Listeria monocytogenes* Vaccination Eliminates Papillomavirus-Induced Tumors and Prevents Papilloma Formation from Viral DNA," *Journal of Virology* 71(11):8467-8474.

Jensen, E.R. et al. (1997). "Recombinant *Listeria monocytogenes* as a Live Vaccine Vehicle and a Probe for Studying Cell-Mediated Immunity," *Immunological Reviews* 158:147-157.

Johnson, J. et al. (Jul. 2004). "Natural Atypical *Listeria innocua* Strains with *Listeria monocytogenes* Pathogenicity Island 1 Genes," *Applied and Environmental Microbiology* 70(7):4256-4266.

Jones, S. et al. (Dec. 1994). "Characterization of *Listeria monocytogenes* Pathogenesis in a Strain Expressing Perfringolysin O in Place of Listeriolysin O," *Infection and Immunity* 62(12):5608-5613.

Karlin, S. et al (Apr. 20, 2004). "Comparative Analysis of Gene Expression Among Low G+C Gram-Positive Genomes," *Proc. Natl. Acad. Sci. USA* 101(16):6182-6187.

Kawamura, K.S. et al. (Jun. 1, 2002). "In Vivo Generation of Cytotoxic T Cells From Epitopes Displayed on Peptide-Based Delivery Vehicles," *The Journal of Immunology* 168(11):5709-5715.

Kocks, C. et al. (Feb. 7, 1992). "*L. monocytogenes*-Induced Actin Assembly Requires the *actA* Gene Product, a Surface Protein," *Cell* 68:521-531.

Köhler, S. et al. (Jun. 1990). "The Gene Coding for Protein p60 of *Listeria monocytogenes* and Its Use as a Specific Probe for *Listeria monocytogenes*," *Infection and Immunity* 58(6):1943-1950.

Köhler, S. et al. (Aug. 1991). "Expression of the *iap* Gene Coding for Protein p60 of *Listeria monocytogenes* Is Controlled on the Post-transcriptional Level," *Journal of Bacteriology* 173(15):4668-4674.

Kolb-Mäurer, A. et al. (Jun. 2000). "*Listeria monocytogenes*-Infected Human Dendritic Cells: Uptake and Host Cell Response," *Infection and Immunity* 68(6):3680-3688.

Kovacsovics-Bankowski, M. et al. (Jun. 1, 1993). "Efficient Major Histocompatibility Complex Class I Presentation of Exogenous Antigen Upon Phagocytosis by Macrophages," *Proc. Natl. Acad. Sci. USA* 90(11):4942-4946.

Lalic-Mülthaler, M. et al. (2001). "In vitro Transcription of PrfA-Dependent and—Independent Genes of *Listeria monocytogenes*," *Molecular Microbiology* 42(1):111-120.

Lampson, L.A. et al. (Jan. 1, 1993). "Exploiting the *lacZ* Reporter Gene for Quantitative Analysis of Disseminated Tumor Growth with the Brain: Use of the *lacZ* Gene Product as a Tumor Antigen, for Evaluation of Antigenic Modulation, and to Facilitate Image Analysis of Tumor Growth in Situ," *Cancer Research* 53(1):176-182.

Landy, A. (Oct. 1993). "Mechanistic and Structural Complexity in the Site-Specific Recombination Pathways of Int and FLP," *Curr. Op. Biotechnol.* 3(5):699-707.

Langer, S.J. et al. (2002). "A Genetic Screen Identifies Novel Non-Compatible *loxP* Sites," *Nucleic Acids Research* 30(14):3067-3077.

Lasa, I. et al. (Nov. 1995). "The Amino-Terminal Part of ActA is Critical for the Actin-Based Motility of *Listeria monocytogenes*; the Central Proline-Rich Region Acts as a Stimulator," *Molecular Microbiology* 18(3):425-436.

Lasa, I. et al. (Apr. 1, 1997). "Identification of Two Regions in the N-Terminal Domain of ActA Involved in the Actin Comet Tail Formation by *Listeria monocytogenes*," *The EMBO Journal* 16(7):1531-1540.

Lauer, P. et al. (Jun. 1, 1999). "Characterization of the Attachment Site of Bacteriophage U153 Within the *Listeria monocytogenes* comK Gene," *Abstracts of the General 99th Meeting of the American Society for Microbiology*, Chicago, IL, May 30-Jun. 3, 1999, p. 446. Abstract M-17.

Lauer, P. et al. (Nov. 1999). "Scanning Alanine Mutagenesis Reveals Multiple Functions for the N-Terminal Region of *Listeria monocytogenes* ActA in Actin-Based Motility," *Molecular Biology of the Cell* 10(Supp.):159a.

Lauer, P. et al. (Dec. 1999). "Scanning Alanine Mutagenesis Reveals Multiple Functions for the N-Terminal Region of *Listeria monocytogenes* ActA in Actin-Based Motility," Abstract 919, *Abstracts presented at the 39th Annual Meeting of the American Soceity for Cell Biology*, Washington, DC, Dec. 11-15, 1999, p. 159a.

Lauer, P. et al. (2001). "Systematic Mutational Analysis of the Amino-Terminal Domain of the *Listeria monocytogenes* ActA Protein Reveals Novel Functions in Actin-Based Motility," *Molecular Microbiology* 42(5):1163-1177.

Lauer, P. et al. (Aug. 2002). "Construction, Characterization, and Use of Two *Listeria monocytogenes* Site-Specific Phage Integration Vectors," *Journal of Bacteriology* 184(15):4177-4186.

Lauer, P. et al. (Feb. 2003). "Construction, Characterization, and Use of Two *Listeria monocytogenes* Site-Specific Phage Integration Vectors," *Journal of Bacteriology* Erratum 185(4):1484.

Lauth, M. et al. (2002). "Stable and Efficient Cassette Exchange Under Non-Selectable Conditions by Combined Use of Two Site-Specific Recombinases," *Nucleic Acids Research* 30(21-e115), seven pages.

Lebrun, M. et al. (1996). "Internalin Must be on the Bacterial Surface to Mediate Entry of *Listeria monocytogenes* into Epithelial Cells," *Molecular Microbiology* 21(3):579-592.

Lecuit, M. et al. (Jun. 1, 2001). "A Transgenic Model for Listeriosis: Role of Internalin in Crossing the Intestinal Barrier," *Science* 292:1722-1725.

Lecuit, M. et al. (Nov. 2002). "Genetically-Modified-Animal Models for Human Infections: the *Listeria* Paradigm," *Trends Mol. Med.* 8(11):537-542.

Lecuit, M. et al. (Apr. 20, 2004). "Targeting and Crossing of the Human Maternofetal Barrier by *Listeria monocytogenes*: Role of Internalin Interaction with Trophoblast E-cadherin," *Proc. Natl. Acad. Sci. USA* 101(16):6152-6157.

Lenz, L.L. et al. (Aug. 2002). "Identification of a Second *Listeria* secA Gene Associated with Protein Secretion and the Rough Phenotype," *Molecular Microbiology* 45(4):1043-1056.

Lenz, L.L. et al. (Oct. 14, 2003). "SecA2-Dependent Secretion of Autolytic Enzymes Promotes *Listeria monocytogenes* Pathogenesis," *Proc. Natl. Acad. Sci. USA* 100(21):12432-12437.

Leong, M. et al. (Feb. 3, 2004). "Recombinant Attenuated *Listeria monocytogenes* Elicit Functional Immune Response Specific to a Heterologous Antigen in the Presence of *Listeria*-Specific Cellular and Humoral Immunity," *Gordon Research Conference on Immunochemistry & Immunobiology Conference*, Buellton, CA, Feb. 1-6, 2004, 20 pages.

Lety, M-A. et al. (2003). "Modification of the Signal Sequence Cleavage Site of Listeriolysin O Does Not Affect Protein Secretion but Impairs the Virulence of *Listeria monocytogenes*," *Microbiology* 149:1249-1255.

Li, W. et al. (Dec. 1, 2004). "Epstein-Barr Virus in Hepatocellular Carcinogenesis," *World J. Gasteroenterol.* 10(23):3409-3413.

Li, Y. et al. (Dec. 2004). "Natural Killer Cells Inhibit Hepatitis C Virus Expression," *Journal of Leukocyte Biology* 76(6):1171-1179.

Liau, L.M. et al. (Apr. 15, 2002). "Tumor Immunity Within the Central Nervous System Stimulated by Recombinant *Listeria monocytogenes* Vaccination," *Cancer Research* 62(8):2287-2293.

Lin, J-J. et al. (Aug. 1992). "(A)BC Excinuclease: the *Escherichia coli* Nucleotide Excision Repair Enzyme," *Molecular Microbiology* 6(16):2219-2224.

Lin, C-W. et al. (2002). "Oral Vaccination with Recombinant *Listeria monocytogenes* Expressing Human Papillomavirus Type 16 E7 Can Cause Tumor Growth in Mice to Regress," *Int. J. Cancer* 102:629-637.

Lingnau, A. et al. (Oct. 1995). "Expression of the *Listeria monocytogenes* EGD *inlA* and *inlB* Genes, Whose Products Mediate Bacterial Entry into Tissue Culture Cell Lines, by PrfA-Dependent and -Independent Mechanisms," *Infection and Immunity* 63(10):3896-3903.

Lippolis, J.D. et al. (Nov. 1, 2002). "Analysis of MHC Class II Antigen Processing by Quantitation of Peptides that Constitute Nested Sets," *The Journal of Immunology* 169(9):5089-5097.

Loessner, M.J. et al. (Apr. 1994). "Structural Proteins and DNA Characteristics of 14 *Listeria* Typing Bacteriophages," *Journal of General Virology* 75(4):701-710.

Loessner, M.J. et al. (2000). "Complete Nucleotide Sequence, Molecular Analysis and Genome Structure of Bacteriophage A118 of *Listeria monocytogenes*: Implications for Phage Evolution," *Molecular Microbiology* 35(2):324-340.

Loh, J. et al. (Jan. 2005). "Natural Killer Cells Utilize Both Perforin and Gamma Interferon To Regulate Murine Cytomegalovirus Infection in the Spleen and Liver," *Journal of Virology* 79(1):661-667.

Luo, Q. et al. (2004). "In vitro Transcription of the *Listeria monocytogenes* Virulence Genes *inlC* and *mpl* Reveals Overlapping PrfA-Dependent and -Independent Promoters that are Differentially Activated by GTP," *Molecular Microbiology* 52(1):39-52.

Machner, M.P. et al. (Oct. 26, 2001). "ActA from *Listeria monocytogenes* Can Interact with Up to Four Ena/VASP Homology 1 Domains Simultaneously," *The Journal of Biological Chemistry* 276(43):40096-40103.

Manohar, M. et al. (Jun. 2001). "Gut Colonization of Mice with *actA*-Negative Mutant of *Listeria monocytogenes* Can Stimulate a Humoral Mucosal Immune Response," *Infection and Immunity* 69(6):3542-3549.

Marchand, J-P. et al. (Jul. 1995). "Actin-Based Movement of *Listeria monoctyogenes*: Actin Assembly Results from the Local Maintenance of Uncapped Filament Barbed Ends at the Bacterium Surface," *The Journal of Cell Biology* 130(2):331-343.

Marquis, H. et al. (Jun. 16, 1997). "Proteolytic Pathways of Activation and Degradation of a Bacterial Phospholipase C During Intracellular Infection by *Listeria monocytogenes*," *The Journal of Cell Biology* 137(6):1381-1392.

Martin, P. et al. (1986). "Nucleotide Sequence of the *tetM* Tetracycline Resistance Determinant of the Streptococcal Conjugative Shuttle Transposon Tn*1545*," *Nucleic Acids Research* 14(17):7047-7058.

Mata, M. et al. (1998). "The MHC Class I-Restricted Immune Response to HIV-gag in BALB/c Mice Selects a Single Epitope That Does Not Have a Predictable MHC-Binding Motif and Binds to $K^d$ Through Interactions Between a Glutamine at P3 and Pocket $D^1$," *The Journal of Immunology* 161:2985-2993.

Mata, M. et al. (1999). "Th1 T Cell Responses to HIV-1 Gag Protein Delivered by a *Listeria monocytogenes* Vaccine Are Similar to Those Induced by Endogenous Listerial Antigens," *The Journal of Immunology* 163:1449-1456.

Mata, M. et al. (Jan. 8, 2001). "Evaluation of a Recombinant *Listeria monocytogenes* Expressing an HIV Protein That Protects Mice Against Viral Challenge," *Vaccine* 19(11-12):1435-1445.

Mayer, M.P.A. et al. (Mar. 1999). "Identification of a Cytolethal Distending Toxin Gene Locus and Features of a Virulence-Associated Region in *Actinobacillus actinomycetemcomitans*," *Infection and Immunity* 67(3):1227-1237.

Merlin, C. et al. (Aug. 2002). "Tools for Characterization of *Escherichia coli* Genes of Unknown Function," *Journal of Bacteriology* 184(16):4573-4581.

Milenbachs Lukowiak, A. et al. (Feb. 2004). "Deregulation of *Listeria monocytogenes* Virulence Gene Expression by Two Distinct and Semi-Independent Pathways," *Microbiology* 150(2):321-333.

Milohanic, E. et al. (Mar. 2003). "Transcriptome Analysis of *Listeria monocytogenes* Identifies Three Groups of Genes Differently Regulated by PrfA," *Molecular Microbiology* 47(6):1613-1625.

Mogilner, A. et al. (Mar. 2003). "Force Generation by Actin Polymerization II: The Elastic Ratchet and Tethered Filaments," *Biophysical Journal* 84(3):1591-1605.

Mollet, B. et al. (Jul. 1993). "Directed Genomic Integration, Gene Replacement, and Integrative Gene Expression in *Streptococcus thermophilus*," *Journal of Bacteriology* 175(14):4315-4324.

Moody, G. et al. (Mar. 2004). "Recombinant *Listeria monocytogenes*-Based Immunotherapy Targeting the Receptor Tyrosine Kinase EphA2," Abstract *presented at the American Association for Cancer Research (AACR)*, Mar. 27-31, 2004, as posted on <http://www.cerus.com/pages/solution/abs155.html>, last visited on Aug. 26, 2004, two pages.

Moors, M.A. et al. (1999). "Stability of the *Listeria monocytogenes* ActA Protein in Mammalian Cells is Regulated by the N-end Rule Pathway," *Cellular Microbiology* 1(3):249-257.

Mourrain, P. et al. (Sep. 1997). "ActA is a Dimer," *Proc. Natl. Acad. Sci. USA* 94:10034-10039.

Mu, D. et al. (1997). "DNA Excision Repair Assays," *in Progress in Nucleic Acid Research and Molecular Biology*, Cohn, W.E. et al. eds., Academic Press, Inc.: San Diego, CA, 56:63-81.

Mueller, K.J. et al. (Apr. 2005). "Pleiotropic Enhancement of Bacterial Pathogenesis Resulting from the Constitutive Activation of the *Listeria monocytogenes* Regulatory Factor PrfA," *Infection and Immunity* 73(4):1917-1926.

Muminova, Z.E. et al. (May 12, 2004). "Characterization of Human Mesothelin Transcripts in Ovarian and Pancreatic Cancer," *BMC Cancer* 4(19) 10 pages.

Nagy, A. (2000). "Cre Recombinase: The Universal Reagent for Genome Tailoring," *Genesis* 26:99-109.

Nakano, M. et al. (2001). "DNA Substrates Influence the Recombination Efficiency Mediated by FLP Recombinase Expressed in Mammalian Cells," *Microbiol. Immunol.* 45(9):657-665.

Neighbors, M. et al. (Aug. 6, 2001). "A Critical Role for Interleukin 18 in Primary and Memory Effector Responses to *Listeria monocytogenes* that Extends Beyond its Effects on Interferon γ Production," *J. Exp. Med.* 194(3):343-354.

Nelson, K.E. et al. (2004, e-pub. Apr. 28, 2004). "Whole Genome Comparisons of Serotype 4b and 1/2a Strains of the Food-Borne Pathogen *Listeria monocytogenes* Reveal New Insights into the Core Genome Components of this Species," *Nucleic Acids Research* 32(8):2386-2395.

Niebuhr, K. et al. (Jul. 1993). "Localization of the ActA Polypeptide of *Listeria monocytogenes* in Infected Tissue Culture Cell Lines: ActA Is Not Associated with Actin 'Comets'," *Infection and Immunity* 61(7):2793-2802.

Noireaux, V. et al. (Mar. 2000). "Growing an Actin Gel on Spherical Surfaces," *Biophysical Journal* 78(3):1643-1654.

Nunes-Düby, S.E. et al. (1998). "Similarities and Differences Among 105 Members of the Int Family of Site-Specific Recombinases," *Nucleic Acids Research* 26(2):391-406.

Ochsenbein, A.F. et al. (Aug. 1999). "A Comparison of T Cell Memory Against the Same Antigen Induced by Virus Versus Intracellular Bacteria," *Proc. Natl. Acad. Sci. USA* 96:9293-9298.

Office Action mailed Jun. 22, 2007, for U.S. Appl. No. 11/396,216, filed Mar. 30, 2006, four pages.

Ohga, S. et al. (2002). "Immunological Aspects of Epstein-Barr Virus Infection," *Crit. Rev. Oncol. Hematol.* 44:203-215.

Olazabal, I.M. et al. (Aug. 20, 2001). "Abp1p and Cortactin, New 'Hand-Holds' for Actin," *The Journal of Cell Biology* 154(4):679-682.

Olazabal, I.M. et al. (Aug. 20, 2002). "Rho-Kinase and Myosin-II Control Phagocytic Cup Formation During CR, but Not FcγR, Phagocytosis," *Current Biology* 12:1413-1418.

O'Riordan, M. et al. (Oct. 17, 2003). "*Listeria* Intracellular Growth and Virulence Require Host-Derived Lipoic Acid," *Science* 302(5644):462-464.

Ouadrhiri, Y. et al. (1999). "Modulation of Intracellular Growth of *Listeria monocytogenes* in Human Enterocyte Caco-2 Cells by Interferon-γ and Interleukin-6: Role of Nitric Oxide and Cooperation with Antibiotics," *The Journal of Infectious Diseases* 180:1195-1204.

Paetzel, M. et al. (Jul. 2000). "The Structure and Mechanism of Bacterial Type I Signal Peptidases—A Novel Antibiotic Target," *Pharmacol. Ther.* 87(1):27-49.

Paglia, P. et al. (1997). "The Defined Attenuated *Listeria monocytogenes* Δmpl2 Mutant is an Effective Oral Vaccine Carrier to Trigger a Long-Lasting Immune Response Against a Mouse Fibrosarcoma," *Eur. J. Immunol.* 27:1570-1575.

Pan, Z-K. et al. (May 1995). "A Recombinant *Listeria monocytogenes* Vaccine Expressing a Model Tumour Antigen Protects Mice Against Lethal Tumour Cell Challenge and Causes Regression of Established Tumours," *Nature Medicine* 1(5):471-477.

Pandiripally, V.K. et al. (Feb. 1999). "Surface Protein p104 is Involved in Adhesion of *Listeria monocytogenes* to Human Intestinal Cell Line, Caco-2," *J. Med. Microbiol.* 48(2):117-124.

Paschen, A. et al. (Dec. 2000). "Human Dendritic Cells Infected by *Listeria monocytogenes*: Induction of Maturation, Requirements for Phagolysosomal Escape and Antigen Presentation Capacity," *Eur. J. Immunol.* 30(12):3447-3456.

Paterson, Y. (2003). "Rational Approaches to Immune Regulation," *Immunologic Research* 27(2-3):451-462.

Paterson, Y. et al. (2004). "Progress Towards the Use of *Listeria monocytogenes* as a Live Bacterial Vaccine Vector for the Delivery of HIV Antigens," *Expert. Rev. Vaccines* 3(4):S119-S134.

Peters, C. et al. (2003). "Tailoring Host Immune Responses to *Listeria* by Manipulation of Virulence Genes—The Interface Between Innate and Acquired Immunity," *FEMS Immunol. Med. Microbial.* 35:243-253.

Peters, C. et al. (2003). "The Induction of HIV Gag-Specific $CD8^+$ T Cells in the Spleen and Gut-Associated Lymphoid Tissue by Parenteral or Mucosal Immunization with Recombinant *Listeria monocytogenes* HIV Gag," *The Journal of Immunology* 170:5176-5187.

Pilgrim, S. et al. (Jun. 2003). "Deletion of the Gene Encoding p60 in *Listeria monocytogenes* Leads to Abnormal Cell Division and Loss of Actin-Based Motility," *Infection and Immunity* 71(6):3473-3484.

Pistor, S. et al. (1994). "The ActA Protein of *Listeria monocytogenes* Acts as a Nucleator Inducing Reorganization of the Actin Cytoskeleton," *The EMBO Journal* 13(4):758-763.

Pistor, S. et al. (2000, e-pub. Aug. 22, 2000). "Mutations of Arginine Residues Within the 146-KKRRK-150 Motif of the ActA Protein of *Listeria monocytogenes* Abolish Intracellular Motility by Interfering with the Recruitment of the Arp2/3 Complex," *Journal of Cell Science* 113:3277-3287.

Portnoy, D.A. et al. (Apr. 1, 1988). "Role of Hemolysin for the Intracellular Growth of *Listeria monocytogenes*," *J. Exp. Med.* 167(4):1459-1471.

Portnoy, D.A. et al. (Aug. 5, 2002). "The Cell Biology of *Listeria monocytogenes* Infection: the Intersection of Bacterial Pathogenesis and Cell-Mediated Immunity," *The Journal of Cell Biology* 158(3):409-414.

Raveneau, J. et al. (Mar. 1992). "Reduced Virulence of a *Listeria monocytogenes* Phospholipase-Deficient Mutant Obtained by Transposon Insertion into the Zinc Metalloprotease Gene," *Infection and Immunity* 60(3):916-921.

Rayevskaya, M. et al (Jan. 2002)."Safety and Immunogenicity in Neonatal Mice of a Hyperattenuated *Listeria* Vaccine Directed Against Human Immunodeficiency Virus," *Journal of Virology* 76(2):918-922.

Ripio, M-T. et al. (Mar. 1997). "A Gly145Ser Substitution in the Transcriptional Activator PrfA Causes Constitutive Overexpression of Virulence Factors in *Listeria monocytogenes*," *Journal of Bacteriology* 179(5):1533-1540.

Roback, J.D. et al. (Nov. 16, 2004). "Immunization with Live-Attenuated *Listeria* Encoding CMV Antigen Induces Extensive Expansion of CMV-Specific CD8+ T-Cells Following HSCT: An Alternative to Adoptive Antiviral Immunotherapy," Abstract No. 2129, Poster Board—Session No. 342-II, *46th Annual Meeting of the American Society of Hematology*, San Diego, CA, Dec. 4-7, 2004, *Blood* 104(11-pt. 1):586A.

Roback, J.D. et al. (Dec. 5, 2004). "Immunization with Live-Attenuated *Listeria* Encoding CMV Antigen Induces Extensive Expansion of CMV-Specific CD8+t-Cells Following HSCT: An Alternative to Adoptive Antiviral Immunotherapy," Abstract No. 2129, Poster Session 342-II, *46th Annual Meeting of the American Society of Hematology*, San Diego, CA, Dec. 4-7, 2004, located at <http://www.abstracts2view.com/hem_sandiego2004/view.php?nu=HEM4L1_4025> last visited Apr. 28, 2006, one page.

Roback, J.D. et al. (Nov. 16, 2005). "Live-Attenuated and Novel Non-Replicating *Listeria* vaccines encoding CMV Antigen Produce Persistent Functional Antiviral Immunity," *47th Annual Meeting of the American Society of Hematology*, Atlanta, GA, Dec. 10-13, 2005, *Blood* 106(11, pt. 1)p. 171A, Abstract 575.

Roberts, M.C. et al. (Jan. 1996). "Transferable Erthromycin Resistance in *Listeria* spp. Isolated from Food," *Applied and Environmental Microbiology* 62(1):269-270.

Rubin, R.H. (Aug. 1997). "Cytomegalovirus Infection in the Liver Transplant Recipient," *Clin. Liver Dis.* 1(2):439-452.

Ryu, B. et al. (Feb. 1, 2002). "Relationships and Differentially Expressed Genes Among Pancreatic Cancers Examined by Large-Scale Serial Analysis of Gene Expression," *Cancer Research* 62(3):819-826.

Saklani-Jusforgues, H. et al. (Mar. 2003). "Enteral Immunization with Attenuated Recombinant *Listeria monocytogenes* as a Live Vaccine Vector: Organ-Dependent Dynamics of CD4 T Lymphocytes Reactive to a *Leishmania major* Tracer Epitope," *Infection and Immunity* 71(3):1083-1090.

Sancar, A. (Dec. 23, 1994). "Mechanisms of DNA Excision Repair," *Science* 266:1954-1956.

Sauer, B. (1993). "Manipulation of Transgenes by Site-Specific Recombination: Use of Cre Recombinase," Chapter 53 *in Methods in Enzymology*, Wassarman, P.M. et al. eds., Academic Press, Inc., San Diego: CA, 225:890-900.

Sauer, B. (1996). "Multiplex Cre/*lox* Recombination Permits Selective Site-Specific DNA Targeting to Both a Natural and an Engineered Site in the Yeast Genome," *Nucleic Acids Research* 24(23):4608-4613.

Saviola, B. et al. (2004, e-pub. Jan. 12, 2004). "Method to Integrate Multiple Plasmids into the Mycobacterial Chromosome," *Nucleic Acids Research* 32(1:e11): pp. 1-4.

Scanlan, M.J. et al. (Jan. 23, 2004). "The Cancer/Testis Genes: Review Standardization, and Commentary," *Cancer Immunity* 4(1): pp. 1-15.

Schafer, R. et al. (Jul. 1, 1992). "Induction of a Cellular Immune Response to a Foreign Antigen by a Recombinant *Listeria monocytogenes* Vaccine," *Journal of Immunology* 149:53-59.

Scheirlinck, T. et al. (Sep. 1989). "Integration and Expression of α-Amylase and Endoglucanase Genes in the *Lactobacillus plantarum* Chromosome," *Applied and Environmental Microbiology* 55(9):2130-2137.

Schlüter, D. et al. (Dec. 1998). "Phosphatidylcholine-Specific Phospholipase C from *Listeria monocytogenes* Is an Important Virulence Factor in Murine Cerebral Listeriosis," *Infection and Immunity* 66(12):5930-5938.

Schlüter, D. et al. (1999). "Immune Reactions to *Listeria monocytogenes* in the Brain," *Immunobiology* 201:188-195.

Schweizer, H.P. (2003). "Applications of the *Saccharomyces cerevisiae* Flp-*FRT* System in Bacterial Genetics," *J. Mol. Microbiol. Biotechnol.* 5:67-77.

Selby, C.P. et al. (Jul. 1990). "Structure and Function of the (A)BC Excinuclease of *Escherichia coli*," *Mutation Research* 236(1):203-211.

Sequence Listing: LMOf6854_2703 Site-Specific Recombinase, Phage Integrase Family, Putative (*Listeria monocytogenes* 1-2a F6854), located at tigr.org, last visited Jan. 16, 2006, p. 542.

Sequence Listing: LMOf6854_2703 Site-Specific Recombinase, Phage Integrase Family, Putative (*Listeria monocytogenes* 1-2a F6854), located at tigr.org, last visited Jan. 16, 2006, p. 784.

Setterblad, N. et al. (2004). "B Cell Lipid Rafts Regulate Both Peptide-Dependent and Peptide-Independent APC-T Cell Interaction," *The Journal of Immunology* 173:1876-1886.

Shen, H. et al. (Apr. 25, 1995). "Recombinant *Listeria monocytogenes* as a Live Vaccine Vehicle for the Induction of Protective Anti-Viral Cell-Mediated Immunity," *Proc. Natl. Acad. Sci. USA* 92:3987-3991.

Shen, Z. et al: (1997). "Cloned Dendritic Cells Can Present Exogenous Antigens on Both MHC Class I and Class II Molecules," *The Journal of Immunology* 158:2723-2730.

Shetron-Rama, L.M. et al. (Mar. 2002). "Intracellular Induction of *Listeria monocytogenes* actA Expression," *Infection and Immunity* 70(3):1087-1096.

Shetron-Rama, L.M. et al. (2003). "Isolation of *Listeria monocytogenes* Mutants with High-Level in vitro Expression of Host Cytosol-Induced Gene Products," *Molecular Microbiology* 48(6):1537-1551.

Shresta, S. et al. (Feb. 5, 2004). "Early Activation of Natural Killer and B Cells in Response to Primary Dengue Virus Infection in A/J Mice," *Virology* 319(1):262-273.

Sibelius, U. et al. (Mar. 1999). "Role of *Listeria monocytogenes* Exotoxins Listeriolysin and Phosphatidylinositol-Specific Phospholipase C in Activation of Human Neutrophils," *Infection and Immunity* 67(3):1125-1130.

Siboo, I.R. et al. (Dec. 2003). "Genomic Organization and Molecular Characterization of SM1, a Temperate Bacteriophase of *Streptococcus mitis*," *Journal of Bacteriology* 185(23):6968-6975.

Škoberne, M. et al. (Aug. 15, 2001). "Dynamic Antigen Presentation Patterns of *Listeria monocytogenes*-Derived CD8 T Cell Epitopes In Vivo," *The Journal of Immunology* 167(4):2209-2218.

Skoble, J. et al. (Nov. 1999). "Identification of Regions in ActA Involved in Arp2/3 Complex-Mediated Actin Nucleation," Abstract 918, (*Abstracts presented at the 39th Annual Meeting of the American Society for Cell Biology*, Washington, DC, Dec. 11-15, 1999), *Molecular Biology of the Cell* 10(Supp):158a.

Skoble, J. et al. (Dec. 1999). "Identification of Regions in ActA Involved in Arp2/3 Complex-Mediated Actin Nucleation," Abstract 918, *Abstracts presented at the 39th Annual Meeting of the American Society for Cell Biology*, Washington, DC, Dec. 11-15, 1999, p. 158a.

Skoble, J. et al. (Aug. 7, 2000). "Three Regions Within ActA Promote Arp2/3 Complex-Mediated Actin Nucleation and *Listeria monocytogenes* Motility," *The Journal of Cell Biology* 150(3):527-537.

Skoble, J. et al. (Oct. 1, 2001). "Pivotal Role of VASP in Arp2/3 Complex-Mediated Actin Nucleation, Actin Branch-Formation, and *Listeria monocytogenes* Motility," *The Journal of Cell Biology* 155(1):89-100.

Slansky, J.E. et al. (Oct. 2000). "Enhanced Antigen-Specific Antitumor Immunity with Altered Peptide Ligands that Stabilize the MHC-Peptide-TCR Complex," *Immunity* 13:529-538.

Smith, G.A. (Oct. 1993). "The Role of the Proline-Rich Repeats of Act A for the Actin Based Motility of *Listeria monocytogenes*," *Abstracts Presented at the American Society for Cell Biology Thirty-third Annual Meeting*, New Orleans, LA, Dec. 11-15, 1993, *Molecular Biology of the Cell* 4(Supp.):149A, Abstract No. 872.

Smith, G.A. et al. (Nov. 1995). "The Two Distinct Phospholipases C of *Listeria monocytogenes* Have Overlapping Roles in Escape from a Vacuole and Cell-to-Cell Spread," *Infection and Immunity* 63(11):4231-4237.

Smith, G.A. et al. (1995). "Asymmetric Distribution of the *Listeria monocytogenes* ActA Protein is Required and Sufficient to Direct Actin-Based Motility," *Molecular Microbiology* 17(5):945-951.

Smith, G.A. et al. (Nov. 1996). "The Tandem Repeat Domain in the *Listeria monocytogenes* ActA Protein Controls the Rate of Actin-Based Motility, the Percentage of Moving Bacteria, and the Localization of Vasodilator-Stimulated Phosphoprotein and Profilin," *The Journal of Cell Biology* 135(3):647-660.

Smith, G.R. (Mar. 1988). "Homologous Recombination in Procaryotes," *Microbiological Reviews* 52(1):1-28.

Smith, K. et al. (1992). "Use of a New Integrational Vector to Investigate Compartment-Specific Expression of the *Bacillus subtilis* spoIIM Gene," *Biochimie* 74:705-711.

Smith, M.C.M. et al. (2002). "Diversity in the Serine Recombinases," *Molecular Microbiology* 44(2):299-307.

Soussi, N. et al. (Mar. 2000). "*Listeria monocytogenes* as a Short-Lived Delivery System for the Induction of Type 1 Cell-Mediated Immunity Against the p36/LACK Antigen of *Leishmania major*," *Infection and Immunity* 68(3):1498-1506.

Soussi, N. et al. (Jun. 21, 2002). "Effect of Intragastric and Intraperitoneal Immunisation with Attenuated and Wild-Type LACK-Expressing *Listeria monocytogenes* on Control of Murine *Leishmania major* Infection," *Vaccine* 20(21-22):2702-2712.

Southwick, F.S. et al. (May 1994). "Arrest of *Listeria* Movement in Host Cells by a Bacterial ActA Analogue: Implications for Actin-Based Motility," *Proc. Natl. Acad. Sci. USA* 91:5168-5172.

Stahl, M.L. et al. (May 1984). "Replacement of the *Bacillus subtilis* Subtilisin Structural Gene with an In Vitro-Derived Deletion Mutation," *Journal of Bacteriology* 158(2):411-418.

Starks, H. et al. (Jul. 1, 2004). "*Listeria monocytogenes* as a Vaccine Vector. Virulence Attenuation or Existing Antivector Immunity Does Not Diminish Therapeutic Efficacy," *The Journal of Immunology* 173:420-427.

Straley, E. et al. (Apr. 2006). "Targeting the Receptor Tyrosine Kinase EphA2 with a Live-Attenuated *Listeria monocytogenes*-based Active Immunotherapy," Abstract No. 1400 *presented at the 97th ACCR Annual Meeting*, Washington, DC, Apr. 1-5, 2006, located at <http://www.abstractsonline.com/viewer/viewAbstractPrintFriendly.asp?CKey={E67A9B...>, last visited Dec. 18, 2006, one page.

Strugnell, R.A. et al. (1990). "Stable Expression of Foreign Antigens from the Chromosome of *Salmonella typhimurium* Vaccine Strains," *Gene* 88(1):57-63.

Sun, R. et al. (Nov. 2004). "Negative Regulation of Liver Regeneration by Innate Immunity (Natural Killer Cells/Interferon-γ)," *Gasteroenterology* 127(5):1525-1539.

Suzuki, T. et al. (Nov. 1, 1999). "Degradation Signals in the Lysine-Asparagine Sequence Space," *The EMBO Journal* 18(21):6017-6026.

Theriot, J.A. et al. (Feb. 11, 1994). "Involvement of Profilin in the Actin-Based Motility of *L. monoclyogenes* in Cells and in Cell-Free Extracts," *Cell* 76(3):505-517.

Theriot, J.A. et al. (1998). "*Listeria monocytogenes*-Based Assays for Actin Assembly Factors," Chapter 11 in *Methods in Enzymology*, Vallee, R.B. ed., Academic Press, Inc.: San Diego, CA, 298:114-122.

Thomas, A.M. et al. (Aug. 2, 2004). "Mesothelin-Specific CD8+ T Cell Responses Provide Evidence of In Vivo Cross-Priming by Antigen-Presenting Cells in Vaccinated Pancreatic Cancer Patients," *J. Exp. Med.* 200(3):297-306.

Thorpe, H.M. et al. (May 1998). "In vitro Site-Specific Integration of Bacteriophage DNA Catalyzed by a Recombinase of the Resolvase/Invertase Family," *Proc. Natl. Acad. Sci. USA* 95:5505-5510.

Torres, D. et al. (Apr. 2004). "Toll-Like Receptor 2 Is Required for Optimal Control of *Listeria monocytogenes* Infection," *Infection and Immunity* 72(4):2131-2139.

Tskvitaria-Fuller, I. et al. (2003). "Regulation of Sustained Actin Dynamics by the TCR and Costimulation as a Mechanism of Receptor Localization," *The Journal of Immunology* 171:2287-2295.

Tvinnereim, A.R. et al. (Jan. 2002). "CD8+-T-Cell Response to Secreted and Nonsecreted Antigens Delivered by Recombinant *Listeria monocytogenes* During Secondary Infection," *Infection and Immunity* 70(1):153-162.

Van Der Mee-Marquet, N. et al. (Sep. 1997). "Evaluation of Seven Experimental Phages for Inclusion in the International Phage Set for the Epidemiological Typing of *Listeria monocytogenes*," *Applied and Environmental Microbiology* 63(9):3374-3377.

Varani, S. et al. (2002). "Cytomegalovirus as a Hepatotropic Virus," *Clin. Lab.* 48(1+2):39-44.

Varshavsky, A. (Oct. 29, 1996). "The N-end Rule: Functions, Mysteries, Uses," *Proc. Natl. Acad. Sci. USA* 93(22):12142-12149.

Vázquez-Boland, J-A. et al. (Jan. 1992). "Nucleotide Sequence of the Lecithinase Operon of *Listeria monocytogenes* and Possible Role of Lecithinase in Cell-to-Cell Spread," *Infection and Immunity* 60(1):219-230.

Vázquez-Boland, J.A. et al. (Jul. 2001). "*Listeria* Pathogenesis and Molecular Virulence Determinants," *Clinical Microbiology Reviews* 14(3):584-640.

Wang, W. et al. (Feb. 1, 1998). "Class I-Restricted Alloreactive Cytotoxic T Lymphocytes Recognize a Complex Array of Specific MHC-Associated Peptides," *The Journal of Immunology* 160(3):1091-1097.

Way, S.S. et al. (2004). "Cutting Edge: Immunity and IFN-γ Production During *Listeria monocytogenes* Infection in the Absence of T-bet," *The Journal of Immunology* 173:5918-5922.

Wei, Z. et al. (Sep. 6, 2005). "*Listeria monocytogenes* Phosphatidylinositol-Specific Phospholipase C has Evolved for Virulence by Greatly Reduced Activity on GPI Anchors," *Proc. Natl. Acad. Sci. USA* 102(36):12927-12931.

Weiskirch, L.M. et al. (1997). "*Listeria monocytogenes*: A Potent Vaccine Vector for Neoplastic and Infectious Disease," *Immunological Reviews* 158:159-169.

Welch, M.D. et al. (Jul. 3, 1998). "Interaction of Human Arp2/3 Complex and the *Listeria monocytogenes* ActA Protein in Actin Filament Nucleation," *Science* 281(5373):105-108.

Welch, M.D. et al. (Nov. 2001). "Interaction Between ActA, the Arp2/3 Complex and VASP Contributes to Actin Nucleation, Network Architecture, and *L. monocytogenes* Motility," *Abstracts from the 41st American Society for Cell Biology Annual Meeting*, Washington, DC, Dec. 8-12, 2001, *Molecular Biology of the Cell* 12(Supp):138A, Abstract No. 750.

Williams, J.R. et al. (Feb. 2000). "Sequence Variations Within PrfA DNA Binding Sites and Effects on *Listeria monocytogenes* Virulence Gene Expression," *Journal of Bacteriology* 182(3):837-841.

Williams, R. et al. (Oct. 2000). "Acute Liver Failure: Established and Putative Hepatitis Viruses and Therapeutic Implications," *J. Gasteroenterol. Hepatol.* 15(Suppl.):G17-G25.

Wirth, R. et al. (Mar. 1986). "Highly Efficient Protoplast Transformation System for *Streptococcus faecalis* and a New *Escherichia coli*-*S. faecalis* Shuttle Vector," *Journal of Bacteriology* 165(3):831-836.

Wong, K.K.Y. et al. (Feb. 2004). "Evidence Implicating the 5' Untranslated Region of *Listeria monocytogenes* actA in the Regulation of Bacterial Actin-Based Motility," *Cellular Microbiology* 6(2):155-166.

Wong, K.K.Y. et al. (Sep. 2004). "A Novel Mutation within the Central *Listeria monocytogenes* Regulator PrfA That Results in Constitutive Expression of Virulence Gene Products," *Journal of Bacteriology* 186(18):6265-6276.

Yang, W. et al. (Jul. 28, 1995). "Crystal Structure of the Site-Specific Recombainase γδ Resolvase Complexed with a 34 bp Cleavage Site," *Cell* 82(2):193-207.

Yoshimura, K. et al. (Jan. 15, 2006). "Selective Targeting of Antitumor Immune Responses with Engineered Live-Attenuated *Listeria monocytogenes*," *Cancer Research* 66(2):1096-1104.

Yu, D. et al. (May 23, 2000). "An Efficient Recombination System for Chromosome Engineering in *Escherichia coli*," *Proc. Natl. Acad. Sci. USA* 97(11):5978-5983.

Zalevsky, J. et al. (Feb. 2, 2001). "Activation of the Arp2/3 Complex by the *Listeria* ActA Protein," *J. Biol. Chem.* 276(5):3468-3475.

Zhang, Y. et al. (Oct. 1998). "A New Logic for DNA Engineering Using Recombination in *Escherichia coli*," *Nature Genetics* 20(2):123-128.

Zhao, S. et al. (Feb. 2002). "Integrative Genetic Element That Reverses the Usual Target Gene Orientation," *Journal of Bacteriology* 184(3):859-860.

Zimmer, M. et al. (Aug. 2002). "Genomic Analysis of *Clostridium perfringens* Bacteriophage Φ3626, Which Integrates into gua4 and Possibly Affects Sporulation," *Journal of Bacteriology* 184(16):4359-4368.

Zimmer, M. et al. (2003). "Genome and Proteome of *Listeria monocytogenes* Phage PSA: An Unusual Case for Programmed + 1 Translational Frameshifting in Structural Protein Synthesis," *Molecular Microbiology* 50(1):303-317.

Zink, R. et al. (Jan. 1992). "Classification of Virulent and Temperate Bacteriophages of *Listeria* spp. on the Basis of Morphology and Protein Analysis," *Applied and Environmental Microbiology* 58(1):296-302.

Bruhn, K.W. et al (2007), "*Listeria* as a Vaccine Vector," *Microbes and Infection* 9(10):1226-1235.

International Preliminary Report on Patentability mailed Jul. 6, 2006, for PCT Application No. PCT/US2004/044080, filed Dec. 23, 2004, 11 pages.

International Search Report mailed Aug. 19, 2005, for PCT Application No. PCT/US2004/044080, filed Dec. 23, 2004, 10 pages.

International Search Report mailed Jan. 10, 2008, for PCT Application No. PCT/US2007/005457, filed Mar. 1, 2007, seven pages.

Non-Final Office Action mailed Jun. 22, 2007, for U.S. Appl. No. 11/396,216, filed Mar. 30, 2006, 4 pages.

Non-Final Office Action mailed Apr. 9, 2008, for U.S. Appl. No. 11/396,216, filed Mar. 30, 2006, 7 pages.

Renzoni, A. et al. (Apr. 1997). "Evidence that PrfA, the Pleiotropic Activator of Virulence Genes in *Listeria monocytogenes*, Can Be Present but Inactive," *Infection and Immunity* 65(4):1515-1518.

Schnupf, P. et al. (2006, e-pub. Oct. 21, 2005). "Phosphorylation, Ubiquitination and Degradation of Listeriolysin O in Mammalian Cells: Role of the PEST-Like Sequence," *Cellular Microbiology* 8(2):353-364.

Schnupf, P. et al. (2006, e-pub. Jul. 12, 2006). "Regulated Translation of Listeriolysin O Controls Virulence of *Listera monocytogens*," *Molecular Microbiolgy* 61(4):999-1012.

Schnupf, P. et al. (May 26, 2007). "Listeriolysin O: A Phagosome-Specific Lysin," *Microbes and Infection*, (Article in Press: doi:10.1016/j.micinf.2007.05.005), twelve pages.

Shen, A. et al. (2005). "The 5' Untranslated Region-Mediated Enhancement of Intracellular Listeriolysin O Production is Required for *Listeria monocytogenes* Pathogenicity," *Molecular Microbiology* 57(5):1460-1473.

Singh, R. et al. (2005). "Fusion to Listeriolysin O and Delivery by *Listeria monocytogenes* Enhances the Immunogenicity of HER-2/neu and Reveals Subdominant Epitopes in the FVB/N Mouse," *The Journal of Immunology* 175:3663-3673.

Singh, R. et al. (2006). "*Listeria monocytogenes* as a Vector for Tumor-Associated Antigens for Cancer Immunotherapy," *Expert Rev. Vaccines* 5(4):541-552.

Souders, N.C. et al. (Feb. 6, 2007). "*Listeria*-based Vaccines can Overcome Tolerance by Expandinng low Avidity CD8+ T Cells Capable of Eradicating a Solid Tumor in a Transgenic Mouse Model of Cancer," *Cancer Immunity* 7(2):1-12.

Written Opinion mailed Aug. 19, 2005, for PCT Application No. PCT/US2004/044080, filed Dec. 23, 2004, 9 pages.

Zenewicz, L.A. et al. (2002). "Nonsecreted Bacterial Proteins Induce Recall CD8 T Cell Responses But Do Not Serve as Protective Antigens," *The Journal of Immunology* 169:5805-5812.

Fig. 7.

| | SS | hMeso | GPI | |
|---|---|---|---|---|
| | | hMesoΔSSΔGPI | | |
| hly | BaP | hMesoΔSSΔGPI | | |
| hly | BaP | hMesoΔSSΔGPI | | 12ras |
| hly | LLO62 | hMesoΔSSΔGPI | | 12ras |
| hly | LLO60opt | hMesoΔSSΔGPI | | 12ras |
| actA | actA-N100 | hMesoΔSSΔGPI | | |
| actA | actA-N100 | hMesoΔSSΔGPI | | 12ra |

Fig. 13

HBSS parental Lm

Lm ΔH1 Δ5

Lm actA promoter-BaPa-hmesothelin (actA locus)

Lm hly promoter-BaPa-hmesothelin (inlB locus)

Lm BaPa ActA N100 hmesothelin

Fig. 15A-G. Harvest splenocytes on day 23 post tumor implant.

FIG. 19
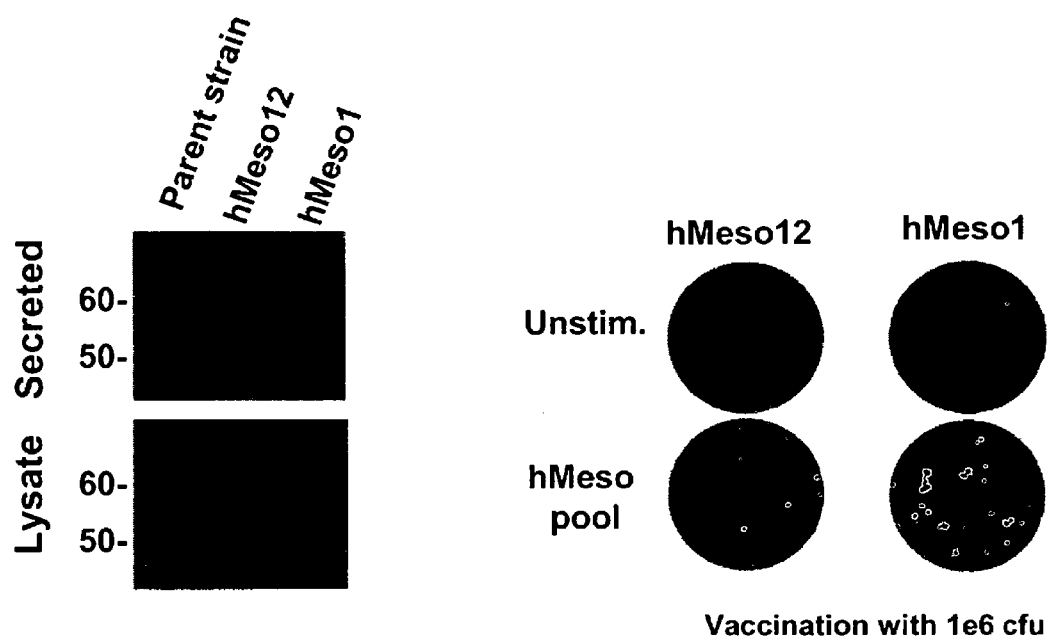
Vaccination with 1e6 cfu
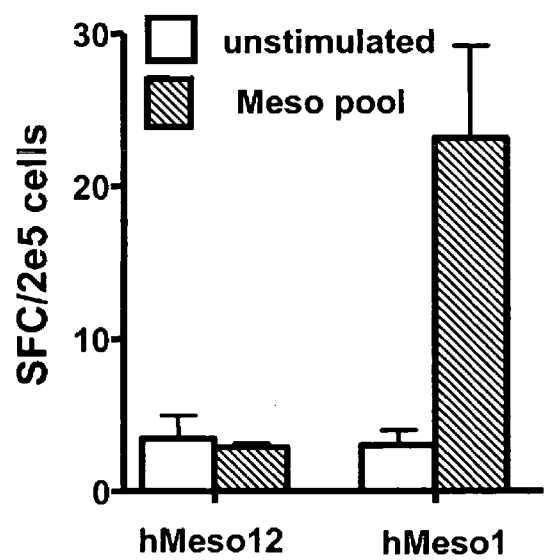

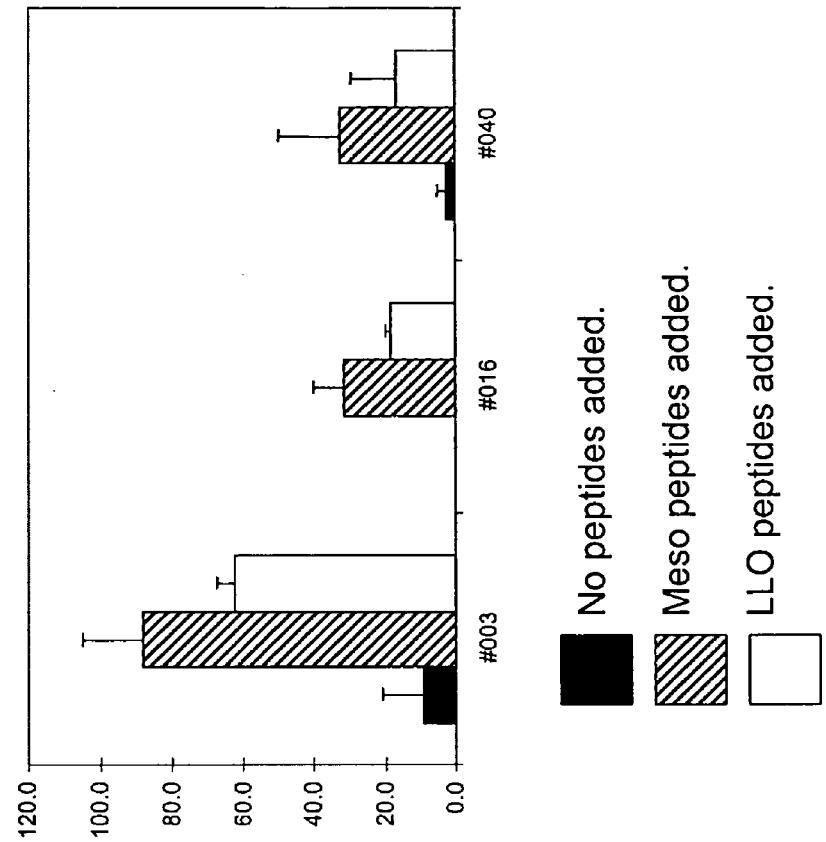
Fig. 23

Fig. 24 hMeso expression by *Listeria* in
broth or in mammalian cells in BHI broth / in J774 cells hMeso-specific
immune responses in Balb/c
relative to hMeso6 hMeso6: *L. monocytogenes* ΔactAΔinlB
encoding actA-N100-hMeso ΔSSΔGPI.

hMeso5: *L. monocytogenes* ΔactAΔinlB
encoding p60-hMeso ΔSSΔGPI.

Fig. 26
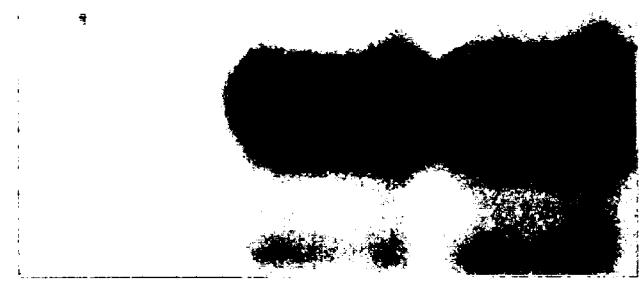
hMeso-specific responses in Balb/c mice relative to hMeso26
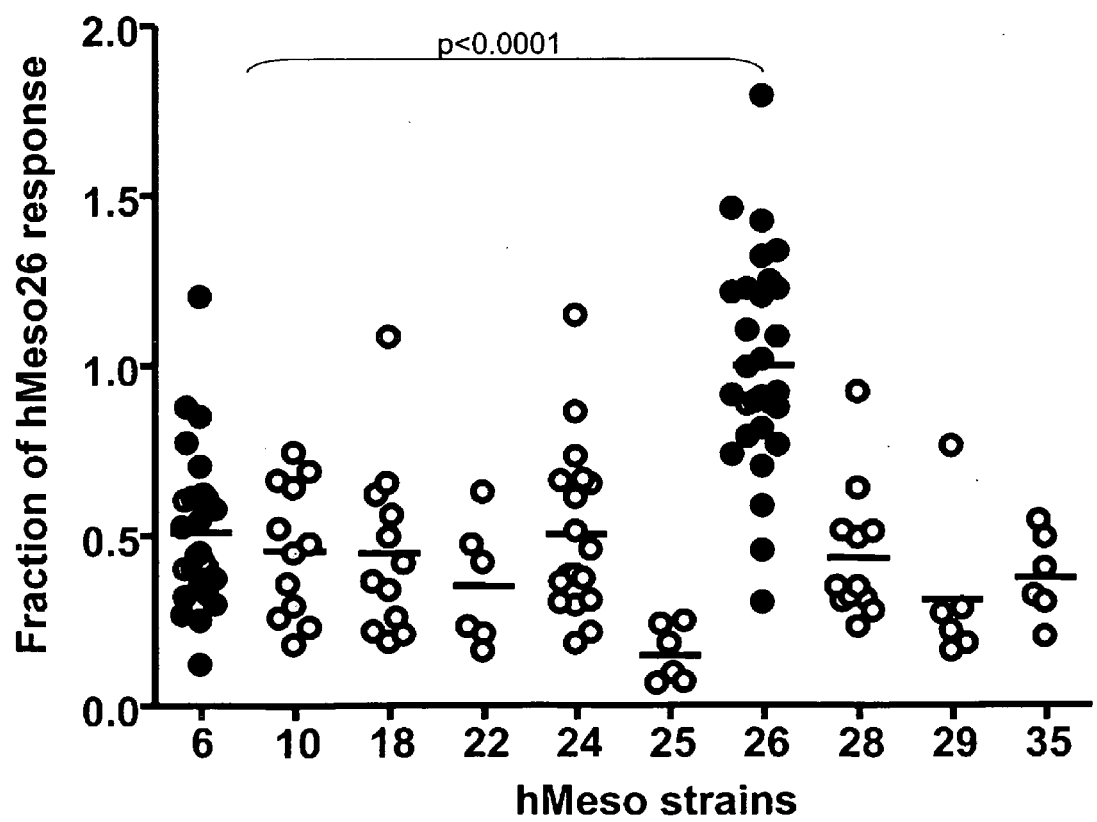

Lung metastases at day19 (inject tumor cells i.v. at t=0 days; *Listeria* i.v. at t=3 days, harvest lungs at t=19days).

Day 0. Inject tumor cells (i.v.).
Day 3. Inject *Listeria* vaccines (i.v.).
Day 19. Harvest lungs.

Fig. 33
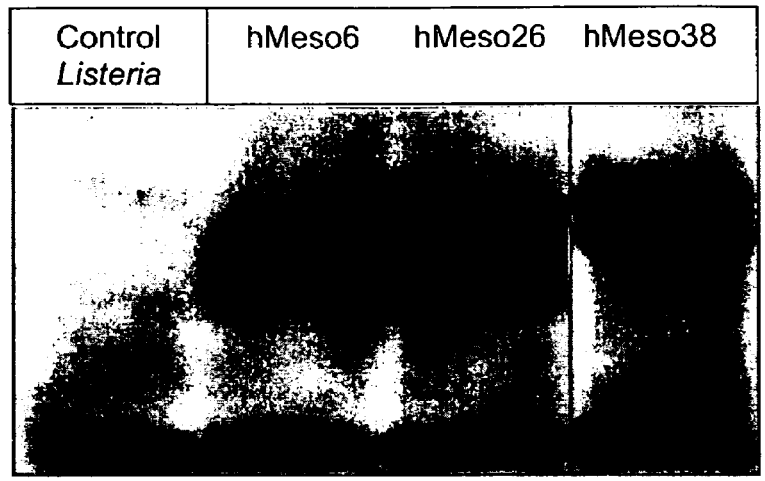
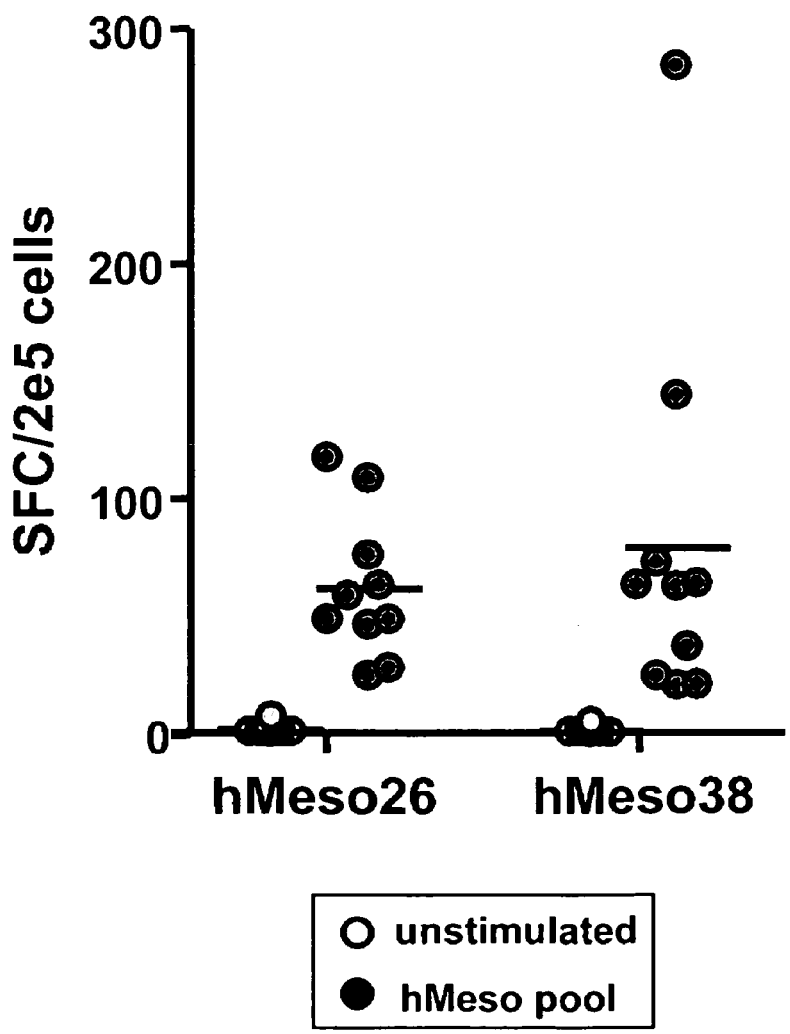
hMeso pool responses in Balb/c (5e6 cfu)
○ unstimulated
● hMeso pool Days –8, -4, and –1. Inject depleting antibodies.
Day 0. Inject tumor cells (i.v.).
Day 3. Inject *Listeria* vaccines (i.v.).
Weekly antibody boosts.
Test survival of mice.

Days −8, −4, −1. Inject depleting antibodies.
Day 0. Inject tumor cells (i.v.).
Day 3. Inject Listeria vaccines (i.v.).
Weekly antibody boosts.
Test survival of mice.

Fig. 40.

```
L.innocua 1231.
                       1                                                  50
U153 int       (1)    MKAAIYIRVSTQEQIEN-YSIQAQTEKLTALCRSKDWDVYDIFIDGGYSG
lin1231        (1)    MTVGIYIRVSTEEQVKEGFSISAQKEKLKAYCTAQGWEDFKFYVDEGKSA
Consensus      (1)    M  AIYIRVST EQI   FSI AQ EKL A C A  WD F  FID G SA
                       51                                                100
U153 int      (50)    SNMNRPALNEMLSKLHE--IDAVVVYRLDRLSRSQRDTITLIEEYFLKNN
lin1231       (51)    KDMHRPLLQEMISHIKKGLIDTVLVYKLDRLTRSVVDLHNLLSIFDEFN-
Consensus     (51)       M RP LNEMIS I   ID VLVYKLDRLSRS  D   LI F    N
                       101                                               150
U153 int      (98)    VEFVSLSETLDTSSPFGRAMIGILSVFAQLERETIRDRMVMGKIXRIEAG
lin1231      (100)    CAFKSATEVYDTSSAMGRFFITIISSVAQFERENTSERVSFGMAEKVRQG
Consensus    (101)        F S SE   DTSS GR  I  IIS AQ ERE    DRM G   KI G
                       151                                               200
U153 int     (148)    LPLTTAKGRTFGYDV-IDTKLYINEEEAKQLQMIYDIFEEEKSITTLQKR
lin1231      (150)    EYIPLAP---FGYTKGTDGKLIVNKIEKEIFLQVVEMVSTGYSLRQTCEY
Consensus    (151)        I A    FGY    D KL IN E      I DI    SI
                       201                                               250
U153 int     (197)    LKKLGFKVKS------YSSYNNWLTNDLYCGYVSYADKVHTKGVHEPIIS
lin1231      (197)    LTNIGLKTRRSNDVWKVSTLIWMLKNPAVYGAIKWNNEIYEN-THEPLID
Consensus    (201)    L  IG K K       SS     L N    G I W  IH    HEPII
                       251                                               300
U153 int     (241)    EEQFYRVQEIFSRMGKNPNMNR-DSASLLNNLVVCGKCGLGFVHRRKDTV
lin1231      (246)    KATFNKVAKILSIRSKSTTSRRGHVHHIFKNRLICPACGKRLSGLRTKYI
Consensus    (251)        F KV   IS   K     R         I N LIC CG    R  I
                       301                                               350
U153 int     (290)    SRGK-KYHYRYYSCKTYKHTHELEKCGNKIWRADKLEELIIDRVNNYSFA
lin1231      (296)    NKNKETFYNNNYRCATCKEHRRPAVQIS----EQKIEKAFIDYISNYTLN
Consensus    (301)     K K   FH   Y C T K            KIE   ID I NYS
                       351                                               400
U153 int     (339)    SRNVDKEDELDSLN--EKLKTEHVKK--KR-------LFDLYISGSYEVS
lin1231      (342)    KANISSKKLDNNLRKQEMIQKEIISLQRKREKFQKAWAADLMNDDEFSKL
Consensus    (351)        NI      L    E I E I   KR         DL       F
                       401                                               450
U153 int     (378)    ELDAMMADIDAQIN---YYEAQIEANEELKKNKKIQENLADLATVDFDSL
lin1231      (392)    MIDTKMEIDAAEDRKKEYDVSLFVSPEDIAK----RNNILRELKINWTSL
Consensus    (401)       ID  M  A    Y  A   A EDI K        NI    I F SL
                       451                           484
U153 int     (425)    EFREKQLYLKSLINKIYIDGEQVTIEWL------
lin1231      (438)    SPTEKTDFISMFIEGIEYVKDDENKAVITKISFL
Consensus    (451)        EK  FI   I I   D       I
```

Fig. 41.

L.innocua 0071.

```
                     1                                                  50
    PSA int     (1)  MKIKKLANGKYCVRLRIKVDGEWKEKRLTDTSETNLMYKASKLLKQVQHD
    lin0071     (1)  -MVKKVKGRRYEGSIEQRSKNSWRMRVTVGYDYKGTPIRADRTTRTKNER
    Consensus   (1)     IKKL   KY   I   K    WK K              KA K   K  N
                     51                                                100
    PSA int    (51)  S--------SSLKEWNFKEFYTLFMKTFKDGKSS--------------Q
    lin0071    (50)  ERERELRNFITELEQNGYTAPARMTFKAFVENEYMPKHAQNNLEVKTWTE
    Consensus  (51)           S L      F      L  K F D
                     101                                               150
    PSA int    (78)  STINLYDLAYNQFVDYFDEKIKLNSIDAVQYQQFINHLSVDYAISTVDTR
    lin0071   (100)  YYKSIVARAYPAFGGVQMDKITTLHIVNLVAKLQKPGARLDVKPTDSDEK
    Consensus (101)       I    AY F    DKI    I  L           LD    S D K
                     151                                               200
    PSA int   (128)  HR--------K----IRAIFNKAVHLGYMKKNPTIGAHISGQDVAKNKA
    lin0071   (150)  KNKPLSPRSIRNIYFAINSVFETAVEWKVIPINPAEGVRLP--KTTKRPP
    Consensus (151)                   I AIF  AV       I   NP G I     K
                     201                                               250
    PSA int   (165)  QFMETDKVHLLLEELAKFHSISRAVIFLAVQTGMRFEEIIALTKKDINFT
    lin0071   (198)  TIYTPAEIELLNAALVKEPLRLQVMIYIALISGCREAELAALEVKHVNLI
    Consensus (201)          I  LL   L K         MIFIAL SG R  EI AL   K IN
                     251                                               300
    PSA int   (215)  KRSITVNKAWDYKYTNTFIDTKTKK---SRVIYIDNSTAQYLHSYLNWHT
    lin0071   (248)  EDELTFEQTLVAKAGEGLLLKESTKNDVAGIVSIPAWLTNLIETYISNEV
    Consensus (251)       IT      K        I  SK    A II I    N I SYI
                     301                                               350
    PSA int   (262)  DYMKEHAIKNPLMLLFITYHNKPVDNASCNKALKKICSTINSEPVTLHKL
    lin0071   (298)  LDLKTEGKWANHKFLFADMEGKPIRPDSIYQRWKRFLERHNLPVIRFHDL
    Consensus (301)     LK  A     LF   K    KPI  S          KK N  I  H L
                     351                                               400
    PSA int   (312)  RHTHTGLCVEAGMDIIYVADRLGHDDINTTLKYYSHLSSNLRQHNQSKVD
    lin0071   (348)  RHTSATLLLNKGRDIKIIQERLRHKSSVTTSNIYAHVLKDTHKDAASDFE
    Consensus (351)  RHT   L L  G DI  I  DRL H    TT   YAHL       S  D
                     401           424
    PSA int   (362)  AFFTLKTDENTTNFTTNATKTTE-
    lin0071   (398)  NPF---------------------
    Consensus (401)   F
```

Fig. 42.

```
L.innocua 1765.

1                                                50
    PSA int    (1)  -------------MKIKKLANGKYCVRLRIKVDGEWKEKR----LTDTS
    lin1765    (1)  MAKNKWQPTKHLGIYEYMTKKGKRYGIRVRYKQGNDYPEINKSGFETIAA
    Consensus  (1)               KY IRLR K    DW E          T   A
                    51                                              100
    PSA int   (33)  ETNLMYKASKLLKQVQHDSSSLKEWNFKEFYTLFMKTFKDGKSSQSTINL
    lin1765   (51)  AKVYKNNIENLKANKKEYVFTNEKLTLNTWFASYMEMFKKKNKSKDTIAN
    Consensus (51)        L  N     S         FF  FM FK    S  TI
                    101                                             150
    PSA int   (83)  YDLAYNQFVDYFDEKIKLNSIDAVQYQQFINHLSVD-YAISTVDTRHRKI
    lin1765  (101)  KYSIYNNHLEIPFGNYYLTDISLDIYEDFLREKIKNGYANNSVKAMHKLM
    Consensus(101)      YNN LD      L I Y   FI       YA  S V    HK I
                    151                                             200
    PSA int  (132)  RAIFNKAVHLGYMKKN-PTIGAHISGQDVAKNKAQFMETDKVHLLLEELA
    lin1765  (151)  KSILNAAVRYEKLEKNRLQFAEIEQLEENEVIELKVLETDEFNVFISACR
    Consensus(151)  KAI N AV     L KN     A      D       LETD    L I
                    201                                             250
    PSA int  (181)  KFHSISRAVIFLAVQTGMRFEEIIALTKKDINFTKRSITVNKAWDYKYTN
    lin1765  (201)  AFFTKYDFTMIYLAVWGMRRGEVMGVKLKNLTFDDAKQQVRITLDSTRTL
    Consensus(201)   F S   I   LA  GMR   E IIAL K  I F      V   D T
                    251                                             300
    PSA int  (231)  TFIDTKTKKS---R-VIYIDNSTAQYLHSYLNWHTDYMKEH--AIKNPLM
    lin1765  (251)  RTPEGKGTKTPAGRRILLIDGEGYRLLKYSVEKAVSIAKDHGSVLHQDDF
    Consensus(251)       D K KS   R  II ID      L  L       KDH   I N
                    301                                             350
    PSA int  (275)  LLFITYHNKPVDNASCNKALKKICSTINSEPVTLHKLRHTHTGLCVEAGM
    lin1765  (301)  IFRNPTSNRPWAVTRMNDLLRKLEKEYDIK-VYPHLLRHNFNTQALLAGA
    Consensus(301)  I      NKP    N    LKKI        V  H LRH      L AG
                    351                                             400
    PSA int  (325)  DIIYVADRLGHDDINTTLKYYSHLSSNLRQHNQSKVDAFFTLKTDENTTN
    lin1765  (350)  NSNDLRKFIGHKNS-SMTDHYSHATDEGREK------LMNTMKDRLSGI-
    Consensus(351)          L  IGH    S   HYSH S  R             TLK
                    401       411
    PSA int  (375)  FTTNATKTTE-
    lin1765  (392)  -----------
    Consensus(401)
```

Fig. 43.

*L.innocua* 2601.

```
                   1                                                  50
     PSA int   (1) MKIKKLLANGKYCVRLRIKVDGEWKEKRLTDTSETNLMYKASKLLKQVQHD
     lin2601   (1) MKIKKMKNGKYTVRLRIKVDGEWKEKRLTDTSETNLMYKASKLLKQVEHD
   Consensus   (1) MKIKKL NGKY VRLRIKVDGEWKEKRLTDTSETNLMYKASKLLKQV HD
                  51                                                 100
     PSA int  (51) SSSLKEWNFKEFYTLFMKTFKDGKSSQSTINLYDLAYNQFVDYFDEKIKL
     lin2601  (51) SNSLKEWNFKEFYSLFMKTFKENKSSQSTINLYDLAYNQFVNYFDEKIKL
   Consensus  (51) S SLKEWNFKEFYSLFMKTFKD KSSQSTINLYDLAYNQFV YFDEKIKL
                 101                                                 150
     PSA int (101) NSIDAVQYQQFINHLSVDYAISTVDTRHRKIRAIFNKAVHLGYMKKNPTI
     lin2601 (101) NSIDAVQYQQFINHLALDYAVATIDTRHRKIRAIFNKAVHLGYMKKNPAL
   Consensus (101) NSIDAVQYQQFINHLALDYAIATIDTRHRKIRAIFNKAVHLGYMKKNP I
                 151                                                 200
     PSA int (151) GAHISGQDVAKNKAQFMETDKVHLLLEELAKFHSISRAVIFLAVQTGMRF
     lin2601 (151) GAHISGHDIAKTKAQYLETDKVHLLLEELAKLHSISRAVIFLAVQTGMRF
   Consensus (151) GAHISG DIAK KAQFLETDKVHLLLEELAK HSISRAVIFLAVQTGMRF
                 201                                                 250
     PSA int (201) EEIIALTKKDINFTKRSITVNKAWDYKYTNTFIDTKTKKSRVIYIDNSTA
     lin2601 (201) EEIIALTKKDINFTKRSISVNKAWDYKYTNTFTDTKTKKSRVIYIDNSTV
   Consensus (201) EEIIALTKKDINFTKRSISVNKAWDYKYTNTF DTKTKKSRVIYIDNST
                 251                                                 300
     PSA int (251) QYLHSYLNWHTDYMKEHAIKNPLMLLFITYHNKPVDNASCNKALKKICST
     lin2601 (251) QYLQSYLAWHADYMKEHAIENPVMLLFITYHNKPVDNASCNKALKKICTT
   Consensus (251) QYL SYL WH DYMKEHAI NPLMLLFITYHNKPVDNASCNKALKKICST
                 301                                                 350
     PSA int (301) INSEPVTLHKLRHTHTGLCVEAGMDIIYVADRLGHDDINTTLKYYSHLSS
     lin2601 (301) INSETVTLHKLRHTHTGLCVEAGMDIIYVADRLGHDDINTTLKYYSHLSS
   Consensus (301) INSE VTLHKLRHTHTGLCVEAGMDIIYVADRLGHDDINTTLKYYSHLSS
                 351                                       385
     PSA int (351) NLRQHNQSKVDAFFTLKTDENTTNFTTNATKTTE-
     lin2601 (351) NLRQQNQSKVDAFFTLKTDENTTKFATNATKTTE-
   Consensus (351) NLRQ NQSKVDAFFTLKTDENTT F TNATKTTE
```

Fig. 44.

*L.monocytogenes* f6854.

```
                        1                                                  50
         PSA int    (1) -MKIKKLANGKYCVRLRIKVDGEWK-----EKRLTDTSETNLMYKASKLL
    lmof6854_2703   (1) MASYVNLGNNKYELRVSKGYDARGKQIRKTKNVTVKTVKALKLELSNFEA
       Consensus    (1)      LAN KY LRL    DA  K          T      L    A
                        51                                                 100
         PSA int   (45) KQVQHDSSSLKEWNFKEFYTLFMKTFKDGKSSQSTINLYDLAYNQFVDYF
    lmof6854_2703  (51) YVYSSDYTEIKDMRFIDFVEKWRLNYAKRELKGNTIDKYNLFLENWIIPY
       Consensus   (51)      D S IKD   F DF   F      F         TI  Y L   NFI  F
                        101                                                150
         PSA int   (95) DEKIKLNSIDAVQYQQFINHLS-VDYAISTVDTRHRKIRAIFNKAVHLGY
    lmof6854_2703 (101) FERKKISKITTMQLLDYFHEVQKKGVGPSALEGHHRVIRSLFKYATLWGI
       Consensus  (101) EK KI   I   MQ   F  L     A S  LD   HR IRAIF  A    G
                        151                                                200
         PSA int  (144) MKKNPTIGAHISGQDVAKNKAQFMETDKVHLLLEELAKFHSISRAVIFLA
    lmof6854_2703 (151) TETDVSLSVKKPTYKVPE--KNIYNRREIEVLIDRIKILQKYQQVMIKLA
       Consensus  (151)          SI       V     N      I  LLID  I        MI LA
                        201                                                250
         PSA int  (194) VQTGMRFEEIIALTKKDINFTKRSITVNKAWDYKYTN--TFIDTKTKKSR
    lmof6854_2703 (199) LYCGLRRGEVIGLTTKDMNYNKNTINVYRAVIKSASEGIKLDETKNKRKR
       Consensus  (201) L  GLR   EIIALT KDINF K SI V  KA   S        DTK KK R
                        251                                                300
         PSA int  (242) VIYIDNSTAQYLHSYLNWHTDYMKEHAIKNP---------LMLLFITYHN
    lmof6854_2703 (249) IVPAPAGLMQEIKELAKEKQKNKDKLGLLWKGTKDLDGKTVVLIFSHDDG
       Consensus  (251) I             Q  I             AI           LMLIF
                        301                                                350
         PSA int  (283) KPVDNASCNKALKKICSTINS--E-PVTLHKLRHTHTGLCVEAGMDIIYV
    lmof6854_2703 (299) TPFTPASVTRMFNRFLEKEENNDLTKISFHDLRHSAASFLLEQGINVKVI
       Consensus  (301)  P    AS  K  K              IS H LRHS     LE GI I  I
                        351                                                400
         PSA int  (330) ADRLGHDDINTTLKYYSHLSSNLRQHNQSKVDAFFTLKTDENTTNFTTNA
    lmof6854_2703 (349) QNILGHSDIKVTLNTYAHITEDGYSEAAKTFDNFYKSSK-----------
       Consensus  (351)    LGH DI  TL   YAHIS            D FF
                        401
         PSA int  (380) TKTTE-
    lmof6854_2703 (388) ------
       Consensus  (401)
```

ENGINEERED *LISTERIA* AND METHODS OF USE THEREOF

CROSS-REFERENCE TO RELATED APPLICATIONS

This application claims the priority benefit of the U.S. Provisional Application Ser. No. 60/784,576, filed on Mar. 21, 2006, and U.S. Provisional Application Ser. No. 60/778,471, filed on Mar. 1, 2006, the contents of each of which are hereby incorporated by reference herein in their entirety.

STATEMENT REGARDING FEDERALLY SPONSORED RESEARCH OR DEVELOPMENT

This invention was made, in part, with U.S. government support under National Cancer Institute NHI 1 K23CA104160-01. The government may have certain rights in the invention.

FIELD OF THE INVENTION

The invention provides engineered *Listeria* bacteria, useful for stimulating the immune system and treating cancers and infections. Also provided are polynucleotides, fusion protein partners, and integration vectors useful for modifying *Listeria* and other bacterial species.

BACKGROUND OF THE INVENTION

Cancers and infections can be treated by administering reagents that modulate the immune system. These reagents include vaccines, cytokines, antibodies, and small molecules, such as CpG oligodeoxynucleotides and imidazoquinolines (see, e.g., Becker (2005) Virus Genes 30:251-266; Schetter and Vollmer (2004) Curr. Opin. Drug Devel. 7:204-210; Majewski, et al. (2005) Int. J. Dermatol. 44:14-19), Hoffmann, et al. (2005) J. Clin. Virol. 32:86-91; Huber, et al. (2005) Infection 33:25-29; Carter (2001) Nature Revs. Cancer 1:118-129; Dechant and Valaerius (2001) Crit. Revs. Oncol. 39:69-77; O'Connor, et al. (2004) Neurology 62:2038-2043). Vaccines, including classical vaccines (inactivated whole organisms, extracts, or antigens), dendritic cell (DC) vaccines, and nucleic acid-based vaccines, are all useful for treating cancers and infections (see, e.g., Robinson and Amara (2005) Nat. Med. Suppl. 11:S25-S32; Plotkin (2005) Nat. Med. Suppl. 11:S5-S11; Pashine, et al. (2005) Nat. Med. Suppl. 11:S63-S68; Larche and Wraith (2005) Nat. Med. Suppl. 11:S69-S76). Another reagent useful for modulating the immune system is *Listeria monocytogenes* (*L. monocytogenes*), and this reagent has proven to be successful in treating cancers and tumors (see, e.g., Brockstedt, et al. (2004) Proc. Natl. Acad. Sci. USA 101:13832-13837; Brockstedt, et al (2005) Nat. Med. 11:853-860); Starks, et al. (2004) J. Immunol. 173:420-427; Shen, et al. (1995) Proc. Natl. Acad. Sci. USA 92:3987-3991).

Recombinant *Listeria* strains have been developed as vaccines against viruses and tumors (see, e.g., Starks, et al. (2004) J. Immunol. 173:420-427; Gunn, et al. (2001) J. Immunol. 167:6471-6479; Ikonomidis, et al. (1994) J. Exp. Med. 180:2209-2218; Mata, et al. (2001) Vaccine 19:1435-1445; Mata and Paterson (1999) J. Immunol. 163:1449-1456; Mata, et al. (1998) J. Immunol. 161:2985-2993; Friedman, et al. (2000) J. Virol. 74:9987-9993; Soussi, et al. (2002) Vaccine 20:2702-2712; Saklani-Jusforgues, et al. (2003) Infect. Immun. 71:1083-1090; Soussi, et al. (2000) Infect. Immunity 68:1498-1506; Tvinnereim, et al. (2002) Infect. Immunity 70:153-162; Rayevskaya, et al. (2002) J. Virol. 76:918-922; Frankel, et al. (1995) J. Immunol. 55:4775-4782; Jensen, et al. (1997) J. Virol. 71:8467-8474; Jensen, et al. (1997) Immunol. Rev. 158:147-157; Lin, et al. (2002) Int. J. Cancer 102:629-637; Peters, et al. (2003) FEMS Immunol. Med. Microbiol. 35:243-253; Peters, et al. (2003) J. Immunol. 170:5176-5187; Paterson (2003) Immunol. Res. 27:451-462; Paterson and Johnson (2004) Expert Rev. Vaccines 3:S119-S134; Ochsenbein, et al. (1999) Proc. Natl. Acad. Sci USA 96:9293-9298; Hess, et al. (2000) Adv. Immunol. 75:1-88).

*L. monocytogenes* has a natural tropism for the liver and spleen and, to some extent, other tissues such as the small intestines (see, e.g., Dussurget, et al. (2004) Ann. Rev. Microbiol. 58:587-610; Gouin, et al. (2005) Curr. Opin. Microbiol. 8:35-45; Cossart (2002) Int. J. Med. Microbiol. 291:401-409; Vazquez-Boland, et al. (2001) Clin. Microbiol. Rev. 14:584-640; Schluter, et al. (1999) Immunobiol. 201:188-195). Where the bacterium resides in the intestines, passage to the bloodstream is mediated by listerial proteins, such as ActA and intemalin A (see, e.g., Manohar, et al. (2001) Infection Immunity 69:3542-3549; Lecuit, et al. (2004) Proc. Natl. Acad. Sci. USA 101:6152-6157; Lecuit and Cossart (2002) Trends Mol. Med. 8:537-542). Once the bacterium enters a host cell, the life cycle of *L. monocytogenes* involves escape from the phagolysosome and to the cytosol. This life cycle contrasts with that of *Mycobacterium*, which remains inside the phagolysosome (see, e.g., Clemens, et al. (2002) Infection Immunity 70:5800-5807; Schluter, et al. (1998) Infect. Immunity 66:5930-5938; Gutierrez, et al. (2004) Cell 119:753-766). *L. monocytogenes'* escape from the phagolysosome is mediated by listerial proteins, such as listeriolysin (LLO), PI-PLC, and PC-PLC (see Portnoy, et al. (2002) J. Cell Biol. 158:409-414).

Vaccines for treating cancers or infections are often ineffective because of a lack of appropriate reagents. The present invention fulfills this need by providing polynucleotides, fusion protein partners, plasmids and bacterial vaccines, useful for enhancing the expression or immune processing of antigens, and for increasing survival to cancers and infections.

SUMMARY OF THE INVENTION

The present invention is based, in part, on the recognition that administering an attenuated *Listeria* to a mammal bearing a tumor results in enhanced survival, where the *Listeria* was engineered to contain a nucleic acid encoding an ActA-based fusion protein linked to a tumor antigen.

In one aspect, the invention provides a polynucleotide comprising a promoter operably linked to a nucleic acid sequence encoding a fusion protein, wherein the fusion protein comprises (a) modified ActA and (b) a heterologous antigen. In some embodiments, the promoter is a bacterial promoter (e.g., a *Listerial* promoter). In some embodiments, the promoter is an ActA promoter. In some embodiments, the modified ActA comprises at least the first 59 amino acids of ActA. In some embodiments, the modified ActA comprises more than the first 59 amino acids of ActA. In some embodiments, the modified ActA comprises less than the first 380 amino acids or less than the first 265 amino acids. In some embodiments, the modified ActA comprises more than the first 59 amino acids of ActA, and less than the first 380 amino acids of ActA. For example, in some embodiments, the modified ActA comprises at least about the first 59 amino acids of ActA, but less than about the first 265 amino acids of ActA. In some embodiments, the modified ActA comprises more than the first 59 amino acids of ActA, but less than about the first 265 amino acids of ActA. In other embodiments, the modified ActA comprises more than the first 59 amino acids of ActA, and less than the first 380 amino acids of ActA. In still further embodiments, the modified ActA comprises at least the first 85 amino acids of ActA and less than the first 125 amino acids of ActA. In some embodiments, the modified ActA comprises amino acids 1-100 of ActA. In some embodiments, the modified ActA consists of amino acids 1-100 of ActA. The heterologous antigen may be non-Listerial. In some embodiments, the heterologous antigen is from, or is derived from, a cancer cell, tumor, or infectious agent. In some embodiments, the heterologous antigen is immunologically cross-reactive with, or shares at least one epitope with, the cancer, tumor, or infectious agent. In some embodiments, the heterologous antigen is a tumor antigen or is derived from a tumor antigen. In some embodiments, the heterologous antigen is, or is derived from, mesothelin. For example, in some embodiments, the heterologous antigen is, or is derived from, human mesothelin. In some embodiments, the Listeria is hMeso26 or hMeso38 (see Table 11 of Example VII, below). In some embodiments, the heterologous antigen does not comprise an EphA2 antigenic peptide. In some embodiments, the nucleic acid sequence encoding the fusion protein is codon-optimized for expression in Listeria. The invention provides plasmids and cells comprising the polynucleotide. The invention further provides a Listeria bacterium (e.g., Listeria monocytogenes) comprising the polynucleotide, as well as vaccines comprising the Listeria. The Listeria bacterium may be attenuated (e.g., an actA deletion mutant or an actA insertion mutant). In some embodiments, the Listeria comprises the polynucleotide in its genome. In some embodiments, the polynucleotide has been integrated into a virulence gene in the Listerial genome. In some embodiments, a polynucleotide (or nucleic acid) has been integrated into a virulence gene in the genome of the Listeria, wherein the integration of the polynucleotide (a) disrupts expression of the virulence gene and/or (b) disrupts a coding sequence of the virulence gene. In some embodiments, the virulence gene is prfA-dependent. In other embodiments, the virulence gene is prfA-independent. In some embodiments, the nucleic acid or the polynucleotide has been integrated into the genome of the Listeria at the actA locus and/or inlB locus. In some embodiments, the Listeria comprises a plasmid comprising the polynucleotide. The invention further provides immunogenic and pharmaceutical compositions comprising the Listeria. The invention also provides methods for stimulating immune responses to the heterologous antigen in a mammal (e.g., a human), comprising administering an effective amount of the Listeria (or an effective amount of a composition comprising the Listeria) to the mammal. For instance, the invention also provides methods for stimulating immune responses to an antigen from, or derived from, a cancer or infectious agent, comprising administering an effective amount of the Listeria (or a composition comprising the Listeria) to a mammal having the cancer or infectious agent, wherein the heterologous antigen shares at least one epitope with or is immunologically cross-reactive with the antigen from, or derived from, the cancer or infectious agent. In some embodiments, inclusion of the modified Act A sequence in the fusion protein enhances the immunogenicity of the Listeria comprising the polynucleotide (e.g., relative to the immunogenicity of Listeria comprising a polynucleotide encoding a fusion protein comprising the heterologous antigen and a non-ActA signal sequence and/or leader sequence instead of the modified ActA). In some embodiments, inclusion of the modified Act A sequence in the fusion protein enhances expression and/or secretion of the heterologous antigen in Listeria (e.g., relative to the expression and/or secretion in Listeria of the heterologous antigen fused to a non-ActA signal sequence and/or leader sequence instead of the modified ActA).

In another aspect, the invention provides a polynucleotide comprising a first nucleic acid encoding a modified ActA (e.g., actA-N-100), operably linked and in frame with, a second nucleic acid encoding a heterologous antigen. In some embodiments, the modified ActA comprises at least the first 59 amino acids of ActA, but less than about the first 265 amino acids of ActA. In some embodiments, the modified ActA comprises more than the first 59 amino acids of ActA, but less than about the first 265 amino acids of ActA. In some embodiments, the first nucleic acid encodes amino acids 1-100 of ActA. In some embodiments, the polynucleotide is genomic. For instance, the polynucleotide may be integrated into the actA or inlB gene. In some alternative embodiments, the polynucleotide is plasmid-based. In some embodiments, the polynucleotide is operably linked with one or more of the following: (a) actA promoter; or (b) a bacterial promoter that is not actA promoter. In some embodiments, the heterologous antigen is, or is derived from, a cancer cell, tumor, or infectious agent. In some embodiments, the heterologous antigen is immunologically cross-reactive with, or shares at least one epitope with, the cancer, tumor, or infectious agent. In some embodiments, the heterologous antigen is, or is derived from, mesothelin (e.g., human mesothelin). The invention further provides a Listeria bacterium e.g., Listeria monocytogenes) comprising the polynucleotide, as well as vaccines comprising the Listeria. In some embodiments, the Listeria is hMeso26 or hMeso38 (see Table 11 of Example VII, below). The invention also provides methods for stimulating immune responses to an antigen from, or derived from, a cancer (e.g., a tumor or pre-cancerous cell) or infectious agent (e.g., a virus, pathogenic bacterium, or parasitic organism), comprising administering the Listeria to a mammal having the cancer or infectious agent, wherein the heterologous antigen shares at least one epitope with or is immunologically cross-reactive with the antigen from, or derived from, the cancer or infectious agent. In some embodiments of the methods, the stimulating is relative to immune response without administering the Listeria. In some embodiments of the methods, the heterologous antigen is from, or is derived from, the cancer cell, tumor, or infectious agent.

In another aspect, the invention provides a polynucleotide comprising a first nucleic acid encoding a modified actA, wherein the modified actA comprises (a) amino acids 1-59 of actA, (b) an inactivating mutation in, deletion of, or truncation prior to, at least one domain for actA-mediated regulation of the host cell cytoskeleton, wherein the first nucleic acid is operably linked and in frame with a second nucleic acid encoding a heterologous antigen. In some embodiments the modified ActA comprises more than the first 59 amino acids of ActA. In some embodiments, the domain is the cofilin homology region (KKRR (SEQ ID NO:23)). In some embodiments, the domain is the phospholipid core binding domain (KVFKKIKDAGKWVRDKI (SEQ ID NO:20)). In some embodiments, the at least one domain comprises all four proline-rich domains (FPPPP (SEQ ID NO:21), FPPPP (SEQ ID NO:21), FPPPP (SEQ ID NO:21), FPPIP (SEQ ID NO:22)) of ActA. In some embodiments, the modified actA is actA-N100. In some embodiments, the polynucleotide is genomic. In some embodiments, the polynucleotide is not genomic. In some embodiments, the polynucleotide is operably linked with one or more of the following: (a) actA promoter; or (b) a bacterial (e.g., listerial) promoter that is not actA promoter. The invention further provides a Listeria bacterium (e.g., Listeria monocytogenes) comprising the polynucleotide, as well as vaccines comprising the *Listeria*. In some embodiments, the *Listeria* is hMeso26 or hMeso38 (see Table 11 of Example VII, below). The invention also provides methods for stimulating immune responses to an antigen from, or derived from, a cancer or infectious agent, comprising administering the *Listeria* to a mammal having the cancer or infectious agent, wherein the heterologous antigen shares at least one epitope with or is immunologically cross-reactive with the antigen from, or derived from, the cancer or infectious agent. In some embodiments, the stimulating is relative to immune response without administering the *Listeria*. In some embodiments, the cancer comprises a tumor or precancerous cell. In some embodiments, the infectious agent comprises a virus, pathogenic bacterium, or parasitic organism. In some embodiments, the heterologous antigen is, or is derived from, a cancer cell, tumor, or infectious agent. In some embodiments, the heterologous antigen is immunologically cross-reactive with, or shares at least one epitope with, the cancer, tumor, or infectious agent. In some embodiments, the heterologous antigen is, or is derived from, mesothelin. For instance, in some embodiments, the heterologous antigen is, or is derived from, human mesothelin. In some embodiments, inclusion of the modified Act A sequence in the polynucleotide enhances expression and/or secretion of the heterologous antigen in *Listeria*. In some embodiments, inclusion of the modified Act A sequence in the polynucleotide enhances the immunogenicity of vaccine compositions comprising the *Listeria*.

In still another aspect, the invention provides a plasmid comprising a first nucleic acid encoding a phage integrase, a second nucleic acid encoding a phage attachment site (attPP' site), and a third nucleic acid encoding a heterologous antigen or regulatory nucleic acid, wherein the plasmid is useful for mediating site-specific integration of the nucleic acid encoding the heterologous antigen at a bacterial attachment site (attBB' site) in a bacterial genome that is compatible with the attPP' site of the plasmid. In some embodiments, each of the nucleic acids is derivable from *L. innocua* 0071, each of the nucleic acids is derivable from *L. innocua* 1765, each of the nucleic acids is derivable from *L. innocua* 2601, or each of the nucleic acids is derivable from *L. monocytogenes* f6854_2703. In some embodiments, the first nucleic acid encodes a phiC31 integrase. In some embodiments, the plasmid is the polynucleotide sequence of pINT; or a polynucleotide hybridizable under stringent conditions to a polynucleotide encoding pINT, wherein the polynucleotide that is hybridizable is capable of mediating site specific integration at the same bacterial attachment site (attBB') in a bacterial genome as that used by pINT. In some embodiments, the bacterial genome is of a *Listeria, Bacillus anthracis*, or *Francisella tularensis*. In some embodiments, the heterologous antigen is, or is derived from, a cancer cell, tumor, or infectious agent. In some embodiments, the regulatory nucleic acid is a bacterial attachment site (attBB'). In some embodiments, the plasmid further comprises a fourth nucleic acid encoding a first lox site, a fifth nucleic acid encoding a second lox site, and a sixth nucleic acid encoding a selection marker, wherein the first lox site and second lox site are operably linked with the sixth nucleic acid, and wherein the operably linked lox sites are useful for mediating Cre recombinase catalyzed excision of the sixth nucleic acid. In some embodiments, the first lox site is a loxP site and the second lox site is a loxP site. In some embodiments, the plasmid further comprises a non compatible bacterial attachment site (attBB'), wherein the non compatible attBB' site is not compatible with the phage attachment site (attPP'). In some embodiments, the plasmid further comprises a first promoter operably linked with the first nucleic acid, and a second promoter operably linked with the third nucleic acid. The invention further provides a method of modifying a bacterial genome, comprising transfecting the bacterium with the plasmid, and allowing integrase-catalyzed integration of the third nucleic acid into the bacterial genome under conditions suitable for integration. In some embodiments of the method, the bacterium is *Listeria, Bacillus anthracis*, or *Francisella tularensis*.

The invention further provides a plasmid comprising: (a) a first nucleic acid encoding a first region of homology to a bacterial genome, (b) a second nucleic acid encoding a second region of homology to the bacterial genome, and (c) a third nucleic acid comprising a bacterial attachment site (attBB'), wherein the third nucleic acid is flanked by the first and second nucleic acids, wherein the first nucleic acid and second nucleic acid are operably linked with each other and able to mediate homologous integration of the third nucleic acid into the bacterial genome. In some embodiments, the bacterial attachment site (attBB') comprises the attBB' of: listerial tRNAArg-attBB'; listerial comK attBB'; *Listeria innocua* 0071; *Listeria innocua* 1231; *Listeria innocua* 1765; *Listeria innocua* 2610; or *Listeria monocytogenes* f6854_2703; or phiC31. In some embodiments, the genome is of a *Listeria, Bacillus anthracis*, or *Francisella tularensis*. In some embodiments, the third nucleic acid encodes a selection marker flanked by a first lox site and a second lox site, wherein the lox sites are recognized as substrates by Cre recombinase and allow Cre recombinase catalyzed excision of the third nucleic acid, and wherein the selection marker is useful for detecting integration of the third nucleic acid into the bacterial genome. In some embodiments, the first lox site is a loxP site, and the second lox site is a loxP site. In some embodiments, the third nucleic acid comprises an antibiotic resistance gene. In some embodiments, the first nucleic acid is homologous to a first region of a virulence factor gene and the second nucleic acid is homologous to a second region of the virulence factor gene, wherein the first and second regions of the virulence factor gene are distinct from each other and do not overlap each other. In some embodiments, the first region of the virulence factor gene covalently contacts or abuts the second region of the virulence factor gene. In other embodiments, the first region of the virulence factor gene is not in covalent contact with, and does not covalently abut, the second region of the virulence factor gene. The invention further provides bacteria modified by integration of the plasmid. In some embodiments, the integration is in a region of the genome that is necessary for mediating growth or spread. In other embodiments, the integration is in a region of the genome that is not necessary for mediating growth or spread.

In yet another aspect, the invention provides a bacterium wherein the genome comprises a polynucleotide containing two operably linked heterologous recombinase binding sites flanking a first nucleic acid, wherein the two sites are: (a) two lox sites; or (b) two Frt sites, and wherein the nucleic acid flanked by the two lox sites is excisable by Cre recombinase, and wherein the nucleic acid flanked by the two Frt sites is excisable by FLP recombinase. In some embodiments, the two lox sites are both loxP sites. In some embodiments, the first nucleic acid encodes a selection marker or a heterologous antigen. In some embodiments, the first nucleic acid encodes an antibiotic resistance gene. In some embodiments, the bacterium is *Listeria, Bacillus anthracis*, or *Francisella tularensis*. the polynucleotide further comprises a second nucleic acid, wherein the second nucleic acid is not flanked by, and is not operably linked with, the first and second heterologous recombinase binding site. In some embodiments, the second nucleic acid encodes one or both of: heterologous antigen; or a bacterial attachment site (attBB'). In some embodiments, the heterologous antigen is, or is derived from, a cancer cell, tumor, or infectious agent. The invention further provides a method of excising the first nucleic acid from the bacterial genome, comprising contacting the genome with Cre recombinase or FLP recombinase, and allowing the recombinase to catalyze excision of the first nucleic acid, under conditions allowing or facilitating excision: (a) wherein the first nucleic acid is flanked by lox sites and the recombinase is Cre recombinase; or (b) wherein the first nucleic acid is flanked by Frt sites and the recombinase is FLP recombinase. In some embodiments, the recombinase is transiently expressed in the bacterium.

In another aspect, the invention provides Listeria (e.g., Listeria monocytogenes) in which the genome comprises a polynucleotide comprising a nucleic acid encoding a heterologous antigen. In some embodiments, the nucleic acid encoding the heterologous antigen has been integrated into the genome by site-specific recombination or homologous recombination. In some embodiments, the site of integration into the genome is the tRNA$^{Arg}$ locus. In some embodiments, the presence of the nucleic acid in the genome attenuates the Listeria. In some embodiments, the nucleic acid encoding the heterologous antigen has been integrated into the locus of a virulence gene. In some embodiments, the nucleic acid encoding the heterologous antigen has been integrated into the actA locus. In some embodiments, the nucleic acid encoding the heterologous antigen has been integrated into the inlB locus. In some embodiments, the genome of the Listeria comprises a first nucleic acid encoding a heterologous antigen that has been integrated into a first locus (e.g., the actA locus) and a second nucleic acid encoding a second heterologous antigen that has been integrated into a second locus (e.g., the inlB locus). The first and second heterologous antigens may be identical to each other or different. In some embodiments, the first and second heterologous antigens differ from each other, but are derived from the same tumor antigen or infectious agent antigen. In some embodiments, the first and second heterologous antigens are each a different fragment of an antigen derived from a cancer cell, tumor, or infectious agent. In some embodiments, the integrated nucleic acid encodes a fusion protein comprising the heterologous antigen and modified ActA. In some embodiments, at least two, at least three, at least four, at least five, at least six, or at least seven nucleic acid sequences encoding heterologous antigens have been integrated into the Listerial genome.

In another aspect, the invention provides a Listeria bacterium comprising a genome, wherein the genome comprises a polynucleotide comprising a nucleic acid encoding a heterologous antigen, wherein the nucleic acid has been integrated into a virulence gene in the genome. In some embodiments, integration of the polynucleotide (a) disrupts expression of the virulence gene; or (b) disrupts a coding sequence of the virulence gene. In some embodiments, all or part of the virulence gene has been deleted. In some embodiments, none of the virulence gene has been deleted. In some embodiments, the integration attenuates the Listeria. In some embodiments, the virulence gene is prfA-dependent. In other embodiments, the virulence gene is prfA-independent. In some embodiments, the virulence gene is necessary for mediated growth or spread of the bacterium. In some embodiments, the virulence gene is not necessary for growth and spread of the bacterium. In some embodiments, the virulence gene is actA or inlB. In some embodiments, the Listeria bacterium is Listeria monocytogenes. In some embodiments, the heterologous antigen is from, or is derived from, a cancer cell, tumor, or infectious agent. In some embodiments, the heterologous antigen is mesothelin (e.g., human mesothelin), or derived from mesothelin. In some embodiments, the nucleic acid encodes a fusion protein comprising the heterologous antigen and a modified ActA. In some embodiments, the bacterium comprises a second nucleic acid encoding a second heterologous antigen that has been integrated into a second virulence gene. The invention provides vaccines comprising the Listeria bacterium. The invention further provides a method for stimulating an immune response to the heterologous antigen in a mammal, comprising administering an effective amount of the Listeria bacterium, or an effective amount of a composition comprising the Listeria bacterium, to the mammal.

In still another aspect, the invention provides a method of producing a Listeria bacterium (e.g., an attenuated bacterium), comprising integrating a polynucleotide into a virulence gene in the genome of the Listeria bacterium, wherein the polynucleotide comprises a nucleic acid encoding a heterologous antigen. In some embodiments, the integration of the polynucleotide (a) disrupts expression of the virulence gene or (b) disrupts a coding sequence of the virulence gene. In some embodiments, the integration of the polynucleotide results in both (a) and (b). In some embodiments the method produces a Listeria bacterium for use in a vaccine. In some embodiments, the polynucleotide is integrated into the virulence gene by homologous recombination. In some embodiments, the polynucleotide is integrated via site-specific recombination. In some embodiments, all or part of the virulence gene is deleted during integration of the polynucleotide. In other embodiments, none of the virulence gene is deleted during the integration. In some embodiments, the virulence gene is actA or inlB. In some embodiments, the heterologous antigen is from, or is derived from, a cancer cell, tumor, or infectious agent. In some embodiments, the heterologous antigen is mesothelin (e.g., human mesothelin), or derived from mesothelin. In some embodiments, the nucleic acid encodes a fusion protein comprising the heterologous antigen and a modified ActA. The invention further provides a Listeria bacterium produced by the method, and vaccine compositions comprising the bacterium. The invention also provides a Listeria bacterium having the properties of a Listeria bacterium produced by the method, as well as vaccines comprising the bacterium. Methods for stimulating an immune response to the heterologous antigen in a mammal, comprising administering an effective amount of the Listeria bacterium, or an effective amount of a composition comprising the Listeria bacterium, are also provided.

In an additional aspect, the invention provides a Listeria bacterium comprising a genome, wherein the genome comprises a polynucleotide comprising a nucleic acid encoding a heterologous antigen, wherein the nucleic acid has been integrated into a gene necessary for mediating growth or spread. In some embodiments, integration of the polynucleotide attenuates the Listeria for growth or spread. In some embodiments, part or all of the gene has been deleted. In some embodiments, none of the gene has been deleted. In some embodiments, the gene is actA. In some embodiments, the Listeria bacterium is Listeria monocytogenes. In some embodiments, the heterologous antigen is from, or is derived from, a cancer cell, tumor, or infectious agent. In some embodiments, the heterologous antigen is mesothelin (e.g., human mesothelin), or derived from mesothelin. In some embodiments, the nucleic acid encodes a fusion protein comprising the heterologous antigen and a modified ActA. The invention provides vaccines comprising the Listeria bacterium. The invention further provides a method for stimulating an immune response to the heterologous antigen in a mammal, comprising administering an effective amount of the

*Listeria* bacterium, or an effective amount of a composition comprising the *Listeria* bacterium, to the mammal.

In still another aspect, the invention provides a method of producing a *Listeria* bacterium (e.g., an attenuated bacterium), comprising integrating a polynucleotide into a gene in the genome of the *Listeria* bacterium that is necessary for mediating growth or spread, wherein the polynucleotide comprises a nucleic acid encoding a heterologous antigen. In some embodiments, the integration of the polynucleotide attenuates the *Listeria* for growth or spread. In some embodiments the method produces a *Listeria* bacterium for use in a vaccine. In some embodiments, the polynucleotide is integrated into the gene by homologous recombination. In some embodiments, the polynucleotide is integrated via site-specific recombination. In some embodiments, all or part of the gene necessary for mediating growth or spread is deleted during integration of the polynucleotide. In other embodiments, none of the gene is deleted during the integration. In some embodiments, the gene necessary for mediating growth or spread is actA. In some embodiments, the heterologous antigen is from, or is derived from, a cancer cell, tumor, or infectious agent. In some embodiments, the heterologous antigen is mesothelin (e.g., human mesothelin), or derived from mesothelin. In some embodiments, the nucleic acid encodes a fusion protein comprising the heterologous antigen and a modified ActA. The invention further provides a *Listeria* bacterium produced by the method, and vaccine compositions comprising the bacterium. The invention also provides a *Listeria* bacterium having the properties of a *Listeria* bacterium produced by the method, as well as vaccines comprising the bacterium. Methods for stimulating an immune response to the heterologous antigen in a mammal, comprising administering an effective amount of the *Listeria* bacterium, or an effective amount of a composition comprising the *Listeria* bacterium, are also provided.

In some embodiments, the invention provides a *Listeria* bacterium containing a polynucleotide comprising a first nucleic acid encoding a fusion protein partner, operably linked and in frame with and a second nucleic acid encoding human mesothelin, or a derivative thereof. The first nucleic acid can encode, e.g., LLO62 (non-codon optimized); LLO26 (codon optimized); LLO441 (non-codon optimized); LLO441 (codon optimized); full length LLO (non-codon optimized); full length LLO (codon optimized); BaPA secretory sequence; *B. subtilis* phoD secretory sequence (Bs phoD SS); p60 (non-codon optimized); p60 (codon optimized); actA (non-codon optimized); actA (codon optimized); actA-N100 (non-codon optimized); actA-N100 (codon optimized); actA (A30R). The second nucleic acid can encode full length human mesothelin; human mesothelin deleted in its signal sequence; human mesothelin deleted in its GPI anchor; or human mesothelin deleted in both the signal sequence and the GPI anchor, where codon-optimized and non-codon optimized versions of mesothelin are provided. In another aspect, the present invention provides the above polynucleotide integrated at the position of the inlB gene, actA gene, hly gene, where integration can be mediated by homologous recombination, and where integration can optionally be with operable linking with the promoter of the inlB, actA, or hly gene. In yet another aspect, the invention provides listerial embodiments where the above polynucleotide is integrated into the listerial genome by way of site-specific integration, e.g., at the tRNA$^{Arg}$ site. Each of the individual embodiments disclosed herein, optionally, encompasses a *Listeria* comprising a constitutively active pfrA gene (prfA*). The listerial constructs are not limited to polynucleotides operably linked with an actA promoter or hly promoter.

What is also encompassed is operable linkages with other bacterial promoters, synthetic promoters, bacteriovirus promoters, and combinations of two or more promoters.

In some embodiments, the heterologous antigen encoded by a nucleic acid in the polynucleotides, *Listeria* bacteria, and/or vaccines described above, or elsewhere herein, does not comprise an EphA2 antigenic peptide. In some embodiments, the heterologous antigen encoded by a nucleic acid in the polynucleotides, *Listeria* bacteria, and/or vaccines, does not comprise full-length EphA2 or an antigenic fragment, analog or derivative thereof.

BRIEF DESCRIPTION OF THE DRAWINGS

FIG. 7 is a schematic disclosing some of the mesothelin constructs of the present invention, including, e.g., any promoters, secretory sequences, fusion protein partners, and so on.

FIG. 13 disclose numbers of tumor metastases on the surfaces of livers, after treating tumor-bearing mice with various preparations of recombinant *L. monocytogenes*. FIG. 13 reveals the raw data (photographs of fixed livers).

FIG. 19 shows secretion of mesothelin and immune responses stimulated by various preparations of recombinant *L. monocytogenes*.

FIG. 23 discloses immune responses stimulated by vaccination with various preparations of recombinant *Listeria*.

FIG. 24 further discloses secretion of mesothelin and immune responses stimulated by various preparations of recombinant *L. monocytogenes*.

FIG. 26 additionally discloses secretion of mesothelin and immune responses stimulated by various preparations of recombinant *L. monocytogenes*. hMeso6: *L. monocytogenes* ΔactAΔinlB encoding actA promoter; actA-N100-hMeso ΔSSΔGPI; integrated at actA locus. hMeso25: *L. monocytogenes* ΔactAΔinlB encoding actA promoter; actA-N100-hMeso ΔSSΔGPI; integrated at inlB locus.

FIG. 33 depicts mesothelin secretion and immune responses stimulated after vaccination with recombinant *L. monocytogenes*.

FIG. 35A illustrates raw data (photographs of fixed livers).

FIG. 40 discloses alignment of a phage integrase of the present invention with a another phage integrase (U153 int: SEQ ID NO: 1; lin 1231: SEQ ID NO:2).

FIG. 41 discloses alignment of yet another phage integrase of the present invention another phage integrase (PSA int: SEQ ID NO:3; lin 0071: SEQ ID NO:4).

FIG. 42 shows alignment of still another phage integrase of the present invention with a different phage integrase (PSA int: SEQ ID NO:5; lin 1765: SEQ ID NO:6).

FIG. 43 discloses alignment of a further phage integrase of the present invention with another phage integrase (PSA int: SEQ ID NO:7; lin 2601: SEQ ID NO:8).

FIG. 44 provides an alignment of an additional phage integrase of the present invention with a nucleic acid encoding another phage integrase (PSA int: SEQ ID NO:119; lmof6854_2703: SEQ ID NO:120).

DETAILED DESCRIPTION

Figure 1:
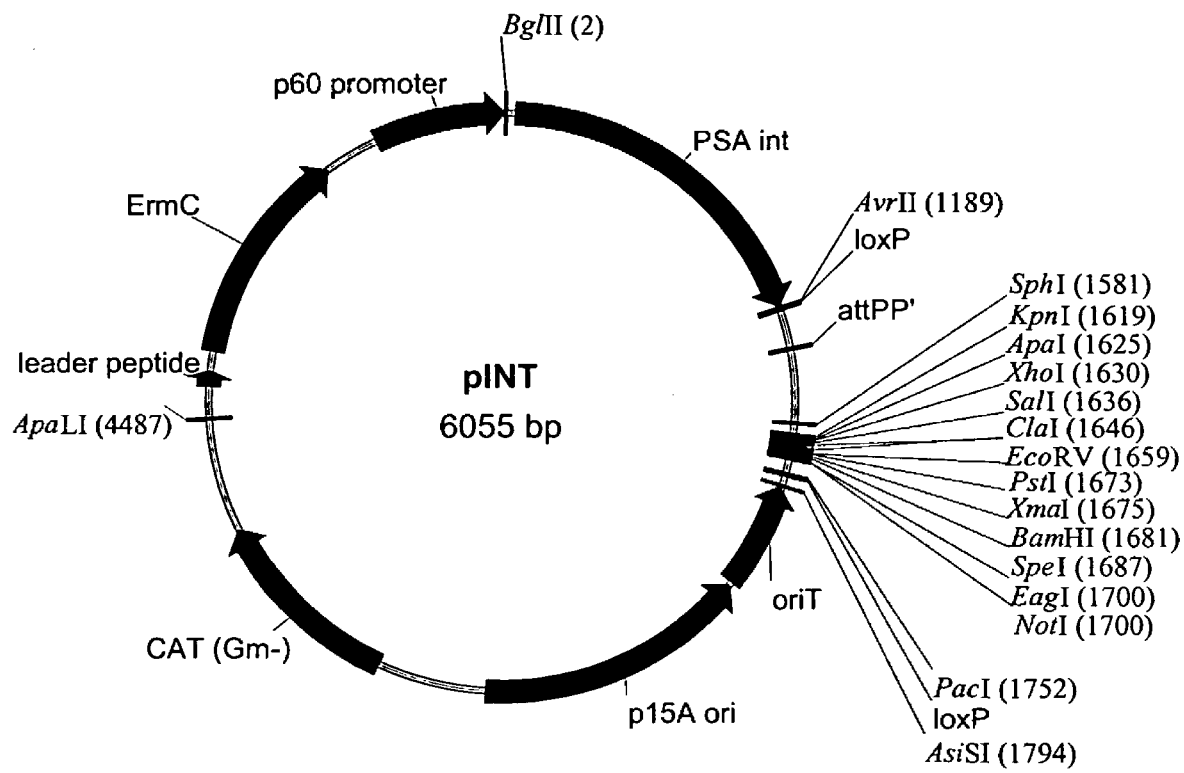
FIG. 1 discloses pINT, a 6055 bp plasmid. Once pINT is integrated in a listerial genome, the *Listeria* can be isolated by erythromycin resistance (ErmC), followed by treatment with Cre recombinase to remove a region of the plasmid encoding the antibiotic resistance genes (CAT and ErmC).

As used herein, including the appended claims, the singular forms of words such as "a," "an," and "the," include their corresponding plural references unless the context clearly dictates otherwise. All references cited herein are incorporated by reference to the same extent as if each individual publication, sequences accessed by a GenBank Accession No., patent application, patent, Sequence Listing, nucleotide or oligo- or polypeptide sequence in the Sequence Listing, as well as figures and drawings in said publications and patent documents, was specifically and individually indicated to be incorporated by reference. The term "present invention" refers to certain embodiments of the present invention, or to some embodiments of the present invention. Unless stated otherwise, the term "present invention" does not necessarily refer to all embodiments of the invention.

I. Definitions.

Abbreviations used to indicate a mutation in a gene, or a mutation in a bacterium comprising the gene, are as follows. By way of example, the abbreviation "*L. monocytogenes* ΔActA" means that part, or all, of the ActA gene was deleted. The delta symbol (Δ) means deletion. An abbreviation including a superscripted minus sign (*Listeria* ActA$^-$) means that the ActA gene was mutated, e.g., by way of a deletion, point mutation, or frameshift mutation, but not limited to these types of mutations. Exponentials are abbreviated, where, for example, "3e7" means $3\times10^7$.

"Administration" as it applies to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration"

also encompasses in vitro and ex vivo treatments, e.g., of a cell, by a reagent, diagnostic, binding composition, or by another cell.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) can encompass GM-CSF, a mutein or derivative of GM-CSF, a peptide mimetic of GM-CSF, a small molecule that mimics the biological function of GM-CSF, or an antibody that stimulates GM-CSF receptor. An antagonist, as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

As used herein, an "analog" in the context of an EphA2 polypeptide (or a fragment of an EphA2 polypeptide) refers to a proteinaceous agent (e.g., a peptide, polypeptide or protein) that possesses a similar or identical function as the EphA2 polypeptide (or fragment of an EphA2 polypeptide), but does not necessarily comprise a similar or identical amino acid sequence or structure of the EphA2 polypeptide (or fragment). An analog of an EphA2 polypeptide that has a similar amino acid sequence to an EphA2 polypeptide refers to a proteinaceous agent that satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of an EphA2 polypeptide; (b) a proteinaceous agent encoded by a nucleotide sequence that hybridizes under stringent conditions to a nucleotide sequence encoding an EphA2 polypeptide of at least 20 amino acid residues, at least 30 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, or at least 150 amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding an EphA2 polypeptide. A proteinaceous agent with similar structure to an EphA2 polypeptide refers to a proteinaceous agent that has a similar secondary, tertiary or quaternary structure of the EphA2 polypeptide.

"Antigen presenting cells" (APCs) are cells of the immune system used for presenting antigen to T cells. APCs include dendritic cells, monocytes, macrophages, marginal zone Kupffer cells, microglia, Langerhans cells, T cells, and B cells (see, e.g., Rodriguez-Pinto and Moreno (2005) Eur. J. Immunol. 35:1097-1105). Dendritic cells occur in at least two lineages. The first lineage encompasses pre-DC1, myeloid DC1, and mature DC1. The second lineage encompasses $CD34^{++}CD45RA^-$ early progenitor multipotent cells, $CD34^{++}CD45RA^+$ cells, $CD34^{++}CD45RA^{++}$ $CD4^+$ $IL-3Ralpha^{++}$ pro-DC2 cells, $CD4^+CD11c^-$ plasmacytoid pre-DC2 cells, lymphoid human DC2 plasmacytoid-derived DC2s, and mature DC2s (see, e.g., Gilliet and Liu (2002) J. Exp. Med. 195:695-704; Bauer, et al. (2001) J. Immunol. 166: 5000-5007; Arpinati, et al. (2000) Blood 95:2484-2490; Kadowaki, et al. (2001) J. Exp. Med. 194:863-869; Liu (2002) Human Immunology 63:1067-1071; McKenna, et al. (2005) J. Virol. 79:17-27; O'Neill, et al. (2004) Blood 104:2235-2246; Rossi and Young (2005) J. Immunol. 175:1373-1381; Banchereau and Palucka (2005) Nat. Rev. Immunol. 5:296-306).

"Attenuation" and "attenuated" encompasses a bacterium, virus, parasite, infectious organism, prion, tumor cell, gene in the infectious organism, and the like, that is modified to reduce toxicity to a host. The host can be a human or animal host, or an organ, tissue, or cell. The bacterium, to give a non-limiting example, can be attenuated to reduce binding to a host cell, to reduce spread from one host cell to another host cell, to reduce extracellular growth, or to reduce intracellular growth in a host cell. Attenuation can be assessed by measuring, e.g., an indicum or indicia of toxicity, the $LD_{50}$, the rate of clearance from an organ, or the competitive index (see, e.g., Auerbuch, et al. (2001) Infect. Immunity 69:5953-5957). Generally, an attenuation results an increase in the $LD_{50}$ and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

"Attenuated gene" encompasses a gene that mediates toxicity, pathology, or virulence, to a host, growth within the host, or survival within the host, where the gene is mutated in a way that mitigates, reduces, or eliminates the toxicity, pathology, or virulence. The reduction or elimination can be assessed by comparing the virulence or toxicity mediated by the mutated gene with that mediated by the non-mutated (or parent) gene. "Mutated gene" encompasses deletions, point mutations, and frameshift mutations in regulatory regions of the gene, coding regions of the gene, non-coding regions of the gene, or any combination thereof.

"Cancerous condition" and "cancerous disorder" encompass, without implying any limitation, a cancer, a tumor, metastasis, angiogenesis of a tumor, and precancerous disorders such as dysplasias.

"Conservatively modified variants" applies to both amino acid and nucleic acid sequences. With respect to particular nucleic acid sequences, a conservatively modified variant refers to nucleic acids encoding identical amino acid sequences, or amino acid sequences that have one or more conservative substitutions. An example of a conservative substitution is the exchange of an amino acid in one of the following groups for another amino acid of the same group (U.S. Pat. No. 5,767,063 issued to Lee, et al.; Kyte and Doolittle (1982) J. Mol. Biol. 157:105-132).

(1) Hydrophobic: Norleucine, Ile, Val, Leu, Phe, Cys, Met;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro;
(6) Aromatic: Trp, Tyr, Phe; and
(7) Small amino acids: Gly, Ala, Ser.

A "derivative" in the context of an EphA2 polypeptide or a fragment of an EphA2 polypeptide refers to a proteinaceous agent that comprises an amino acid sequence of an EphA2 polypeptide or a fragment of an EphA2 polypeptide that has been altered by the introduction of amino acid residue substitutions, deletions or additions (i.e., mutations). The term "derivative" in the context of EphA2 proteinaceous agents also refers to an EphA2 polypeptide or a fragment of an EphA2 polypeptide which has been modified, i.e, by the covalent attachment of any type of molecule to the polypeptide. For example, but not by way of limitation, an EphA2 polypeptide or a fragment of an EphA2 polypeptide may be modified, e.g., by glycosylation, acetylation, pegylation, phosphorylation, amidation, derivatization by known protecting/blocking groups, proteolytic cleavage, linkage to a cellular ligand or other protein, etc. A derivative of an EphA2 polypeptide or a fragment of an EphA2 polypeptide may be modified by chemical modifications using techniques known to those of skill in the art, including, but not limited to, specific chemical cleavage, acetylation, formylation, metabolic synthesis of tunicamycin, etc. Further, a derivative of an EphA2 polypeptide or a fragment of an EphA2 polypeptide may contain one or more non-classical amino acids. In one embodiment, a polypeptide derivative possesses a similar or identical function as an EphA2 polypeptide or a fragment of an EphA2 polypeptide described herein. In another embodiment, a derivative of EphA2 polypeptide or a fragment of an EphA2 polypeptide has an altered activity when compared to an unaltered polypeptide. For example, a derivative of an EphA2 polypeptide or fragment thereof can differ in phosphorylation relative to an EphA2 polypeptide or fragment thereof.

"Effective amount" encompasses, without limitation, an amount that can ameliorate, reverse, mitigate, prevent, or diagnose a symptom or sign of a medical condition or disorder. Unless dictated otherwise, explicitly or by context, an "effective amount" is not limited to a minimal amount sufficient to ameliorate a condition.

"EphA2 antigenic peptides" (sometimes referred to as "EphA2 antigenic polypeptides"), are defined and described in U.S. Patent Publication No. 2005/0281783 A1, which is hereby incorporated by reference herein in its entirety, including all sequences contained therein. EphA2 is a 130 kDa receptor tyrosine kinase expressed in adult epithelia (Zantek et al. (1999) Cell Growth & Differentiation 10:629; Lindberg et al. (1990) Molecular & Cellular Biology 10:6316). An "EphA2 antigenic peptide" or an "EphA2 antigenic polypeptide" refers to an EphA2 polypeptide, or a fragment, analog or derivative thereof comprising one or more B cell epitopes or T cell epitopes of EphA2. The EphA2 polypeptide may be from any species. For example the EphA2 polypeptide may be a human EphA2 polypeptide. The term "EphA2 polypeptide" includes the mature, processed form of EphA2, as well as immature forms of EphA2. In some embodiments, the EphA2 polypeptide is the sequence shown in SEQ ID NO:2 of U.S. Patent Publication No. 2005/0281783 A1. Examples of the nucleotide sequence of human EphA2 can be found in the GenBank database (see, e.g., Accession Nos. BC037166, M59371 and M36395). Examples of the amino acid sequence of human EphA2 can also be found in the GenBank database (see, e.g., Accession Nos. NP$_{004422}$, AAH37166, and AAA53375). Additional examples of amino acid sequences of EphA2 include those listed as GenBank Accession Nos. NP$_{034269}$ (mouse), AAH06954 (mouse), XP$_{345597}$ (rat), and BAB63910 (chicken).

An "extracellular fluid" encompasses, e.g., serum, plasma, blood, interstitial fluid, cerebrospinal fluid, secreted fluids, lymph, bile, sweat, fecal matter, and urine. An "extracelluar fluid" can comprise a colloid or a suspension, e.g., whole blood or coagulated blood.

The term "fragments" in the context of EphA2 polypeptides include an EphA2 antigenic peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of an EphA2 polypeptide.

"Gene" refers to a nucleic acid sequence encoding an oligopeptide or polypeptide. The oligopeptide or polypeptide can be biologically active, antigenically active, biologically inactive, or antigenically inactive, and the like. The term gene encompasses, e.g., the sum of the open reading frames (ORFs) encoding a specific oligopeptide or polypeptide; the sum of the ORFs plus the nucleic acids encoding introns; the sum of the ORFs and the operably linked promoter(s); the sum of the ORFS and the operably linked promoter(s) and any introns; the sum of the ORFS and the operably linked promoter(s), intron(s), and promoter(s), and other regulatory elements, such as enhancer(s). In certain embodiments, "gene" encompasses any sequences required in cis for regulating expression of the gene. The term gene can also refer to a nucleic acid that encodes a peptide encompassing an antigen or an antigenically active fragment of a peptide, oligopeptide, polypeptide, or protein. The term gene does not necessarily imply that the encoded peptide or protein has any biological activity, or even that the peptide or protein is antigenically active. A nucleic acid sequence encoding a non-expressable sequence is generally considered a pseudogene. The term gene also encompasses nucleic acid sequences encoding a ribonucleic acid such as rRNA, tRNA, or a ribozyme.

"Growth" of a *Listeria* bacterium encompasses, without limitation, functions of bacterial physiology and genes relating to colonization, replication, increase in listerial protein content, increase in listerial lipid content. Unless specified otherwise explicitly or by context, growth of a *Listeria* encompasses growth of the bacterium outside a host cell, and also growth inside a host cell. Growth related genes include, without implying any limitation, those that mediate energy production (e.g., glycolysis, Krebs cycle, cytochromes), anabolism and/or catabolism of amino acids, sugars, lipids, minerals, purines, and pyrimidines, nutrient transport, transcription, translation, and/or replication. In some embodiments, "growth" of a *Listeria* bacterium refers to intracellular growth of the *Listeria* bacterium, that is, growth inside a host cell such as a mammalian cell. While intracellular growth of a *Listeria* bacterium can be measured by light microscopy or colony forming unit (CFU) assays, growth is not to be limited by any technique of measurement. Biochemical parameters such as the quantity of a listerial antigen, listerial nucleic acid sequence, or lipid specific to the *Listeria* bacterium, can be used to assess growth. In some embodiments, a gene that mediates growth is one that specifically mediates intracellular growth. In some embodiments, a gene that specifically mediates intracellular growth encompasses, but is not limited to, a gene where inactivation of the gene reduces the rate of intracellular growth but does not detectably, substantially, or appreciably, reduce the rate of extracellular growth (e.g., growth in broth), or a gene where inactivation of the gene reduces the rate of intracellular growth to a greater extent than it reduces the rate of extracellular growth. To provide a non-limiting example, in some embodiments, a gene where inactivation reduces the rate of intracellular growth to a greater extent than extracellular growth encompasses the situation where inactivation reduces intracellular growth to less than 50% the normal or maximal value, but reduces extracellular growth to only 1-5%, 5-10%, or 10-15% the maximal value. The invention, in certain aspects, encompasses a *Listeria* attenuated in intracellular growth but not attenuated in extracellular growth, a *Listeria* not attenuated in intracellular growth and not attenuated in extracellular growth, as well as a *Listeria* not attenuated in intracellular growth but attenuated in extracellular growth.

"Immune condition" or "immune disorder" encompasses a disorder, condition, syndrome, or disease resulting from ineffective, inappropriate, or pathological response of the immune system, e.g., to a persistent infection or to a persistent cancer (see, e.g., Jacobson, et al. (1997) Clin. Immunol. Immunopathol. 84:223-243). "Immune condition" or "immune disorder" encompasses, e.g., pathological inflammation, an inflammatory disorder, and an autoimmune disorder or disease. "Immune condition" or "immune disorder" also can refer to infections, persistent infections, cancer, tumors, precancerous disorders, cancers that resist irradication by the immune system, and angiogenesis of tumors. "Immune condition" or "immune disorder" also encompasses cancers induced by an infective agent, including the non-limiting examples of cancers induced by hepatitis B virus, hepatitis C virus, simian virus 40 (SV40), Epstein-Barr virus, papillomaviruses, polyomaviruses, Kaposi's sarcoma herpesvirus, human T-cell leukemia virus, and *Helicobacter pylori* (see, e.g., Young and Rickinson (2004) Nat. Rev. Cancer 4:757-768; Pagano, et al. (2004) Semin. Cancer Biol. 14:453-471; Li, et al. (2005) Cell Res. 15:262-271).

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$, stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

"Ligand" refers to a small molecule, peptide, polypeptide, or membrane associated or membrane-bound molecule, that is an agonist or antagonist of a receptor. "Ligand" also encompasses a binding agent that is not an agonist or antagonist, and has no agonist or antagonist properties. By convention, where a ligand is membrane-bound on a first cell, the receptor usually occurs on a second cell. The second cell may have the same identity (the same name), or it may have a different identity (a different name), as the first cell. A ligand or receptor may be entirely intracellular, that is, it may reside in the cytosol, nucleus, or in some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

"Nucleic acid" refers to deoxyribonucleotides or ribonucleotides and polymers thereof in either single stranded, double-stranded form, or multi-stranded form. Non-limiting examples of a nucleic acid are a, e.g., cDNA, mRNA, oligonucleotide, and polynucleotide. A particular nucleic acid sequence can also implicitly encompasses "allelic variants" and "splice variants."

"Operably linked" in the context of a promoter and a nucleic acid encoding a mRNA means that the promoter can be used to initiate transcription of that nucleic acid.

The terms "percent identity" and "% identity" refer to the percentage of sequence similarity found by a comparison or alignment of two or more amino acid or nucleic acid sequences. Percent identity can be determined by a direct comparison of the sequence information between two molecules by aligning the sequences, counting the exact number of matches between the two aligned sequences, dividing by the length of the shorter sequence, and multiplying the result by 100. An algorithm for calculating percent identity is the Smith-Waterman homology search algorithm (see, e.g., Kann and Goldstein (2002) Proteins 48:367-376; Arslan, et al. (2001) Bioinformatics 17:327-337).

"Precancerous condition" encompasses, without limitation, dysplasias, preneoplastic nodules; macroregenerative nodules (MRN); low-grade dysplastic nodules (LG-DN); high-grade dysplastic nodules (HG-DN); biliary epithelial dysplasia; foci of altered hepatocytes (FAH); nodules of altered hepatocytes (NAH); chromosomal imbalances; aberrant activation of telomerase; re-expression of the catalytic subunit of telomerase; expression of endothelial cell markers such as CD31, CD34, and BNH9 (see, e.g., Terracciano and Tomillo (2003) Pathologica 95:71-82; Su and Bannasch (2003) Toxicol. Pathol. 31:126-133; Rocken and Carl-McGrath (2001) Dig. Dis. 19:269-278; Kotoula, et al. (2002) Liver 22:57-69; Frachon, et al. (2001) J. Hepatol. 34:850-857; Shimonishi, et al. (2000) J. Hepatobiliary Pancreat. Surg. 7:542-550; Nakanuma, et al. (2003) J. Hepatobiliary Pancreat. Surg. 10:265-281). Methods for diagnosing cancer and dysplasia are disclosed (see, e.g., Riegler (1996) Semin. Gastrointest. Dis. 7:74-87; Benvegnu, et al. (1992) Liver 12:80-83; Giannini, et al. (1987) Hepatogastroenterol. 34:95-97; Anthony (1976) Cancer Res. 36:2579-2583).

By "purified" and "isolated" is meant, when referring to a polypeptide, that the polypeptide is present in the substantial absence of the other biological macromolecules with which it is associated in nature. The term "purified" as used herein means that an identified polypeptide often accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the polypeptides present. The weights of water, buffers, salts, detergents, reductants, protease inhibitors, stabilizers (including an added protein such as albumin), and excipients, and molecules having a molecular weight of less than 1000, are generally not used in the determination of polypeptide purity. See, e.g., discussion of purity in U.S. Pat. No. 6,090,611 issued to Covacci, et al.

"Peptide" refers to a short sequence of amino acids, where the amino acids are connected to each other by peptide bonds. A peptide may occur free or bound to another moiety, such as a macromolecule, lipid, oligo- or polysaccharide, and/or a polypeptide. Where a peptide is incorporated into a polypeptide chain, the term "peptide" may still be used to refer specifically to the short sequence of amino acids. A "peptide"

may be connected to another moiety by way of a peptide bond or some other type of linkage. A peptide is at least two amino acids in length and generally less than about 25 amino acids in length, where the maximal length is a function of custom or context. The terms "peptide" and "oligopeptide" may be used interchangeably.

"Protein" generally refers to the sequence of amino acids comprising a polypeptide chain. Protein may also refer to a three dimensional structure of the polypeptide. "Denatured protein" refers to a partially denatured polypeptide, having some residual three dimensional structure or, alternatively, to an essentially random three dimensional structure, i.e., totally denatured. The invention encompasses reagents of, and methods using, polypeptide variants, e.g., involving glycosylation, phosphorylation, sulfation, disulfide bond formation, deamidation, isomerization, cleavage points in signal or leader sequence processing, covalent and non-covalently bound cofactors, oxidized variants, and the like. The formation of disulfide linked proteins is described (see, e.g., Woycechowsky and Raines (2000) Curr. Opin. Chem. Biol. 4:533-539; Creighton, et al. (1995) Trends Biotechnol. 13:18-23).

"Recombinant" when used with reference, e.g., to a nucleic acid, cell, animal, virus, plasmid, vector, or the like, indicates modification by the introduction of an exogenous, non-native nucleic acid, alteration of a native nucleic acid, or by derivation in whole or in part from a recombinant nucleic acid, cell, virus, plasmid, or vector. Recombinant protein refers to a protein derived, e.g., from a recombinant nucleic acid, virus, plasmid, vector, or the like. "Recombinant bacterium" encompasses a bacterium where the genome is engineered by recombinant methods, e.g., by way of a mutation, deletion, insertion, and/or a rearrangement. "Recombinant bacterium" also encompasses a bacterium modified to include a recombinant extra-genomic nucleic acid, e.g., a plasmid or a second chromosome, or a bacterium where an existing extra-genomic nucleic acid is altered.

"Sample" refers to a sample from a human, animal, placebo, or research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

A "selectable marker" encompasses a nucleic acid that allows one to select for or against a cell that contains the selectable marker. Examples of selectable markers include, without limitation, e.g.: (1) A nucleic acid encoding a product providing resistance to an otherwise toxic compound (e.g., an antibiotic), or encoding susceptibility to an otherwise harmless compound (e.g., sucrose); (2) A nucleic acid encoding a product that is otherwise lacking in the recipient cell (e.g., tRNA genes, auxotrophic markers); (3) A nucleic acid encoding a product that suppresses an activity of a gene product; (4) A nucleic acid that encodes a product that can be readily identified (e.g., phenotypic markers such as beta-galactosidase, green fluorescent protein (GFP), cell surface proteins, an epitope tag, a FLAG tag); (5) A nucleic acid that can be identified by hybridization techniques, for example, PCR or molecular beacons.

"Specifically" or "selectively" binds, when referring to a ligand/receptor, nucleic acid/complementary nucleic acid, antibody/antigen, or other binding pair (e.g., a cytokine to a cytokine receptor) indicates a binding reaction which is determinative of the presence of the protein in a heterogeneous population of proteins and other biologics. Thus, under designated conditions, a specified ligand binds to a particular receptor and does not bind in a significant amount to other proteins present in the sample. Specific binding can also mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with any other binding compound.

In a typical embodiment an antibody will have an affinity that is greater than about $10^9$ liters/mol, as determined, e.g., by Scatchard analysis (Munsen, et al. (1980) Analyt. Biochem. 107:220-239). It is recognized by the skilled artisan that some binding compounds can specifically bind to more than one target, e.g., an antibody specifically binds to its antigen, to lectins by way of the antibody's oligosaccharide, and/or to an Fc receptor by way of the antibody's Fc region.

"Spread" of a bacterium encompasses "cell to cell spread," that is, transmission of the bacterium from a first host cell to a second host cell, as mediated, for example, by a vesicle. Functions relating to spread include, but are not limited to, e.g., formation of an actin tail, formation of a pseudopod-like extension, and formation of a double-membraned vacuole.

The "target site" of a recombinase is the nucleic acid sequence or region that is recognized, bound, and/or acted upon by the recombinase (see, e.g., U.S. Pat. No. 6,379,943 issued to Graham, et al.; Smith and Thorpe (2002) Mol. Microbiol. 44:299-307; Groth and Calos (2004) J. Mol. Biol. 335:667-678; Nunes-Duby, et al. (1998) Nucleic Acids Res. 26:391-406).

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual (see, e.g., U.S. Pat. No. 5,888,530 issued to Netti, et al.).

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, and/or prolonging survival. For instance, in some embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

"Vaccine" encompasses preventative vaccines. Vaccine also encompasses therapeutic vaccines, e.g., a vaccine administered to a mammal that comprises a condition or disorder associated with the antigen or epitope provided by the vaccine.

II. General.

The present invention provides reagents and methods useful for the treatment and diagnosis of cancer, tumors, precancerous disorders, and infections. Provided are nucleic acids, *Listeria* bacteria, and vaccines comprising a *Listeria* bacterium. The invention encompasses listerial cells that have been modified in vitro, including during storage, or in vivo, including products of bacterial cell division and products of bacterial deterioration.

Provided are nucleic acids encoding at least one heterologous antigen (heterologous to the *Listeria* bacterium). The heterologous antigen can be derived from a tumor, cancer cell, or and/or infective agent, e.g., a virus, bacterium, or protozoan. The heterologous antigen can also be a listerial antigen, for example, where the antigen is expressed in greater amounts than that which naturally occurs within the *Listeria* bacterium, where the listerial antigen is operably linked with a non-native regulatory sequence, or where the listerial antigen is modified to be attenuated or to increase its antigenicity.

Where a *Listeria* contains a nucleic acid encoding a heterologous antigen, the term "heterologous" encompasses, but is not necessarily limited to, an antigen from, or derived from: (1) A non-listerial organism; (2) An antigen of synthetic origin; (3) An antigen of listerial origin where the nucleic acid is integrated at a position in the listerial genome that is different from that found in the wild type; and (4) An antigen of listerial origin, but where the nucleic acid is operably linked with a regulatory sequence not normally used in a wild type *Listeria*. The preceding commentary also applies to the term "heterologous antigen," when used, for example, in the context of a viral vector. Here, heterologous antigen encompasses antigens that are not from, and not derived from, that viral vector, as well as, for example, antigens from the viral vector that are controlled by a non-native nucleic acid regulatory sequence.

Provided are reagents and methods for stimulating the mammalian immune system, for reducing the number and/or size of tumors, for reducing metastasis, and for reducing titer of an infectious organism. The present invention also provides reagents and methods for improving survival of a cell, tissue, organ, or mammal, to a cancer or infection. The present invention also provides reagents and methods for improving survival of a cell (in vivo or in vitro), a tissue (in vivo or in vitro), an organ (in vivo or in vitro), an organism, a mammal, a veterinary subject, a research subject, or a human subject, to a cancer, tumor, or infection. What is encompassed is administration that is in vivo or in vitro, survival of the cell, tissue, or organ in vitro or in vivo, or any combination thereof. Any combination includes, e.g., administration that is in vivo where subsequent survival is in vitro, or administration that is in vitro and where subsequent survival is in vivo.

Provided is a *Listeria* comprising a polynucleotide encoding at least one heterologous antigen wherein the one polynucleotide is genomic. Also encompassed is a *Listeria* comprising a polynucleotide encoding at least one heterologous antigen, wherein the polynucleotide is genomic and not residing on a plasmid within the *Listeria*. Moreover, encompassed is a *Listeria* comprising a polynucleotide encoding at least one heterologous antigen, wherein the polynucleotide resides on a plasmid within the *Listeria*. Furthermore, what is provided is a *Listeria* comprising a polynucleotide encoding at least one heterologous antigen, where the polynucleotide resides on a plasmid and does not occur integrated in the genome. In another aspect, the present invention provides a *Listeria* comprising a polynucleotide encoding at least one heterologous antigen, where the polynucleotide is integrated in the genome and also separately resides in a plasmid.

The mouse is an accepted model for human immune response. In detail, mouse T cells are a model for human T cells, mouse dendritic cells (DCs) are a model for human DCs, mouse NK cells are a model for human NK cells, mouse NKT cells are a model for human NKT cells, mouse innate response is an accepted model for human innate response, and so on. Model studies are disclosed, for example, for $CD8^+$ T cells, central memory T cells, and effector memory T cells (see, e.g., Walzer, et al. (2002) J. Immunol. 168:2704-2711); the two subsets of NK cells (see, e.g., Chakir, et al. (2000) J. Immunol. 165:4985-4993; Smith, et al. (2000) J. Exp. Med. 191:1341-1354; Ehrlich, et al. (2005) J. Immunol. 174:1922-1931; Peritt, et al. (1998) J. Immunol. 161:5821-5824); NKT cells (see, e.g., Couedel, et al. (1998) Eur. J. Immunol. 28:4391-4397; Sakamoto, et al. (1999) J. Allergy Clin. Immunol. 103:S445-S451; Saikh, et al. (2003) J. Infect. Dis. 188:1562-1570; Emoto, et al. (1997) Infection Immunity 65:5003-5009; Taniguchi, et al. (2003) Annu. Rev. Immunol. 21:483-513; Sidobre, et al. (2004) Proc. Natl. Acad. Sci. 101: 12254-12259); monocytes/macrophages (Sunderkotter, et al. (2004) J. Immunol. 172:4410-4417); the two lineages of DCs (Boonstra, et al. (2003) J. Exp. Med. 197:101-109; Donnenberg, et al. (2001) Transplantation 72:1946-1951; Becker (2003) Virus Genes 26:119-130; Carine, et al. (2003) J. Immunol. 171:6466-6477; Penna, et al. (2002) J. Immunol. 169:6673-6676; Alferink, et al. (2003) J. Exp. Med. 197:585-599).

Mouse innate response, including the Toll-Like Receptors (TLRs), is a model for human innate immune response, as disclosed (see, e.g., Janssens and Beyaert (2003) Clinical Microb. Revs. 16:637-646). Mouse neutrophils are an accepted model for human neutrophils (see, e.g., Kobayashi, et al. (2003) Proc. Natl. Acad. Sci. USA 100:10948-10953; Torres, et al. (2004) 72:2131-2139; Sibelius, et al. (1999) Infection Immunity 67:1125-1130; Tvinnereim, et al. (2004) J. Immunol. 173:1994-2002). Murine immune response to *Listeria* is an accepted model for human response to *Listeria* (see, e.g., Kolb-Maurer, et al. (2000) Infection Immunity 68:3680-3688; Brzoza, et al. (2004) J. Immunol. 173:2641-2651; Esplugues, et al. (2005) Blood February 3 (epub ahead of print); Paschen, et al. (2000) Eur. J. Immunol. 30:3447-3456; Way and Wilson (2004) J. Immunol. 173:5918-5922; Ouadrhiri, et al. (1999) J. Infectious Diseases 180:1195-1204; Neighbors, et al. (2001) J. Exp. Med. 194:343-354; Calorini, et al. (2002) Clin. Exp. Metastasis 19:259-264; Andersson, et al. (1998) J. Immunol. 161:5600-5606; Flo, et al. (2000) J. Immunol. 164:2064-2069; Calorini, et al. (2002) Clin. Exp. Metastasis 19:259-264; Brzoza, et al. (2004) J.

Immunol. 173:2641-2651; Brzoza, et al. (2004) J. Immunol. 173:2641-2651; Cleveland, et al. (1996) Infection Immunity 64:1906-1912; Andersson, et al. (1998) J. Immunol. 161: 5600-5606).

U.S. Patent Publication Nos. 2004/0228877 and 2004/0197343, each of which is incorporated by reference herein in its entirety, describe the use of *Listeria* useful in some embodiments of the present invention. U.S. Patent Publication No. 2005/0249748, incorporated by reference herein in its entirety, further describes *Listeria* and polynucleotides useful in some embodiments of the present invention.

(a). Secretory or Signal Sequences.

The present invention embraces a nucleic acid encoding a secretory sequence, or encoding a listerial protein, or a fragment thereof, suitable for use as a fusion protein partner. What is encompassed is a nucleic acid encoding:

i. a secretory sequence,
ii. a signal sequence,
iii. a listerial polypeptide containing its native secretory sequence,
iv. a listerial protein with its native secretory sequence replaced with that of another listerial protein,
v. a listerial protein with its native secretory sequence replaced with the secretory sequence of a non-listerial bacterial protein,
vi. a non-secreted listerial protein, or fragment thereof, not containing any secretory sequence; and
vii. a non-listerial bacterial secretory sequence fused with, and in frame with, a non-secreted listerial protein, or fragment thereof.

These embodiments can encompass the following listerial proteins, and fragments or domains thereof:

i. Listeriolysin (LLO). The secretory signal sequence of listeriolysin O (hly gene) has been identified (see, e.g., Lety, et al. (2003) Microbiol. 149:1249-1255).

ii. ActA. The ribosomal binding site, promoter, and signal sequence have been identified for listerial ActA. The ribosomal binding site occurs 6 bp upstream of the start codon of the ActA gene (Vazquez-Boland, et al. (1992) Infect. Immunity 60:219-230).

iii. Internalins. All of the internalin (Inl) proteins contain an N-terminal sequence of 30-35 amino acids with characteristics of bacterial signal peptides (see, e.g., Dramsi, et al. (1997) Infect. Immunity 65:1615-1625).

iv. p60 (iap gene). A 27-amino acid region between the start codon and nucleotide 524 functions as a signal sequence, and directs transport of p60 across the *Listeria* cell membrane (Kohler, et al. (1990) Infect. Immunity 58:1943-1950). Kohler, et al., supra, also disclose a purine-rich ribosome (16S RNA) binding site of the p60 mRNA of *L. monocytogenes*.

Table 1 discloses a number of non-limiting examples of signal peptides for use in fusing with a fusion protein partner sequence such as a heterologous antigen. The SignalP algorithm can be used to determine signal sequences in Gram positive bacteria. This program is available on the world wide web at: cbs.dtu.dk/services/SignalP/. Signal peptides tend to contain three domains: a positively charged N-terminus (1-5 residues long); a central hydrophobic domain (7-15 residues long); and a neutral but polar C-terminal domain (see, e.g., Lety, et al. (2003) Microbiology 149:1249-1255; Paetzel, et al. (2000) Pharmacol. Ther. 87:27-49). As signal peptides and secretory sequences encoded by *Listeria* genome, or by a genome or plasmid of another bacterium, are not necessarily codon optimized for optimal expression in *Listeria*, the present invention also provides nucleic acids originating from the *Listeria* genome, or from a genome or plasmid of another bacterium, that are altered by codon optimized for expressing by a *L. monocytogenes*. The present invention is not to be limited to polypeptide and peptide antigens that are secreted, but also embraces polypeptides and peptides that are not secreted or cannot be secreted from a *Listeria* or other bacterium.

TABLE 1

Bacterial signal pathway. Signal peptides are identified by the signal peptidase site.

| Signal peptidase site (cleavage site represented by') | Gene | Genus/species |
| --- | --- | --- |
| secA1 pathway | | |
| TEA'KD | hly (LLO) | *Listeria monocytogenes* |
| VYA'DT (SEQ ID NO: 127) | Usp45 | *Lactococcus lactis* (see, e.g., Steidler, et al. (2003) Nat. Biotech. 21: 785-789; Schotte, et al. (2000) Enzyme Microb. Technol. 27: 761-765). |
| IQA'EV (SEQ ID NO: 128) | pag (protective antigen) | *Bacillus anthracis* |
| secA2 pathway | | |
| ASA'ST (SEQ ID NO: 129) | iap (invasion-associated protein) p60 | *Listeria monocytogenes* |
| VGA'FG (SEQ ID NO: 130) | NamA lmo2691 (autolysin) | *Listeria monocytogenes* |
| AFA'ED (SEQ ID NO: 131) | *BA_0281 (NLP/P60 Family) | *Bacillus anthracis* |
| VQA'AE (SEQ ID NO: 132) | *atl (autolysin) | *Staphylococcus aureus* |
| Tat pathway | | |
| DKA'LT (SEQ ID NO: 133) | lmo0367 | *Listeria monocytogenes* |
| VGA'FG (SEQ ID NO: 134) | PhoD (alkaline phosphatase) | *Bacillus subtillis* |

*Bacterial autolysins secreted by sec pathway (not determined whether secA1 or secA2).
Secretory sequences are encompassed by the indicated nucleic acids encoded by the *Listeria* EGD genome (GenBank Acc. No. NC_003210) at, e.g., nucleotides 45434-456936 (inlA); nucleotides 457021-457125 (inlB); nucleotides 1860200-1860295 (inlC); nucleotides 286219-287718 (inlE); nucleotides 205819-205893 (hly gene; LLO) (see also GenBank Acc. No. P13128); nucleotides 209470-209556 (ActA) (see also GenBank Acc. No. S20887).
The referenced nucleic acid sequences, and corresponding translated amino acid sequences, and the cited amino acid sequences, and the corresponding nucleic acid sequences associated with or cited in that reference, are incorporated by reference herein in their entirety.

(b). Codon Optimization.

The present invention, in certain embodiments, provides codon optimization of a nucleic acid heterologous to *Listeria*, or of a nucleic acid endogenous to *Listeria*. The optimal codons utilized by *L. monocytogenes* for each amino acid are shown (Table 2). A nucleic acid is codon-optimized if at least one codon in the nucleic acid is replaced with a codon that is more frequently used by *L. monocytogenes* for that amino acid than the codon in the original sequence.

Normally, at least one percent of any non-optimal codons are changed to provide optimal codons, more normally at least five percent are changed, most normally at least ten percent are changed, often at least 20% are changed, more often at least 30% are changed, most often at least 40%, usually at least 50% are changed, more usually at least 60% are changed, most usually at least 70% are changed, optimally at least 80% are changed, more optimally at least 90% are changed, most optimally at least 95% are changed, and conventionally 100% of any non-optimal codons are codon-optimized for *Listeria* expression (Table 2).

TABLE 2

Optimal codons for expression in *Listeria*.

| | Amino Acid | | | | | | | | |
|---|---|---|---|---|---|---|---|---|---|
| | A | R | N | D | C | Q | E | G | H | I |
| Optimal *Listeria* codon | GCA | CGU | AAU | GAU | UGU | CAA | GAA | GGU | CAU | AUU |

| | Amino Acid | | | | | | | | |
|---|---|---|---|---|---|---|---|---|---|
| | L | K | M | F | P | S | T | W | Y | V |
| Optimal *Listeria* codon | UUA | AAA | AUG | UUU | CCA | AGU | ACA | UGG | UAU | GUU |

(c). Virulence Factors and Attenuation.

*L. monocytogenes* expresses various genes and gene products that contribute to invasion, growth, or colonization of the host (Table 3). Some of these are classed as "virulence factors." These virulence factors include ActA, listeriolysin (LLO), protein 60 (p60), internalin A (inlA), intemalin B (inlB), phosphatidylcholine phospholipase C (PC-PLC), phosphatidylinositol-specific phospholipase C (PI-PLC; plcA gene). A number of other internalins have been characterized, e.g., InlC2, InlD, InlE, and InlF (Dramsi, et al. (1997) Infect. Immunity 65:1615-1625). Mpl, a metalloprotease that processes proPL-PLC to active PL-PLC, is also a virulence factor (Chakraborty, et al. (2000) Int. J. Med. Microbiol. 290:167-174; Williams, et al. (2000) J. Bact. 182:837-841). In some embodiments, a virulence gene is a gene that encodes a virulence factor. Without limiting the present invention to the attenuated genes disclosed herein, the present invention supplies a *Listeria* that is altered, mutated, or attenuated in one or more of the sequences of Table 3.

DNA repair genes can also be the target of an attenuating mutation. Mutating or deleting a DNA repair gene can result in an attenuated bacterium (see, e.g., Darwin and Nathan (2005) Infection Immunity 73:4581-4587).

TABLE 3

| Sequences of *L. monocytogenes* nucleic acids and proteins. | | |
|---|---|---|
| Protein/Gene | Nucleotides | GenBank Acc. No. |
| Actin assembly inducing protein precursor (ActA gene) | 209470-211389 (coding sequence) 209456-211389 (gene) | NC_003210 |
| ActA in various *L. monocytogenes* subtypes. | — | AF497169; AF497170; AF497171; AF497172; AF497173; AF497174; AF497175; AF497176; AF497177; AF497178; AF497179; AF497180; AF497181; AF497182; AF497183 (Lasa, et al. (1995) Mol. Microbiol. 18: 425-436). |
| Listeriolysin O precursor (LLO) (hly gene) | 205819-207408 | NC_003210 |
| Internalin A (InlA) | 454534-456936 | NC_003210 |
| Internalin B (inlB) | 457021-458913 | NC_003210 |
| SvpA | — | Bierne, et al. (2004) J. Bacteriol. 186: 1972-1982; Borezee, et al. (2000) Microbiology 147: 2913-2923. |
| p104 (a.k.a. LAP) | | Pandiripally, et al. (1999) J. Med. Microbiol. 48: 117-124; Jaradat, et al. (2003) Med. Microbiol. Immunol. 192: 85-91. |
| Phosphatidylinositol-specific phospholipase C (PI-PLC) (plcA gene) | 204624-205577 | NC_003210 |
| Phosphatidylcholine-specific phospholipase C (PC-PLC) (plcB gene) | 1-3031 | X59723 |
| Zinc metalloprotease precursor (Mpl) | 207739-209271 | NC_003210 |
| p60 (protein 60; invasion associated protein (iap)). | Complement of 618932-620380 | NC_003210 (Lenz, et al. (2003) Proc. Natl. Acad. Sci. USA 100: 12432-12437). |

TABLE 3-continued

Sequences of *L. monocytogenes* nucleic acids and proteins.

| Protein/Gene | Nucleotides | GenBank Acc. No. |
| --- | --- | --- |
| Sortase | 966245-966913 | NC_003210 |
| Listeriolysin positive regulatory protein (PrfA gene) | 203607-203642 | NC_003210 |
| Listeriolysin positive regulatory protein (PrfA gene) | 1-801 | AY318750 |
| PrfB gene | 2586114-2587097 | NC_003210 |
| FbpA gene | 570 amino acids | Dramsi, et al. (2004) Mol. Microbiol. 53: 639-649. |
| Auto gene | — | Cabanes, et al. (2004) Mol. Microbiol. 51: 1601-1614. |
| Ami (amidase that mediates adhesion) | — | Dussurget, et al. (2004) Annu. Rev. Microbiol. 58: 587-610; |
| dlt operon (dltA; dltB; dltC; dltD). | 487-2034 (dltA) | GenBank Acc. No: AJ012255 (Abachin, et al. (2002) Mol. Microbiol. 43: 1-14.) |
| prfA boxes | — | Dussurget, et al. (2002) Mol. Microbiol. 45: 1095-1106. |
| Htp (sugar-P transporter) | 1-1386 | GenBank Acc. No. AJ315765 (see, e.g., Milohanic, et al. (2003) Mol. Microbiol. 47: 1613-1625). |

The referenced nucleic acid sequences, and corresponding translated amino acid sequences, and the cited amino acid sequences, and the corresponding nucleic acid sequences associated with or cited in that reference, are incorporated by reference herein in their entirety.

Listeriolysin (LLO) biology is described (see, e.g., Glomski, et al. (2003) Infect. Immun. 71:6754-6765; Gedde, et al. (2000) Infect. Immun. 68:999-1003; Glomski, et al. (2002) J. Cell Biol. 156:1029-1038; Dubail, et al. (2001) Microbiol. 147:2679-2688; Dramsi and Cosssart (2002) J. Cell Biol. 156:943-946). ActA biochemistry and physiology is disclosed (see, e.g., Machner, et al. (2001) J. Biol. Chem. 276: 40096-40103; Lauer, et al. (2001) Mol. Microbiol. 42:1163-1177; Portnoy, et al. (2002) J. Cell Biol. 158:409-414). Intemalin biochemistry and physiology is available (see, e.g., Bierne and Cossart (2000) J. Cell Sci. 115:3357-3367; Schluter, et al. (1998) Infect. Immun. 66:5930-5938; Dormann, et al. (1997) Infect. Immun. 65:101-109). Sortase proteins are described (see, e.g., Bierne, et al. (2002) Mol. Microbiol. 43:869-881). Two phospholipases, PI-PLC (encoded by plcA gene) and PC-PLC (encoded by plcB gene) are disclosed (see, e.g., Camilli, et al. (1993) Mol. Microbiol. 8:143-157; Schulter, et al. (1998) Infect. Immun. 66:5930-5938). Protein p60 is described (Pilgrim, et al. (2003) Infect. Immun. 71:3473-3484).

The invention also contemplates a *Listeria* attenuated in at least one regulatory factor, e.g., a promoter or a transcription factor. The following concerns promoters. ActA expression is regulated by two different promoters (Lauer, et al. (2002) J. Bacteriol. 184:4177-4186). Together, inlA and inlB are regulated by five promoters (Lingnau, et al. (1995) Infect. Immun. 63:3896-3903). The transcription factor prfA is required for transcription of a number of *L. monocytogenes* genes, e.g., hly, plcA, ActA, mpl, prfA, and iap. PrfA's regulatory properties are mediated by, e.g., the PrfA-dependent promoter (PinlC) and the PrfA-box. The present invention, in certain embodiments, provides a nucleic acid encoding inactivated, mutated, or deleted in at least one of ActA promoter, inlB promoter, PrfA, PinlC, PrfA-box, and the like (see, e.g., Lalic-Mullthaler, et al. (2001) Mol. Microbiol. 42:111-120; Shetron-Rama, et al. (2003) Mol. Microbiol. 48:1537-1551; Luo, et al. (2004) Mol. Microbiol. 52:39-52). PrfA can be made constitutively active by a Gly145Ser mutation, Gly155Ser mutation, or Glu77Lys mutation (see, e.g., Mueller and Freitag (2005) Infect. Immun. 73:1917-1926; Wong and Freitag (2004) J. Bacteriol. 186:6265-6276; Ripio, et al. (1997) J. Bacteriol. 179:1533-1540).

Attenuation can be effected by, e.g., heat-treatment or chemical modification. Attenuation can also be effected by genetic modification of a nucleic acid that modulates, e.g., metabolism, extracellular growth, or intracellular growth, genetic modification of a nucleic acid encoding a virulence factor, such as listerial prfA, ActA, listeriolysin (LLO), an adhesion mediating factor (e.g., an internalin such as inlA or inlB), mpl, phosphatidylcholine phospholipase C (PC-PLC), phosphatidylinositol-specific phospholipase C (PI-PLC; plcA gene), any combination of the above, and the like. Attenuation can be assessed by comparing a biological function of an attenuated *Listeria* with the corresponding biological function shown by an appropriate parent *Listeria*.

The present invention, in other embodiments, provides a *Listeria* that is attenuated by treating with a nucleic acid targeting agent, such as a cross-linking agent, a psoralen, a nitrogen mustard, cis-platin, a bulky adduct, ultraviolet light, gamma irradiation, any combination thereof, and the like. Typically, the lesion produced by one molecule of cross-linking agent involves cross-linking of both strands of the double helix. The *Listeria* of the invention can also be attenuated by mutating at least one nucleic acid repair gene, e.g., uvrA, uvrB, uvrAB, uvrc, uvrD, uvrAB, phrA, and/or a gene mediating recombinational repair, e.g., recA. Moreover, the invention provides a *Listeria* attenuated by both a nucleic acid targeting agent and by mutating a nucleic acid repair gene. Additionally, the invention encompasses treating with a light sensitive nucleic acid targeting agent, such as a psoralen, and/or a light sensitive nucleic acid cross-linking agent, such as psoralen, followed by exposure to ultraviolet light (see, e.g., U.S. Pat. Publ. Nos. U.S.2004/0228877 and U.S.2004/0197343 of Dubensky, et al.).

(d). *Listeria* Strains.

The invention supplies a number of listerial species and strains for making or engineering an attenuated *Listeria* of the present invention (Table 4). The *Listeria* of the present invention is not to be limited by the species and strains disclosed in this table.

TABLE 4

Strains of *Listeria* suitable for use in the present invention, e.g., as a vaccine or as a source of nucleic acids.

| | |
|---|---|
| *L. monocytogenes* 10403S wild type. | Bishop and Hinrichs (1987) J. Immunol. 139: 2005-2009; Lauer, et al. (2002) J. Bact. 184: 4177-4186. |
| *L. monocytogenes* DP-L4056 (phage cured). The prophage-cured 10403S strain is designated DP-L4056. | Lauer, et al. (2002) J. Bact. 184: 4177-4186. |
| *L. monocytogenes* DP-L4027, which is DP-L2161, phage cured, deleted in hly gene. | Lauer, et al. (2002) J. Bact. 184: 4177-4186; Jones and Portnoy (1994) Infect. Immunity 65: 5608-5613. |
| *L. monocytogenes* DP-L4029, which is DP-L3078, phage cured, deleted in ActA. | Lauer, et al. (2002) J. Bact. 184: 4177-4186; Skoble, et al. (2000) J. Cell Biol. 150: 527-538. |
| *L. monocytogenes* DP-L4042 (delta PEST) | Brockstedt, et al. (2004) Proc. Natl. Acad. Sci. USA 101: 13832-13837; supporting information. |
| *L. monocytogenes* DP-L4097 (LLO-S44A). | Brockstedt, et al. (2004) Proc. Natl. Acad. Sci. USA 101: 13832-13837; supporting information. |
| *L. monocytogenes* DP-L4364 (delta lplA; lipoate protein ligase). | Brockstedt, et al. (2004) Proc. Natl. Acad. Sci. USA 101: 13832-13837; supporting information. |
| *L. monocytogenes* DP-L4405 (delta inlA). | Brockstedt, et al. (2004) Proc. Natl. Acad. Sci. USA 101: 13832-13837; supporting information. |
| *L. monocytogenes* DP-L4406 (delta inlB). | Brockstedt, et al. (2004) Proc. Natl. Acad. Sci. USA 101: 13832-13837; supporting information. |
| *L. monocytogenes* CS-L0001 (delta ActA-delta inlB). | Brockstedt, et al. (2004) Proc. Natl. Acad. Sci. USA 101: 13832-13837; supporting information. |
| *L. monocytogenes* CS-L0002 (delta ActA-delta lplA). | Brockstedt, et al. (2004) Proc. Natl. Acad. Sci. USA 101: 13832-13837; supporting information. |
| *L. monocytogenes* CS-L0003 (L461T-delta lplA). | Brockstedt, et al. (2004) Proc. Natl. Acad. Sci. USA 101: 13832-13837; supporting information. |
| *L. monocytogenes* DP-L4038 (delta ActA-LLO L461T). | Brockstedt, et al. (2004) Proc. Natl. Acad. Sci. USA 101: 13832-13837; supporting information. |
| *L. monocytogenes* DP-L4384 (S44A-LLO L461T). | Brockstedt, et al. (2004) Proc. Natl. Acad. Sci. USA 101: 13832-13837; supporting information. |
| *L. monocytogenes*. Mutation in lipoate protein ligase (LplA1). | O'Riordan, et al. (2003) Science 302: 462-464. |
| *L. monocytogenes* DP-L4017 (10403S hly (L461T) point mutation in hemolysin gene. | U.S. Provisional Pat. Appl. Ser. No. 60/490,089 filed Jul. 24, 2003. |
| *L. monocytogenes* EGD. | GenBank Acc. No. AL591824. |
| *L. monocytogenes* EGD-e. | GenBank Acc. No. NC_003210. ATCC Acc. No. BAA-679. |
| *L. monocytogenes* strain EGD, complete genome, segment 3/12 | GenBank Acc. No. AL591975 |
| *L. monocytogenes*. | ATCC Nos. 13932; 15313; 19111-19120; 43248-43251; 51772-51782. |
| *L. monocytogenes* DP-L4029 deleted in uvrAB. | U.S. Provisional Pat. Appl. Ser. No. 60/541,515 filed Feb. 2, 2004; U.S. Provisional Pat. Appl. Ser. No. 60/490,080 filed Jul. 24, 2003. |
| *L. monocytogenes* DP-L4029 deleted in uvrAB treated with a psoralen. | U.S. Provisional Pat. Appl. Ser. No. 60/541,515 filed Feb. 2, 2004. |
| *L. monocytogenes* ActA-/inlB - double mutant. | Deposited with ATCC on Oct. 3, 2003. Acc. No. PTA-5562. |
| *L. monocytogenes* lplA mutant or hly mutant. | U.S. Pat. Applic. No. 20040013690 of Portnoy, et al. |
| *L. monocytogenes* DAL/DAT double mutant. | U.S. Pat. Applic. No. 20050048081 of Frankel and Portnoy. |
| *L. monocytogenes* str. 4b F2365. | GenBank Acc. No. NC_002973. |
| *Listeria ivanovii* | ATCC No. 49954 |
| *Listeria innocua* Clip11262. | GenBank Acc. No. NC_003212; AL592022. |
| *Listeria innocua*, a naturally occurring hemolytic strain containing the PrfA-regulated virulence gene cluster. | Johnson, et al. (2004) Appl. Environ. Microbiol. 70: 4256-4266. |
| *Listeria seeligeri*. | Howard, et al. (1992) Appl. Eviron. Microbiol. 58: 709-712. |
| *Listeria innocua* with *L. monocytogenes* pathogenicity island genes. | Johnson, et al. (2004) Appl. Environ. Microbiol. 70: 4256-4266. |
| *Listeria innocua* with *L. monocytogenes* internalin A gene, e.g., as a plasmid or as a genomic nucleic acid. | See, e.g., Lingnau, et al. (1995) Infection Immunity 63: 3896-3903; Gaillard, et al. (1991) Cell 65: 1127-1141). |

The present invention encompasses reagents and methods that comprise the above listerial strains, as well as these strains that are modified, e.g., by a plasmid and/or by genomic integration, to contain a nucleic acid encoding one of, or any combination of, the following genes: hly (LLO; listeriolysin); iap (p60); inlA; inlB; inlC; dal (alanine racemase); daaA (dat; D-amino acid aminotransferase); plcA; plcB; ActA; or any nucleic acid that mediates growth, spread, breakdown of a single walled vesicle, breakdown of a double walled vesicle, binding to a host cell, uptake by a host cell. The present invention is not to be limited by the particular strains disclosed above.

(e). Antigens.

The present invention, in certain embodiments, provides a nucleic acid encoding at least one antigen, an antigen with one or more conservative changes, one or more epitopes from a specified antigen, or a peptide or polypeptide that is immunologically cross-reactive with an antigen (Table 5). The nucleic acids and antigens of the invention are not to be limited to those disclosed in the table.

TABLE 5

| Antigen | Reference |
|---|---|
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein A (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621). |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. U S A. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; | De Backer, et al. (1999) Cancer Res. 59: 3157-3165; Scarcella, et al. (1999) Clin. Cancer Res. 5: 335-341. |

TABLE 5-continued

Antigens.

| Antigen | Reference |
|---|---|
| GAGE-7; GAGE-8; GAGE-65; GAGE-11; GAGE-13; GAGE-7B. | |
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyltranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985 NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 melanoma cell antigens. | GenBank Acc. No. NM_206956; NM_206955; NM_206954; NM_206953; NM_006115; NM_00536; NM_004988; AY148486; U10340; U10339; M77481. See, e g., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastreenterol. 10: 3394-3398. |
| NA88-A. | Moreau-Aubry, et al. (2000) J. Exp. Med. 191: 1617-1624. |

TABLE 5-continued

Antigens.

| Antigen | Reference |
|---|---|
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. |
| BCL2; BLC6; CD10 protein. | Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |
| Spas-1. | U.S. Published Pat. Appl. No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type | Clements, et al. (2003) Clin. Colorectal Cancer 3: 113-120; Gulmann, et al. |

TABLE 5-continued

Antigens.

| Antigen | Reference |
|---|---|
| forms of adenomatous polyposis coli (APC); beta-catenin; c-met; p53; E-cadherin; cyclooxygenase-2 (COX-2). | (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| *Francisella tularensis* antigens | |
| Francisella tularensis A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27:922-926; Porsch-Ozcurumez, et al. (2004) Clin. Diagnostic. Lab. Immunol. 11:1008-1015). Antigenic components of *F.tularensis* include, e.g., 80 antigens, including 10 kDa and 60 kDa chaperonins (Havlasova, et al. (2002) Proteomics 2:857-86), nucleoside diphosphate kinase, isocitrate dehydrogenase, RNA-binding protein Hfq, the chaperone ClpB (Havlasova, et al. (2005) Proteomics 5:2090-2103). See also, e.g., Oyston al. (2005) Adv. Drug Deliv. Rev. 57:1403-1414; Biagini, et al. (2005) Anal. Bioanal. Chem. 382:1027-1034. |
| Malarial antigens | |
| Circumsporozoite protein (CSP); SSP2; HEP17; Exp-1 orthologs found in P. falciparum; and LSA-1. | See, e.g., Haddad, et al. (2004) Infection Immunity 72:1594-1602; Hoffman, et al. (1997) Vaccine 15:842-845; Oliveira-Ferreira and Daniel-Ribeiro (2001) Mem. Inst. Oswaldo Cruz, Rio de Janeiro 96:221-227. CSP (see, e.g., GenBank Acc. No. AB121024). SSP2 (see, e.g., GenBank Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1 (MSP1); 195A; BVp42. | See, e.g., Stirnadel, et al. (2000) Int. J. Epidemiol. 29:579-586; Krzych, et al. (1995) J. Immunol. 155:4072-4077. See also, Good, et al. (2004) Immunol. Rev. 201:254-267; Good, et al. (2004) Ann. Rev. Immunol. 23:69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, el al. (2005) Protein Expr. Purif. 41:186-198. AMA1 (see, e.g., GenBank Acc. No. A'13; AJ494905; AJ490565). |
| Viruses and viral antigens | |
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. NC_004102; AJ238800; AJ238799; AJ132997; AJ132996; AJ000009; D84263). |
| Human papillomavirus, including all 200+ subtypes (classed in 16 groups), such as the high risk subtypes 16, 18, 30, 31, 33, 45. | See, e.g., Trimble, et al. (2003) Vaccine 21:4036-4042; Kim, et al. (2004) Gene Ther. 11:1011-1018; Simon, et al. (2003) Eur. J. Obstet. Gynecol. Reprod. Biol. 109:219-223; Jung, et al. (2004) J. Microbiol. 42:255-266; Damasus-Awatai and Freeman-Wang (2003) Curr. Opin. Obstet. Gynecol. 15:473-477; Jansen and Shaw (2004) Annu. Rev. Med. 55:319-331; Roden and Wu (2003) Expert Rev. Vaccines 2:495-516; de Villiers, et al. (2004) Virology 324:17-24; Hussain and Paterson (2005) Cancer Immunol. Immunother. 54:577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes IIa, IIb, IIc, and IId. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), and | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |

TABLE 5-continued

Antigens.

| Antigen | Reference |
| --- | --- |
| Toroviruses. | |
| Rubella virus. | GenBank Acc. Nos. NC_001545; AF435866. |
| Mumps virus, including the genotypes A, C, D, G, H, and I. | See, e.g., Orvell, et a l. (2002) J. Gen. Virol. 83: 2489-2496. See, e.g., GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank Acc. Nos. AY421768; AY790926: X67706. |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV | See, e.g., Oberste, et al. (2004) J. Virol. 78: 855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank Acc. No. NC_003899; AY722102); Western equine encephalitis (NC_003908). |
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC_001806 (herpesvirus 1); NC_001798 (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virol. 66: 235-240. |
| HIV-1 including group M (including subtypes A to J)and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank Acc. No. V01555). |
| Reovirus, including serotypes and strains 1, | See, e.g., Barthold, et al. (1993) Lab. Anim. Sci. 43: 425-430; Roner, et al. (1995) Proc. Natl. Acad. Sci. USA 92: 12362-12366; Kedl, et |

TABLE 5-continued

Antigens.

| Antigen | Reference |
|---|---|
| 2, and 3, type 1 Lang, type 2 Jones, and type 3 Dearing. | al. (1995) J. Virol. 69: 552-559. GenBank Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| Rhinovirus, including all serotypes. | Human rhinovirus 2 (GenBank Acc. No. X02316); Human rhinovirus B (GenBank Acc. No. NC_001490); Human rhinovirus 89 (GenBank Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Varicella-zoster virus, including strains and genotypes Oka, Dumas, European, Japanese, and Mosaic. | See, e.g., Loparev, et al. (2004) J. Virol. 78: 8349-8358; Carr, et al. (2004) J. Med. Virol. 73: 131-136; Takayama and Takayama (2004) J. Clin. Virol. 29: 113-119. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. Marburg virus (see, e.g., GenBank Acc. No. NC_001608). Ebola virus (see, e.g., GenBank Acc. Nos. NC_006432; AY769362; NC_002549; AF272001; AF086833). |
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GenBank Acc. Nos. NC_001611; Y16780; X72086; X69198). |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human | Human parainfluenza virus 2 (see, e.g., GenBank Acc. Nos. AB176531; |

TABLE 5-continued

Antigens.

| Antigen | Reference |
|---|---|
| parainfluenzaviruses (HPV), including HPV types 1-56. | NC003443). Human parainfluenza virus 3 (see, e.g., GenBank Acc. No. NC_001796). |
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see, e.g., GenBank Acc. Nos. AY626144(. Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. Nno. AY627895). |
| Influenza A virus subtypes, e.g., swine viruses (SIV): H1N1 influenzaA and swine influenza virus. | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., Wentworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957); human rotavirus A strain major inner capsid protein (see, e.g., GenBank Acc. No. AY601554). |
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank Acc. No. AY134748). |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

The present invention provides, but is not limited by, an attenuated *Listeria* comprising a nucleic acid that encodes at least one of the above-disclosed antigens, or at least one antigen encoded by one of the above-disclosed complete genomes. The present invention encompasses nucleic acids encoding mutants, muteins, splice variants, fragments, truncated variants, soluble variants, extracellular domains, intracellular domains, mature sequences, and the like, of the disclosed antigens. Provided are nucleic acids encoding epitopes, oligo- and polypeptides of these antigens. Also provided are codon optimized embodiments, that is, optimized for expression in *Listeria*. The cited references, GenBank Acc. Nos., and the nucleic acids, peptides, and polypeptides disclosed therein, are all incorporated herein by reference in their entirety.

In some embodiments, the antigen is non-Listerial. In some embodiments, the antigen is from a cancer cell, tumor, or infectious agent. In some embodiments, the antigen is derived from an antigen from a cancer cell, tumor, or infectious agent. In some embodiments, an antigen that is "derived from" another antigen is a fragment or other derivative of the antigen. In some embodiments, the derived antigen comprises a fragment of at least 8 amino acids, at least 12 amino acids, at least 20 amino acids, at least 50 amino acids, at least 75 amino acids, at least 100 amino acids, or at least 200 amino acids. In some embodiments, the derivative of the antigen has at least about 80% identity, at least about 85% identity, at least about 90% identity, at least about 95% identity, or at least about 98% identity to the antigen from which it is derived, or a fragment thereof. In some embodiments, a derived antigen comprises an antigen deleted of its signal sequence and/or membrane anchor. In some embodiments, an antigen derived from another antigen comprises at least one MHC class I epitope and/or at least one MHC class II epitope from the original antigen. In some embodiments, the antigen is a tumor antigen.

In some embodiments, the antigen is mesothelin, or derived from mesothelin. In some embodiments, the mesothelin is human. In some embodiments, the mesothelin is full-length (e.g., full length human mesothelin). In some embodiments, the antigen derived from mesothelin comprises mesothelin (e.g., human mesothelin) deleted in its signal sequence, deleted in its GPI anchor, or deleted in both the signal sequence and the GPI anchor. The polynucleotide encoding the mesothelin may be codon-optimized or non-codon optimized for expression in *Listeria*.

In some embodiments, the antigen (e.g., heterologous antigen) does not comprise an EphA2 antigenic peptide (sometimes referred to as an "EphA2 antigenic polypeptide"), as defined and described in U.S. Patent Publication No. 2005/0281783 A1, which is hereby incorporated by reference herein in its entirety, including all sequences contained therein. In some embodiments, the EphA2 antigenic peptide excluded from use in the methods and compositions described herein can be any EphA2 antigenic peptide that is capable of eliciting an immune response against EphA2-expressing cells involved in a hyperproliferative disorder. Thus, in some embodiments, the excluded EphA2 antigenic peptide can be an EphA2 polypeptide (e.g., the EphA2 polypeptide of SEQ ID NO:2 in U.S. Patent Publication No. 2005/0281783 A1, incorporated by reference herein in its entirety), or a fragment or derivative of an EphA2 polypeptide that (1) displays ability to bind or compete with EphA2 for binding to an anti-EphA2 antibody, (2) displays ability to generate antibody which binds to EphA2, and/or (3) contains one or more T cell epitopes of EphA2. In some embodiments, the EphA2 antigenic peptide is a sequence encoded by one of the following nucleotide sequences, or a fragment or derivative thereof: Genbank Accession No. NM_004431 (Human); Genbank Accession No. NM_010139 (Mouse); or Genbank Accession No. AB038986 (Chicken, partial sequence). In some embodiments, the EphA2 antigenic peptide is full-length human EphA2 (e.g., SEQ ID NO:2 of U.S. Patent Publication No. 2005/0281783 A1, the polypeptide sequence shown in FIGS. 46A-B of the present application). In some embodiments, the EphA2 antigenic peptide comprises the extracellular domain of EphA2 or the intracellular domain of EphA2. In some embodiments, the EphA2 antigenic peptide consists of full-length EphA2 or a fragment thereof with a substitution of valine to methionine at amino acid residue 646 of EphA2. In some embodiments, the EphA2 antigenic peptide sequence consists of an amino acid sequence that exhibits at least about 65% sequence similarity to human EphA2, at least 70% sequence similarity to human EphA2, or at least about 75% sequence similarity to human EphA2. In some embodiments, the EphA2 polypeptide sequence consists of an amino acid sequence that exhibits at least 85% sequence similarity to human EphA2, at least 90% sequence similarity to human EphA2, or at least about 95% sequence similarity to human EphA2. In some embodiments, the excluded EphA2 antigenic peptide consists of at least 10, 20, 30, 40, 50, 75, 100, or 200 amino acids of an EphA2 polypeptide. In some embodiments, the EphA2 antigenic peptide consists of at least 10, 20, 30, 40, 50, 75, 100, or 200 contiguous amino acids of an EphA2 polypeptide.

The invention supplies methods and reagents for stimulating immune response to infections, e.g., infections of the liver. These include infections from hepatotropic viruses and viruses that mediate hepatitis, e.g., hepatitis B virus, hepatitis C virus, and cytomegalovirus. The invention contemplates methods to treat other hepatotropic viruses, such as herpes simplex virus, Epstein-Barr virus, and dengue virus (see, e.g., Ahlenstiel and Rehermann (2005) Hepatology 41:675-677; Chen, et al. (2005) J. Viral Hepat. 12:38-45; Sun and Gao (2004) Gasteroenterol. 127:1525-1539; Li, et al. (2004) J. Leukoc. Biol. 76:1171-1179; Ahmad and Alvarez (2004) J. Leukoc. Biol. 76:743-759; Cook (1997) Eur. J. Gasteroenterol. Hepatol. 9:1239-1247; Williams and Riordan (2000) J. Gasteroenterol. Hepatol. 15 (Suppl.)G17-G25; Varani and Landini (2002) Clin. Lab. 48:39-44; Rubin (1997) Clin. Liver Dis. 1:439-452; Loh, et al. (2005) J. Virol. 79:661-667; Shresta, et al. (2004) Virology 319:262-273; Fjaer, et al. (2005) Pediatr. Transplant 9:68-73; Li, et al. (2004) World J. Gasteroenterol. 10:3409-3413; Collin, et al. (2004) J. Hepatol. 41:174-175; Ohga, et al. (2002) Crit. Rev. Oncol. Hematol. 44:203-215).

In another aspect, the present invention provides methods and reagents for the treatment and/or prevention of parasitic infections, e.g., parasitic infections of the liver. These include, without limitation, liver flukes (e.g., *Clonorchis, Fasciola hepatica, Opisthorchis*), *Leishmania, Ascaris lumbricoides, Schistosoma*, and helminths. Helminths include, e.g., nematodes (roundworms), cestodes (tapeworms), and trematodes (flatworms or flukes) (see, e.g., Tliba, et al. (2002) Vet. Res. 33:327-332; Keiser and Utzinger (2004) Expert Opin. Pharmacother. 5:1711-1726; Kaewkes (2003) ActA Trop. 88:177-186; Srivatanakul, et al. (2004) Asian Pac. J. Cancer Prev. 5:118-125; Stuaffer, et al. (2004) J. Travel Med. 11:157-159; Nylen, et al. (2003) Clin. Exp. Immunol. 131:457-467; Bukte, et al. (2004) Abdom. Imaging 29:82-84; Singh and Sivakumar (2003) 49:55-60; Wyler (1992) Parisitol. Today 8:277-279; Wynn, et al. (2004) Immunol. Rev. 201:156-167; Asseman, et al. (1996) Immunol. Lett. 54:11-20; Becker, et al. (2003) Mol. Biochem. Parasitol. 130:65-74; Pockros and Capozza (2005) Curr. Infect. Dis. Rep. 7:61-70; Hsieh, et al. (2004) J. Immunol. 173:2699-2704; Korten, et al. (2002) J. Immunol. 168:5199-5206; Pockros and Capozza (2004) Curr. Gasteroenterol. Rep. 6:287-296).

Yet another aspect of the present invention provides methods and reagents for the treatment and/or prevention of bacterial infections, e.g., by hepatotropic bacteria. Provided are methods and reagents for treating, e.g., *Mycobacterium tuberculosis, Treponema pallidum*, and *Salmonella* spp (see, e.g., Cook (1997) Eur. J. Gasteroenterol. Hepatol. 9:1239-1247; Vankayalapati, et al. (2004) J. Immunol. 172:130-137; Sellati, et al. (2001) J. Immunol. 166:4131-4140; Jason, et al. (2000) J. Infectious Dis. 182:474-481; Kirby, et al. (2002) J. Immunol. 169:4450-4459; Johansson and Wick (2004) J. Immunol. 172:2496-2503; Hayashi, et al. (2004) Intern. Med. 43:521-523; Akcay, et al. (2004) Int. J. Clin. Pract. 58:625-627; de la Barrera, et al. (2004) Clin. Exp. Immunol. 135:105-113).

In a further embodiment, the heterologous of the present invention is derived from Human Immunodeficiency Virus (HIV), e.g., gp120; gp160; gp41; gag antigens such as p24gag or p55 gag, as well as protein derived from the pol, env, tat, vir, rev, nef, vpr, vpu, and LTR regions of HIV. The heterologous antigens contemplated include those from herpes simplex virus (HSV) types 1 and 2, from cytomegalovirus, from Epstein-Barr virus, or Varicella Zoster Virus. Also encompassed are antigens derived from a hepatitis virus, e.g., hepatitis A, B, C, delta, E, or G. Moreover, the antigens also encompass antigens from Picornaviridae (poliovirus; rhinovirus); Caliciviridae; Togaviridae (rubella; dengue); Flaviviridae; Coronaviridae; Reoviridae; Birnaviridae; Rhabdoviridae; Orthomyxoviridae; Filoviridae; Paramyxoviridae (mumps; measle); Bunyviridae; Arenaviridae; Retroviradae (HTLV-I; HIV-1); Papillovirus, tick-borne encephalitis viruses, and the like.

In yet another aspect, the present invention provides reagents and methods for the prevention and treatment of bacterial and parasitic infections, e.g., *Salmonella, Neisseria, Borrelia, Chlamydia, Bordetella,* plasmodium, *Toxoplasma, Mycobacterium tuberculosis, Bacillus anthracis, Yersinia pestis,* Diphtheria, Pertussis, Tetanus, bacterial or fungal pneumonia, Otitis Media, Gonorrhea, Cholera, Typhoid, Meningitis, Mononucleosis, Plague, Shigellosis, Salmonellosis, Legionaire's Disease, Lyme disease, Leprosy, Malaria, Hookworm, Onchocerciasis, Schistosomiasis, Trypanasomes, Leshmania, Giardia, Amoebiasis, Filariasis, Borelia, and Trichinosis (see, e.g., Despommier, et al. (2000) Parasitic Dieases, 4$^{th}$ ed., Apple Trees Productions, New York, N.Y.; U.S. Government (2002) 21st Century Collection Centers for Disease Control (CDC) Emerging Infectious Diseases (EID)—Comprehensive Collection from 1995 to 2002 with Accurate and Detailed Information on Dozens of Serious Virus and Bacteria Illnesses—Hantavirus, Influenza, AIDS, Malaria, TB, Pox, Bioterrorism, Smallpox, Anthrax, Vaccines, Lyme Disease, Rabies, West Nile Virus, Hemorrhagic Fevers, Ebola, Encephalitis (Core Federal Information Series).

The present invention, at least in some embodiments, provides reagents and methods for treating a disorder or condition, or stimulating an immune response to a disorder or condition, that comprises both a cancer and infection. In some viral infections, for example, an antigen can be both a tumor antigen and a viral antigen (see, e.g., Montesano, et al. (1990) Cell 62:435-445; Ichaso and Dilworth (2001) Oncogene 20:7908-7916; Wilson, et al. (1999) J. Immunol. 162:3933-3941; Daemen, et al. (2004) Antivir. Ther. 9:733-742; Boudewijn, et al. (2004) J. Natl. Cancer Inst. 96:998-1006; Liu, et al. (2004) Proc. Natl. Acad. Sci. USA 101: 14567-14571).

(f). DNA Repair Mutants and Nucleic Acid Targeting Agents.

The present invention, in other embodiments, provides *Listeria* mutants, where the mutant is defective in repair of DNA damage, including, e.g., the repair of UV-light induced DNA damage, radiation induced damage, interstrand cross-links, intrastrand cross-links, covalent adducts, bulky adduct-modified DNA, deamidated bases, depurinated bases, depyrimidinated bases, oxidative damage, psoralen adducts, cisplatin adducts, combinations of the above, and the like (Mu and Sancar (1997) Prog. Nucl. Acid Res. Mol. Biol. 56:63-81; Sancar (1994) Science 266:1954-1956; Lin and Sancar (1992) Mol. Microbiol. 6:2219-2224; Selby and Sancar (1990) 236:203-211; Grossman (1994) Ann. N.Y. Acad. Sci. 726:252-265). Provided is a *Listeria* mutated in, e.g., uvrA, uvrB, uvrAB, uvrc, any combination of the above, and the like.

Moreover, what is provided is a *Listeria* that comprises at least one interstrand cross-link in its genomic DNA, or at least two, at least three, at least four, at least five, at least ten, at least 20, at least 30, at least 40, at least 50, at least 100, or more, cross-links in its genomic DNA.

One embodiment of the present invention comprises *Listeria* uvrAB engineered to express a heterologous antigen, where the engineered bacterium is treated with a nucleic acid cross-linking agent, a psoralen compound, a nitrogen mustard compound, 4'-(4-amino-2-oxa)butyl-4,5',8-trimethylpsoralen, or beta-alanine,N-(acridine-9-yl),2-[bis(2-chloroethyl)amino]ethyl ester (see, e.g., U.S. Publ. Pat. Appl. No. US 2004/0197343 of Dubensky; Brockstedt, et al (2005) Nat. Med. 11:853-860).

(g) Hybridization Under Stringent Conditions.

Hybridization of a plasmid to a variant of that plasmid, bearing at least one mutation, can be accomplished under the following stringent conditions. The plasmid can be between 2-3 kb, 3-4 kb, 4-5 kb, 5-6 kb, 6-7 kb, and so on. The mutation can consist of 1-10 nucleotides (nt), 10-20 nt, 20-30 nt, 30-40 nt, 40-50 nt, 50-60 nt, 60-70 kb, 70-80 kb, 80-90 kb, 90-100 kb, and the like.

Stringent conditions for hybridization in formamide can use the following hybridization solution: 48 ml formamide; 24 ml 20 times SSC; 1.0 ml 2 M Tris Cl, pH 7.6; 1.0 ml 100 times Denhardt's solution; 5.0 ml water; 20 ml 50% dextran sulfate, 1.0 ml 10% sodium dodecylsulfate (total volume 100 ml). Hybridization can be for overnight at 42° C. (see, e.g., (1993) Current Protocols in Molecular Biology, Suppl. 23, pages 6.3.3-6.3.4). More stringent hybridization conditions comprise use of the above buffer but at the temperature of 43°, 44°, 45°, 46°, 47°, 48°, 49°, 50°, 51°, 52°, 53°, 54°, and the like.

Stringent hybridization under aqueous conditions are 1% bovine serum albumin; 1 mM EDTA; 0.5 M NaHPO$_4$, pH 7.2, 7% sodium dodecyl sulfate, with overnight incubation at 65° C. More stringent aqueous hybridization conditions comprise the use of the above buffer, but at a temperature of 66°, 67°, 68°, 69°, 70°, 71°, 72°, 73°, 74°, 75°, and so on (see, e.g., (1993) Current Protocols in Molecular Biology, Suppl. 23, pages 6.3.3-6.3.4).

Increasing formamide concentration increases the stringency of hybridization. Mismatches between probe DNA and target DNA slows down the rate of hybridization by about 2-fold, for every 10% mismatching. Similarly, the melting temperature of mismatched DNA duplex decreases by about one degree centigrade for every 1.7% mismatching (Anderson (1999) Nucleic Acid Hybridization, Springer-Verlag, New York, N.Y., pp. 70-72; Tijssen (1993) Hybridization with Nucleic Acid Probes, Elsevier Publ. Co., Burlington, Mass.; Ross (ed.) (1998) Nucleic Acid Hybridization: Essential Techniques, John Wiley and Sons, Hoboken, N.J.; U.S. Pat. No. 6,551,784 issued to Fodor, et al.).

The invention encompasses a variant first plasmid that hybridizes under stringent conditions to a second plasmid of the present invention, where both plasmids are functionally equivalent, and where hybridization is determinable by hybridizing the first plasmid directly to the second plasmid, or by hybridizing oligonucleotide probes spanning the entire length (individually or as a collection of probes) of the first variant plasmid to the second plasmid, and so on.

The skilled artisan will be able to adjust, or elevate, the hybridization temperature to allow distinction between a probe nucleic acid and a target nucleic acid where the sequences of the probe and target differ by 5-10 nucleotides, 10-15 nucleotides, 15-20 nucleotides, 20-25 nucleotides, 25-30 nucleotides, 30-35 nucleotides, 35-40 nucleotides, 40-45 nucleotides, 45-50 nucleotides, 50-55 nucleotides, 55-60 nucleotides, 60-65 nucleotides, 65-70 nucleotides, 70-80 nucleotides, and the like.

III. Some Detailed Embodiments of the Invention (a). Integration by Site-Specific Recombination and By Homologous Recombination.

In some embodiments, nucleic acids, polynucleotides, bacterial genomes including listerial genomes, and bacteria including *Listeria* and *Bacillus anthracis*, of the present invention are modified by site-specific recombination and/or by homologous recombination. Site specific recombinases are described (see, e.g., Landy (1993) Curr. Op. Biotechnol. 3:699-707; Smith and Thorpe (2002) Mol. Microbiol. 44:299-307; Groth and Calos (2004) J. Mol. Biol. 335:667-678; Nunes-Duby, et al. (1998) Nucleic Acids Res. 26:391-406; Sauer (1993) Methods Enzymol. 225:890-900). Transposition is distinguished from site-specific recombination (see, e.g., Hallett and Sherratt (1997) FEMS Microbiol. Rev. 21:157-178; Grindley (1997) Curr. Biol. 7:R608-R612).

A. Site-Specific Recombination.

The present invention provides systems for mediating site-specific integration into a nucleic acid, vector, or genome. By "system" is meant, a first nucleic acid encoding an integrase, as well as the expressed integrase polypeptide, a second nucleic acid encoding a phage attachment site (attPP'), and a third nucleic acid encoding a corresponding bacterial attachment site (attBB'). Generally, any given attPP' site corresponds to, or is compatible with, a particular attBB' site. The availability of the integration systems of the present invention allow for the integration of one or more nucleic acids into any given polynucleotide or genome.

The integration site of the present invention can be implanted at a pre-determined position in a listerial genome by way of site-specific integration at an existing site (e.g., at the tRNA$^{Arg}$ integration site or the comK integration site). In addition, or in the alternative, the integration system site can be implanted at a pre-determined location by way of homologous integration.

Homologous recombination can result in deletion of material from the integration site, or no deletion of material, depending on the design of the regions of homology (the "homologous arms"). Any deletion that occurs, during homologous recombination corresponds to the region of the target DNA that resides in between regions of the target DNA that can hybridize with the "homologous arms." Homologous recombination can be used to implant an integration site (attBB') within a bacterial genome, for future use in site-specific recombination.

FIG. 1 discloses a strategy for preparing the plasmid, pINT, for use in site-directed integration into a bacterial genome. pINT contains a chloramphenicol resistance gene and an erythromycin resistance gene (see, e.g., Roberts, et al. (1996) Appl. Environ. Microbiol. 62:269-270). When pINT mediates site-specific integration of a nucleic acid into the listerial genome, the antibiotic resistance genes can be subsequently eliminated by transient exposure to Cre recombinase. As shown in FIG. 1, the antibiotic resistance genes reside in between a first loxP site and a second loxP site. Cre recombinase can catalyze removal of material residing in between the two loxP sites. Transient expression of Cre recombinase can be effected by electroporation by a plasmid encoding Cre recombinase, or by any number of other techniques.

The Listeria genome or chromosome of the present invention is modified using the plasmids pPL1, pPL2, and/or pINT1 (Lauer, et al. (2002) J. Bact. 184:4177-4186). The plasmid pPL1 (GenBank Acc. No. AJ417488) comprises a nucleic acid encoding U153 integrase, where this integrase catalyzes integration at the comK-attBB' location of the listerial genome (Lauer, et al. (2002) J. Bact. 184:4177-4186). The structure of comK is available (nucleotides 542-1114 of GenBank Acc. No. AF174588). pPL1 contains a number of restriction sites suitable for inserting a cassette. For example, in some embodiments, a cassette of the present invention encodes at least one heterologous antigen and a loxP-flanked region, where the loxP-flanked region comprises: a first nucleic acid encoding an integrase and a second nucleic acid encoding an antibiotic resistance factor. Some of the restriction sites are disclosed in Table 6. Restriction sites can also be introduced de novo by standard methods.

TABLE 6

Restriction sites in pPL1 and pPL2.

| pPL1 | | pPL2 | |
|---|---|---|---|
| Site | Cut position | Site | Cut position |
| HindII | 56 | HindII | 56 |
| SmaI | 95 | SmaI | 95 |
| BamHI | 99 | BamHI | 99 |
| HindIII | 69 | ClaI | 64 |
| NotI | 118 | NotI | 118 |
| SalI | 54 | SalI | 54 |

TABLE 6-continued

Restriction sites in pPL1 and pPL2.

| pPL1 | | pPL2 | |
|---|---|---|---|
| Site | Cut position | Site | Cut position |
| KpnI | 37 | SpeI | 105 |
| PstI | 91 | KpnI | 37 |
| SacI | 139 | PstI | 91 |
| AatII | 5 and 175 | SacI | 139 |
| BalI | 490 (in chloramphenicol resistance gene) | AatII | 5 and 175 |
| ScaI | 340 (in chloramphenicol resistance gene) | AvaI | 48 and 93 |
| BaeI | 3942 and 3975 (in U153 integrase gene) | BalI | 490 (in chloramphenicol resistance gene) |
| BsePI | 3753 (in U153 integrase gene) | ScaI | 340 (in chloramphenicol resistance gene) |
| MluI | 4074 (in U153 integrase gene) | AflIII | 3259 and 4328 (in PSA integrase gene) |
| — | — | SnaBI | 4077 and 4177 (in PSA integrase gene) |
| — | — | Eam1105I | 3263 (in PSA integrase gene) |
| — | — | BseYI | 4357 (in PSA integrase gene) |
| — | — | SwaI | 3353 (in PSA integrase gene) |
| — | — | BglII | 4150 (in PSA integrase gene) |

The skilled artisan will appreciate that the techniques used for preparing pPL1 and pPL2, and for using pPL1 and pPL2 to mediate site-specific integration, can be applied to the integrases, phage attachment sites (attPP'), and bacterial attachment sites (attBB'), of the present invention.

pPL2 (GenBank Acc. No. AJ417499) comprises a nucleic acid encoding PSA integrase, where this integrase catalyzes integration at the tRNA$^{Arg}$ gene of the L. monocytogenes genome (Lauer, et al. (2002) J. Bact. 184:4177-4186). The 74 nucleotide tRNA$^{Arg}$ gene is found at nucleotide 1,266,675 to 1,266,748 of L. monocytogenes strain EGD genome (see, e.g., GenBank Acc. No. NC_003210), and at nucleotides 1,243,907 to 1,243,980 of L. monocytogenes strain 4bF265 (see, e.g., GenBank Acc. No. NC_002973). pPL2 contains a number of restriction sites suitable for inserting a cassette. The present invention provides a cassette encoding, e.g., a heterologous antigen and loxP-flanked region, where the loxP-flanked region comprises: a first nucleic acid encoding an integrase and a second nucleic acid encoding an antibiotic-resistance factor. Some of the restriction sites are disclosed in Table 6. Standard methods can be used to introduce other restriction sites de novo.

A first embodiment of site-specific recombination involves integrase-catalyzed site-specific integration of a nucleic acid at an integration site located at a specific tRNA$^{Arg}$ region of the Listeria genome.

A second embodiment uses integration of a nucleic acid at the ComK region of the Listeria genome.

Additional embodiments comprise prophage attachment sites where the target is found at, e.g., tRNA-Thr4 of L. monocytogenes F6854 φ F6854.3 (nucleotides 277,661-277710 of L. monocytogenes EGD GenBank Acc. No. AL591983.1), tRNA-Lys4 of L. innocua 11262 φ 11262.1 (nucleotides 115,501-115,548 of GenBank Acc. No. AL596163.1); similar to L. monocytogenes 1262 of L. innocua 11262 phi11262.3; intergenic of L. innocua 11262 φ11262.4 (nucleotides 162,123-162,143 of GenBank Acc. No. AL596169.1); and tRNA-Arg4 of L. innocua 11262 φ 11262.6 (nucleotides 15908-15922 of GenBank Acc. No.

AL596173.1 of *L. innocua* or nucleotides 145,229-145,243 of GenBank Acc. No. AL591983.1 of *L. monocytogenes* EGD) (see, e.g., Nelson, et al. (2004) Nucleic Acids Res. 32:2386-2395)

A further embodiment of site-specific recombination comprises insertion of a loxP sites (or Frt site) by site-specific intregration at the tRNA$^{Arg}$ region or ComK region, where insertion of the loxP sites is followed by Cre recombinase-mediated insertion of a nucleic acid into the *Listeria* genome.

pPL1 integrates at the comK-attBB' chromosomal location (6,101 bp; GenBank Acc. No. AJ417488). This integration is catalyzed by U153 integrase. The *L. monocytogenes* comK gene is disclosed (nucleotides 542-1114 of GenBank Acc. No. AF174588). The pPL1 integration site comprises nucleotides 2694-2696 of the plasmid sequence AJ417488. The following two PCR primers bracket the attachment site comK-attBB' of the *Listeria* genome: Primer PL60 is 5'-TGA AGT AAA CCC GCA CAC GATC-3' (SEQ ID NO:9); Primer PL61 is 5'-TGT AAC ATG GAG GTT CTG GCA ATC-3' (SEQ ID NO:10). The primer pair PL60 and PL61 amplifies comK-attBB' resulting in a 417 bp product in non-lysogenic strains, e.g., DP-L4056.

pPL2 integrates at the tRNA$^{Arg}$-attBB' chromosomal location (6,123 bp; GenBank Acc. No. AJ417449). This integration is catalyzed by PSA integrase. pPL2 is similar to pPL1, except that the PSA phage attachment site and U153 integrase of pPL1 were deleted and replaced with PSA integrase and the PSA phage attachment site. The pPL2 integration site comprises a 17 bp region that resides at nucleotides 2852-2868 of the plasmid pPL2 (AJ417449), with the corresponding bacterial region residing at nucleotides 1,266,733-1,266,749 of *L. monocytogenes* strain EGD genome (GenBank Acc. No. NC_003210).

For listeriophage A118, a phage closely related to U153 listeriophage, the attB position resides at nucleotides 187-189 of the 573 bp comK ORF (Loessner, et al. (2000) Mol. Microbiol. 35:324-340). This 573 bp ORG (nucleotide 542-1114 of GenBank Acc. No. AF174588) and the attB site (nucleotide 701-757 of GenBank Acc. No. AF174588) are both disclosed in GenBank Acc. No. AF174588. The attP site resides in the listeriophage A118 genome at nucleotides 23500-23444 (GenBank Acc. No. AJ242593).

The present invention provides reagents and methods for catalyzing the integration of a nucleic acid, e.g., a plasmid, at an integration site in a *Listeria* genome. The *L. monocytogenes* genome is disclosed (see, e.g., GenBank Acc. No. NC_003210; GenBank Acc. No. NC_003198, He and Luchansky (1997) Appl. Environ. Microbiol. 63:3480-3487, Nelson, et al. (2004) Nucl. Acids Res. 32:2386-2395; Buchrieser, et al. (2003) FEMS Immunol. Med. Microbiol. 35:207-213; Doumith, et al. (2004) Infect. Immun. 72:1072-1083; Glaser, et al. (2001) Science 294:849-852).

Suitable enzymes for catalyzing integration of a nucleic acid into a *Listeria* genome include, e.g., U153 integrase (see, e.g., complement of nucleotides 2741-4099 of GenBank Acc. No. AJ417488; Lauer, et al. (2002) J. Bact. 184:4177-4186)) and PSA integrase (see, e.g., complement of nucleotides 19,413-20,567 of PSA phage genome (37,618 bp genome) (GenBank Acc. No. NC_003291)).

A similar or identical nucleotide sequence for tRNA$^{Arg}$ gene, and for the core integration site that is found within this gene, has been disclosed for a number of strains of *L. monocytogenes*. The *L. monocytogenes* strain EGD complete genome (2,944,528 bp total) (GenBank Acc. No. NC_003210) contains an integration site in the tRNA$^{Arg}$ gene. The 74 nucleotide tRNA$^{Arg}$ gene is found at nucleotide 1,266,675 to 1,266,748 of GenBank Acc. No. NC_003210. Similarly, the tRNA$^{Arg}$ gene occurs in *L. monocytogenes* strain 4bF265 (GenBank Acc. No. NC_002973) at nucleotides 1,243,907 to 1,243,980. The sequence of tRNA$^{Arg}$ gene for *L. monocytogenes* strain WSLC 1042 is disclosed in Lauer, et al. (2002) J. Bact. 184:4177-4186. Lauer, et al., supra, disclose the bacterial core integration site and the corresponding phage core integration site.

Residence in a functional cluster establishes function of nucleic acids residing in that cluster. The function of a bacterial gene, or bacteriophage gene, can be identified according to its grouping in a functional cluster with other genes of known function, its transcriptional direction as relative to other genes of similar function, and occurrence on one operon with other genes of similar function (see, e.g., Bowers, et al. (2004) Genome Biology 5:R35.1-R35.13). For example, the gene encoding phage integrase has been identified in the genomes of a number of phages (or phages integrated into bacterial genomes), where the phage integrase gene resides in a lysogeny control cluster, where this cluster contains a very limited number of genes (three genes to nine genes) (see, e.g., Loessner, et al. (2000) Mol. Microbiol. 35:324-340; Zimmer, et al. (2003) Mol. Microbiol. 50:303-317; Zimmer, et al. (2002) J. Bacteriol. 184:4359-4368).

The phage attachment site (attPP') resides essentially immediately adjacent to the phage integrase gene. According to Zhao and Williams, the integrase gene (int) and attP are typically adjacent, facilitating their co-evolution (Zhao and Williams (2002) J. Bacteriol. 184:859-860). For example, in phiC31 phage, phage integrase is encoded by nucleotide (nt): 38,447 to 40,264, while the attP site resides nearby at nt 38,346 to 38,429. PhiC31 phage integrase does not require cofactors for catalyzing the integration reaction, and can function in foreign cellular environments, such as mammalian cells (see, e.g., Thorpe and Smith (1998) Proc. Natl. Acad. Sci. USA 95:5505-5510; Groth, et al. (2000) Proc. Natl. Acad. Sci. USA 97:5995-6000; GenBank Acc. No. AJ006589). Furthermore, for phage SM1, phage HP1, phage phi3626, for various actinomycete bacteriophages (intM gene), phage lambda, and for phage Aa phi23, the integrase gene and attP site are located immediately next to each other. The integrase gene and attP site can occur together in small group of genes known as a "lysogeny control cluster." Methods for determining the genomic location, approximate size, maximally active size, and/or minimal size of an attPP' site (or attP site) are available (see, e.g., Zimmer, et al. (2002) J. Bacteriol. 184:4359-4368; Siboo, et al. (2003) J. Bacteriol. 185:6968-6975; Mayer, et al. (1999) Infection Immunity 67:1227-1237; Alexander, et al. (2003) Microbiology 149: 2443-2453; Hoess and Landy (1978) Proc. Natl. Acad. Sci. USA 75:5437-5441; Resch (2005) *Sequence and analysis of the DNA genome of the temperate bacteriophage Aaphi23*, Inauguraldissertation, Univ. Basel; Campbell (1994) Ann. Rev. Microbiol. 48:193-222).

The present invention provides a vector for use in modifying a listerial genome, where the vector encodes phiC31 phage integrase, phiC31 attPP' site, and where the listerial genome was modified to include the phiC31 attBB' site. A bacterial genome, e.g., of *Listeria* or *B. anthracis*, can be modified to include an attBB' site by homologous recombination. The phiC31 attBB' site is disclosed by Thorpe and Smith (1998) Proc. Natl. Acad. Sci. USA 95:5505-5510. The amino acid sequence of phiC31 integrase is disclosed below (GenBank Acc. No. AJ414670):

```
                                                     (SEQ ID NO: 11)
MTQGVVTGVDTYAGAYDRQSRERENSSAASPATQRSANEDKAADLQREVE
RDGGRFRFVGHFSEAPGTSAFGTAERPEFERILNECRAGRLNMIIVYDVS
RFSRLKVMDAIPIVSELLALGVTIVSTQEGVFRQGNVMDLIHLIMRLDAS
HKESSLKSAKILDTKNLQRELGGYVGGKAPYGFELVSETKEITRNGRMVN
VVINKLAHSTTPLTGPFEFEPDVIRWWWREIKTHKHLPFKPGSQAAIHPG
SITGLCKRMDADAVPTRGETIGKKTASSAWDPATVMRILRDPRIAGFAAE
VIYKKKPDGTPTTKIEGYRIQRDPITLRPVELDCGPIIEPAEWYELQAWL
DGRGRGKGLSRGQAILSAMDKLYCECGAVMTSKRGEESIKDSYRCRRRKV
VDPSAPGQHEGTCNVSMAALDKFVAERIFNKIRHAEGDEETLALLWEAAR
RFGKLTEAPEKSGERANLVAERADALNALEELYEDRAAGAYDGPVGRKHF
RKQQAALTLRQQGAEERLAELEAAEAPKLPLDQWFPEDADADPTGPKSWW
GRASVDDKRVFVGLFVDKIVVTKSTTGRGQGTPIEKRASITWAKPPTDDD
EDDAQDGTEDVAA (GenBank Acc. No.

AJ414670)
```

The present invention provides the following relevant phiC31 target attBB' sites, and functional variants thereof:

```
                                                     (SEQ ID NO: 12)
TGACGGTCTCGAAGCCGCGGTGCGGGTGCCAGGGCGTGCCCTTGGGCTCC
CCGGGCGCGTACTCCACCTCACCCATCTGGTCCA
(see, e.g., Thorpe and
Smith (1998) Proc. Natl.
Acad. Sci. USA 95:5505-5510).

(SEQ ID NO: 13)
gtcgacgatgtaggtcacggtctcgaagccgcggtgcgggtgccagggcg
tgcccttgggctccccgggcgcgtactccacctcacccatctggtccatc
atgatgaacgggtcgaggtggcggtagt
(GenBank Acc. No. X60952)

tgatcccggcgaacgcgcggcgcaccgggaagccctcgccctcgaaaccg
ctgggcgcggtggtcacggtgagcacgggacgtgcgacggcgtcggcggg
tgcggatacgcggggcagcgtcagcgggttctcgacggtcacggcgggca
tgtcgac
```

Furthermore, the invention provides the following relevant phiC31 attPP' sites, and functional variants thereof:

```
                                                     (SEQ ID NO: 14)
AAGGGGTTGTGACCGGGGTGGACACGTACGCGGGTGCTTACGACCGTCAG
TCGCGC

GAGCGCGAGAATTC
(see, e.g., GenBank Acc.
Nos. X57036 and AJ006589;
Thorpe and Smith (1998)
Proc. Natl. Acad. Sci.
USA 95: 5505-5510).
```

The present invention encompasses a vector that encodes a phage integrase and a functionally active attPP' site, but does not encode the phage integrase and attPP' site of pPL1. Also encompassed is a vector that encodes a phage integrase and a functionally active attPP' site, but does not encode the phage integrase and attPP' site of pPL2. Moreover, the present invention encompasses a vector that encodes a phage integrase and a functionally active attPP' site, but does not encode the phage integrase and attPP' site of pPL1 or of pPL2.

The present invention encompasses a vector useful for integrating a heterologous nucleic acid into a bacterial genome that encodes a phage integrase and a functionally active attPP' site, but does not encode the phage integrase and attPP' site of U153 phage. Also encompassed is a vector, useful for integrating a heterologous nucleic acid into a bacterial genome, that encodes a phage integrase and a functionally active attPP' site, but does not encode the phage integrase and attPP' site of PSA phage. Moreover, the present invention encompasses a vector, useful for integrating a heterologous nucleic acid into a bacterial genome, that encodes a phage integrase and a functionally active attPP' site, but does not encode the phage integrase and attPP' site from any of U153 phage and PSA phage. In another aspect, the present invention encompasses a vector, useful for integrating a heterologous nucleic acid into a bacterial genome, that encodes a phage integrase and a functionally active attPP' site, but does not encode the phage integrase and attPP' site of A118 phage. Further encompassed by the invention is a vector, useful for integrating a heterologous nucleic acid into a bacterial genome, that encodes a phage integrase and a functionally active attPP' site, but does not encode the phage integrase and attPP' site from any of A118 phage, U153 phage, or PSA phage.

B. Homologous Recombination.

The target site for homologous recombination can be an open reading frame, a virulence gene, a gene of unknown function, a pseudogene, a region of DNA shown to have no function, a gene that mediates growth, a gene that mediates spread, a regulatory region, a region of the genome that mediates listerial growth or survival, a gene where disruption leads to attenuation, an intergenic region, and the like.

To give a first example, once a nucleic acid encoding an antigen (operably linked with a promoter) is implanted into a virulence gene, the result is two fold, namely the inactivation of the virulence gene, plus the creation of an expressable antigen.

The invention provides a *Listeria* bacterium comprising an expression cassette, integrated via homologous recombination (or by allelic exchange, and the like), in a listerial virulence gene. Integration can be with or without deletion of a corresponding nucleic acid from the listerial genome.

The expression cassette can be operably linked with one or more promoters of the virulence gene (promoters already present in the parental or wild type *Listeria*). Alternatively, the expression cassette can be operably linked with both: (1) One or more promoters supplied by the expression cassette; and (2) One or more promoters supplied by the parent or wild type *Listeria*.

In some embodiments, the expression cassette can be operably linked with one or more promoters supplied by the expression cassette, and not at all operably linked with any promoter of the *Listeria*.

Without implying any limitation, the virulence factor gene can be one or more of actA, inlB, both actA and inlB, as well as one or more of the genes disclosed in Table 3. In another aspect, homologous recombination can be at the locus of one or more genes that mediate growth, spread, or both growth and spread.

In another aspect, the invention provides a *Listeria* bacterium having a polynucleotide, where the polynucleotide comprises a nucleic acid (encoding a heterologous antigen) integrated at the locus of a virulence factor. In some embodiments, integration is by homologous recombination. In some embodiments, the invention provides integration in a regulatory region of the virulence factor gene, in an open reading frame (ORF) of the virulence factor gene, or in both a regulatory region and the ORF of the virulence factor. Integration can be with deletion or without deletion of all or part of the virulence factor gene.

Expression of the nucleic acid encoding the heterologous antigen can be mediated by the virulence factor's promoter, where this promoter is operably linked and with the nucleic acid. For example, a nucleic acid integrated in the actA gene can be operably linked with the actA promoter. Also, a nucleic acid integrated at the locus of the inlB gene can be operably linked and in frame with the inlB promoter. In addition, or as an alternative, the regulation of expression of the open reading frame can be mediated entirely by a promoter supplied by the nucleic acid.

The expression cassette and the above-identified nucleic acid can provide one or more listerial promoters, one or more bacterial promoters that are non-listerial, an actA promoter, an inlB promoter, and any combination thereof. The promoter mediates expression of the expression cassette. Also, the promoter mediates expression of the above-identified nucleic acid. Moreover, the promoter is operably linked with the ORF.

In some embodiments, integration into the virulence gene, or integration at the locus of the virulence gene, results in deletion of all or part of the virulence gene, and/or disruption of regulation of the virulence gene. In some embodiments, integration results in an attenuation of the virulence gene, or in inactivation of the virulence gene. Moreover, the invention provides a promoter that is prfA-dependent, a promoter that is prfA-independent, a promoter of synthetic origin, a promoter of partially synthetic origin, and so on.

Provided is a method for manufacturing the above-disclosed *Listeria*. Also provided are methods of using the above-disclosed *Listeria* for expressing the expression cassette or for expressing the above-identified nucleic acid. Moreover, in some embodiments, what is provided are methods for stimulating a mammalian immune system, comprising administering the above-disclosed *Listeria* to a mammal.

To give another example, once a bacterial attachment site (attBB') is implanted in a virulence gene, the result is two fold, namely the inactivation of that gene, plus the creation of a tool that enables efficient integration of a nucleic acid at that attBB' site.

In directing homologous integration of the pKSV7 plasmid, or another suitable plasmid, into the listerial genome, the present invention provides a region of homology that is normally at least 0.01 kb, more normally at least 0.02 kb, most normally at least 0.04 kb, often at least 0.08 kb, more often at least 0.1 kb, most often at least 0.2 kb, usually at least 0.4 kb, most usually at least 0.8 kb, generally at least 1.0 kb, more generally at least 1.5 kb, and most generally at least 2.0 kb.

Figure 2:
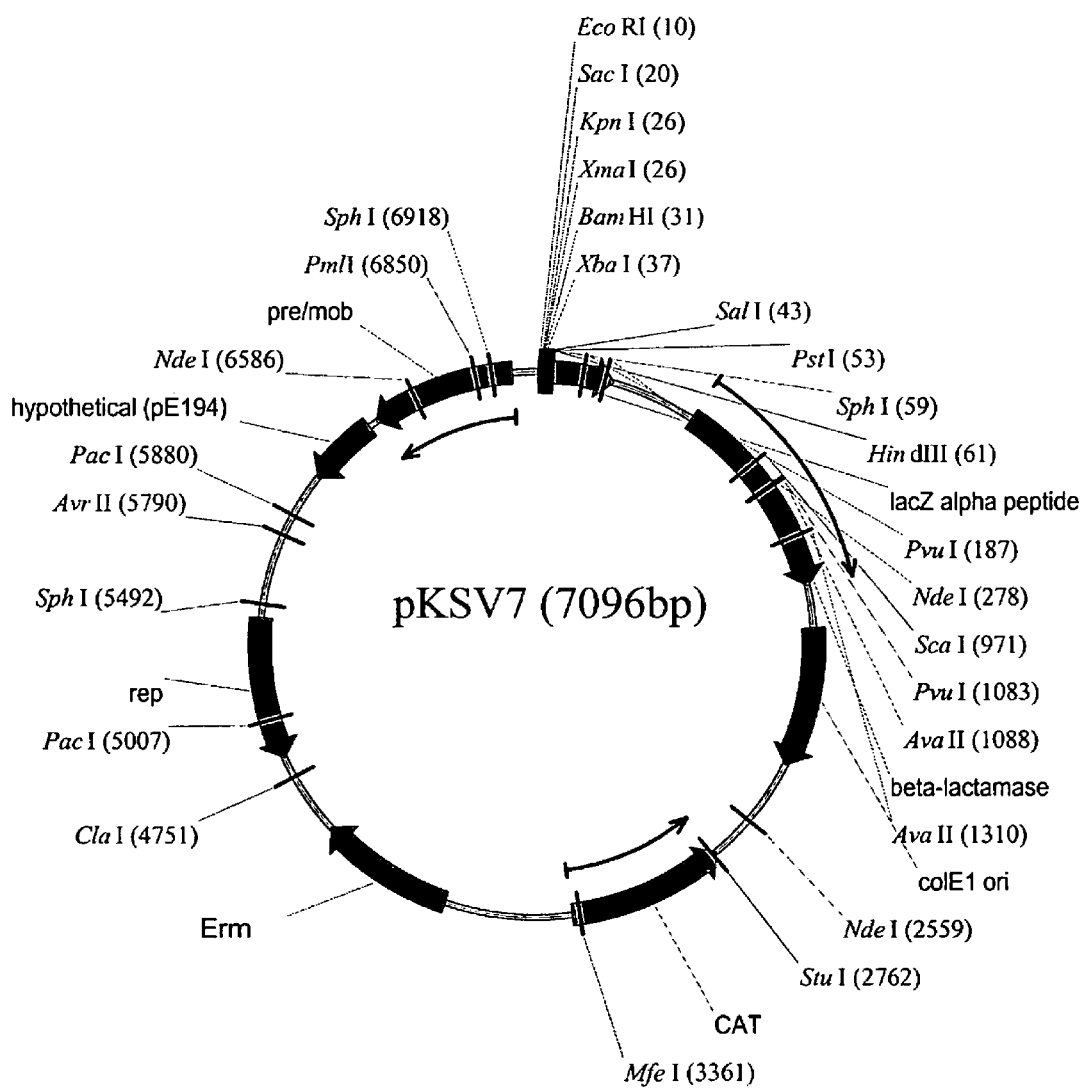
FIG. 2 shows pKSV7, a 7096 plasmid that mediates homologous recombination.

FIG. 2 demonstrates a strategy using pKSV7 in homologous recombination into a bacterial genome. In Step 1, the plasmid crosses over with a region of homology in the genome. In Step 2, the plasmid integrates into the genome, producing a merodiploid intermediate. WXYZ represents any sequence in the pKSV7, such as an antibiotic-resistance encoding gene. Step 3 shows a second crossover, while Step 4 shows elimination of the "body" of the pKSV7 plasmid and elimination of WXYZ. Subsequent treatment with Cre recombinase, e.g., by transient expression of Cre recombination, catalyzes removal of material between the loxP sites.

Figure 3:
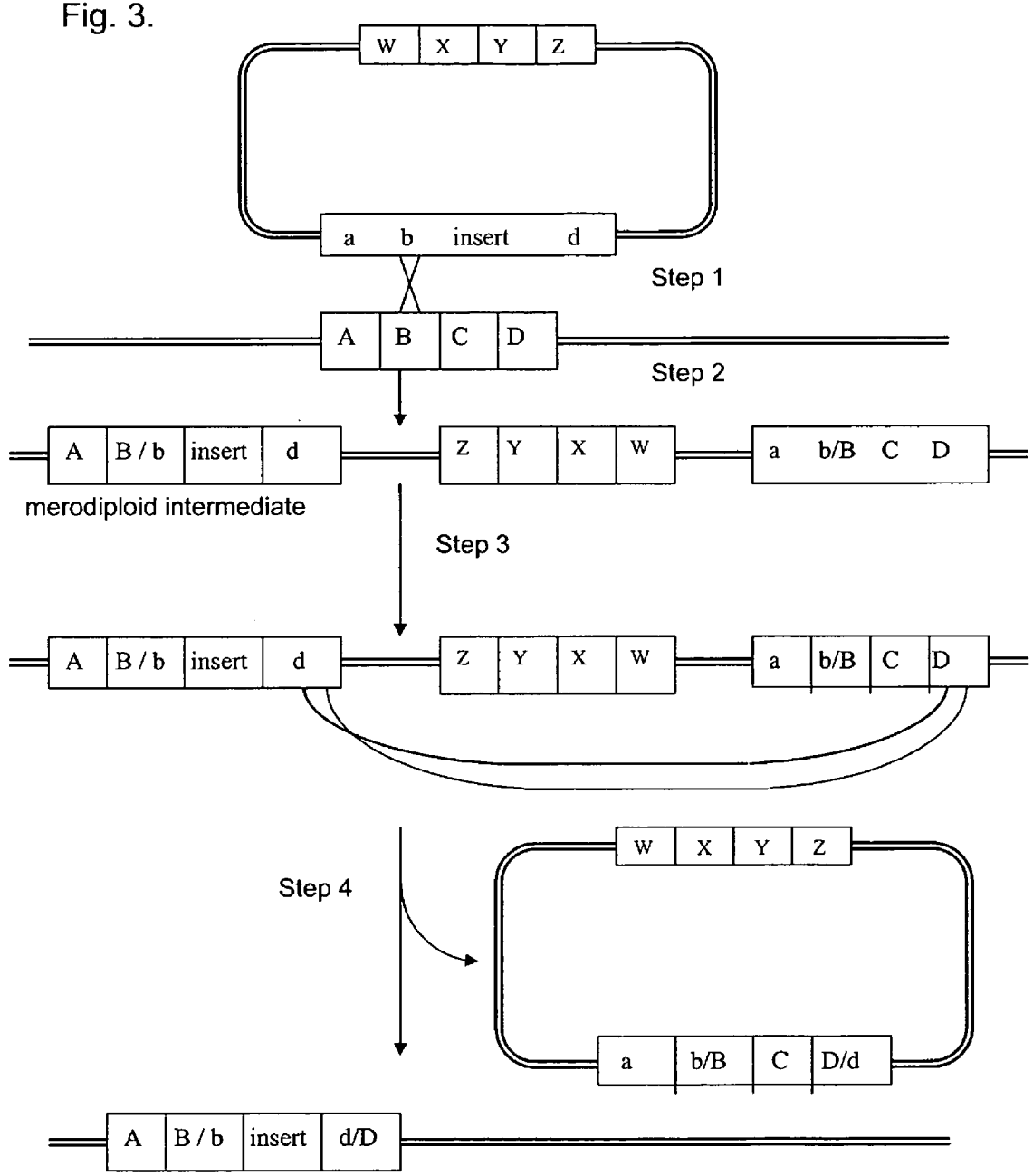
FIG. 3 shows steps, or intermediates, occurring with pKSV7-mediated homologous recombination into a bacterial genome.

FIG. 3 shows a method for preparing an insert, where the insert is placed into pKSV7. The insert mediates homologous recombination into a listerial genome, resulting in integration of various elements into the listerial genome (nucleic acids encoding an antigen, loxP sites, and an antibiotic resistance gene). Subsequent treatment with Cre recombinase catalyzes removal of material between the loxP sites.

Figure 4:
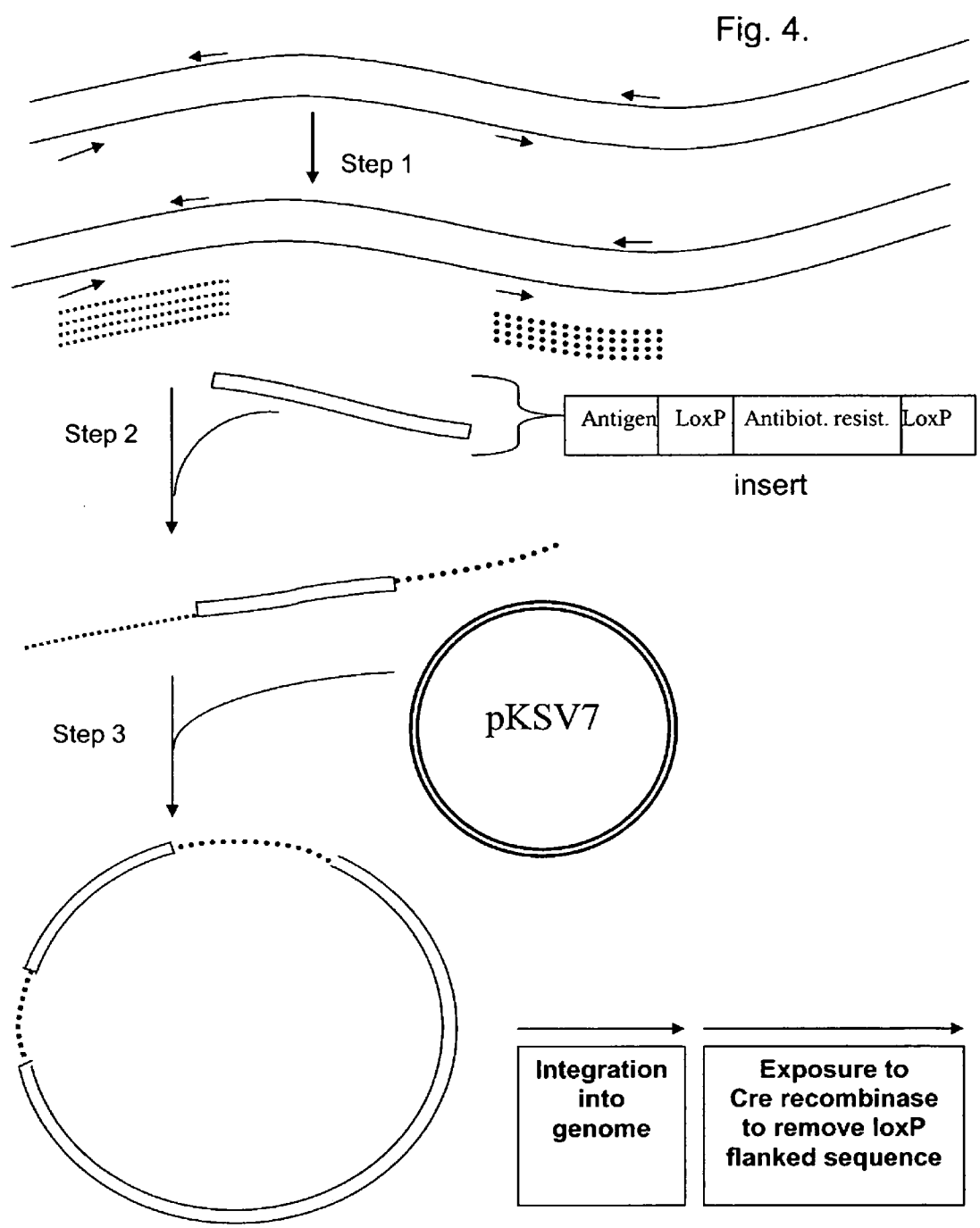
FIG. 4 discloses a method for preparing an insert bearing homologous arms, where the insert bearing the homologous arms is placed into pKSV7. The loxP-flanked region is bracketed by the homologous arms. After integration into a bacterial genome, transient exposure to Cre recombinase catalyzes removal of the antibiotic resistance gene. Integration occurs with deletion of part of the genome, corresponding to the region between areas matching the homologous arms.

FIG. 4 shows a method for preparing an insert, where the insert is placed into pKSV7. The insert mediates homologous recombination into a listerial genome, resulting in integration of various elements into the listerial genome (nucleic acid encoding an antigen). Nucleic acids encoding loxP sites and an antibiotic resistance gene are encoded by a modified pKSV7. Subsequent treatment with Cre recombinase, e.g., by transient expression of Cre recombination, catalyzes removal of material between the loxP sites.

Figure 5:
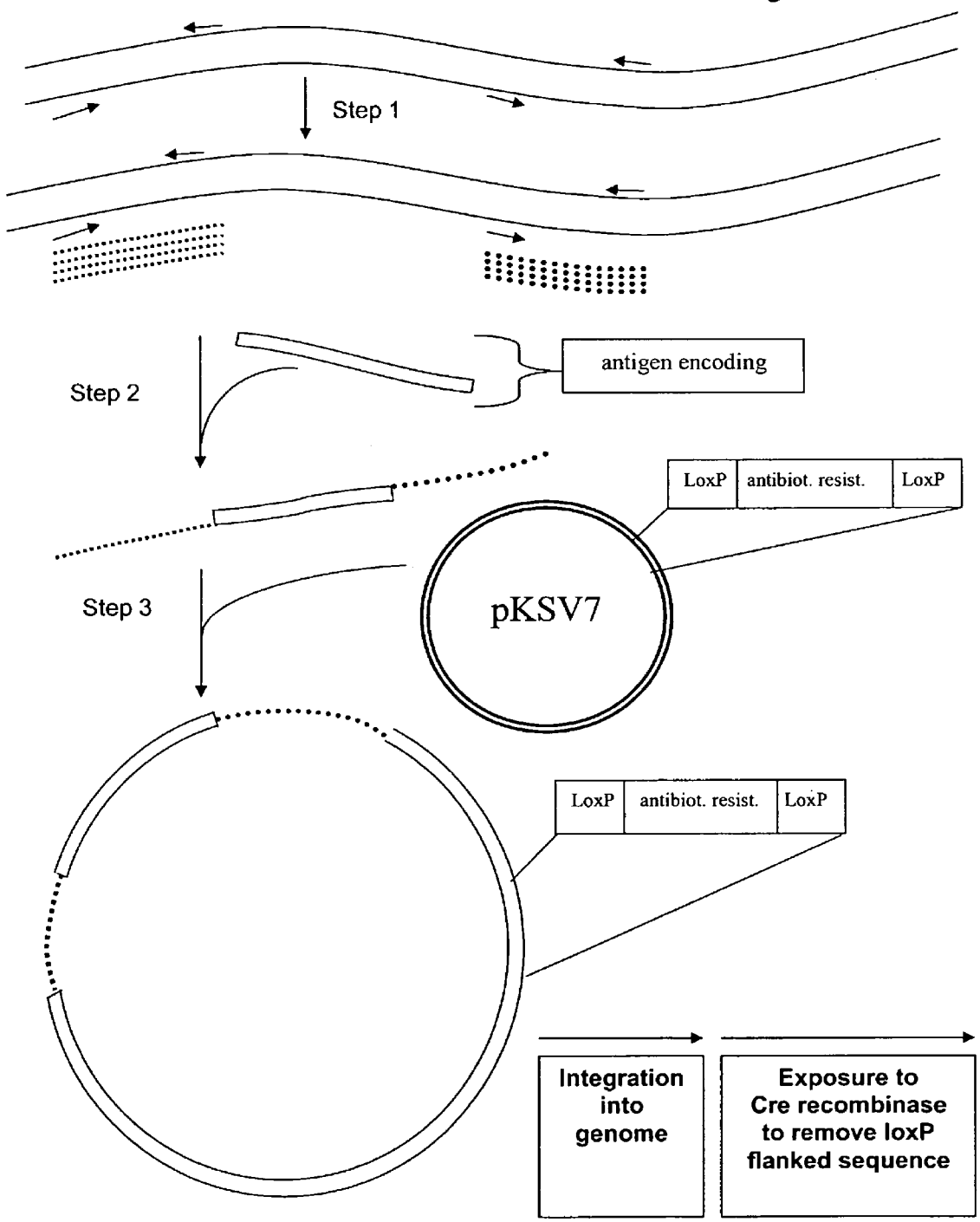
FIG. 5 shows an alternate method for preparing an insert bearing homologous arms, where the insert bearing homologous arms is placed into pKSV7. The loxP-flanked region resides outside the homologous arms. After integration into a bacterial genome, transient exposure to Cre recombinase catalyzes removal of the antibiotic resistance gene (or other selection marker). Integration occurs with deletion of part of the genome, corresponding to the region between areas matching the homologous arms.

FIG. 5 discloses an embodiment that results in only integration with no deletion. Subsequent treatment with Cre recombinase, e.g., by transient expression of Cre recombination, catalyzes removal of material between the loxP sites.

The reagents and methods of the present invention, prepared by homologous recombination, are not limited to use of pKSV7, or to derivatives thereof. Other vectors suitable for homologous recombination are available (see, e.g., Merlin, et al. (2002) J. Bacteriol. 184:4573-4581; Yu, et al. (2000) Proc. Natl. Acad. Sci. USA 97:5978-5983; Smith (1988) Microbiol. Revs. 52:1-28; Biswas, et al. (1993) J. Bact. 175:3628-3635; Yu, et al. (2000) Proc. Natl. Acad. Sci. USA 97:5978-5983; Datsenko and Wannter (2000) Proc. Natl. Acad. Sci. USA 97:6640-6645; Zhang, et al. (1998) Nature Genetics 20:123-128).

For integrating a nucleic acid by way of homologous recombination, bacteria are electroporated with a pKSV7, where the pKSV7 encodes a heterologous protein or where the pKSV7 contains an expression cassette. Bacteria are selected by plating on BHI agar media (or media not based on animal proteins) containing a suitable antibiotic, e.g., chloramphenicol (0.01 mg/ml), and incubated at the permissive temperature of 30° C. Single cross-over integration into the bacterial chromosome is selected by passaging several individual colonies for multiple generations at the non-permissive temperature of 41° C. in medium containing the antibiotic. Finally, plasmid excision and curing (double cross-over) is achieved by passaging several individual colonies for multiple generations at the permissive temperature of 30° C. in BHI media not containing the antibiotic.

Homologous recombination can be used to insert a nucleic acid into a target DNA, with or without deletion of material from the target DNA. A vector that mediates homologous recombination includes a first homologous arm (first nucleic acid), a second homologous arm (second nucleic acid), and a third nucleic acid encoding a heterologous antigen that resides in between the two homologous arms. Regarding the correspondence of the homologous arms and the target genomic DNA, the target regions can abut each other or the target regions can be spaced apart from each other. Where the target regions abut each other, the event of homologous recombination merely results in insertion of the third nucleic acid. But where the target regions are spaced apart from each other, the event of homologous recombination results in insertion of the third nucleic acid and also deletion of the DNA residing in between the two target regions.

Homologous recombination at the inlB gene can be mediated by pKSV7, where the pKSV7 contains the following central structure. The following central structure consists essentially of a first homologous arm (upstream of inlB gene in a *L. monocytogenes* genome), a region containing KpnI and BamHI sites (underlined), and a second homologous arm (downstream of inlB gene in *L. monocytogenes*). The region containing KpnI and BamHI sites is suitable for receiving an insert, where the insert also contains KpnI and BamHI sites at the 5'-prime and 3'-prime end (or 3'-end and 5'-end):

(SEQ ID NO: 15)
```
CCAAATTAGCGATCTTACACCATTGGCTAATTTAACAAGAATCACCCAAC
TAGGGTTGAATGATCAAGCATGGACAAATGCACCAGTAAACTACAAAGCA
AATGTATCCATTCCAAACACGGTGAAAAATGTGACTGGCGCTTTGATTGC
ACCTGCTACTATTAGCGATGGCGGTAGTTACGCAGAACCGGATATAACAT
GGAACTTACCTAGTTATACAAATGAAGTAAGCTATACCTTTAGCCAACCT
GTCACTATTGGAAAAGGAACGACAACATTTAGTGGAACCGTGACGCAGCC
ACTTAAGGCAATTTTTAATGCTAAGTTTCATGTGGACGGCAAAGAAACAA
CCAAAGAAGTGGAAGCTGGGAATTTATTGACTGAACCAGCTAAGCCCGTA
AAAGAAGGTCACACATTTGTTGGTTGGTTTGATGCCCAAACAGGCGGAAC
```

-continued
```
TAAGTGGAATTTCAGTACGGATAAAATGCCGACAAATGACATCAATTTAT
ATGCACAATTTAGTATTAACAGCTACACAGCAACCTTTGAGAATGACGGT
GTAACAACATCTCAAACAGTAGATTATCAAGGCTTGTTACAAGAACCTAC
ACCACCAACAAAAGAAGGTTATACTTTCAAAGGCTGGTATGACGCAAAAA
CTGGTGGTGACAAGTGGGATTTCGCAACTAGCAAAATGCCTGCTAAAAAC
ATCACCTTATATGCCCAATATAGCGCCAATAGCTATACAGCAACGTTTGA
TGTTGATGGAAAATCAACGACTCAAGCAGTAGACTATCAAGGACTTCTAA
AAGAACCAAAGGCACCAACGAAAGCCGGATATACTTTCAAAGGCTGGTAT
GACGAAAAAACAGATGGGAAAAAATGGGATTTTGCGACGGATAAAATGCC
AGCAAATGACATTACGCTGTACGCTCAATTTACGAAAAATCCTGTGGCAC
CACCAACAACTGGAGGGAACACACCGCCTACAACAAATAACGGCGGGAAT
ACTACACCACCTTCCGCAAATATACCTGGAAGCGACACATCTAACACATC
AACTGGGAATTCAGCCAGCACAACAAGTACAATGAACGCTTATGACCCTT
ATAATTCAAAAGAAGCTTCACTCCCTACAACTGGCGATAGCGATAATGCG
CTCTACCTTTTGTTAGGGTTATTAGCAGTAGGAACTGCAATGGCTCTTAC
TAAAAAAGCACGTGCTAGTAAATAGAAGTAGTGTAAAGAGCTAGATGTGG
TTTTCGGACTATATCTAGCTTTTTTATTTTTAATAACTAGAATCAAGGA
GAGGATAGTGGTACCTTGGTGAGCTCCCTACGAAAAGCTACAACTTTAAA
TTCATGAAAAAAGAACTGATTCGCTGAAAACGGATCAGTTCTTTTTTCTT
TAGACTTATTTTTACAAAAACTTTTCGATAATTTCCATATTCTGGGGTCT
GTCTTTGCTTTCAAGTACAGAAATATCACGAACAATGCTATCTAATTTAA
TTTTTTCCATTTCAAATTCTATTTTTTGTTGGAGCAGATCGTATTTACTC
GTAAGAACTTGTTGGATATTGGCTCCGACAACGCAGTCTGGGTTGGTTTT
TGGATCAACGTGAATTAAATTCGTATTGCCTTCTATACTCTTATAAACAT
CAAGCAGTGAAATTTCTTCTGGTGGTCTAGCAAGAATCGGATTTGCTTTG
CCAGTCTGCGTAGTAATTAAATCAGCTTTTTTTAAATTACTCATGATTTT
TCTAATGTTAGCAGGATTTGTTTTTACGCTACCAGCAATAATTTCACTCG
ATAACAAATTCGTATTTTTAAAAATTTCTATATAAGCCAAAATGTGGATA
GCATCGCTAAATTGGATAGAGTATTTCATTTTTTTCAATCCTTTCAAATT
TTCTCCTTGACTTATCTTATCATAATGTTTATTATAAAGGTGTAAATTAT
AAATGTACAGCTTTAGTGTTAAAAAATTTAAAGGAGTGGTTTAAATGACT
TATTTAGTAACTGGTGCAACAGGTGGACTTGGAGGCTACGCATTAAATTA
TTTGAAAGAGCTGGTTCCCATGTCCGATATTTATGCTTTAGTTCGTAGCG
AAGAAAAAGGTACAGACTTGAAAGCAGCAGGATTTAATATCCGTATTGGT
GATTATAGTGATGTAGAATCAATGAAGCAAGCATTCGCAGGCATCGACCG
CGTATTATTTGTTTCAGGAGCACCTGGTAATCGCCAAGTAGAACACGAAA
ATGTGGTAAATGCGGCAAAAGAAGCAGGCGTTTCTTACATCGCTTACACA
AGTTTCGCGGGCGCAGATAAATCCACAAGCGCTTTAGCAGAAGATCATTT
CTTTACCGAAAAAGTAATCGAAAAATCCGGAATCGCGCACACTTTCTTGC
GTAACAACTGGTACTTCGAAAATGAAATGCCGATGATCGGTGGCGCATTG
AGTGCTGGAAATTTGTATACGCTGCTGAAAATGAAAAGTTGGCTGGGC
ATTAAAACGCGAATACGCAGAAGTAGCCGCAAAAGCTGTTGCGGACGCTG
ACTTCCCAGAAATCCTTGAATTATCTGGCCCACTCAATCGTAATC
ATGTCATAGCTGTTTCCTGTGTGAAATTGTTATCCGCTCACAATTCCACA
CAACATACGAGCCGGAAGCATAAAGTGTAAAGCCTGGGGTGCCTAATGAG
TGAGCTAACTCACATTAATTGCGTTGCGCTCACTGCCCGCTTTCCAGTCG
GGAAACCTGTCGTGCCAGCTGGACTAAAAGGCATGCAATTCA
```

The following is the region of the "central region" that contains KpnI and BamHI sites for inserting an expression cassette: GGTACCTTGGTGAGCTC (SEQ ID NO: 121).

The upstream homologous arm is shown below (upstream of inlB gene). The present sequences are from *L. monocytogenes* 10403S. The following provides comparison with another listerial strain, *L. monocytogenes* 4bF2365. In this strain, the inlB gene resides at nt 196,241-198,133 (GenBank AE017323; segment 2 of 10 segments). The upstream homologous arm, disclosed here for *L. monocytogenes* 10403S, has a corresponding sequence in *L. monocytogenes* 4bF2365 at nt 194,932 to 196,240 (GenBank AE017323; segment 2 of 10 segments). The downstream homologous arm, disclosed here for *L. monocytogenes* 10403S, has a corresponding (but not totally identical) sequence in *L. monocytogenes* 4bF2365 at nt 198,134 to 199,629 (GenBank AE017323; segment 2 of 10 segments).

```
                                        (SEQ ID NO: 16)
(upstream homologous arm)
CCAAATTAGCGATCTTACACCATTGGCTAATTTAACAAGAATCACCCAAC
TAGGGTTGAATGATCAAGCATGGACAAATGCACCAGTAAACTACAAAGCA
AATGTATCCATTCCAAACACGGTGAAAAATGTGACTGGCGCTTTGATTGC
ACCTGCTACTATTAGCGATGGCGGTAGTTACGCAGAACCGGATATAACAT
GGAACTTACCTAGTTATACAAATGAAGTAAGCTATACCTTTAGCCAACCT
GTCACTATTGGAAAAGGAACGACAACATTTAGTGGAACCGTGACGCAGCC
ACTTAAGGCAATTTTTAATGCTAAGTTTCATGTGGACGGCAAAGAAACAA
```

-continued

```
CCAAAGAAGTGGAAGCTGGGAATTTATTGACTGAACCAGCTAAGCCCGTA
AAAGAAGGTCACACATTTGTTGGTTGGTTTGATGCCCAAACAGGCGGAAC
TAAGTGGAATTTCAGTACGGATAAAATGCCGACAAATGACATCAATTTAT
ATGCACAATTTAGTATTAACAGCTACACAGCAACCTTTGAGAATGACGGT
GTAACAACATCTCAAACAGTAGATTATCAAGGCTTGTTACAAGAACCTAC
ACCACCAACAAAAGAAGGTTATACTTTCAAAGGCTGGTATGACGCAAAAA
CTGGTGGTGACAAGTGGGATTTCGCAACTAGCAAAATGCCTGCTAAAAAC
ATCACCTTATATGCCCAATATAGCGCCAATAGCTATACAGCAACGTTTGA
TGTTGATGGAAAATCAACGACTCAAGCAGTAGACTATCAAGGACTTCTAA
AAGAACCAAAGGCACCAACGAAAGCCGGATATACTTTCAAAGGCTGGTAT
GACGAAAAAACAGATGGGAAAAAATGGGATTTTGCGACGGATAAAATGCC
AGCAAATGACATTACGCTGTACGCTCAATTTACGAAAAATCCTGTGGCAC
CACCAACAACTGGAGGGAACACACCGCCTACAACAAATAACGGCGGGAAT
ACTACACCACCTTCCGCAAATATACCTGGAAGCGACACATCTAACACATC
AACTGGGAATTCAGCCAGCACAACAAGTACAATGAACGCTTATGACCCTT
ATAATTCAAAAGAAGCTTCACTCCCTACAACTGGCGATAGCGATAATGCG
CTCTACCTTTTGTTAGGGTTATTAGCAGTAGGAACTGCAATGGCTCTTAC
TAAAAAAGCACGTGCTAGTAAATAGAAGTAGTGTAAAGAGCTAGATGTGG
TTTTCGGACTATATCTAGCTTTTTTATTTTTTAATAACTAGAATCAAGGA
GAGGATAGT
```

The downstream homologous arm is shown below (downstream of inlB gene):

```
                                        (SEQ ID NO: 17)
(downstream homologous arm)
CCTACGAAAAGCTACAACTTTAAATTCATGAAAAAAGAACTGATTCGCTG
ACGGATCAGTTCTTTTTTCTTTAGACTTATTTTTACAAAAACTTTTCGAT
AATTTCCATATTCTGGGGTCTGTCTTTGCTTTCAAGTACAGAAATATCAC
GAACAATGCTATCTAATTTAATTTTTTCCATTTCAAATTCTATTTTTTGT
TGGAGCAGATCGTATTTACTCGTAAGAACTTGTTGGATATTGGCTCCGAC
AACGCAGTCTGGGTTGGTTTTTGGATCAACGTGAATTAAATTCGTATTGC
CTTCTATACTCTTATAAACATCAAGCAGTGAAATTTCTTCTGGTGGTCTA
GCAAGAATCGGATTTGCTTTGCCAGTCTGCGTAGTAATTAAATCAGCTTT
TTTTAAATTACTCATGATTTTTCTAATGTTAGCAGGATTTGTTTTTACGC
TACCAGCAATAATTTCACTCGATAACAAATTCGTATTTTTAAAAATTTCT
ATATAAGCCAAAATGTGGATAGCATCGCTAAATTGGATAGAGTATTTCAT
TTTTTTCAATCCTTTCAAATTTTCTCCTTGACTTATCTTATCATAATGTT
TATTATAAAGGTGTAAATTATAAATGTACAGCTTTAGTGTTAAAAAATTT
AAAGGAGTGGTTTAAATGACTTATTTAGTAACTGGTGCAACAGGTGGACT
TGGAGGCTACGCATTAAATTATTTGAAAGAGCTGGTTCCCATGTCCGATA
TTTATGCTTTAGTTCGTAGCGAAGAAAAAGGTACAGACTTGAAAGCAGCA
GGATTTAATATCCGTATTGGTGATTATAGTGATGTAGAATCAATGAAGCA
AGCATTCGCAGGCATCGACCGCGTATTATTTGTTTCAGGAGCACCTGGTA
ATCGCCAAGTAGAACACGAAAATGTGGTAAATGCGGCAAAAGAAGCAGGC
GTTTCTTACATCGCTTACACAAGTTTCGCGGGCGCAGATAAATCCACAAG
CGCTTTAGCAGAAGATCATTTCTTTACCGAAAAAGTAATCGAAAAATCCG
GAATCGCGCACACTTTCTTGCGTAACAACTGGTACTTCGAAAATGAAATG
CCGATGATCGGTGGCGCATTGAGTGCTGGAAAATTTGTATACGCTGCTGA
AAATGGAAAAGTTGGCTGGGCATTAAAACGCGAATACGCAGAAGTAGCCG
CAAAAGCTGTTGCGGACGCTGACTTCCCAGAAATCCTTGAATTATCTGGC
CCACTCATGCAATTCGTAATCATGTCATAGCTGTTTCCTGTGTGAAATTG
TTATCCGCTCACAATTCCACACAACATACGAGCCGGAAGCATAAAGTGTA
AAGCCTGGGGTGCCTAATGAGTGAGCTAACTCACATTAATTGCGTTGCGC
TCACTGCCCGCTTTCCAGTCGGGAAACCTGTCGTGCCAGCTGGACTAAAA
GGCATGCAATTCA
```

Regarding insertion at the ActA gene in a listerial genome, the following discloses a suitable upstream and downstream homologous arms for mediating homologous-recombination integration at the ActA locus of *L. monocytogenes* 10403S:

```
                                        (SEQ ID NO: 18)
(upstream homologous arm)
AGAATTTAGTTCCGCAGTGGATGCTCATTTTTACGCAAGTGAAGTGTACG
AATACTATAAAAATGTCCACCAACTAGAGAGTCTAGATGGTAAAGGTGGA
GAAATTGATTCGTTTGTCCATTATGGCTTGAATTGCAATAATGCCTTTTG
GGATGGCCAAGAAATTCTTTATGGAGATGGGGACAAAAAGAATTTCAAAC
CATTTTCATGCGCCAAAACTATTGTTGGTCATGAACTAACGCATGCAGTT
ATCCAGTATTCGGCGGGATTGGAATACGAAGGGCAATCAGGTGCGCTAAA
CGAGTCGTTCGCCGATGTTTTTGGTTATTTTATTGCGCCAAATCATTGGT
TGATTGGTGAGGATGTCTGTGTGCGTGGGTCGCGAGATGGGCGAATAAGA
AGCATTAAAGATCCTGACAAATATAATCAAGCGGCTCATATGAAGGATTA
CGAATCGCTTCCAATCACAGAGGAAGGCGACTGGGGCGGAGTTCATTATA
ATAGTGGTATCCCGAATAAAGCAGCCTATAATACTATCNCTAAACTTGGA
AAAGAAAAAACAGAACAGCTTTATTTTCGCGCCTTAAAGTACTATTTAAC
GAAAAAATCCCAGTTTACCGATGCGAAAAAAGCGCTTCAACAAGCAGCGA
```

-continued
AAGATTTATATGGTGAAGATGCTTCTAAAAAAGTTGCTGAAGCTTGGGAA
GCAGTTGGGGTTAACTGATTAACAAATGTTAGAGAAAAATTAATTCTCCA
AGTGATATTCTTAAAATAATTCATGAATATTTTTCTTATATTAGCTAAT
TAAGAAGATAATTAACTGCTAATCCAATTTTTAACGGAATAAATTAGTGA
AAATGAAGGCCGAATTTTCCTTGTTCTAAAAAGGTTGTATTAGCGTATCA
CCAGGAGGGAGTATAA
```

The following discloses a suitable downstream homologous arm, for mediating insertion at the listerial ActA gene:

```
                                                    (SEQ ID NO: 19)
(homologous downstream arm)
AAACACAGAACGAAAGAAAAAGTGAGGTGAATGATATGAAATTCAAAAAT
GTGGTTCTAGGTATGTGCTTGACCGCAAGTGTTCTAGTCTTTCCGGTAAC
GATAAAAGCAAATGCCTGTTGTGATGAATACTTACAAACACCCGCAGCTC
CGCATGATATTGACAGCAAATTACCACATAAACTTAGTTGGTCCGCGGAT
AACCCGACAAATACTGACGTAAATACGCACTATTGGCTTTTTAAACAAGC
GGAAAAAATACTAGCTAAAGATGTAAATCATATGCGAGCTAATTTAATGA
ATGAACTTAAAAAATTCGATAAACAAATAGCTCAAGGAATATATGATGCG
GATCATAAAAATCCATATTATGATACTAGTACATTTTTATCTCATTTTTA
TAATCCTGATAGAGATAATACTTATTTGCCGGGTTTTGCTAATGCGAAAA
TAACAGGAGCAAAGTATTTCAATAATCGGTGACTGATTACCGAGAAGGG
AAATTTGACACAGCGTTTTATAAATTAGGCCTAGCAATCCATTATTATAC
GGATATTAGTCAACCTATGCACGCCAATAATTTTACCGCAAATATCACC
CTCCAGGCTACCACTGTGCATATGAAAATTACGTAGATACCATTAAACAC
AATTATCAAGCAACGGAAGACATGGTAGCAAAAAGATTTTGCTCAGATGA
CGTGAAAGACTGGCTCTATGAAAATGCGAAAAGGGCGAAAGCGGACTACC
CGAAAATAGTCAATGCGAAAACTAAAAAATCATATTTAGTAGGAAATTCC
GAATGGAAAAAGGATACAGTGGAACCTACTGGAGCTAGACTAAGAGATTC
ACAGCAAACTTTGGCAGGTTTTTTAGAATTTTGGTCTAAAAAAACAAATG
AATAACAATATTTAGGAATACATTCTTATCCACTCGTTAGCGGGTGGATA
TATTTTATGGGGAGGAAGTAAGCCAAATGTATATAAAAGGGAGGTTAATC
TTTTTCTTTGTAATGTTAGTAATCGCGTTATGTTCCGAAGGGC
```

(b). LoxP-Flanked Antibiotic Resistance Genes.

The present invention, in some embodiments, provides reagents and methods for mediating the rapid or efficient excision of a first nucleic acid from a bacterial genome. The method depends on recombinase-mediated excision, where the recombinase recognizes heterologous recombinase binding sites that flank the first nucleic acid. The heterologous recombinase binding sites can be, for example, a pair of loxP sites or a pair of frt sites. To provide a non-limiting example, the first nucleic acid can encode a selection marker such as an antibiotic resistance gene.

The reagents of this embodiment include plasmids comprising two heterologous recombinase binding sites that flank the first nucleic acid; a bacterial genome comprising two heterologous recombinase bindings sites that flank the first nucleic acid; and a bacterium containing a genome comprising two heterologous recombinase bindings sites that flank the first nucleic acid.

The method of this embodiment is set forth in the following steps:

i. Transfect a bacterium with a plasmid, where the plasmid can mediate integration of a first nucleic acid (flanked by a pair of heterologous recombinase binding sites) into the bacterial genome;

ii. Allow integration of the first nucleic acid (flanked by two heterologous recombinase binding sites) into the bacterial genome. Without implying any limitation as to the mechanism, integration can be by way of site-specific recombination or homologous recombination;

iii. Select for the bacterium containing the integrated first nucleic acid. Where the first nucleic acid encodes an antibiotic resistance gene, selection can involve culturing the bacterium in a medium containing the antibiotic. The selection step can result in a genotypically pure bacterium;

iv. Treat the genotypically pure bacterium with conditions that facilitate recombinase-catalyzed excision of the first nucleic acid from the bacterial genome. Where the pair of heterologous recombinase binding sites are loxP sites, the recombinase can be Cre recombinase. Cre recombinase can be introduced into the bacterium by transfecting with a plasmid encoding this enzyme. In one embodiment, expression of Cre recombinase is transient. Cre recombinase and FLP recombinase use the same enzymatic reaction mechanism, and mediate precise site-specific excision between a pair of their specific target sequences;

v. After allowing for Cre recombinase-catalyzed excision of the first nucleic, the bacterium can be cultured until the plasmid is lost by dilution or nuclease action;

vi. The resulting bacterium can be identified by the presence of the first nucleic acid in the genome. Also, the resulting bacterium can be identified by the loss of one of the two heterologous recombinase binding sites from the genome, that is, only one of the two sites will be left.

The above disclosure is not intended to limit the method to the recited steps, is not intended to limit the method to the disclosed order of steps, and is not intended to mean that all of these steps must occur. The invention is not necessarily limited to two heterologous recombinase binding sites. Polynucleotides containing two loxP sites and two Frt sites can be used, for example, where the two loxP sites flank a first nucleic acid, and the two Frt sites flank a second nucleic acid, and where transient expression of Cre recombinase allows excision of the first nucleic acid, and where transient expression of FLP recombinase (perhaps at a different time) results in excision of the second nucleic acid.

The canonical DNA target site for site-specific recombinases consists of two recombinase binding sites, where the two recombinase binding sites flank a core region (spacer region). The present invention provides two canonical DNA target sites (a pair of canonical DNA target sites), where the sites flank a first nucleic acid. LoxP is one type of canonical DNA target site. LoxP has two 13 bp recombinase binding sites (13 bp inverted repeats) that flank an 8 bp core region or spacer. Thus, each loxP site is a sequence of 34 continuous nucleotides (34 bp).

Cre recombinase and FLP recombinase are members of the integrase family of site-specific recombinases. Cre and FLP recombinase utilize a tyrosine residue to catalyze DNA cleavage. Cre recombinase recognizes lox sites, while FLP recombinase recognizes Frt sites.

Guidance for designing alternate and variant Lox sites and Frt sites is available. Where an alternate spacer region is desired, the skilled artisan will recognize that Cre recombinase-mediated excision is likely to require identical spacer regions in the first lox site and the second lox site (see, e.g., Araki, et al. (2000) Nucleic Acids Res. 30:e103; Nagy (2000) Genetics 26:99-109; Guo, et al. (1997) Nature 389:40-46; Sauer (1993) Methods Enzymol. 225:890-900; Langer, et al. (2002) Nucleic Acids Res. 30:3067-3077; Lath, et al. (2002) Nucleic Acids Res. 30:e115; Baer and Bode (2001) Curr. Opinion Biotechnol. 12:473-480; Nakano, et al. (2001) Microbiol. Immunol. 45:657-665).

The present invention contemplates a polynucleotide comprising a first lox site and a second lox site, where the pair of lox sites flanks a first nucleic acid, and where the first nucleic acid can encode, e.g., a selection marker, antibiotic resistance gene, regulatory region, or antigen. Also contemplated is a polynucleotide comprising a first lox site and a second lox site, where the pair of lox sites flanks a first nucleic acid, and where the first nucleic acid can encode, e.g., a selection marker, antibiotic resistance gene, regulatory region, or antigen.

The skilled artisan will readily appreciate that variant Lox sites where the recombinase binding site is under 13 bp are available, in light of reports that Cre recombinase can function with a recombinase binding site as short as 8-10 bp.

An alternate lox site, loxY is available, to provide a non-limiting example. The present invention contemplates a polynucleotide comprising a first loxY site and a second loxY site, where the pair of loxY sites flanks a first nucleic acid, and where the first nucleic acid can encode, e.g., a selection marker, an antibiotic resistance gene, a regulatory region, or an antigen, and so on. Note also, that the core region of loxP has alternating purine and pyrimidine bases. However, this alternating pattern is necessary for recognition by Cre recombinase, and the present invention encompasses LoxP site variants with mutated core regions (see, e.g., Sauer (1996) Nucleic Acids Res. 24:4608-4613; Hoess, et al. (1986) Nucleic Acids Res. 14:2287-2300).

The Frt site contains three 13 bp symmetry elements and one 8 bp core region (48 bp altogether). FLP recombinase recognizes Frt as a substrate, as well as variant Frt sites, including Frt sites as short as 34 bp, and Frt site with variant core regions (see, e.g., Schweizer (2003) J. Mol. Microbiol. Biotechnol. 5:67-77; Bode, et al. (2000) Biol. Chem. 381: 801-813).

The present invention provides a polynucleotide containing a first loxP site and an operably linked second loxP site, wherein the first and second loxP sites flank a first nucleic acid, to provide a non-limiting example. It will be appreciated that the invention encompasses other heterologous recombinase binding sites, such as variants of loxP, as well as frt sites and fit site variants.

The term "operably linked," as it applies to a first loxP site and a second loxP site, where the two loxP sites flank a first nucleic acid, encompasses the following. Here, "operably linked" means that Cre recombinase is able to recognize the first loxP site and the second loxP site as substrates, and is able to catalyze the excision of the first nucleic acid from the bacterial genome. The term "operably linked" is not to be limited to loxP sites, as it encompasses any "heterologous recombinase binding sites" such as other lox sites, or frt sites. Also, the term "operably linked" is not to be limited to recombinase-catalyzed excision, the term also embraces recombinase-catalyzed integration. Moreover, the term "operably linked" is not to be limited to nucleic acids residing in a genome—also encompassed are nucleic acids residing in plasmids, intermediates used in genetic engineering, and the like.

Nucleic acids encoding recombinases are disclosed in Table 7A, and nucleic acid target sites recognized by these recombinases appear in Table 7B.

TABLE 7A

Recombinases.

| Recombinase | Location and GenBank Accession No. |
|---|---|
| Cre recombinase | Nucleotides 5347–6195 (exon 1) and 6262–6465 (exon 1) of GenBank Acc. No. AJ627603. |
| FLP recombinase | Complement of nucleotides 4426–5697 of GenBank Acc. No. AF048702. |
| FLP recombinase | Complement of nucleotides 6054–7325 of GenBank Acc. No. AY597273. |

TABLE 7A-continued

Recombinases.

| Recombinase | Location and GenBank Accession No. |
|---|---|
| FLP recombinase | Nucleotides 5570–6318, 1–523 of GenBank Acc. No. J01347. The upstream region of the coding sequence begins at nucleotide 5570, while the downstream region of the coding sequence ends at nucleotide 523. |

TABLE 7B

Binding sites for recombinases.

| Target site | Location and GenBank Accession No. |
|---|---|
| | Target sites of FLP recombinase |
| Frt | Nucleotides 260–307 of GenBank Acc. No. AY562545. |
| Frt | Nucleotides 464–511 of GenBank Acc. No. AY597272. |
| Frt | Nucleotides 3599–3646 of GenBank Acc. No. AY423864. |
| | Target sites of Cre recombinase |
| LoxP | Nucleotides 415–448 of GenBank Acc. No. AF143506. |
| LoxP | Nucleotides 118–151 of GenBank Acc. No. U51223. |
| LoxP | Nucleotides 1050–1083 of GenBank Acc. No. AY093430. |
| LoxP | Nucleotides 759–792 of GenBank Acc. No. AJ401047. |

The referenced nucleic acid sequences, and corresponding translated amino acid sequences, and the cited amino acid sequences, and the corresponding nucleic acid sequences associated with or cited in that reference, are incorporated by reference herein in their entirety.

Nucleic acid sequences encoding various antibiotic resistance factors are disclosed (Table 8). Typical sequences are those encoding resistance to an antibiotic that is toxic to *Listeria* e.g., chloramphenicol acetyltransferase (CAT) (Table 8).

A first nucleic acid encoding the antibiotic resistance factor is operably linked to a ribosome binding site, a promoter, and contains a translation start site, and/or a translation stop site, and is flanked by two heterologous recombinase binding sites.

The invention provides a polynucleotide containing a pair of operably linked loxP sites flanking a first nucleic acid, and a second nucleic acid (not flanked by the loxP sites), where the polynucleotide consists of a first strand and a second strand, and where the first nucleic acid has a first open reading frame (ORF) and the second nucleic acid has a second open reading frame (ORF). In one aspect, the first ORF is on the first strand, and the second ORF is also on the first strand. In another aspect, the first ORF is on the first strand and the second ORF is on the second strand. Yet another aspect provides a first ORF on the second strand and the second ORF on the first strand. Moreover, both ORFs can reside on the second strand. The present invention, in one aspect, provides a plasmid comprising the above-disclosed polynucleotide. Also provided is a *Listeria* containing the above-disclosed polynucleotide, where the polynucleotide can be on a plasmid and/or integrated in the genome. Each of the above-disclosed embodiments can comprise heterologous recombinase binding sites other than loxP. For example, lox variants, Frt sites, Frt variants, and recombinase binding sites unrelated to lox or Frt are available.

TABLE 8

Antibiotic resistance genes.

| Antibiotic resistance gene. | GenBank Accession No. |
|---|---|
| Chloramphenicol (chloramphenicol acetyltransferase; CAT). | Complement of nucleotides 312-971 of GenBank Acc. No. AJ417488 (pPL1 of Lauer, et al.). |
| Chloramphenicol | Complement of nucleotides 4898-5548 of GenBank |

TABLE 8-continued

Antibiotic resistance genes.

| Antibiotic resistance gene. | GenBank Accession No. |
|---|---|
| (CAT). Chloramphenicol | Acc. No. AJ417488 (pPL1 of Lauer, et al.). |
| (CAT). Chloramphenicol | Complement of nucleotides 312-971 of GenBank Acc. No. AJ417449 (pPL2 of Lauer, et al.). |
| (CAT). Chloramphenicol | Complement of nucleotides 4920-5570 of GenBank Acc. No. AJ417449 (pPL2 of Lauer, et al.). |
| (CAT). Chloramphenicol | Nucleotides 3021-3680 of GenBank Acc. No. AJ007660. |
| Penicillin (penicillin-binding protein 2). | Nucleotides 25-1770 of GenBank Acc. No. X59629. |
| Erythromycin (erythromycin resistance determinant). | Nucleotides 864-1601 of GenBank Acc. No. AY680862. |
| Ampicillin (penicillin beta-1ActAmase). | Complement of nucleotides 3381-4311 of GenBank Acc. No. AJ401049. |
| Tetracycline (tetracycline resistance protein). | Complement of nucleotides of 4180-5454 of GenBank Acc. No. AY608912. |
| Gentamycin (aminoglycoside acetyltransferase). | Complement of nucleotides 1326-1859 of GenBank Acc. No. EVE414668. |

(c). ActA Fusion Protein Partners, and Derivatives Thereof.
  i. General.

The present invention, in certain aspects, provides a polynucleotide comprising a first nucleic acid encoding a modified ActA, operably linked and in frame with a second nucleic acid encoding a heterologous antigen. The invention also provides a *Listeria* containing the polynucleotide, where expression of the polynucleotide generates a fusion protein comprising the modified ActA and the heterologous antigen. The modified ActA can include the natural secretory sequence of ActA, a secretory sequence derived from another listerial protein, a secretory sequence derived from a non-listerial bacterial protein, or the modified ActA can be devoid of any secretory sequence.

The ActA-derived fusion protein partner finds use in increasing expression, increasing stability, increasing secretion, enhancing immune presentation, stimulating immune response, improving survival to a tumor, improving survival to a cancer, increasing survival to an infectious agent, and the like.

In one aspect, the invention provides a polynucleotide comprising a promoter operably linked to a nucleic acid sequence encoding a fusion protein, wherein the fusion protein comprises (a) modified ActA and (b) a heterologous antigen. In some embodiments, the promoter is ActA promoter. In some embodiments, the modified ActA comprises at least the first 59 amino acids of ActA. In some embodiments, the modified ActA comprises more than the first 59 amino acids of ActA. In some embodiments, the modified ActA is a fragment of ActA comprising the signal sequence of ActA (or is derived from a fragment of ActA comprising the signal sequence of ActA). In some embodiments, the modified ActA comprises at least the first 59 amino acids of ActA, but less than about the first 265 amino acids of ActA. In some embodiments, the modified ActA comprises more than the first 59 amino acids of ActA, but less than about the first 265 amino acids of ActA. In other words, in some embodiments, the modified ActA sequence corresponds to an N-terminal fragment of ActA (including the ActA signal sequence) that is truncated somewhere between amino acid 59 and about amino acid 265 of the ActA sequence. In some embodiments, the modified ActA comprises the first 59 to 200 amino acids of ActA, the first 59 to 150 amino acids of ActA, the first 59 to 125 amino acids of ActA, or the first 59 to 110 amino acids of ActA. In some embodiments, the modified ActA consists of the first 59 to 200 amino acids of ActA, the first 59 to 150 amino acids of ActA, the first 59 to 125 amino acids of ActA, or the first 59 to 110 amino acids of ActA. In some embodiments, the modified ActA comprises about the first 65 to 200 amino acids of ActA, about the first 65 to 150 amino acids of ActA, about the first 65 to 125 amino acids of ActA, or about the first 65 to 110 amino acids of ActA. In some embodiments, the modified ActA consists of about the first 65 to 200 amino acids of ActA, about the first 65 to 150 amino acids of ActA, about the first 65 to 125 amino acids of ActA, or about the first 65 to 110 amino acids of ActA. In some embodiments, the modified ActA comprises the first 70 to 200 amino acids of ActA, the first 80 to 150 amino acids of ActA, the first 85 to 125 amino acids of ActA, the first 90 to 110 amino acids of ActA, the first 95 to 105 amino acids of ActA, or about the first 100 amino acids of ActA. In some embodiments, the modified ActA consists of the first 70 to 200 amino acids of ActA, the first 80 to 150 amino acids of ActA, the first 85 to 125 amino acids of ActA, the first 90 to 110 amino acids of ActA, the first 95 to 105 amino acids of ActA, or about the first 100 amino acids of ActA. In some embodiments, the modified ActA comprises amino acids 1-100 of ActA. In some embodiments, the modified ActA consists of amino acids 1-100 of ActA. In some embodiments, the heterologous antigen is, or is derived from, a cancer cell, tumor, or infectious agent. In some embodiments, the heterologous antigen is immunologically cross-reactive with, or shares at least one epitope with, the cancer, tumor, or infectious agent. In some embodiments, the heterologous antigen is a tumor antigen or is derived from a tumor antigen. In some embodiments, the heterologous antigen is, or is derived from, human mesothelin. In some embodiments, the nucleic acid sequence encoding the fusion protein is codon-optimized for expression in *Listeria*. The invention provides plasmids and cells comprising the polynucleotide. The invention further provides a *Listeria* bacterium e.g., *Listeria monocytogenes*) comprising the polynucleotide, as well as vaccines comprising the *Listeria*. In some embodiments, the genomic DNA of the *Listeria* comprises the polynucleotide. In some embodiments, the polynucleotide is positioned in the genomic DNA at the site of the actA gene or the site of the inlB gene. In some embodiments, the *Listeria* comprises a plasmid comprising the polynucleotide. The invention further provides immunogenic and pharmaceutical compositions comprising the *Listeria*. The invention also provides methods for stimulating immune responses to the heterologous antigen in a mammal (e.g., a human), comprising administering an effective amount of the *Listeria*

(or an effective amount of a composition comprising the *Listeria*) to the mammal. For instance, the invention also provides methods for stimulating immune responses to an antigen from, or derived from, a cancer or infectious agent, comprising administering an effective amount of the *Listeria* (or a composition comprising the *Listeria*) to a mammal having the cancer or infectious agent, wherein the heterologous antigen shares at least one epitope with or is immunologically cross-reactive with the antigen from, or derived from, the cancer or infectious agent.

In another aspect, the invention provides a polynucleotide comprising a first nucleic acid encoding a modified ActA, operably linked and in frame with, a second nucleic acid encoding a heterologous antigen. In some embodiments, the modified ActA comprises at least the first 59 amino acids of ActA, but less than about the first 265 amino acids of ActA. In some embodiments, the modified ActA comprises the first 59 to 200 amino acids of ActA, the first 59 to 150 amino acids of ActA, the first 59 to 125 amino acids of ActA, or the first 59 to 110 amino acids of ActA. In some embodiments, the modified ActA comprises the first 70 to 200 amino acids of ActA, the first 80 to 150 amino acids of ActA, the first 85 to 125 amino acids of ActA, the first 90 to 110 amino acids of ActA, the first 95 to 105 amino acids of ActA, or about the first 100 amino acids of ActA. In some embodiments, the first nucleic acid encodes amino acids 1-100 of ActA. In some embodiments, the polynucleotide is genomic. In some alternative embodiments, the polynucleotide is plasmid-based. In some embodiments, the polynucleotide is operably linked with a promoter. For instance, the polynucleotide may be operably linked with one or more of the following: (a) actA promoter; or (b) a bacterial promoter that is not actA promoter. In some embodiments, the heterologous antigen is, or is derived from, a cancer cell, tumor, or infectious agent. In some embodiments, the heterologous antigen is immunologically cross-reactive with, or shares at least one epitope with, the cancer, tumor, or infectious agent. In some embodiments, the heterologous antigen is, or is derived from human mesothelin. The invention further provides a *Listeria* bacterium e.g., *Listeria monocytogenes*) comprising the polynucleotide, as well as vaccines comprising the *Listeria*. In some embodiments, the *Listeria* is hMeso26 or hMeso38 (see Table 11 of Example VII, below). The invention also provides methods for stimulating immune responses to an antigen from, or derived from, a cancer or infectious agent, comprising administering the *Listeria* to a mammal having the cancer or infectious agent, wherein the heterologous antigen shares at least one epitope with or is immunologically cross-reactive with the antigen from, or derived from, the cancer or infectious agent.

In another aspect, the invention provides a polynucleotide comprising a first nucleic acid encoding a modified actA, where the modified actA comprises (a) amino acids 1-59 of actA, (b) an inactivating mutation in, deletion of, or truncation prior to, at least one domain for actA-mediated regulation of the host cell cytoskeleton, wherein the first nucleic acid is operably linked and in frame with a second nucleic acid encoding a heterologous antigen. In some embodiments, the domain is the cofilin homology region (KKRR (SEQ ID NO:23)). In some embodiments, the domain is the phospholipid core binding domain (KVFKKIKDAGKWVRDKI (SEQ ID NO:20)). In some embodiments, at least one domain comprises all four proline-rich domains (FPPPP (SEQ ID NO:21), FPPPP (SEQ ID NO:21), FPPPP (SEQ ID NO:21), FPPIP (SEQ ID NO:22)) of ActA. In some embodiments, the modified actA is actA-N100. In some embodiments, the polynucleotide is genomic. In some embodiments, the polynucleotide is not genomic. In some embodiments, the polynucleotide is operably linked with one or more of the following: (a) actA promoter; or (b) a bacterial (e.g., listerial) promoter that is not actA promoter. The invention further provides a *Listeria* bacterium (e.g., *Listeria monocytogenes*) comprising the polynucleotide, as well as vaccines comprising the *Listeria*. In some embodiments, the *Listeria* is hMeso26 or hMeso38 (see Table 11 of Example VII, below). The invention also provides methods for stimulating immune responses to an antigen from, or derived from, a cancer or infectious agent, comprising administering the *Listeria* to a mammal having the cancer or infectious agent, wherein the heterologous antigen shares at least one epitope with or is immunologically cross-reactive with the antigen from, or derived from, the cancer or infectious agent. In some embodiments, the stimulating is relative to immune response without administering the *Listeria*. In some embodiments, the cancer comprises a tumor or pre-cancerous cell. In some embodiments, the infectious agent comprises a virus, pathogenic bacterium, or parasitic organism. In some embodiments, the heterologous antigen is, or is derived from, a cancer cell, tumor, or infectious agent. In some embodiments, the heterologous antigen is immunologically cross-reactive with, or shares at least one epitope with, the cancer, tumor, or infectious agent. In some embodiments, the heterologous antigen is, or is derived from, human mesothelin.

In some embodiments, what is provided is a polynucleotide comprising a first nucleic acid encoding a modified ActA comprising at least amino acids 1-59 of ActA, further comprising at least one modification in a wild type ActA sequence, wherein the at least one modification is an inactivating mutation in, deletion of, or truncation at or prior to, a domain specifically used for ActA-mediated regulation of the host cell cytoskeleton, wherein the first nucleic acid is operably linked and in frame with a second nucleic acid encoding a heterologous antigen.

Also encompassed is the above polynucleotide, where the at least one modification is an inactivating mutation in, deletion of, or termination at, comprising the cofilin homology region KKRR (SEQ ID NO:23). Moreover, what is encompassed is the above polynucleotide where the at least one modification is an inactivating mutation in, deletion of, or termination at, comprising the phospholipid core binding domain (KVFKKIKDAGKWVRDKI (SEQ ID NO:20)).

In yet another aspect, what is contemplated is the above polynucleotide, wherein the at least one modification comprises an inactivating mutation in, or deletion of, in each of the first proline-rich domain (FPPPP (SEQ ID NO:21)), the second proline-rich domain (FPPPP (SEQ ID NO:21)), the third proline-rich domain (FPPPP (SEQ ID NO:21)), and the fourth proline-rich domain (FPPIP (SEQ ID NO:22)), or a termination at the first proline-rich domain. In another aspect, what is provided is the above polynucleotide where the modified ActA is ActA-N100.

Yet another embodiment provides a *Listeria* bacterium comprising one or more of the above polynucleotide. The polynucleotide can be genomic, it can be plasmid-based, or it can reside on both a plasmid and the listerial genome. Also provided is the above *Listeria* where the polynucleotide is not genomic, as well as the above *Listeria* where the polynucleotide is not plasmidic. The *Listeria* can be *Listeria monocytogenes, L. innocua*, or some other listerial species.

Moreover, what is supplied by yet another embodiment, is a method of stimulating immune response to an antigen from, or derived from, a tumor, cancer cell, or infectious agent, comprising administering to a mammal the above-disclosed *Listeria* and where the heterologous antigen is shares at least one epitope with the antigen derived from the tumor, cancer cell, or infectious agent. What is also supplied is the above method, where the stimulating is relative to antigen-specific immune response in absence of the administering the *Listeria* (specific to the antigen encoded by the second nucleic acid).

Optionally, the heterologous antigen can be identical to the antigen from (or derived from) the tumor, cancer cell, or infectious agent.

The following embodiments relate to nucleic acids encoding the modified ActA called ActA-N100. ActA-N100 encompasses a nucleic acid encoding amino acids 1-100 of ActA, as well as the polypeptide expressed from this nucleic acid. (This numbering includes all of the secretory sequence of ActA.) What is provided is a polynucleotide comprising a first nucleic acid encoding ActA-N100 operably linked and in frame with a second nucleic acid encoding a heterologous antigen.

Yet another embodiment provides a *Listeria* bacterium comprising one or more of the above polynucleotide. The polynucleotide can be genomic, it can be plasmid-based, or it can reside on both a plasmid and the listerial genome. Also provided is the above *Listeria* where the polynucleotide is not genomic, as well as the above *Listeria* where the polynucleotide is not plasmidic. The *Listeria* can be *Listeria monocytogenes*, *L. innocua*, or some other listerial species.

Methods for using ActA-N100 are also available. Provided is a method for stimulating immune response to an antigen from, or derived from, a tumor, cancer cell, or infectious agent, comprising administering to a mammal the above-disclosed *Listeria*, and wherein the heterologous antigen is shares at least one epitope with the antigen derived from the tumor, cancer cell, or infectious agent. What is also provided is the above method, where the stimulating is relative to antigen-specific immune response in absence of the administering the *Listeria* (specific to the antigen encoded by the second nucleic acid). Alternatively, the heterologous antigen can be identical to the antigen from, or derived from, the tumor, cancer cell, or infectious agent.

In some embodiments, the modified ActA consists of a fragment of ActA or other derivative of ActA in which the ActA signal sequence has been deleted. In some embodiments, the polynucleotides comprising nucleic acids encoding a fusion protein comprising such a modified ActA and the heterologous antigen further comprise a signal sequence that is not the ActA signal sequence. The ActA signal sequence is MGLNRFMRAMMVVFITANCITINPDIIFA (SEQ ID NO:125). In some embodiments, the modified ActA consists of amino acids 31-100 of ActA (i.e., ActA-N100 deleted of the signal sequence).

ii. Nucleic Acids Encoding Modified ActA.

The present invention provides a polynucleotide comprising a first nucleic acid encoding a modified ActA, operatively linked and in frame with a second nucleic acid encoding a heterologous antigen. ActA contains a number of domains, each of which plays a part in binding to a component of the mammalian cytoskeleton, where the present invention contemplates removing one or more of these domains.

ActA contains a number of domains, including an N-terminal domain (amino acids 1-234), proline-rich domain (amino acids 235-393), and a C-terminal domain (amino acids 394-610). The first two domains have distinct effects on the cytoskeleton (Cicchetti, et al. (1999) J. Biol. Chem. 274: 33616-33626). The proline-rich domain contains four proline-rich motifs. The proline-rich motifs are docking sites for the Ena/VASP family of proteins. Deletion of proline-rich domains of ActA strongly reduces actin filament assembly (Cicchetti, et al. (1999) J. Biol. Chem. 274:33616-33626). Machner, et al., provides guidance for designing mutated proline-rich motifs that can no longer dock, where this guidance can be put to use for embodiments of the present invention (Machner, et al. (2001) J. Biol. Chem. 276:40096-40103). For example, the phenylalanine of the proline-rich motifs is critical. The present invention, in an alternate embodiment, provides a polynucleotide comprising a first nucleic acid encoding ActA, where the codons for the phenylalaline in each proline-rich motif is changed to an alanine codon, operably linked and in frame with a second nucleic acid encoding at least one heterologous antigen. In another aspect, the first nucleic acid encoding ActA comprises a proline to alanine mutation in only the first proline-rich motif, in only the second proline-rich motif, in only the third proline-rich motif, in only the fourth proline-rich motif, or any combination thereof. In another aspect, a nucleic acid encoding an altered ActA can encompass a mutation in a codon for one or more proline-rich motifs in combination with a mutation or deletion in, e.g., cofilin homology region and/or the core binding sequence for phospholipids interaction.

What is also embraced, is a mutation of proline to another amino acid, e.g., serine. The above guidance in designing mutations is not to be limited to changing the proline-rich motifs, but applies as well to the cofilin homology region, the core binding sequence for phospholipids interaction, and any other motifs or domains that contribute to interactions of ActA with the mammalian cytoskeleton.

ActA contains a domain that is a "core binding sequence for phospholipids interaction" at amino acids 185-201 of ActA, where the function in phospholipids binding was demonstrated by binding studies (Cicchetti, et al. (1999) J. Biol. Chem. 274:33616-33626). According to Cicchetti, et al., supra, phospholipids binding regulates the activities of actin-binding proteins.

ActA contains a cofilin homology region KKRR (SEQ ID NO:23). Mutations of the KKRR (SEQ ID NO:23) region abolishes the ActA's ability to stimulate actin polymerization (see, e.g., Baoujemaa-Paterski, et al. (2001) Biochemistry 40:11390-11404; Skoble, et al. (2000) J. Cell. Biol. 150:527-537; Pistor, et al. (2000) J. Cell Sci. 113:3277-3287).

The following concerns expression, by *L. monocytogenes*, of truncated actA derivatives truncated down from amino acid 263 to amino acid 59. Unlike other truncated derivatives, actA N59 was not expressed whereas all of the longer ones were expressed (Skoble, J. (unpublished)). The next longest derivative tested was actA-N101. Fusion protein constructs expressed from actA promoter, consisting of a first fusion protein partner that is actA secretory sequence, and a second fusion protein partner, resulted in much less protein secretion than where the first fusion protein partner was actA-N100. Regarding deletion constructs, good expression was also found where the first fusion protein partner was soluble actA with amino acids 31-59 deleted. Moreover, good expression was found where the first fusion protein partner was soluble actA with amino acids 31-165 deleted (Skoble, J. (unpublished)).

The present invention, in certain embodiments, provides a polynucleotide comprising a first nucleic acid encoding a modified ActA, comprising at least one modification, wherein the at least one modification is an inactivating mutation in, deletion of, or termination of the ActA polypeptide sequence at or prior to, a domain required for ActA-mediated regulation of the host cell cytoskeleton, and a second nucleic acid encoding a heterologous antigen. The modified ActA can be one resulting in impaired motility and/or decreased plaque size, and includes a nucleic acid encoding one of the mutants 34, 39, 48, and 56 (Lauer, et al. (2001) Mol. Microbiol. 42:1163-1177). The present invention also contemplates a nucleic acid encoding one of the ActA mutants 49, 50, 51, 52, and 54. Also provides is a nucleic acid encoding one of the ActA mutants 40, 41, 42, 43, 44, 45, 45, and 47. Provided are mutants in the actin monomer binding region AB region, that is, mutants 41, 42, 43, and 44 (Lauer, et al. (2001) Mol. Microbiol. 42:1163-1177).

In another aspect, the modified ActA of the present invention can consist a deletion mutant, can comprise a deletion mutant, or can be derived from a deletion mutant ActA that is unable to polymerize actin in cells and/or unable to support plaque formation, or supported only sub-maximal plaque formation. These ActA deletion mutants include the nucleic acids encoding Δ31-165; Δ136-200; Δ60-165; Δ136-165; Δ146-150, Δ31-58; Δ60-101; and Δ202-263 and the like (Skoble, et al. (2000) J. Cell Biol. 150:527-537). Encompassed are nucleic acids encoding ActA deletion mutants that have narrower deletions and broader deletions. The following set of examples, which discloses deletions at the cofilin homology region, can optionally to each the ActA deletions set forth herein. The present invention provides nucleic acids encoding these deletions at the cofilin homology region: Δ146-150; Δ145-150; Δ144-150; Δ143-150; Δ142-150; Δ141-150; Δ140-150; Δ139-150; Δ138-150; Δ137-150; Δ136-150, and the like. Also encompassed are nucleic acids encoding ActA with the deletions: Δ146-150; Δ146-151; Δ146-152; Δ146-153; Δ146-154; Δ146-155; Δ146-156; Δ146-157; Δ146-158; Δ146-159; Δ146-160; and so on. Moreover, also embraced are nucleic acids encoding the deletion mutants: Δ146-150; Δ145-151; Δ144-152; Δ143-153; Δ142-154; Δ141-155; Δ140-156; Δ139-157; Δ138-158; Δ137-159; Δ136-160, and the like. Where there is a deletion at both the N-terminal end of the region in question, and at the C-terminal end, the sizes of these two deletions need not be equal to each other.

Deletion embodiments are also provided, including but not limited to the following. What is provided is a nucleic acid encoding full length actA, an actA missing the transmembrane anchor, or another variant of actA, where the actA is deleted in a segment comprising amino acids (or in the alternative, consisting of the amino acids): 31-59, 31-60, 31-61, 31-62, 31-63, 31-64, 31-65, 31-66, 31-67, 31-68, 31-69, 31-70, 31-71, 31-72, 31-73, 31-74, 31-75, 31-76, 31-77, 31-78, 31-79, 31-80, 31-81, 31-82, 31-83, 31-84, 31-85, 31-86, 31-87, 31-88, 31-89, 31-90, 31-91, 31-92, 31-93, 31-94, 31-95, 31-96, 31-97, 31-98, 31-99, 31-100, 31-101, 31-102, 31-103, 31-104, 31-105, 31-106, 31-107, 31-108, 31-109, 31-110, 31-111, 31-112, 31-113, 31-114, 31-115, 31-116, 31-117, 31-118, 31-119, 31-120, 31-121, 31-122, 31-123, 31-124, 31-125, 31-126, 31-127, 31-128, 31-129, 31-130, 31-131, 31-132, 31-133, 31-134, 31-135, 31-136, 31-137, 31-138, 31-139, 31-140, 31-141, 31-142, 31-143, 31-144, 31-145, 31-146, 31-147, 31-148, 31-149, 31-150, 31-151, 31-152, 31-153, 31-154, 31-155, 31-156, 31-157, 31-158, 31-159, 31-160, 31-161, 31-162, 31-163, 31-164, 31-165, and the like.

In yet another aspect, what is supplied is a polypeptide containing a first nucleic acid encoding an actA derivative, and a second nucleic acid encoding a heterologous nucleic acid, where the actA derivative is soluble actA comprising a deletion or conservative amino acid mutation, and where the deletion or conservative amino acid mutation comprises (or in another embodiment, where the deletion consists of) amino acid: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, and so on.

What is also provided, in other embodiments, is a polynucleotide comprising a first nucleic acid encoding an altered ActA, operably linked and in frame with a second nucleic acid, encoding a heterologous antigen, where the first nucleic acid is derived from, for example, ΔActA3 (amino acids 129-153 deleted); ΔActA9 (amino acids 142-153 deleted); ΔActA6 (amino acids 68-153 deleted); ΔActA7 (amino acids 90-153 deleted); or ΔActA8 (amino acids 110-153 deleted), and so on (see, e.g., Pistor, et al. (2000) J. Cell Science 113:3277-3287).

A number of derivatives of ActA, encompassing the start methionine (N-terminus) and prematurely terminated, resulting in a novel C-terminus. Some of these derivatives are reported in Skoble, et al. (2000) J. Cell Biol. 150:527-537). Nucleic acids encoding these derivatives were introduced into L. monocytogenes, to test expression. The ActA derivative terminating at amino acid 59 (ActA-N59) was not expressed by L. monocytogenes. In contrast, ActA-N101, and longer derivatives of ActA, were expressed. Fusion proteins (expressed from the ActA promoter) consisting of only the ActA signal sequence and a fusion protein partner, showed much less secretion than fusion proteins consisting of ActA-N100 and a fusion protein partner.

The truncation, deletion, or inactivating mutation, can reduce or eliminate the function of one or more of ActA's four $FP_4$ domains ((E/D)FPPPX(D/E)) (SEQ ID NO:135). ActA's $FP_4$ domains mediate binding to the following proteins: mammalian enabled (Mena); Ena/VASP-like protein (Evl); and vasodilator-stimulated phosphoprotein (VASP) (Machner, et al. (2001) J. Biol. Chem. 276:40096-40103). Hence, the nucleic acid of the present invention encodes a truncated ActA, deleted or mutated in one or more of its $FP_4$ domains, thereby reducing or preventing biding to Mena, Evl, and/or VASP. Provided is a nucleic acid encoding a truncated, partially deleted or mutated ActA and a heterologous antigen, where the truncation, partial deletion, or mutation, occurs at amino acids 236-240; amino acids 270-274; amino acids 306-310; and/or amino acids 351-355 of ActA (numbering of Machner, et al. (2001) J. Biol. Chem. 276:40096-40103).

The present invention provides a polynucleotide comprising a first nucleic acid encoding an ActA variant, and a second nucleic acid encoding at least one heterologous antigen, where the ActA variant is ActA deleted in or mutated in one "long repeat," two long repeats, or all three long repeats of ActA. The long repeats of ActA are 24-amino acid sequences located in between the $FP_4$ domains (see, e.g., Smith, et al. (1996) J. Cell Biol. 135:647-660). The long repeats help transform actin polymerization to a force-generating mechanism.

As an alternate example, what is provided is a nucleic acid encoding the following ActA-based fusion protein partner, using consisting language: What is provided is a nucleic acid encoding a fusion protein partner consisting of amino acids 1-50 of human actA (for example, GenBank Acc. No. AY512476 or its equivalent, where numbering begins with the start amino acid), amino acids 1-60; 1-61; 1-62; 1-63; 1-64; 1-65; 1-66; 1-67; 1-68; 1-69; 1-70; 1-72; 1-73; 1-74;

1-75; 1-76; 1-77; 1-78; 1-79; 1-80; 1-81; 1-82; 1-83; 1-84; 1-85; 1-86; 1-87; 1-88; 1-89; 1-90; 1-91; 1-92; 1-93; 1-94; 1-95; 1-96; 1-97; 1-98; 1-99; 1-100; 1-101; 1-102; 1-103; 1-104; 1-105; 1-106; 1-107; 1-108; 1-109; 1-110; 1-111; 1-112; 1-113; 1-114; 1-115; 1-116; 1-117; 1-118; 1-119; 1-120; 1-121; 1-122; 1-123; 1-124; 1-125; 1-126; 1-127; 1-128; 1-129; 1-130; 1-131; 1-132; 1-133; 1-134; 1-135; 1-136; 1-137; 1-138; 1-139; 1-140; 1-141; 1-142; 1-143; 1-144; 1-145; 1-146; 1-147; 1-148; 1-149; 1-150; 1-151; 1-152; 1-153; 1-154; 1-155; 1-156; 1-157; 1-158; 1-159; 1-160, and so on.

Figure 6:
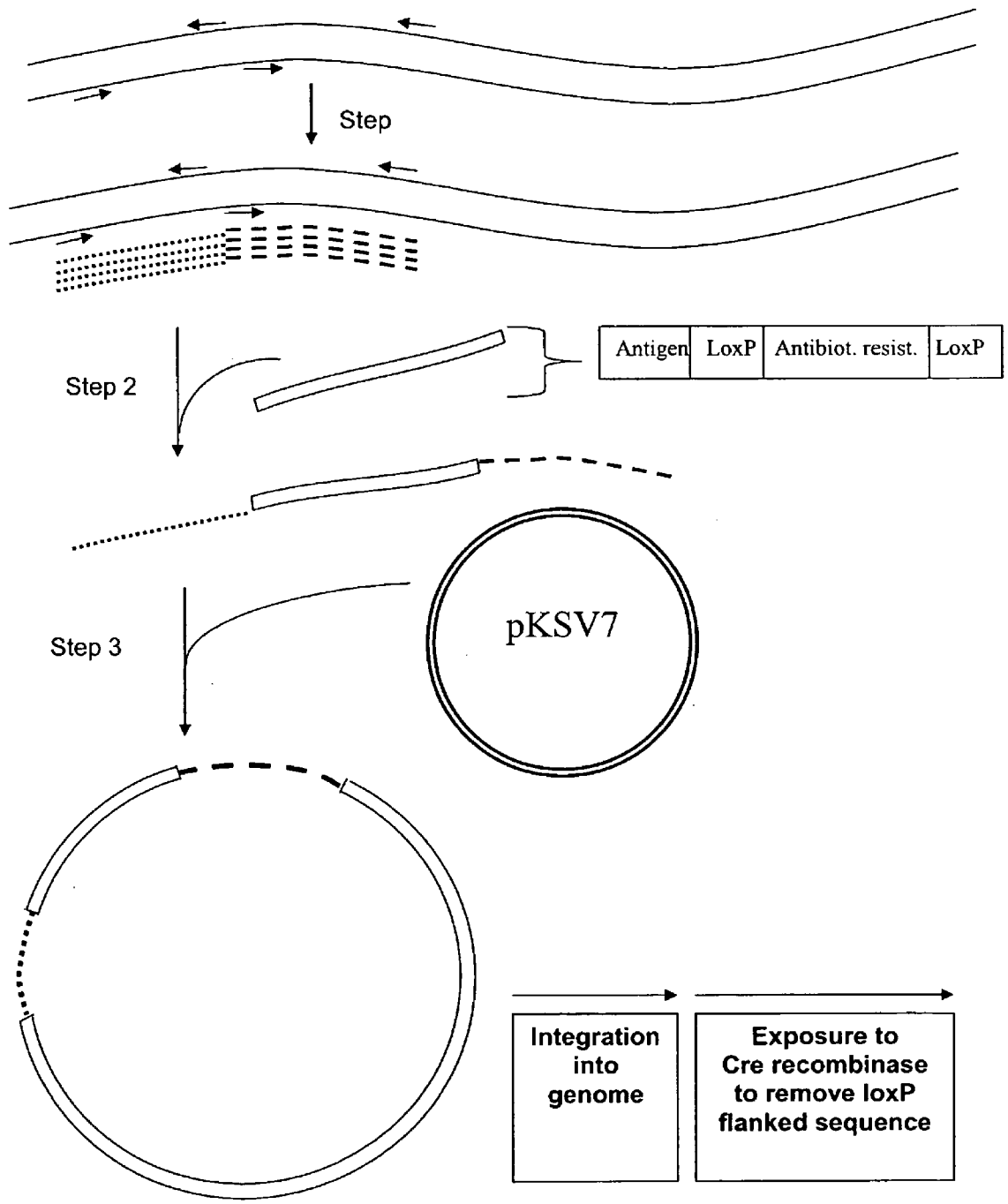
FIG. 6 discloses the preparation of an insert bearing homologous arms, where the insert bearing homologous arms is placed into pKSV7. The loxP-flanked region resides in between the homologous arms. In vectors prepared according to this figure, integration is not followed by deletion of any corresponding region of the genome.

As yet another alternate example, what is provided is a nucleic acid encoding the following ActA-based fusion protein partner, using comprising language: What is provided is a nucleic acid encoding a fusion protein partner comprising amino acids 1-50 of human actA (for example, GenBank Acc. No. AY512476 or its equivalent, where numbering begins with the start amino acid), amino acids 1-60; 1-61; 1-62; 1-63; 1-64; 1-65; 1-66; 1-67; 1-68; 1-69; 1-70; 1-72; 1-73; 1-74; 1-75; 1-76; 1-77; 1-78; 1-79; 1-80; 1-81; 1-82; 1-83; 1-84; 1-85; 1-86; 1-87; 1-88; 1-89; 1-90; 1-91; 1-92; 1-93; 1-94; 1-95; 1-96; 1-97; 1-98; 1-99; 1-100; 1-101; 1-102; 1-103; 1-104; 1-105; 1-106; 1-107; 1-108; 1-109; 1-110; 1-111; 1-112; 1-113; 1-114; 1-115; 1-116; 1-117; 1-118; 1-119; 1-120; 1-121; 1-122; 1-123; 1-124; 1-125; 1-126; 1-127; 1-128; 1-129; 1-130; 1-131; 1-132; 1-133; 1-134; 1-135; 1-136; 1-137; 1-138; 1-139; 1-140; 1-141; 1-142; 1-143; 1-144; 1-145; 1-146; 1-147; 1-148; 1-149; 1-150; 1-151; 1-152; 1-153; 1-154; 1-155; 1-156; 1-157; 1-158; 1-159; 1-160, and so on.

The contemplated nucleic acids encoding an actA-based fusion protein partner include nucleic acids encoding the actA-based fusion protein partner, where one or more nucleotides is altered to provide one or more conservative amino acid changes. What is contemplated is one conservative amino acid change, two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more, conservative amino acid changes. Moreover, what is contemplated is a nucleic acid encoding the actA-based fusion protein partner, comprising at least one mutation encoding at least one short deletion, or at least one short insertion, or any combination thereof.

Regarding the identity of the nucleic acid encoding ActA, and derivatives thereof, the codon for the start methionine can be a valine start codon. In other words, *Listeria* uses a valine start codon to encode methionine.

The contemplated invention encompasses ActA, and ActA deleted in one or more cytoskeleton-binding domains, ActA-N100 fusion protein partners, from all listerial species, including *L. monocytogenes* and *L. ivanovii* (Gerstel, et al. (1996) Infection Immunity 64:1929-1936; GenBank Acc. No. X81135; GenBank Acc. No. AY510073).

iii. Abnormal Cell Physiology Produced By Wild Type ActA.

The modified ActA, of at least some embodiments of the invention, is changed to reduce or eliminate its interaction with the mammalian cytoskeleton. While the physiological function of ActA is to bind to the mammalian cytoskeleton and to allow actin-mediated movement of the *Listeria* bacterium through the cytoplasm, this binding is reduced or eliminated in the ActA component of the fusion protein.

Expression of soluble ActA in mammalian cytoplasm, by way of eukaryotic expression vectors, results in abnormalities of the cytoskeleton, e.g., "redistribution of F-actin," and sequestration of the recombinant ActA at the location of "membrane protrusions." In other words, the normal location of F-actin was changed, where its new location was in membrane protrusions. Moreover, "ActA stain co-distributed with that of F-actin in membrane protrusions." Other abnormalities in mammalian cells included "loss of stress fibres." It was observed that "the amino-terminal part of ActA is involved in the nucleation of actin filaments while the segment including the proline-rich repeat region promotes or controls polymerization" (Friederich, et al. (1995) EMBO J. 14:2731-2744). Moreover, according to Olazabal and Machesky, overexpressing a protein demonstrated to be similar to ActA, the WASP protein, causes "defects in actin organization that lead to malfunctions of cells" (Olazabal and Machesky (2001) J. Cell Biol. 154:679-682). The title of a publication ("*Listeria* protein ActA mimics WASP family proteins") indicates this similarity (Boujemaa-Paterski, et al. (2001) Biochemistry 40:11390-11404).

Introducing certain domains of ActA into a mammalian cell disrupts the host cell cytoplasm. In detail, microinjecting ActA's repeat oligoproline sequence induces "loss of stress fibers," "dramatic retraction of peripheral membranes," and "accumulation of filamentous actin near the retracting peripheral membrane" (Southwick and Purich (1994) Proc. Natl. Acad. Sci. USA 91:5168-5172). ActA, a protein expressed by *Listeria*, sequesters or "highjacks" or utilizes various cytoskeleton related proteins, including the Arp2/3 complex and actin (Olazabal, et al. (2002) Curr. Biol. 12:1413-1418; Zalevsky, et al. (2001) J. Biol. Chem. 276:3468-3475; Brieher, et al. (2004) J. Cell Biol. 165:233-242).

The ActA-based fusion protein partner, of the present invention, has a reduced polypeptide length when compared to ActA lacking the transmembrane domain. The ActA-based fusion protein partner provides reduced disruption of actin-dependent activity such as immune presentation, host cell proliferation, cell polarity, cell migration, endocytosis, sealing of detached vesicles, movement of endocytotic vesicles, secretion, cell polarity, and response to wounds (wound healing) (see, e.g., Setterblad, et al. (2004) J. Immunol. 173:1876-1886; Tskvitaria-Fuller, et al. (2003) J. Immunol. 171:2287-2295). Without implying any limitation on the invention, reduced disruption in this context is relative to that found with full-length ActA, with ActA deleted only in the transmembrane domain, or with ActA truncated at the transmembrane domain. ActA lacking the membrane anchor sequence produces a "discernable redistribution of actin" in mammalian cells (see, e.g., Pistor, et al. (1994) EMBO J. 13:758-763).

Actin-dependent activities of the cell include immune cell functions, wound healing, capping, receptor internalization, phagocytosis, Fc-receptor clustering and Fc-receptor mediated phagocytosis, utilize actin (see, e.g., Kwiatkowska, et al. (2002) J. Cell Biol. 116:537-550; Ma, et al. (2001) J. Immunol. 166:1507-1516; Fukatsu, et al. (2004) J. Biol. Chem. 279:48976-48982; Botelho, et al. (2002) J. Immunol. 169: 4423-4429; Krishnan, et al. (2003) J. Immunol. 170:4189-4195; Gomez-Garcia and Kornberg (2004) Proc. Natl. Acad. Sci. USA 101:15876-15880; Kusner, et al. (2002) J. Biol. Chem. 277:50683-50692; Roonov-Jessen and Peterson (1996) J. Cell Biol. 134:67-80; Choma, et al. (2004) J. Cell Science 117:3947-3959; Miki, et al. (2000) Am. J. Physiol. Lung Cell. Mol. Physiol. 278:L13-L18; Fujimoto, et al. (2000) Traffic 1:161-171; Zualmann, et al. (2000) J. Cell Biol. 150:F111-F116; Olazabal, et al. (2002) Curr. Biol. 12:1413-1418; Magdalena, et al. (2003) Molecular Biology of the Cell 14:670-684).

ActA is degraded (in the mammalian cytoplasm) by way of the "N-end rule pathway." (see, e.g., Moors, et al. (1999) Cellular Microbiol. 1:249-257; Varshavsky (1996) Proc. Natl. Acad. Sci. USA 93:12142-12149).

iv. Polynucleotide Constructs Based on Modified ActA, and *Listeria* Containing the Polynucleotide Constructs The present invention, in some embodiments, encompasses a polynucleotide comprising a first nucleic acid encoding actA-N100 operably linked and in frame with a second nucleic acid encoding a heterologous antigen, such as human mesothelin, or a derivative thereof. Human mesothelin was expressed from a number of constructs, where these constructs were created by site-directed integration or homologous integration into the *Listeria* genome. Some of these constructs are shown in FIG. 6. FIG. 6 discloses naturally occurring human mesothelin, which contains a signal sequence and a GPI-sequence. The signal sequence and GPI-sequence was deleted in the following examples, where the naturally occurring signal sequence was replaced with the *Bacillus anthracis* Protective Antigen secretory sequence (BaPA), with LLO-62, with LLO-60$_{codon\ optimized}$ (LLO-60$_{opt}$), or with ActA-N100 (FIG. 6). The sequence of ActA-N100 includes the naturally occurring secretory sequence of ActA.

B. Rare Codons of ActA; Immunogenicity of ActA.

The ActA coding region contains a number of codons that are non-optimal for *L. monocytogenes*. Of these, a number occur in the listerial genome at a frequency of 25% or less than that of the most commonly used codon. The following provides a codon analysis for *L. monocytogenes* 10403S ActA. In the codons encoding amino acids 101-400, rare codons for glutamate (GAG) occur 12 times; rare codons for lysine (AAG) occurs three times; rare codons for isoleucine (ATA) occurs three times; rare codons for arginine (CGG) occurs once; rare codons for glutamine (CAG) occurs once; and rare codons for leucine (CTG; CTC) occurs three times. The following commentary relates to non-optimal codons, not just to rare codons. Moreover, in the codons encoding amino acids 101-400 (300 codons), non-optimal codons (this is in addition to the rare codons) occur 152 times (out of 300 codons total).

ActA is a major target for immune response by humans exposed to *L. monocytogenes* (see, e.g., Grenningloh, et al. (1997) Infect. Immun. 65:3976-3980). In some embodiments, the present invention provides an ActA-based fusion protein partner, where the ActA-based fusion protein partner has reduced immunogenicity, e.g., contains fewer epitopes than full-length ActA or is modified to provide epitopes of reduced immunogenicity.

The reagents and methods of the present invention provide a nucleic acid encoding an ActA, a truncated ActA, and/or a mutated ActA (e.g., a point mutation or a deletion), having a reduced number of antigenic epitopes, or that lacks one or more regions of increased antigenicity. Regions of increased antigenicity, as determined by a Welling plot, include amino acids 85-90; 140-150; 160-190; 220-230; 250-260; 270-280; 305-315; 350-370; 435-445; 450-460; 490-520; 545-555; and 595-610, of GenBank Acc. No. X59723. ActA has been identified as an immunogenic protein (see, e.g., Grenningloh, et al. (1997) Infection Immunity 65:3976-3980; Darji, et al. (1998) J. Immunol. 161:2414-2420; Niebuhr, et al. (1993) Infect. Immun. 61:2793-2802; Lingnau, et al. (1995) Infect. Immun. 63:3896-3903). The immunogenic properties of ActA increase with expression of soluble forms of actin, e.g., actin lacking all or part of its C-terminal region (amino acids 394-610 using numbering of Mourrain, et al. (1997) Proc. Natl. Acad. Sci. USA 94:10034-10039) (see also, e.g., Darji, et al. (1998) J. Immunol. 161:2414-2420; Cicchetti, et al. (1999) J. Biol. Chem. 274:33616-33626). Hence, where a truncated, partially deleted, or mutated ActA of the present invention lacks (or functionally lacks) a domain used for membrane-binding, thereby resulting in increased immunogenicity, the present invention provides for further truncations or mutations in order to reduce immunogenicity of the truncated ActA.

C. Assays to Measure Binding of ActA Derivatives, to Cytoskeletal Proteins, and ActA-Dependent Movement of *Listeria*.

Assays for determining recruiting of actin, or other proteins, to ActA, or to variants of ActA, are available. Recruiting can reasonably be assessed by bacterial movement assays, that is, assays that measure actin-dependent rate of *Listeria* movement in eukaryotic cell extracts or inside a eukaryotic cell (see, e.g., Marchand, et al. (1995) J. Cell Biol. 130:331-343). Bacterial movement assays can distinguish between *Listeria* expressing wild type ActA, and *Listeria* expressing mutant versions of ActA, for example, mutant ActA that lacks FP$_4$ domains (Smith, et al. (1996) J. Cell Biol. 135:647-660).

Recruitment can also be assessed by measuring local actin concentration at the surface of ActA-coated beads or at the surface of ActA-expressing bacteria. Bead-based assays are described (see, e.g., Machner, et al. (2001) J. Biol. Chem. 276:40096-40103; Fradelizi, et al. (2001) Nature Cell Biol. 3:699-707; Theriot, et al. (1994) Cell 76:505-517; Smith, et al. (1995) Mol. Microbiol. 17:945-951; Cameron, et al. (1999) Proc. Natl. Acad. Sci. USA 96:4908-4913). Ultracentrifugation can assess the number of cytoskeletal proteins bound to ActA (see, e.g., Machner, et al., supra).

Assays available to the skilled artisan include, e.g., the spontaneous actin polymerization assay; the elongation from the barbed end assay; and the elongation from the pointed end (see, e.g., Zalevsky, et al. (2001) J. Biol. Chem. 276:3468-3475). Methods are also available for assessing polarity of ActA-induced actin polymerization (see, e.g., Mogilner and Oster (2003) Biophys. J. 84:1591-1605; Noireauz, et al. (2000) Biophys. J. 78:1643-1654).

(d). SecA2-Secreted Proteins for Use as Fusion Protein Partner.

The present invention provides a family of SecA2 listerial secretory proteins useful as fusion protein partners with a heterologous antigen. The secretory protein-derived fusion protein partner finds use in increasing expression, increasing stability, increasing secretion, enhancing immune presentation, stimulating immune response, improving survival to a tumor, improving survival to a cancer, increasing survival to an infectious agent, and the like.

The contemplated listerial secretory proteins include p60 autolysin; N-acetyl-muramidase (NamA); penicillin-binding protein 2B (PBP-2B) (GenBank Acc. No. NC_003210); pheromone transporter (OppA) (complement to nt 184,539-186,215 of GenBank Acc. No. AL591982); maltose/maltodextrin ABC transporter (complement to nt 104,857-105,708 of GenBank Acc. No. AL591982); antigenic lipoprotein (Csa) (nt 3646-4719 of GenBank Acc. No. AL591982); and conserved lipoprotein, e.g., of *L. monocytogenes* EGD (see, e.g., Lenz, et al. (2003) Proc. Natl. Acad. Sci. USA 100: 12432-12437; Lenz and Portnoy (2002) Mol. Microbiol. 45:1043-1056).

p60 is encoded by an open reading frame of 1,452 bp, has an N-terminal signal sequence, an SH3 domain in the N-terminal region, a central region containing threonine-asparagine repeats, and a C-terminal region encompassing the autolysin catalytic site (see, e.g., Pilgrim, et al. (2003) Infect. Immun. 71:3473-3484). p60 is also known as invasion-associated protein (iap) (GenBank Acc. No. X52268; NC_003210).

The present invention provides a polynucleotide comprising a first nucleic acid encoding p60, or a p60 derivative, and a second nucleic acid encoding a heterologous antigen. The p60 or p60 derivatives encompass a full length p60 protein (e.g., from *L. monocytogenes, L. innocua, L. ivanovii, L. seeligeri, L. welshimeri, L. murrayi*, and/or *L. grayi*), truncated p60 proteins consisting essentially of the N-terminal 70 amino acids; a truncated p60 protein deleted in the region that catalyses hydrolysis; signal sequences from a p60 protein; or a p60 protein with its signal sequence replaced with a different signal sequence (e.g., the signal sequence of ActA, LLO, PFO, or BaPA), and a second nucleic acid encoding a heterologous antigen. The p60 signal sequence (27 amino acids) is: MNMKKATIAATAGIAVTAFAAPTIASA (SEQ ID NO:24) (Bubert, et al. (1992) J. Bacteriol. 174:8166-8171; Bubert, et al. (1992) Appl. Environ. Microbiol. 58:2625-2632; J. Bacteriol. 173:4668-4674). The N-acetyl-muramidase signal sequence (52 amino acids) is: MDRKFIKPGIILLIVAFLV-VSINVGAETGGSRTAQVNLTTSQQAFIDEILPA (SEQ ID NO:25) (nt 2679599 to 2681125 of GenBank Acc. No. NC_003210; GenBank Acc. No. AY542872; nt 2765101 to 2766627 of GenBank Acc. No. NC_003212; Lenz, et al. (2003) Proc. Natl. Acad. Sci. USA 100:12432-12437).

The present invention provides a p60 variant, for example, where the codons for amino acids 69 (L) and 70 (Q) are changed to provide a unique Pst I restriction site, where the Pst I site finds use in insertion a nucleic acid encoding a heterologous antigen.

Contemplated is nucleic acid encoding a fusion protein comprising a SecA2-pathway secreted protein and a heterologous antigen. Also contemplated is a nucleic acid encoding a fusion protein comprising a derivative or truncated version of a SecA2-pathway secreted protein and a heterologous antigen. Moreover, what is contemplated is a *Listeria* bacterium comprising a nucleic acid encoding a fusion protein comprising a SecA2-pathway secreted protein and a heterologous antigen, or comprising a nucleic acid encoding a fusion protein comprising a derivative or truncated version of a SecA2-pathway secreted protein and a heterologous antigen.

(e) Mesothelin.

Human mesothelin cDNA is 2138 bp, contains an open reading frame of 1884 bp, and encodes a 69 kD protein. The mesothelin precursor protein contains 628 amino acids, and a furin cleavage site (RPRFRR at amino acids 288-293). Cleavage of the 69 kd protein generates a 40 kD membrane-bound protein (termed "mesothelin") plus a 31 kD soluble protein called megakaryocyte-potentiating factor (MPF). Mesothelin has a lipophilic sequence at its C-terminus, which is removed and replaced by phosphatidyl inositol, which causes mesothelin to be membrane-bound. Mesothelin contains a glycosylphosphatidyl inositol anchor signal sequence near the C-terminus. Mesothelin's domains, expression of mesothelin by cancer and tumor cells, and antigenic properties of mesothelin, are described (see, e.g., Hassan, et al. (2004) Clin. Cancer Res. 10:3937-3942; Ryu, et al. (2002) Cancer Res. 62:819-826; Thomas, et al. (2003) J. Exp. Med. 200:297-306; Argani, et al. (2001) Clin. Cancer Res. 7:3862-3868; Chowdhury, et al. (1998) Proc. Natl. Acad. Sci. USA 95:669-674; Chang and Pastan (1996) Proc. Natl. Acad. Sci. USA 93:136-140; Muminova, et al. (2004) BMC Cancer 4:19; GenBank Acc. Nos. NM_005823 and NM_013404; U.S. Pat. No. 5,723,318 issued to Yamaguchi, et al.).

Human mesothelin, deleted in mesothelin's signal sequence, is shown below:

```
                                          (SEQ ID NO: 26)
RTLAGETGQEAAPLDGVLTNPPNISSLSPRQLLGFPCAEVSGLSTERV
RELAVALAQKNVKLSTEQLRCLAHRLSEPPEDLDALPLDLLLFLNPDA
FSGPQACTRFFSRITKANVDLLPRGAPERQRLLPAALACWGVRGSLLS
EADVRALGGLACDLPGRFVAESAEVLLPRLVSCPGPLDQDQQEAARAA
LQGGGPPYGPPSTWSVSTMDALRGLLPVLGQPILRSWQGIVAAWRQRS
SRDPSWRQPERTILRPRFRREVEKTACPSGKKAREIDESLWYKKWELE
ACVDAALLATQMDRVNAIPFTYEQLDVLKIHKLDELYPQGYPESVIQH
LGYLFLKMSPEDIRKWNVTSLETLKALLEVNKGHEMSPQVATLIDRFV
KGRGQLDKDTLDTLTAFYPGYLCSLSPEELSSVPPSSJWAVRPQDLDT
CDPRQLDVLYPKARLAFQNMNGSEYFVKIQSFLGGAPTEDLKALSQQN
VSMDLATFMKLRTDAVLPLTVAEVQKLLGPHVEGLKAEERHRPVRDWI
LRQRQDDLDTLGLGLQGGIPNGYLVLDLSVQEALSGTPCLLGPGPVLT
VLALLLASTLA
```

Human mesothelin, deleted in mesothelin's signal sequence and also deleted in mesothelin's GPI-anchor, is disclosed below:

```
                                          (SEQ ID NO: 27)
RTLAGETGQEAAPLDGVLTNPPNISSLSPRQLLGFPCAEVSGLSTERV
RELAVALAQKNVKLSTEQLRCLAHRLSEPPEDLDALPLDLLLFLNPDA
FSGPQACTRFFSRITKANVDLLPRGAPERQRLLPAALACWGVRGSLLS
EADVRALGGLACDLPGRFVAESAEVLLPRLVSCPGPLDQDQQEAARAA
LQGGGPPYGPPSTWSVSTMDALRGLLPVLGQPIIRSIPQGIVAAWRQR
SSRDPSWRQPERTILRPRFRREVEKTACPSGKXAREDESLWYKKWELE
ACVDAALLATQMDRVNAIPFTYEQLDVLKIHKLDELYPQGYPESVIQH
LGYLFLKMSPEDIRKWNVTSLETLKALLEVNKGHEMSPQVATLIDRFV
KGRGQLDKDTLDTLTAFYPGYLCSLSPEELSSVPPSSIWAVRPQDLDT
CDPRQLDVLYPKARLAFQNMNGSEYFVKIQSFLGGAPTEDLKALSQQN
VSMDLATFMKLRTDAVLPLTVAEVQKLLGPHVEGLKAEERHRPVRDWI
LRQRQDDLDTLGLGLQG
```

The following documents are hereby incorporated by reference (see, e.g., U.S. Pat. No. 5,723,318 issued to Yamaguchi, et al.; U.S. Pat. No. 6,153,430 issued to Pastan, et al.; U.S. Pat. No. 6,809,184 issued to Pastan, et al.; U.S. Patent Applic. Publ. Pub. No.: US 2005/0214304 of Pastan, et al.; International Publ. No. WO 01/95942 of Pastan, et al.).

(f) Site of Integration

The present invention provides a polynucleotide comprising a first nucleic acid that mediates growth or spread in a wild type or parent *Listeria*, wherein the first nucleic acid is modified by integration of a second nucleic acid encoding at least one antigen. In one aspect, the integration results in attenuation of the *Listeria*. In another aspect, the integration does not result in attenuation of the *Listeria*. In yet another aspect, the parent *Listeria* is attenuated, and the integration results in further attenuation. Furthermore, as another non-limiting example, the parent *Listeria* is attenuated, where the integration does not result in further measurable attenuation.

Embodiments further comprising modification by integrating in the first nucleic acid, a third nucleic acid encoding at least one antigen, a fourth nucleic acid encoding at least one antigen, a fifth nucleic acid encoding at least one antigen, or the like, are also provided.

Without implying any limitation, the antigen can be a heterologous antigen (heterologous to the *Listeria*), a tumor antigen or an antigen derived from a tumor antigen, an infectious agent antigen or an antigen derived from an infectious agent antigen, and the like.

The first nucleic acid can be the actA gene or inlB gene. Integration can be at a promoter or regulatory region of actA or inlB, and/or in the open reading frame of actA or inlB, where the integration attenuates the *Listeria*, as determinable under appropriate conditions. Integration can be accompanied by deletion of a part or all of the promoter or regulatory region of actA or inlB, or with deletion of part or all of the open reading frame of actA or inlB, or with deletion of both the promoter or regulatory region plus part or all of the open reading frame of actA or inlB, where the integration attenuates the *Listeria*, as determinable under appropriate conditions.

For each of the above-disclosed embodiments, the present invention provides a *Listeria* bacterium containing the polynucleotide. The polynucleotide can be genomic.

In some embodiments, the first nucleic acid that is modified by integration of a second nucleic acid encoding at least one antigen mediates growth or spread in a wild type or parent *Listeria*. In some embodiments, the first nucleic acid that is modified mediates cell to cell spread. In some embodiments, the first nucleic acid is actA.

In some embodiments, the first nucleic acid that is modified by integration of a second nucleic acid encoding at least one antigen, comprises a gene identified as one of the following: hly gene (encodes listeriolysin O; LLO); internalin A; internalin B; actA; SvpA; p104 (a.k.a. LAP); IplA; phosphatidylinositol-specific phospholipase C (PI-PLC) (plcA gene); phosphatidylcholine-specific phospholipase C (PC-PLC) (plcB gene); zinc metalloprotease precursor (Mpl gene); p60 (protein 60; invasion associated protein (iap); sortase; listeriolysin positive regulatory protein (PrfA gene); PrfB gene; FbpA gene; Auto gene; Ami (amidase that mediates adhesion); dlt operon (dltA; dltB; dltC; dltD); any prfA boxe; or Htp (sugar-P transporter).

Moreover, what is embraced is a *Listeria* comprising the above polynucleotide. The polynucleotide can be genomic. In one aspect, the *Listeria* can be *Listeria monocytogenes*. Provided is each of the above-disclosed embodiments, wherein the integration results in attenuation of the *Listeria*, as determinable under appropriate conditions. Also provided is each of the above-disclosed embodiments, wherein the integration does not result in attenuation of the *Listeria*, as determinable under appropriate conditions. In yet another aspect, the parent *Listeria* is attenuated, and the integration results in further attenuation. Furthermore, as another example, the parent *Listeria* is attenuated, where the integration does not result in further measurable attenuation.

In another aspect, first nucleic acid can be genomic. In another aspect, the integration can be mediated by homologous recombination, where the integration does not result in any deletion of the first nucleic acid, where the integration results in deletion of all or part of the first nucleic acid, where the first nucleic acid contains a promoter or other regulatory region and where the second nucleic acid is operably linked and/or in frame with the promoter or other regulatory region, and where the first nucleic acid contains a promoter or other regulatory region and where the second nucleic acid is not at all operably linked and/or in frame with the promoter or other regulatory region.

The term "gene modified by integration" encompasses, but is not limited to, "a locus of integration that is the gene."

What is also embraced by the present invention is a polynucleotide comprising a first nucleic acid that mediates growth or spread in a wild type or parent *Listeria*, where the first nucleic acid comprises all or part of a pathogenicity island or virulence gene cluster, wherein the all or part of the pathogenicity island or virulence gene cluster is modified by integration of a second nucleic acid encoding at least one antigen, wherein the integration results in attenuation of the *Listeria*, as determinable under appropriate conditions. Pathogenicity islands and virulence gene clusters are disclosed (see, e.g., Chakraborty, et al. (2000) Int. J. Med. Microbiol. 290:167-174; Vazquez-Boland, et al. (2001) Clin. Microbiol. Revs. 14:584-640). The gene that mediates growth and spread is not limited to a gene that specifically mediates virulence, but encompasses growth-mediating genes such those that mediate energy production (e.g., glycolysis, Krebs cycle, cytochromes), anabolism and/or catabolism of amino acids, sugars, lipids, minerals, purines, and pyrimidines, and genes that mediate nutrient transport, transcription, translation, and/or replication, and the like.

In another aspect, what is provided is a polynucleotide comprising a first nucleic acid that mediates growth or spread in a wild type or parent *Listeria*, wherein the nucleic acid is modified by integration of a plurality of nucleic acids encoding an antigen or antigens.

The integration can be within the second nucleic acid without any corresponding deletion of the second nucleic acid. Alternatively, the integration can be within the second nucleic acid with a corresponding deletion of the second nucleic acid, or a portion thereof. Where the first nucleic acid in the wild type or parent *Listeria* comprises a promoter and/or other regulatory site, the integration can be in the promoter and/or regulatory site.

Where the first nucleic acid comprises a promoter and/or other regulatory site, the present invention provides an integrated second nucleic acid, where the second nucleic acid comprises a coding region that is operably linked and in-frame with the promoter and/or regulatory site. As an alternative, the present invention provides an integrated second nucleic acid, where the second nucleic acid comprises a coding region that is not operably linked and in-frame with the promoter and/or regulatory site. Provided is each of the above embodiments, where the integrated nucleic acid (second nucleic acid) comprises a promoter and/or regulatory site, where the promoter and/or regulatory site can take the place of, or alternatively can operate in addition to, a promoter and/or other regulatory site present in the first nucleic acid.

In one aspect, the first nucleic acid comprises (or in the alternative, consists of) a promoter or other regulatory element, and the second nucleic acid is operably linked with the promoter and/or other regulatory element. In another aspect, the second nucleic encoding an antigen further comprises a promoter and/or other regulatory element.

The first nucleic acid need not encode any polypeptide, as the first nucleic acid can be a regulatory region or box. The following concerns integration as mediated by, for example, homologous integration. The invention provides the above polynucleotide, wherein the second nucleic acid is integrated without deletion of any of the first nucleic acid.

In one embodiment, the first nucleic acid mediates growth but not spread. In another embodiment, the first nucleic acid mediates spread but not growth. In yet another embodiment, the first nucleic acid mediates both growth and spread. In one aspect, the integration reduces or eliminates the growth, reduces or eliminates the spread, or reduces or eliminates both growth and spread.

Moreover, in one embodiment the first nucleic acid has the property that its inactivation results in at least 10% reduction of growth, sometimes in at least 20% reduction of growth, typically in at least 30% reduction of growth, more typically in least 40% reduction of growth, most typically in at least 50% reduction in growth, often in at least 60% reduction in growth, more often in at least 70% reduction in growth, most often in at least 80% reduction in growth, conventionally at least 85% reduction in growth, more conventionally at least 90% reduction in growth, and most conventionally in at least 95% reduction in growth, and sometimes in at least 99% reduction in growth. In one aspect, the growth can be measured in a defined medium, in a broth medium, in agar, within a host cell, in the cytoplasm of a host cell, and the like.

Moreover, in one embodiment the first nucleic acid has the property that its inactivation results in at least 10% reduction of cell-to-cell spread, sometimes in at least 20% reduction of spread, typically in at least 30% reduction of spread, more typically in least 40% reduction of spread, most typically in at least 50% reduction in spread, often in at least 60% reduction in spread, more often in at least 70% reduction in spread, most often in at least 80% reduction in spread, conventionally at least 85% reduction in spread, more conventionally at least 90% reduction in spread, and most conventionally in at least 95% reduction in spread, and sometimes in at least 99% reduction in spread. In one aspect, the growth can be measured in a defined medium, in a broth medium, in agar, within a host cell, in the cytoplasm of a host cell, and the like.

Provided is a *Listeria* bacterium comprising each of the above-disclosed polynucleotides. In one aspect, the *Listeria* is *Listeria monocytogenes*. Without implying any limitation, the present invention contemplates each of the above polynucleotides that is genomic, plasmid based, or that is present in both genomic and plasmid based forms.

In each of the above-disclosed embodiments, integration can be mediated by site-specific integration. Site-specific integration involves a plasmidic attPP' site, which recognizes a genomic attBB' site. In certain embodiments, the attBB' site can be naturally present in a gene that mediates growth or spread. In other embodiments, the attBB' site can be integrated, e.g., by homologous integration, in the gene that mediates growth or spread, followed by site-specific integration of the above-disclosed second nucleic acid.

The present invention provides a *Listeria* containing a polynucleotide comprising a first nucleic acid that, in the wild type *Listeria* or parent *Listeria*, mediates growth or spread, or both growth and spread, wherein the nucleic acid is modified by integration of a second nucleic acid encoding an antigen. Yet one further example of each of the embodiments disclosed herein provides an integration that reduces or eliminates growth, reduces or eliminates spread, or reduces or eliminates both growth and spread.

What is also embraced is a polynucleotide comprising a first nucleic acid that mediates growth or spread of a wild type or parental *Listeria*, and where the first nucleic acid comprises a signal sequence or secretory sequence, wherein the first nucleic acid is modified by integration of a second nucleic acid encoding at least one antigen, and wherein the integration results an in attenuation of the *Listeria*, and where the integration operably links the signal or secretory sequence (encoded by the first nucleic acid) with an open reading frame encoding by the second nucleic acid. In one aspect, the above integration results in deletion of all of the polypeptide encoded by the first nucleic acid, except for the signal or secretory sequence encoded by the first nucleic acid (where the signal or secretory sequence remains intact).

Genomes comprising each of the polynucleotide embodiments described herein are further contemplated. Moreover, what is provided is a listerial genome comprising each of the above embodiments. Furthermore, the invention supplies a *Listeria* bacterium comprising each of the polynucleotide embodiments described herein.

In one embodiment, the invention provides *Listeria* (e.g., *Listeria monocytogenes*) in which the genome comprises a polynucleotide comprising a nucleic acid encoding a heterologous antigen. In some embodiments, the nucleic acid encoding the heterologous antigen has been integrated into the genome by site-specific recombination or homologous recombination. In some embodiments, the presence of the nucleic acid in the genome attenuates the *Listeria*. In some embodiments, the nucleic acid encoding the heterologous antigen has been integrated into the locus of a virulence gene. In some embodiments, the nucleic acid encoding the heterologous antigen has been integrated into the actA locus. In some embodiments, the nucleic acid encoding the heterologous antigen has been integrated into the inlB locus. In some embodiments, the genome of the *Listeria* comprises a first nucleic acid encoding a heterologous antigen that has been integrated into a first locus (e.g., the actA locus) and a second nucleic acid encoding a second heterologous antigen that has been integrated into a second locus (e.g., the inlB locus). The first and second heterologous antigens may be identical to each other or different. In some embodiments, the first and second heterologous antigens differ from each other, but are derived from the same tumor antigen or infectious agent antigen. In some embodiments, the first and second heterologous antigens are each a different fragment of an antigen derived from a cancer cell, tumor, or infectious agent. In some embodiments, the integrated nucleic acid encodes a fusion protein comprising the heterologous antigen and modified ActA. In some embodiments, at least two, at least three, at least four, at least five, at least six, or at least seven nucleic acid sequences encoding heterologous antigens have been integrated into the Listerial genome.

In some embodiments, a polynucleotide (or nucleic acid) described herein has been integrated into a virulence gene in the genome of the *Listeria*, wherein the integration of the polynucleotide (a) disrupts expression of the virulence gene; and/or (b) disrupts a coding sequence of the virulence gene. In some embodiments, the *Listeria* is attenuated by the disruption of the expression of the virulence gene and/or the disruption of the coding sequence of the virulence gene attenuates the *Listeria*. In some embodiments, the virulence gene is necessary for mediating growth or spread. In other embodiments, the virulence gene is not necessary for mediating growth or spread. In some embodiments, the virulence gene is a prfA-dependent gene. In some embodiments, the virulence gene is not a prfA-dependent gene. In some embodiments, the virulence gene is actA or inlB. In some embodiments, the expression of the virulence gene in which the polynucleotide/nucleic acid is integrated is disrupted at least 10%, at least 25%, at least 50%, at least 75%, at least 90%, or about 100% (relative to the expression of the virulence gene in the absence of the integrated polynucleotide/nucleic acid, as determined by measuring expression levels. Disruption of the coding sequence of the virulence gene encompasses alterations of the coding sequence of any kind including frame-shift mutations, truncations, insertions, deletions, or replacements/substitutions. In some embodiments, all or part of the virulence gene is deleted during integration of the polynucleotide into the virulence gene. In other embodiments, none of the virulence gene is deleted during integration of the polynucleotide. In some embodiments, part or all of the coding sequence of the virulence gene is replaced by the integrated polynucleotide.

In some embodiments, multiple polynucleotides described herein have been integrated into the *Listeria* genome at one or more different sites. The multiple polynucleotides may be the same or different. In some embodiments, a first polynucleotide described herein has been integrated into the actA locus and/or a second polynucleotide described herein has been integrated into the inlB locus. In some embodiments, a first polynucleotide described herein has been integrated into the actA locus and a second polynucleotide described herein has been integrated into the inlB locus. The heterologous antigen encoded by the first polynucleotide may be the same or different as that encoded by the second polynucleotide. In some embodiments, the two heterologous antigens encoded by the integrated antigens differ, but are derived from the same antigen.

IV. Therapeutic Compositions and Uses (a). Therapeutic Compositions.

The attenuated *Listeria*, vaccines, small molecules, biological reagents, and adjuvants that are provided herein can be administered to a host, either alone or in combination with a pharmaceutically acceptable excipient, in an amount sufficient to induce an appropriate immune response to an immune disorder, cancer, tumor, or infection. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression.

"Pharmaceutically acceptable excipient" or "diagnostically acceptable excipient" includes but is not limited to, sterile distilled water, saline, phosphate buffered solutions, amino acid-based buffers, or bicarbonate buffered solutions. An excipient selected and the amount of excipient used will depend upon the mode of administration. Administration may be oral, intravenous, subcutaneous, dermal, intradermal, intramuscular, mucosal, parenteral, intraorgan, intralesional, intranasal, inhalation, intraocular, intramuscular, intravascular, intranodal, by scarification, rectal, intraperitoneal, or any one or combination of a variety of well-known routes of administration. The administration can comprise an injection, infusion, or a combination thereof. Administration of the *Listeria* of the present invention by a non-oral route can avoid tolerance (see, e.g., Lecuit, et al. (2001) Science 292:1722-1725; Kirk, et al. (2005) Transgenic Res. 14:449-462; Faria and Weiner (2005) Immunol. Rev. 206:232-259; Kraus, et al. (2005) J. Clin. Invest. 115:2234-2243; Mucida, et al. (2005) J. Clin. Invest. 115:1923-1933). Methods are available for administration of *Listeria*, e.g., intravenously, subcutaneously, intramuscularly, intraperitoneally, orally, mucosal, by way of the urinary tract, by way of a genital tract, by way of the gastrointestinal tract, or by inhalation (Dustoor, et al. (1977) Infection Immunity 15:916-924; Gregory and Wing (2002) J. Leukoc. Biol. 72:239-248; Hof, et al. (1997) Clin. Microbiol. Revs. 10:345-357; Schluter, et al. (1999) Immunobiol. 201:188-195; Hof (2004) Expert Opin. Pharmacother. 5:1727-1735; Heymer, et al. (1988) Infection 16(Suppl. 2):S106-S111; Yin, et al. (2003) Environ. Health Perspectives 111:524-530).

The following applies, optionally, to each of the embodiments disclosed herein. Provided is an administered reagent that is pure or purified, for example where the administered reagent can be administered to a mammal in a pure or purified form, i.e., alone, as a pharmaceutically acceptable composition, or in an excipient. Moreover, the following also can apply, optionally, to each of the embodiments disclosed herein. Provided is an administered reagent that is pure or purified, where the administered reagent can be administered in a pure or purified form, i.e., alone, as a pharmaceutically acceptable composition, or in an excipient, and where the reagent is not generated after administration (not generated in the mammal). In one embodiment, what might optionally apply to each of the reagents disclosed herein, is a polypeptide reagent that is administered as a pure or purified polypeptide (e.g., alone, as a pharmaceutically acceptable composition, or in an excipient), where the administered polypeptide reagent is not administered in the form of a nucleic acid encoding that polypeptide, and as a consequence, there is no administered nucleic acid that can generate the polypeptide inside the mammal.

The *Listeria* of the present invention can be stored, e.g., frozen, lyophilized, as a suspension, as a cell paste, or complexed with a solid matrix or gel matrix.

An effective amount for a particular patient may vary depending on factors such as the condition being treated, the overall health of the patient, the route and dose of administration and the severity of side affects. An effective amount for a particular patient may vary depending on factors such as the condition being treated, the overall health of the patient, the route and dose of administration and the severity of side affects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The *Listeria* of the present invention can be administered in a dose, or dosages, where each dose comprises at least 1000 *Listeria* cells/kg body weight; normally at least 10,000 cells; more normally at least 100,000 cells; most normally at least 1 million cells; often at least 10 million cells; more often at least 100 million cells; typically at least 1 billion cells; usually at least 10 billion cells; conventionally at least 100 billion cells; and sometimes at least 1 trillion *Listeria* cells/kg body weight. The present invention provides the above doses where the units of *Listeria* administration is colony forming units (CFU), the equivalent of CFU prior to psoralen-treatment, or where the units are number of *Listeria* cells.

The *Listeria* of the present invention can be administered in a dose, or dosages, where each dose comprises between $10^7$ and $10^8$ *Listeria* per 70 kg body weight (or per 1.7 square meters surface area; or per 1.5 kg liver weight); $2 \times 10^7$ and $2 \times 10^8$ *Listeria* per 70 kg body weight (or per 1.7 square meters surface area; or per 1.5 kg liver weight); $5 \times 10^7$ and $5 \times 10^8$ *Listeria* per 70 kg body weight (or per 1.7 square meters surface area; or per 1.5 kg liver weight); $10^8$ and $10^9$ *Listeria* per 70 kg body weight (or per 1.7 square meters surface area; or per 1.5 kg liver weight); between $2.0 \times 10^8$ and $2.0 \times 10^9$ *Listeria* per 70 kg (or per 1.7 square meters surface area, or per 1.5 kg liver weight); between $5.0 \times 10^8$ to $5.0 \times 10^9$ *Listeria* per 70 kg (or per 1.7 square meters surface area, or per 1.5 kg liver weight); between $10^9$ and $10^{10}$ *Listeria* per 70 kg (or per 1.7 square meters surface area, or per 1.5 kg liver weight); between $2 \times 10^9$ and $2 \times 10^{10}$ *Listeria* per 70 kg (or per 1.7 square meters surface area, or per 1.5 kg liver weight); between $5 \times 10^9$ and $5 \times 10^{10}$ *Listeria* per 70 kg (or per 1.7 square meters surface area, or per 1.5 kg liver weight); between $10^{11}$ and $10^{12}$ *Listeria* per 70 kg (or per 1.7 square meters surface area, or per 1.5 kg liver weight); between $2 \times 10^{11}$ and $2 \times 10^{12}$ *Listeria* per 70 kg (or per 1.7 square meters surface area, or per 1.5 kg liver weight); between $5 \times 10^{11}$ and $5 \times 10^{12}$ *Listeria* per 70 kg (or per 1.7 square meters surface area, or per 1.5 kg liver weight); between $10^{12}$ and $10^{13}$ *Listeria* per 70 kg (or per 1.7 square meters surface area); between $2 \times 10^{12}$ and $2 \times 10^{13}$ *Listeria* per 70 kg (or per 1.7 square meters surface area, or per 1.5 kg liver weight); between $5 \times 10^{12}$ and $5 \times 10^{13}$ *Listeria* per 70 kg (or per 1.7 square meters surface area, or per 1.5 kg liver weight); between $10^{13}$ and $10^{14}$ *Listeria* per 70 kg (or per 1.7 square meters surface area, or per 1.5 kg liver weight); between $2 \times 10^{13}$ and $2 \times 10^{14}$ *Listeria* per 70 kg (or per 1.7 square meters surface area, or per 1.5 kg liver weight); $5 \times 10^{13}$ and $5 \times 10^{14}$ *Listeria* per 70 kg (or per 1.7 square meters surface area, or per 1.5 kg liver weight); between $10^{14}$ and $10^{15}$ *Listeria* per 70 kg (or per 1.7 square meters surface area, or per 1.5 kg liver weight); between $2 \times 10^{14}$ and $2 \times 10^{15}$ *Listeria* per 70 kg (or per 1.7 square meters surface area, or per 1.5 kg liver weight); and so on, wet weight.

The mouse liver, at the time of administering the *Listeria* of the present invention, weighs about 1.5 grams. Human liver weighs about 1.5 kilograms.

Also provided is one or more of the above doses, where the dose is administered by way of one injection every day, one injection every two days, one injection every three days, one injection every four days, one injection every five days, one injection every six days, or one injection every seven days, where the injection schedule is maintained for, e.g., one day only, two days, three days, four days, five days, six days, seven days, two weeks, three weeks, four weeks, five weeks, or longer. The invention also embraces combinations of the above doses and schedules, e.g., a relatively large initial dose of *Listeria*, followed by relatively small subsequent doses of *Listeria*, or a relatively small initial dose followed by a large dose.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The present invention encompasses a method of administering *Listeria* that is oral. Also provided is a method of administering *Listeria* that is intravenous. Moreover, what is provided is a method of administering *Listeria* that is intramuscular. The invention supplies a *Listeria* bacterium, or culture or suspension of *Listeria* bacteria, prepared by growing in a medium that is meat based, or that contains polypeptides derived from a meat or animal product. Also supplied by the present invention is a *Listeria* bacterium, or culture or suspension of *Listeria* bacteria, prepared by growing in a medium that does not contain meat or animal products, prepared by growing on a medium that contains vegetable polypeptides, prepared by growing on a medium that is not based on yeast products, or prepared by growing on a medium that contains yeast polypeptides.

The present invention encompasses a method of administering *Listeria* that is not oral. Also provided is a method of administering *Listeria* that is not intravenous. Moreover, what is provided is a method of administering *Listeria* that is not intramuscular. The invention supplies a *Listeria* bacterium, or culture or suspension of *Listeria* bacteria, prepared by growing in a medium that is not meat based, or that does not contain polypeptides derived from a meat or animal product. Also supplied by the present invention is a *Listeria* bacterium, or culture or suspension of *Listeria* bacteria, prepared by growing in a medium based on vegetable products, that contains vegetable polypeptides, that is based on yeast products, or that contains yeast polypeptides.

Methods for co-administration with an additional therapeutic agent, e.g., a small molecule, antibiotic, innate immunity modulating agent, tolerance modulating agent, cytokine, chemotherapeutic agent, or radiation, are well known in the art (Hardman, et al. (eds.) (2001) Goodman and Gilman's The Pharmacological Basis of Therapeutics, $10^{th}$ ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

The present invention provides reagents for administering in conjunction with an attenuated *Listeria*. These reagents include biological reagents such as: (1) Cytokines, antibodies, dendritic cells, attenuated tumor cells cells; (2) Small molecule reagents such as 5-fluorouracil, methotrexate, paclitaxel, docetaxel, cis-platin, gemcitabine; (3) Reagents that modulate regulatory T cells, such as cyclophosphamide, anti-CTLA4 antibody, anti-CD25 antibody (see, e.g., Hawryfar, et al. (2005) J. Immunol. 174:344-3351); and (4) Vaccines (including polypeptide vaccines, nucleic acid vaccines, attenuated tumor cell vaccines, and dendritic cell vaccines). The reagents can be administered with the *Listeria* or independently (before or after) the *Listeria*. For example, the reagent can be administered immediately before (or after) the *Listeria*, on the same day as, one day before (or after), one week before (or after), one month before (or after), or two months before (or after) the *Listeria*, and the like.

Biological reagents or macromolecules of the present invention encompass an agonist or antagonist of a cytokine, a nucleic acid encoding an agonist or antagonist of a cytokine, a cell expressing a cytokine, or an agonistic or antagonistic antibody. Biological reagents include, without limitation, a TH-1 cytokine, a TH-2 cytokine, IL-2, IL-12, FLT3-ligand, GM-CSF, IFNgamma, a cytokine receptor, a soluble cytokine receptor, a chemokine, tumor necrosis factor (TNF), CD40 ligand, or a reagent that stimulates replacement of a proteasome subunit with an immunoproteasome subunit.

The present invention encompasses biological reagents, such cells engineered to express at least one of the following: GM-CSF, IL-2, IL-3, IL-4, IL-12, IL-18, tumor necrosis factor-alpha (TNF-alpha), or inducing protein-10. Other contemplated reagents include agonists of B7-1, B7-2, CD28, CD40 ligand, or OX40 ligand (OX40L), and novel forms engineered to be soluble or engineered to be membrane-bound (see, e.g., Karnbach, et al. (2001) J. Immunol. 167: 2569-2576; Greenfield, et al. (1998) Crit. Rev. Immunol. 18:389-418; Parney and Chang (2003) J. Biomed. Sci. 10:37-43; Gri, et al. (2003) J. Immunol. 170:99-106; Chiodoni, et al. (1999) J. Exp. Med. 190:125-133; Enzler, et al. (2003) J. Exp. Med. 197:1213-1219; Soo Hoo, et al. (1999) J. Immunol 162:7343-7349; Mihalyo, et al. (2004) J. Immunol. 172: 5338-5345; Chapoval, et al. (1998) J. Immunol. 161:6977-6984).

Without implying any limitation, the present invention provides the following biologicals. MCP-1, MIP1-alpha, TNF-alpha, and interleukin-2, for example, are effective in treating a variety of tumors (see, e.g., Nakamoto, et al. (2000) Anticancer Res. 20(6A):4087-4096; Kamada, et al. (2000) Cancer Res. 60:6416-6420; Li, et al. (2002) Cancer Res. 62:4023-4028; Yang, et al. (2002) Zhonghua Wai Ke Za Zhi 40:789-791; Hoving, et al. (2005) Cancer Res. 65:4300-4308; Tsuchiyama, et al. (2003) Cancer Gene Ther. 10:260-269; Sakai, et al. (2001) Cancer Gene Ther. 8:695-704).

The present invention provides reagents and methods encompassing an Flt3-ligand agonist, and an Flt3-ligand agonist in combination with *Listeria*. Flt3-ligand (Fms-like thyrosine kinase 3 ligand) is a cytokine that can generate an antitumor immune response (see, e.g., Dranoff (2002) Immunol. Revs. 188:147-154; Mach, et al. (2000) Cancer Res. 60:3239-3246; Furumoto, et al. (2004) J. Clin. Invest. 113:774-783; Freedman, et al. (2003) Clin. Cancer Res. 9:5228-5237; Mach, et al. (2000) Cancer Res. 60:3239-3246).

In another embodiment, the present invention contemplates administration of a dendritic cell (DC) that expresses at least one tumor antigen, or infectious disease antigen. Expression by the DC of an antigen can be mediated by way of, e.g., peptide loading, tumor cell extracts, fusion with tumor cells, transduction with mRNA, or transfected by a vector (see, e.g., Klein, et al. (2000) J. Exp. Med. 191:1699-1708; Conrad and Nestle (2003) Curr. Opin. Mol. Ther. 5:405-412; Gilboa and Vieweg (2004) Immunol. Rev. 199:251-263; Paczesny, et al. (2003) Semin. Cancer Biol. 13:439-447; Westermann, et al. (1998) Gene Ther. 5:264-271).

The methods and reagents of the present invention also encompass small molecule reagents, such as 5-fluorouracil, methotrexate, irinotecan, doxorubicin, prednisone, dolostatin-10 (D10), combretastatin A-4, mitomycin C (MMC), vincristine, colchicines, vinblastine, cyclophosphamide, fungal beta-glucans and derivatives thereof, and the like (see, e.g., Hurwitz, et al. (2004) New Engl. J. Med. 350:2335-2342; Pelaez, et al. (2001) J. Immunol. 166:6608-6615; Havas, et al. (1990) J. Biol. Response Modifiers 9:194-204; Turk, et al. (2004) J. Exp. Med. 200:771-782; Ghiringhelli, et al. (2004) Eur. J. Immunol. 34:336-344; Andrade-Mena (1994) Int. J. Tissue React. 16:95-103; Chrischilles, et al. (2003) Cancer Control 10:396-403). Also encompassed are compositions that are not molecules, e.g., salts and ions.

Provided are analogues of cyclophosphamide (see, e.g., Jain, et al. (2004) J. Med. Chem. 47:3843-3852; Andersson, et al. (1994) Cancer Res. 54:5394-5400; Borch and Canute (1991) J. Med. Chem. 34:3044-3052; Ludeman, et al. (1979) J. Med. Chem. 22:151-158; Zon (1982) Prog. Med. Chem. 19:205-246).

Also embraced by the invention are small molecule reagents that stimulate innate immune response, e.g., CpG oligonucleotides, imiquimod, and alphaGalCer. CpG oligonucleotides mediate immune response via TLR9 (see, e.g., Chagnon, et al. (2005) Clin. Cancer Res. 11:1302-1311; Speiser, et al. (2005) J. Clin. Invest. February 3 (epub ahead of print); Mason, et al. (2005) Clin. Cancer Res. 11:361-369; Suzuki, et al. (2004) Cancer Res. 64:8754-8760; Taniguchi, et al. (2003) Annu. Rev. Immunol. 21:483-513; Takeda, et al. (2003) Annu. Rev. Immunol. 21:335-376; Metelitsa, et al. (2001) J. Immunol. 167:3114-3122).

Other useful small molecule reagents include those derived from bacterial peptidoglycan, such as certain NOD2 ligands (McCaffrey, et al. (2004) Proc. Natl. Acad. Sci. USA 101:11386-11391).

The invention includes reagents and methods for modulating activity of T regulatory cells (Tregs; suppressor T cells). Attenuation or inhibition of Treg cell activity can enhance the immune system's killing of tumor cells. A number of reagents have been identified that inhibit Treg cell activity. These reagents include, e.g., cyclophosphamide (a.k.a. Cytoxan®; CTX), anti-CD25 antitobody, modulators of GITR-L or GITR, a modulator of Forkhead-box transcription factor (Fox), a modulator of LAG-3, anti-IL-2R, and anti-CTLA4 (see, e.g., Pardoll (2003) Annu. Rev. Immunol. 21:807-839; Ercolini, et al. (2005) J. Exp. Med. 201:1591-1602; Haeryfar, et al. (2005) J. Immunol. 174:3344-3351; Mihalyo, et al. (2004) J. Immunol. 172:5338-5345; Stephens, et al. (2004) J. Immunol. 173:5008-5020; Schiavoni, et al. (2000) Blood 95:2024-2030; Calmels, et al. (2004) Cancer Gene Ther. October 08 (epub ahead of print); Mincheff, et al. (2004) Cancer Gene Ther. September 17 [epub ahead of print]; Muriglan, et al. (2004) J. Exp. Med. 200:149-157; Stephens, et al. (2004) J. Immunol. 173:5008-5020; Coffer and Burgering (2004) Nat. Rev. Immunol. 4:889-899; Kalinichenko, et al. (2004) Genes Dev. 18:830-850; Cobbold, et al. (2004) J. Immunol. 172:6003-6010; Huang, et al. (2004) Immunity 21:503-513). CTX shows a bimodal effect on the immune system, where low doses of CTX inhibit Tregs (see, e.g., Lutsiak, et al. (2005) Blood 105:2862-2868).

CTLA4-blocking agents, such as anti-CTLA4 blocking antibodies, can enhance immune response to cancers, tumors, pre-cancerous disorders, infections, and the like (see, e.g., Zubairi, et al. (2004) Eur. J. Immunol. 34:1433-1440; Espenschied, et al. (2003) J. Immunol. 170:3401-3407; Davila, et al. (2003) Cancer Res. 63:3281-3288; Hodi, et al. (2003) Proc. Natl. Acad. Sci. USA 100:4712-4717). Where the present invention uses anti-CTLA4 antibodies, and the like, the invention is not necessarily limited to use for inhibiting Tregs, and also does not necessarily always encompass inhibition of Tregs.

Lymphocyte activation gene-3 (LAG-3) blocking agents, such as anti-LAG-3 antibodies or soluble LAG-3 (e.g., LAG-3 Ig), can enhance immune response to cancers or infections. Anti-LAG-3 antibodies reduce the activity of Tregs (see, e.g., Huang, et al. (2004) Immunity 21:503-513; Triebel (2003) Trends Immunol. 24:619-622; Workman and Vignali (2003) Eur. J. Immunol. 33:970-979; Cappello, et al. (2003) Cancer Res. 63:2518-2525; Workman, et al. (2004) J. Immunol. 172:5450-5455; Macon-Lemaitre and Triebel (2005) Immunology 115:170-178).

Vaccines comprising a tumor antigen, a nucleic acid encoding a tumor antigen, a vector comprising a nucleic acid encoding a tumor antigen, a cell comprising a tumor antigen, a tumor cell, or an attenuated tumor cell, are encompassed by the invention. Provided are reagents derived from a nucleic acid encoding a tumor antigen, e.g., a codon optimized nucleic acid, or a nucleic acid encoding two or more different tumor antigens, or a nucleic acid expressing rearranged epitopes of a tumor antigen, e.g., where the natural order of epitopes is ABCD and the engineered order is ADBC, or a nucleic acid encoding a fusion protein comprising at least two different tumor antigens.

Where an administered antibody, binding compound derived from an antibody, cytokine, or other therapeutic agent produces toxicity, an appropriate dose can be one where the therapeutic effect outweighs the toxic effect. Generally, an optimal dosage of the present invention is one that maximizes therapeutic effect, while limiting any toxic effect to a level that does not threaten the life of the patient or reduce the efficacy of the therapeutic agent. Signs of toxic effect, or anti-therapeutic effect include, without limitation, e.g., anti-idiotypic response, immune response to a therapeutic antibody, allergic reaction, hematologic and platelet toxicity, elevations of aminotransferases, alkaline phosphatase, creatine kinase, neurotoxicity, nausea, and vomiting (see, e.g., Huang, et al. (1990) Clin. Chem. 36:431-434).

An effective amount of a therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

The reagents and methods of the present invention provide a vaccine comprising only one vaccination; or comprising a first vaccination; or comprising at least one booster vaccination; at least two booster vaccinations; or at least three booster vaccinations. Guidance in parameters for booster vaccinations is available (see, e.g., Marth (1997) Biologicals 25:199-203; Ramsay, et al. (1997) Immunol. Cell Biol. 75:382-388; Gherardi, et al. (2001) Histol. Histopathol. 16:655-667; Leroux-Roels, et al. (2001) ActA Clin. Belg. 56:209-219; Greiner, et al. (2002) Cancer Res. 62:6944-6951; Smith, et al. (2003) J. Med. Virol. 70:Suppl. 1:S38-S41; Sepulveda-Amor, et al. (2002) Vaccine 20:2790-2795).

Provided is a first reagent that comprises a *Listeria* bacterium (or *Listeria* vaccine), and a second reagent that comprises, e.g., a cytokine, a small molecule such as cyclophosphamide or methotrexate, or a vaccine, such as an attenuated tumor cell or attenuated tumor cell expressing a cytokine. Provided are the following methods of administration of the first reagent and the second reagent.

The *Listeria* and the second reagent can be administered concomitantly, that is, where the administering for each of these reagents can occur at time intervals that partially or fully overlap each other. The *Listeria* and second reagent can be administered during time intervals that do not overlap each other. For example, the first reagent can be administered within the time frame of t=0 to 1 hours, while the second reagent can be administered within the time frame of t=1 to 2 hours. Also, the first reagent can be administered within the time frame of t=0 to 1 hours, while the second reagent can be administered somewhere within the time frame of t=2-3 hours, t=3-4 hours, t=4-5 hours, t=5-6 hours, t=6-7 hours, t=7-8 hours, t=8-9 hours, t=9-10 hours, and the like. Moreover, the second reagent can be administered somewhere in the time frame of t=minus 2-3 hours, t=minus 3-4 hours, t=minus 4-5 hours, t=5-6 minus hours, t=minus 6-7 hours, t=minus 7-8 hours, t=minus 8-9 hours, t=minus 9-10 hours, and the like:

To provide another example, the first reagent can be administered within the time frame of t=0 to 1 days, while the second reagent can be administered within the time frame of t=1 to 2 days. Also, the first reagent can be administered within the time frame of t=0 to 1 days, while the second reagent can be administered somewhere within the time frame of t=2-3 days, t=3-4 days, t=4-5 days, t=5-6 days, t=6-7 days, t=7-8 days, t=8-9 days, t=9-10 days, and the like. Moreover, the second reagent can be administered somewhere in the time from of t=minus 2-3 days, t=minus 3-4 days, t=minus 4-5 days, t=minus 5-6 days, t=minus 6-7 days, t=minus 7-8 days, t=minus 8-9 days, t=minus 9-10 days, and the like.

In another aspect, administration of the *Listeria* can begin at t=0 hours, where the administration results in a peak (or maximal plateau) in plasma concentration of the *Listeria*, and where administration of the second reagent is initiated at about the time that the concentration of plasma *Listeria* reaches said peak concentration, at about the time that the concentration of plasma *Listeria* is 95% said peak concentration, at about the time that the concentration of plasma *Listeria* is 90% said peak concentration, at about the time that the concentration of plasma *Listeria* is 85% said peak concentration, at about the time that the concentration of plasma *Listeria* is 80% said peak concentration, at about the time that the concentration of plasma *Listeria* is 75% said peak concentration, at about the time that the concentration of plasma *Listeria* is 70% said peak concentration, at about the time that the concentration of plasma *Listeria* is 65% said peak concentration, at about the time that the concentration of plasma *Listeria* is 60% said peak concentration, at about the time that the concentration of plasma *Listeria* is 55% said peak concentration, at about the time that the concentration of plasma *Listeria* is 50% said peak concentration, at about the time that the concentration of plasma *Listeria* is 45% said peak concentration, at about the time that the concentration of plasma *Listeria* is 40% said peak concentration, at about the time that the concentration of plasma *Listeria* is 35% said peak concentration, at about the time that the concentration of plasma *Listeria* is 30% said peak concentration, at about the time that the concentration of plasma *Listeria* is 25% said peak concentration, at about the time that the concentration of plasma *Listeria* is 20% said peak concentration, at about the time that the concentration of plasma *Listeria* is 15% said peak concentration, at about the time that the concentration of plasma *Listeria* is 10% said peak concentration, at about the time that the concentration of plasma *Listeria* is 5% said peak concentration, at about the time that the concentration of plasma *Listeria* is 2.0% said peak concentration, at about the time that the concentration of plasma *Listeria* is 0.5% said peak concentration, at about the time that the concentration of plasma *Listeria* is 0.2% said peak concentration, or at about the time that the concentration of plasma *Listeria* is 0.1%, or less than, said peak concentration.

In another aspect, administration of the second reagent can begin at t=0 hours, where the administration results in a peak (or maximal plateau) in plasma concentration of the second reagent and where administration of the *Listeria* is initiated at about the time that the concentration of plasma level of the second reagent reaches said peak concentration, at about the time that the concentration of plasma second reagent is 95% said peak concentration, at about the time that the concentration of plasma second reagent is 90% said peak concentration, at about the time that the concentration of plasma second reagent is 85% said peak concentration, at about the time that the concentration of plasma second reagent is 80% said peak concentration, at about the time that the concentration of plasma second reagent is 75% said peak concentration, at about the time that the concentration of plasma second reagent is 70% said peak concentration, at about the time that the concentration of plasma second reagent is 65% said peak concentration, at about the time that the concentration of plasma second reagent is 60% said peak concentration, at about the time that the concentration of plasma second reagent is 55% said peak concentration, at about the time that the concentration of plasma second reagent is 50% said peak concentration, at about the time that the concentration of plasma second reagent is 45% said peak concentration, at about the time that the concentration of plasma second reagent is 40% said peak concentration, at about the time that the concentration of plasma second reagent is 35% said peak concentration, at about the time that the concentration of plasma second reagent is 30% said peak concentration, at about the time that the concentration of plasma second reagent is 25% said peak concentration, at about the time that the concentration of plasma second reagent is 20% said peak concentration, at about the time that the concentration of plasma second reagent is 15% said peak concentration, at about the time that the concentration of plasma second reagent is 10% said peak concentration, at about the time that the concentration of plasma second reagent is 5% said peak concentration, at about the time that the concentration of plasma reagent is 2.0% said peak concentration, at about the time that the concentration of plasma second reagent is 0.5% said peak concentration, at about the time that the concentration of plasma second reagent is 0.2% said peak concentration, or at about the time that the concentration of plasma second reagent is 0.1%, or less than, said peak concentration. As it is recognized that alteration of the *Listeria* or second reagent may occur in vivo, the above concentrations can be assessed after measurement of intact reagent, or after measurement of an identifiable degradation product of the intact reagent.

Formulations of therapeutic and diagnostic agents may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

The invention also provides a kit comprising a *Listeria* cell, a listerial cell culture, or a lyophilized cell preparation, and a compartment. In addition, the present invention provides a kit comprising a *Listeria* cell, listerial cell culture, or a lyophilized cell preparation and a reagent. Also provided is a kit comprising a *Listeria* cell, a listerial cell culture, or a lyophilized cell preparation and instructions for use or disposal. Moreover, the present invention provides a kit comprising a *Listeria* cell, a listerial cell culture, or lyophilized cell preparation, and compartment and a reagent. Provided is a kit comprising *Listeria* bacteria, and instructions for using the *Listeria* bacteria with a small molecule anti-cancer agent, and/or small molecule immunomodulating agent (e.g., cyclophosphamide), and/or a small molecule anti-infection agent, and the like. Also provided is a kit comprising *Listeria* bacteria, and/or instructions for administering the *Listeria*, and/or instructions for monitoring immune response to the administered *Listeria*, and/or instructions for monitoring immune response to a heterologous antigen encoded by the administered *Listeria*.

(b). Uses.

The invention provides, in certain embodiments, a modified *Listeria* bacterium, e.g., *L. monocytogenes*, engineered to express at least one heterologous antigen. The invention is useful for enhancing immune response, stimulating immune response, enhancing immune presentation, increasing stability of an expressed mRNA or polypeptide, increasing proteolytic processing of an expressed polypeptide, increasing immune response to a mutated self antigen, increasing survival to a cancer or infection, and for treating a cancer or infection. The invention is also useful for enhanced expression of a heterologous antigen, e.g., for industry, agriculture, or medicine.

For methods to stimulate, enhance, or increase immune response to a cancer, tumor, or infectious agent; and for methods to stimulate, enhance, or increase survival to a cancer, tumor, or infectious agent; an increase can occur with administration of a *Listeria* containing a nucleic acid encoding a heterologous antigen. For purposes of providing an experimental control, the increase can be relative to response with administration of a *Listeria* not containing a nucleic acid encoding that particular heterologous antigen. As another alternative, the increase can be relative to response with administering a *Listeria* not containing any nucleic acid that encodes a heterologous antigen, e.g., a parental or wild type *Listeria*. As still another alternative, the increase can be relative to response without administering any *Listeria*.

For methods to stimulate, enhance, or increase immune response to a cancer, tumor, or infectious agent; and for methods to stimulate, enhance, or increase survival to a cancer, tumor, or infectious agent; an increase can occur with administration of a *Listeria* (containing or not containing a nucleic acid encoding a heterologous antigen) with an immune modulator, such as an agonist antibody, a cytokine, or an antibody that specifically binds to an antigen of the cancer, tumor, or infectious agent. For purposes of providing an experimental control, the increase can be relative to response with administration of a *Listeria* but without administering the immune modulator. As an alternative, the increase can be relative to any response with administering the immune modulator, but without administering any *Listeria*. As still another alternative, the increase can be relative to response without administering any *Listeria* and without administering the immune modulator.

The invention provides a *Listeria* bacterium, or a *Listeria* strain, that is killed but metabolically active (KBMA) (see, e.g., Brockstedt, et al (2005) Nat. Med. 11:853-860). A KBMA *Listeria* bacterium is metabolically active, but cannot form a colony, e.g., on agar. An inactivating mutation in at least one DNA repair gene, e.g., $\Delta uvrAB$, enables killing of *Listeria* using concentrations of a nucleic acid cross-linking agent (e.g., psoralen) at low concentrations, where these concentrations are sufficient to prevent colony formation but not sufficient to substantially impair metabolism, or to detectably impair metabolism. The result of limited treatment with psoralen/UVA light, and/or of treatment with a nucleic acid cross-linking agent that is highly specific for making interstrand genomic cross links, is that the bacterial cells are killed but remain metabolically active.

The present invention results in the reduction of the number of abnormally proliferating cells, reduction in the number of cancer cells, reduction in the number of tumor cells, reduction in the tumor volume, reduction of the number of infectious organisms or pathogens per unit of biological fluid or tissue (e.g., serum), reduction in viral titer (e.g., serum), where it is normally reduced by at least 5%, more normally reduced by at least 10%, most normally reduced by at least 15%, typically reduced by at least 20%, more typically reduced by at least 25%, most typically reduced by at least 30%, usually reduced by at least 40%, more usually reduced by at least 50%, most usually reduced by at least 60%, conventionally reduced by at least 70%, more conventionally reduced by at least 80%, most conventionally reduced by at least 90%, and still most conventionally reduced by at least 99%. The unit of reduction can be, without limitation, number of tumor cells/mammalian subject; number of tumor cells/liver; number of tumor cells/spleen; mass of tumor cells/mammalian subject; mass of tumor cells/liver; mass of tumor cells/spleen; number of viral particles or viruses or titer per gram of liver; number of viral particles or viruses or titer per cell; number of viral particles or viruses or titer per ml of blood; and the like.

The growth medium used to prepare a *Listeria* can be characterized by chemical analysis, high pressure liquid chromatography (HPLC), mass spectroscopy, gas chromatography, spectroscopic methods, and the like. The growth medium can also be characterized by way of antibodies specific for components of that medium, where the component occurs as a contaminant with the *Listeria*, e.g., a contaminant in the listerial powder, frozen preparation, or cell paste. Antibodies, specific for peptide or protein antigens, or glycolipid, glycopeptide, or lipopeptide antigens, can be used in ELISA assays formulated for detecting animal-origin contaminants. Antibodies for use in detecting antigens, or antigenic fragments, of animal origin are available (see, e.g., Fukuta, et al. (1977) Jpn. Heart J. 18:696-704; DeVay and Adler (1976) Ann. Rev. Microbiol. 30:147-168; Cunningham, et al. (1984) Infection Immunity 46:34-41; Kawakita, et al. (1979) Jpn. Cir. J. 43:452-457; Hanly, et al. (1994) Lupus 3:193-199; Huppi, et al. (1987) Neurochem. Res. 12:659-665; Quackenbush, et al. (1985) Biochem. J. 225:291-299). The invention supplies kits and diagnostic methods that facilitate testing the *Listeria*'s influence on the immune system. Testing can involve comparing one strain of *Listeria* with another strain of *Listeria*, or a parent *Listeria* strain with a mutated *Listeria* strain. Methods of testing comprise, e.g., phagocytosis, spreading, antigen presentation, T cell stimulation, cytokine response, host toxicity, $LD_{50}$, and efficacy in ameliorating a pathological condition.

The present invention provides methods to increase survival of a subject, host, patient, test subject, experimental subject, veterinary subject, and the like, to a cancer, a tumor, a precancerous disorder, an immune disorder, and/or an infectious agent. The infectious agent can be a virus, bacterium, or parasite, or any combination thereof. The method comprises administering an attenuated *Listeria*, for example, as a suspension, bolus, gel, matrix, injection, or infusion, and the like. The administered *Listeria* increases survival, as compared to an appropriate control (e.g., nothing administered or an administered placebo, and the like) by usually at least one day; more usually at least four days; most usually at least eight days, normally at least 12 days; more normally at least 16 days; most normally at least 20 days, often at least 24 days; more often at least 28 days; most often at least 32 days, conventionally at least 40 days, more conventionally at least 48 days; most conventionally at least 56 days; typically by at least 64 days; more typically by at least 72 days; most typically at least 80 days; generally at least six months; more generally at least eight months; most generally at least ten months; commonly at least 12 months; more commonly at least 16 months; and most commonly at least 20 months, or more.

Each of the above disclosed methods contemplates administering a composition comprising a *Listeria* and an excipient, a *Listeria* and a carrier, a *Listeria* and buffer, a *Listeria* and a reagent, a *Listeria* and a pharmaceutically acceptable carrier, a *Listeria* and an agriculturally acceptable carrier, a *Listeria* and a veterinarily acceptable carrier, a *Listeria* and a stabilizer, a *Listeria* and a preservative, and the like.

The present invention provides reagents and methods for treating conditions that are both cancerous (neoplasms, malignancies, cancers, tumors, and/or precancerous disorders, dysplasias, and the like) and infectious (infections). Provided are reagents and methods for treating disorders that are both cancerous (neoplasms, malignancies, cancers, tumors, and/or precancerous disorders, dysplasias, and the like) and infectious. With infection with certain viruses, such as papillomavirus and polyoma virus, the result can be a cancerous condition, and here the condition is both cancerous and infectious. A condition that is both cancerous and infectious can be detected, as a non-limiting example, where a viral infection results in a cancerous cell, and where the cancerous cell expresses a viral-encoded antigen. As another non-limiting example, a condition that is both cancerous and infectious is one where immune response against a tumor cell involves specific recognition against a viral-encoded antigen (See, e.g., Montesano, et al. (1990) Cell 62:435-445; Ichaso and Dilworth (2001) Oncogene 20:7908-7916; Wilson, et al. (1999) J. Immunol. 162:3933-3941; Daemen, et al. (2004) Antivir. Ther. 9:733-742; Boudewijn, et al. (2004) J. Natl. Cancer Inst. 96:998-1006; Liu, et al. (2004) Proc. Natl. Acad. Sci. USA 101:14567-14571).

The following embodiments relate to the individual embodiments disclosed herein.

The present invention, in certain embodiments, comprises a method of stimulating the immune system against an infectious disorder, where the infectious disorder is a *Listeria* infection. Also comprised, is a method of stimulating the immune system against an infectious disorder, where the infectious disorder is not a *Listeria* infection, that is, excludes *Listeria* infections.

Each of the embodiments encompasses, as an alternate or additional reagent, a *Listeria* that is not attenuated. Also, each of the embodiments encompasses, as an alternate or additional reagent, a *Listeria* that is attenuated. Each of the embodiments encompasses, as an alternate or additional method, using a *Listeria* that is not attenuated. Also, each of the embodiments encompasses, as an alternate or additional method, using a *Listeria* that is attenuated.

Each of the embodiments disclosed herein encompasses methods and reagents using a *Listeria* that comprises a nucleic acid encoding at least one tumor antigen, a *Listeria* that comprises a nucleic acid encoding at least one cancer antigen, a *Listeria* that comprises a nucleic acid encoding at least one heterologous antigen, as well as a *Listeria* that expresses at least one tumor antigen, cancer antigen, and/or heterologous antigen.

Each of the embodiments disclosed herein encompasses methods and reagents using a *Listeria* that does not comprise a nucleic acid encoding a tumor antigen, a *Listeria* that does not comprise a nucleic acid encoding a cancer antigen, a *Listeria* that does not comprise a nucleic acid encoding a heterologous antigen, as well as a *Listeria* that does not express a tumor antigen, cancer antigen, and/or a heterologous antigen.

Each of the embodiments disclosed herein encompasses methods and reagents using a *Listeria* that comprises a nucleic acid encoding an antigen from a non-listerial infectious organism. Each of the above-disclosed embodiments encompasses methods and reagents using a *Listeria* that comprises a nucleic acid encoding at least one antigen from a virus, parasite, bacterium, tumor, self-antigen derived from a tumor, or non-self antigen derived from a tumor.

Each of the embodiments disclosed herein encompasses methods and reagents using a *Listeria* that does not comprise a nucleic acid encoding an antigen from a non-listerial infectious organism. Each of the above-disclosed embodiments encompasses methods and reagents using a *Listeria* that does not comprise a nucleic acid encoding at least one antigen from a virus, parasite, bacterium, tumor, self-antigen derived from a tumor, or non-self antigen derived from a tumor.

Each of the embodiments disclosed herein also encompasses a *Listeria* that is not prepared by growing on a medium based on animal protein, but is prepared by growing on a different type of medium. Each of the above-disclosed embodiments also encompasses a *Listeria* that is not prepared by growing on a medium containing peptides derived from animal protein, but is prepared by growing on a different type of medium. Moreover, each of the above-disclosed embodiments encompasses administration of a *Listeria* by a route that is not oral or that is not enteral. Additionally, each of the above-disclosed embodiments includes administration of a *Listeria* by a route that does not require movement from the gut lumen to the lymphatics or bloodstream.

Each of the embodiments disclosed herein further comprises a method wherein the *Listeria* are not injected directly into the tumor or are not directly injected into a site that is affected by the cancer, precancerous disorder, tumor, or infection.

Additionally, each of the embodiments disclosed herein encompasses administering the *Listeria* by direct injection into a tumor, by direct injection into a cancerous lesion, and/or by direct injection into a lesion of infection. Also, the invention includes each of the above embodiments, where administration is not by direct injection into a tumor, not by direct injection into a cancerous lesion, and/or not by direct injection into a lesion of infection.

Provided is a vaccine where the heterologous antigen, as in any of the embodiments disclosed herein, is a tumor antigen or is derived from a tumor antigen. Also provided is a vaccine where the heterologous antigen, as in any of the embodiments disclosed herein, is a cancer antigen, or is derived from a cancer antigen. Moreover, what is provided is a vaccine where the heterologous antigen, as in any of the embodiments disclosed herein, is an antigen of an infectious organism, or is derived from an antigen of an infectious organism, e.g., a virus, bacterium, or multi-cellular organism.

A further embodiment provides a nucleic acid where the heterologous antigen, as in any of the embodiments disclosed herein, is a tumor antigen or derived from a tumor antigen. Also provided is a nucleic acid where the heterologous antigen, as in any of the embodiments disclosed herein, is a cancer antigen, or is derived from a cancer antigen. Moreover, what is provided is a nucleic acid, where the heterologous antigen, as in any of the embodiments disclosed herein, is an antigen of an infectious organism, or is derived from an antigen of an infectious organism, e.g., a virus, bacterium, or multi-cellular organism.

In another embodiment, what is provided is a *Listeria* where the heterologous antigen, as in any of the embodiments disclosed herein, is a tumor antigen or derived from a tumor antigen. Also provided is a *Listeria* where the heterologous antigen, as in any of the examples disclosed herein, is a cancer antigen, or is derived from a cancer antigen. Moreover, what is provided is a *Listeria*, where the heterologous antigen, as in any of the embodiments disclosed herein, is an antigen from an infectious organism or derived from an antigen of an infectious organism, e.g., a virus, bacterium, parasite, or multi-cellular organism.

Each of the above-disclosed embodiments also encompasses an attenuated *Listeria* that is not prepared by growing on a medium based on animal or meat protein, but is prepared by growing on a different type of medium. Provided is an attenuated *Listeria* not prepared by growing on a medium based on meat or animal protein, but is prepared by growing on a medium based on yeast and/or vegetable derived protein.

Unless specified otherwise, each of the embodiments disclosed herein encompasses a bacterium that does not contain a nucleic acid encoding a heterologous antigen. Also, unless specified otherwise, each of the embodiments disclosed herein encompasses a bacterium that does not contain a nucleic acid encoding a heterologous regulatory sequences. Optionally, every one of the embodiments disclosed herein encompasses a bacterium that contains a nucleic acid encoding a heterologous antigen and/or encoding a heterologous regulatory sequence.

The following concerns bacterial embodiments, e.g., of *Listeria, Bacillus anthracis*, or another bacterium, that encode secreted antigens, non-secreted antigens, secreted antigens that are releasable from the bacterium by a mechanism other than secretion, and non-secreted antigens that are releasable by a mechanism other than secretion. What is embraced is a bacterium containing a polynucleotide comprising a nucleic acid, where the nucleic acid encodes a polypeptide that contains a secretory sequence and is secreted under appropriate conditions; where the nucleic acid encodes a polypeptide that does not contain a secretory sequence; where the nucleic acid does contain a secretory sequence and where the polypeptide is releasable by some other mechanism such as enzymatic damage or perforation to the cell membrane or cell wall; and where the nucleic acid encodes a polypeptide that does not contain any secretory sequence but where the polypeptide is releasable by some other mechanism, such as enzymatic damage or perforation to the cell membrane and/or cell wall.

Without implying any limitation, as to narrowness or breadth, of the present invention, the invention can be modified by the skilled artisan to comprise any one of the following embodiments, or to consist of any one of the following embodiments (Table 10).

TABLE 10

Spread of the bacterium of the present invention, i.e., transmission of a bacterium from a first host cell to a second host cell.

Without implying any limitation to the bacterium of the present invention, e.g., with regard to its ability to spread from cell to cell, the spread of the bacterium of the present invention can encompass one or more of the following. Without implying any lack of limitation to the bacterium of the present invention, e.g., with regard to its ability to spread from cell to cell, the spread of the bacterium of the present invention can encompass one or more of the following.

| | | |
|---|---|---|
| The spread of the bacterium of the present invention can be | at most 1%; at most 5%; at most 10%; at most 20%; at most 30%; at most 40%; at most 50%; at most 60%; at most 70%; at most 80%; at most 90%; at most 95%; at most 100%; at most 200%; at most 300%; at most 400%; at most 500%, | as compared to the spread of a suitable control or parent bacterium. |
| The spread of the bacterium of the present invention can be | at least 1%; at least 5%; at least 10%; at least 20%; at least 30%; at least 40%; at least 50%; at least 60%; at least 70%; at least 80%; at least 90%; at least 95%; at least 100%; at least 200%; at least 300%; at least 400%; at least 500%, | as compared to the spread of a suitable control or parent bacterium. |
| The spread of the bacterium of the present invention can be | 0 to 1%; 1% to 5%; 5% to 10%; 10% to 20%; 20% to 30%; 30% to 40%; 40% to 50%; 50% to 60%; 60% to 70%; 70% to 80%; 80% to 90%; 90% to 95%; | as compared to the spread of a suitable control or parent bacterium. |

TABLE 10-continued

Spread of the bacterium of the present invention, i.e., transmission of a bacterium from a first host cell to a second host cell.

90% to 100%; 100% to 200%; 200% to 300%; 300% to 400%; 400% to 500%, or greater than 500%, Growth of the *Listeria* strain of the present invention. Without implying any limitation to the present invention, e.g., as to narrowness or to breadth, the present invention can encompass any one, or any of combination, of the following embodiments. Without implying any lack of limitation to the present invention, the present invention can encompass any one, or any combination, of the following embodiments.

| | | |
|---|---|---|
| Growth of the *Listeria* strain of the present invention is at least | 0.1%; 0.5%; 1.0%; 5%; 10%; 15%; 20%; 25%; 30%; 35%; 40%; 45%; 50%; 55%; 60%; 65%; 70%; 75%; 80%; 85%; 90%; 95%; 99%; 99.5%; 99.5%, 2-fold; 5-fold; 10-fold; or greater than 10-fold, | as compared with the parent *Listeria* or with a suitable control *Listeria*. |
| Growth of the *Listeria* strain of the present invention is at most | not detectable, 0.1%; 0.5%; 1.0%; 5%; 10%; 15%; 20%; 25%; 30%; 35%; 40%; 45%; 50%; 55%; 60%; 65%; 70%; 75%; 80%; 85%; 90%; 95%; 99%; 99.5%; 99.5%, 2-fold; 5-fold; 10-fold; or greater than 10-fold, | as compared with the parent *Listeria* or with a suitable control *Listeria*. |
| Growth of the *Listeria* strain of the present invention is less than | 0.1%; 0.5%; 1.0%; 5%; 10%; 15%; 20%; 25%; 30%; 35%; 40%; 45%; 50%; 55%; 60%; 65%; 70%; 75%; 80%; 85%; 90%; 95%; 99%; 99.5%; or 99.5%; 2-fold; 5-fold; 10-fold; or greater than 10-fold, | as compared with the parent *Listeria* or with a suitable control *Listeria*. |
| Growth of the *Listeria* strain of the present invention is more than | 0.1%; 0.5%; 1.0%; 5%; 10%; 15%; 20%; 25%; 30%; 35%; 40%; 45%; 50%; 55%; 60%; 65%; 70%; 75%; 80%; 85%; 90%; 95%; 99%; 99.5%; 99.5%, 2-fold; 5-fold; 10-fold; or greater than 10-fold, | as compared with the parent *Listeria* or with a suitable control *Listeria*. |
| Growth of the *Listeria* of the present invention is between | 0-0.1%; 0.1-0.5%; 0.5-1.0%; 1.0-5%; 5-10%; 10-15%; 15-20%; 20-25%; 25-30%; 30-35%; 35-40%; 40-45%; 45-50%; 50-55%; 55-60%; 60-65%; 65-70%; 70-75%; 75-80%; 80-85%; 85-90%; 90-95%; 95-99%; 99-99.5%; 99.5-99.5%, 99.5%-greater, 100% to 2-fold; 2-fold to 10-fold; 10-fold to greater than 10-fold, | as compared with the parent *Listeria* or with a suitable control *Listeria*. |

Growth of the *Listeria* strain of the present invention.

| | | |
|---|---|---|
| Extracellular growth of the *Listeria* strain of the present invention is at least | 0.1%; 0.5%; 1.0%; 5%; 10%; 15%; 20%; 25%; 30%; 35%; 40%; 45%; 50%; 55%; 60%; 65%; 70%; 75%; 80%; 85%; 90%; 95%; 99%; 99.5%; or greater than 99.5%, 100%, 2-fold greater; 5-fold greater; or 10-fold greater, | as compared with intracellular growth of the same *Listeria* strain. |
| Extracellular growth of the *Listeria* strain of the present invention is | 0-0.1%; 0.1-0.5%; 0.5-1.0%; 1.0-5%; 5-10%; 10-15%; 15-20%; 20-25%; 25-30%; 30-35%; 35-40%; 40-45%; 45-50%; 50-55%; 55-60%; 60-65%; 65-70%; 70-75%; 75-80%; 80-85%; 85-90%; 90-95%; 95-99%; 99-99.5%; 99.5-100%, 100-200%; 200-500%; 500-1000%; or greater than 1000%, | as compared with intracellular growth of the same *Listeria* strain. |

Growth related genes. A growth related gene of the present invention can include, but is not necessarily limited in narrowness or in breadth, by the following.

| | | |
|---|---|---|
| A growth related gene embraces one that stimulates the rate of intracellular growth by | the same amount, by at least 10% greater; by at least 20% greater; by at least 30% greater; by at least 40% greater; by at least 50% greater; by at least 60% greater; by at least 70% greater; by at least 80% greater; by at least 90% greater; by at least TABLE 10-continued Spread of the bacterium of the present invention, i.e., transmission of a bacterium from a first host cell to a second host cell.

Growth of a *Listeria* strain of the present invention can be compared with a parent, or suitable control, *Listeria* strain, where only intracellular growth is compared. Growth of a *Listeria* strain of the present invention can be compared with a parent, or suitable control, *Listeria* strain, where only extracellular growth is compared. Growth of a *Listeria* strain of the present invention can be compared with a parent, or suitable control, *Listeria* strain, where intracellular growth of the present invention strain is compared with extracellular growth of a parent or suitable control strain.
Growth of a *Listeria* strain of the present invention can be compared with a parent, or suitable control, *Listeria* strain, where extracellular growth of the present invention strain is compared with intracellular growth of a parent or suitable control strain.
Metabolically active bacteria. Without implying any limitation to the present invention, e.g., as to narrowness or to breadth, the present invention can encompass any one, or any of combination, of the following embodiments. Without implying any lack of limitation to the present invention, e.g., as to narrowness or to breadth, the present invention can encompass any one, or any of combination, of the following embodiments.

| | | |
|---|---|---|
| A metabolically active but colony formation impaired (and/or cell division or replication impaired) *Listeria* bacterium of the present invention encompasses a *Listeria* bacterium where the rate of colony formation, cell division, and/or replication is under 40% that of a parent or control *Listeria* bacterium, | and where metabolism is greater than 10-fold; 10-fold to 5-fold; 5-fold to 4-fold; 4-fold to 2-fold; 2-fold to 100%; essentially 100%; 100% to 95%; 95% to 90%; 90% to 80%; 80% to 70%; 70% to 60%; 60% to 50%; 50% to 40%, | that of the control or parent *Listeria* bacterium. |
| A metabolically active but colony formation impaired (and/or cell division or replication impaired) *Listeria* bacterium of the present invention encompasses a *Listeria* bacterium where the rate of colony formation, cell division, and/or replication is under 30% that of a parent or control *Listeria* bacterium, | and where metabolism is greater than 10-fold; 10-fold to 5-fold; 5-fold to 4-fold; 4-fold to 2-fold; 2-fold to 100%; essentially 100%; 100% to 95%; 95% to 90%; 90% to 80%; 80% to 70%; 70% to 60%; 60% to 50%; 50% to 40%; or 40% to 30, | that of the control or parent *Listeria* bacterium. |
| A metabolically active but colony formation impaired (and/or cell division or replication impaired) *Listeria* bacterium of the present invention encompasses a *Listeria* bacterium where the rate of colony formation, cell division, and/or replication is under 20% that of a parent or control *Listeria* bacterium, | and where metabolism is greater than 10-fold; 10-fold to 5-fold; 5-fold to 4-fold; 4-fold to 2-fold; 2-fold to 100%; essentially 100%; 100% to 95%; 95% to 90%; 90% to 80%; 80% to 70%; 70% to 60%; 60% to 50%; 50% to 40%; 40% to 30; or 30 to 20%, | that of the control or parent *Listeria* bacterium. |
| A metabolically active but colony formation impaired (and/or cell division or replication impaired) *Listeria* bacterium of the present invention encompasses a *Listeria* bacterium where the rate of colony formation, cell division, and/or replication is under 10% that of a parent or control *Listeria* bacterium, | and where metabolism is greater than 10-fold; 10-fold to 5-fold; 5-fold to 4-fold; 4-fold to 2-fold; 2-fold to 100%; essentially 100%; 100% to 95%; 95% to 90%; 90% to 80%; 80% to 70%; 70% to 60%; 60% to 50%; 50% to 40%; 40% to 30; 30 to 20%; or 20 to 10%, | that of the control or parent *Listeria* bacterium. |
| A metabolically active but colony formation impaired (and/or cell division or replication impaired) *Listeria* bacterium of the present invention encompasses a *Listeria* bacterium where the rate of colony formation, cell division, and/or replication is under 5% that of a parent or control *Listeria* bacterium, | and where metabolism is greater than 10-fold; 10-fold to 5-fold; 5-fold to 4-fold; 4-fold to 2-fold; 2-fold to 100%; essentially 100%; 100% to 95%; 95% to 90%; 90% to 80%; 80% to 70%; 70% to 60%; 60% to 50%; 50% to 40%; 40% to 30; 30 to 20%; 20 to 10%; or 10 to 5%, Metabolically active bacteria. | that of the control or parent *Listeria* bacterium. |
| A metabolically active but colony formation impaired (and/or cell division or replication impaired) *Listeria* bacterium of the present invention encompasses a *Listeria* bacterium where the rate of colony formation, cell division, and/or replication is under 1% that of a parent or control *Listeria* bacterium, | and where metabolism is greater than 10-fold; 10-fold to 5-fold; 5-fold to 4-fold; 4-fold to 2-fold; 2-fold to 100%; essentially 100%; 100% to 95%; 95% to 90%; 90% to 80%; 80% to 70%; 70% to 60%; 60% to 50%; 50% to 40%; 40% to 30; 30 to 20%; 20-10%; 10-5%; or 5% to 1%, | that of the control or parent *Listeria* bacterium. |

A "killed but metabolically active" (KMBA) bacterium, is a *Listeria* bacterium that is unable to form colonies and where metabolism is, e.g., 10-fold to 5-fold (an indicator of metabolism occurring at a level higher than normally found); 5-fold to 4-fold; 4-fold to 2-fold; 2-fold to 100%; essentially 100%; 100% to 95%; 95% to 90%; 90% to 80%; 80% to 70%; 70% to 60%; 60% to 50%; 50% to 40%; 40% to 30; 30 to 20%; 20 to 10%; or 10 to 5%, that of a control or parent *Listeria* bacterium. In another aspect, a KBMA bacterium is a *Listeria* bacterium where the rate of colony formation is under 1% that of a control or parent *Listeria* bacterium, and where metabolism is, e.g., 10-fold to 5-fold; 5-fold to 4-fold; 4-fold to 2-fold; 2-fold to 100%; essentially 100%; 100% to 95%; 95% to 90%; 90% to 80%; 80% to 70%; 70% to 60%; 60% to 50%; 50% to 40%; 40% to 30; 30 to 20%; 20 to 10%; or 10 to 5%, that of the control or parent *Listeria* bacterium. In yet another aspect, a KBMA bacterium is a *Listeria* bacterium where the rate of colony formation is under 2% that of a control or parent *Listeria* bacterium, and where metabolism is, e.g., 10-fold to 5-fold; 5-fold to 4-fold; 4-fold to 2-fold; 2-fold to 100%; essentially 100%; 100% to 95%; 95% to 90%; 90% to 80%; 80% to 70%; 70% to 60%; 60% to 50%; 50% to 40%; 40% to 30; 30 to 20%; 20 to 10%; or 10 to 5%, that of the control or parent *Listeria* bacterium. In another embodiment, a KBMA bacterium is a *Listeria* bacterium where the rate of colony formation is under 5% that of a control or parent *Listeria* bacterium, and where metabolism is, e.g., 10-fold to 5-fold; 5-fold to 4-fold; 4-fold to 2-fold; 2-fold to 100%; essentially 100%; 100% to 95%; 95% to 90%; 90% to 80%; 80% to 70%; 70% to 60%; 60% to 50%; 50% to 40%; 40% to 30; 30 to 20%; 20 to 10%; or 10 to 5%, that of the control or parent *Listeria* bacterium.

The rate of metabolism can be measured by various indicia, e.g., translation, respiration, secretion, transport, fermentation, glycolysis, amino acid metabolism, or the Krebs cycle. Various indicia of metabolism for *L. monocytogenes* are disclosed (see, e.g., Karlin, et al. (2004) Proc. Natl. Acad. Sci. USA 101:6182-6187; Gilbreth, et al. (2004) Curr. Microbiol. 49:95-98). Often, metabolism is assessed with intact bacteria by way of radioactive, heavy isotope, or fluorescent tagged metabolites. The skilled artisan can choose a suitable gene for measuring translation, or a suitable enzyme for measuring glycolysis, amino acid metabolism, or the Krebs cycle. A heat-killed bacterium generally is essentially or totally metabolically inactive. Residual apparent metabolic activity of an essentially or totally metabolically inactive bacterium can be due, e.g., to oxidation of lipids, oxidation of sulfhydryls, reactions catalyzed by heavy metals, or to enzymes that are stable to heat-treatment.

(c) Methods for Assessing Immune Response; Methods of Diagnosis.

Reagents and methods useful for determining, assessing, monitoring, and/or diagnosing immune response are available. The present invention, in some situations, provides the following methods for diagnosing a mammalian subject administered with the compositions of the present invention. In other aspects, what is provided are the following methods for assessing immune response to one or more of the administered compositions of the present invention. These methods, which can be applied, e.g., in vivo, in vitro, ex vivo, in utero; to living or deceased mammals; to cells; to recombinant, chimeric, or hybrid cells; to biological fluids, to isolated nucleic acids, and the like, include:

i. Methods for measuring cellular parameters. What can be measured includes effector T cells; central memory T cells ($T_{CM}$); effector memory T cells ($T_{EM}$), and constituents thereof. What can be measured are biological functions of these cells including cytotoxic function, expression of markers, affinity for antigen, number of cells in a biological compartment such as serum, preferred location in the body such as in lymph node or spleen, and rate of response when exposed or re-exposed to antigen.

ii. Methods for measuring antibodies. What can be measured is affinity maturation of antibodies (see, e.g., McHeyzer-Williams and McHeyzer-Williams (2005) Ann. Rev. Immunol. 23:487-513), antibody titer or isotype, including IgG ($IgG_1$; $IgG_2$; $IgG_3$; $IgG_4$); IgA ($IgA_1$; $IgA_2$); IgM; IgD; IgE; isotype switching of antibodies, for example, decreases in IgM and increases in IgG (see, e.g., Hasbold, et al. (2004) Nature Immunol. 5:55-63; Ryffel, et al. (1997) J. Immunol. 158:2126-2133; Lund, et al. (2002) J. Immunol. 169:5236-5243; Palladino, et al. (1995) J. Virol. 69:2075-2081; Karrer, et al. (2000) J. Immunol. 164:768-778); isotype switching that is a function of Th1-type or Th2-type response (Delale, et al. (2005) J. Immunol. 175:6723-6732; McKenzie, et al. (1999) J. Exp. Med. 189:1565-1572; Fayette, et al. (1997) J. Exp. Med. 185:1909-1918).

iii. Parameters of B cells. What can be measured includes naive B cells (high in membrane IgD and low in CD27), memory B cells (low in IgD and high in CD27), and constituents of these cells (see, e.g., Fecteau and Neron (2003) J. Immunol. 171:4621-4629). What can be measured is formation of memory B cells within germinal centers (see, e.g., Ohkubo, et al. (2005) J. Immunol. 174:7703-7710). What can be measured includes terminally differentiated B cells, for example, cell's ability to respond to CXCL12 (see, e.g., Roy, et al. (2002) J. Immunol. 169:1676-1682). What can be measured includes commitment antibody-secreting cells (ASCs) (see, e.g., Hasbold, et al. (2004) Nature Immunol. 5:55-63).

iv. Parameters of T cells. What can be measured is affinity of a peptide for T cell receptor, affinity maturation of T cell receptor (see, e.g., Rees, et al. (1999) Proc. Natl. Acad. Sci. USA 96:9781-9786; McKinney, et al. (2004) J. Immunol. 173:1941-1950). What can be measured is affinity of a cytotoxic T cell for a target cell (see, e.g., Montoya and Del Val (1999) J. Immunol. 163:1914-1922). What can be measured includes markers, for example, effector memory T cells ($T_{EM}$) can be identified as $CD62L^{LOW}$ and $CCR7^{LOW}$, where these cells show immediate effector function with antigen re-encounter. Central memory T cells ($T_{CM}$) can be identified by relatively high expression of CD62L and CCR7, where the cells show a relatively slow activation kinetics. Other available markers include, e.g., CCL4, CCL5, XCL1, granulysin, granzyme A, granzyme B, and so on (see, e.g., Chtanova, et al. (2005) J. Immunol. 175:7837-7847; Kondrack, et al. (2003) J. Exp. Med. 198:1797-1806; Huster, et al. (2004) Proc. Natl. Acad. Sci. USA 101:5610-5615; Ahmadzadeh, et al. (2001) J. Immunol. 166:926-935; Goldrath, et al. (2004) Proc. Natl. Acad. Sci. USA 101:16885-16890; Wherry, et al. (2003) Nature Immunol. 4:225-234; Sallusto, et al. (2004) Ann. Rev. Immunol. 22:745-763). Different types of immune cells, as well as different stages of maturation of a particular cell, or different stages of activation of a cell, can be distinguished by titrating with a reagent specific to any given marker (see, e.g., Ahmadzah, et al. (2001) J. Immunol. 166:926-935).

v. Parameters of antigen presenting cells (APCs), including dendritic cells (DCs). What can be measured is mmoles of peptide presented (or bound) per mmole MHC Class I. Moreover, what can be measured is mmoles peptide presented or bound per mmol of MHC Class II. Also, what can be measured is the amino acid sequence of the bound peptides (see, e.g., Velazquez, et al. (2001) J. Immunol. 166:5488-5494). In addition, what can be measured is relative ability of the APC to present epitopes derived from peptides versus epitopes derived from proteins, as well as ability to present epitopes acquired from low levels of peptides versus high levels of peptides and, in other aspects, the identity of the APC suitable for presentation (see, e.g., Constant, et al. (1995) J. Immunol. 154:4915-4923).

Guidance is available for the skilled artisan in designing diagnostic appropriate controls (see, e.g., Wilson (1991) An Introduction to Scientific Research, Dover Publications, Mineola, N.Y.).

The broad scope of this invention is best understood with reference to the following examples, which are not intended to limit the invention to any specific embodiments.

EXAMPLES

I. General Methods

Standard methods of biochemistry and molecular biology are described (see, e.g., Maniatis, et al. (1982) Molecular Cloning, A Laboratory Manual, Cold Spring Harbor Press, Cold Spring Harbor, N.Y.; Sambrook and Russell (2001) Molecular Cloning, 3$^{rd}$ ed., Cold Spring Harbor Laboratory Press, Cold Spring Harbor, N.Y.; Wu (1993) Recombinant DNA, Vol. 217, Academic Press, San Diego, Calif.; Innis, et al. (eds.) (1990) PCR Protocols: A Guide to Methods and Applications, Academic Press, N.Y. Standard methods are also found in Ausbel, et al. (2001) Curr. Protocols in Mol. Biol., Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). Methods for producing fusion proteins are described (see, e.g., Invitrogen (2005) Catalogue, Carlsbad, Calif.; Amersham Pharmacia Biotech. (2005) Catalogue, Piscataway, N.J.; Liu, et al. (2001) Curr. Protein Pept. Sci. 2:107-121; Graddis, et al. (2002) Curr. Pharm. Biotechnol. 3:285-297).

Splice overlap extension PCR, and other methods, for creating mutations, restriction sites, loxP sites, and the like, are described (see, e.g., Horton, et al. (1990) Biotechniques 8:528-535; Horton, et al. (1989) Gene 77:61-68; Horton (1995) Mol Biotechnol. 3:93-99; Cutrone and Langer (2001) J. Biol. Chem. 276:17140-17148; Cox, et al. (2002) Nucleic Acids Res. 30:e108; Warrens, et al. (1997) Gene 186:29-35; Guo and Bi (2002) Methods Mol. Biol. 192:111-119; Johnson (2000) J. Microbiol. Methods 41:201-209; Lantz, et al. (2000) Biotechnol. Annu. Rev. 5:87-130; Gustin and Burk (2000) Methods Mol. Biol. 130:85-90; QuikChange® Mutagenesis Kit, Stratagene, La Jolla, Calif.). Engineering codon preferences of signal peptides, secretory proteins, and heterologous antigens, to fit the optimal codons of a host are described (Sharp, et al. (1987) Nucl. Acids Res. 15:1281-1295; Uchijima, et al. (1998) J. Immunol. 161:5594-5599). Engineering codon preferences of signal peptides, secretory proteins, and heterologous antigens, to fit the optimal codons of a host are described (Sharp, et al. (1987) Nucl. Acids Res. 15:1281-1295; Uchijima, et al. (1998) J. Immunol. 161:5594-5599). Polynucleotides and nucleic acids are available, e.g., from Blue Heron Biotechnology, Bothell, Wash.).

Methods for effecting homologous recombination in, e.g., bacteria, phages, and plasmids, are available (see, e.g., Kuzminov (1999) Microb. Mol. Biol. Rev. 63:751-813; Camerini-Otero and Hsieh (1995) Annu. Rev. Genet. 29:509-552; Amundsen and Smith (2003) Cell 112:741-744; Cox (2001) Annu. Rev. Genet. 35:53-82; Quiberoni, et al. (2001) Res. Microbiol. 152:131-139; Fernandez, et al. (2000) Res. Microbiol. 151:481-486; Wedland (2003) Curr. Genet. 44:115-123; Muttucumaru and Parish (2004) Curr. Issues Mol. Biol. 6:145-157; Bhattacharyya, et al. (2004) Infect. Genet. Evol. 4:91-98).

A number of transducing listeriophages, as well as techniques for infecting *L. monocytogenes* with listeriophages are available. These listeriophages include, e.g., P35, U153, and derivatives thereof (see, e.g., Lauer, et al. (2002) J. Bact. 184:4177-4186; Hodgson (2000) Mol. Microbiol. 35:312-323; Mee-Marquet, et al. (1997) Appl. Environ. Microbiol. 63:3374-3377; Zink and Loessner (1992) Appl. Environ. Microbiol. 58:296-302; Loessner, et al. (1994) Intervirol. 37:31-35; Loessner, et al. (1994) J. Gen. Virol. 75:701-710; Loessner, et al. (2000) Mol. Microbiol. 35:324-340).

Methods for using electroporation and *E. coli*-mediated conjugation for introducing nucleic acids into *Listeria* are described. Plasmids suitable for introducing a nucleic acid into a bacterium include, e.g., pPL1 (GenBank assession no: AJ417488), pPL2 (Acc. No. AJ417449), pLUCH80, pLUCH88, and derivatives thereof (see, e.g., Lauer, et al. (2002) J. Bact. 184:4177-4186; Wilson, et al. (2001) Infect. Immunity 69:5016-5024; Chesneau, et al. (1999) FEMS Microbiol. Lett. 177:93-100; Park and Stewart (1990) Gene 94:129-132; Luchansky, et al. (1988) Mol. Microbiol. 2:537-646; He and Luchansky (1997) Appl. Environ. Microbiol. 63:3480-3487).

Methods for protein purification such as immunoprecipitation, column chromatography, electrophoresis, isoelectric focusing, centrifugation, and crystallization, are described (Coligan, et al. (2000) Current Protocols in Protein Science, Vol. 1, John Wiley and Sons, Inc., New York). Chemical analysis, chemical modification, post-translational modification, and glycosylation of proteins is described. See, e.g., Coligan, et al. (2000) Current Protocols in Protein Science, Vol. 2, John Wiley and Sons, Inc., New York; Walker (ed.) (2002) Protein Protocols Handbook, Humana Press, Towota, N.J.; Lundblad (1995) Techniques in Protein Modification, CRC Press, Boca Raton, Fla. Techniques for characterizing binding interactions are described (Coligan, et al. (2001) Current Protocols in Immunology, Vol. 4, John Wiley and Sons, Inc., New York; Parker, et al. (2000) J. Biomol. Screen. 5:77-88; Karlsson, et al. (1991) J. Immunol. Methods 145: 229-240; Neri, et al. (1997) Nat. Biotechnol. 15:1271-1275; Jonsson, et al. (1991) Biotechniques 11:620-627; Friguet, et al. (1985) J. Immunol. Methods 77:305-319; Hubble (1997) Immunol. Today 18:305-306; Shen, et al. (2001) J. Biol. Chem. 276:47311-47319).

Software packages for determining, e.g., antigenic fragments, leader sequences, protein folding, functional domains, glycosylation sites, and sequence alignments, are available (see, e.g., Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) Bioinformatics 16:741-742; Menne, et al. (2000) Bioinformatics Applications Note 16:741-742; Wren, et al. (2002) Comput. Methods Programs Biomed. 68:177-181; von Heijne (1983) Eur. J. Biochem. 133:17-21; von Heijne (1986) Nucleic Acids Res. 14:4683-4690). Methods for determining coding sequences (CDS) are available (Furono, et al. (2003) Genome Res. 13:1478-1487).

Computer algorithms (e.g., BIMAS; SYFPEITHI) for identifying peptides that bind to MHC Class I and/or MHC Class II are available (Thomas, et al. (2004) J. Exp. Med. 200:297-306). These algorithms can provide nucleic acids of the present invention that encode proteins comprising the identified peptides.

Sequences of listerial proteins and nucleic acids can be found on the world wide web at: (1) ncbi.nlm.nih.gov; (2) genolist.Pasteur.fr (with clicking on "listilist"); and (3) tigr.org (with clicking on "databases," then on "comprehensive microbial resource").

Methods are available for assessing internalization of a *Listeria* by an APC, and for assessing presentation of listerial-encoded antigens by the APC. Methods are also available for presentation of these antigens to T cell, and for assessing antigen-dependent priming of the T cell. A suitable APC is murine DC 2.4 cell line, while suitable T cell is the B3Z T cell hybridoma (see, e.g., U.S. Provisional Pat. Appl. Ser. No. 60/490,089 filed Jul. 24, 2003; Shen, et al. (1997) J. Immunol. 158:2723-2730; Kawamura, et al. (2002 J. Immunol. 168: 5709-5715; Geginat, et al. (2001) J. Immunol. 166:1877-1884; Skoberne, et al. (2001) J. Immunol. 167:2209-2218; Wang, et al. (1998) J. Immunol. 160:1091-1097; Bullock, et al. (2000) J. Immunol. 164:2354-2361; Lippolis, et al. (2002) J. Immunol. 169:5089-5097). Methods for preparing dendritic cells (DCs), ex vivo modification of the DCs, and administration of the modified DCs, e.g., for the treatment of a cancer, pathogen, or infective agent, are available (see, e.g., Ribas, et al. (2004) J. Immunother. 27:354-367; Gilboa and Vieweg (2004) Immunol. Rev. 199:251-263; Dees, et al. (2004) Cancer Immunol. Immunother. 53:777-785; Eriksson, et al. (2004) Eur. J. Immunol. 34:1272-1281; Goldszmid, et al. (2003) J. Immunol. 171:5940-5947; Coughlin and Vonderheide (2003) Cancer Biol. Ther. 2:466-470; Colino and Snapper (2003) Microbes Infect. 5:311-319).

Assays for *Listeria* plaque size, $LD_{50}$, and motility are described. Plaque diameter is a function of a bacterium's ability to grow, to move from cell to cell, and to escape from a secondary vesicle formed in an adjacent cell (see, e.g., Lauer, et al. (2001) Mol. Microbiol. 42:1163-1177; Theriot, et al. (1994) Cell 76:505-517; Theriot, et al. (1998) Meth. Enzymol. 298:114-122; Portnoy, et al. (1988) J. Exp. Med. 167:1459-1471).

Elispot assays and intracellular cytokine staining (ICS) for characterizing immune cells are available (see, e.g., Lalvani, et al. (1997) J. Exp. Med. 186:859-865; Waldrop, et al. (1997) J. Clin. Invest. 99:1739-1750; Hudgens, et al. (2004) J. Immunol. Methods 288:19-34; Goulder, et al. (2001) J. Virol. 75:1339-1347; Goulder, et al. (2000) J. Exp. Med. 192:1819-1831; Anthony and Lehman (2003) Methods 29:260-269; Badovinac and Harty (2000) J. Immunol. Methods 238:107-117). The "tetramer staining" method is also available (see, e.g., Serbina and Pamer (2003) Curr. Opin. Immunol. 15:436-442; Skinner and Haase (2002) J. Immunol. Methods 268:29-34; Pittet, et al. (2001) Int. Immunopharmacol. 1:1235-1237).

Methods are available for determining if an antigen or epitope is presented via direct presentation or by cross-presentation. These methods include use of TAP-deficient mice with administration of cells (from another source) that contain an antigen of interest. Another method involves preparing a mouse genetically deficient in an MHC Class I or Class II molecule that is required for presenting a specific epitope, e.g., MHC Class I H-$2^b$, and administering H-$2^b$ expressing antigen presenting cells (APCs) (from another source) that contain the antigen of interest (or that were pulsed with an epitope of interest) (see, e.g., van Mierlo, et al. (2004) J. Immunol. 173:6753-6759; Pozzi, et al. (2005) J. Immunol. 175:2071-2081).

Methods for determining binding affinities, binding specificities, and affinity maturation are available. The present invention provides methods for stimulating and/or diagnosing affinity maturation, as it applies to, e.g., maturation of antibodies and/or of T cells (see, e.g., Chen, et al. (2004) J. Immunol. 173:5021-5027; Rees, et al. (1999) Proc. Natl. Acad. Sci. USA 96:9781-9786; Busch and Pamer (1999) J. Exp. Med. 189:701-709; Ploss, et al. (2005) J. Immunol. 175:5998-6005; Brams, et al. (1998) J. Immunol. 160:2051-2058; Choi, et al. (2003) J. Immunol. 171:5116-5123).

Methods for using animals in the study of cancer, metastasis, and angiogenesis, and for using animal tumor data for extrapolating human treatments are available (see, e.g., Hirst and Balmain (2004) Eur J Cancer 40:1974-1980; Griswold, et al. (1991) Cancer Metastasis Rev. 10:255-261; Hoffman (1999) Invest. New Drugs 17:343-359; Boone, et al. (1990) Cancer Res. 50:2-9; Moulder, et al. (1988) Int. J. Radiat. Oncol. Biol. Phys. 14:913-927; Tuveson and Jacks (2002) Curr. Opin. Genet. Dev. 12:105-110; Jackson-Grusby (2002) Oncogene 21:5504-5514; Teicher, B. A. (2001) Tumor Models in Cancer Research, Humana Press, Totowa, N.J.; Hasan, et al. (2004) Angiogenesis 7:1-16; Radovanovic, et al. (2004) Cancer Treat. Res. 117:97-114; Khanna and Hunter (2004) Carcinogenesis September 9 [epub ahead of print]; Crnic and Christofori (2004) Int. J. Dev. Biol. 48:573-581).

Colorectal cancer hepatic metastases can be generated using primary hepatic injection, portal vein injection, or whole spleen injection of tumor cells (see, e.g., Suh, et al. (1999) J. Surgical Oncology 72:218-224; Dent and Finley-Jones (1985) Br. J. Cancer 51:533-541; Young, et al. (1986) J. Natl. Cancer Inst. 76:745-750; Watson, et al. (1991) J. Leukoc. Biol. 49:126-138).

Example II

Vectors for Use in Mediating Site-Specific Recombination and Homologous Recombination The *Listeria monocytogenes* strains used in the present work are described (see, Brockstedt, et al. (2004) Proc. Natl. Acad. Sci. USA 101:13832-13837). *L. monocytogenes* ΔActAΔinlB was deposited with American Type Culture Collection (ATCC) at PTA-5562. *L. monocytogenes* ΔActAΔuvrAB is available from ATCC at PTA-5563. Yeast medium without glucose contained 25 grams/L yeast extract (Bacto®yeast extract) (BD Biosciences, Sparks, Md.); 9 grams/L potassium phosphate monobasic, pH 7.2.

Homologous recombination can be mediated by pKSV7 (SEQ ID NO:3) (see also, Smith and Youngman (1992) Biochimie 74:705-711; Camilli, et al. (1993) Mol. Microbiol. 8:143-157; Camilli (1992) *Genetic analysis of Listeria monocytogenes Determinants of Pathogenesis*, Univ. of Pennsylvania, Doctoral thesis).

```
(SEQ ID NO: 28, pKSV7)
CTCGCGGATTGTTGATGATTACGAAAATATTAAGAGCACAGACTATTACA
CAGAAAATCAAGAATTAAAAAAACGTAGAGAGAGTTTGAAAGAAGTAGTG
AATACATGGAAAGAGGGGTATCACGAAAAAAGTAAAGAGGTTAATAAATT
AAAGCGAGAGAATGATAGTTTGAATGAGCAGTTGAATGTATCAGAGAAAT
TTCAAGATAGTACAGTGACTTTATATCGTGCTGCGAGGGCGAATTTCCCT
GGGTTTGAGAAAGGGTTTAATAGGCTTAAAGAGAAATTCTTTAATGATTC
CAAATTCGAGCGTGTGGGACAGTTTATGGATGTTGTACAGGATAATGTCC
AGAAGGTCGATAGAAAGCGTGAGAAACAGCGTACAGACGATTTAGAGATG
TAGAGGTACTTTTATGCCGAGAAAACTTTTTGCGTGTGACAGTCCTTAAA
ATATACTTAGAGCGTAAGCGAAAGTAGTAGCGACAGCTATTAACTTTCGG
TTGCAAAGCTCTAGGATTTTTTAATGGACGCAGCGCATCACACGCAAAAAG
GAAATTGGAATAAATGCGAAATTTGAGATGTTAATTAAAGACCTTTTTGA
GGTCTTTTTTTCTTAGATTTTTGGGGTTATTTAGGGGAGAAAACATAGGG
GGGTACTACGACCTCCCCCCTAGGTGTCCATTGTCCATTGTCCAAACAAA
TAAATAAATATTGGGTTTTTAATGTTAAAAGGTTGTTTTTTATGTTAAAG
TGAAAAAAACAGATGTTGGGAGGTACAGTGATGGTTGTAGATAGAAAAGA
AGAGAAAAAGTTGCTGTTACTTTAAGACTTACACAGAAGAAAATGAGAT
ATTAAATAGAATCCAAGAAAAATATAATATTAGCAAATCAGATGCACCGG
TATTCTAATAAAAAATATGYRMAGGAGGAATACSGTGCATTTTAACAAAA
AAAGATAGACAGCACTGGCATGCTGCCTATCTATGACTAAATTTTGTTAA
ATGTATTAGCACCGTTATTATATCATGAGCGAAAATGTAATAAAAGAAAC
TGAAAACAAGAAAAATTCAAGAGGACGTAATTGGACATTTGTTTTATATC
CAGAATCAGCAAAAGCCGAGTGGTTAGAGTATTTAAAAGAGTTACACATT
CAATTTGTAGTGTCTCCATTACATGATAGGGATACTGATACAGAAGATAG
GATGAAAAAAGAGCATTATCATATTCTAGTGATGTATGAGGGTAATAAAT
CTTATGAACAGATAAAAATAATTACAGAAGAATTGAATGCGACTATTCCG
CAGATTGCAGGAAGTGTGAAAGGTCTTGTGAGATATATGCTTCACATGGA
CGATCCTAATAAATTTAAATATCAAAAAGAAGATATGATAGTTTATGCCG
GTGTAGATGTTGATGAATTATTAAAGAAAACAACAACAGATAGATATAAA
TTAATTAAAGAAATGATTGAGTTTATTGATGAACAAGGAATCGTAGAATT
TAAGAGTTTAATGGATTATGCAATGAAGTTTAAATTTGATGATTGGTTCC
CGCTTTTATGTGATAACTCGGCGTATGTTGTTTATTCAAGAATATATAAAATCA
AATCGGTATAAATCTGACCGATAGATTTTGAATTTAAGAGTGTCACAAGA
CACTCTTTTTTCGCACCAACGAAAACTGGTTTAAGCCGACTGCGCAAAAG
ACATAATCGATTCACAAAAAATAGGCACACGAAAAACAAGTTAAGGGATG
CAGTTTATGCATCCCTTANCTTACTTATTAAATAATTTATAGCTATTGAA
AAGAGATAAGAATTGTTCAAGCTAATATTGTTTAAATCGTCCATTCCTGC
ATGTTTTANGGAAWTGTTAANTTGATTTTTTGTAATATTTTCTKGTATYC
TTTGTTAMCCCATTTCATAACGAAATAATTATACTTTTGTTTATCTTTGT
GTGATATTCTTGATTTTTTCTACTTAATCTGATAAGTGAGCTATTCACT
TTAGGTTTAGGATGAAAATATTCTCTTGGAACCATACTTAATATAGAAAT
ATCAACTTCTGCCATTAAAAGTAATGCCAATGAGCGTTTTGTATTTAATA
ATCTTTTAGCAAACCCGTATTCCACGATTAAATAAATCTCATTAGCTATA
CTATCAAAAACAATTTTGCGTATTATATCCGTACTTATGTTATAAGGTAT
ATTACCATATATTTTATAGGATTGGTTTTTAGGAAATTTAAACTGCAATA
TATCCTTGTTTAAAACTTGGAAATTATCGTGATCTTCCTTCAGGTTATGA
CCATCTGTGCCAGTTCGTAATGTCTGGTCAACTTTCCGACTCTGAGAAAC
TTCTGGAATCGCTAGAGAATTTCTGGAATGGGATTCAGGAGTGGACAGAA
CGACACGGATATATAGTGGATGTGTCAAAACGCATACCATTTTGAACGAT
GACCTCTAATAATTGTTAATCATGTTGGTTACGTATTTATTAACTTCTCC
TAGTATTAGTAATTATCATGGCTGTCATGGCGCATTAACGGAATAAAGGG
TGTGCTTAAATCGGGCCATTTTGCGTAATAAGAAAAAGGATTAATTATGA
GCGAATTGAATTAATAATAAGGTAATAGATTTACATTAGAAAATGAAAGG
GGATTTTATGCGTGAGAATGTTACAGTCTATCCCGGCAATAGTTACCCTT
ATTATYWSGATAAGAANGAAAGGATTTTTCGCTACGCTCAATCCTTTAAA
AAAACACAAAAGACCACATTTTTTAATGTGGTCTTTTATTCTTCAACTAA
AGCACCCATTAGTTCAACAAACGAAAATTGGATAARGTGGGATATTTTWA
AWATAATWTATKTATGTTACAGTAATATTGACTTTTAAAAAAGGATTGAT
TCTAATGAGAAAGCAGACAAGTAAGCCTCCTAAATTCACTTTAGATAAA
AATTTAGGAGGCATATCAAATGAACTTTAATAAAATTGATTTAGACAATT
GGAAGAGAAAAGAGATATTTAATCATTATTTGAACCAACAAACGACTTTT
AGTATAACCACAGAAATTGATATTAGTGTTTTATACCGAAACATAAAACA
```

-continued
AGAAGGATATAAATTTTACCCTGCATTTATTTTCTTAGTGACAAGGGTGA
TAAACTCAAATACAGCTTTTAGAACTGGTTACAATAGCGACGGAGAGTTA
GGTTATTGGGATAAGTTAGAGCCACTTTATACAATTTTTGATGGTGTATC
TAAAACATTCTCTGGTATTTGGACTCCTGTAAAGAATGACTTCAAAGAGT
TTTATGATTTATACCTTTCTGATGTAGAGAAATATAATGGTTCGGGGAAA
TTGTTTCCCAAAACACCTATACCTGAAAATGCTTTTTCTCTTTCTATTAT
TCCATGGACTTCATTTACTGGGTTTAACTTAAATATCAATAATAATAGTA
ATTACCTTCTACCCATTATTACNGCAGGAAANTTCATTAATAANGGTAAT
TCAATATATTTACCGCTATCTTTACAGGTACATCATTCTGTTTGTGATGG
TTATCATGCNGGATTGTTTATGAACTCTATTCAGGAATTGTCAGATAGGC
CTAATGACTGGCTTTTATATATGAGATAATGCCGACTGTACTTTTTACRG
TCGGTTTTCTAACGATMCATTAATAGGTMCGAAAAAGCMACTTTTTTKSC
GCTTAAAACCAGTCATACCAATAACTTAAGGGTAACTAGCCTCGCCGGAA
AGAGCGAAAATGCCTCACATTTGTGCCACCTAAAAAGGAGCGATTTACAT
ATGAGTTATGCAGTTTGTAGAATGCAAAAAGTGAAATCAGCTGCATTAAT
GAATCGGCCAACGCGCGGGGAGAGGCGGTTTGCGTATTGGGCGCTCTTCC
GCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGG
ATAACGCAGGAAAGAACATGTGAGCAAAAGGCCAGCAAAAGGCCAGGAAC
CGTAAAAAGGCCGCGTTGCTGGCGTTTTTCCATAGGCTCCGCCCCCCTGA
CGAGCATCACAAAAATCGACGCTCAAGTCAGAGGTGGCGAAACCCGACAG
GACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGG
TGTAGGTCGTTCGCTCCAAGCTGGGCTGTGTGCACGAACCCCCCGTTCAG
CCCGACCGCTGCGCCTTATCCGGTAACTATCGTCTTGAGTCCAACCCGGT
AAGACACGACTTATCGCCACTGGCAGCAGCCACTGGTAACAGGATTAGCA
GAGCGAGGTATGTAGGCGGTGCTACAGAGTTCTTGAAGTGGTGGCCTRSS
YACKSSKMYCCTAGAAGAACAGTATTTGGTATCTGCGCTCTGCTGAAGCC
AGTTACCTTCGGAAAAAGAGTTGGTAGCTCTTGATCCGGCAAAMAAACCA
CCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGC
TCAGTGGAACGAAAACTCACGTTAAGGGATTTTGGTCATGAGATTATCAA
AAAGGATCTTCACCTAGATCCTTTTAAATTAAAAATGAAGTTTTAAATCA
ATCTAAAGTATATATGAGTAAACTTGGTCTGACAGTTACCAATGCTTAAT
CAGTGAGGCACCTATCTCAGCGATCTGTCTATTTCGTTCATCCATAGTTG
CCTGACTCCCCGTCGTGTAGATAACTACGATACGGGAGGGCTTACCATCT
GGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGC
TACAGGCATCGTGGTGTCACGCTCGTCGTTTGGTATGGCTTCATTCAGCT
CCGGTTCCCAACGATCAAGGCGAGTTACATGATCCCCCATGTTGTGCAAA
AAAGCGGTTAGCTCCTTCGGTCCTCCGATCGTTGTCAGAAGTAAGTTGGC
CGCAGTGTTATCACTCATGGTTATGGCAGCACTGCATAATTCTCTTACTG
TCATGCCATCCGTAAGATGCTTTTCTGTGACTGGTGRKKASTCWCMCMAG
TCATTCTGAGAATAGTGTATGCGGCGACCGAGTTGCTCTTGCCCNGGSGT
CAATACGGGATAATACCGCSCCACATAGCARAACTTTAAAAGTGCTCATC
ATTGGAAAACGTTCTTCGGGGCGAAAACTCTCAAGGATCTTACCGCTGTT
GAGATCCAGTTCGATGTAACCCACTCGTGCACCCAACTGATCTTCAGCAT
CTTTTACTTTCACCAGCGTTTCTGGGTGAGCAAAAACAGGAAGGCAAAAT
GCCGCAAAAAAGGGAATAAGGGCGACACGGAAATGTTGAATACTCATACT
CTTCCTTTTTCAATATTATTGAAGCATTTATCAGGGTTATTGTCTCATGA
GCGGATACATATTTGAATGTATTTAGAAAAATAAACAAATAGGGGTTCCG
CGCACATTTCCCCGAAAAGTGCCACCTGACGTCTAAGAAACCATTATTAT
CATGACATTAACCTATAAAAATAGGCGTATCACGAGGCCCTTTCGTCTCG
CGCGTTTCGGTGATGACGGTGAAAACCTCTGACACATGCAGCTCCCGGAG
ACGGTCACAGCTTGTCTGTAAGCGGATGCCGGGAGCAGACAAGCCCGTCA
GGGCGCGTCAGCGGGTGTTGGCGGGTGTCGGGGCTGGCTTAACTATGCGG
CATCAGAGCAGATTGTACTGAGAGTGCACMATATGCGGTGTGAAATACCG
CACAGATGCGTAAGGAGAAAATACCGCATCAGGCGCCATTCGCCATTCAG
GCTGCGCAACTGTTGGGAAGGGCGATCGGTGCGGGCCTCTTCGCTATTAC
GCCAGCTGGCGAAAGGGGGATGTGCTGCAAGGCGATTAAGTTGGGTAACG
CCAGGGTTTTYCCAGTCACGACGTTGTAAAACGACGGCCAGTGCCAAGCT
TGCATGCCTGCAGGTCGACTCTAGAGGATCCCNGGGTACCGAGCTCGAA
TTCGTAATCATGTCATAGCTGTTTCCTGTGTGAAATTGTTATCCGCTCAC
AATTCCACACAACATACGAGCGGAAGCATAAAGTGTAAAGCCTGGGGTG
CCTAATGAGTGAGCTAACTCACATTAATTGCGTTGCGCTCACTGCCCGCT
TTCCAGTCGGGAAACCTGTCGTGCCAGCTGGACTAAAAGGCATGCAATTT
CATAATCAAAGAGAGCGAAAAAGTAGAACGAATGATGATATTGACCATGA
GCGAACACGTGAAAATTATGATTTGAAAAATGATAAAAATATTGATTACA
ACGAACGTGTCAAAGAAATTATTGAATCACAAAAAACAGGTACAAGAAAA
ACGAGGAAAGATGCTGTTCTTGTAAATGAGTTGCTAGTAACATCTGACCG
AGATTTTTTGAGCAACTGGATCAGTACAAGAAAGATACTGTATTTCATA
AACAGGAACTGCAAGAAGTTAAGGATGAGTTACAGAAGGCAAATAAGCAG
TTACAGAGTGGAATAGAGCATATGAGGTCTACGAAACCCTTTGATTATGA
AAATGAGCGTACAGGTTTGTTCTCTGACGTGAAGAGACTGGTAGAAAGA
TATTAACTGCTGATGAATTTGAACGCCTGCAAGAAACAATCTCTTCGAAC
GGATTGTTGATGATTACGAAATATAAGAGCCCGACTATTCCCAGAAATCA
GAATTAAAAACGTAGAGAGAG.

Site-specific integration can be mediated by pPL1, pPL2, pINT, or variants thereof (see, e.g., Lauer, et al. (2002) J. Bacteriol. 184:4177-4186; Int. Appl. No. PCT/US03/13492 (Int. Publ. No. WO 03/092600) of Portnoy, Calendar, and Lauer).

The pINT plasmid has loxP sites that allow the specific removal of most of the plasmid from the listerial chromosome, leaving behind the attP and MCS (multiple cloning site), and the contents of the multi-cloning site (MCS) (e.g., an antigen cassette). pINT can work differently from pPL2 as follows. Up to a 100 microliters aliquot of a 10:1 dilution of a pPL2 conjugation can be plated on double selection plates. Plating up to a 100 microliters aliquot of a 10:1 dilution of a pPL2 conjugation generally results in 50-100 colonies. Plating more than 100 microliters of a 10:1 dilution of pPL2 conjugation gives little or no colonies due to a background growth from the E. coli donor. pINT, on the other hand, can be plated without diluting and even concentrating the conjugation mix because erythromycin (Erm) is more selective than chloramphenicol against E. coli. The use of pINT broadens the dynamic range for successful integration by approximately 2 logs.

(SEQ ID NO: 29)
pINT vector.
AGATCTCCAAAAATAAACAGGTGGTGGTATTAATGAAGATAAAAAAATTA
GCAAACGGTAAATATTGTGTTCGCCTACGTATAAAAGTCGATGGTGAATG
GAAAGAAAAGCGTTTGACAGATACAAGTGAAACAAACTTAATGTATAAAG
CATCTAAATTATTAAAACAAGTTCAGCATGATAGTAGTTCTCTGAAAGAA
TGGAACTTCAAAGAATTTTATACGCTATTCATGAAAACATTTAAAGATGG
GAAAAGTAGTCAATCTACTATTAATTTATACGATCTTGCTTATAATCAAT
TCGTTGATTATTTCGATGAAAAAATTAAATTTAATTCGATTGATGCGGTT
CAATATCAACAATTTATTAATCATTTATCTGTAGACTATGCAATATCCAC
TGTAGACACCAGACACCGCAAATTAGAGCGATTTTTAACAAGGCTGTTC
ATTTAGGTTACATGAAGAAAACCCCACTATAGGGGCTCATATAAGCGGA
CAGGACGTAGCGAAAAATAAAGCACAATTTATGGAAACAGACAAAGTTCA
TTTACTATTAGAAGAACTTGCAAAATTTCATTCTATATCACGAGCAGTTA
TCTTTCTAGCTGTCCAGACAGGCATGAGGTTCGAAGAAATTATTGCACTA
ACAAAGAAGGATATTAATTTCACTAAACGTTCAATAACTGTGAATAAAGC
TTGGGATTACAAGTACACTAATACATTCATTGATACCAAAACAAAAAAAT
CACGAGTGATCTATATTGATAACTCTACCGCTCAATATTTACATTCGTAT
TTAAATTGGCATACTGAATATATGAAGGAACATGCTATTAAGAATCCATT
GATGTTATTATTCATCACTTACCACAATAAGCCAGTAGACAACGCGTCTT
GTAATAAAGCTTTGAAGAAGATATGTAGTACAATCAATTCTGAACCAGTG
ACATTACACAAGCTACGACATACGCATACACAGGCTTATGTGTAGAAGCGGG
TATGGATATTATTTATGTAGCTGATAGGCTTGGTCATGATGACATTAATA
CAACATTAAAATACTATAGTCATCTAAGCTCTAATTTAAGACAACATAAT
CAGTCCAAAGTAGATGCTTTTTTCACACTAAAAACAGATGAAAATACCAC
AAATTTTACCACAAATGCCACAAAAACAACGGAATAACCTAGGATAACTT
CGTATAATGTATGCTATACGAAGTTATATGCATGGGTATTATACGATATA
AAAAAAACTCCAAAACATTCATCCGCCCTTTAATATCAAGGCTTTTCAAC
GTTTTAGAGATTTCTTTACATTACTATTTAACGTCCTGAGAGGGATTAAC
ACACACTGATATAAAGCCATTTAGGATATATATACCACAAATAATACCAC
AAACATTTTATGTAATAATAAATATTATTTATTACATTGAAATAAAT
ATTCGTTATAAATAGTTTTTATATCAAGATGTTTTTTCTCAAGGTTTTA
TAAAATGACTTTAATTCTTTTGTTTCAAGTAGTCCAGAGAAGATTTTTTC
AACAGCGTTCTTCTTTCCCTCCACGCATGCGACGTCAATACGACTCACTA
TAGGGCGAATTGGGTACCGGGCCCCCCCTCGAGGTCGACGGTATCGATAA
GCTTGATATCGAATTCCTGCAGCCCGGGGGATCCACTAGTTCTAGAGCGG
CCGCCACCGCGGTGGAGCTCCAGCTTTTGTTCCCTTTAGTGAGGGTTAAT
TAAATAACTTCGTATAATGTATGCTATACGAAGTTATGCGATCGCCTCTC
GCCTGTCCCCTCAGTTCAGTAATTTCCTGCATTTGCCTGTTTCCAGTCGG
TAGATATTCCACAAAACAGCAGGGAAGCAGCGCTTTTCCGCTGCATAACC
CTGCTTCGGGGTCATTATAGCGATTTTTTCGGTATATCCATCCTTTTTCG
CACGATATACAGGATTTTGCCAAAGGGTTCGTGTAGACTTTCCTTGGTGT
ATCCAACGGCGTCAGCCGGCAGGATAGGTGAAGTAGGCCCACCCGCGAA
CGGGTGTTCCTTCTTCACTGTCCCTTATTCGCACCTGGCGGTGCTCAACG
GGAATCCTGCTCTGCGAGGCTGGCCGGCTACCGCCGGCGTAACAGATGAG
GGCAAGCGGCGGAGAATTACAACTTATATCGTATGGGGCTGACTTCAGGT
GCTACATTTGAAGAGATAAATTGCACTGAAATCTAGAAATATTTTATCTG
ATTAATAAGATGATCTTCTTGAGATCGTTTTGGTCTGCGCGTAATCTCTT
GCTCTGAAAACGAAAAAACCGCCTTGCAGGGCGGTTTTTCGAAGGTTCTC
TGAGCTACCAACTCTTTGAACCGAGGTAACTGGCTTGGAGGAGCGCAGTC
ACCAAAACTTGTCCTTTCAGTTTAGCCTTAACCGGCGCATGACTTCAAGA
CTAACTCCTCTAAATCAATTACCAGTGGCTGCTGCCAGTGGTGCTTTTGC -continued
```
ATGTCTTTCCGGGTTGGACTCAAGACGATAGTTACCGGATAAGGCGCAGC
GGTCGGACTGAACGGGGGTTCGTGCATACAGTCCAGCTTGGAGCGAACT
GCCTACCCGGAACTGAGTGTCAGGCGTGGAATGAGACAAACGCGGCCATA
ACAGCGGAATGACACCGGTAAACCGAAAGGCAGGAACAGGAGAGCGCACG
AGGGAGCCGCCAGGGGGAAACGCCTGGTATCTTTATAGTCCTGTCGGGTT
TCGCCACCACTGATTTGAGCGTCAGATTTCGTGATGCTTGTCAGGGGGGC
GGAGCCTATGGAAAAACGGCTTTGCCGCGGCCCTCTCACTTCCCTGTTAA
GTATCTTCCTGGCATCTTCCAGGAAATCTCCGCCCCGTTCGTAAGCCATT
TCCGCTCGCCGCAGTCGAACGACCGAGCGTAGCGAGTCAGTGAGCGAGGA
AGCGGAATATATCCTGTATCACATATTCTGCTGACGCACCGGTGCAGCCT
TTTTTCTCCTGCCACATGAAGCACTTCACTGACACCCTCATCAGTGCCAA
CATAGTAAGCCAGTATACACTCCGCTAGCGCTGATGTCCGGCGGTGCTTT
TGCCGTTACGCACCACCCCGTCAGTAGCTGAACAGGAGGGACAGCTGATA
GAAACAGAAGCCACTGGAGCACCTCAAAAACACCATCATACACTAAATCA
GTAAGTTGGCAGCATCACCCGACGCACTTTGCGCCGAATAAATACCTGTG
ACGGAAGATCACTTCGCAGAATAAATAAATCCTGGTGTCCCTGTTGATAC
CGGGAAGCCCTGGGCCAACTTTTGGCGAAAATGAGACGTTGATCGGCACG
TAAGAGGTTCCAACTTTCACCATAATGAAATAAGATCACTACCGGGCGTA
TTTTTTGAGTTATCGAGATTTTCAGGAGCTAAGGAAGCTAAAATGGAGAA
AAAAATCACTGGATATACCACCGTTGATATATCCCAATGGCATCGTAAAG
AACATTTTGAGGCATTTCAGTCAGTTGCTCAATGTACCTATAACCAGACC
GTTCAGCTGGATATTACGGCCTTTTTAAAGACCGTAAAGAAAAATAAGCA
CAAGTTTTATCCGGCCTTTATTCACATTCTTGCCCGCCTGATGAATGCTC
ATCCGCAATTCCGTATGGCAATGAAAGACGGTGAGCTGGTGATATGGGAT
AGTGTTCACCCTTGTTACACCGTTTTCCATGAGCAAACTGAAACGTTTTC
ATCGCTCTGGAGTGAATACCACGACGATTTCCGGCAGTTTCTACACATAT
ATTCGCAAGATGTGGCGTGTTACGGTGAAAACCTGGCCTATTTCCCTAAA
GGGTTTATTGAGAATATGTTTTTCGTCTCAGCCAATCCCTGGGTGAGTTT
CACCAGTTTTGATTTAAACGTGGCCAATATGGACAACTTCTTCGCCCCCG
TTTTCACCATGGGCAAATATTATACGCAAGGCGACAAGGTGCTGATGCCG
CTGGCGATTCAGGTTCATCATGCCGTTTGTGATGGCTTCCATGTCGGCAG
AATGCTTAATGAATTACAACAGTACTGCGATGAGTGGCAGGGCGGGCGT
AATTTTTTTAAGGCAGTTATTGGTGCCCTTAAACGCCTGGTTGCTACGCC
TGAATAAGTGATAATAAGCGGATGAATGGCAGAAATTCGAAAGCAAATTC
GACCCGGTCGTCGGTTCAGGGCAGGGTCGTTAAATAGCGACGTCTAAGAA
ACCATTATTATCATGACATTAACCTATAAAAATAGGCGTATCACGAGGCC
CTTTCGTCTCGCGCGTTTCGGTGATGACGGTGAAAACCTCTGACACATGC
AGCTCCCGGAGACGGTCACAGCTTGTCTGTAAGCGGATGCCGGGAGCAGA
CAAGCCCGTCAGGGCGCGTCAGCGGGTGTTGGCGGGTGTCGGGCTGGCT
TAACTATGCGGCATCAGAGCAGATTGTACTGAGAGTGCACAATCGCATCC
GATTGCAGTATAAATTTAACGATCACTCATCATGTTCATATTTATCAGAG
CTCGTGCTATAATTATACTAATTTTATAAGGAGGAAAAATATGGGCATT
TTTAGTATTTTTGTAATCAGCACAGTTCATTATCAACCAAACAAAAAATA
AGTGGTTATAATGAATCGTTAATAAGCAAAATTCATATAACCAAATTAAA
GAGGGTTATAATGAACGAGAAAATATAAAACACAGTCAAAACTTTATTA
CTTCAAAACATAATATAGATAAAATAATGACAAATATAAGATTAAATGAA
CATGATAATATCTTTGAAATCGGCTCAGGAAAAGGCCATTTTACCCTTGA
ATTAGTAAAGAGGTGTAATTTCGTAACTGCCATTGAAATAGACCATAAAT
TATGCAAAACTACAGAAAATAAACTTGTTGATCACGATAATTTCCAAGTT
TTAAACAAGGATATATTGCAGTTTAAATTTCCTAAAAACCAATCCTATAA
AATATATGGTAATATACCTTATAACATAAGTACGGATATAATACGCAAAA
TTGTTTTTGATAGTATAGCTAATGAGATTTATTTAATCGTGGAATACGGG
TTTGCTAAAAGATTATTAAATACAAAACGCTCATTGGCATTACTTTTAAT
GGCAGAAGTTGATATTTCTATATTAAGTATGGTTCCAAGAGAATATTTTC
ATCCTAAACCTAAAGTGAATAGCTCACTTATCAGATTAAGTAGAAAAAAA
TCAAGAATATCACACAAAGATAAACAAAAGTATAATTATTTCGTTATGAA
ATGGGTTAACAAAGAAATACAAGAAAATATTTACAAAAAATCAATTTAACA
ATTCCTTAAAACATGCAGGAATTGACGATTTAAACAATATTAGCTTTGAA
CAATTCTTATCTCTTTTCAATAGCTATAAATTATTTAATAAGTAAGTTAA
GGGATGCATAAACTGCATCCCTTAACTTGTTTTTCGTGTGCCCGATCGGT
GCGGGCCTCTTCGCTATTACGCCAGCTGGCGAAAGGGGATGTGCTGCAA
GGCGATTAAGTTGGGTAACGCCAGGGTTTTCCCAGTCACGACGTTGTAAA
ACGACGGCCAGTGCCAAGCTAGCTTTCGATCATCATAATTCTGTCTCATT
ATATAACATCCTCCATACCTTCTATTATAGAATACCATAAACTCATCTGG
CAATTCATTTCGAGTCACGAAGAACGGAAAAACTGCCGGTTTTTATATTA
CAAATGTATTAAGTTTTTCTATTAACAAAAAACAATAGGTTTCCCATAGC
GAAAGTTGTTGATTAACGTTCACATCCCACTTACACTATAAAGGTTTACC
CAGCAATACATCTCAAGCCCTAAGAATACACGTTCGCTTTTCAACTGTTA
CAGAATTATTACAAATAGTTGGTATAGTCCTCTTTAGCCTTTGGAGCTAT
TATCTCATCATTTGTTTTTAGGTGAAAACTGGGTAAACTTAGTATTAAT
CAATATAAAATTAATTCTCAAATACTTAATTACGTACTGGGATTTTCTGA
AAAAA
```

Example III

ActA-Based Fusion Protein Partners, Including ActA Derivatives that are Truncated or Deleted in One or More Motifs The present invention, in some embodiments, provides reagents and methods comprising a first nucleic acid encoding an ActA-based fusion protein partner operably linked to and in frame with a second nucleic acid encoding at least one heterologous antigen. Provided is a nucleic acid that can hybridize under stringent conditions to any of the disclosed nucleic acids.

What is encompassed is a first nucleic acid and second nucleic acid that are operably linked with each other, and in frame with each other. In this context, "operably linked with each other" means that any construct comprising the first and second nucleic acids encode a fusion protein. In another embodiment, the second nucleic acid can be embedded in the first nucleic acid.

The ActA-based fusion protein partner can comprise one or more of the following. "Consisting" embodiments are also available, and here the ActA-based fusion protein partner can consist of one or more of the following embodiments:

(1) ActA-N100 (amino acids 1-100 of GenBank Acc. No. X59723, or of a similar or homologous ActA sequence).

(2) Full length ActA, where a nucleic acid encoding at least one heterologous antigen is connected to (and in frame with) the C-terminus of full length ActA, residing at an internal position of ActA, or both connected to the C-terminus of the full length ActA and also residing at an internal position of ActA.

(3) A truncated ActA that normally supports less than 90% the activity of nucleating the Arp2/3 complex, as compared with the activity of full length ActA; conventionally supports less than 80% the nucleating activity of full length ActA; characteristically supports less than 70% the nucleating activity of full length ActA; typically supports less than 60% the nucleating activity of full length ActA; more typically supports less than 50% the nucleating activity of full length ActA; most typically supports less than 40% the nucleating activity of full length ActA; often supports less than 30% the nucleating activity of full length ActA; more often supports less than 20% the nucleating activity of full length ActA; most often supports less than 10% the nucleating activity of full length ActA; usually supports less than 5% the nucleating activity of full length ActA; more usually supports less than 2% the nucleating activity of full length ActA; and most usually is undetectable in any ability to nucleate the Arp2/3 complex. The reduced, or eliminated, nucleation activity of progressively truncated ActA was demonstrated by Skoble (Skoble, et al. (2000) J. Cell Biol. 150:527-537). It was demonstrated that ActA truncated at amino acid-101, and ActA truncated at amino acid-135, have little or no nucleating activity, while ActA truncated at amino acids 165, 201, and 263, are as potent as full length ActA in nucleating the Arp2/3 complex.

(4) A truncated ActA, wherein the ActA is truncated at about amino acid-40; truncated at about amino acid-45; truncated at about amino acid-50; truncated at about amino acid-55; truncated at about amino acid-60; truncated at about amino acid-65; truncated at about amino acid-70; truncated at about amino acid-75; truncated at about amino acid-80; truncated at about amino acid-85; truncated at about amino acid-90; truncated at about amino acid-95; truncated at about amino acid-100; truncated at about amino acid-105; truncated at about amino acid-110; truncated at about amino acid-115;

truncated at about amino acid-120; truncated at about amino acid-125; truncated at about amino acid-130; truncated at about amino acid-135; truncated at about amino acid-140; truncated at about amino acid-145; truncated at about amino acid-150; truncated at about amino acid-150; truncated at about amino acid-155; and truncated at about amino acid-160. The term "about" in this context means plus or minus one amino acid, plus or minus two amino acids, plus or minus three amino acids, plus or minus four amino acids, or plus or minus five amino acids.

(5) ActA secretory sequence (amino acids 1-29 of GenBank Acc. No. X59723, or of a similar or homologous ActA sequence).

(6) Does not comprise an ActA secretory sequence (amino acids 1-29 of GenBank Acc. No. X59723, or of a similar or homologous ActA sequence).

(7) ActA secretory sequence and the mature N-terminal domain (amino acids 1-263 of GenBank Acc. No. X59723, or of a similar or homologous ActA sequence).

(5) Mature N-terminal domain without the secretory sequence (amino acids 30-263 of GenBank Acc. No. X59723, or of a similar or homologous ActA sequence).

(9) ActA sequence with reduced ability to directly stimulate actin polymerization. The reduced ability can be, e.g., normally at most 90% maximal, more normally at most 80% maximal, most normally at most 70% maximal, usually at most 60% maximal, more usually at most 50% maximal, most usually at most 40% maximal, often at most 30% maximal, more often at most 20% maximal, most often at most 10% maximal, and typically at most 5% maximal.

(10) ActA sequence with a reduced ability to bind to a member of the Ena/VASP family of proteins (mammalian Enabled (Mena); Ena/VASP-like protein (Evl); vasodilator-stimulated phosphoprotein (VASP) (see, e.g., Machner, et al. (2001) J. Biol. Chem. 276:40096-40103). The reduced ability can be, e.g., normally at most 90% maximal, more normally at most 80% maximal, most normally at most 70% maximal, usually at most 60% maximal, more usually at most 50% maximal, most usually at most 40% maximal, often at most 30% maximal, more often at most 20% maximal, most often at most 10% maximal, and typically at most 5% maximal.

(11) ActA that is truncated at the point of, deleted in, or mutated in amino acids 93-98 of GenBank Acc. No. X59723, or of a similar or homologous ActA sequence (LKEKAE (SEQ ID NO: 124)) (homologous to actin binding domain of caldesmon (see, e.g., Pistor, et al. (2000) J. Cell Science 113:3277-3287; Lasa, et al. (1997) EMBO J. 16:1531-1540).

(12) ActA that is truncated at the point of, deleted in, or mutated in, amino acids 126-155 (PAIQ, etc.) of GenBank Acc. No. X59723, or of a similar or homologous ActA sequence, that are critical for ActA dimer formation (see, e.g., Mourrain, et al. (1997) Proc. Natl. Acad. Sci. USA 94:10034-10039).

(13) ActA that is truncated at the point of, deleted in, or mutated in, amino acids 121-170 of GenBank Acc. No. X59723, or of a similar or homologous ActA sequence (minimal ARP2/3 activating domain) (see, e.g., Zalevsky, et al. (2001) J. Biol. Chem. 276:3468-3475).

(14) ActA that is truncated at the point of, deleted in, or mutated in, amino acids 146-150 KKRRK (SEQ ID NO:30)) of GenBank Acc. No. X59723, or of a similar or homologous ActA sequence (a region essential for recruiting Arp2/3 complex) (Lasa, et al. (1997) EMBO J. 16:1531-1540; Pistor, et al. (2000) J. Cell Science 113:3277-3287).

(15) ActA that is truncated at the point of, deleted in, or mutated in, amino acids 41-46 DEWEEE (SEQ ID NO:31) of GenBank Acc. No. X59723, or of a similar or homologous ActA sequence (a region involved in Arp2/3 complex binding) (see, e.g., Boujemaa-Paterski, et al. (2001) Biochemistry 40:11390-11404).

(16) ActA that is truncated at the point of, deleted in, or mutated in, amino acids 481-492 (DRLADLRDRGTG (SEQ ID NO:32)), which is a vinculin homology region. Vinculin mediates cell-to-cell spread of S. flexneri (see, e.g., Kocks, et al. (1992) Cell 68:521-531).

(17) ActA that is truncated at the point of, deleted in, or mutated in, the cofilin homology domain (IKKKRRKA-IASSD (SEQ ID NO:33)) (amino acids 145-156 of GenBank Acc. No. X59723, or of a similar or homologous ActA sequence) (see, e.g., Skoble, et al. (2000) J. Cell Biol. 150: 527-537).

(18) ActA that is truncated at the point of, deleted in, or mutated in, amino acids 50-125 of GenBank Acc. No. X59723, or of a similar or homologous ActA sequence (continuity of filament elongation region) (see, e.g., Lasa, et al. (1997) EMBO J. 16:1531-1540).

(16) ActA that is truncated at the point of, deleted in, or mutated in, the first $FP_4$ motif (amino acids 265-269, or 264-269, and the like), second $FP_4$ motif (amino acids 300-304, or 299-304, and the like), third $FP_4$ motif (amino acids 335-339, or 334-339, and the like), fourth $FP_4$ motif (amino acids 380-384, or 379-384, and the like), all four $FP_4$ motifs, or any combination of the above, where the amino acids refer to GenBank Acc. No. X59723, or a similar or homologous ActA sequence (see, e.g., Machner, et al. (2001) J. Biol. Chem. 276:40096-40103). The $FP_4$ motifs enhance actin polymerization and bacterial motility by recruiting focal contact proteins (e.g., VASP and Mena) and profilin, which promote elongation of filaments nucleated by interactions between motifs at the N-terminal region of ActA and Arp2/3 complex (see, e.g., Welch, et al. (1998) Science 281:105-108; Skoble, et al. (2000) J. Cell Biol. 150:527-537); Pistor, et al. (2000) J. Cell Science 113:3277-3287).

(17) ActA that is truncated at the point of, deleted in, or mutated in, amino acids 136-165 of GenBank Acc. No. X59723, or of a similar or homologous ActA sequence (cofilin homology region, a region that stimulates Arp2/3 complex) (see, e.g., Lauer, et al. (2001) Mol. Microbiol. 42:1163-1177).

(18) ActA that is truncated at the point of, deleted in, or mutated in, the "acidic stretch," that is, amino acids 31-58 (TDSED (SEQ ID NO:34), etc.) of GenBank Acc. No. X59723, or of a similar or homologous ActA sequence. The acidic stretch contributes to actin polymerization, movement of *Listeria* in the host cell cytoplasm, cell to cell spreading, and to plaque size (see, e.g., Skoble, et al. (2000) J. Cell Biol. 150:527-537; Lauer, et al. (2001) Mol. Microbiol. 42:1163-1177).

(19) ActA that is truncated at the point of, deleted in, or mutated in, amino acids 60-101 (AB region, an actin binding domain) of GenBank Acc. No. X59723, or of a similar or homologous ActA sequence (see, e.g., Lauer, et al. (2001) Mol. Microbiol. 42:1163-1177).

(20) ActA that is truncated at the point of, deleted in, or containing the mutation of mutant 34 (no movement; no plaque) amino acids 117-121 (KKRRK (SEQ ID NO:30)) of GenBank Acc. No. X59723, or of a similar or homologous ActA sequence (Lauer, et al. (2001) Mol. Microbiol. 42:1163-1177.

(21) ActA that is truncated at the point of, deleted in, or containing the mutation of mutant 34 (no movement; no plaque) amino acids 244-249 (DKSAGLID (SEQ ID NO:123)) of GenBank Acc. No. X59723, or of a similar or homologous ActA sequence. The mutation can be, e.g., replacement of the D, K, and D by alanines (Lauer, et al. (2001) Mol. Microbiol. 42:1163-1177).

(22) ActA that is truncated at the point of, deleted in, or containing the mutation of mutants 39, 47-52, 54 and/or 48 (reduced movement) (Lauer, et al. (2001) Mol. Microbiol. 42:1163-1177).

(23) ActA that is truncated at the point of, deleted in, or mutated in, amino acids 264-390 (central repeat region) of GenBank Acc. No. X59723, or of a similar or homologous ActA sequence (see, e.g., Lauer, et al. (2001) Mol. Microbiol. 42:1163-1177; Skoble, et al. (2000) J. Cell Biol. 150:527-537; Skoble, et al. (2001) J. Cell Biol. 155:89-100).

The present invention provides an ActA-based fusion protein partner that can comprise any one, or any combination of, the above-disclosed embodiments. "Consisting" embodiments are also available, and here the ActA-based fusion protein partner can consist of one or more of the above-disclosed embodiments.

When provided with the present disclosure, the skilled artisan can envision and prepare embodiments containing conservative modifications, or modifications where one or more amino acids is deleted, or where one or more amino acids is replaced with alanine, and the like.

In the present context, "fusion protein partner" encompasses, but is not limited to, a nucleic acid encoding a polypeptide, or the polypeptide itself, that occurs as a fusion protein with a heterologous antigen, where the fusion protein partner enhances, e.g., transcription, translation, stability, processing by an antigen presenting cell (APC), presentation by an APC, immune presentation, cytotoxic T cell response, CD8⁺ T cell response, CD4⁺ T cell response, reduction in tumor size, number, or metastasis, increase in survival to a tumor or infective agent, and the like.

The present invention provides nucleic acids and polypeptides of ActA-N100, and fusion proteins thereof, including fusion proteins that comprise at least one antigen. Without implying any limitation on the invention, the at least one antigen can comprise mesothelin, H-ras, a mesothelin derivative, a H-ras derivative, or any combination thereof. The nucleic acid encoding at least one antigen can be operably linked to, and in frame with, the N-terminus of an ActA-based fusion protein partner. Alternatively, the nucleic acid encoding the at least one antigen can be operably linked to, and in frame with, the C-terminus of the ActA fusion protein partner. Or the nucleic acid encoding the at least one antigen can be operably linked with, and reside within a nucleic acid encoding an ActA-based fusion protein partner.

Example IV

Building Blocks Used for Assembling Nucleic Acids Encoding ActA Fusion Proteins The following discloses nucleic acids and polypeptides used for making constructs that contain ActA-N100 as a fusion protein partner. Sequences codon optimized for expression in *L. monocytogenes*, and non-codon optimized sequences, are identified.

| | |
|---|---|
| Nucleic acid | GTGGGATTAAATAGATTTATGCGTGCGATGATGGTAGT |
| encoding | TTTCATTACTGCCAACTGCATTACGATTAACCCCGACA |
| ActA-N100 native | TAATATTTGCAGCGACAGATAGCGAAGATTCCAGTCTA |
| sequence (not | AACACAGATGAATGGGAAGAAGAAAAAACAGAAGAGCA |
| codon optimized), | GCCAAGCGAGGTAAATACGGGACCAAGATACGAAACTG |
| including Shine- | CACGTGAAGTAAGTTCACGTGATATTGAGGAACTAGAA |
| Dalgarno | AAATCGAATAAAGTGAAAAATACGAACAAAGCAGACCT |
| sequence.<br>(SEQ ID NO: 122) | AATAGCAATGTTGAAAGCAAAAGCAGAGAAAGGT |
| ActA promoter | AAGCTTGGGAAGCAGTTGGGGTTAACTGATTAACAAATGTTAGAGAA |
| *L. monocytogenes* | AAATTAATTCTCCAAGTGATATTCTTAAAATAATTCATGAATATTTT |
| 10403S. | TTCTTATATTAGCTAATTAAGAAGATAATTAACTGCTAATCCAATTT |
| (SEQ ID NO: 35) | TTAACGGAATAAATTAGTGAAAATGAAGGCCGAATTTTCCTTGTTCT |
| | AAAAAGGTTGTATTAGCGTATCACGAGGAGGGAGTATAA |
| ActA-N100 native | GTGGGATTAAATAGATTTATGCGTGCGATGATGGTAGTTTTCAT |
| sequence (not codon | TACTGCCAACTGCATTACGATTAACCCCGACATAATATTTGCAG |
| optimized), | CGACAGATAGCGAAGATTCCAGTCTAAACACAGATGAATGGGAA |
| including Shine- | GAAGAAAAAACAGAAGAGCAGCCAAGCGAGGTAAATACGGGACC |
| Dalgarno sequence, | AAGATACGAAACTGCACGTGAAGTAAGTTCACGTGATATTGAGG |
| with human | AACTAGAAAAATCGAATAAAGTGAAAAATACGAACAAAGCAGAC |
| mesothelin (codon | CTAATAGCAATGTTGAAAGCAAAAGCAGAGAAAGGTGGATCCCG |
| optimized) with SS | TACATTAGCAGGTGAAACAGGTCAAGAAGCAGCACCACTTGACG |
| deleted and GPI | GTGTATTAACGAATCCACCAAATATATCAAGTTTAAGTCCACGT |

| | |
|---|---|
| deleted. The BamHI (GGATCC) and SacI (GAGCTC) sites are shown in BOLD. (SEQ ID NO: 36) | CAATTATTAGGTTTTCCATGTGCAGAAGTTTCAGGTTTAAGTAC<br>AGAACGTGTCCGTGAGTTAGCAGTTGCATTAGCACAAAAAAACG<br>TTAAATTATCTACAGAACAGTTACGTTGTTTAGCCCATAGATTA<br>AGCGAACCACCAGAAGACTTAGATGCACTTCCTTTAGACCTTCT<br>TTTATTCTTAAATCCAGATGCATTTTCAGGACCACAAGCATGTA<br>CACGTTTTTTTAGTCGAATTACAAAAGCCAATGTTGATTTATTA<br>CCTCGTGGGGCTCCTGAAAGACAACGTTTATTACCTGCTGCATT<br>AGCATGCTGGGGTGTTCGCGGTAGCTTATTAAGTGAAGCCGATG<br>TTCGTGCTTTAGGGGGTTTAGCATGTGATTTACCTGGTCGTTTC<br>GTTGCAGAATCAGCAGAAGTGTTATTACCGAGATTAGTTTCATG<br>CCCAGGACCTTTAGATCAAGATCAACAAGAGGCAGCTAGAGCAG<br>CTCTTCAAGGAGGAGGCCCACCATATGGCCCACCAAGTACATGG<br>AGTGTTTCTACAATGGATGCGTTAAGAGGTTTATTACCGGTTTT<br>AGGACAACCAATTATTCGTAGTATTCCACAAGGCATTGTAGCAG<br>CATGGCGTCAACGTAGTTCTCGTGATCCGTCTTGGCGACAACCA<br>GAACGTACAATTCTACGTCCAAGATTTCGTAGAGAAGTAGAAAA<br>AACGGCGTGTCCTAGTGGCAAAAAAGCACGTGAAATTGATGAAA<br>GTTTAATTTTTTATAAAAAATGGGAATTAGAAGCATGTGTCGAT<br>GCAGCATTACTAGCTACACAAATGGATCGTGTTAATGCTATTCC<br>ATTCACATATGAACAATTAGATGTTTTAAAGCATAAATTAGACG<br>AATTATATCCACAAGGTTATCCAGAATCAGTTATTCAACATTTA<br>GGTTACTTATTTTTAAAAATGAGTCCAGAAGACATACGCAAATG<br>GAATGTTACAAGTTTAGAAACATTAAAAGCGCTTTTAGAAGTTA<br>ACAAAGGTCATGAAATGAGTCCACAAGTTGCTACGTTAATTGAT<br>AGATTCGTTAAAGGCCGTGGTCAATTAGATAAAGATACTTTAGA<br>TACATTAACAGCATTTTATCCTGGCTACTTATGCAGTTTATCAC<br>CAGAAGAATTAAGTTCCGTTCCACCGAGTAGTATCTGGGCAGTT<br>CGTCCGCAAGATTTAGATACATGCGACCCACGTCAATTAGATGT<br>TTTATATCCAAAAGCAAGATTAGCTTTCCAAAATATGAACGGTA<br>GTGAATATTTCGTAAAAATTCAATCCTTTTTAGGTGGTGCACCA<br>ACTGAAGATCTAAAAGCATTAAGCCAACAAAATGTAAGTATGGA<br>TTTAGCTACGTTTATGAAATTACGTACAGATGCAGTTCTACCAT<br>TAACAGTTGCAGAAGTTCAAAAATTATTAGGTCCACACGTAGAA<br>GGATTAAAAGCAGAAGAACGTCACCGTCCAGTTCGCGATTGGAT<br>TTTACGTCAACGTCAAGATGATTTAGATACATTAGGTTTAGGTT<br>TACAAGGCTAAGAGCTC |
| Nucleic acid encoding full-length ActA *L. monocytogenes* | GTGGGATTAAATAGATTTATGCGTGCGATGATGGTAGTTTT<br>C 10403S.
(SEQ ID NO: 37)

GGTAAATACGGGACCAAGATACGAAACTGCACGTGAAGTA

AGTTCACGTGATATTGAGGAACTAGAAAAATCGAATAAAG

TGAAAAATACGAACAAAGCAGACCTAATAGCAATGTTGAA

AGCAAAAGCAGAGAAAGGTCCGAATAACAATAATAACAAC

GGTGAGCAAACAGGAAATGTGGCTATAAATGAAGAGGCTTC

AGGAGTCGACCGACCAACTCTGCAAGTGGAGCGTCGTCATC

CAGGTCTGTCATCGGATAGCGCAGCGGAAATTAAAAAAGA

AGAAAAGCCATAGCGTCGTCGGATAGTGAGCTTGAAAGCCT

TACTTATCCAGATAAACCAACAAAAGCAAATAAGAGAAAAG

TGGCGAAAGAGTCAGTTGTGGATGCTTCTGAAAGTGACTTAG

ATTCTAGCATGCAGTCAGCAGACGAGTCTACACCACAACCTT

TAAAAGCAAATCAAAAACCATTTTTCCCTAAAGTATTTAAAA

AAATAAAAGATGCGGGGAAATGGGTACGTGATAAAATCGAC

GAAAATCCTGAAGTAAAGAAAGCGATTGTTGATAAAAGTGC

AGGGTTAATTGACCAATTATTAACCAAAAAGAAAAGTGAAG

AGGTAAATGCTTCGGACTTCCCGCCACCACCTACGGATGAAG

AGTTAAGACTTGCTTTGCCAGAGACACCGATGCTTCTCGGTTT

TAATGCTCCTACTCCATCGGAACCGAGCTCATTCGAATTTCCG

CCGCCACCTACGGATGAAGAGTTAAGACTTGCTTTGCCAGAG

ACGCCAATGCTTCTTGGTTTTAATGCTCCTGCTACATCGGAAC

CGAGCTCATTCGAATTTCCACCGCCTCCAACAGAAGATGAAC

TAGAAATTATGCGGGAAACAGCACCTTCGCTAGATTCTAGTT

TTACAAGCGGGGATTTAGCTAGTTTGAGAAGTGCTATTAATC

GCCATAGCGAAAATTTCTCTGATTTCCCACTAATCCCAACAG

AAGAAGAGTTGAACGGGAGAGGCGGTAGACCAACATCTGAA

GAATTTAGTTCGCTGAATAGTGGTGATTTTACAGATGACGAA

AACAGCGAGACAACAGAAGAAGAAATTGATCGCCTAGCTGA

TTTAAGAGATAGAGGAACAGGAAAACACTCAAGAAATGCGG

GTTTTTTACCATTAAATCCATTTATTAGTAGCCCTGTTCCTTCA

TTAACTCCAAAGGTACCGAAAATAAGCGCGCCGGCTCTGATA

AGTGACATAACTAAAAAAGCGCCATTTAAGAATCCATCACAG

CCATTAAATGTGTTTAATAAAAAAACTACAACGAAAACAGTG

ACTAAAAAACCAACCCCTGTAAAGACCGCACCAAAGCTAGCA

GAACTTCCTGCCACAAAACCACAAGAAACCGTACTTAGGGAA

AATAAAACACCCTTTATAGAAAAACAAGCAGAAACAAACAAG

CAGTCAATCAATATGCCGAGCCTACCAGTAATCCAAAAAGAA

GCTACAGAGAGCGATAAAGAGGAAATGAAACCACAAACCGA

GGAAAAAATGGTAGAGGAAAGCGAATCAGCTAATAACGCAA

ACGGAAAAAATCGTTCTGCTGGCATTGAAGAAGGAAAACTAA

TTGCTAAAAGTGCAGAAGACGAAAAAGCGAAGGAAGAACCA

GGGAACCATACGACGTTAATTCTTGCAATGTTAGCTA

| | |
|---|---|
| | TTGGCGTGTTCTCTTTAGGGGCGTTTATCAAAATTATT |
| | CAATTAAGAAAAAATAATTAA |
| ActA polypeptide from *L. monocytogenes* 10403S. (SEQ ID NO: 38) | VGLNRFMRANMVVFITANCITINPDIIFAATDSEDSSLNTDEWEEEKT EEQPSEVNTGPRYETAREVSSRDIEELEKSNKVKNTNKADLIAMLKAK AEKGPNNNNNNGEQTGNVAINEEASGVDRPTLQVERRHPGLSSDSAAE IKKRRKAIASSDSELESLTYPDKPTKANKRKVAKESVVDASESDLDSS MQSADESTPQPLKANQKPFFPKVFKKIKDAGKWVRDKTDENPEVKKAI VDKSAGLIDQLLTKKKSEEVNASDFPPPPTDEELRLALPETPMLLGFN APTPSEPSSFEFPPPPPTDEELRLALPETPMLLGFNAPATSEPSSFEFP PPPTEDELEIMRETAPSLDSSFTSGDLASLRSAINRHSENFSDFPLIP TEEELNGRGGRPTSEEFSSLNSGDFTDDENSETTEEEIDRLADLRDRG TGKHSRNAGFLPLNPFISSPVPSLTPKVPKISAPALISDITKKAPFKN PSQPLNVFNKKTTTKTVTKKPTPVKTAPKLAELPATKPQETVLRENKT PFIEKQAETNKQSINNPSLPVIQKEATESDKEEMKPQTEEKMVEESES ANNANGKNRSAGIEEGKLIAKSAEDEKAKEEPGNHTTLILAMLAIGVF SLGAFIKIIQLRKNN |
| Nucleic acid encoding ActA-N100 fragment used in our constructs, including promoter and restriction enzyme sites (KpnI site and BamHI site underlined, promoter sequence lowercase, N100 ORF sequence in UPPERCASE). (SEQ ID NO: 39) | <u>Ggtacc</u>gggaagcagttgggggttaactgattaacaaatgttagagaaa Aattaattctccaagtgatattcttaaaataattcatgaatatttttt Cttatattagctaattaagaagataattaactgctaatccaattttta Acggaataaattagtgaaaatgaaggccgaattttccttgttctaaaa AggttgtattagcgtatcacgaggagggagtataaGTGGGATTAAATA GATTTATGCGTGCGATGATGGTAGTTTTCATTACTGCCAACTGCATTA CGATTAACCCCGACATAATATTTGCAGCGACAGATAGCGAAGATTCCA GTCTAAACACAGATGAATGGGAAGAAGAAAAAACAGAAGAGCAGCCAA GCGAGGTAAATACGGGACCAAGATACGAAACTGCACGTGAAGTAAGTT CACGTGATATTGAGGAACTAGAAAAATCGAATAAAGTGAAAAATACGA ACAAAGCAGACCTAATAGCAATGTTGAAAGCAAAAGCAGAGAAAGGT <u>ggatcc</u> |
| Amino acid sequence of ActA-N100. The nucleic acid encoding ActA-N100 contains a valine codon at the N-terminus, but the *Listeria* actually biosynthesizes a polypeptide starting with methionine, not valine. (SEQ ID NO: 40) | VGLNRFMRAMMVVFITANCITINPDIIFAATDSEDSS LNTDEWEEEKTEEQPSEVNTGPRYETAREVSSRDIEE LEKSNKVKNTNKADLIAMLKAKAEKG |
| Amino acid | VGLNRFMRAMMVVFITANCITINPDIIFAATDSEDSSLNTDEWEE |

-continued

| | |
|---|---|
| sequence of fusion protein of ActA-N100 with human mesothelin (ss deleted; GPI deleted). The nucleic acid encoding ActA-N100, or a fusion protein thereof, contains a valine codon at the N-terminus, but the *Listeria* actually biosynthesizes a polypeptide starting with methionine, not valine. The BamHI site adds two amino acids (GS). (SEQ ID NO: 41) | EKTEEQPSEVNTGPRYETAREVSSRDIEELEKSNKVKNTNKADLI<br>AMLKAKAEKGGSRTLAGETGQEAAPLDGVLTNPPNISSLSPRQLL<br>GFPCAEVSGLSTERVRELAVALAQKNVKLSTEQLRCLAHRLSEPP<br>EDLDALPLDLLLFLNPDAFSGPQACTRFFSRITKANVDLLPRGA<br>PERQRLLPAALACWGVRGSLLSEADVRALGGLACDLPGRFVAES<br>AEVLLPRLVSCPGPLDQDQQEAARAALQGGGPPYGPPSTWSVST<br>MDALRGLLPVLGQPIIRSIPQGIVAAWRQRSSRDPSWRQPERTI<br>LRPRFRREVEKTACPSGKKAREIDESLIFYKKWELEACVDAALL<br>ATQMDRVNAIPFTYEQLDVLKHKLDELYPQGYPESVIQHLGYLF<br>LKMSPEDIRKWNVTSLETLKALLEVNKGHEMSPQVATLIDRFVK<br>GRGQLDKDTLDTLTAFYPGYLCSLSPEELSSVPPSSIWAVRPQD<br>LDTCDPRQLDVLYPKARLAFQNMNGSEYFVKIQSFLGGAPTEDL<br>KALSQQNVSMDLATFMKLRTDAVLPLTVAEVQKLLGPHVEGLKA<br>EERHRPVRDWILRQRQDDLDTLGLGLQG |
| Nucleic acid sequence of 12ras. (SEQ ID NO: 42) | GCCATGACAGAATATAAATTAGTTGTAGTTGGTGCAGA<br>TGGTGTTGGTAAAAGTGCATTAACAATTCAATTAATTC<br>AATAA |
| Amino acid sequence of 12ras. (SEQ ID NO: 43) | AMTEYKLVVVGADGVGKSALTIQLIQ |
| Nucleic acid of fusion protein of ActA-N100 with codon optimized human mesothelin (deleted SS; deleted GPI) and 12ras. 12ras is fused to the 3'-end of mesothelin (deleted in SS; deleted in GPI). The mesothelin-ras fusion construct is codon optimized | GTGGGATTAAATAGATTTATGCGTGCGATGATGGTAGTTTTCATTA<br>CTGCCAACTGCATTACGATTAACCCCGACATAATATTTGCAGCGAC<br>AGATAGCGAAGATTCCAGTCTAAACACAGATGAATGGGAAGAAGAA<br>AAAACAGAAGAGCAGCCAAGCGAGGTAAATACGGGACCAAGATACG<br>AAACTGCACGTGAAGTAAGTTCACGTGATATTGAGGAACTAGAAAA<br>ATCGAATAAAGTGAAAAATACGAACAAAGCAGACCTAATAGCAATG<br>TTGAAAGCAAAAGCAGAGAAAGGTGGATCCCGTACATTAGCAGGTG<br>AAACAGGTCAAGAAGCAGCACCACTTGACGGTGTATTAACGAATCC<br>ACCAAATATATCAAGTTTAAGTCCACGTCAATTATTAGGTTTTCCA<br>TGTGCAGAAGTTTCAGGTTTAAGTACAGAACGTGTCCGTGAGTTAG<br>CAGTTGCATTAGCACAAAAAAACGTTAAATTATCTACAGAACAGTT<br>ACGTTGTTTAGCCCATAGATTAAGCGAACCACCAGAAGACTTAGAT<br>GCACTTCCTTTAGACCTTCTTTTATTCTTAAATCCAGATGCATTTT<br>CAGGACCACAAGCATGTACACGTTTTTTTAGTCGAATTACAAAAGC<br>CAATGTTGATTTATTACCTCGTGGGGCTCCTGAAAGACAACGTTTA<br>TTACCTGCTGCATTAGCATGCTGGGGTGTTCGCGGTAGCTTATTAA |

| | -continued |
|---|---|
| and cloned (as a | GTGAAGCCGATGTTCGTGCTTTAGGGGGTTTAGCATGTGATTTACC |
| BamHI-SacI | TGGTCGTTTCGTTGCAGAATCAGCAGAAGTGTTATTACCGAGATTA |
| fragment) | GTTTCATGCCCAGGACCTTTAGATCAAGATCAACAAGAGGCAGCTA |
| downstream of the | GAGCAGCTCTTCAAGGAGGAGGCCCACCATATGGCCCACCAAGTAC |
| ActA-N100-fusion | ATGGAGTGTTTCTACAATGGATGCGTTAAGAGGTTTATTACCGGTT |
| protein partner. | TTAGG

| | |
|---|---|
| | VTSLETLKALLEVNKGHEMSPQVATLIDRFVKGRGQLD |
| | KDTLDTLTAFYPGYLCSLSPEELSSVPPSSIWAVRPQD |
| | LDTCDPRQLDVLYPKARLAFQNMNGSEYFVKIQSFLGG |
| | APTEDLKALSQQNVSMDLATFMKLRTDAVLPLTVAEVQ |
| | KLLGPHVEGLKAEERHRPVRDWILRQRQDDLDTLGLGL |
| | QGAMTEYKLVVVGADGVGKSALTIQLIQ |
| ActA promoter and ActA-N100: N100 coding sequence is native. Tumor antigens are inserted at the BamHI site (GGATCC). (SEQ ID NO: 46) | AAGCTTGGGAAGCAGTTGGGGTTAACTGATTAACAAATGTTAGAGAAAAA TTAATTCTCCAAGTGATATTCTTAAAATAATTCATGAATATTTTTTCTTA TATTAGCTAATTAAGAAGATAATTAACTGCTAATCCAATTTTTAACGGAA TAAATTAGTGAAAATGAAGGCCGAATTTTCCTTGTTCTAAAAAGGTTGTA TTAGCGTATCACGAGGAGGGAGTATAAGTGGGATTAAATAGATTTATGCG TGCGATCATGGTAGTTTTCATTACTGCCAACTGCATTACGATTAACCCCG ACATAATATTTGCAGCGACAGATAGCGAAGATTCCAGTCTAAACACAGAT GAATGGGAAGAAGAAAAAACAGAAGAGCAGCCAAGCGAGGTAAATACGGG ACCAAGATACGAAACTGCACGTGAAGTAAGTTCACGTGATATTGAGGAAC TAGAAAAATCGAATAAAGTGAAAAATACGAACAAAGCAGACCTAATAGCA ATGTTGAAAGCAAAAGCAGAGAAAGGTGGATCC |
| Amino acid sequence of ActAN100: the BamHI site adds two amino acids (GS). (SEQ ID NO: 47) | VGLNRFMRAMMVVFITANCITINPDIIFAATDSEDSSLNTDEWEEEK TEEQPSEVNTGPRYETAREVSSRDIEELEKSNKVKNTNKADLIAMLK AKAEKGGS |

Example V

Building Blocks Used for Assembling Listeriolysin (LLO; hly Gene) Fusion Proteins

| | |
|---|---|
| Nucleic acid of LLO open reading frame (ORF) from wild type *Listeria* 10403S. (SEQ ID NO: 48) | Atgaaaaaaataatgctagttttta ttacacttatattagttagtcta Ccaattgcgcaacaaactgaagcaaaggatgcatctgcattcaataaa Gaaaattcaatttcatccatggcaccaccagcatctccgcctgcaagt Cctaagacgccaatcgaaaagaaacacgcggatgaaatcgataagtat Atacaaggattggattacaataaaaacaatgtattagtataccacgg Agatgcagtgacaaatgtgccgccaagaaaaggttacaaagatggaa Atgaatatattgttgtggagaaaaagaagaaatccatcaatcaaat Aatgcagacattcaagttgtgaatgcaatttcgagcctaacctatcc Aggtgctctcgtaaaagcgaattcggaattagtagaaaatcaaccag Atgttctccctgtaaaacgtgattcattaacactcagcattgatttg CcaggtatgActAatcaagacaataaaatcgttgtaaaaaatgccac Taaatcaaacgttaacaacgcagtaaatacattagtggaaagatgga Atgaaaaatatgctcaagcttatccaaatgtaagtgcaaaaattgat Tatgatgacgaaatggcttacagtgaatcacaattaattgcgaaatt |

|  | Tggtacagcatttaaagctgtaaataatagcttgaatgtaaacttcg |
|---|---|
|  | Gcgcaatcagtgaagggaaaatgcaagaagaagtcattagttttaaa |
|  | CaaatttActAtaacgtgaatgttaatgaacctacaagaccttccag |
|  | AtttttcggcaaagctgttActAaagagcagttgcaagcgcttggag |
|  | Tgaatgcagaaaatcctcctgcatatatctcaagtgtggcgtatggc |
|  | CgtcaagtttatttgaaattatcaActAattcccatagtActAaagt |
|  | Aaaagctgcttttgatgctgccgtaagcggaaaatctgtctcaggtg |
|  | AtgtagaActAacaaatatcatcaaaaattcttccttcaaagccgta |
|  | Atttacggaggttccgcaaaagatgaagttcaaatcatcgacggcaa |
|  | Cctcggagacttacgcgatattttgaaaaaaggcgctacttttaatc |
|  | Gagaaacaccaggagttcccattgcttatacaacaaacttcctaaaa |
|  | Gacaatgaattagctgttattaaaaacaactcagaatatattgaaac |
|  | Aacttcaaaagcttatacagatggaaaaattaacatcgatcactctg |
|  | Gaggatacgttgctcaattcaacatttcttgggatgaagtaaattat |
|  | Gatcctgaaggtaacgaaattgttcaacataaaaactggagcgaaaa |
|  | Caataaaagcaagctagctcatttcacatcgtccatctatttgcctg |
|  | Gtaacgcgagaaatattaatgtttacgctaaagaatgcactggttta |
|  | Gcttgggaatggtggagaacggtaattgatgaccggaacttaccact |
|  | Tgtgaaaaatagaaatatctccatctggggcaccacgctttatccga |
|  | Aatatagtaataaagtagataatccaatcgaataa |
| Codon | Atgaaaaaaataatgctagtctttattacattaattttagtaagtctaccaattgca |
| optimized | Caacaaaccgaagctaaagatgcatcagcgttcaacaaagaaaattcaattagttca |
| LLO | Atggccccaccagcttctccaccagcatctccaaaaacaccaattgaaaaaaaacat |
| (GGATCC is | Gcagacgaaattgataaatatattcaaggtttagattacaataagaataacgttta |
| a BamHI site | Gtataccacggcgatgcagtaacaaatgtacctccaagaaaaggctataaagacgga |
| added at the | Aatgaatatattgttgttgaaaaaaaaaagaaatctattaatcaaaacaatgccgac |
| 3' end for in- | Atccaagtagttaacgcgattagctcattgacgtatccaggcgcccttgtaaaagct |
| frame | Aactctgaattagtggaaaatcaaccagacgtacttccagtcaaacgtgatagtcta |
| fusions). | Accttaagtattgatttaccaggaatgacaaatcaagataacaaaattgttgttaaa |
| (SEQ ID NO: 49) | AatgcaActAaatccaatgtaaataatgcagttaacacattagtagaacgatggaac |
|  | Gaaaaatacgcacaggcatacccaaatgtatcagctaaaattgattacgacgacgaa |
|  | Atggcctactcagaaagtcaattaattgctaaatttggtacagcattcaaagcagtc |
|  | Aataatagtttaaatgtaaattttggagcgatctctgaaggaaagatgcaggaagaa |
|  | Gtaatttcattcaaacaaatttattataatgttaacgtaaatgaaccaacccgtcct |
|  | TcccgtttctttggcaaagcagttActAaagaacaattacaagcActAggtgtgaat |
|  | Gcagaaaacccaccggcatatatttcaagcgtcgcttacggacgacaagtttactta |
|  | Aaattatctacaaacagtcatagtacaaaagtaaaagcagcattcgatgcagctgtg |
|  | Tcaggaaaatcagttagtggagatgtagaattaaccaatattattaaaaattcgagt |
|  | Tttaaagctgttatttatggaggttctgcaaaagatgaagtacaaattattgacgga |
|  | Aacttaggcgatttacgtgacatttaaaaaaaggcgcaacatttaatagagaaaca |

-continued

|  | |
|---|---|
| | Ccaggggttccaattgcttatacaactaattttcttaaagataatgaacttgcagta |
| | Attaaaaacaattcagaatacattgaaacaacttcgaaagcatatacagacggaaaa |
| | Attaatattgatcactcaggagggtacgttgcacaatttaatattagttgggatgaa |
| | GtaaActAtgatccagaaggcaatgaaattgtacaacataaaaattggtctgaaaat |
| | AacaaatctaaActAgcacactttaccagttctatctatttaccaggaaatgctcgc |
| | AatattaatgtttacgcaaaagaatgtaccggattagcatgggaaTGGTGGcgcaca |
| | Gttattgacgaccgcaatcttcctctagtaaaaaacagaaacatcagcatttgggga |
| | acaacgctttatccgaaatacagtaataaagttgataatccaattgaa GGATCC |
| One mutant variation on codon optimized LLO (as a translational fusion- GGATCC is a BamHI site added at the 3' end for in-frame fusions; mutant variation is in CAPS, changes TGGTGG to TTTTTT amino acid changes WW to FF). (SEQ ID NO: 50) | Atgaaaaaaataatgctagtctttattacattaattttagtaagtctaccaattgc Acaacaaaccgaagctaaagatgcatcagcgttcaacaaagaaaattcaattagtt Caatggccccaccagcttctccaccagcatctccaaaaacaccaattgaaaaaaaa Catgcagacgaaattgataaatatattcaaggtttagattacaataagaataacgt Tttagtataccacggcgatgcagtaacaaatgtacctccaagaaaaggctataaag Acggaaatgaatatattgttgttgaaaaaaaaagaaatctattaatcaaaacaat Gccgacatccaagtagttaacgcgattagctcattgacgtatccaggcgcccttgt Aaaagctaactctgaattagtggaaaatcaaccagacgtacttccagtcaaacgtg Atagtctaaccttaagtattgatttaccaggaatgacaaatcaagataacaaaatt GttgttaaaaatgcaActAaatccaatgtaaataatgcagttaacacattagtaga Acgatggaacgaaaaatacgcacaggcatacccaaatgtatcagctaaaattgatt Acgacgacgaaatggcctactcagaaagtcaattaattgctaaatttggtacagca Ttcaaagcagtcaataatagtttaaatgtaaattttggagcgatctctgaaggaaa Gatgcaggaagaagtaatttcattcaaacaaatttattataatgttaacgtaaatg AaccaacccgtccttcccgtttctttggcaaagcagttActAaagaacaattacaa GcActAggtgtgaatgcagaaaacccaccggcatatatttcaagcgtcgcttacgg Acgacaagtttacttaaaattatctacaaacagtcatagtacaaaagtaaaagcag Cattcgatgcagctgtgtcaggaaaatcagttagtggagatgtagaattaaccaat Attattaaaaattcgagttttaaagctgttatttatggaggttctgcaaaagatga Agtacaaattattgacggaaacttaggcgatttacgtgacattttaaaaaaggcg CaacatttaatagagaaacaccaggggttccaattgcttatacaActAattttctt Aaagataatgaacttgcagtaattaaaaacaattcagaatacattgaaacaacttc Gaaagcatatacagacggaaaaattaatattgatcactcaggagggtacgttgcac AatttaatattagttgggatgaagtaaActAtgatccagaaggcaatgaaattgta CaacataaaaattggtctgaaaataacaaatctaaActAgcacactttaccagttc Tatctatttaccaggaaatgctcgcaatattaatgtttacgcaaaagaatgtaccg GattagcatgggaaTTTTTTcgcacagttattgacgaccgcaatcttcctctagta Aaaaacagaaacatcagcatttggggaacaacgctttatccgaaatacagtaataa agttgataatccaattgaa GGATCC |
| Nucleic acid of LLO59 (not codon optimized). | ATGAAAAAAATAATGCTAGTTTTTATTACACTTATATT AGTTAGTCTACCAATTGCGCAACAAACTGAAGCAAAGG ATGCATCTGCATTCAATAAAGAAAATTCAATTTCATCC ATGGCACCACCAGCATCTCCGCCTGCAAGTCCTAAGAC |

| | |
|---|---|
| (SEQ ID NO: 51) | GCCAATCGAAAAGAAACACGCGGAT |
| Nucleic acid of LLO59, codon optimized for expression in *Listeria*. (SEQ ID NO: 52) | ATGAAAAAAATTATGTTAGTTTTTATTACATTAATTTT AGTTAGTTTACCAATTGCACAACAAACAGAAGCAAAAG ATGCAAGTGCATTTAATAAAGAAAATAGTATTAGTAGT ATGGCACCACCAGCAAGTCCACCAGCAAGTCCAAAAAC ACCAATTGAAAAAAAACATGCAGAT |
| Amino acids of LLO59. (SEQ ID NO: 53) | MKKIMLVFITLILVSLPIAQQTEAKDASAFNKENSISS MAPPASPPASPKTPIEKKHAD |
| Nucleic acid of LLO59, codon optimized for expression in *Listeria*, with codon optimized human mesothelin (deleted SS; deleted GPI), cloned in frame with LLO as a BamHi/SacI fragment. The BamHI (GGATCC) and SacI (GAGCTC) sites are indicated in BOLD. This construct can be called: LLOopt59-hMesothelin (deleted SS; deleted gpi) fusion. (SEQ ID NO: 54) | ATGAAAAAAATTATGTTAGTTTTTATTACATTAATTTTAGTTAGTTTA CCAATTGCACAACAAACAGAAGCAAAAGATGCAAGTGCATTTAATAAA GAAAATAGTATTAGTAGTATGGCACCACCAGCAAGTCCACCAGCAAGT CCAAAAACACCAATTGAAAAAAAACATGCAGATGGATCCCGTACATTA GCAGGTGAAACAGGTCAAGAAGCAGCACCACTTGACGGTGTATTAACG AATCCACCAAATATATCAAGTTTAAGTCCACGTCAATTATTAGGTTTT CCATGTGCAGAAGTTTCAGGTTTAAGTACAGAACGTGTCCGTGAGTTA GCAGTTGCATTAGCACAAAAAAACGTTAAATTATCTACAGAACAGTTA CGTTGTTTAGCCCATAGATTAAGCGAACCACCAGAAGACTTAGATGCA CTTCCTTTAGACCTTCTTTTATTCTTAAATCCAGATGCATTTTCAGGA CCACAAGCATGTACACGTTTTTTTAGTCGAATTACAAAAGCCAATGTT GATTTATTACCTCGTGGGGCTCCTGAAAGACAACGTTTATTACCTGCT GCATTAGCATGCTGGGGTGTTCGCGGTAGCTTATTAAGTGAAGCCGAT GTTCGTGCTTTAGGGGGTTTAGCATGTGATTTACCTGGTCGTTTCGTT GCAGAATCAGCAGAAGTGTTATTACCGAGATTAGTTTCATGCCCAGGA CCTTTAGATCAAGATCAACAAGAGGCAGCTAGAGCAGCTCTTCAAGGA GGAGGCCCACCATATGGCCCACCAAGTACATGGAGTGTTTCTACAATG GATGCGTTAAGAGGTTTATTACCGGTTTTAGGACAACCAATTATTCGT AGTATTCCACAAGGCATTGTAGCAGCATGGCGTCAACGTAGTTCTCGT GATCCGTCTTGGCGACAACCAGAACGTACAATTCTACGTCCAAGATTT CGTAGAGAAGTAGAAAAAACGGCGTGTCCTAGTGGCAAAAAAGCACGT GAAATTGATGAAAGTTTAATTTTTTATAAAAAATGGGAATTAGAAGCA TGTGTCGATGCAGCATTACTAGCTACACAAATGGATCGTGTTAATGCT ATTCCATTCACATATGAACAATTAGATGTTTTAAAGCATAAATTAGAC GAATTATATCCAAAGGTTATCCAGAATCAGTTATTCAACATTTAGGT TACTTATTTTTAAAAATGAGTCCAGAAGACATACGCAAATGGAATGTT ACAAGTTTAGAAACATTAAAAGCGCTTTTAGAAGTTAACAAAGGTCAT GAAATGAGTCCACAAGTTGCTACGTTAATTGATAGATTCGTTAAAGGC CGTGGTCAATTAGATAAAGATACTTTAGATACATTAACAGCATTTTAT CCTGGCTACTTATGCAGTTTATCACCAGAAGAATTAAGTTCCGTTCCA CCGAGTAGTATCTGGGCAGTTCGTCCGCAAGATTTAGATACATGCGAC |

-continued

```
                  CCACGTCAATTAGATGTTTTATATCCAAAAGCAAGATTAGCTTTCCAA

AATATGAACGGTAGTGAATATTTCGTAAAAATTCAATCCTTTTTAGGT

GGTGCACCAACTGAAGATCTAAAAGCATTAAGCCAACAAAATGTAAGT

ATGGATTTAGCTACGTTTATGAAATTACGTACAGATGCAGTTCTACCA

TTAACAGTTGCAGAAGTTCAAAAATTATTAGGTCCACACGTAGAAGGA

TTAAAAGCAGAAGAACGTCACCGTCCAGTTCGCGATTGGATTTTACGT

CAACGTCAAGATGATTTAGATACATTAGGTTTAGGTTTACAAGGCTA

AGAGCTC
```

| | |
|---|---|
| Amino acids of fusion protein of LLO59, codon optimized, with codon optimized human mesothelin (de

| | |
|---|---|
| shown in BOLD. This sequence can be called: LLOnat59 hMesothelin (deleted SS; deleted gpi) fusion. "nat" means natural, not codon optimized. Regarding the amino acid sequences, the amino acid encoded by this sequence is the same as that encoded by the corresponding sequence where mesothelin is codon optimized. (SEQ ID NO: 56) | CCACCATATGGCCCACCAAGTACATGGAGTGTTTCTACAATGG ATGCGTTAAGAGGTTTATTACCGGTTTTAGGACAACCAATTAT TCGTAGTATTCCACAAGGCATTGTAGCAGCATGGCGTCAACGT AGTTCTCGTGATCCGTCTTGGCGACAACCAGAACGTACAATTC TACGTCCAAGATTTCGTAGAGAAGTAGAAAAAACGGCGTGTCC TAGTGGCAAAAAAGCACGTGAAATTGATGAAAGTTTAATTTTT TATAAAAAATGGGAATTAGAAGCATGTGTCGATGCAGCATTAC TAGCTACACAAATGGATCGTGTTAATGCTATTCCATTCACATA TGAACAATTAGATGTTTTAAAGCATAAATTAGACGAATTATAT CCACAAGGTTATCCAGAATCAGTTATTCAACATTTAGGTTACT TATTTTTAAAAATGAGTCCAGAAGACATACGCAAATGGAATGT TACAAGTTTAGAAACATTAAAAGCGCTTTTAGAAGTTAACAAA GGTCATGAAATGAGTCCACAAGTTGCTACGTTAATTGATAGAT TCGTTAAAGGCCGTGGTCAATTAGATAAAGATACTTTAGATAC ATTAACAGCATTTTATCCTGGCTACTTATGCAGTTTATCACCA GAAGAATTAAGTTCCGTTCCACCGAGTAGTATCTGGGCAGTTC GTCCGCAAGATTTAGATACATGCGACCCACGTCAATTAGATGT TTTATATCCAAAAGCAAGATTAGCTTTCCAAAATATGAACGGT AGTGAATATTTCGTAAAAATTCAATCCTTTTTAGGTGGTGCAC CAACTGAAGATCTAAAAGCATTAAGCCAACAAAATGTAAGTAT GGATTTAGCTACGTTTATGAAATTACGTACAGATGCAGTTCTA CCATTAACAGTTGCAGAAGTTCAAAAATTATTAGGTCCACACG TAGAAGGATTAAAAGCACAAGAACGTCACCGTCCAGTTCGCGA TTGGATTTTACGTCAACGTCAAGATGATTTAGATACATTAGGT TTAGGTTTACAAGGCTAAGAGCTC |
| hly promoter. (SEQ ID NO: 57) | GGTACCTCCTTTGATTAGTATATTCCTATCTTAAAGTTACT TTTATGTGGAGGCATTAACATTTGTTAATGACGTCAAAAGG ATAGCAAGACTAGAATAAAGCTATAAAGCAAGCATATAATA TTGCGTTTCATCTTTAGAAGCGAATTTCGCCAATATTATAA TTATCAAAAGAGAGGGGTGGCAAACGGTATTTGGCATTATT AGGTTAAAAAATGTAGAAGGAGAGTGAAACCC |
| Nucleic acid for codon-optimized BaPA signal peptide. (SEQ ID NO: 58) | ATGAAAAAACGTAAAGTTTTAATTCCATTAATGGCATTAAGTACAA TTTTAGTTAGTAGTACAGGTAATTTAGAAGTTATTCAAGCAGAAGT TGGATCC |
| Amino acids of BaPA signal peptide. (SEQ ID NO: 59) | MKK

| | -continued |
|---|---|
| BaPA signal | AGCTATAAAGCAAGCATATAATATTGCGTTTCATCTTTAGAAGCGAATTT |
| peptide are | CGCCAATATTATAATTATCAAAAGAGAGGGGTGGCAAACGGTATTTGGCA |
| fused | TTATTAGGTTAAAAAATGTAGAAGGAGAGTGAAACCCATGAAAAAACGTA |
| seamlessly | AAGTTTTAATTCCATTAATGGCATTAAGTACAATTTTAGTTAGTAGTACA |
| together. The hly promoter and BaPA signal peptide are fused seamlessly together (no restriction sites) and the promoter-signal peptide assembly is inserted into plasmids as a KpnI (GGTACC)- BamHI (GGATCC) fragment. The tumor antigen is inserted at the BamHI site. (SEQ ID NO: 60) | GGTAATTTAGAAGTTATTCAAGCAGAAGTTGGATCC |

Example VI

Building Blocks Used for Assembling p60 Fusion Proteins and Fusion Proteins Other Polypeptides that Mediate SecA2-Dependent Secretion The present invention provides a polynucleotide comprising a first nucleic acid encoding a protein secreted by a SecA2-dependent pathway and a second nucleic acid encoding a heterologous antigen. Autolysins, such as p60 and NamA (N-acetyl-muramidase), are proteins secreted from *Listeria* by the SecA2-dependent pathway (Lenz, et al. (2003) Proc. Natl. Acad. Sci. USA 100:12432-12437). In one embodiment, the fusion protein partner (e.g., p60 or NamA) retains its enzymatic or structural activity. In another embodiment, the fusion protein partner lacks its enzymatic or structural activity. Yet another embodiment places or insertes a nucleic acid encoding a heterologous protein between the signal sequence (SS) and nucleic acids encoding the cell wall binding domains (LysSM) and catalytic domains Lyz-2 (NamA) and p60-dom (p60).

The following discloses, as a non-limiting example, nucleic acids encoding fusion proteins comprising p60 and human mesothelin (hMeso). Mesothelin was inserted into *Listeria*'s p60 protein as follows. A nucleic acid encoding mesothelin was inserted into a nucleic acid encoding p60, so that when expressed, mesothelin would be inserted into p60 at amino acid 70. A polynucleotide encoding the resulting fusion protein was prepared for use in expression by a *Listeria* bacterium.

In another embodiment, protein chimera contained optimal codons for expression in *Listeria* in the p60 amino acids 1-70 as well as in the entire mesothelin coding sequence. In yet another embodiment, the p60-human mesothelin protein chimera was functionally linked to the *L. monocytogenes* hly promoter, incorporated into the pPL2 vector, which was used subsequently to generate recombinant *L. monocytogenes* strains expressing and secreting human mesothelin.

The sequence of the first 70 amino acids of p60 from *L. monocytogenes*, strain 10403S is disclosed.

```
                                          (SEQ ID NO: 61)
M N M K K A T I A A T A G I A V T A F A A P T I A
S A S T V V V E A

G D T L W G I A Q S K G T T V D A I K K A N N L T
T D K I V P G Q K

L Q
```

The synthesized DNA sequence corresponding to the hly promoter-70 N-terminal p60 amino acids is shown below. The codons encoding p60 amino acid residues 69 (L) and 70 (Q), were modified to contain a unique Pst I enzyme recognition sequence, to facilitate functional insertion of a heterologous sequence (e.g., a nucleic acid encoding mesothelin). Moreover, the 5' end of the synthesized sub-fragment contains a unique KpnI enzyme recognition sequence.

At this point in the commentary on vector synthesis, the nucleic acid sequence corresponds to the following:

hly promoter-p60 (70 N-terminal amino acids of p60).

The unique PstI site (CTGCAG) is visible at the 3'-end.

```
                                          (SEQ ID NO: 62)
GGTACCTCCTTTGATTAGTATATTCCTATCTTAAAGTTACTTTTATGTGG
AGGCATTAACATTTGTTAATGACGTCAAAAGGATAGCAAGACTAGAATAA
AGCTATAAAGCAAGCATATAATATTGCGTTTCATCTTTAGAAGCGAATTT
CGCCAATATTATAATTATCAAAAGAGAGGGGTGGCAAACGGTATTTGGCA
TTATTAGGTTAAAAAATGTAGAAGGAGAGTGAAACCCATGAATATGAAAA
AAGCTACGATTGCAGCTACAGCCGGCATTGCCGTAACAGCTTTTGCAGCA
CCAACTATTGCCTCAGCCTCTACAGTTGTTGTCGAAGCAGGAGACACATT
ATGGGGAATCGCACAATCAAAAGGTACAACGGTTGATGCTATTAAAAAAG
CGAATAATTTAACAACAGATAAAATCGTGCCAGGTCAAAAACTGCAG.
```

The 447 bp KpnI and PstI digested sub-fragment is ligated into the corresponding KpnI and PstI sites of the pPL2 vector, treated by digestion with KpnI and PstI enzymes and digestion with calf intestinal alkaline phosphatase (CIAP). This plasmid is known as pPL2-hlyP-Np60 CodOp. Subsequently, the remainder of the native p60 gene was cloned into the pPL2-hlyP-Np60 CodOp plasmid, between the unique Pst I and BamHI sites. The remainder of the p60 gene was cloned by PCR, using a proof-reading containing thermostable polymerase, and the following primer pair:

Forward primer:

```
5'-CGC CTGCAGGTAAATAATGAGGTTGCTG (SEQ ID NO: 63)
```

Reverse primer:

```
5'-CGCGGATCCTTAATTATACGCGACCGAAG (SEQ ID NO: 64)
```

The 1241 bp amplicon is digested with PstI and BamHI, and the purified 1235 bp is ligated into the pPL2-hlyP-Np60 CodOp plasmid, digested with PstI and BamHI, and treated with CIAP. The resulting plasmid contains the full p60 gene with optimal codons corresponding to amino acids 1-77, and native codons corresponding to amino acids 78-478. The full p60 gene is linked functional to the *L. monocytogenes* hly promoter.

At this point in the commentary on vector synthesis, the nucleic acid sequence corresponds to the following:

hly promoter-p60-[70 N-terminal amino acids 1-77 of p60 (codon optimized)]-[PstI]-[C-terminal amino acids 78-478 of p60 (non-codon optimized)].

At this point, the construct has not yet received a nucleic acid encoding a heterologous antigen. In commentary to follow, the unique PstI site will receive a nucleic acid encoding a heterologous antigen (mesothelin). This plasmid, which contains full length p60, but with the N-terminal region codon optimized, and the C-terminal region non-codon optimized, is known as: pPL2-hlyP-Np60 CodOp (1-77). The sequence of the KpnI-BamHI sub-fragment that contains the hlyP linked functionally to the p60 encoding sequence is shown below (SEQ ID NO:65). The expected sequence of the pPL2-hlyP-Np60 CodOp(1-77) plasmid was confirmed by sequencing.

```
                                           (SEQ ID NO: 65)
GGTACCTCCTTTGATTAGTATATTCCTATCTTAAAGTTACTTTTATGTGG
AGGCATTAACATTTGTTAATGACGTCAAAAGGATAGCAAGACTAGAATAA
AGCTATAAAGCAAGCATATAATATTGCGTTTCATCTTTAGAAGCGAATTT
CGCCAATATTATAATTATCAAAAGAGAGGGGTGGCAAACGGTATTTGGCA
TTATTAGGTTAAAAAATGTAGAAGGAGAGTGAAACCCATGAATATGAAAA
AAGCTACGATTGCAGCTACAGCCGGCATTGCCGTAACAGCTTTTGCAGCA
CCAACTATTGCCTCAGCCTCTACAGTTGTTGTCGAAGCAGGAGACACATT
ATGGGGAATCGCACAATCAAAAGGTACAACGGTTGATGCTATTAAAAAAG
CGAATAATTTAACAACAGATAAAATCGTGCCAGGTCAAAAACTGCAGGTA
AATAATGAGGTTGCTGCTGCTGAAAAAACAGAGAAATCTGTTAGCGCAAC
TTGGTTAAACGTCCGTACTGGCGCTGGTGTTGATAACAGTATTATTACGT
CCATCAAAGGTGGAACAAAAGTAACTGTTGAAACAACCGAATCTAACGGC
TGGCACAAAATTACTTACAACGATGGAAAAACTGGTTTCGTTAACGGTAA
ATACTTAACTGACAAAGCAGTAAGCACTCCAGTTGCACCAACACAAGAAG
TGAAAAAAGAAACTACTACTCAACAAGCTGCACCTGTTGCAGAAACAAAA
ACTGAAGTAAAACAAACTACACAAGCAACTACACCTGCGCCTAAAGTAGC
AGAAACGAAAGAAACTCCAGTAATAGATCAAAATGCTACTACACACGCTG
TCAAAAGCGGTGACACTATTTGGGCTTTATCCGTAAAATACGGTGTTTCT
GTTCAAGACATTATGTCATGGAATAATTTATCTTCTTCTTCTATTTATGT
AGGTCAAAAGCTTGCTATTAAACAAACTGCTAACACAGCTACTCCAAAAG
CAGAAGTGAAAACGGAAGCTCCAGCAGCTGAAAAACAAGCAGCTCCAGTA
GTTAAAGAAAATACTAACACAAATACTGCTACTACAGAGAAAAAAGAAAC
AGCAACGCAACAACAAACAGCACCTAAAGCACCAACAGAAGCTGCAAAAC
CAGCTCCTGCACCATCTACAAACACAAATGCTAATAAAACGAATACAAAT
ACAAATACAAACAATACTAATACACCATCTAAAAATACTAATACAAACTC
AAATACTAATACGAATACAAACTCAAATACGAATGCTAATCAAGGTTCTT
CCAACAATAACAGCAATTCAAGTGCAAGTGCTATTATTGCTGAAGCTCAA
AAACACCTTGGAAAAGCTTATTCATGGGGTGGTAACGGACCAACTACATT
TGATTGCTCTGGTTACACTAAATATGTATTTGCTAAAGCGGGTATCTCCC
TTCCACGTACATCTGGCGCACAATATGCTAGCACTACAAGAATTTCTGAA
```

-continued

```
TCTCAAGCAAAACCTGGTGATTTAGTATTCTTCGACTATGGTAGCGGAAT
TTCTCACATTGGTATTTATGTTGGTAATGGTCAAATGATTAACGCGCAAG
ACAATGGCGTTAAATACGATAACATCCACGGCTCTGGCTGGGGTAAATAT
CTAGTTGGCTTCGGTCGCGTATAATAAGGATCC.
```

The next step in the construction is the functional insertion of a heterologous protein encoding sequence at the unique PstI site of plasmid as pPL2-hlyP-Np60 CodOp(1-77).

A nucleic acid encoding human mesothelin that was codon-optimized for optimal expression in *L. monocytogenes* was inserted into the unique PstI site of plasmid as pPL2-hlyP-Np60 CodOp (1-77). Specifically, full-length mesothelin, or mesothelin that was deleted of the signal peptide and GPI linker domains (mesothelin ΔSP/ΔGPI) was cloned from a plasmid that contains the full-length human mesothelin, containing optimal codons for expression in *L. monocytogenes*, using a thermostable polymerase with proof-reading activity, and the primer pair shown below. The present invention provides for other nucleic acids encoding antigens other than mesothelin or in addition to mesothelin, for use in the present protocol. Moreover, the present invention provides for codon-optimization of nucleic acids encoding an antigen, codon-optimization of nucleic acids encoding a fusion protein partner, and/or codon-optimization of nucleic acids encoding a fusion protein partner.

The skilled artisan will understand that expressions that recite "an antigen was inserted into a polypeptide," or expressions to that effect, can encompass "a first nucleic acid encoding an antigen was inserted into a second nucleic acid encoding a polypeptide," and the like.

PCR Primers used to amplify full length human mesothelin:

Forward Primer (huMeso 3F):

```
5'-AAACTGCAGGCATTGCCAACTGCACGTCC (SEQ ID NO: 66)
```

Reverse Primer (hMeso 1935R):

```
                                         (SEQ ID NO: 67)
5'-AAACTGCAGAGCTAATGTACTGGCTAATAATAATGCTAAC
```

PCR primers used to amplify human mesothelin (ΔSS-ΔGPI anchor).

Forward Primer (huMeso 133F):

```
                                          (SEQ D NO: 68)
5'-CGCCTGCAGCGTACATTAGCAGGTGAAACAGG
```

Reverse Primer (huMeso 1770R):

```
                                         (SEQ ID NO: 69)
5'-CGCCTGCAGGCCTTGTAAACCTAAACCTAATGTATC
```

In viewing the following embodiments of mesothelin, the skilled artisan will recognize that the disclosed nucleic acids and polypeptides of mesothelin can be inserted or used in into a variety of polypeptide constructs including fusion proteins, nucleic acids encoding fusion proteins and the like, multicistronic constructs, plasmids, vectors, fusion proteins, bacterial vaccines, and the like.

| | |
|---|---|
| Nucleic acid of the signal peptide of human mesothelin. (SEQ ID NO: 70) | GCATTGCCAACTGCACGTCCATTAC -continued

|  | |
|---|---|
| | GGCAGTTCGTCCGCAAGATTTAGATACATGCGACCCACGTCAA |
| | TTAGATGTTTTATATCCAAAAGCAAGATTAGCTTTCCAAAATA |
| | TGAACGGTAGTGAATATTTCGTAAAAATTCAATCCTTTTTAGG |
| | TGGTGCACCAACTGAAGATCTAAAAGCATTAAGCCAACAAAAT |
| | GTAAGTATGGATTTAGCTACGTTTATGAAATTACGTACAGATG |
| | CAGTTCTACCATTAACAGTTGCAGAAGTTCAAAAATTATTAGG |
| | TCCACACGTAGAAGGATTAAAAGCAGAAGAACGTCACCGTCCA |
| | GTTCGCGATTGGATTTTACGTCAACGTCAAGATGATTTAGATA |
| | CATTAGGTTTAGGTTTACAAGGCGGTATTCCGAATGGATATTT |
| | AGTGTTAGATTTATCTGTTCAAGAAGCATTAAGTGGTACACCG |
| | TGTTTATTAGGTCCAGGTCCAGTTTTAACAGTGTTAGCATTAT |
| | TATTAGCCAGTACATTAGCTTAAGAGCTC |
| Amino acids of full length human mesothelin. (SEQ ID NO: 73) | ALPTARPLLGSCGTPALGSLLFLLFSLGWVQPSRTLAG ETGQEAAPLDGVLTNPPNISSLSPRQLLGFPCAEVSGL STERVRELAVALAQKNVKLSTEQLRCLAHRLSEPPEDL DALPLDLLLFLNPDAFSGPQACTRFFSRITKANVDLLP RGAPERQRLLPAALACWGVRGSLLSEADVRALGGLACD LPGRFVAESAEVLLPRLVSCPGPLDQDQQEAARAALQG GGPPYGPPSTWSVSTMDALRGLLPVLGQPIIRSIPQGI VAAWRQRSSRDPSWRQPERTILRPRFRREVEKTACPSG KKAREIDESLIFYKKWELEACVDAALLATQMDRVNAIP FTYEQLDVLKHKLDELYPQGYPESVIQHLGYLFLKMSP EDIRKWNVTSLETLKALLEVNKGHEMSPQVATLIDRFV KGRGQLDKDTLDTLTAFYPGYLCSLSPEELSSVPPSSI WAVRPQDLDTCDPRQLDVLYPKARLAFQNMNGSEYFVK IQSFLGGAPTEDLKALSQQNVSMDLATFMKLRTDAVLP LTVAEVQKLLGPHVEGLKAEERHRPVRDWILRQRQDDL DTLGLGLQGGIPNGYLVLDLSVQEALSGTPCLLGPGPV LTVLALLLASTLA |
| Human mesothelin nucleic acid (codon optimized), deleted SS, deleted GPI anchor. This is a cassette encoding human mesothelin, where the | GGATCCCGTACATTAGCAGGTGAAACAGGTCAAGAAGCAGCACC ACTTGACGGTGTATTAACGAATCCACCAAATATATCAAGTTTAA GTCCACGTCAATTATTAGGTTTTCCATGTGCAGAAGTTTCAGGT TTAAGTACAGAACGTGTCCGTGAGTTAGCAGTTGCATTAGCACA AAAAAACGTTAAATTATCTACAGAACAGTTACGTTGTTTAGCCC ATAGATTAAGCGAACCACCAGAAGACTTAGATGCACTTCCTTTA GACCTTCTTTTATTCTTAAATCCAGATGCATTTTCAGGACCACA AGCATGTACACGTTTTTTTAGTCGAATTACAAAAGCCAATGTTG ATTTATTACCTCGTGGGGCTCCTGAAAGACAACGTTTATTACCT GCTGCATTAGCATGCTGGGGTGTTCGCGGTAGCTTATTAAGTGA AGCCGATGTTCGTGCTTTAGGGGGTTTAGCATGTGATTTACCTG GTCGTTTCGTTGCAGAATCAGCAGAAGTGTTATTACCGAGATTA |

| | |
|---|---|
| cassette contains the restriction sites 5'-BamHI and 3'-SacI. (SEQ ID NO: 74) | GTTTCATGCCCAGGACCTTTAGATCAAGATCAACAAGAGGCAGC TAGAGCAGCTCTTCAAGGAGGAGGCCCACCATATGGCCCACCAA GTACATGGAGTGTTTCTACAATGGATGCGTTAAGAGGTTTATTA CCGGTTTTAGGACAACCAATTATTCGTAGTATTCCACAAGGCAT TGTAGCAGCATGGCGTCAACGTAGTTCTCGTGATCCGTCTTGGC GACAACCAGAACGTACAATTCTACGTCCAAGATTTCGTAGAGAA GTAGAAAAAACGGCGTGTCCTAGTGGCAAAAAAGCACGTGAAAT TGATGAAAGTTTAATTTTTTATAAAAAATGGGAATTAGAAGCAT GTGTCGATGCAGCATTACTAGCTACACAAATGGATCGTGTTAAT GCTATTCCATTCACATATGAACAATTAGATGTTTTAAAGCATAA ATTAGACGAATTATATCCACAAGGTTATCCAGAATCAGTTATTC AACATTTAGGTTACTTATTTTTAAAAATGAGTCCAGAAGACATA CGCAAATGGAATGTTACAAGTTTAGAAACATTAAAAGCGCTTTT AGAAGTTAACAAAGGTCATGAAATGAGTCCACAAGTTGCTACGT TAATTGATAGATTCGTTAAAGGCCGTGGTCAATTAGATAAAGAT ACTTTAGATACATTAACAGCATTTTATCCTGGCTACTTATGCAG TTTATCACCAGAAGAATTAAGTTCCGTTCCACCGAGTAGTATCT GGGCAGTTCGTCCGCAAGATTTAGATACATGCGACCCACGTCAA TTAGATGTTTTATATCCAAAAGCAAGATTAGCTTTCCAAAATAT GAACGGTAGTGAATATTTCGTAAAAATTCAATCCTTTTTAGGTG GTGCACCAACTGAAGATCTAAAAGCATTAAGCCAACAAAATGTA AGTATGGATTTAGCTACGTTTATGAAATTACGTACAGATGCAGT TCTACCATTAACAGTTGCAGAAGTTCAAAAATTATTAGGTCCAC ACGTAGAAGGATTAAAAGCAGAAGAACGTCACCGTCCAGTTCGC GATTGGATTTTACGTCAACGTCAAGATGATTTAGATACATTAGG TTTAGGTTTACAAGGCTAAGAGCTC |
| Human mesothelin amino acid, deleted SS, deleted GPI anchor. (SEQ ID NO: 75) | RTLAGETGQEAAPLDGVLTNPPNISSLSPRQLLGFPCA EVSGLSTERVRELAVALAQKNVKLSTEQLRCLAHRLSE PPEDLDALPLDLLLFLNPDAFSGPQACTRFFSRITKAN VDLLPRGAPERQRLLPAALACWGVRGSLLSEADVRALG GLACDLPGRFVAESAEVLLPRLVSCPGPLDQDQQEAAR AALQGGGPPYGPPSTWSVSTMDALRGLLPVLGQPIIRS IPQGIVAAWRQRSSRDPSWRQPERTILRPRFRREVEKT ACPSGKKAREIDESLIFYKKWELEACVDAALLATQMDR VNAIPFTYEQLDVLKHKLDELYPQGYPESVIQHLGYLF LKMSPEDIRKWNVTSLETLKALLEVNKGHEMSPQVATL IDRFVKGRGQLDKDTLDTLTAFYPGYLCSLSPEELSSV PPSSIWAVRPQDLDTCDPRQLDVLYPKARLAFQNMNGS |

EYFVKIQSFLGGAPTEDLKALSQQNVSMDLATFMKLRT

DAVLPLTVAEVQKLLGPHVEGLKAEERHRPVRDWILRQ

RQDDLDTLGLGLQG

The PCR amplicons of 1932 bps (full-length mesothelin) and 1637 bps (mesothelin ΔSP/ΔGPI) were purified, digested with PstI, purified, and ligated into the unique PstI site of plasmid pPL2-hlyP-Np60 CodOp(1-77), treated by digestion with PstI, and digestion with CIAP. The consistent amino terminus to carboxy terminus orientation of the p60 and Mesothelin domains was confirmed by restriction endonuclease mapping. These plasmids are known as pPL2-hlyP-Np60 CodOp(1-77)-mesothelin and pPL2-hlyP-Np60 CodOp(1-77)-mesothelin ΔSP/ΔGPI, and were introduced into selected *L. monocytogenes* strains.

The sequence of the KpnI-BamHI sub-fragment of plasmid pPL2-hlyP-Np60 CodOp(1-77)-mesothelin containing the hly promoter linked functionally to the p60-human mesothelin protein chimera encoding gene has the sequence shown below.

```
                                          (SEQ ID NO: 136)
GGTACCTCCTTTGATTAGTATATTCCTATCTTAAAGTTACTTTTATGTGG
AGGCATTAACATTTGTTAATGACGTCAAAAGGATAGCAAGACTAGAATAA
AGCTATAAAGCAAGCATATAATATTGCGTTTCATCTTTAGAAGCGAATTT
CGCCAATATTATAATTATCAAAAGAGAGGGGTGGCAAACGGTATTTGGCA
TTATTAGGTTAAAAAATGTAGAAGGAGAGTGAAACCCATGAATATGAAAA
AAGCTACGATTGCAGCTACAGCCGGCATTGCCGTAACAGCTTTTGCAGCA
CCAACTATTGCCTCAGCCTCTACAGTTGTTGTCGAAGCAGGAGACACATT
ATGGGGAATCGCACAATCAAAAGGTACAACGGTTGATGCTATTAAAAAAG
CGAATAATTTAACAACAGATAAAATCGTGCCAGGTCAAAAACTGCAGGCA
TTGCCAACTGCACGTCCATTACTAGGTAGTTGCGGTACACCAGCACTAGG
TTCTTTATTATTTTTGTTATTTTCTCTAGGTTGGGTTCAACCAAGTCGTA
CATTAGCAGGTGAAACAGGTCAAGAAGCAGCACCACTTGACGGTGTATTA
ACGAATCCACCAAATATATCAAGTTTAAGTCCACGTCAATTATTAGGTTT
TCCATGTGCAGAAGTTTCAGGTTTAAGTACAGAACGTGTCCGTGAGTTAG
CAGTTGCATTAGCACAAAAAAACGTTAAATTATCTACAGAACAGTTACGT
TGTTTAGCCCATAGATTAAGCGAACCACCAGAAGACTTAGATGCACTTCC
TTTAGACCTTCTTTTATTCTTAAATCCAGATGCATTTTCAGGACCACAAG
CATGTACACGTTTTTTTAGTCGAATTACAAAAGCCAATGTTGATTTATTA
CCTCGTGGGGCTCCTGAAAGACAACGTTTATTACCTGCTGCATTAGCATG
CTGGGGTGTTCGCGGTAGCTTATTAAGTGAAGCCGATGTTCGTGCTTTAG
GGGGTTTAGCATGTGATTTACCTGGTCGTTTCGTTGCAGAATCAGCAGAA
GTGTTATTACCGAGATTAGTTTCATGCCCAGGACCTTTAGATCAAGATCA
ACAAGAGGCAGCTAGAGCAGCTCTTCAAGGAGGAGGCCCACCATATGGCC
CACCAAGTACATGGAGTGTTTCTACAATGGATGCGTTAAGAGGTTTATTA
CCGGTTTTAGGACAACCAATTATTCGTAGTATTCCACAAGGCATTGTAGC
AGCATGGCGTCAACGTAGTTCTCGTGATCCGTCTTGGCGACAACCAGAAC
GTACAATTCTACGTCCAAGATTTCGTAGAGAAGTAGAAAAAACGGCGTGT
CCTAGTGGCAAAAAAGCACGTGAAATTGATGAAAGTTTAATTTTTTATAA
AAAATGGGAATTAGAAGCATGTGTCGATGCAGCATTACTAGCTACACAAA
TGGATCGTGTTAATGCTATTCCATTCACATATGAACAATTAGATGTTTTA
AAGCATAAATTAGACGAATTATATCCACAAGGTTATCCAGAATCAGTTAT
TCAACATTTAGGTTACTTATTTTTAAAAATGAGTCCAGAAGACATACGCA
AATGGAATGTTACAAGTTTAGAAACATTAAAAGCGCTTTTAGAAGTTAAC
AAAGGTCATGAAATGAGTCCACAAGTTGCTACGTTAATTGATAGATTCGT
TAAAGGCCGTGGTCAATTAGATAAAGATACTTTAGATACATTAACAGCAT
TTTATCCTGGCTACTTATGCAGTTTATCACCAGAAGAATTAAGTTCCGTT
CCACCGAGTAGTATCTGGGCAGTTCGTCCGCAAGATTTAGATACATGCGA
CCCACGTCAATTAGATGTTTTATATCCAAAAGCAAGATTAGCTTTCCAAA
ATATGAACGGTAGTGAATATTTCGTAAAAATTCAATCCTTTTTAGGTGGT
GCACCAACTGAAGATCTAAAAGCATTAAGCCAACAAAATGTAAGTATGGA
TTTAGCTACGTTTATGAAATTACGTACAGATGCAGTTCTACCATTAACAG
TTGCAGAAGTTCAAAAATTATTAGGTCCACACGTAGAAGGATTAAAAGCA
GAAGAACGTCACCGTCCAGTTCGCGATTGGATTTTACGTCAACGTCAAGA
TGATTTAGATACATTAGGTTTAGGTTTACAAGGCGGTATTCCGAATGGAT
ATTTAGTGTTAGATTTATCTGTTCAAGAAGCATTAAGTGGTACACCGTGT
TTATTAGGTCCAGGTCCAGTTTTAACAGTGTTAGCATTATTATTAGCCAG
TACATTAGCTCTGCAGGTAAATAATGAGGTTGCTGCTGCTGAAAAAACAG
AGAAATCTGTTAGCGCAACTTGGTTAAACGTCCGTACTGGCGCTGGTGTT
GATAACAGTATTATTACGTCCATCAAAGGTGGAACAAAAGTAACTGTTGA
```

-continued

```
AACAACCGAATCTAACGGCTGGCACAAAATTACTTACAACGATGGAAAAA
CTGGTTTCGTTAACGGTAAATACTTAACTGACAAAGCAGTAAGCACTCCA
GTTGCACCAACACAAGAAGTGAAAAAAGAAACTACTACTCAACAAGCTGC
ACCTGTTGCAGAAACAAAAACTGAAGTAAAACAAACTACACAAGCAACTA
CACCTGCGCCTAAAGTAGCAGAAACGAAAGAAACTCCAGTAATAGATCAA
AATGCTACTACACACGCTGTCAAAAGCGGTGACACTATTTGGGCTTTATC
CGTAAAATACGGTGTTTCTGTTCAAGACATTATGTCATGGAATAATTTAT
CTTCTTCTTCTATTTATGTAGGTCAAAAGCTTGCTATTAAACAAACTGCT
AACACAGCTACTCCAAAAGCAGAAGTGAAAACGGAAGCTCCAGCAGCTGA
AAAACAAGCAGCTCCAGTAGTTAAAGAAAATACTAACACAAATACTGCTA
CTACAGAGAAAAAAGAAACAGCAACGCAACAACAAACAGCACCTAAAGCA
CCAACAGAAGCTGCAAAACCAGCTCCTGCACCATCTACAAACACAAATGC
TAATAAAACGAATACAAATACAAATACAAACAATACTAATACACCATCTA
AAAATACTAATACAAACTCAAATACTAATACGAATACAAACTCAAATACG
AATGCTAATCAAGGTTCTTCCAACAATAACAGCAATTCAAGTGCAAGTGC
TATTATTGCTGAAGCTCAAAAACACCTTGGAAAAGCTTATTCATGGGGTG
GTAACGGACCAACTACATTTGATTGCTCTGGTTACACTAAATATGTATTT
GCTAAAGCGGGTATCTCCCTTCCACGTACATCTGGCGCACAATATGCTAG
CACTACAAGAATTTCTGAATCTCAAGCAAAACCTGGTGATTTAGTATTCT
TCGACTATGGTAGCGGAATTTCTCACATTGGTATTTATGTTGGTAATGGT
CAAATGATTAACGCGCAAGACAATGGCGTTAAATACGATAACATCCACGG
CTCTGGCTGGGGTAAATATCTAGTTGGCTTCGGTCGCGTATAATAAGGAT
CC.
```

The sequence of the KpnI-BamHI sub-fragment of plasmid pPL2-hlyP-Np60 CodOp(1-77)-mesothelin ΔSS/ΔGPI containing the hly promoter linked functionally to the p60-human mesothelin ΔSS/ΔGPI protein chimera encoding gene has the sequence shown below.

```
                                           (SEQ ID NO: 76)
GGTACCTCCTTTGATTAGTATATTCCTATCTTAAAGTTACTTTTATGTGG
AGGCATTAACATTTGTTAATGACGTCAAAAGGATAGCAAGACTAGAATAA
AGCTATAAAGCAAGCATATAATATTGCGTTTCATCTTTAGAAGCGAATTT
CGCCAATATTATAATTATCAAAAGAGAGGGGTGGCAAACGGTATTTGGCA
TTATTAGGTTAAAAAATGTAGAAGGAGAGTGAAACCCATGAATATGAAAA
AAGCTACGATTGCAGCTACAGCCGGCATTGCCGTAACAGCTTTTGCAGCA
CCAACTATTGCCTCAGCCTCTACAGTTGTTGTCGAAGCAGGAGACACATT
ATGGGGAATCGCACAATCAAAAGGTACAACGGTTGATGCTATTAAAAAAG
CGAATAATTTAACAACAGATAAAATCGTGCCAGGTCAAAAACTGCAGCGT
ACATTAGCAGGTGAAACAGGTCAAGAAGCAGCACCACTTGACGGTGTATT
AACGAATCCACCAAATATATCAAGTTTAAGTCCACGTCAATTATTAGGTT
TTCCATGTGCAGAAGTTTCAGGTTTAAGTACAGAACGTGTCCGTGAGTTA
GCAGTTGCATTAGCACAAAAAAACGTTAAATTATCTACAGAACAGTTACG
TTGTTTAGCCCATAGATTAAGCGAACCACCAGAAGACTTAGATGCACTTC
CTTTAGACCTTCTTTTATTCTTAAATCCAGATGCATTTTCAGGACCACAA
GCATGTACACGTTTTTTTAGTCGAATTACAAAAGCCAATGTTGATTTATT
ACCTCGTGGGGCTCCTGAAAGACAACGTTTATTACCTGCTGCATTAGCAT
GCTGGGGTGTTCGCGGTAGCTTATTAAGTGAAGCCGATGTTCGTGCTTTA
GGGGGTTTAGCATGTGATTTACCTGGTCGTTTCGTTGCAGAATCAGCAGA
AGTGTTATTACCGAGATTAGTTTCATGCCCAGGACCTTTAGATCAAGATC
AACAAGAGGCAGCTAGAGCAGCTCTTCAAGGAGGAGGCCCACCATATGGC
CCACCAAGTACATGGAGTGTTTCTACAATGGATGCGTTAAGAGGTTTATT
ACCGGTTTTAGGACAACCAATTATTCGTAGTATTCCACAAGGCATTGTAG
CAGCATGGCGTCAACGTAGTTCTCGTGATCCGTCTTGGCGACAACCAGAA
CGTACAATTCTACGTCCAAGATTTCGTAGAGAAGTAGAAAAAACGGCGTG
TCCTAGTGGCAAAAAAGCACGTGAAATTGATGAAAGTTTAATTTTTTATA
AAAAATGGGAATTAGAAGCATGTGTCGATGCAGCATTACTAGCTACACAA
ATGGATCGTGTTAATGCTATTCCATTCACATATGAACAATTAGATGTTTT
AAAGCATAAATTAGACGAATTATATCCACAAGGTTATCCAGAATCAGTTA
TTCAACATTTAGGTTACTTATTTTTAAAAATGAGTCCAGAAGACATACGC
AAATGGAATGTTACAAGTTTAGAAACATTAAAAGCGCTTTTAGAAGTTAA
CAAAGGTCATGAAATGAGTCCACAAGTTGCTACGTTAATTGATAGATTCG
TTAAAGGCCGTGGTCAATTAGATAAAGATACTTTAGATACATTAACAGCA
TTTTATCCTGGCTACTTATGCAGTTTATCACCAGAAGAATTAAGTTCCGT
TCCACCGAGTAGTATCTGGGCAGTTCGTCCGCAAGATTTAGATACATGCG
ACCCACGTCAATTAGATGTTTTATATCCAAAAGCAAGATTAGCTTTCCAA
AATATGAACGGTAGTGAATATTTCGTAAAAATTCAATCCTTTTTAGGTGG
TGCACCAACTGAAGATCTAAAAGCATTAAGCCAACAAAATGTAAGTATGG
```

-continued
```
ATTTAGCTACGTTTATGAAATTACGTACAGATGCAGTTCTACCATTAACA
GTTGCAGAAGTTCAAAAATTATTAGGTCCACACGTAGAAGGATTAAAAGC
AGAAGAACGTCACCGTCCAGTTCGCGATTGGATTTTACGTCAACGTCAAG
ATGATTTAGATACATTAGGTTTAGGTTTACAAGGCCTGCAGGTAAATAAT
GAGGTTGCTGCTGCTGAAAAAACAGAGAAATCTGTTAGCGCAACTTGGTT
AAACGTCCGTACTGGCGCTGGTGTTGATAACAGTATTATTACGTCCATCA
AAGGTGGAACAAAAGTAACTGTTGAAACAACCGAATCTAACGGCTGGCAC
AAAATTACTTACAACGATGGAAAAACTGGTTTCGTTAACGGTAAATACTT
AACTGACAAAGCAGTAAGCACTCCAGTTGCACCAACACAAGAAGTGAAAA
AAGAAACTACTACTCAACAAGCTGCACCTGTTGCAGAAACAAAAACTGAA
GTAAAACAAACTACACAAGCAACTACACCTGCGCCTAAAGTAGCAGAAAC
GAAAGAAACTCCAGTAATAGATCAAAATGCTACTACACACGCTGTCAAAA
GCGGTGACACTATTTGGGCTTTATCCGTAAAATACGGTGTTTCTGTTCAA
GACATTATGTCATGGAATAATTTATCTTCTTCTTCTATTTATGTAGGTCA
AAAGCTTGCTATTAAACAAACTGCTAACACAGCTACTCCAAAAGCAGAAG
TGAAAACGGAAGCTCCAGCAGCTGAAAAACAAGCAGCTCCAGTAGTTAAA
GAAAATACTAACACAAATACTGCTACTACAGAGAAAAAAGAAACAGCAAC
GCAACAACAAACAGCACCTAAAGCACCAACAGAAGCTGCAAAACCAGCTC
CTGCACCATCTACAAACACAAATGCTAATAAAACGAATACAAATACAAAT
ACAAACAATACTAATACACCATCTAAAAATACTAATACAAACTCAAATAC
TAATACGAATACAAACTCAAATACGAATGCTAATCAAGGTTCTTCCAACA
```
```
ATAACAGCAATTCAAGTGCAAGTGCTATTATTGCTGAAGCTCAAAAACAC
CTTGGAAAAGCTTATTCATGGGGTGGTAACGGACCAACTACATTTGATTG
CTCTGGTTACACTAAATATGTATTTGCTAAAGCGGGTATCTCCCTTCCAC
GTACATCTGGCGCACAATATGCTAGCACTACAAGAATTTCTGAATCTCAA
GCAAAACCTGGTGATTTAGTATTCTTCGACTATGGTAGCGGAATTTCTCA
CATTGGTATTTATGTTGGTAATGGTCAAATGATTAACGCGCAAGACAATG
GCGTTAAATACGATAACATCCACGGCTCTGGCTGGGGTAAATATCTAGTT
GGCTTCGGTCGCGTATAATAAGGATCC.
```

Example VII

ActA-N100-Based Fusion Proteins; LLO-Based Fusion Proteins (Synthesis; Vaccination; Immunogenicity)

Table 11 discloses some of the bacterial strains that were prepared. The bacteria were used for vaccination into tumor-bearing mice. Where indicated, vaccination resulted in anti-tumor immune responses, reduction in tumor number and size, and increased survival.

TABLE 11

Recombinant *L. monocytogenes* bacteria of the present invention. "Delta" means deleted. The E30R mutation and the E30M mutation, where indicated, occur in the *Bacillus* Protective Antigen (BaPA) secretory sequence. The S28D mutation and S28R mutation, where indicated, occur in p60.

| Strain (trivial name) | Construct | Genetic background | Locus of integration | Promoter | Secretory sequence (SS) |
|---|---|---|---|---|---|
| — | Full length (FL) hMesothelin | ΔActA ΔinlB | tRNA Arg | Hly | BaPA |
| hMeso1 | hMeso [deltaSS deltaGPI] | ΔActA ΔinlB | tRNA Arg | Hly | BaPA |
| hMeso2 | HMeso[deltaSS deltaGPI] | ΔActA ΔinlB prfA* | tRNA Arg | Hly | BaPA |
| hMeso3 | hMeso [deltaSS deltaGPI] | ΔActA ΔinlB | ActA | ActA | BaPA |
| hMeso4 | HMeso [deltaSS deltaGPI] | ΔActA ΔinlB | inlB | Hly | BaPA |
| hMeso5 | p60-hMeso [deltaSS deltaGPI] | ΔActA ΔinlB | tRNA Arg | Hly | p60 |
| hMeso6 | ActA-N100 hMeso [deltaSS deltaGPI] | ΔActA ΔinlB | ActA | act | ActA |
| hMeso8 | hMeso [deltaSS deltaGPI]-rasG12D | ΔActA ΔinlB | tRNA Arg | hly | BaPA |
| hMeso10 | ActA-N100 hMeso [deltaSS deltaGPI]-rasG12D | ΔActA ΔinlB | ActA | ActA | ActA |
| hMeso11 | HMeso [deltaSS deltaGPI]-rasG12D | ΔActA ΔinlB | inlB | Hly | BaPA |
| hMeso12 | hMeso [deltaSS deltaGPI]-rasG12D | ΔActA ΔinlB | tRNA Arg | Hly | BaPA (E30R) |
| hMeso13 | hMeso [deltaSS deltaGPI]-rasG12D | ΔActA ΔinlB | tRNA Arg | hly | BaPA (E30M) |
| hMeso14 | LLO62-hMeso [deltaSS deltaGPI]-rasG12D | ΔActA ΔinlB | tRNAArg | hly | LLO(62) |
| hMeso15 | LLOopt62 hMeso [deltaSS deltaGPI]-rasG12D | ΔActA ΔinlB | tRNA Arg | Hly | LLO(opt62) |
| hMeso18 | A30R ActA-N100-hMeso [deltaSS deltaGPI]-12ras (the ras has a G12D mutation) | ΔActA ΔinlB | ActA | ActA | ActA (A30R) |
| hMeso19 | S28D p60hMeso [deltaSS deltaGPI] | ΔActA ΔinlB | tRNA Arg | hly | p60 |
| hMeso20 | S28R deltap60hMeso [deltaSS deltaGPI] | ΔActA ΔinlB | tRNA Arg | hly | p60 |
| hMeso22 | LLO441-hMeso [deltaSS deltaGPI]-rasG12D | ΔActA ΔinlB | tRNA Arg | hly | LLO |
| hMeso26 | ActA-N100 hMeso [deltaSS deltaGPI] | ΔActA ΔinlB | inlB | ActA | ActA |
| hMeso31 | ActA-N100 (A30R in ActA-N100)-hMeso [deltaSS deltaGPI] diploid | ΔActA ΔinlB | ActA and inlB | ActA and ActA | ActA and ActA |
| hMeso32 | ActA-N100-hMeso [deltaSS deltaGPI] diploid | ΔActA ΔinlB | inlB and tRNA$^{Arg}$ | ActA and ActA | ActA and ActA |
| hMeso33 | ActA-N100 deltaSS (containing GPI) | ΔActA ΔinlB | tRNA$^{Arg}$ integrated with pINT | ActA | ActA |

TABLE 11-continued

Recombinant *L. monocytogenes* bacteria of the present invention. "Delta" means deleted. The E30R mutation and the E30M mutation, where indicated, occur in the *Bacillus* Protective Antigen (BaPA) secretory sequence. The S28D mutation and S28R mutation, where indicated, occur in p60.

| Strain (trivial name) | Construct | Genetic background | Locus of integration | Promoter | Secretory sequence (SS) |
|---|---|---|---|---|---|
| hMeso37 | ActA-N100 [deltaSS] (containing GPI) | ΔActA ΔinlB | tRNA$^{Arg}$ integrated with pINT | ActA | ActA |
| hMeso38 | ActA-N100-hmeso [deltaSS] (not deleted in GPI). (hmeso33allele) | ΔActA ΔinlB | inlB | ActA | ActA |
| hMeso40 (see Table 12) | hMeso26 with this additional integration: pINT-ActA-N100-db12ras3 | ΔActA ΔinlB | inlB and tRNA$^{Arg}$ | ActA and ActA | ActA and ActA |
| hMeso41 (see Table 12) | hmeso26 with this additional integration: pINT-ActA-N100-dbl-12ras4 | ΔActA ΔinlB | inlB and tRNA$^{Arg}$ | ActA and ActA | ActA and ActA |
| hMeso42 (see Table 12) | hMeso26 with this additional integration: pINT-ActA-N100-dbl-12ras5 | ΔActA ΔinlB | inlB and tRNA$^{Arg}$ | ActA and ActA | ActA and ActA |
| hMeso43 (see Table 12) | hMeso26 with this additional integration: pINT-ActA-N100-db1-12ras6 | ΔActA ΔinlB | inlB and tRNA$^{Arg}$ | ActA and ActA | ActA and ActA | hMeso37 differs from hMeso33 in that hMeso37 was treated with a plasmid encoding Cre recombinase to effect removal of loxP-flanked DNA. Cre recombinase was provided via the plasmid pCON2. pCON2 is temperature sensitive. Shifting temperature results in removal of loxP-flanked DNA and results in loss of pCON2 from the cell. pCON is described (see, e.g., Behari, et al. (1998) J. Bacteriol. 180: 6316–6324; Milenbachs, et al. (2004) Microbiology 150: 321–333).
Where a polynucleotide is integrated at the ActA locus, the ActA gene is deleted during homologous recombination, unless otherwise specified. Where a polynucleotide is integrated at the ActA locus, and where the construct comprises a fusion protein that includes ActA-N100, and where the secretory sequence is listed as the ActA secretory sequence, the ActA secretory sequence comes from the ActA-N100 fusion protein partner (not from the genomic ActA gene, for the reason that the genomic ActA gene was deleted during homologous recombination), as in hMeso6, hMeso10, and hMeso18.

TABLE 12

Sequences in expression cassettes of hMeso40, hMeso41, hMeso42, and hMeso43. "ActA-N100" indicates that the ActA-N100 sequence immediately precedes the indicated amino acids that follow.

Db112ras3 sequence of hMeso40
(ActA-N100)GSAKVLEEDEEEALPTARPLLGSCGTPALGSLLFLLFSLGWVQ
PSRTLAGETGQEAAEEDEEEADLVLAKVLMTEYKLVVVGADGVGKSALTIQLIQ
ADLVLAKVLMTEYKLVVVGAVGVGKSALTIQLIQADLVLAKVLESIINFEKLAD
LVAEQKLISEEDLV
(SEQ ID NO: 77)

Db112ras4 sequence of hMeso41
(ActAN100)GSAKVLEEDEEETPALGSLLFLLFSLGWVQPEEDEEEADLVLAK
VLMTEYKLVVVGADGVGKSALTIQLIQADLVLAKVLMTEYKLVVVGAVGVGKSA
LTIQLIQADLVLAKVLESIINFEKLADLVAEQKLISEEDLV
(SEQ ID NO: 78)

Db112ras5 sequence of hMeso42
(ActAN100)GSAKVLMTEYKLVVVGADGVGKSALTIQLIQADLVLAKVLMTEY
KLVVVGAVGVGKSALTIQLIQADLVLAKVLEEDEEEALPTARPLLGSCGTPALG
SLLFLLFSLGWVQPSRTLAGETGQEAAEEDEEEADLVLAKVLESIINFEKLADL
VAEQKLISEEDLV
(SEQ ID NO: 79)

Db112ras6 sequence of hMeso43
(ActAN100)GSAKVLMTEYKLVVVGADGVGKSALTIQLIQADLVLAKVLMTEY
KLVVVGAVGVGKSALTIQLIQADLVLAKVLEEDEEETPALGSLLFLLFSLGWVQ
PEEDEEEADLVLAKVLESIINFEKLADLVAEQKLISEEDLV
(SEQ ID NO: 80)

TABLE 12-continued

Sequences in expression cassettes of hMeso40, hMeso41, hMeso42, and hMeso43. "ActA-N100" indicates that the ActA-N100 sequence immediately precedes the indicated amino acids that follow.

| | |
|---|---|
| | Identification of details within above sequences |
| rasG12D (a.k.a. 12rasD) | MTEYKLVVVGADGVGKSALTIQLIQ (SEQ ID NO: 81) |
| rasG12V (a.k.a. 12rasV) | MTEYKLVVVGAVGDGKSALTIQLIQ (SEQ ID NO: 82) |
| Meso secretory sequence (MesoSS) | ALPTARPLLGSCGTPALGSLLFLLFSLGWVQPSRTLAGETGQEAA (SEQ ID NO: 83) |
| MesoA2 epitope occurring within MesoSS | TPALGSLLFLLFSLGWVQP (SEQ ID NO: 84) |
| Spacer | EEDEEE (SEQ ID NO: 85) |

The following *Listeria* ΔActA ΔinlB constructs, suitable as control constructs, were found not to detectably express: (1) hMeso deltaSS deltaGPI ras (the ras had a G12D mutation). This construct had an ActA promoter, BaPA signal sequence, with an ActA locus of integration; (2) A30R ActA-N100 hMeso ΔSSΔGPI ras (the ras had a G12D mutation). This construct had an ActA promoter, BaPA signal sequence, with an ActA locus of integration; and (3) A30L ActA-N100 hMeso ΔSSΔGPI ras (the ras had a G12D mutation). This particular construct had an ActA promoter, ActA signal sequence, with an ActA locus of integration.

Promoters of the present invention can include one or more of the following operably linked with a nucleic acid encoding an antigen: hly, ActA, p60, pHyper, and so on. pHyper is disclosed (see, e.g., U.S. Pat. Appl. 2005/0147621 of Higgins, et al.). The present invention provides signal sequences, such as one or more of the signal sequence of LLO, ActA, BaPA, BsPhoD, p60, and so on. Fusion protein partners of the present invention can include one or more of $LLO_{1-62}$, $LLO_{1-441}$, ActA-N100, p60, $PFO_{1-390}$, $BaPA_{1-82}$, and the like.

Constructs containing an ActA-based fusion protein partner or an LLO-based fusion protein partner were synthesized as follows. When synthesis was complete, the construct was integrated into the genome of *L. monocytogenes*. While integration was mediated by vectors such as pKSV7, pPL2, and pINT, the present invention is not limited to any particular integration vector or mechanism of integration. Various polynucleotides were assembled in a modular fashion, that is, by ligating prefabricated nucleic acids together on the pKSV7 scaffold. These prefabricated nucleic acids were as follows:

The ActA promoter/ActA-N100/human Mesothelin ΔSSΔGPI construct was assembled using the following components: A first polynucleotide consisting of a first nucleic acid encoding native listerial ActA promoter sequence (including the Shine Dalgarno site) connected directly to a second nucleic acid encoding ActA-N100 (the first polynucleotide had a 5'-HindIII site and a 3'-BamHI site.) A second polynucleotide consisted of human Mesothelin ΔSSΔGPI (5'-BamHI site and 3'-SacI site). The pKSV7 received an insert consisting of the first polynucleotide connected directly to the second polynucleotide. In a variation of this construct, the second polynucleotide consisted of a first nucleic acid encoding human Mesothelin ΔssΔGPI connected directly to a second nucleic acid encoding 12ras (5'-BamHI site and 3'-SacI site). Human mesothelin is intended as a non-limiting example.

The hly promoter/LLO62/human Mesothelin ΔSSΔGPI/12ras construct was assembled using the following components. LLO62 means a nucleic acid encoding amino acids 1-62 of listeriolysin (LLO). A first polynucleotide was prepared that consisted of a first nucleic acid encoding native listerial hly promoter sequence (including the Shine Dalgarno site) connected directly to a second nucleic acid encoding LLO62 (the first polynucleotide had a 5'-KpnI site and a 3'-BamHI site). A second polynucleotide was prepared that consisted of a first nucleic acid encoding human Mesothelin ΔSSΔGPI connected directly to a second nucleic acid encoding 12ras (the second polynucleotide had a 5'-BamHI site and a 3'-SacI site.) The pKSV7 received an insert consisting of the first polynucleotide connected directly to the second polynucleotide. A variation of this construct used LLO60 (codon optimized) in place of LLO62.

FIG. 7 discloses a number of embodiments of the present invention, including LLO-based fusion proteins and actA-N100-based fusion proteins.

FIG. 8 discloses expression of various constructs from cell cultures of engineered *Listeria*. In this context, expression means protein biosynthesis and secretion into the medium, where the indicated construct had been integrated into the listerial genome. Expression was conducted in a medium containing yeast extract without glucose at a bacterial density corresponding to $OD_{600}$=0.8. The term pPL2 indicates that the construct was inserted by way of site-specific recombination using the vector pPL2, pKSV7 means that the construct was inserted by homologous recombination using the vector pKSV7 (see Table 13).

The antibody for detecting mesothelin expression was a rabbit polyclonal antibody, produced by immunizing rabbit with three peptides from human mesothelin, where the antibody was purified by a single peptide that is completely conserved between mouse and human mesothelin (SEADVRALGGLAC (SEQ ID NO:86)).

TABLE 13

Figure 8:
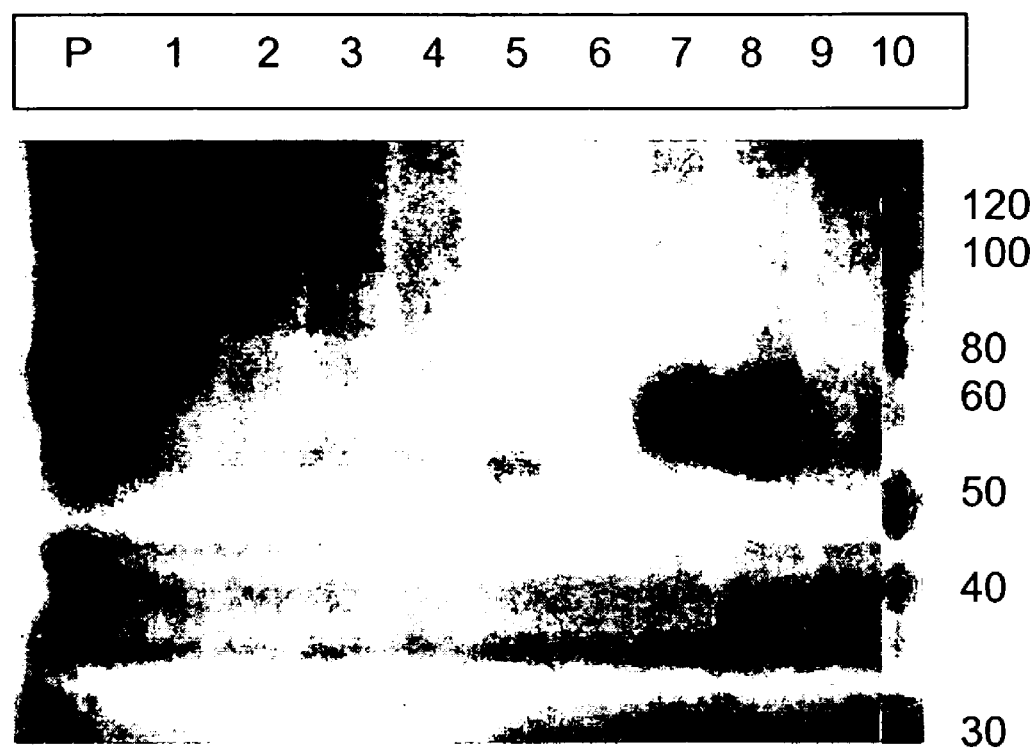
FIG. 8 is a gel showing expression of mesothelin from various listerial constructs.

Legend for FIG. 8.

| | Construct | Promoters | Secretory sequences (SS) of construct: | Integration mediated by: |
|---|---|---|---|---|
| Lane P. | Parent L. monocytogenes ΔActAΔinlB. | N.A. | N.A. | N.A. |
| Lane 1. | pPL2 LLO BaPA ΔSS hMeso ΔSSΔGPI-12-ras. | hly | LLO | pPL2 |
| Lane 2. | pPL2 LLO BaPA E30R hMeso ΔSSΔGPI-12-ras. | hly | LLO and BaPA | pPL2 |
| Lane 3. | pPL2 LLO BaPA E30M hMeso ΔSSΔGPI-12-ras. | hly | LLO and BaPA | pPL2 |
| Lane 4. | pPL2 LLO$_{natural}$ hmeso ΔSSΔGPI-12-ras. | hly | LLO | pPL2 |
| Lane 5. | pPL2 LLO$_{opt}$ hmeso ΔSSΔGPI-12-ras. | hly | LLO | pPL2 |
| Lane 6. | pKSV7 ActA::ActA-N100 mMeso ΔSSΔGPI. | ActA | ActA | pKSV7 |
| Lane 7. | pKSV7 ActA:: ActA-N100 hMeso ΔSSΔGPI-12-ras. | ActA | ActA | pKSV7 |
| Lane 8. | pKSV7 ActA:: ActA N100 hMeso ΔSSΔGPI. | ActA | ActA | pKSV7 |
| Lane 9. | pKSV7 inlB::BaPA hMeso ΔSSΔGPI-12-ras. | inlB | BaPA | pKSV7 |
| Lane 10. | Molecular weight markers. | N.A. | N.A. | N.A. |

The double colon of "ActA::ActA-N100" means that the locus of insertion was the ActA gene.
LLO means listeriolysin. The hly gene encodes listeriolysin.

The results from the gel (FIG. 8) show proteins in the supernatant (secreted proteins).

Lane P, a control experiment using the parental *Listeria*, does not show any obvious stained band.

Lanes 1-4 show little or no bands.

Lane 5 shows some secretion of LLO$_{opt}$ hmeso ΔSSΔGPI-12-ras, where integration was by pPL2-mediated integration in the listerial tRNA$^{Arg}$ gene.

Lane 6, which represents an attempt to secrete mouse mesothelin, does not show any obvious stained band.

Lane 7 shows marked secretion of the ActA-N100 hMeso ΔSSΔGPI-12-ras, where integration was mediated by pKSV7 at the ActA site of the listerial genome.

Lane 8 shows even greater secretion, where the construct was ActA N100 hMeso ΔSSΔGPI, and where integration was mediated by pKSV7 at the ActA site of the listerial genome (FIG. 7).

Lane 9 shows little or no band.

Figure 9:
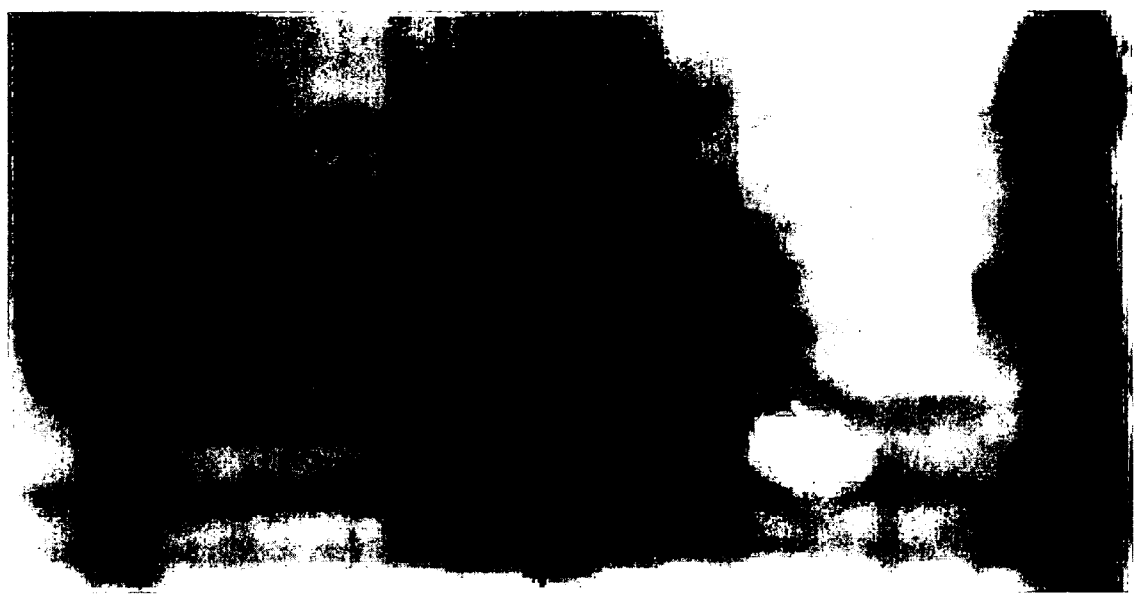
FIG. 9 is a gel showing expression of mesothelin from a number of listerial constructs.

FIG. 9 demonstrates protein secretion from *L. monocytogenes* ΔActAΔinlB, where the *Listeria* expressed various fusion proteins comprising human mesothelinΔSSΔGPI. All mesothelin constructs were expressed from *L. monocytogenes* by nucleic acids codon optimized for *L. monocytogenes*. Various constructs were prepared for the secretion study (see Table 14). In these experiments also, the antibody for detecting mesothelin expression was a rabbit polyclonal antibody, produced by immunizing rabbit with three peptides from human mesothelin, where the antibody was purified by a single peptide that is completely conserved between mouse and human mesothelin (SEADVRALGGLAC (SEQ ID NO:86)).

TABLE 14

Legend for FIG. 9. Western blot analysis for secretion of human mesothelin (hMeso).

| Lane | Construct | Promoters | Secretory sequences (SS) of construct: | Integration mediated by: |
|---|---|---|---|---|
| P. | Patent *L. monocytogenes* ΔActAΔinlB (no mesothelin). | N.A. | N.A. | N.A. |
| 1. | *L. monocytogenes* ΔActAΔinlB LLO441$_{opt}$ human mesothelinΔSSΔGPI-12-ras | ActA | LLO | pPL2. |
| 2. | *L. monocytogenes* ΔActAΔinlB ActA::BaPA ActA-N100(A30R)-human mesothelinΔSSΔGPI (clone 2.25). | ActA | BaPA | pKSV7 at ActA locus. |
| 3. | *L. monocytogenes* ΔActAΔinlB ActA::BaPA ActA-N100 (A30R)-human mesothelinΔSSΔGPI (clone 2.69). | ActA | BaPA | pKSV7 at ActA locus. |
| 4. | *L. mnonocytogenes* ΔActAΔinlB ActA::BaPA ActA-N100 (A30R)-human mesothelinΔSSΔGPI-12-ras (clone 1.1) | ActA | BaPA. | pKSV7 at ActA locus. |

TABLE 14-continued

Legend for FIG. 9. Western blot analysis for secretion of human mesothelin (hMeso).

| Lane | Construct | Promoters | Secretory sequences (SS) of construct: | Integration mediated by: |
|---|---|---|---|---|
| 5. | L. monocytogenes ΔActAΔinlB ActA::ActA-N100 (A30R)-human mesothelinΔSSΔGPI (clone 1.46). A30R indicates mutation in the ActA upon which ActA-N100 is based. | ActA | ActA | pKSV7 at ActA locus. |
| 6. | L. monocytogenes ΔActAΔinlB ActA::ActA-N100 (A30R)-human mesothelinΔSSΔGPI (clone 2.14). A30R indicates mutation in the ActA upon which ActA-N100 is based. | ActA | ActA | pKSV7 at ActA locus. |
| 7. | L. monocytogenes ΔActAΔinlB inlB::ActAN100-human mesothelinΔSSΔGPI (clone BH77). ActA-N100 is based on wild type ActA. | inlB | ActA | pKSV7 at inlB locus. |
| 8. | L. monocytogenes ΔActAΔinlB inlB::ActAN100-human mesothelinΔSSΔGPI (clone BH78). ActA-N100 is based on wild type ActA. | inlB | ActA | pKSV7 at inlB locus. |
| 9. | L. monocytogenes ΔActAΔinlB inlB::ActA-N100(A30R)-human mesothelinΔSSΔGPI (clone BH85). A30R indicates mutation the ActA upon which ActA-N100 is based. | inlB | ActA | pKSV7 at inlB locus. |
| 10. | L. monocytogenes ΔActAΔinlB inlB::ActA-N100(A30R)-human mesothelinΔSSΔGPI (clone BH85). A30R indicates mutation the ActA upon which ActA-N100 is based. | inlB | ActA | pKSV7 at ActA locus. |
| 11. | L. monocytogenes ΔActAΔinlB ActA-N100 Ndegcon-human mesothelin (clone A11-2). | ActA | ActA. | pKSV7 at ActA locus. |
| 12. | L. monocytogenes ΔActAΔinlB ActA-N100 Ndegcon-human mesothelin (clone A11-2). | ActA | ActA. | pKSV7 at ActA locus. |
| 13. | L. monocytogenes ΔActAΔinlB ActA-N100 Ndegcon human mesothelinΔSSΔGPI-12-ras (clone 1-3). | ActA | ActA. | pKSV7 at ActA locus. |
| 14. | Molecular weight markers. | N.A. | N.A. | N.A. |

N.A. means not applicable.
The double colon found in "inlB::ActAN100" indicates the locus of the construct, i.e., at the inlB gene. "Ndegcon" refers to constructs that include consensus sequences modeled after the sequences set forth by Suzuki and Varshavsky (1999) EMBO J. 18: 6017-6026.

The construct used for Lane 1 used LLO441 as the source of secretory sequence, where the nucleic acid for LLO441 had been codon optimized for expression in L. monocytogenes, and where the heterologous antigen was human mesothelinΔSSΔGPI (Lane 1). This construct produced the highest level of secretion in this particular experiment (Lane 1). The high molecular weight material shown in the western blot represents $LLO_{441}$ fused to mesothelin, where the lower molecular weight material likely represents degradation products.

The constructs used for Lanes 2 and 4 were based on ActA-N100, but with the ActA's signal sequence deleted and replaced with the signal sequence of BaPA. Expression from these constructs was relatively low (Lanes 2 and 4) (FIG. 9).

All of the remaining constructs contained full-length ActA-N100 as the source of secretory sequence, but where ActA-N100 had an A30R mutation (Lane 5); where ActA-N100 had no mutation (Lane 7); where ActA-N100 had an A30R mutation (Lane 9); and where ActA-N100 had four mutations (designated "Ndegcon") (Lane 11). The four mutations in ActA-N100 designated by "Ndegcon" were Arg-29, Lys-32, Lys-37, and Lys-44. The Ndegcon was situated (or inserted) in between ActA-N100 and the mesothelin.

Secreted protein was collected by precipitation with trichloroacetic acid from mid-exponential cultures grown in yeast extract without glucose.

Figure 10:
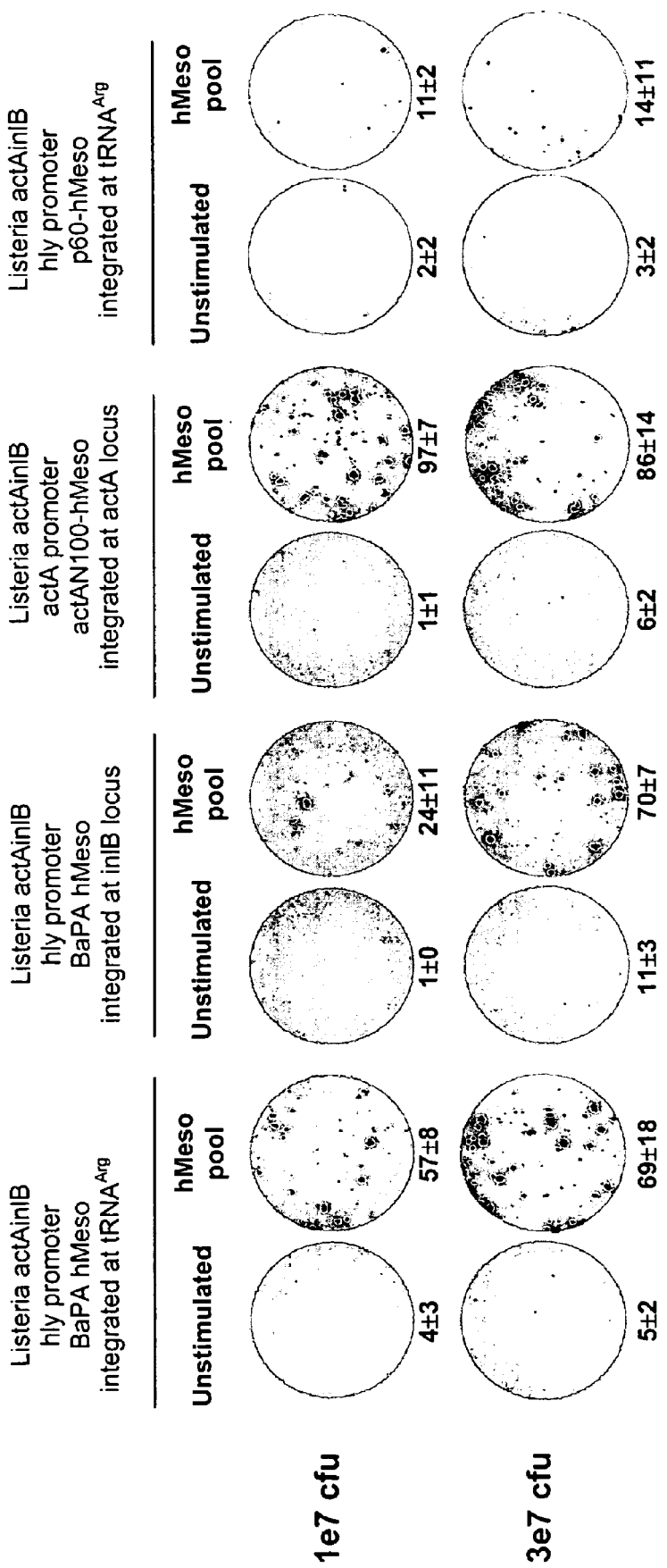
FIGS. 10-12 show expression of interferon-gamma (IFN-gamma) from spot forming cell (SFC) assays, and compare immune responses where mice had been vaccinated with various numbers (colony forming units; c.f.u.) of engineered *L. monocytogenes*.

FIG. 10 shows immune stimulation, as determined after a single vaccination with the indicated L. monocytogenes ΔActAΔinlB construct, where spleens were harvested seven days after vaccination and used as the source of splenocytes. Mesothelin-specific immune responses were found after vaccination with each of the four constructs: (1) hly promoter was operably linked with BaPA signal sequence and hMeso (integrated at $tRNA^{Arg}$ locus); (2) hly promoter was operably linked with BaPA signal sequence and hMeso (integrated at inlB locus); (3) ActA promoter was operably linked with ActA-N100 and hMeso (integrated at ActA); and (4) hly promoter was operably linked with p60 and hMeso (integrated at $tRNA^{Arg}$ locus).

The results indicate a role of the ActA promoter in stimulating immune response; a role of the ActA-N100 fusion partner in enhancing immune response; as well as a role of integration at ActA locus in increasing immune response; and demonstrate enhanced ability to stimulate immune response where the ActA promoter is operably linked with ActA-N100 fusion protein partner and integration is at ActA locus (FIG. 10).

Further details of the above study are described as follows. Mice were injected with Listeria, followed by a period of time (7 days) to allow the Listeria to be taken up and processed by antigen presenting cells (APCs). After uptake of the Listeria, the APC presented Listeria-encoded antigens to T cells, resulting in the activation and clonal expansion of the T cells. Spleens were removed, and the splenocytes (including T cells and APCs) were isolated. To the isolated splenocytes was added either buffer or a pool of human mesothelin peptides (0.002 mg/ml final concentration of pool). After adding the peptides, the dendritic cells (DCs) in the splenocyte preparation were allowed to present peptide to any activated T cells. Successful presentation resulted in the T cell's secretion of interferon-gamma, as reflected by signals in spot forming assays (spot forming cells; SFC) (FIG. 10).

Figure 11:
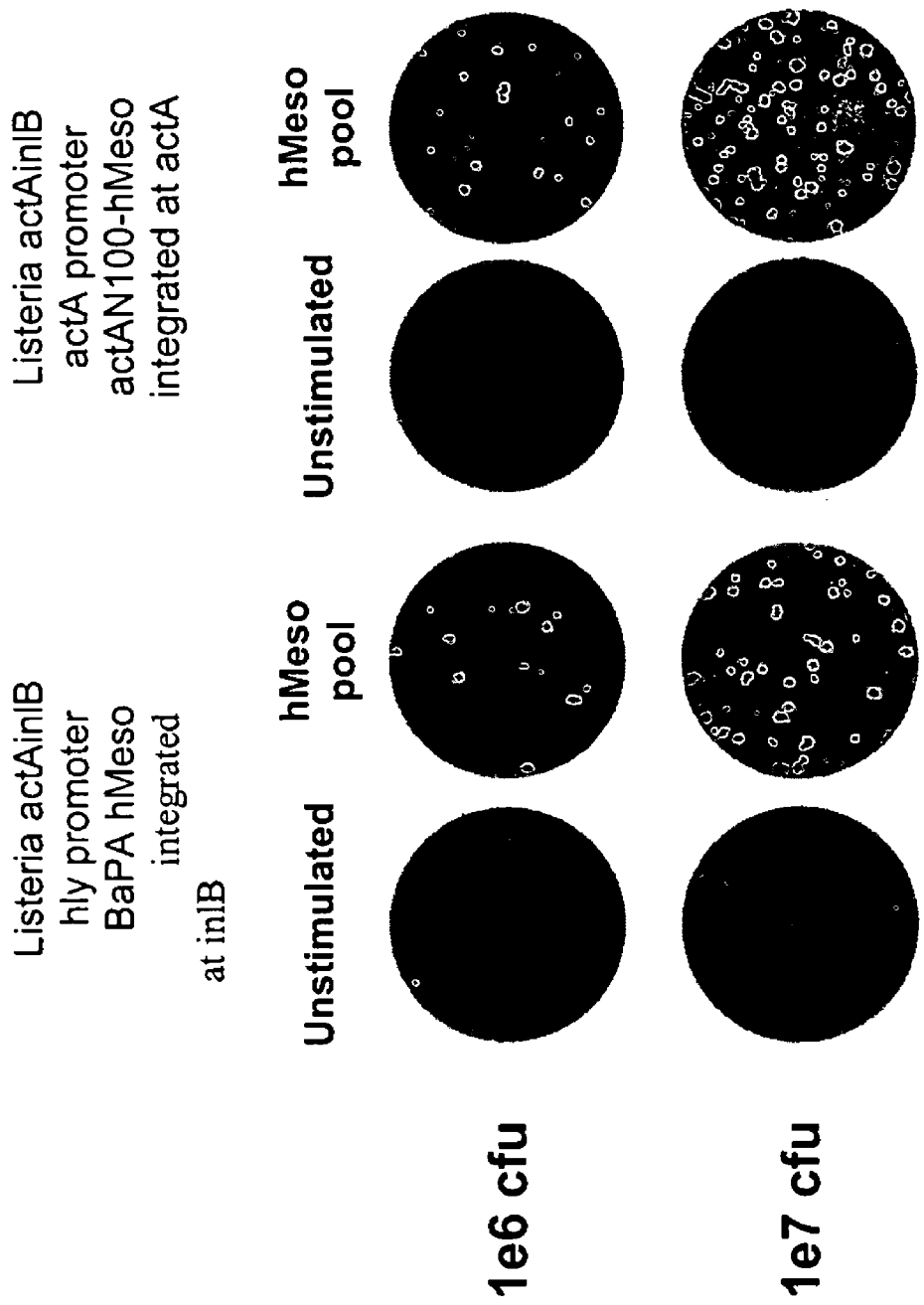
Figure 12:
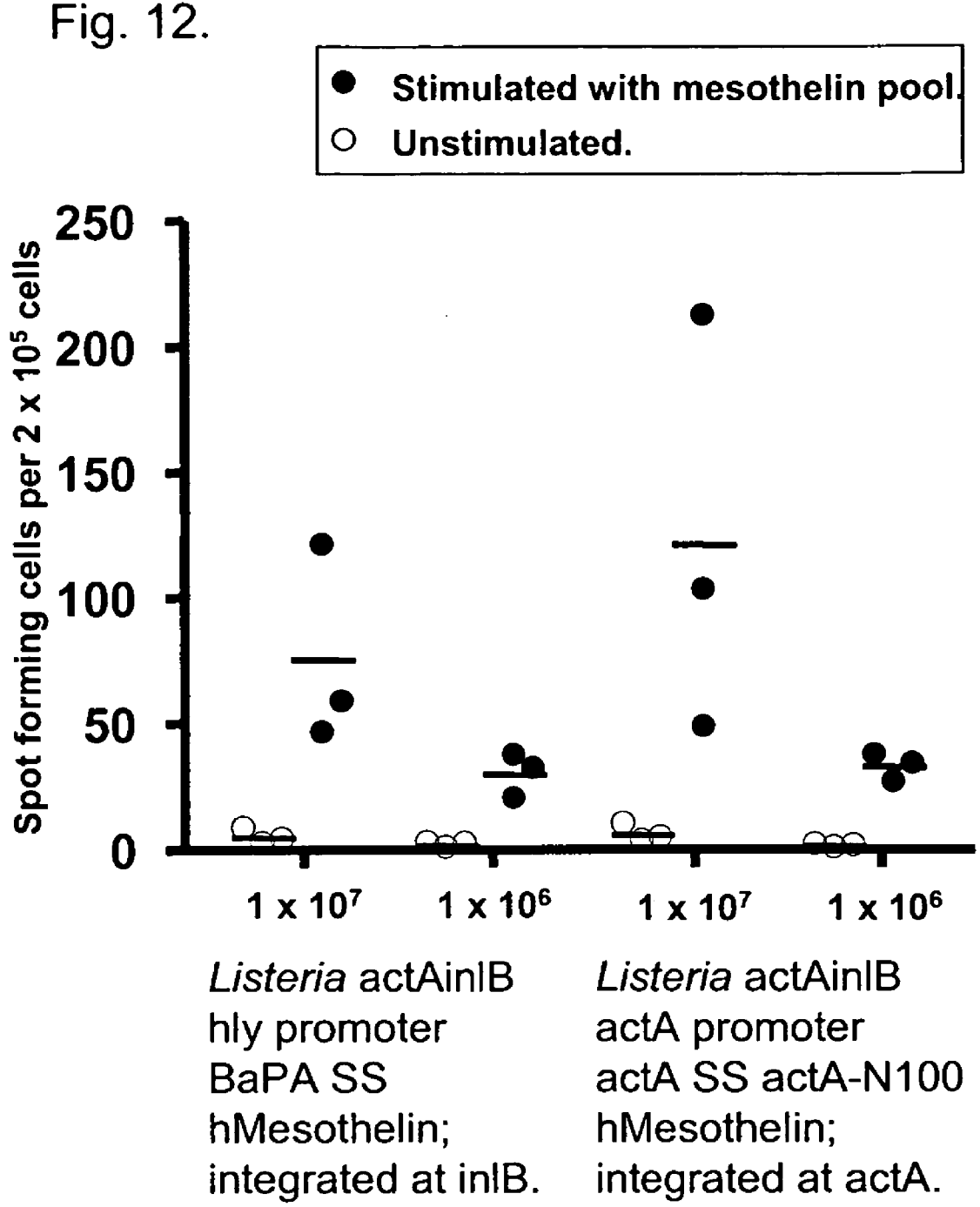

The mesothelin peptide pool (also known as 15×11 pool) consisted of 153 different peptides, all of them 15 mers, spanning the entire sequence of human mesothelin, where succeeding peptides overlapped by eleven amino acids. The results demonstrated that interferon-gamma (IFGgamma) expression was greater where the peptide pool had been added to the splenocytes, than where no peptide pool was used. FIGS. 10-12 compare immune response where mice were vaccinated with $1\times10^7$ CFU or $3\times10^7$ CFU (FIG. 10); $1\times10^6$ CFU or $1\times10^7$ CFU (FIG. 11); or $1\times10^6$ CFU or $1\times10^7$ CFU of L. monocytogenes (FIG. 12). In most cases disclosed here, immune response was greater where mice were injected with greater numbers of bacteria.

FIGS. 11 and 12 disclose similar studies using spot forming cell assays.

The raw data (photographs of spot forming cell assays) from FIG. 11 are graphed in FIG. 12. FIG. 12 discloses the number of cells that produce an IFNgamma signal (spot forming cell; SPC) per number of splenocytes. The data disclose comparable mesothelin-specific immune responses, where the construct was with hly promoter operably linked with BAPA signal sequence and hMeso (inlB locus), or where the construct was with ActA promoter operably linked with ActA signal sequence and ActA-N100 and hMeso (ActA locus).

Figure 14:
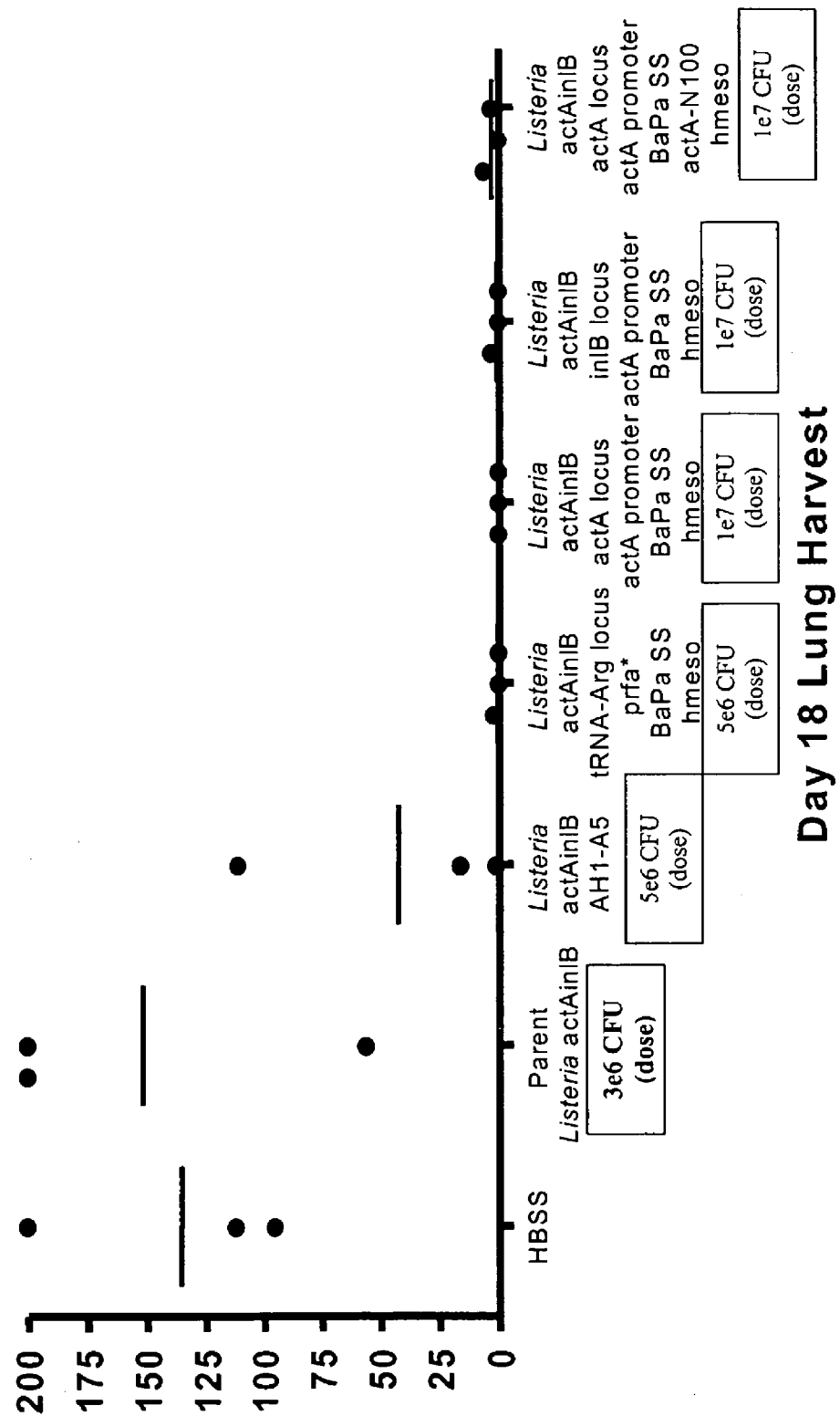
FIG. 14 also disclose numbers of tumor metastases on the surfaces of livers, after treatment of tumor-bearing mice with various preparations of recombinant *L. monocytogenes*.

FIGS. 13-14 disclose tumor metastasis data. The study measured metastasis of CT-26 human mesothelin expressing cells to the lungs. At t=0 days, CD-26 tumor cells were injected i.v. (2e5 cells). At t=3 days, mice were administered the indicated Listeria vaccine. At t=18 days, lungs were harvested. "2e5 cells" means $2\times10^5$ cells.

Tumor cell-inoculated mice were treated as follows: (1) Salt water only (HBSS); (2) L. monocytogenes ΔActAΔinlB encoding no heterologous antigen (negative control); (3) L. monocytogenes ΔActAΔinlB encoding the AH1-A5 peptide derived from the gp70 tumor antigen (an antigen different from mesothelin—positive control); and (4)-(7) Listeria ΔActAΔinlB encoding various mesothelin constructs. The AH1-A5 peptide is derived from the gp70 tumor antigen. AH1-A5 is used as a positive control in the present experiments (see, e.g., Brockstedt, et al. (2004) Proc. Natl. Acad. Sci. USA 101:13832-13837; Slansky, et al. (2000) Immunity 13:529-538).

FIG. 14 reveals equivalent effects of the four mesothelin-expressing Listeria constructs in eliminating tumor metastasis.

TABLE 15

Groups of mice challenged with CT26 tumor cells and treated with Listeria vaccines.

| Group | Listeria vaccine | Site of integraton. |
|---|---|---|
| 1 | Hanks Buffered Salt Solution only (HBSS) (no Listeria) (negative control). | no Listeria |
| 2 | L. monocytogenes ΔActAΔinlB (parental strain) (negative control). | none |
| 3 | L. monocytogenes ΔActAΔinlB-OVA-AH1-A5. The AH1-A5 epitope was inserted in-frame within OVA by using a unique AvaII site (expressed from hly promoter as part of pPL2 vector) (positive control). | tRNA$^{Arg}$ locus |
| 4 | L. monocytogenes ΔActAΔinlB prfA* (E77K)-BaPa signal sequence-human Mesothelin ΔSSΔGPI (see, e.g., Mueller and Freitag (2005) Infect. Immun. 73: 1917-1926). | ActA locus |
| 5 | L. monocytogenes ΔActAΔinlB-BaPa signal sequence-human mesothelin ΔSSΔGPI (expressed from ActA promoter). | ActA locus |
| 6 | L. monocytogenes ΔActAΔinlB-BaPa signal sequence-human mesothelin ΔSSΔGPI (expressed from hly promoter). | inlB locus |
| 7 | L. monocytogenes ΔActAΔinlB-ActA signal sequence-ActA-N100-human mesothelin ΔSSΔGPI (expressed from ActA promoter). | ActA locus |

Figure 15:
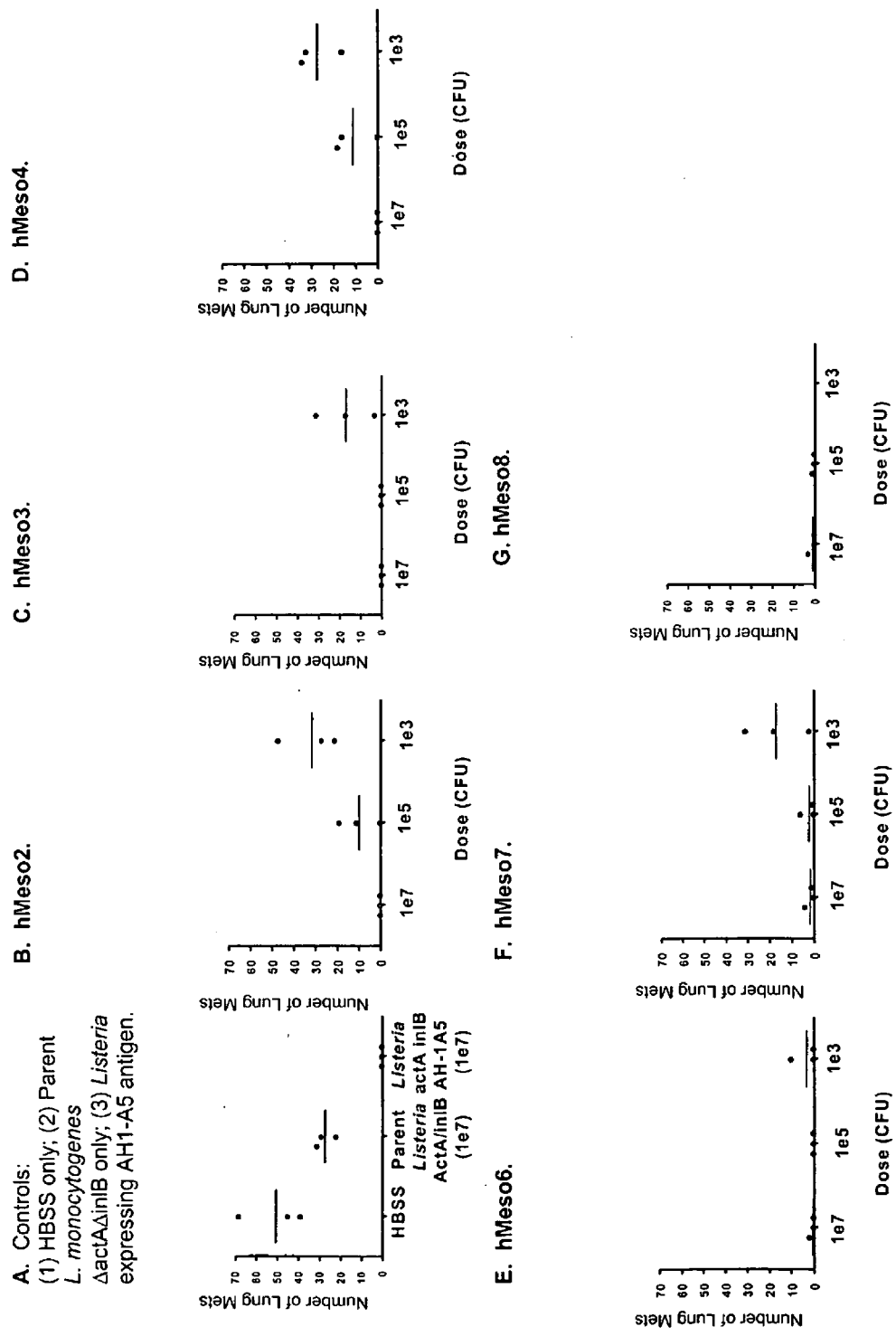
FIG. 15 further disclose numbers of tumor metastases on the surfaces of livers, after treating tumor-bearing mice with recombinant *L. monocytogenes*.

FIG. 15 demonstrates that various mesothelin-expressing Listeria are effective in reducing lung tumors, where three different doses of each mesothelin-expressing Listeria were tested. hMeso6 is more effective than, for example, hMeso2 or hMeso4, in stopping lung metastasis (FIG. 15).

Figure 16:
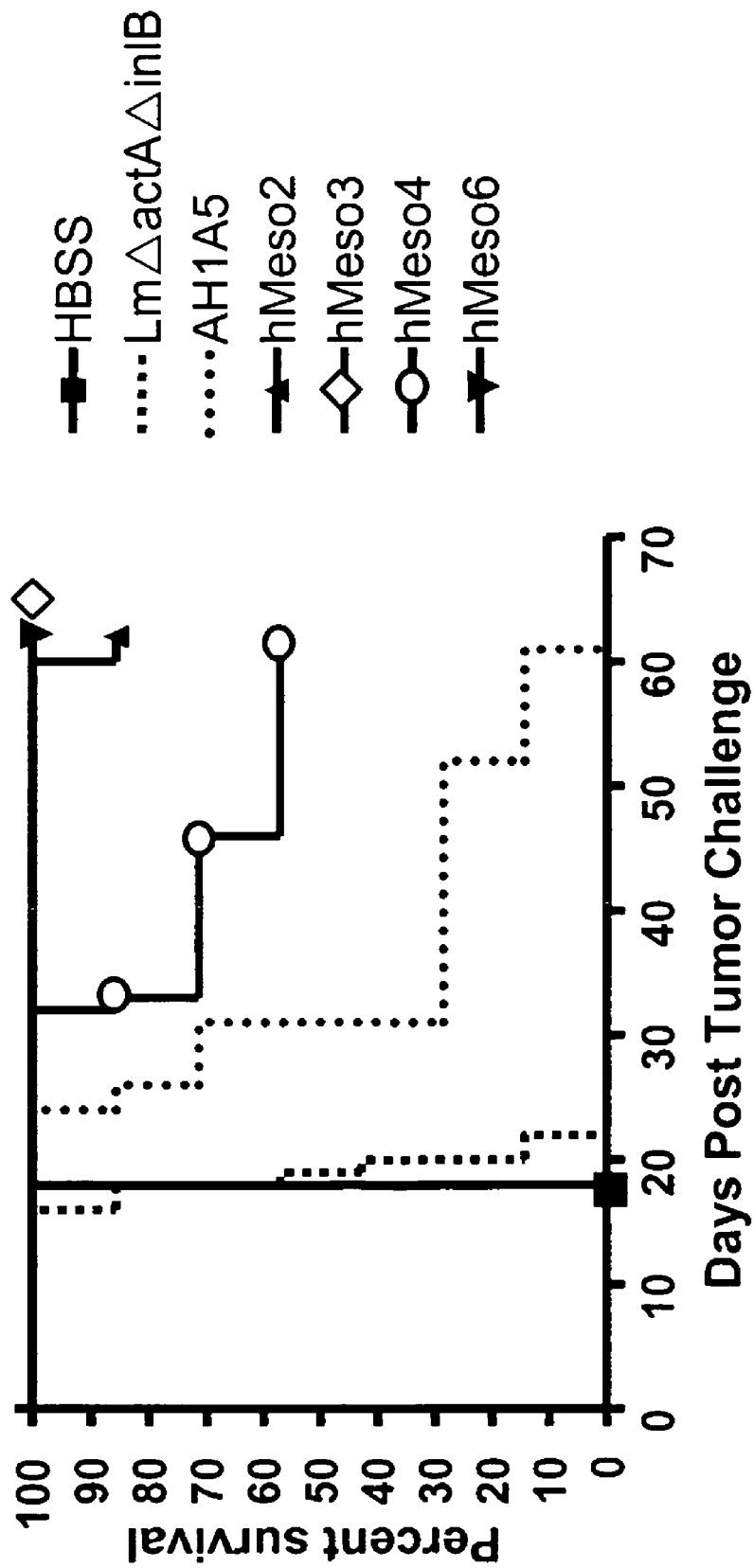
FIG. 16 demonstrates increased survival to tumors by tumor-bearing mice with treatment with various preparations of recombinant *L. monocytogenes*.

FIG. 16 discloses survival to tumors with various listerial vaccines. With negative control treatments (HBSS; parental Listeria), none of the mice survived beyond 22 days. The positive control Listeria expressed an antigen derived from gp70. The antigen (AH1-A5) was derived from the immunodominant antigen from CT26 cells (Slansky, et al. (2000) Immunity 13:529-538). Mice treated with the positive control vaccine survived up to or beyond 60 days (FIG. 16).

Figure 17:
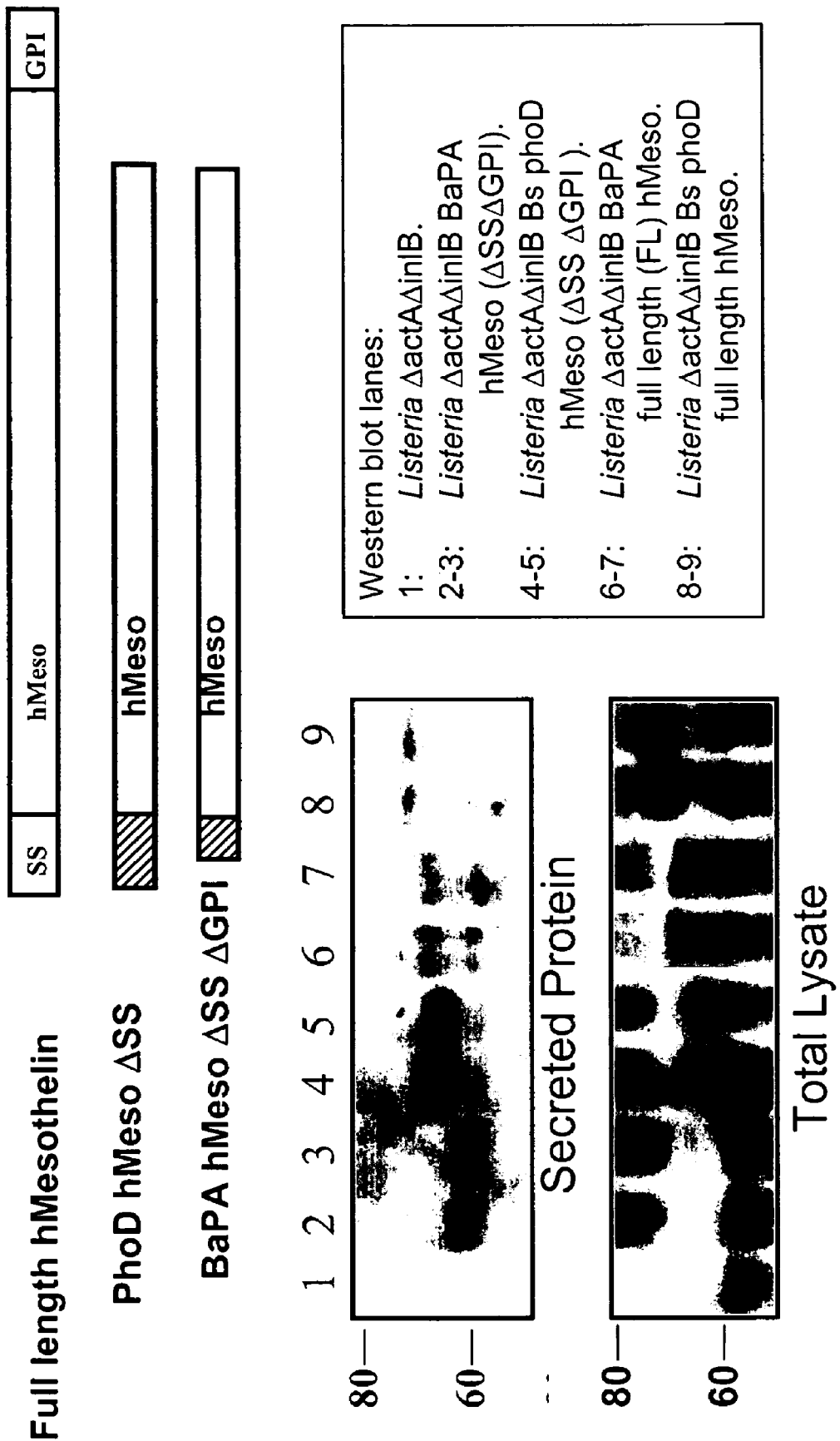
FIG. 17 illustrates mesothelin constructs and secretion of mesothelin by various preparations of recombinant *L. monocytogenes*.

FIG. 17 discloses gels, with western blot analysis, for detecting secreted mesothelin (top blot) and total expressed mesothelin (lower blot). L. monocytogenes ΔActAΔinlB engineered to contain a polynucleotide encoding the indicated secretory sequences and antigens were cultured, and the total or secreted mesothelin was measured. The secretory sequences were BaPA or Bs phoD, as indicated. The antigens were full length (FL) human mesothelin or human mesothelin deleted in its secretory sequence and GPI anchor (hMesoΔSSΔGPI), as indicated. The results indicate that total expression was somewhat greater with Bs phoD (lanes 4-5; lower gel) than with BaPA (lanes 2-3; lower gel). The results also demonstrate that, at least with the Bs phoD containing constructs, secretion was greater with hMeso (ΔSSΔGPI) (lanes 4-5; top gel) than with full length hMeso (lanes 8-9; top gel).

Figure 18:
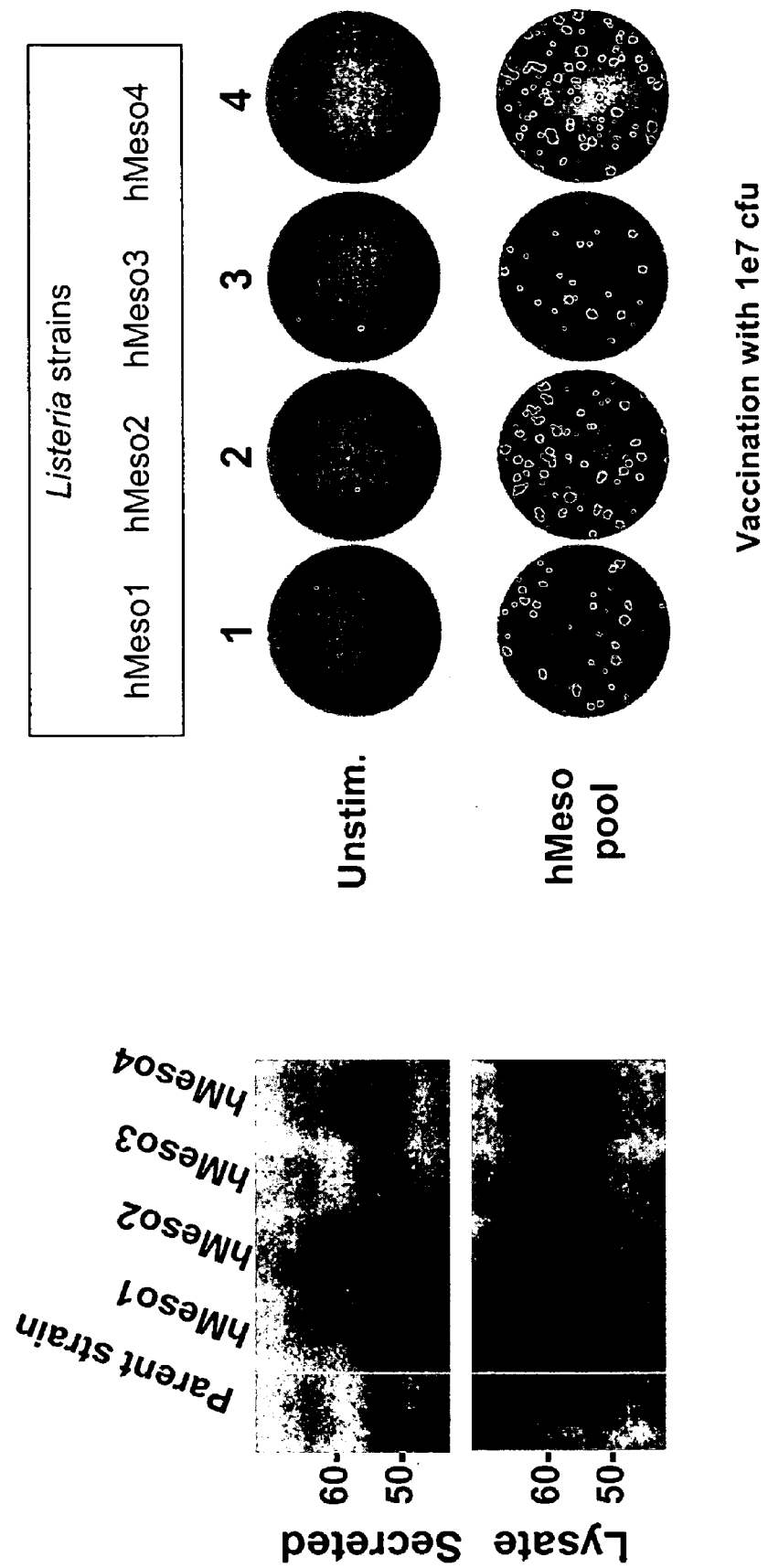
FIG. 18 discloses secretion of mesothelin and immune responses stimulated by various preparations of recombinant *L. monocytogenes*.

FIG. 18 compares the mesothelin-specific immune response to vaccination with hMeso1, hMeso2, hMeso3, and hMeso4. Side-by-side comparison of hMeso1 and hMeso2 reveals that a Listeria construct comprising a nucleic acid encoding for constitutively active PrfA (prfA*) increases immune response, as compared to a Listeria construct not comprising that nucleic acid. Side-by-side comparisons of hMeso1 and hMeso4 reveals that increased immune response is found with genomic integration at the inlB locus (hMeso4), as compared to immune response where genomic integration is at the tRNA$^{Arg}$ locus (hMeso1). Comparison of immune response to hMeso3 and hMeso4 suggests that immune response can be enhanced by using hly promoter, as compared to immune response with ActA promoter. Elispot analysis was used to assess immune response. Splenocytes (plus or minus stimulation of splenocytes with a pool of mesothelin peptides) for elispot assays, where the elispot assays measured IFNgamma expression.

The gels of FIG. 18 disclose western blots sensitive to total expression of mesothelin or to secretion of mesothelin. hMeso2 produced the highest levels of secretion, indicating the usefulness of the following combination for increasing secretion: (1) prfA* nucleic acid; (2) Integration at tRNAArg locus; (3) The hly promoter; and (4) BaPa secretory sequence. Again, the usefulness of the prfA* nucleic acid is demonstrated.

FIG. 19 compares immune response to hMeso12 and hMeso1. Mesothelin-specific immune response is depicted by the raw data (elispot assays) and by histograms showing the number of spot forming splenocytes per 2×10$^5$ spenocytes. The results indicate that the ras sequence present in the fusion protein of hMeso ΔSSΔGPI (hMeso12) results in lower immune response (elispot assays) and lower expression (western blots), as compared to results where the fusion protein did not comprise ras (hMeso1) (FIG. 19).

Mice were vaccinated with the two strains (hMeso12 or hMeso1), and splenocytes were removed and used for elispot assays, where assay mixtures were pulsed with the standard hMeso pool of peptides. As disclosed above, hMeso1 (the BaPA secretory sequence is wild type) stimulated a greater mesothelin-specific immune response than hMeso12 (the BaPA secretory sequence is E30R).

Figure 20:
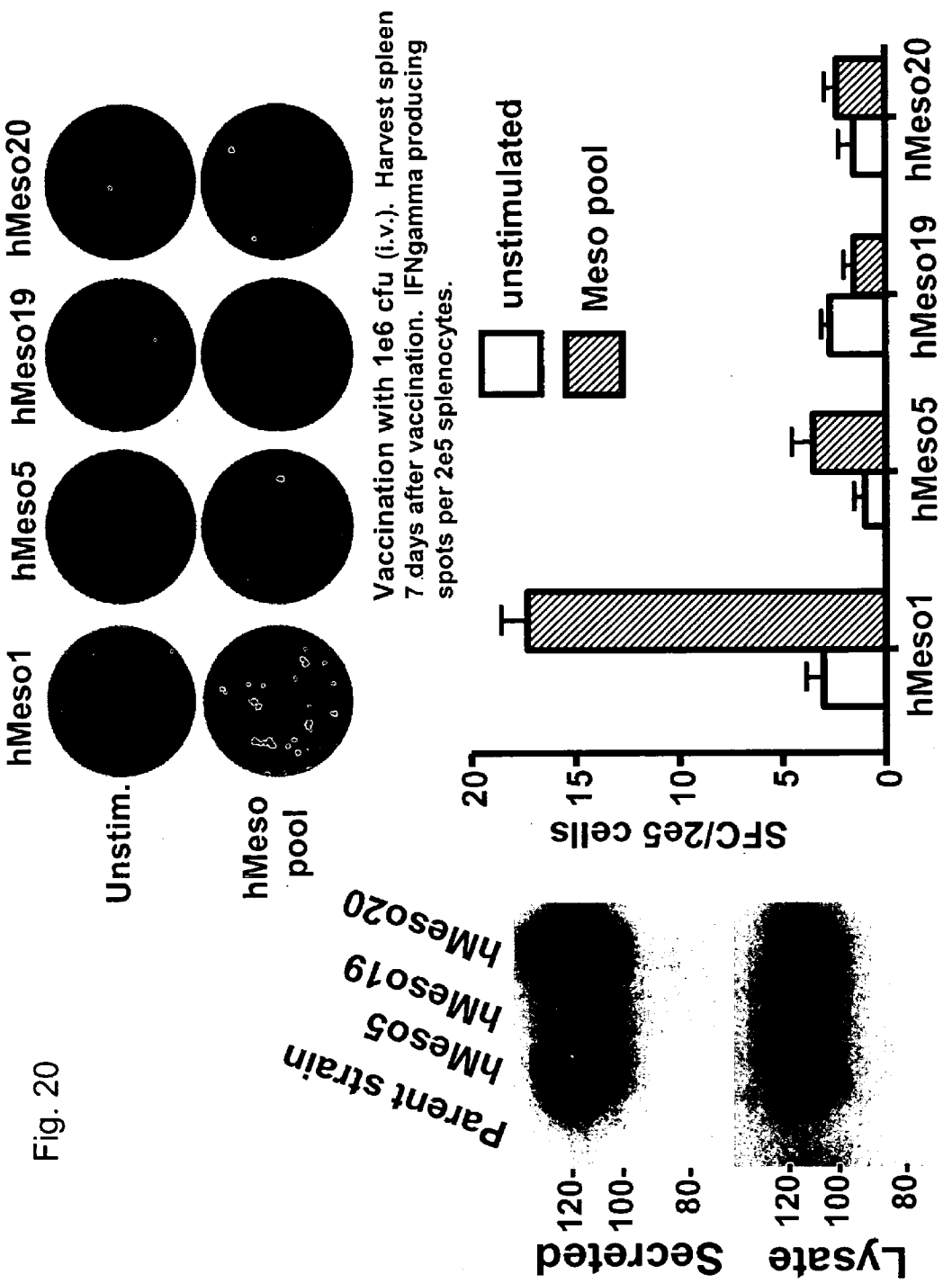
FIG. 20 further reveals mesothelin expression and immune responses stimulated by various preparations of recombinant *L. monocytogenes*.
Figure 21:
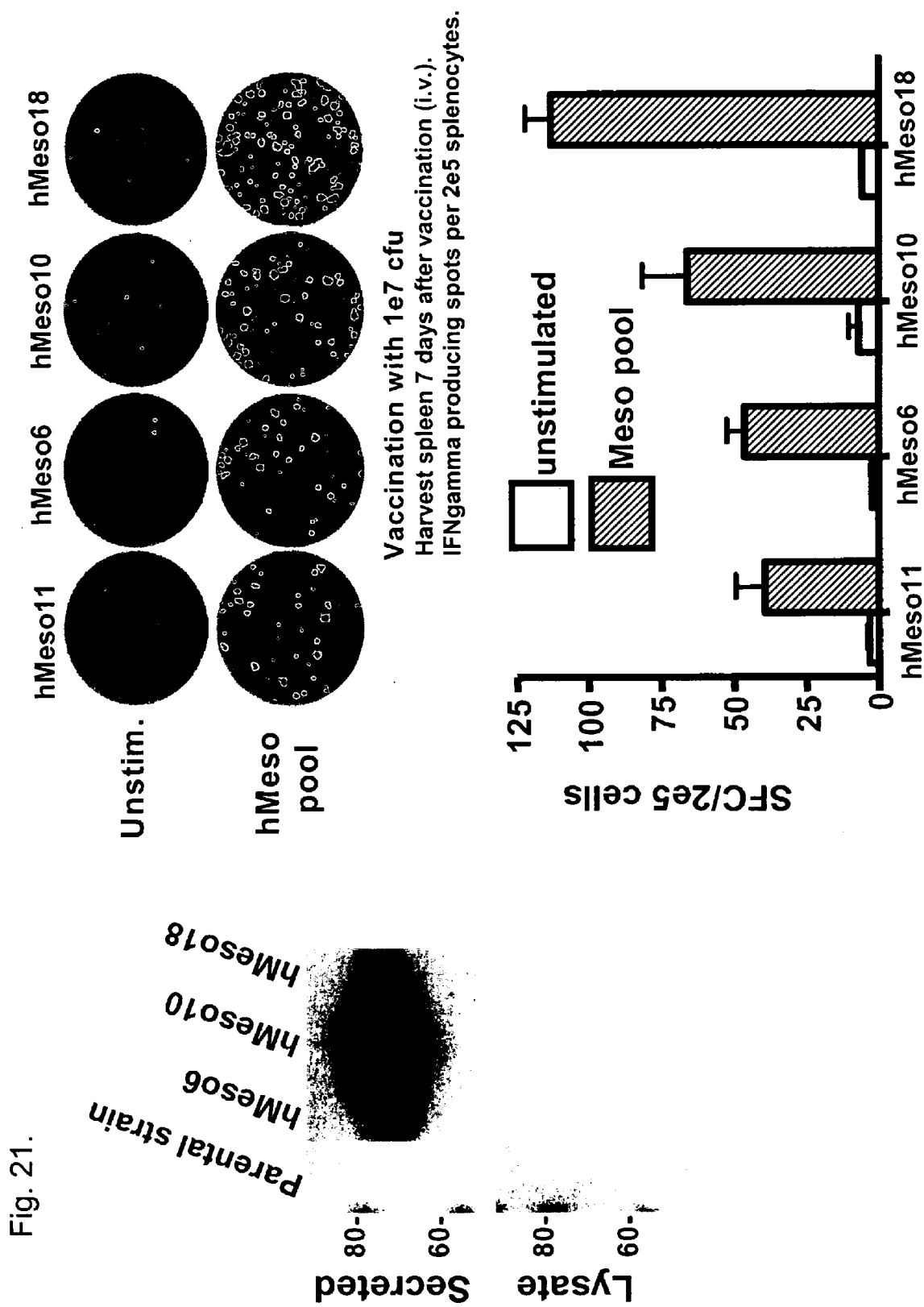
FIG. 21 additionally illustrates secretion of mesothelin and immune responses stimulated by various preparations of recombinant *L. monocytogenes*.
Figure 22:
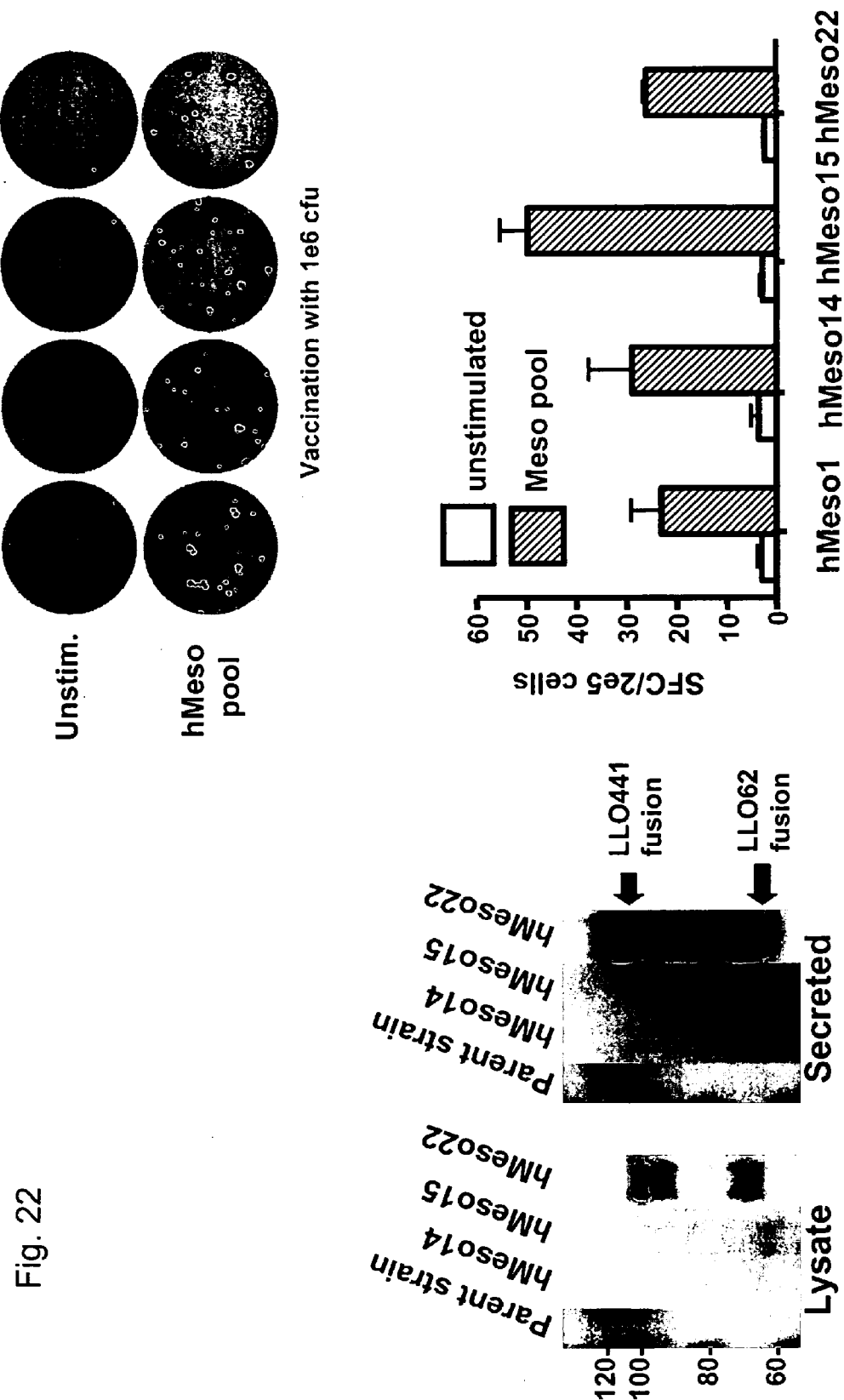
FIG. 22 demonstrates mesothelin expression and immune responses stimulated by various preparations of recombinant *L. monocytogenes*.
Figure 25:
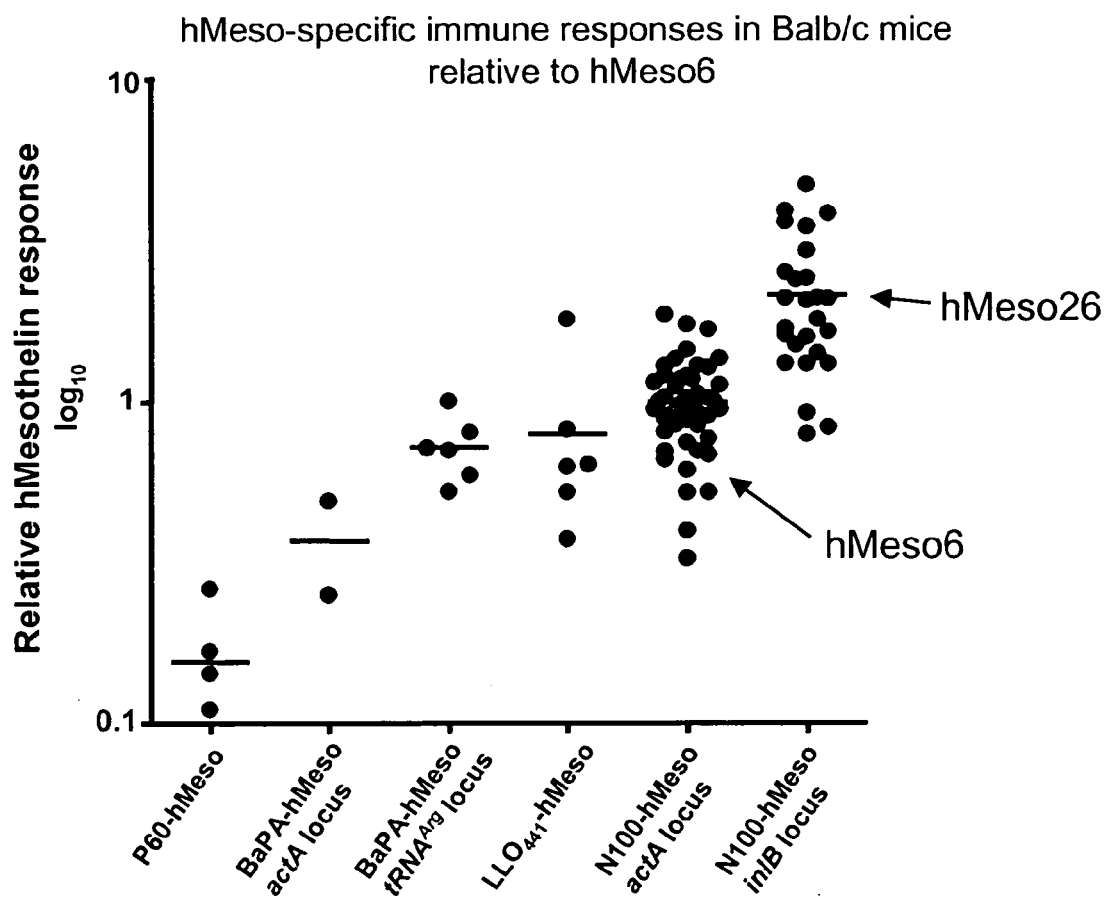
FIG. 25 reveals immune responses stimulated after vaccination with a number of preparations of recombinant *Listeria*.
Figure 27:
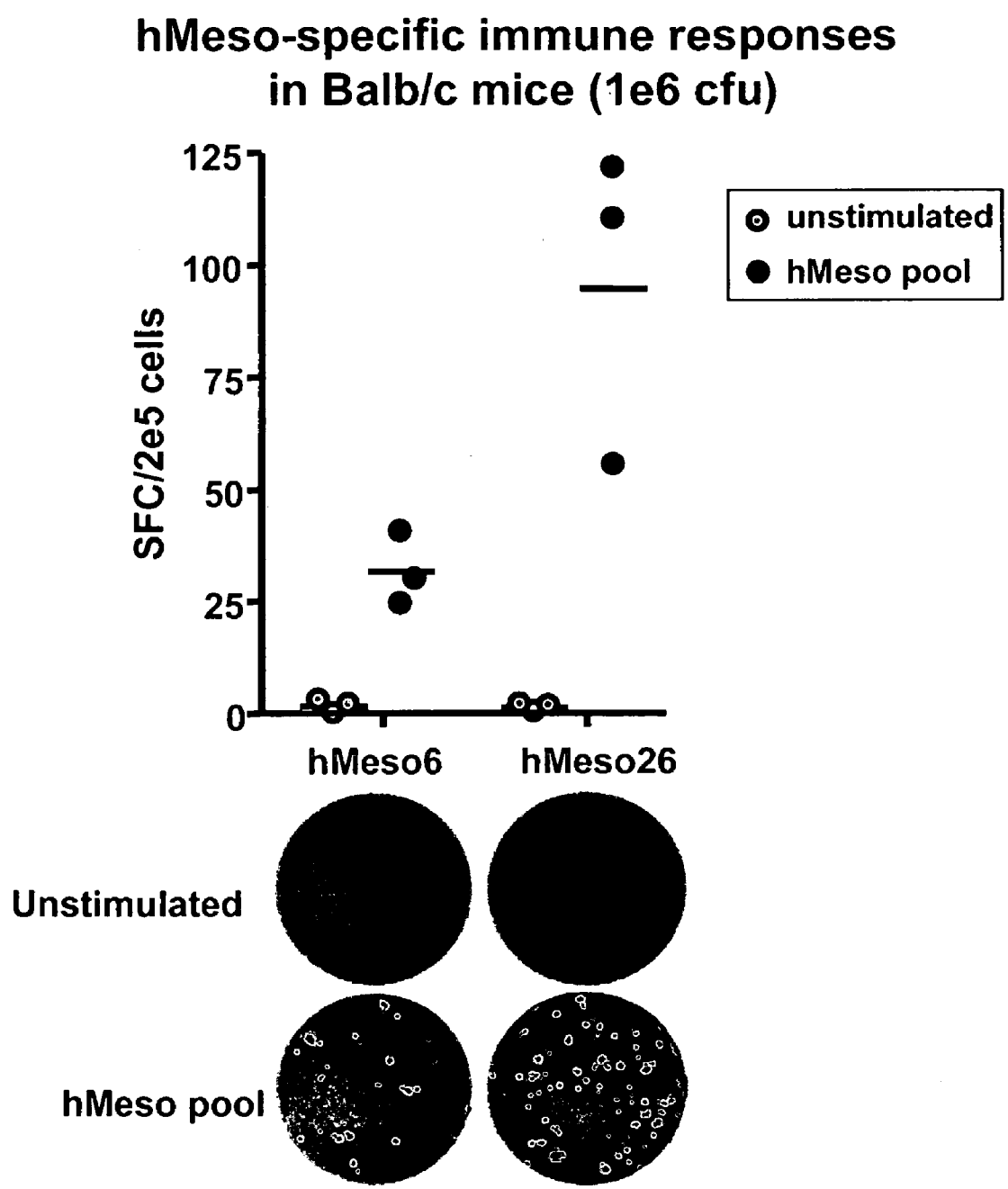
FIG. 27 further demonstrates secretion of mesothelin and immune responses stimulated by various preparations of recombinant *L. monocytogenes*.
Figure 28:
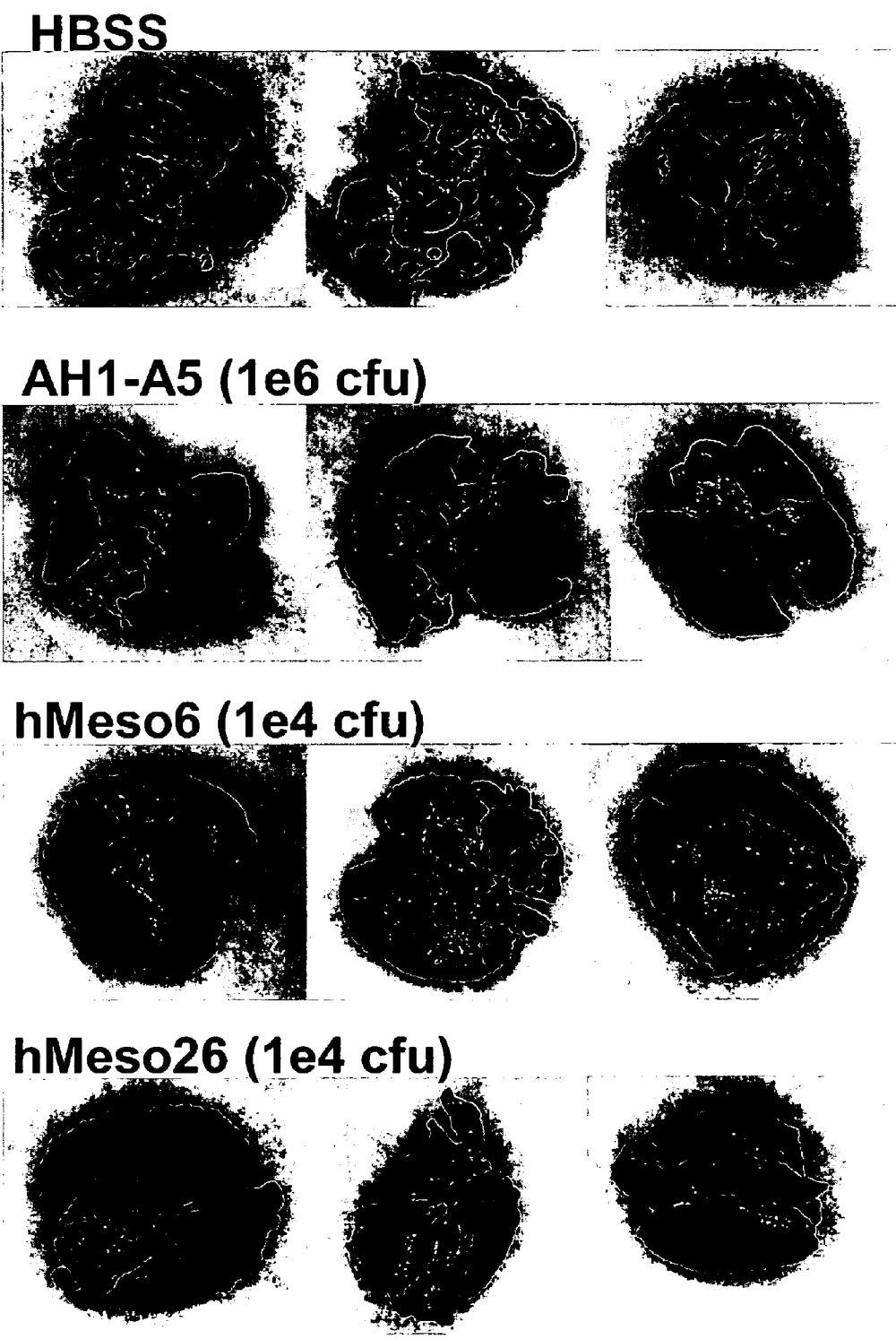
FIG. 28 shows photographs of fixed lungs.
Figure 29:
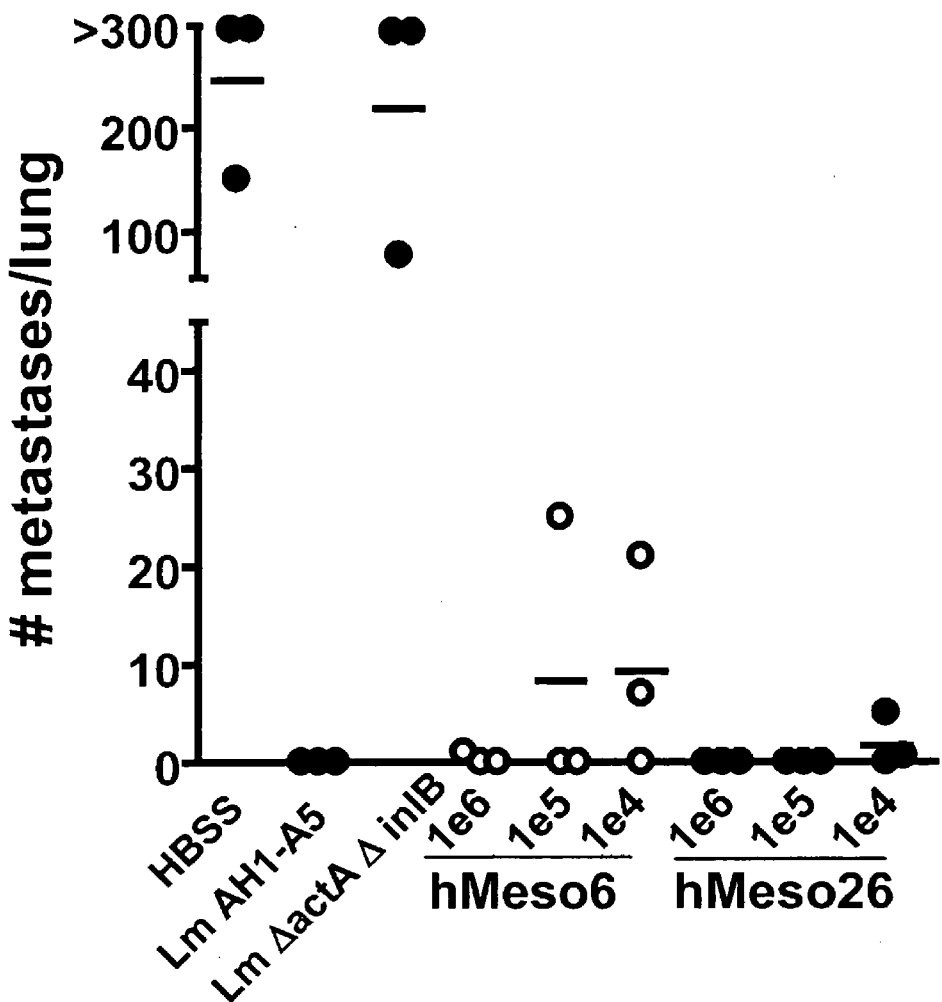
FIG. 29 shows a histogram of data from the photographs of fixed lung.
Figure 30:
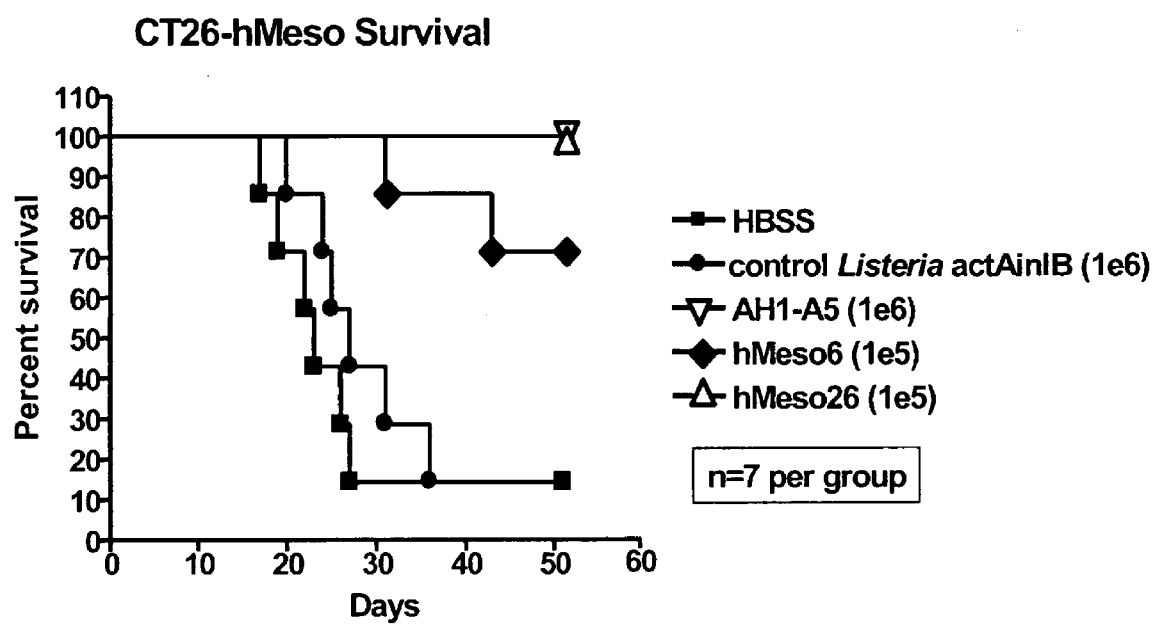
FIG. 30 reveals the effectiveness of various preparations of recombinant *Listeria* in improving survival of tumor-bearing mice.
Figure 31:
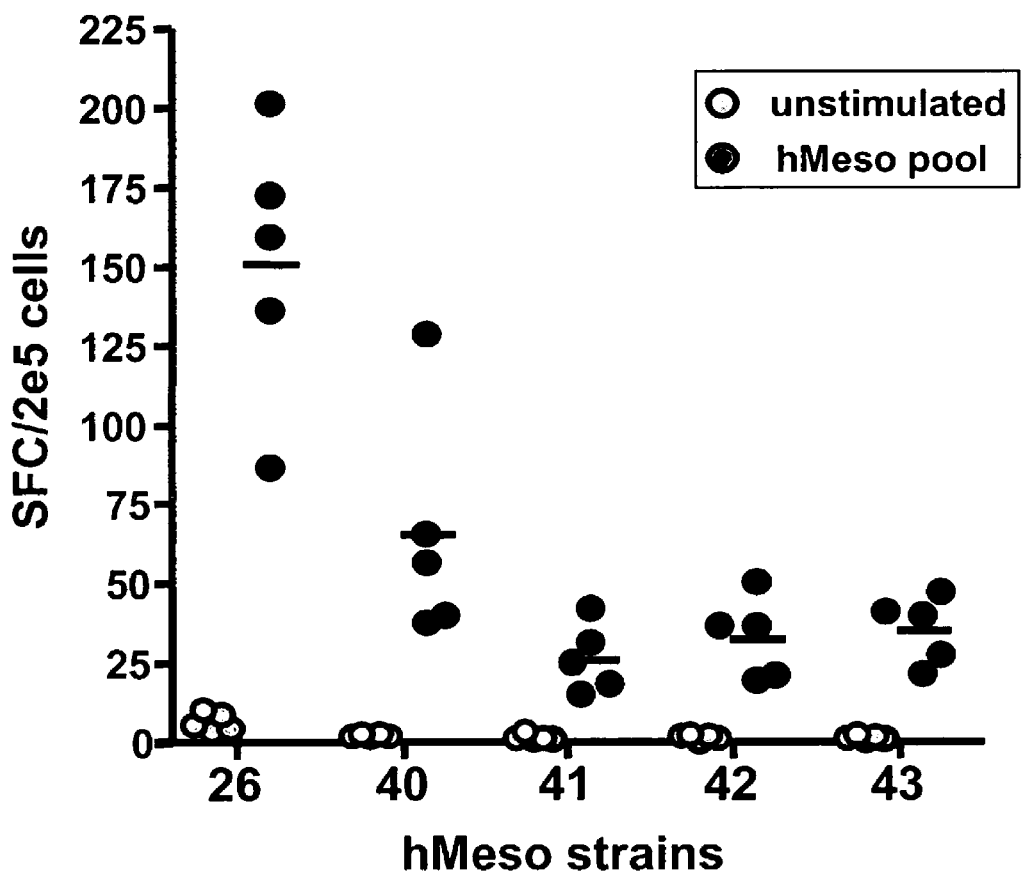
FIG. 31 discloses secretion of mesothelin and immune responses stimulated by various preparations of recombinant *L. monocytogenes*.
Figure 32:
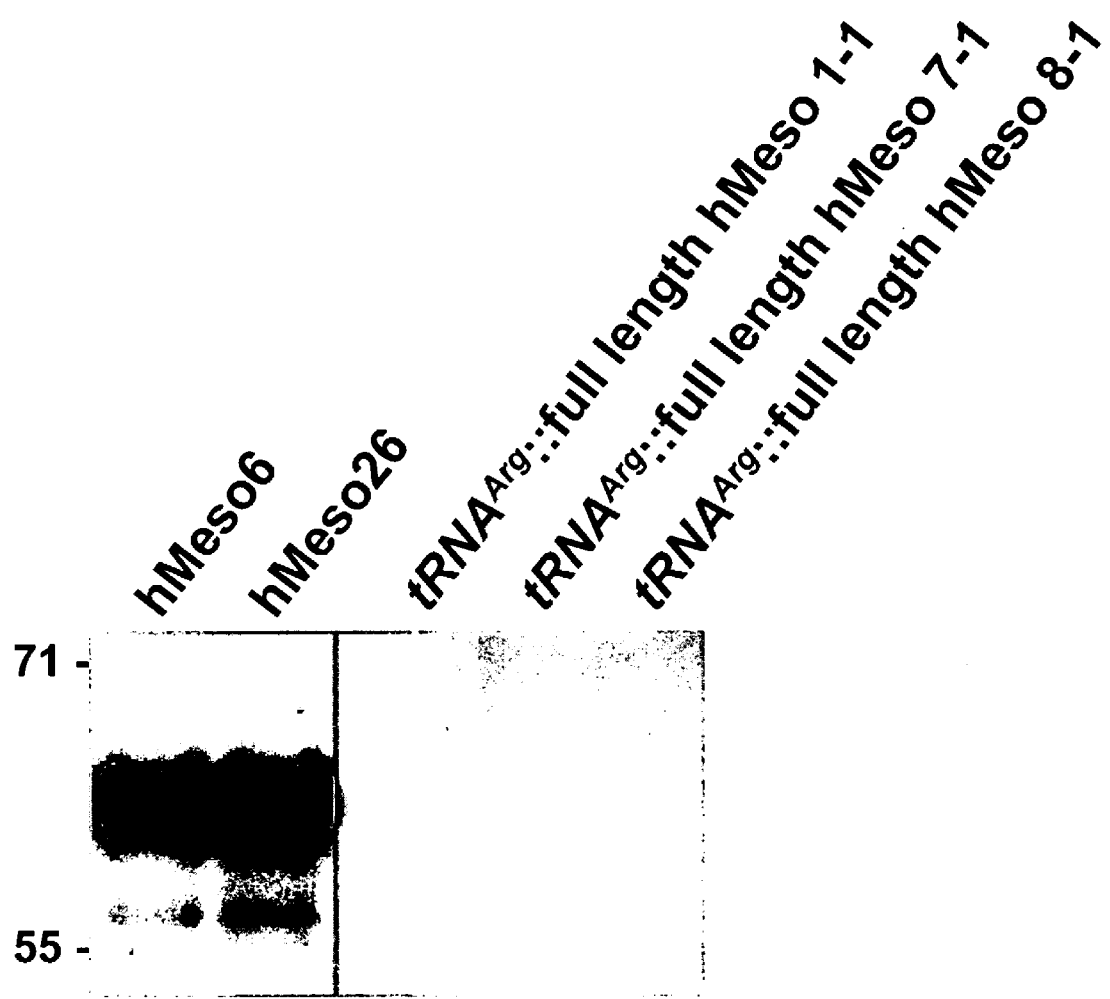
FIG. 32 compares mesothelin expression from various preparations of recombinant *Listeria*.

FIG. 20 compares immune response to hMeso1, hMeso5, hMeso19, and hMeso20. The results demonstrate that the greatest mesothelin-specific immune response was to hMeso1, where there was also some detectable mesothelin-specific response to hMeso5. The results demonstrate that BaPA secretory sequence results in greater immune response, as compared to p60 secretory sequence, or to derivatives of p60 secretory sequence. The gel demonstrates that the p60 secretory sequence supports secretion of mesothelin. See lanes labeled hMeso5 or hMeso20 (FIG. 20).

FIG. 21 compares immune responses to hMeso11, hMeso6, hMeso10, and hMeso18. Mesothelin-specific immune responses occurred with each of these vaccines, where the highest responses were provoked by hMeso10 and hMeso18. In comparing hMeso6 and hMeso10, it can be seen that the ras (hMeso10) can enhance mesothelin-specific immune response. Here, both *Listeria* strains ActA secretory sequence was used, ActA promoter was used, and ActA locus of integration was used. The high degree of immune response to hMeso18 can be due to the use of the ActA (A30R) secretory sequence. The present invention provides a *Listeria* containing a polynucleotide comprising a first nucleic acid encoding ActA (A30R), operably linked with and in frame with a second nucleic acid encoding a heterologous antigen, e.g., an antigen derived from a tumor, such as mesothelin antigen, or an antigen derived from an infectious agent. The gel reveals that the hMeso18 *Listeria* strain secreted relatively low amounts of mesothelin, as compared with secretion by hMeso10 and hMeso6 (FIG. 21).

FIG. 22 compares immune responses to hMeso1, hMeso14, hMeso15, and hMeso22. Mesothelin-specific immune responses to hMeso1, hMeso14, and hMeso22 were comparable, while that to hMeso15 was greater. The secretory sequences (SS) of each these four vaccine strains are different. The secretory sequences (SS) of hMeso1 is BAPA; hMeso14 (LLO62); hMeso15 (LLO opt62); hMeso22 (LLO441).

FIG. 23 reveals immune response in healthy human volunteers, to listeriolysin (LLO) and to mesothelin. Immune response to epitopes of LLO and to mesothelin was found in all three subjects tested.

FIG. 24 illustrates expression of human mesothelin by hMeso6 or hMeso5, in BHI broth and in J774 macrophages, where expression was assessed by gel separation and detection by the western blot method. The results demonstrate relatively low expression by hMeso6 in broth (and high expression by hMeso5 in broth), and relatively high expression by hMeso6 inside mammalian cells (and low expression by hMeso5 inside mammalian cells). The graph demonstrates relatively high immune response (meso-specific response; elispot assays) after vaccination with hMeso6, and low immune response after vaccination with hMeso5 (FIG. 24).

FIG. 25 discloses mesothelin-specific immune response, where mice had been vaccinated with *Listeria* containing a polynucleotide comprising a first nucleic acid encoding p60, BaPA, LLO441, ActA-N100, as indicated, and a second nucleic acid encoding hMeso. Integration was at the $tRNA^{Arg}$ locus, ActA locus, or inlB locus, of the listerial genome, as indicated.

FIG. 26 illustrates in vivo expression of mesothelin from J774 macrophages, as detected by western blotting using an anti-mesothelin antibody. Similar in vivo expression occurred when the J744 macrophages were infected with hMeso6 or with hMeso26.

FIG. 26, as well as FIG. 27, shows show that mesothelin-specific mounted after vaccination with various engineered *Listeria* were greater with the hMeso26 strain than with the other tested strains.

FIGS. 28 (photographs of lungs), 29 (histograms of lung data), and 30 (mouse survival) reveal the successful treatment of lung tumors by administering hMeso6 and hMeso26. Mice were treated with a negative control (HBSS); positive control (*Listeria* expressing AH1-A5); or the indicated numbers of hMeso6 or hMeso26. The tumors were induced by an injection with CT26 cells. The results demonstrate that both hMeso6 and hMeso26 were effective in reducing tumor metastasis, where hMeso26 was more effective than hMeso6 (FIG. 30).

FIG. 31 compares expression, and immune responses to vaccination, with various *Listeria* strains engineered to contain integrated expression cassettes at different points in the listerial genome. The control bacterium (*L. monocytogenes* ΔActAΔinlB) contained no expression cassette, while hMeso26 contained only one integrated expression cassette. The strains hMeso40, hMeso41, hMeso42, and hMeso43, each contained two different expression cassettes (integrated at two different points in the genome), where expression from these *Listeria* strains and immune response to these *Listeria* strains are shown (FIG. 31).

FIG. 32 shows in vivo expression of mesothelin, that is, in vivo within J744 macrophages, after infection with (1) hMeso6; (2) hMeso26; or (3) *L. monocytogenes* ΔActAΔinlB (three identical constructs) bearing an expression cassette encoding full length human mesothelin, and integrated at tRNA$^{Arg}$ locus. The three identical constructs, or siblings, are labeled 1-1, 7-1, and 8-1.

FIG. 33 discloses in vivo expression of mesothelin by hMeso6, hMeso26, and hMeso38 within J774 murine macrophages (gels with western blots). The control bacterium was *L. monocytogenes* ΔActAΔinlB. Also shown are mesothelin-specific immune responses (elispot assays). The results demonstrate comparable expression of mesothelin where hMeso6, hMeso26, and hMeso38 are located in macrophages, and comparable immune response to hMeso26 and hMeso38.

Figure 34:
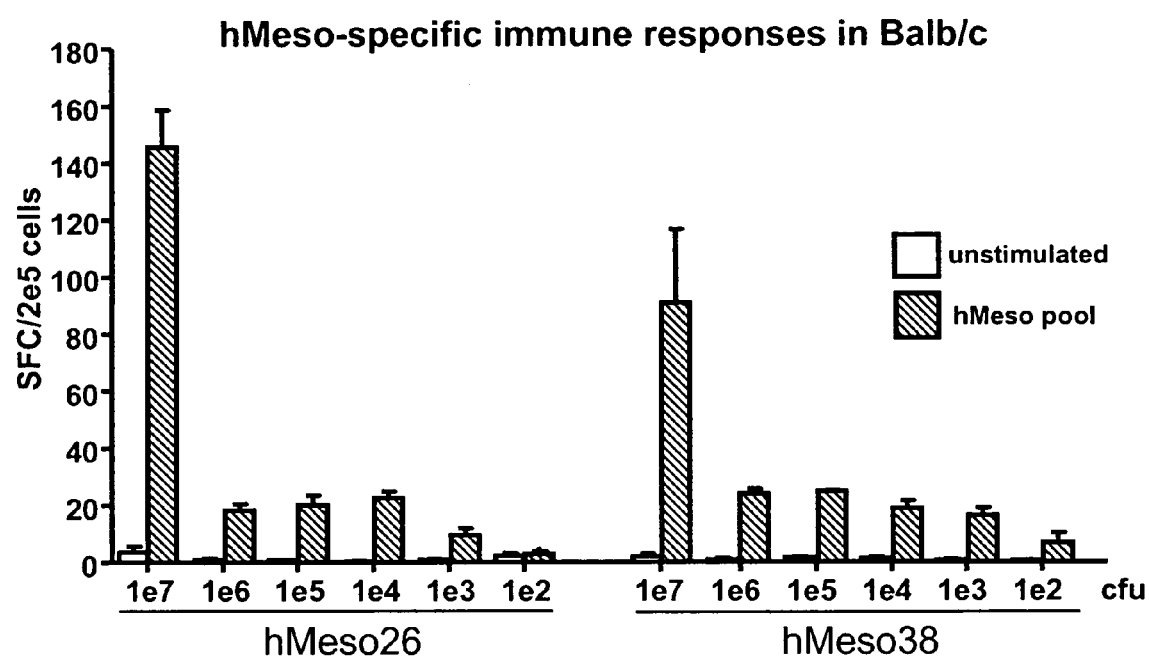
FIG. 34 demonstrates immune response stimulated after vaccination with the preparations and doses of recombinant *Listeria*.

FIG. 34 discloses mesothelin-specific immune response generated seven days after a single injection of hMeso26 or hMeso38, at the indicated doses. The dose response curves reveal a marked increase in going from one million bacteria to ten million bacteria. The dose response curves found with the two strains are similar to each other (FIG. 34). The present invention provides hMeso26; hMeso38; a vaccine comprising hMeso26 and/or hMeso38; a method of administering hMeso26 and/or hMeso38 to a mammalian subject; a method of stimulating mesothelin-specific immune response against a cancer or tumor comprising administering hMeso26 and/or hMeso38; a method of increasing survival to a cancer or tumor comprising administering hMeso26 and/or hMeso28, and so on (FIG. 34).

Figure 35A:
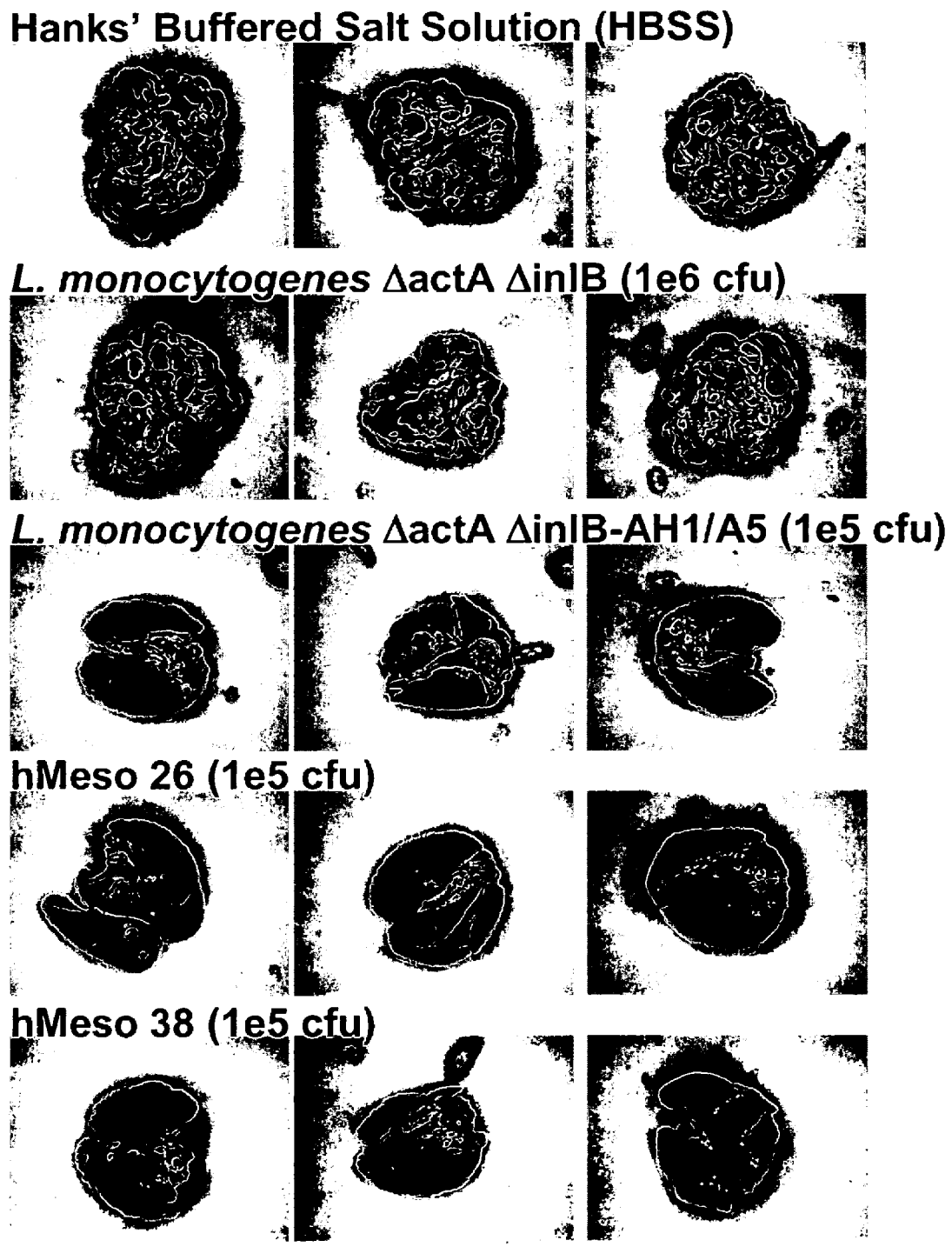
FIGS. 35A and 35B disclose numbers of tumor metastases on livers, after treatment of tumor-bearing mice with various preparations of recombinant *L. monocytogenes*.
Figure 35B:
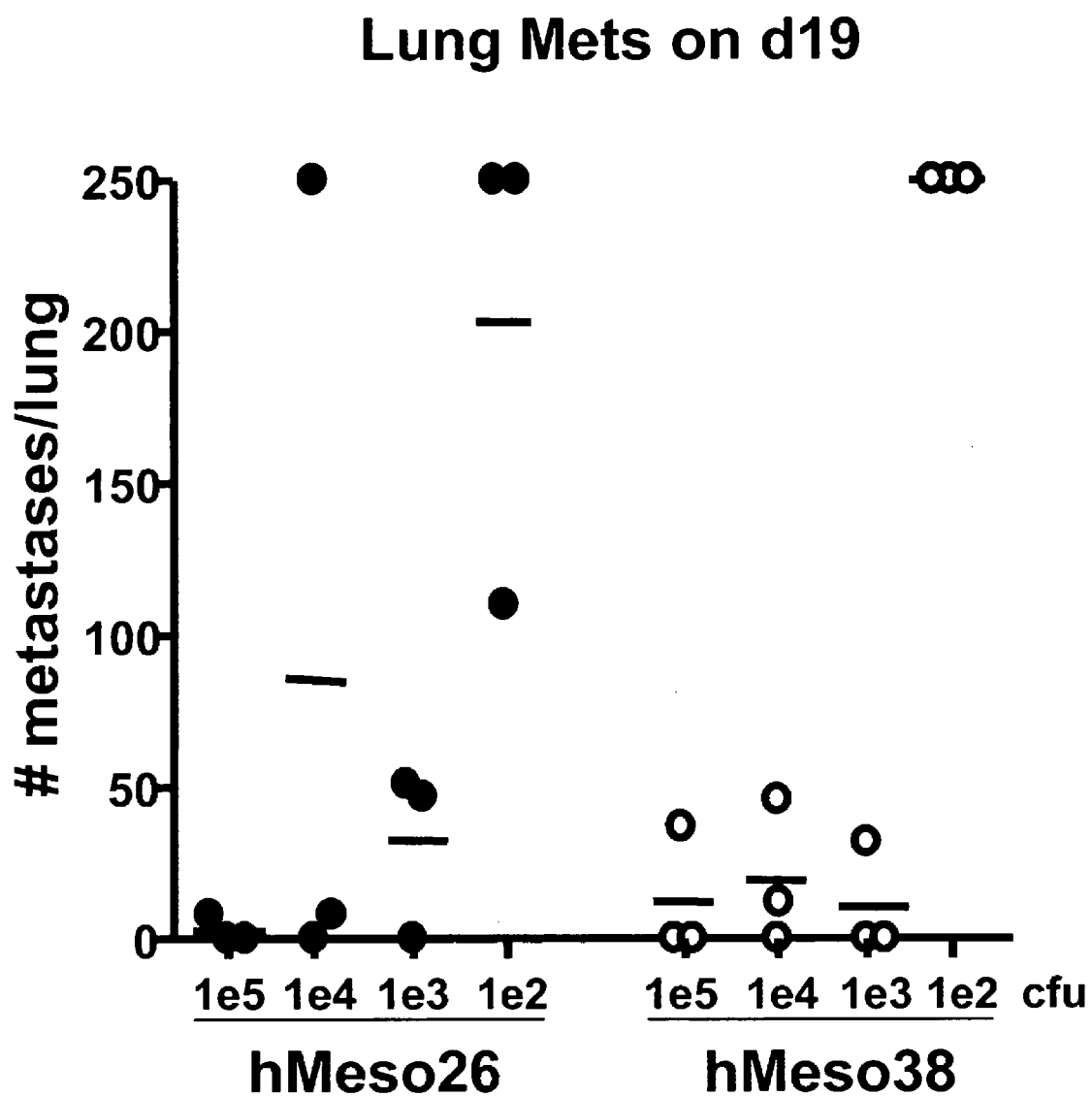

FIGS. 35A and 35B continue the narrative on hMeso26 and hMeso38, and shows photographs of fixed lungs. Tumor cells were injected at t=0 days. *Listeria* vaccines were injected (i.v.) at T=3 days. Lungs were harvested at t=19 days, where the histograph quantitates the metastasis results represented by the lung photographs (FIG. 35A,B). With titration of mice with the indicated numbers of bacteria, the results show similar responses for both listerial strains, hMeso26 and hMeso38.

Figure 36:
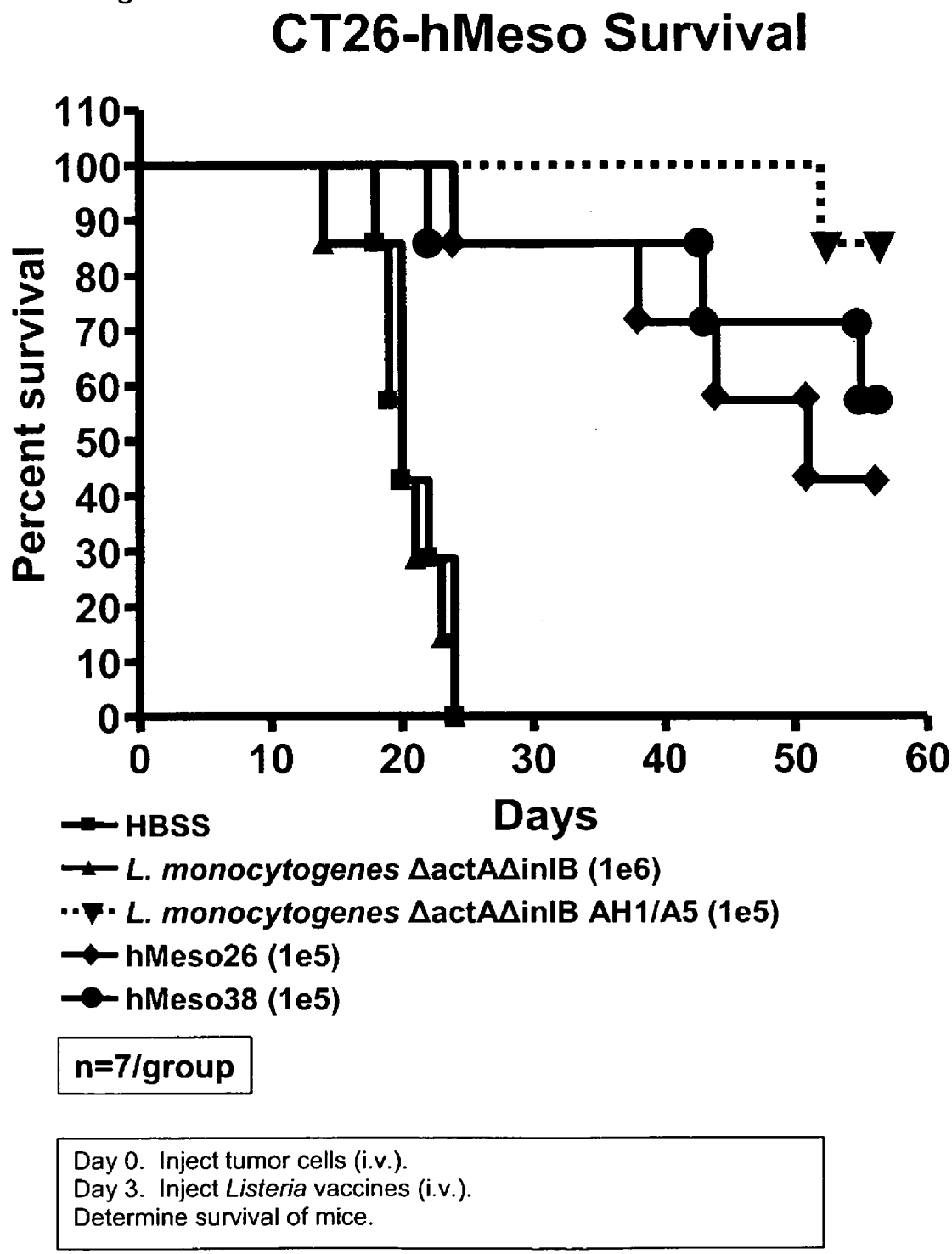
FIG. 36 demonstrates the effectiveness of various preparations of recombinant *Listeria* in improving survival of tumor-bearing mice.

FIG. 36 also continues the narrative of *Listeria* strains hMeso26 and hMeso38. The results demonstrate that both strains result in similar increases in survival to innoculated CT26 tumor cells.

Figure 37:
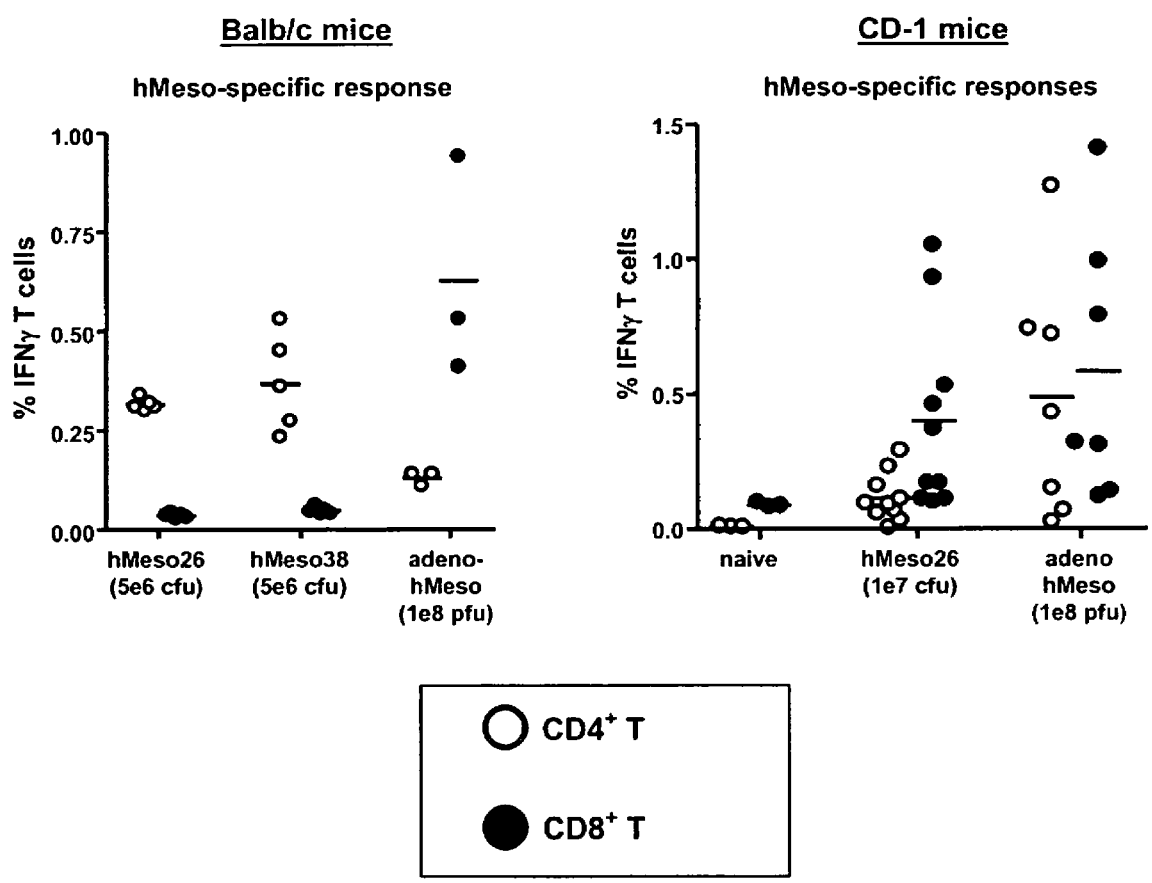
FIG. 37 discloses immune response after vaccination with various preparations of recombinant *Listeria*, and compares $CD4^+$ T cell and $CD8^+$ T cell responses.

FIG. 37 dissects mesothelin-specific immune response to *Listeria* strains hMeso26 and hMeso38 into CD4$^+$ T cell response and CD8$^+$ T cell response. Immune response was monitored by intracellular staining assays (ICS). Both strains of *Listeria* were tested with Balb/c mice, while only the hMeso26 *Listeria* strain was tested with CD-1 mice. The results demonstrate that the proportion of immune response that is CD4$^+$ T cell response, or CD8$^+$ T cell response, can differ in different strains of mice.

Figure 38:
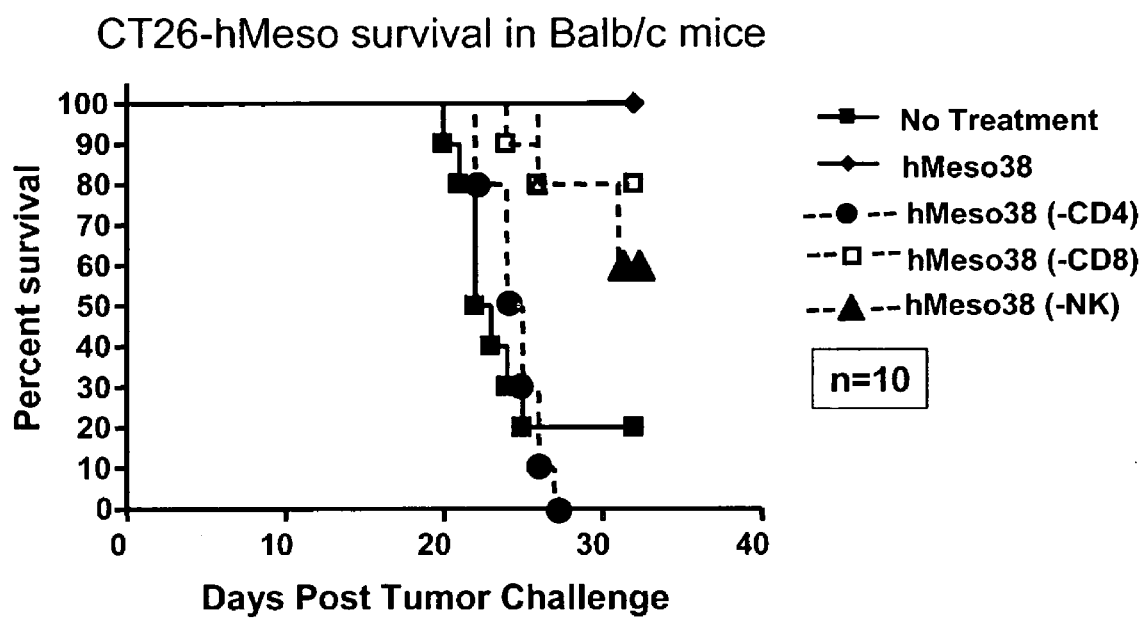
FIG. 38 reveals survival of tumor-bearing mice to the tumors after vaccination with various preparations of recombinant *Listeria*.
Figure 39:
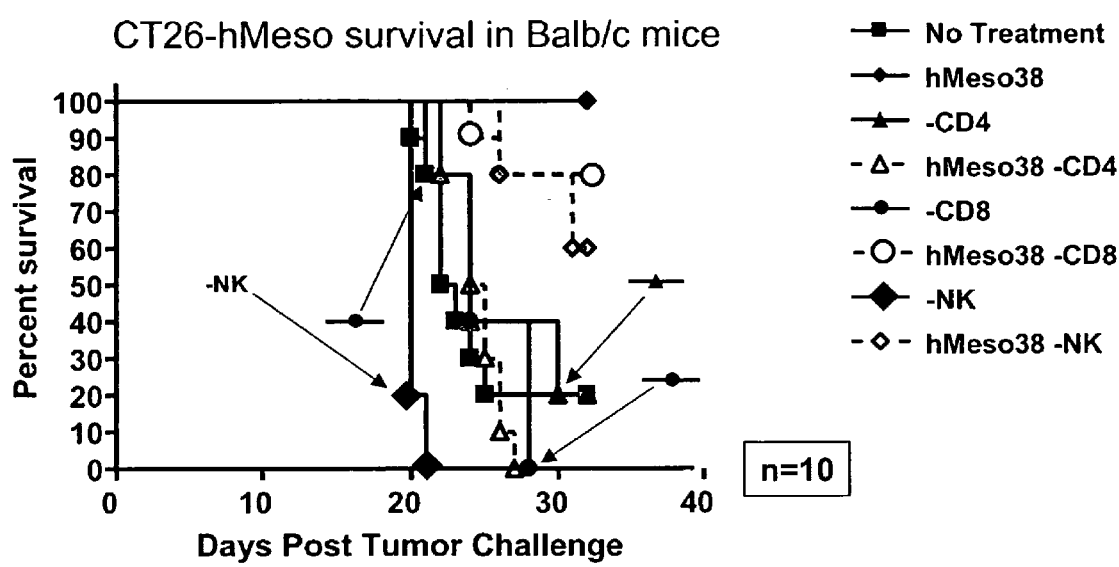
FIG. 39 further illustrates survival of tumor-bearing mice to the tumors after vaccination with various preparations of recombinant *Listeria*.

FIG. 38 demonstrates that hMeso38 increases survival to tumors, and dissects the contribution to survival by cells that are CD4+, CD8+, and NK cells. Mice were treated with antibodies that depleted one of CD4+ cells, CD8+ cells, or NK cells. Treating with the anti-CD8 antibodies resulted in only slight impairment of hMeso38-mediated increased survival. Treating with anti-NK cell antibodies resulted in moderate impairments of hMeso38-mediated increased survival. Treating with anti-CD4 antibodies resulted in a large impairment in hMeso38-medacated increased survival (FIG. 38). Antibody-mediated depletion of the mouse's cells were effected by administering antibodies on t=minus 8 days, minus 4 days, and on minus 1 days. At t=0 days, mice were injected (i.v.) with tumor cells. At t=3 days, mice were injected with *Listeria* vaccine (i.v.). Weekly antibody boosts were given to provoke depletion of the mouse's cells. FIG. 39 shows a similar experiment, but where only antibody was administered, where only hMeso38 was administered, or where both hMeso38 and the indicated antibody were administered.

The above-disclosed data are not intended to limit the present invention to embodiments comprising *L. monocytogenes* ΔActAΔinlB containing a nucleic acid encoding human mesothelin. The present invention provides other attenuated listerial vaccine platforms, e.g., KBMA *L. monocytogenes*, *L. monocytogenes* ΔinlB; *L. monocytogenes* ΔActA; *L. monocytogenes* Δhly; KBMA *L. monocytogenes* ΔinlB; KBMA *L. monocytogenes* ΔActA; KBMA *L. monocytogenes* ΔActAΔinlB; KBMA *L. monocytogenes* Δhly. Moreover, what is also provided are constructs encoding antigens other than, or in addition to, human mesothelin.

Example VIII

Nucleic Acids Encoding Phage Integrases, Phage Attachment Sites (attPP'), and Bacterial Attachment Sites (attBB')

Site-specific integration of a first nucleic acid into a polynucleotide can be mediated by a phage integrase, an attPP' site residing in the first nucleic acid, and a corresponding or compatible attBB' site residing in the polynucleotide. The present invention provides a number of nucleic acids, encoding phage integrases, attPP' sites, and attBB' sites, useful for mediating integration of a first nucleic acid into a polynucleotide, where the polynucleotide can be a plasmid or bacterial genome, to provide some non-limiting examples.

FIG. 40, FIG. 41, FIG. 42, FIG. 43, and FIG. 44, disclose the amino acid sequences of some of the phage integrases of the present invention. What is encompassed is polynucleotides encoding these phage integrases, nucleic acids that hybridize under stringent conditions to these polynucleotides where the nucleic acids encode functional phage integrases. Also encompassed are other polynucleotides that are bracketed by a pair of PCR primers, where the pair of PCR primers corresponds exactly to two positions of a polynucleotide encoding a phage integrase of the present invention.

Provided are nucleic acids encoding the following phage integrases, the phage integrase polypeptides, nucleic acids encoding relevant phage attachment sites (attPP') and nucleic acids encoding corresponding bacterial attachment sites (attBB'). The present invention encompasses the following integrases: (1) *L. innocua* 0071 integrase; (2) *L. innocua* 1231 integrase; (3) *L. innocua* 1765 integrase; (4) *L. innocua* 2610 integrase; and (5) *L. monocytogenes* f685_2703 integrase.

Identification of a nucleic acids encoding integrases, attPP' sites, and attBB' sites, was according to the following multi-step procedure. Candidate nucleic acid sequences were initially acquired, and homologies can be identified, using, e.g., the protein or nucleotide BLAST feature on the world wide web at ncbi.nlm.nih.gov, and using the completed microbial genomes feature on the world wide web at tigr.org.

Step 1. Novel phage integrase sequences were identified as follows. Nucleic acids of a known phage integrase were used to search for a similar sequence in a listerial genome, where the listerial genome harbors a prophage. The known phage integrases sequences used at this step of the search were those encoding PSA integrase and U153 integrase.

Step 2. Once a nucleic acid encoding a new phage integrase is identified, review the DNA 3-prime to the nucleic acid encoding the integrase for the appearance of an attachment site. The attachment site typically takes the form of a hybrid of the phage attachment site and the bacterial attachment site (attPB'). The attachment site takes the form of this hybrid because the phage has integrated itself into the listerial genome.

Step 3. Regions of the listerial genome containing a putative attPB' site were compared with the corresponding region of another listerial strain or listerial species, where this other listerial strain or species is not expected to contain an integrated phage. The crossover point (crossover point in between phage sequence and bacterial sequence in attPB') takes the form of a discontinuity. The crossover point can occur in an open reading frame or in an intergenic region.

Step 4. The sequence of nucleotides residing immediately downstream from (immediately 3-prime end of) the integrase gene, and upstream to the crossover point, is identified as phage-derived sequence, and constitutes "a first half" of the phage attachment site.

Step 5. The "second half" of the phage attachment site can be identified by reviewing the nucleic acid sequences residing upstream to (5-prime to) the integrase gene, comparing with the corresponding regions of a listerial strain or species expected not to contain any integrated phage (no integrated phage in the genomic region of interest), and identifying a region of discontinuity. The combination of the first half of the phage attachment site and the second half of the phage attachment site is attPP'.

Step 6. Phage attachment sites and bacterial attachment sites typically contain a region of identity, for example, of between three to 10, 20, 30, or more nucleotides. A region of identity can help in finding the general location of the phage attachment site and bacterial attachment site.

Step 7. Where the listerial species of interest is a species other than *L. monocytogenes*, e.g., *L. innocua*, the identified bacterial attachment site in the *L. innocua* genome can be used as a computer-probe to search the *L. monocytogenes* genome for homologous sequences. The result of this search of the *L. monocytogenes* genome where the result of the probe will be the bacterial attachment site (attBB').

Step 8. Where the region of identity is relatively long, e.g., 40-50 nucleotides, this region of identity can constitute the entire phage attachment site (attPP') and entire bacterial attachment site (attBB').

Most site-specific integrases are of the tyrosine recombinase family or serine recombinase family. About 100 phage-encoded integrase genes have been identified. These genes, encoded by the phage genome, can be found in the phage genome and/or also with a bacterial genome after integration of the phage into the bacterial genome.

The serine recombinases have a catalytic domain at the N-terminus, which includes a number of invariant residues, including Arg-8, Ser-10, and Arg-68. The N-terminal catalytic domain is followed by a region of about 220 amino acids, which contains at least ten conserved residues (including three cysteines). This region is followed by about 125 amino acids on non-conserved residues, by a 30-amino acid region rich in Leu, Ile, Val, and/or Met, and finally a C-terminal tail of 4-200 amino acids in length (see, e.g., Smith and Thorpe (2002) Mol. Microbiol. 44:299-307; Nunes-Darby, et al. (1998) Nucleic Acids Res. 26:391-406; Esposito and Scocca (1997) Nucleic Acids Res. 25:3605-3614).

Phage integrases of the tyrosine recombinase family can be identified by a conserved R-H-R-Y motif. The R-H-R-Y motif is a hallmark for the integrase family of recombinases. The histidine (H) can be substituted by arginine, lysine, asparagine, or tyrosine. In phage lambda integrase, for example, the amino acids of the R-H-R-Y motif occur at amino acids R212, H308, R311, and Y342 (see, e.g., GenBank Acc. No. P03700) (Nunes-Duby, et al., supra). Phage integrases are further identified by Box I (see, e.g., A202-G225 of phage lambda integrase), Box II (see, e.g., T306-D344 of phage lambda integrase), and by certain motifs occurring before or between Box I and Box II. Box II can include the consensus sequence LLGH (SEQ ID NO:137), where the glycine (G) can be replaced by A, S, or T (Nunes-Duby, et al., supra). In addition to the Box I motif and Box II motif, three "patches" of conserved sequences occur in prokaryotic integrases, such as phage integrases. Patch I is upstream of Box I, and has the consensus sequence LT-EEV-LL (SEQ ID NO:88). In phage lambda integrase, Patch I has the sequence LTADEYLKIY (SEQ ID NO:87) (amino acids 180-189 of GenBank Acc. No. P03700). Patch II is lysine (K235 of phage lambda integrase) flanked on both sides by serine, threonine, glycine, or methionine. In phage lambda integrase, Patch II occurs as SKT, while in Cre recombinase Patch II occurs as TKT, and in XerD recombinase it occurs as GKG. Patch III, which occurs between Boxes I and II, is $[D,E]-[F,Y,W,V,L,I,A]_{3-6}[S,T]$ (SEQ ID NOS:89, 138, 139, and 140). In phage lambda integrase, Patch III occurs at amino acids 269-274 (Nunes-Duby, et al., supra). In using a candidate phage integrase sequence as a query sequence, for comparison with established phage integrase sequences, it might be useful to introduce a gap or extension to bring Box I and Box II into alignment.

The conserved R-H-R-Y motif (Table 16) resides in the phage integrases of the present invention. The positions were determined by manual inspection. Esposito and Scocca provide additional conserved sequences within Box I (a.k.a. Box A) and Box II (a.k.a. Box B) (Esposito and Scocca (1997) Nucleic Acids Res. 25:3605-3614). Esposito and Scocca disclose that Arginine (in Box I (Box A) of the R-H-R-Y motif) resides in the following context: TGLRXTEL (SEQ ID NO:91), and that the histidine and the second arginine (in Box II (Box B) of the R-H-R-Y motif) reside in the following context: HXLRHAXATXLXXXG (SEQ ID NO:90). The histidine (H) and second arginine (R) of the R-H-R-Y motif is bolded and underlined. Sequences corresponding to these two contexts can readily be found, by manual inspection, in Boxes I and II of *L. innocua* 0071. Esposito and Scocca place the Tyrosine (Y) of the R-H-R-Y motif in a motif identified as Box C, where the Box C of Esposito and Scooca is: VXXX-LGHXXXXXTXXYXH (SEQ ID NO:92). The Y of the of R-H-R-Y motif is bolded and underlined. Inspection of the *L. innocua* 0071 integrase sequence demonstrates that the Box C consensus sequence resides in *L. innocua* 0071 integrase of the present invention.

Inspection reveals that Esposito and Scocca's Box B and Box C exists in *L. innocua* 1765 integrase of the present invention. Furthermore, inspection demonstrates that Esposito and Scocca's Box A resides in *L. innocua* 2601 integrase of the present invention. In addition, inspection of the *L. monocytogenes* f6854__2703 integrase sequence shows the occurrence of Box A, B, and C. Taken together, the consensus sequences of Nunes-Duby, et al., supra, and of Esposito and Scocca, supra, confirm the identified sequences as phage integrases. Inspection of PSA phage integrase sequence reveals motifs similar to Esposito and Scocca's Boxes A, B, and C.

*L. innocua* 1231 integrase of the present can be identified as a serine recombinase. Yang and Steitz disclosed a number of invariant motifs, and conservatively substituted motifs, of the serine recombinase family (Yang and Steitz (1995) Cell 82:193-207). The YxRVSTxxQ (SEQ ID NO:93) motif of Yang and Steitz occurs in *L. innocua* 1231 integrase. Also, the VLVxxLDRLxR (SEQ ID NO:141) motif of Yang and Steitz can be found in *L. innocua* 1231 integrase. Furthermore, Yang and Steitz's VAQAERxxxxERxxxG (SEQ ID NO:94) motif is found in *L. innocua* 1231 integrase of the present invention.

TABLE 16

| | Conserved R-H-R-Y motifs in phage integrases. | | | |
|---|---|---|---|---|
| | Arginine (R) | Histidine (H) | Arginine (R) | Tyrosine (Y) |
| *L. innocua* 0071 integrase. | 382 | 595 | 598 | 631 |
| *L. innocua* 1765 integrase. | 241 | 334 | 337 | 369 |
| *L.innocua* 2601 integrase (90.9% identical to PSA integrase). | 199 | 309 | 312 | 344 |
| *L. monocytogenes* nf6854_2703 integrase. | 204 | 328 | 331 | 364 |
| Lambda phage. GenBank Acc. No. P03700. | 212 | 308 | 311 | 342 |
| PSAphage. GenBank Acc. No. CAC85582. | 199 | 309 | 312 | 344 |
| *L. innocua* 0071 integrase. Coding sequence plus Shine Dalgarno and terminator. See, e.g., GenBank Acc. No. AL596163.1 (Segment 1/12). (SEQ ID NO: 95) | AggagggcttatLtATGGTAAAAAAAGTAAAAGGTAGGCGTTATGACGGTTCTATT GAACAACGTAGCAAAAATTCATGGCGTATGCGCGTGACTGTAGGCTATGACTACAA AGGTACGCCGATTCGAGCTGACAGAACGACGCGAACAAAAAATGAGAGGGAGCGAG GCAAGAATGACATTTAAAGCATTTGTTGAGAATGAGTATATGCCGAAACATGCACA AAATAACCTAGAAGTTAAAACCTCGACAGAATACTACAAATCTATAGTAGCAAGAG CTTACCCAGCCTTTGGCGGCGTTCAAATGGATAAAATAACTACACTTCATATAGTT AACTTAGTCGCAAAATTACAAAAGCCCGGCGCAAGATTAGATGTTAAACCTACAGA TTCAGACGAAAAGAAAAATAAGCCGCTTTCGCCGCGATCTATCAGAAATATTTATT TTGCGATAAATTCAGTATTTGAAACTGCGGTTGAGTGGAAAGTAATCCCAATTAAC CCCGCAGAGGGTGTAAGGCTTCCAAAAACAACTAAAAGACCGCCTACTATTTATAC TCCTGCTGAAATTGAATTGTTAAATGCAGCTCTAGTGAAAGAGCCACTTAGATTGC AAGTAATGATTTATATAGCGCTGATTTCAGGTTGTAGAGAAGCTGAATTAGCAGCA TTAGAAGTAAAACACGTGAACTTAATAGAAGATGAGCTAACATTCGAACAAACGCT AGTTGCAAAAGCAGGAGAAGGTTTACTTCTTAAAGAATCAACTAAGAATGATGTAG CTGGGATAGTTTCTATACCCGCTTGGTTAACTAATTTAATAGAAAACATATATAAGC AATGAAGTTTTAGACCTAAAAACTGAAGGGAAATGGGCCAATCACAAATTTTTATT CGCCGACATGGAAGGCAAACCGATTAGGCCTGATTCGATTTATCAGCGTTGGAAAC GATTTTTAGAAAGACACAACTTGCCGGTGATTCGTTTTCATGATTTGCGTCACACA TCTGCTACACTTTTATTGAACAAAGGTAGAGATATAAAAATTATCCAAGAGCGGCT TAGACATAAATCTAGTGTGACCACTTCAAACATTTATGCACATGTTTTGAAAGATA CGCACAAAGATGCAGCTAGCGATTTTGAGAACCCTTTTTAAgctttctgccccacc tctgccccacttaataaaaaaaggcaattttaaActAaaatttcacaaacaaaaaa ccgcttaaacgctttgtttaggcgg |
| Coding sequence only of integrase. *L. innocua* 0071. (SEQ ID NO: 96) | ATGGTAAAAAAAGTAAAAGGTAGGCGTTATGAGGGTTCTATTGAACAACGTAGCAA AAATTCATGGCGTATGCGCGTGACTGTAGGCTATGACTACAAAGGTACGCCGATTC GAGCTGACAGAACGACGCGAACAAAAAATGAGAGGGAGCGAGAAAGAGAGTTAAGA AATTTCATCACAGAATTAGAGCAAAATGGATATACAGCTCCTGCAAGAATGACATT TAAAGCATTTGTTGAGAATGAGTATATGCCGAAACATGCACAAAATAACCTAGAAG TTAAAACCTGGACAGAATACTACAAATCTATAGTAGCAAGAGCTTACCCAGCCTTT GGCGGCGTTCAAATGGATAAAATAACTACACTTCATATAGTTAACTTAGTCGCAAA ATTACAAAAGCCCGGCGCAAGATTAGATGTTAAACCTACAGATTCAGACGAAAAGA AAAATAAGCCGCTTTCGCCGCGATCTATCAGAAATATTTATTTTGCGATAAATTCA GTATTTGAAACTGCGGTTGAGTGGAAAGTAATCCCAATTAACCCCGCAGAGGGTGT AAGGCTTCCAAAAACAACTAAAAGACCGCCTACTATTTATACTCCTGCTGAAATTG AATTGTTAAATGCAGCTCTAGTGAAAGAGCCACTTAGATTGCAAGTAATGATTTAT ATAGCGCTGATTTCAGGTTGTAGAGAAGCTGAATTAGCAGCATTAGAAGTAAAACA CGTGAACTTAATAGAAGATGAGCTAACATTCGAACAAACGCTAGTTGCAAAAGCAG GAGAAGGTTTACTTCTTAAAGAATCAACTAAGAATGATGTAGCTGGGATAGTTTCT ATACCCGCTTGGTTAACTAATTTAATAGAAACATATATAAGCAATGAAGTTTTAGA CCTAAAAACTGAAGGGAAATGGGCCAATCACAAATTTTTATTCGCCGACATGGAAG GCAAACCGATTAGGCCTGATTCGATTTATCAGCGTTGGAAACGATTTTTAGAAAGA CACAACTTGCCGGTGATTCGTTTTCATGATTTGCGTCACACATCTGCTACACTTTT ATTGAACAAAGGTAGAGATATAAAAATTATCCAAGAGCGGCTTAGACATAAATCTA GTGTGACCACTTCAAACATTTATGCACATGTTTTGAAAGATACGCACAAAGATGCA GCTAGCGATTTTGACAACCCTTTTTAA |
| *L. innocua* 0071 integrase amino acid sequence. (SEQ ID NO: 97) | MVKKVKGRRYEGSIEQRSKNSWRNRVTVGYDYKGTPIRADRTTRTKNERERERELR HFITELEQNGYTAPARMTFKAFVENEYMPKHAQNNLEVKTWTEYYKSIVARAYPAF GGVQMDKITTLHIVNLVAKLQKPGARLDVKPTDSDEKKNKPLSPRSIRNIYFAINS VFETAVEWKVIPINPAEGVRLPKTTKRPPTIYTPAEIELLNAALVKEPLRLQVMIY IALISGCREAELAALEVKHVNLIEDELTFEQTLVAKAGEGLLLKESTKNDVAGIVS IPAWLTNLIETYISNEVLDLKTEGKWANHKFLFADMEGKPIRPDSIYQRWKRFLER HNLPVIRFHDLRHTSATLLLNKGRDIKIIQERLRHKSSVTTSNIYAHVLKDTHKDA ASDFENPF |

TABLE 16-continued

Conserved R-H-R-Y motifs in phage integrases.

| | Arginine (R) | Histidine (H) | Arginine (R) | Tyrosine (Y) |
|---|---|---|---|---|

*L. innocua* 0071. Bacterial attachment site (between *L. monocytogenes* f2365_0095 & *L. monocytogenes* f2365_0096, in the tRNA-lys gene (attachment site underlined). (SEQ ID NO: 98)

taccgaaaaatatagccgcagcgagtggctgcggctgtgttttatcgctgaattat
ggtataatattttttgtcggaatacgacaacgggttgttagctcagttggtagagC
agctgactcttaatcagcgggtcggggttcgaaaccctcacaacccataaaaaca
aacgccagtgactgttaaagtcgttggtgttttgtcgttttacgggcaaaatgtt
aataatttcaataataagctgatttctttttgattatttatcgattacatagaaaa
taagtggaatttcaaagtatctaataatttActAcatgatatacaaaaggagttgt
ttca

*L. innocua* 0071 phage attachment site. (Common sequence between phage and chromosome (attP and attB)). (SEQ ID NO: 99)

ACTCTTAATCAGCGGGTCGGGGGTTCGAAACCCTCACAACCCATA

*L. innocua* 1231 integrase nucleic acid sequence. *L. innocua* Clip 11262 complete genome GenBank Acc. No. AL596168.1 (segment 6/12 nucleotides 29,995 to 28,563). (SEQ ID NO: 100)

TggaggtgagaaagttcATGACTGTAGGGATTTATATAAGGGTTTCC
ACTGAAGAACAAGTGAAGGAACGCTTTTCTATATCAGCACAGAAAGA
GAAGTTAAAAGCATATTGCACAGCGCAAGGATGGGAAGATTTCAAGT
TTTACGTCGATGAAGGTAAATCAGCAAAAGATATGCACCGCCCTCTT
CTACAAGAAATGATTTCACATATAAAAAAAGGACTTATAGACACAGT
CCTAGTATATAAATTGGATCGTCTTACTAGGTCCGTTGTAGATTTGC
ATAATTTATTAAGTATATTTGATGAATTTAACTGTGCATTTAAAAGC
GCTACTGAAGTCTACGATACTTCTTCCGCTATCGGCAGATTTTTTAT
TACAATAATAAGTTCAGTTGCTCAATTTGAAAGAGAGAATACCTCTG
AACGAGTTAGCTTTGGGATGGCTGAGAAAGTGCGTCAAGGAGAATAT
ATTCCTCTCGCTCCCTTCGGTTATACTAAGGGGACTGACGGAAAACT
AATAGTAAATAAAATAGAAAAAGAAATATTTTTACAAGTAGTTGAAA
TGGTTTCAACCGGTTATTCTTTACGACAAACTTGTGAATATTTAACA
AATATTGGTTTGAAAACAAGGCGTTCAAATGATGTGTGGAAAGTATC
TACATTAATTTGGATGTTAAAAAAATCCTGCTGTCTACGGAGCGATAA
AATGGAATAATGAAATATATGAAAATACACATGAGCCTCTAATCGAT
AAGGCAACATTTAATAAAGTAGCCAAAATACTATCAATAAGAAGTAA
ATCAACAACAAGCCGTCGTGGACACGTTCATCACATTTTTAAAAATA
GATTAATTTGTCCAGCTTGTGGAAAAAAGATTATCTGGATTAAGAACA
AAATATATAAATAAAAAATAAGGAAACTTTTTATAACAATAACTATCG
TTGTGCTACCTGCAAAGAACATAGACGTCCAGCAGTACAGATAAGCG
AGCAAAAAATAGAGAAAGCATTTATTGATTATATTTCAAACTATACA
CTCAATAAAGCAAATATCTCTTCTAAAAAAATTAGATAATAATTTGAG
AAAACAAGAAATGATTCAAAAAGAAATTATTTCACTTCAAAGAAAAC
GTGAAAAGTTTCAGAAAGCATGGGCTGCTGACCTTATGAATGATGAT
GAATTTTCTAAATTAATGATTGATACAAAAATGGAGATTGATGCTGC
AGAAGATAGAAAAAAAGAATATGACGTATCATTATTTGTATCTCCTG
AAGATATTGCTAAAAGAAATAACATTCTTCGTGAACTAAAAAATAAAT
TGGACTTCATTATCTCCTACTGAAAAAACAGATTTTATAAGTATGTT
TATTGAAGGAATTGAATATGTAAAAGATGATGAAAATAAAGCGGTTA
TAACGAAAATAAGTTTTTTATAA

*L. innocua* 1231 integrase amino acid sequence. (SEQ ID NO: 101)

MTVGIYIRVSTEEQVKEGFSISAQKEKLKAYCTAQGWEDFKFYVDEGKSA
KDMHRPLLQEMISHIKKGLIDTVLVYKLDRLTRSVVDLHNLLSIFDEFNC
AFKSATEVYDTSSAMGRFFITIISSVAQFERENTSERVSFGMAEKVRQGE
YIPLAPFGYTKGTDGKLIVNKIEKEIFLQVVEMVSTGYSLRQTCEYLTNI
GLKTRRSNDVWKVSTLIWMLKNPAVYGAIKWNNEIYENTHEPLIDKATFN
KVAKILSIRSKSTTSRRGHVHHIFKNRLICPACGKRLSGLRTKYINKNKE
TFYNNNYRCATCKEHRRPAVQISEQKIEKAFIDYISNYTLNKANISSKKL
DNNLRKQEMIQKEIISLQRKREKFQKAWAADLMNDDEFSKLMIDTKMEID
AAEDRKKEYDVSLFVSPEDIAKRNNILRELKINWTSLSPTEKTDFISMFI
EGIEYVKDDENKAVITKISFL

*L. innocua* 1231 phage attachment site attPP'. This site resides in

Taaataattgtcagtcaatcaaaagaattatttataggtttttgtcaaata
Tggtgatgtgtacttataacccatttttcttgcaataaaagcttgtgttatt
ccccgttcta TABLE 16-continued Conserved R-H-R-Y motifs in phage integrases.

| | Arginine (R) | Histidine (H) | Arginine (R) | Tyrosine (Y) |
|---|---|---|---|---|

L. mono-cytogenes strain 4bF2365 (complement to 2495122 to 2495193), and is essentially the same as a sequence found in L. mono-cytogenes strain EGD (nt 145171 to 145423 of GenBank Acc. No. AL591983.1 segment 11/12). (SEQ ID NO: 102)

L. innocua 1231 attachment site attBB' within L. mono-cytogenes 1263: (SEQ ID NO: 103)
Ttcataaaagaatttcaaatcgcacattaaaatttcacttagaataa
Cagcattttttgtgtgatagtctaacagttcctttttcaatgttactg
Taacctgatgtgtacctatagcccatccgtcgcgcaatgaaagcttg
Ggtgattcctcgctgcaatcgtaattctcgaatttttgttgtattaa
ttcttctggtgtctactgttttcat L. innocua 1765 integrase. See also L. innocua Clip 11262 complete genome, segment 7/12 (nucleotide 210,321 to 211,089). (SEQ ID NO: 104)
AggatgaaagagaATGGCAAAGAACAAATGGCAACCCACTAAA
CATTTAGGAATTTATGAATACATGACTAAAAAAGGAAAGCGTT
ATGGGATACGAGTTCGTTATAAGCAAGGTAATGATTATCCTGA
AATAAATAAATCTGGTTTTGAGACAATTGCAGCTGCAAAAGTTT
ATAAAAACAACATTGAAAATTTGAAAGCTAATAAAAAAGAATAT
GTTTTTACAAATGAAAAATTAACATTAAATACTTGGTTTGCTTC
TTACATGGAAATGTTTAAAAAGAAAAACAAAAGTAAAGACACAA
TAGCGAATAAATATAGTATTTATAATAATCACTTAGAAATCCCT
TTTGGTAATTACTATTTAACTGATATAAGTTTAGATATTTACGA
AGACTTTTTGCGCGAAAAAATTAAAAATGGATACGCAAACAACT
CAGTCAAAGCGATGCATAAATTAATGAAAAGCATTTTAAACGCT
GCTGTTAGATATGAGAAACTAGAAAAAAACAGACTTCAATTTGC
TGAAATAGAGCAATTAGAAGAAAATGAAGTTATTGAGCTTAAGG
TATTAGAAACAGATGAGTTTAATGTATTTATATCAGCTTGTAGA
GCATTTTTTACTAAATATGATTTTACAATGATTTATCTTGCAGT
TTGGGGGATGCGTCGCGGTGAAGTTATGGGGGTAAAACTTAAAA
ATCTTACTTTTGATGATGCTAAACAACAAGTACGTATTACACTA
GATTCCACTCGAACCCTTCGTACTCCCGAGGGAAAAGGTACGAA
AACACCAGCTGGTAGAAGAATATTACTAATAGACGGCGAAGGTT
ATCGACTACTTAAATATTCGGTAGAAAAAAGCGGTTAGCATTGCT
AAAGACCATGGATCTGTTTTGCACCAGGATGATTTTATTTTTAG
AAACCCAACTTCTAATCGTCCTTGGGCGGTTACGCGTATGAATG
ATTTACTACGAAAATTAGAAAAAGAATACGACATAAAAGTTTAC
CCTCATCTATTACGCCATAACTTTAATACTCAGGCATTATTGGC
TGGAGCTAATAGCAATGATTTACGAAAATTTATTGGCCACAAAA
ACAGTAGCATGACTGATCATTATTCACATGCGACAGACGAGGGA
CGAGAAAAAATTAATGAATACGATGAAAGACAGATTGTCAGGAAT
CTAG L. innocua 1765 integrase amino acid sequence. (SEQ ID NO: 105)
MAKNKWQPTKHLGTYEYMTKKGKRYGIRVRYKQGNDYPEINKSGFETIAA
AKVYKNNIENLKANKKEYVFTNEKLTLNTWFASYMEMFKKKNKSKDTIAN
KSILNAAVRYEKLEKNRLQFAEIEQLEENEVIELKVLETDEFNVFISACR
AFFTKYDFTMIYLAVWGMRRGEVMGVKLKNLTFDDAKQQVRITLDSTRTL
RTPEGKGTKTPAGRRILLIDGEGYRLLKYSVEKAVSIAKDHGSVLHQDDF
IFRNPTSNRPWAVTRMNDLLRKLEKEYDIKVYPHLLRHNFNTQALLAGAN
SNDLRKFIGHKNSSMTDHYSHATDEGREKLMNTMKDRLSGI L. innocua 1765 Phage attachment site. (SEQ ID NO: 106)
Aaaattgtgggataaaaattaaatataaaaatatcccacaaa
Aaatcccacaatagtttgatattgtatgatattcaaatgaaa
Tcaaaaaaataaaaaccccgtatttcctaagaaaatacgggg
ttttgatatcatataaaatcaattaaaaattgac L. innocua 1765. bacterial attachment site. This sequence resides in L. monocytogenes EGDe (complete genome) GenBank Acc. No. AL591824 at nt 1,705,630 to nt 1,706,203. Similar sequences occur in L. mono-cytogenes strain 4bF2365 (nt 216008 to 216262
Tcttgttgcctccttttgtaatcaatagttgcaatgcaa
Gagtatcataaaaaagcgatgtataaccaaaaatgtaatg
aaatgtccgattcttgtcgtgaacgActAgaaaatggagc
ttatttagagatattcttacacaacgtgagtatcattaag
tttttttggtcataagataatactcattatgagttActAtt
cacattttaaacattcctgtttctatttatcacaaaaaat
acatatcaatccaagatatgcgttatttcacttatgaata
ttccttatttatttaattatttatcagtttttatttattac
taggtgaataatatagtataattattcacctacgacagac
gagacacgagaaaaattaatgaatacgatgaaagacagat
tgtcaggaatctagaaaattgtgggataaaaattaaatat
aaaaatatcccacaaaaatcccacaataatttgatattg
tatgatattcaaatgaaatcaaaaaatcaaaacccccgca
ttttcctaagaaaatacggggttttgatatcatataaaatc
gatttaaaatggac TABLE 16-continued Conserved R-H-R-Y motifs in phage integrases.

| | Arginine (R) | Histidine (H) | Arginine (R) | Tyrosine (Y) |
|---|---|---|---|---| of section 6) and
in *L. innocua*
Clip11262
nt 77369 to 77270.
(SEQ ID NO: 107)

*L. innocua* 2610.
Integrase gene from
*L. innocua*. The
present invention
also provides the
nucleic acid and
polypeptide
of *L. innocua*
Clip11262 complete
genome segment
11/12 GenBank
Acc. No.
AL596173.1
(nucleotides
14,676 to 15,804).
(SEQ ID NO: 108)

ATGAAAATAAAAAAAAATGAAAAATGGTAAATATACTGTTCGTTTGCGTAT
TAAAGTTGATGGAGAGTGGAAAGAAAAACGTTTGACAGATACAAGTGAAA
CAAATTTGATGTACAAAGCATCAAAATTATTAAAACAAGTTGAACATGAT
AGTAATTCACTAAAAGAATGGAATTTCAAAGAATTCTATTCGCTATTTAT
ACTTAGCTTATAATCAGTTCGTTAATTATTTCGACGAAAAAATAAAGTTA
AATTCAATTGACGCTGTTCAATATCAGCAATTTATTAATCATTTAGCATT
AGATTACGCTGTCGCTACTATAGATACCAGACACCGCAAAATTAGAGCGA
TTTTCAATAAAGCCGTCCATTTAGGTTACATGAAAAAAAACCCTGCTCTG
GGCGCTCACATAAGCGGTCATGATATAGCAAAAACAAAAGCGCAATATTT
AGAAACAGATAAAGTACATCTATTATTAGAAGAGCTTGCAAAACTTCATT
CTATATCAAGAGCAGTTATTTTTTTAGCAGTTCAAACAGGAATGCGATTT
GAAGAAATTATTGCACTGACAAAAAAAGATATTAATTTTACTAAACGTTC
TATATCAGTGAATAAGGCATGGGATTATAAATACACTAACACGTTTACGG
ACACTAAAACAAAAAAGTCACGAGTAATCTATATTGATAATTCAACTGTT
CAATATTTACAGTCTTACCTTGCTTGGCATGCTGATTATATGAAAGAGCA
TGCAATTGAAAATCCGGTGATGTTGTTATTCATTACTTATCACAATAAAC
CTGTTGACAACGCTTCATGTAACAAAGCACTGAAGAAAATATGTACTACA
ATTAATTCTGAAACAGTAACATTACACAAGCTTCGACACACGCACACAGG
TCTATGTGTAGAGGCTGGTATGGATATTATTTATGTAGCTGACAGGCTTG
GTCATGATGATATTAATACAACATTAAAATATTATAGTCATCTGAGTTCT
AATTTACGACAACAAAATCAATCTAAAGTAGATGCTTTTTTCACACTAAA
AACAGATGAAAATACCACAAAATTTGCCACAAATGCCACAAAAACAACGG
AA

*L. innocua* 2610
integrase,
amino acid
sequence (90.9%
identical to PSA
integrase).
(SEQ ID NO: 109)

MKIKKMKNGKYTVRLRIKVDGEWKEKRLTDTSETNLMYKASKLLKQVEHD
SNSLKEWNFKEFYSLFMKTFKENKSSQSTINLYDLAYNQFVNYFDEKIKL
NSIDAVQYQQFINHLALDYAVATIDTRHRKIRAIFNKAVHLGYMKKNPAL
GAHTSGHDIAKTKAQYLETDKVHLLLEELAKLHSISRAVIFLAVQTGMRF
EEIIALTKKDINFTKRSISVNKAWDYKYTNTFTDTKTKKSRVIYIDNSTV
QYLQSYLAWHADYMKEHAIENPVMLLFITYHNKPVDNASCNKALKKICTT
INSETVTLHKLRHTHTGLCVEAGMDIIYVADRLGHDDINTTLKYYSHLSS
NLRQQNQSKVDAFFTLKTDENTTKFATNATKTTE

*L. innocua* 2610.
This sequence is
an attBB site
from *L. innocua*.
Attachment site
(tRNA-Arg5 gene
plus surrounding
sequences,
integrates *Listeria
innocua* strain).
Core attachment
site in bold
(atgccctcggaggga).
(SEQ ID NO: 110)

Taaaacgggtattgcaaggtataaaaaaatctctaaaacattcgtttatc
CtttaatatcaaggatttccaacgttttagagatttctttacatcActAc
Ttaaatgccctcggagggaatcgaaccccccattttaagaaccggaatctta
Cgtgctatccgttgcaccacgagggctttatgtacaaagaaaatgtttac
Cgtacgaataataattatagcgaaattcgtatgtttttacaagctttatt
Ttgaatgaagaagccagcgcatcctgagatttgctggcttcaatagtta Core attachment site
(in bold).
(SEQ ID NO: 111)

atgccctcggaggga

This sequence is an
attBB' site from
*L. monocytogenes*
f2365. Attachment
site of
non-integrated
strain (*L. mono-
cytogenes* F2365;
attachment site in
tRNA-Arg5 gene
underlined. Core att
site is in BOLD
(atgccctcggaggga).
(SEQ ID NO:112)

Taaaatgaaaaaacatcttacaacatggcttttgccagatgtgggatgt
Ttttttagtatgccctcggagggaaatcgaaccccccattttaagaaccgg
Aatcttacgtgctatccgttgcaccacgagggctatatgtaggccagaa
Atgcttaccgtacgaataataattatagcgaaattcgtagtgttttaca
Agtttttattttaaatgaagaagccagcgcctccaaagatttgctggctc
aagtatta

*L. monocytogenes*
f6854_2703
integrase 2680803:
2681963 (Most of
this sequence is
available at
tigr.org).

ATGGCTAGCTATGTAAATTTAGGAAATAATAAATATGAGCTAAGAGTTT
CAAAGGGATATGATGCACGTGGAAAACAAATACGCAAAACAAAAAACGT
CACAGTTAAAACAGTAAAAGCGTTAAAACTAGAACTTTCTAATTTTGAA
GCTTATGTCTATTCAAGCGATTACACAGAAATAAAAGATATGCGATTTA
TTGACTTTGTGGAAAAATGGCGCTTAAATTACGCAAAAAGAGAACTAAA
AGGTAATACTATTCATAAGTATAACCTCTTTCTCGAAAACTGGATTATA
CCTTATTTTGAGAGGAAGAAAATAAGTAAAATTACAACTATGCAGTTGC

TABLE 16-continued

Conserved R-H-R-Y motifs in phage integrases.

| | Arginine (R) | Histidine (H) | Arginine (R) | Tyrosine (Y) |
|---|---|---|---|---|

| | |
|---|---|
| (SEQ ID NO:113) | TCGACTACTTTCATGAAGTTCAAAAAAAAGGAGTTGGTCCAAGCGCTTT<br>AGAGGGACATCATCGAGTTATAAGAAGTTTATTTAAATATGCTACCTTG<br>TGGGGAATTACTGAAACAGACGTATCTTTATCAGTGAAAAAACCTACCT<br>ATAAAGTGCCAGAAAAAAATATTTATAATAGACGAGAAATAGAAGTGTT<br>AATAGATCGCATTAAGATATTACAAAAATATCAACAAGTAATGATTAAA<br>TTAGCGCTATACTGCGGTCTTAGACGTGGCGAAGTTATCGGTTTAACAA<br>CTAAAGATATGAATTACAATAAAAATACAATTAACGTTTATAGAGCGGT<br>TATAAAGAGTGCTAGCGAAGGTATAAAACTAGATGAAACTAAAAATAAG<br>CGAAAAAGAATTGTCCCCGCTCCCGCTGGACTGATGCAAGAAATTAAAG<br>AACTTGCAAAAGAAAAGCAAAAAAACAAAGATAAATTAGGTTTGTTGTG<br>GAAAGGAACAAAAGATTTAGATGGGAAAACTGTTGTATTAATTTTCAGT<br>CATGACGACGGCACCCCCTTTACCCCCGCTTCTGTCACTAGAATGTTTA<br>ATCGATTTTTAGAGAAAGAAGAAAATAACGATCTTACTAAAATATCATT<br>TCATGATTTGCGTCATTCTGCTGCAAGCTTCCTTCTCGAACAAGGTATT<br>AATGTAAAAGTCATTCAAAACATTTTAGGACATTCAGACATTAAAGTTA<br>CATTAAATACGTATGCACATATCACTGAAGATGGTTACTCAGAAGCAGC<br>AAAAACTTTTGATAATTTCTATAAATCTAGTAAA |
| L. monocytogenes f6854_2703 integrase 2,680,803: 2,681,963. (SEQ ID NO:114) | MASYVNLGNNKYELRVSKGYDARGKQIRKTKNVTVKTVKALKLELSNFEA<br>YVVYSSDYTEIKDMRFIDFVEKWRLNYAKRELKGNTIDKYNLFLENWIIPY<br>FERKKISKITTMQLLDYFHEVQKKGVGPSALEGHHRVIRSLFKYATLWGI<br>TETDVSLSVKKPTYKVPEKNIYNRREIEVLIDRIKILQKYQQVMIKLALY<br>CGLRRGEVIGLTTKDMNYNKNTINVYRAVIKSASEGIKLDETKNKRKRIV<br>PAPAGLMQEIKELAKEKQKNKDKLGLLWKGTKDLDGKTVVLIFSHDDGTP<br>FTPASVTRMFNRFLEKEENNDLTKISFHDLRHSAASFLLEQGINVKVIQN<br>ILGHSDIKVTLNTYAHITEDGYSEAAKTFDNFYKSSK |
| L. monocytogenes f6854_2703. Phage attachment site. (SEQ ID NO:115) | TaaggtgtcgaataaggtgttttgctattttaggcaaataaAaaaagc<br>Ttcgcatattagcgaaacacctacagcaccaacgttttatattaagcca<br>Cttgtcggatttgaaccgacgacccctccttaccatggaagtgctcta<br>Ccaactgagctaaagcggcagcaaagcctttcaaataaaaaaatggctc<br>Cacaggcaggactcgaacctgcgaccgatcggttaacagccgattgctc<br>Taccaactgagctactgtggaataataaattgcccggcagcgacctact<br>CtcgcaggggaagcccccaActAccattggcgcagagaagcttaActA<br>CcgtgttcgggatgggaacgggtgtgaccttctcgccataActAccaga<br>CaatattgagttgttgaaagattgctctctcaaaActAgagaagaaagt<br>Gttcagttaggtaacttcgtttcattttttggttaagtcctcgatcgat<br>Tagtatttgtccgctccatgtatcgctacacttccactccaaacctatc<br>Tacctgatcatctttcagggatcttactttccgaagaaatgggaaatct<br>Catcttgagggggcttcacgcttagatgctttcagcgtttatccctgc<br>Cacacatagctacccagcgatgctcctggcggaacaactggtacaccag<br>CggtgtgtccatcccggtcctctcgtActAaggacagctcctctcaaat<br>Ttcctgcgcccgcgacggataggggaccgaactgtctcacgacgttctga<br>Acccagctcgcgtgccgctttaatgggcgaacagcccaacccttgggac<br>CgActAca |
| Phage attachment site (attPP'). Phi6854.3 attachment site is within the tRNA-Thr-4 gene Phage attachment site highlighted in bold and underlined, and is annotated as a phage attachment site in the F2365 genome (Nelson, et al. (2004) Nucleic Acids Res. 332:2386-2395). (SEQ ID NO:116) | AaaaacaccccacccgttctgttattatacccatagtataatcGatttatActAc<br>CtAttcaagatatccataataaatatcattattCttttaaacaatAaaaaaagcct<br>cgcAtActAgcgaaacatAcaaattatccatatattat<br>ttaagccacttgtcggatttgaaccgacgacccttccttaccatggaag<br>tgctctaccaactgagCtaaagcggcagcaaagcctttcaaataaaaaaatgg<br>ctccacaggcaggactCgaacctgcgaCcGatcggttaacagccgattgct<br>ctaccaactgagctactgtGgaataataaattgcccggcagcgacctactctcg<br>caggggaagcccccaActAccattggcgcagagaagcttaa |
| Phage (attPP') Phi6854.3 attachment site | AaaaacaccccacccgttctgttattatacccatagtataatcGatttat<br>ActAcctAttCaagatatccataataaatatcattattCttttaaacaatA<br>aaaaaagcctcgcAtActAgcgaaacatAcaaattatccatatattattta |
| (same as above) is | <div style="border:1px solid black;padding:2px">agccacttgtcggatttgaaccgacgacccttccttaccatggaagtgctctaccaact</div> |
| within the tRNA-Thr-4 gene, where the tRNA-Thr-4 gene is shown outlined in a box. | gagCtaaagcggcagcaaagcctttcaaataaaaaaatggctccacaggcaggact<br>CgaacctgcgaCcGatcggttaacagccgattgctctaccaactgagctactgt<br>Ggaataataaattgcccggcagcgacctactctcgcaggggaagcccccaact<br>Accattggcgcagagaagcttaa |

TABLE 16-continued

Conserved R-H-R-Y motifs in phage integrases.

| | Arginine (R) | Histidine (H) | Arginine (R) | Tyrosine (Y) |
|---|---|---|---|---|

(SEQ ID NO:117)
Bacterial (attBB')
Phi6854.3
attachment site is within the tRNA- Thr-4 gene
Phage attachment
site highlighted in
bold and
underlined, and is
annotated as a
phage attachment
site in the F2365
genome (Nelson, et
al., supra). tRNA
Thr-4 gene is outlined.

Aaaaacaccccacccgttctgttattatacccatagtataatcgatttat
ActAcctattcaagatatccataataaatatcattattcttttaaacaata
aaaaaagcctcgcatActAgcgaaacatacaaattatccatatattat ttaagccacttgtcggatttgaaccgacgaccccttccttaccatggaagtgctctaccaact gagctaaagcggcagcaaagcctttcaaataaaaaaatggctccacaggcaggactcgaacct
gcgaccgatcggttaacagccgattgctctaccaactgagctactgtggaataataaattgcc
cggcagcgacctactctcgcaggggggaagcccccaActAccattggcgcagagaagcttaa (SEQ ID NO:118)

Nucleic acid sequences can be found on the world wide web at tigr.org and, clicking:
(1) Comprehensive microbial resources;
(2) Searches;
(3) CMR BLAST; and
(4) inputting a listerial integrase sequence as a query sequence.
If an accession number is known, a sequence can be found on the world wide web at tigr.org, by clicking:
(1) Comprehensive microbial resource;
(2) Genomes;
(3) *Listeria monocyto* genes 1/2a F6854;
(4) Searches;
(5) Locus;
(6) typing "LMOf6854_2703" in the box; and
(7) clicking at TIGR sequences on the sidebar.

A phage attachment site (attPP') or bacterial attachment site (attBB') of the present invention can be implanted into a polynucleotide by way of site-specific recombination, homologous recombination, by use of restriction sites, by methods of synthetic organic chemistry, or by other methods. In particular, where homologous recombination is used, an attBB' site can be implanted into a virulence gene, where integration results in a simple insertion or, alternatively, in insertion with deletion of a corresponding region of the virulence gene.

Thus, the present invention provides methods for implanting a phage attachment site (attPP') into a plasmid. Provided are methods for implanting a bacterial attachment site (attBB') into a plasmid, as well as downstream methods where the plasmid can later be used to transfer the attBB' into a bacterial genome. In one aspect, the plasmid contains a first nucleic acid encoding an attPP' site and a second nucleic acid encoding a heterologous antigen. In this case, the invention contemplates methods for incorporating the second nucleic acid into an attBB' site residing in a target polynucleotide, where the target polynucleotide can be a bacterial genome.

The target polynucleotide of site-specific recombination, homologous recombination, or engineering by using restriction sites, is not to be limited to virulence genes, but also encompasses without limitation any polynucleotide, plasmid, episome, extrachromosomal element, bacterial genome, listerial genome, genome of *Bacillus anthracis*, or genome of *Francisella tularensis*.

The present invention encompasses a nucleic acid encoding a phage integrase, an attPP' site, or an attBB' site, where the nucleic acid can hybridize under stringent condition to one of the nucleic acids claimed as part of the present invention, that is, to one of the nucleic acids encoding a phage integrase, attPP' site, or attBB site, and where the hybridizing polynucleotide can encode a functional phage integrase, attPP' site, or attBB' site.

Also encompassed is a nucleic acid derived from a polymerase chain reaction (PCR), where the pair of PCR primers matches exactly and brackets a functional region of one of the nucleic acids of the present invention, disclosed herein, encoding a phage integrase, attPP' site, or attBB site. The PCR reaction can be carried out in silico. The present invention encompasses a nucleic acid derived from the PCR reaction, where the nucleic acid encodes a functional phage integrase, attPP' site, or attBB' site. The PCR primers can be designed to bracket the entire nucleic acid encoding the phage integrase, attPP' site, or attBB' site, disclosed herein, or they can be designed to bracket a shorter, functionally active, part of the nucleic acid.

Many modifications and variations of this invention, as will be apparent to one of ordinary skill in the art, can be made to adapt to a particular situation, material, composition of matter, process, process step or steps, to preserve the objective, spirit, and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of the equivalents to which such claims are entitled; and the invention is not to be limited by the specific embodiments that have been presented herein by way of example.

SEQUENCE LISTING

<160> NUMBER OF SEQ ID NOS: 141

<210> SEQ ID NO 1
<211> LENGTH: 452
<212> TYPE: PRT
<213> ORGANISM: Bacteriophage U153
<220> FEATURE:
<221> NAME/KEY: VARIANT
<222> LOCATION: 142
<223> OTHER INFORMATION: Xaa = Any Amino Acid

<400> SEQUENCE: 1

```
Met Lys Ala Ala Ile Tyr Ile Arg Val Ser Thr Gln Glu Gln Ile Glu
  1               5                  10                  15

Asn Tyr Ser Ile Gln Ala Gln Thr Glu Lys Leu Thr Ala Leu Cys Arg
             20                  25                  30

Ser Lys Asp Trp Asp Val Tyr Asp Ile Phe Ile Asp Gly Gly Tyr Ser
         35                  40                  45

Gly Ser Asn Met Asn Arg Pro Ala Leu Asn Glu Met Leu Ser Lys Leu
     50                  55                  60

His Glu Ile Asp Ala Val Val Val Tyr Arg Leu Asp Arg Leu Ser Arg
 65                  70                  75                  80

Ser Gln Arg Asp Thr Ile Thr Leu Ile Glu Gly Tyr Phe Leu Lys Asn
                 85                  90                  95

Asn Val Glu Phe Val Ser Leu Ser Glu Thr Leu Asp Thr Ser Ser Pro
            100                 105                 110

Phe Gly Arg Ala Met Ile Gly Ile Leu Ser Val Phe Ala Gln Leu Glu
        115                 120                 125

Arg Glu Thr Ile Arg Asp Arg Met Val Met Gly Lys Ile Xaa Arg Ile
    130                 135                 140

Glu Ala Gly Leu Pro Leu Thr Thr Ala Lys Gly Arg Thr Phe Gly Tyr
145                 150                 155                 160

Asp Val Ile Asp Thr Lys Leu Tyr Ile Asn Glu Glu Glu Ala Lys Gln
                165                 170                 175

Leu Gln Met Ile Tyr Asp Ile Phe Glu Glu Lys Ser Ile Thr Thr
            180                 185                 190

Leu Gln Lys Arg Leu Lys Lys Leu Gly Phe Lys Val Lys Ser Tyr Ser
        195                 200                 205

Ser Tyr Asn Asn Trp Leu Thr Asn Asp Leu Tyr Cys Gly Tyr Val Ser
    210                 215                 220

Tyr Ala Asp Lys Val His Thr Lys Gly Val His Glu Pro Ile Ile Ser
225                 230                 235                 240

Glu Glu Gln Phe Tyr Arg Val Gln Glu Ile Phe Ser Arg Met Gly Lys
                245                 250                 255

Asn Pro Asn Met Asn Arg Asp Ser Ala Ser Leu Leu Asn Asn Leu Val
            260                 265                 270

Val Cys Gly Lys Cys Gly Leu Gly Phe Val His Arg Arg Lys Asp Thr
        275                 280                 285

Val Ser Arg Gly Lys Lys Tyr His Tyr Arg Tyr Tyr Ser Cys Lys Thr
    290                 295                 300

Tyr Lys His Thr His Glu Leu Glu Lys Cys Gly Asn Lys Ile Trp Arg
305                 310                 315                 320

Ala Asp Lys Leu Glu Glu Leu Ile Ile Asp Arg Val Asn Asn Tyr Ser
                325                 330                 335

Phe Ala Ser Arg Asn Val Asp Lys Glu Asp Glu Leu Asp Ser Leu Asn
```

```
              340             345             350
Glu Lys Leu Lys Thr Glu His Val Lys Lys Arg Leu Phe Asp Leu
            355             360             365

Tyr Ile Ser Gly Ser Tyr Glu Val Ser Glu Leu Asp Ala Met Met Ala
370             375             380

Asp Ile Asp Ala Gln Ile Asn Tyr Tyr Glu Ala Gln Ile Glu Ala Asn
385             390             395             400

Glu Glu Leu Lys Lys Asn Lys Lys Ile Gln Glu Asn Leu Ala Asp Leu
            405             410             415

Ala Thr Val Asp Phe Asp Ser Leu Glu Phe Arg Glu Lys Gln Leu Tyr
            420             425             430

Leu Lys Ser Leu Ile Asn Lys Ile Tyr Ile Asp Gly Glu Gln Val Thr
            435             440             445

Ile Glu Trp Leu
    450

<210> SEQ ID NO 2
<211> LENGTH: 471
<212> TYPE: PRT
<213> ORGANISM: Listeria innocua

<400> SEQUENCE: 2

Met Thr Val Gly Ile Tyr Ile Arg Val Ser Thr Glu Glu Gln Val Lys
1               5               10              15

Glu Gly Phe Ser Ile Ser Ala Gln Lys Glu Lys Leu Lys Ala Tyr Cys
            20              25              30

Thr Ala Gln Gly Trp Glu Asp Phe Lys Phe Tyr Val Asp Glu Gly Lys
        35              40              45

Ser Ala Lys Asp Met His Arg Pro Leu Leu Gln Glu Met Ile Ser His
    50              55              60

Ile Lys Lys Gly Leu Ile Asp Thr Val Leu Val Tyr Lys Leu Asp Arg
65              70              75              80

Leu Thr Arg Ser Val Val Asp Leu His Asn Leu Leu Ser Ile Phe Asp
            85              90              95

Glu Phe Asn Cys Ala Phe Lys Ser Ala Thr Glu Val Tyr Asp Thr Ser
            100             105             110

Ser Ala Met Gly Arg Phe Phe Ile Thr Ile Ile Ser Ser Val Ala Gln
            115             120             125

Phe Glu Arg Glu Asn Thr Ser Glu Arg Val Ser Phe Gly Met Ala Glu
130             135             140

Lys Val Arg Gln Gly Glu Tyr Ile Pro Leu Ala Pro Phe Gly Tyr Thr
145             150             155             160

Lys Gly Thr Asp Gly Lys Leu Ile Val Asn Lys Ile Glu Lys Glu Ile
            165             170             175

Phe Leu Gln Val Val Glu Met Val Ser Thr Gly Tyr Ser Leu Arg Gln
            180             185             190

Thr Cys Glu Tyr Leu Thr Asn Ile Gly Leu Lys Thr Arg Arg Ser Asn
            195             200             205

Asp Val Trp Lys Val Ser Thr Leu Ile Trp Met Leu Lys Asn Pro Ala
    210             215             220

Val Tyr Gly Ala Ile Lys Trp Asn Asn Glu Ile Tyr Glu Asn Thr His
225             230             235             240

Glu Pro Leu Ile Asp Lys Ala Thr Phe Asn Lys Val Ala Lys Ile Leu
            245             250             255

Ser Ile Arg Ser Lys Ser Thr Thr Ser Arg Arg Gly His Val His His
```

```
                260             265             270
Ile Phe Lys Asn Arg Leu Ile Cys Pro Ala Cys Gly Lys Arg Leu Ser
            275             280             285
Gly Leu Arg Thr Lys Tyr Ile Asn Lys Asn Lys Glu Thr Phe Tyr Asn
        290             295             300
Asn Asn Tyr Arg Cys Ala Thr Cys Lys Glu His Arg Arg Pro Ala Val
305             310             315             320
Gln Ile Ser Glu Gln Lys Ile Glu Lys Ala Phe Ile Asp Tyr Ile Ser
                325             330             335
Asn Tyr Thr Leu Asn Lys Ala Asn Ile Ser Ser Lys Lys Leu Asp Asn
            340             345             350
Asn Leu Arg Lys Gln Glu Met Ile Gln Lys Glu Ile Ile Ser Leu Gln
        355             360             365
Arg Lys Arg Glu Lys Phe Gln Lys Ala Trp Ala Ala Asp Leu Met Asn
    370             375             380
Asp Asp Glu Phe Ser Lys Leu Met Ile Asp Thr Lys Met Glu Ile Asp
385             390             395             400
Ala Ala Glu Asp Arg Lys Lys Glu Tyr Asp Val Ser Leu Phe Val Ser
                405             410             415
Pro Glu Asp Ile Ala Lys Arg Asn Asn Ile Leu Arg Glu Leu Lys Ile
            420             425             430
Asn Trp Thr Ser Leu Ser Pro Thr Glu Lys Thr Asp Phe Ile Ser Met
        435             440             445
Phe Ile Glu Gly Ile Glu Tyr Val Lys Asp Asp Glu Asn Lys Ala Val
    450             455             460
Ile Thr Lys Ile Ser Phe Leu
465             470

<210> SEQ ID NO 3
<211> LENGTH: 434
<212> TYPE: PRT
<213> ORGANISM: Bacteriophage PSA

<400> SEQUENCE: 3

Met Lys Ile Lys Lys Leu Ala Asn Gly Lys Tyr Cys Val Arg Leu Arg
1               5                   10                  15
Ile Lys Val Asp Gly Glu Trp Lys Glu Lys Arg Leu Thr Asp Thr Ser
            20                  25                  30
Glu Thr Asn Leu Met Tyr Lys Ala Ser Lys Leu Leu Lys Gln Val Gln
        35                  40                  45
His Asp Ser Ser Ser Leu Lys Glu Trp Asn Phe Lys Glu Phe Tyr Thr
    50                  55                  60
Leu Phe Met Lys Thr Phe Lys Asp Gly Lys Ser Ser Gln Ser Thr Ile
65                  70                  75                  80
Asn Leu Tyr Asp Leu Ala Tyr Asn Gln Phe Val Asp Tyr Phe Asp Glu
                85                  90                  95
Lys Ile Lys Leu Asn Ser Ile Asp Ala Val Gln Tyr Gln Gln Phe Ile
            100                 105                 110
Asn His Leu Ser Val Asp Tyr Ala Ile Ser Thr Val Asp Thr Arg His
        115                 120                 125
Arg Lys Ile Arg Ala Ile Phe Asn Lys Ala Val His Leu Gly Tyr Met
    130                 135                 140
Lys Lys Asn Pro Thr Ile Gly Ala His Ile Ser Gly Gln Asp Val Ala
145                 150                 155                 160
Lys Asn Lys Ala Gln Phe Met Glu Thr Asp Lys Val His Leu Leu Leu
```

```
                     165                 170                 175
Glu Glu Leu Ala Lys Phe His Ser Ile Ser Arg Ala Val Ile Phe Leu
            180                 185                 190

Ala Val Gln Thr Gly Met Arg Phe Glu Glu Ile Ile Ala Leu Thr Lys
        195                 200                 205

Lys Asp Ile Asn Phe Thr Lys Arg Ser Ile Thr Val Asn Lys Ala Trp
    210                 215                 220

Asp Tyr Lys Tyr Thr Asn Thr Phe Ile Asp Thr Lys Thr Lys Lys Ser
225                 230                 235                 240

Arg Val Ile Tyr Ile Asp Asn Ser Thr Ala Gln Tyr Leu His Ser Tyr
                245                 250                 255

Leu Asn Trp His Thr Asp Tyr Met Lys Glu His Ala Ile Lys Asn Pro
            260                 265                 270

Leu Met Leu Leu Phe Ile Thr Tyr His Asn Lys Pro Val Asp Asn Ala
        275                 280                 285

Ser Cys Asn Lys Ala Leu Lys Lys Ile Cys Ser Thr Ile Asn Ser Glu
    290                 295                 300

Pro Val Thr Leu His Lys Leu Arg His Thr His Thr Gly Leu Cys Val
305                 310                 315                 320

Glu Ala Gly Met Asp Ile Ile Tyr Val Ala Asp Arg Leu Gly His Asp
                325                 330                 335

Asp Ile Asn Thr Thr Leu Lys Tyr Tyr Ser His Leu Ser Asn Leu
            340                 345                 350

Arg Gln His Asn Gln Ser Lys Val Asp Arg His Thr His Thr Gly Leu
        355                 360                 365

Cys Val Glu Ala Gly Met Asp Ile Ile Tyr Val Ala Asp Arg Leu Gly
    370                 375                 380

His Asp Asp Ile Asn Thr Thr Leu Lys Tyr Tyr Ser His Leu Ser Ser
385                 390                 395                 400

Asn Leu Arg Gln His Asn Gln Ser Lys Val Asp Ala Phe Phe Thr Leu
                405                 410                 415

Lys Thr Asp Glu Asn Thr Thr Asn Phe Thr Thr Asn Ala Thr Lys Thr
            420                 425                 430

Thr Glu

<210> SEQ ID NO 4
<211> LENGTH: 400
<212> TYPE: PRT
<213> ORGANISM: Listeria innocua

<400> SEQUENCE: 4

Met Val Lys Lys Val Lys Gly Arg Arg Tyr Glu Gly Ser Ile Glu Gln
1               5                   10                  15

Arg Ser Lys Asn Ser Trp Arg Met Arg Val Thr Val Gly Tyr Asp Tyr
            20                  25                  30

Lys Gly Thr Pro Ile Arg Ala Asp Arg Thr Thr Arg Thr Lys Asn Glu
        35                  40                  45

Arg Glu Arg Glu Arg Glu Leu Arg Asn Phe Ile Thr Glu Leu Glu Gln
    50                  55                  60

Asn Gly Tyr Thr Ala Pro Ala Arg Met Thr Phe Lys Ala Phe Val Glu
65                  70                  75                  80

Asn Glu Tyr Met Pro Lys His Ala Gln Asn Asn Leu Glu Val Lys Thr
                85                  90                  95

Trp Thr Glu Tyr Tyr Lys Ser Ile Val Ala Arg Ala Tyr Pro Ala Phe
            100                 105                 110
```

```
Gly Gly Val Gln Met Asp Lys Ile Thr Thr Leu His Ile Val Asn Leu
            115                 120                 125

Val Ala Lys Leu Gln Lys Pro Gly Ala Arg Leu Asp Val Lys Pro Thr
    130                 135                 140

Asp Ser Asp Glu Lys Lys Asn Lys Pro Leu Ser Pro Arg Ser Ile Arg
145                 150                 155                 160

Asn Ile Tyr Phe Ala Ile Asn Ser Val Phe Glu Thr Ala Val Glu Trp
                165                 170                 175

Lys Val Ile Pro Ile Asn Pro Ala Glu Gly Val Arg Leu Pro Lys Thr
            180                 185                 190

Thr Lys Arg Pro Pro Thr Ile Tyr Thr Pro Ala Glu Ile Glu Leu Leu
    195                 200                 205

Asn Ala Ala Leu Val Lys Glu Pro Leu Arg Leu Gln Val Met Ile Tyr
    210                 215                 220

Ile Ala Leu Ile Ser Gly Cys Arg Glu Ala Glu Leu Ala Ala Leu Glu
225                 230                 235                 240

Val Lys His Val Asn Leu Ile Glu Asp Glu Leu Thr Phe Glu Gln Thr
                245                 250                 255

Leu Val Ala Lys Ala Gly Glu Gly Leu Leu Lys Glu Ser Thr Lys
            260                 265                 270

Asn Asp Val Ala Gly Ile Val Ser Ile Pro Ala Trp Leu Thr Asn Leu
    275                 280                 285

Ile Glu Thr Tyr Ile Ser Asn Glu Val Leu Asp Leu Lys Thr Glu Gly
    290                 295                 300

Lys Trp Ala Asn His Lys Phe Leu Phe Ala Asp Met Glu Gly Lys Pro
305                 310                 315                 320

Ile Arg Pro Asp Ser Ile Tyr Gln Arg Trp Lys Arg Phe Leu Glu Arg
                325                 330                 335

His Asn Leu Pro Val Ile Arg Phe His Asp Leu Arg His Thr Ser Ala
            340                 345                 350

Thr Leu Leu Leu Asn Lys Gly Arg Asp Ile Lys Ile Gln Glu Arg
    355                 360                 365

Leu Arg His Lys Ser Ser Val Thr Thr Ser Asn Ile Tyr Ala His Val
    370                 375                 380

Leu Lys Asp Thr His Lys Asp Ala Ala Ser Asp Phe Glu Asn Pro Phe
385                 390                 395                 400

<210> SEQ ID NO 5
<211> LENGTH: 434
<212> TYPE: PRT
<213> ORGANISM: Bacteriophage PSA

<400> SEQUENCE: 5

Met Lys Ile Lys Lys Leu Ala Asn Gly Lys Tyr Cys Val Arg Leu Arg
 1               5                  10                  15

Ile Lys Val Asp Gly Glu Trp Lys Glu Lys Arg Leu Thr Asp Thr Ser
            20                  25                  30

Glu Thr Asn Leu Met Tyr Lys Ala Ser Lys Leu Leu Lys Gln Val Gln
        35                  40                  45

His Asp Ser Ser Ser Leu Lys Glu Trp Asn Phe Lys Glu Phe Tyr Thr
50                  55                  60

Leu Phe Met Lys Thr Phe Lys Asp Gly Lys Ser Ser Gln Ser Thr Ile
65                  70                  75                  80

Asn Leu Tyr Asp Leu Ala Tyr Asn Gln Phe Val Asp Tyr Phe Asp Glu
                85                  90                  95
```

```
Lys Ile Lys Leu Asn Ser Ile Asp Ala Val Gln Tyr Gln Gln Phe Ile
            100                 105                 110

Asn His Leu Ser Val Asp Tyr Ala Ile Ser Thr Val Asp Thr Arg His
            115                 120                 125

Arg Lys Ile Arg Ala Ile Phe Asn Lys Ala Val His Leu Gly Tyr Met
130             135                 140

Lys Lys Asn Pro Thr Ile Gly Ala His Ile Ser Gly Gln Asp Val Ala
145             150                 155                 160

Lys Asn Lys Ala Gln Phe Met Glu Thr Asp Lys Val His Leu Leu Leu
                165                 170                 175

Glu Glu Leu Ala Lys Phe His Ser Ile Ser Arg Ala Val Ile Phe Leu
            180                 185                 190

Ala Val Gln Thr Gly Met Arg Phe Glu Glu Ile Ile Ala Leu Thr Lys
            195                 200                 205

Lys Asp Ile Asn Phe Thr Lys Arg Ser Ile Thr Val Asn Lys Ala Trp
210             215                 220

Asp Tyr Lys Tyr Thr Asn Thr Phe Ile Asp Thr Lys Thr Lys Lys Ser
225             230                 235                 240

Arg Val Ile Tyr Ile Asp Asn Ser Thr Ala Gln Tyr Leu His Ser Tyr
                245                 250                 255

Leu Asn Trp His Thr Asp Tyr Met Lys Glu His Ala Ile Lys Asn Pro
            260                 265                 270

Leu Met Leu Leu Phe Ile Thr Tyr His Asn Lys Pro Val Asp Asn Ala
            275                 280                 285

Ser Cys Asn Lys Ala Leu Lys Lys Ile Cys Ser Thr Ile Asn Ser Glu
            290                 295                 300

Pro Val Thr Leu His Lys Leu Arg His Thr His Thr Gly Leu Cys Val
305             310                 315                 320

Glu Ala Gly Met Leu Leu Phe Ile Thr Tyr His Asn Lys Pro Val Asp
                325                 330                 335

Asn Ala Ser Cys Asn Lys Ala Leu Lys Lys Ile Cys Ser Thr Ile Asn
            340                 345                 350

Ser Glu Pro Val Thr Leu His Lys Leu Arg His Thr His Thr Gly Leu
            355                 360                 365

Cys Val Glu Ala Gly Met Asp Ile Ile Tyr Val Ala Asp Arg Leu Gly
370             375                 380

His Asp Asp Ile Asn Thr Thr Leu Lys Tyr Tyr Ser His Leu Ser Ser
385             390                 395                 400

Asn Leu Arg Gln His Asn Gln Ser Lys Val Asp Ala Phe Phe Thr Leu
                405                 410                 415

Lys Thr Asp Glu Asn Thr Thr Asn Phe Thr Thr Asn Ala Thr Lys Thr
            420                 425                 430

Thr Glu

<210> SEQ ID NO 6
<211> LENGTH: 441
<212> TYPE: PRT
<213> ORGANISM: Listeria innocua

<400> SEQUENCE: 6

Met Ala Lys Asn Lys Trp Gln Pro Thr Lys His Leu Gly Ile Tyr Glu
1               5                   10                  15

Tyr Met Thr Lys Lys Gly Lys Arg Tyr Gly Ile Arg Val Arg Tyr Lys
            20                  25                  30
```

Gln Gly Asn Asp Tyr Pro Glu Ile Asn Lys Ser Gly Phe Glu Thr Ile
              35                  40                  45

Ala Ala Ala Lys Val Tyr Lys Asn Asn Ile Glu Asn Leu Lys Ala Asn
 50                  55                  60

Lys Lys Glu Tyr Val Phe Thr Asn Glu Lys Leu Thr Leu Asn Thr Trp
 65                  70                  75                  80

Phe Ala Ser Tyr Met Glu Met Phe Lys Lys Lys Asn Lys Ser Lys Asp
                 85                  90                  95

Thr Ile Ala Asn Ala Lys Val Tyr Lys Asn Asn Ile Glu Asn Leu Lys
                100                 105                 110

Ala Asn Lys Lys Glu Tyr Val Phe Thr Asn Glu Lys Leu Thr Leu Asn
            115                 120                 125

Thr Trp Phe Ala Ser Tyr Met Glu Met Phe Lys Lys Lys Asn Lys Ser
130                 135                 140

Lys Asp Thr Ile Ala Asn Lys Tyr Ser Ile Tyr Asn Asn His Leu Glu
145                 150                 155                 160

Ile Pro Phe Gly Asn Tyr Tyr Leu Thr Asp Ile Ser Leu Asp Ile Tyr
                165                 170                 175

Glu Asp Phe Leu Arg Glu Lys Ile Lys Asn Gly Tyr Ala Asn Asn Ser
            180                 185                 190

Val Lys Ala Met His Lys Leu Met Lys Ser Ile Leu Asn Ala Ala Val
        195                 200                 205

Arg Tyr Glu Lys Leu Glu Lys Asn Arg Leu Gln Phe Ala Glu Ile Glu
210                 215                 220

Gln Leu Glu Glu Asn Glu Val Ile Glu Leu Lys Val Leu Glu Thr Asp
225                 230                 235                 240

Glu Phe Asn Val Phe Ile Ser Ala Cys Arg Ala Phe Phe Thr Lys Tyr
                245                 250                 255

Asp Phe Thr Met Ile Tyr Leu Ala Val Trp Gly Met Arg Arg Gly Glu
            260                 265                 270

Val Met Gly Val Lys Leu Lys Asn Leu Thr Phe Asp Asp Ala Lys Gln
        275                 280                 285

Gln Val Arg Ile Thr Leu Asp Ser Thr Arg Thr Leu Arg Thr Pro Glu
290                 295                 300

Gly Lys Gly Thr Lys Thr Pro Ala Gly Arg Arg Ile Leu Leu Ile Asp
305                 310                 315                 320

Gly Glu Gly Tyr Arg Leu Leu Lys Tyr Ser Val Glu Lys Ala Val Ser
                325                 330                 335

Ile Ala Lys Asp His Gly Ser Val Leu His Gln Asp Phe Ile Phe
            340                 345                 350

Arg Asn Pro Thr Ser Asn Arg Pro Trp Ala Val Thr Arg Met Asn Asp
        355                 360                 365

Leu Leu Arg Lys Leu Glu Lys Glu Tyr Asp Ile Lys Val Tyr Pro His
370                 375                 380

Leu Leu Arg His Asn Phe Asn Thr Gln Ala Leu Leu Ala Gly Ala Asn
385                 390                 395                 400

Ser Asn Asp Leu Arg Lys Phe Ile Gly His Lys Asn Ser Ser Met Thr
                405                 410                 415

Asp His Tyr Ser His Ala Thr Asp Glu Gly Arg Glu Lys Leu Met Asn
            420                 425                 430

Thr Met Lys Asp Arg Leu Ser Gly Ile
        435                 440

<210> SEQ ID NO 7

<211> LENGTH: 384
<212> TYPE: PRT
<213> ORGANISM: Bacteriophage PSA

<400> SEQUENCE: 7

Met Lys Ile Lys Lys Leu Ala Asn Gly Lys Tyr Cys Val Arg Leu Arg
1               5                   10                  15

Ile Lys Val Asp Gly Glu Trp Lys Glu Lys Arg Leu Thr Asp Thr Ser
            20                  25                  30

Glu Thr Asn Leu Met Tyr Lys Ala Ser Lys Leu Leu Lys Gln Val Gln
        35                  40                  45

His Asp Ser Ser Ser Leu Lys Glu Trp Asn Phe Lys Glu Phe Tyr Thr
    50                  55                  60

Leu Phe Met Lys Thr Phe Lys Asp Gly Lys Ser Ser Gln Ser Thr Ile
65                  70                  75                  80

Asn Leu Tyr Asp Leu Ala Tyr Asn Gln Phe Val Asp Tyr Phe Asp Glu
                85                  90                  95

Lys Ile Lys Leu Asn Ser Ile Asp Ala Val Gln Tyr Gln Gln Phe Ile
            100                 105                 110

Asn His Leu Ser Val Asp Tyr Ala Ile Ser Thr Val Asp Thr Arg His
        115                 120                 125

Arg Lys Ile Arg Ala Ile Phe Asn Lys Ala Val His Leu Gly Tyr Met
    130                 135                 140

Lys Lys Asn Pro Thr Ile Gly Ala His Ile Ser Gly Gln Asp Val Ala
145                 150                 155                 160

Lys Asn Lys Ala Gln Phe Met Glu Thr Asp Lys Val His Leu Leu Leu
                165                 170                 175

Glu Glu Leu Ala Lys Phe His Ser Ile Ser Arg Ala Val Ile Phe Leu
            180                 185                 190

Ala Val Gln Thr Gly Met Arg Phe Glu Glu Ile Ile Ala Leu Thr Lys
        195                 200                 205

Lys Asp Ile Asn Phe Thr Lys Arg Ser Ile Thr Val Asn Lys Ala Trp
    210                 215                 220

Asp Tyr Lys Tyr Thr Asn Thr Phe Ile Asp Thr Lys Thr Lys Lys Ser
225                 230                 235                 240

Arg Val Ile Tyr Ile Asp Asn Ser Thr Ala Gln Tyr Leu His Ser Tyr
                245                 250                 255

Leu Asn Trp His Thr Asp Tyr Met Lys Glu His Ala Ile Lys Asn Pro
            260                 265                 270

Leu Met Leu Leu Phe Ile Thr Tyr His Asn Lys Pro Val Asp Asn Ala
        275                 280                 285

Ser Cys Asn Lys Ala Leu Lys Lys Ile Cys Ser Thr Ile Asn Ser Glu
    290                 295                 300

Pro Val Thr Leu His Lys Leu Arg His Thr His Thr Gly Leu Cys Val
305                 310                 315                 320

Glu Ala Gly Met Asp Ile Ile Tyr Val Ala Asp Arg Leu Gly His Asp
                325                 330                 335

Asp Ile Asn Thr Thr Leu Lys Tyr Tyr Ser His Leu Ser Ser Asn Leu
            340                 345                 350

Arg Gln His Asn Gln Ser Lys Val Asp Ala Phe Phe Thr Leu Lys Thr
        355                 360                 365

Asp Glu Asn Thr Thr Asn Phe Thr Thr Asn Ala Thr Lys Thr Thr Glu
    370                 375                 380

<210> SEQ ID NO 8

<211> LENGTH: 384
<212> TYPE: PRT
<213> ORGANISM: Listeria innocua

<400> SEQUENCE: 8

Met Lys Ile Lys Lys Met Lys Asn Gly Lys Tyr Thr Val Arg Leu Arg
1               5                   10                  15

Ile Lys Val Asp Gly Glu Trp Lys Glu Lys Arg Leu Thr Asp Thr Ser
            20                  25                  30

Glu Thr Asn Leu Met Tyr Lys Ala Ser Lys Leu Leu Lys Gln Val Glu
        35                  40                  45

His Asp Ser Asn Ser Leu Lys Glu Trp Asn Phe Lys Glu Phe Tyr Ser
    50                  55                  60

Leu Phe Met Lys Thr Phe Lys Glu Asn Lys Ser Ser Gln Ser Thr Ile
65                  70                  75                  80

Asn Leu Tyr Asp Leu Ala Tyr Asn Gln Phe Val Asn Tyr Phe Asp Glu
                85                  90                  95

Lys Ile Lys Leu Asn Ser Ile Asp Ala Val Gln Tyr Gln Gln Phe Ile
            100                 105                 110

Asn His Leu Ala Leu Asp Tyr Ala Val Ala Thr Ile Asp Thr Arg His
        115                 120                 125

Arg Lys Ile Arg Ala Ile Phe Asn Lys Ala Val His Leu Gly Tyr Met
    130                 135                 140

Lys Lys Asn Pro Ala Leu Gly Ala His Ile Ser Gly His Asp Ile Ala
145                 150                 155                 160

Lys Thr Lys Ala Gln Tyr Leu Glu Thr Asp Lys Val His Leu Leu Leu
                165                 170                 175

Glu Glu Leu Ala Lys Leu His Ser Ile Ser Arg Ala Val Ile Phe Leu
            180                 185                 190

Ala Val Gln Thr Gly Met Arg Phe Glu Glu Ile Ile Ala Leu Thr Lys
        195                 200                 205

Lys Asp Ile Asn Phe Thr Lys Arg Ser Ile Ser Val Asn Lys Ala Trp
    210                 215                 220

Asp Tyr Lys Tyr Thr Asn Thr Phe Thr Asp Thr Lys Thr Lys Lys Ser
225                 230                 235                 240

Arg Val Ile Tyr Ile Asp Asn Ser Thr Val Gln Tyr Leu Gln Ser Tyr
                245                 250                 255

Leu Ala Trp His Ala Asp Tyr Met Lys Glu His Ala Ile Glu Asn Pro
            260                 265                 270

Val Met Leu Leu Phe Ile Thr Tyr His Asn Lys Pro Val Asp Asn Ala
        275                 280                 285

Ser Cys Asn Lys Ala Leu Lys Lys Ile Cys Thr Thr Ile Asn Ser Glu
    290                 295                 300

Thr Val Thr Leu His Lys Leu Arg His Thr His Thr Gly Leu Cys Val
305                 310                 315                 320

Glu Ala Gly Met Asp Ile Ile Tyr Val Ala Asp Arg Leu Gly His Asp
                325                 330                 335

Asp Ile Asn Thr Thr Leu Lys Tyr Tyr Ser His Leu Ser Ser Asn Leu
            340                 345                 350

Arg Gln Gln Asn Gln Ser Lys Val Asp Ala Phe Phe Thr Leu Lys Thr
        355                 360                 365

Asp Glu Asn Thr Thr Lys Phe Ala Thr Asn Ala Thr Lys Thr Thr Glu
    370                 375                 380

<210> SEQ ID NO 9

```
<211> LENGTH: 22
<212> TYPE: DNA
<213> ORGANISM: Artificial Sequence
<220> FEATURE:
<223> OTHER INFORMATION: Primer

<400> SEQUENCE: 9
tgaagtaaac ccgcacacga tc                                              22

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
tgtaacatgg aggttctggc aatc                                            24

<210> SEQ ID NO 11
<211> LENGTH: 613
<212> TYPE: PRT
<213> ORGANISM: Bacteriophage phiC31

<400> SEQUENCE: 11
```

Met Thr Gln Gly Val Val Thr Gly Val Asp Thr Tyr Ala Gly Ala Tyr
 1               5                   10                  15

Asp Arg Gln Ser Arg Glu Arg Glu Asn Ser Ser Ala Ala Ser Pro Ala
                20                  25                  30

Thr Gln Arg Ser Ala Asn Glu Asp Lys Ala Ala Asp Leu Gln Arg Glu
            35                  40                  45

Val Glu Arg Asp Gly Gly Arg Phe Arg Phe Val Gly His Phe Ser Glu
        50                  55                  60

Ala Pro Gly Thr Ser Ala Phe Gly Thr Ala Glu Arg Pro Glu Phe Glu
65                  70                  75                  80

Arg Ile Leu Asn Glu Cys Arg Ala Gly Arg Leu Asn Met Ile Ile Val
                85                  90                  95

Tyr Asp Val Ser Arg Phe Ser Arg Leu Lys Val Met Asp Ala Ile Pro
            100                 105                 110

Ile Val Ser Glu Leu Leu Ala Leu Gly Val Thr Ile Val Ser Thr Gln
        115                 120                 125

Glu Gly Val Phe Arg Gln Gly Asn Val Met Asp Leu Ile His Leu Ile
130                 135                 140

Met Arg Leu Asp Ala Ser His Lys Glu Ser Ser Leu Lys Ser Ala Lys
145                 150                 155                 160

Ile Leu Asp Thr Lys Asn Leu Gln Arg Glu Leu Gly Gly Tyr Val Gly
                165                 170                 175

Gly Lys Ala Pro Tyr Gly Phe Glu Leu Val Ser Glu Thr Lys Glu Ile
            180                 185                 190

Thr Arg Asn Gly Arg Met Val Asn Val Val Ile Asn Lys Leu Ala His
        195                 200                 205

Ser Thr Thr Pro Leu Thr Gly Pro Phe Glu Phe Glu Pro Asp Val Ile
    210                 215                 220

Arg Trp Trp Arg Glu Ile Lys Thr His Lys His Leu Pro Phe Lys
225                 230                 235                 240

Pro Gly Ser Gln Ala Ala Ile His Pro Gly Ser Ile Thr Gly Leu Cys
                245                 250                 255

Lys Arg Met Asp Ala Asp Ala Val Pro Thr Arg Gly Glu Thr Ile Gly
            260                 265                 270

Lys Lys Thr Ala Ser Ser Ala Trp Asp Pro Ala Thr Val Met Arg Ile
            275                 280                 285

Leu Arg Asp Pro Arg Ile Ala Gly Phe Ala Glu Val Ile Tyr Lys
        290                 295                 300

Lys Lys Pro Asp Gly Thr Pro Thr Thr Lys Ile Glu Gly Tyr Arg Ile
305                 310                 315                 320

Gln Arg Asp Pro Ile Thr Leu Arg Pro Val Glu Leu Asp Cys Gly Pro
                325                 330                 335

Ile Ile Glu Pro Ala Glu Trp Tyr Glu Leu Gln Ala Trp Leu Asp Gly
                340                 345                 350

Arg Gly Arg Gly Lys Gly Leu Ser Arg Gly Gln Ala Ile Leu Ser Ala
            355                 360                 365

Met Asp Lys Leu Tyr Cys Glu Cys Gly Ala Val Met Thr Ser Lys Arg
370                 375                 380

Gly Glu Glu Ser Ile Lys Asp Ser Tyr Arg Cys Arg Arg Arg Lys Val
385                 390                 395                 400

Val Asp Pro Ser Ala Pro Gly Gln His Glu Gly Thr Cys Asn Val Ser
                405                 410                 415

Met Ala Ala Leu Asp Lys Phe Val Ala Glu Arg Ile Phe Asn Lys Ile
                420                 425                 430

Arg His Ala Glu Gly Asp Glu Glu Thr Leu Ala Leu Leu Trp Glu Ala
            435                 440                 445

Ala Arg Arg Phe Gly Lys Leu Thr Glu Ala Pro Glu Lys Ser Gly Glu
        450                 455                 460

Arg Ala Asn Leu Val Ala Glu Arg Ala Asp Ala Leu Asn Ala Leu Glu
465                 470                 475                 480

Glu Leu Tyr Glu Asp Arg Ala Ala Gly Ala Tyr Asp Gly Pro Val Gly
                485                 490                 495

Arg Lys His Phe Arg Lys Gln Gln Ala Ala Leu Thr Leu Arg Gln Gln
            500                 505                 510

Gly Ala Glu Glu Arg Leu Ala Glu Leu Glu Ala Ala Glu Ala Pro Lys
        515                 520                 525

Leu Pro Leu Asp Gln Trp Phe Pro Glu Asp Ala Asp Ala Asp Pro Thr
    530                 535                 540

Gly Pro Lys Ser Trp Trp Gly Arg Ala Ser Val Asp Asp Lys Arg Val
545                 550                 555                 560

Phe Val Gly Leu Phe Val Asp Lys Ile Val Thr Lys Ser Thr Thr
                565                 570                 575

Gly Arg Gly Gln Gly Thr Pro Ile Glu Lys Arg Ala Ser Ile Thr Trp
                580                 585                 590

Ala Lys Pro Pro Thr Asp Asp Glu Asp Ala Gln Asp Gly Thr
            595                 600                 605

Glu Asp Val Ala Ala
    610

<210> SEQ ID NO 12
<211> LENGTH: 84
<212> TYPE: DNA
<213> ORGANISM: Artificial Sequence
<220> FEATURE:
<223> OTHER INFORMATION: phiC31 target attBB' site

<400> SEQUENCE: 12
tgacggtctc gaagccgcgg tgcgggtgcc agggcgtgcc cttgggctcc ccgggcgcgt      60
actccacctc acccatctgg tcca                                            84

<210> SEQ ID NO 13
<211> LENGTH: 285
<212> TYPE: DNA
<213> ORGANISM: Artificial Sequence
<220> FEATURE:
<223> OTHER INFORMATION: phiC31 target attBB' site

<400> SEQUENCE: 13
gtcgacgatg taggtcacgg tctcgaagcc gcggtgcggg tgccagggcg tgcccttggg    60
ctccccgggc gcgtactcca cctcacccat ctggtccatc atgatgaacg ggtcgaggtg   120
gcggtagttg atcccggcga acgcgcggcg caccgggaag ccctcgccct cgaaaccgct   180
gggcgcggtg gtcacggtga gcacgggacg tgcgacggcg tcggcgggtg cggatacgcg   240
gggcagcgtc agcgggttct cgacggtcac ggcgggcatg tcgac                   285

<210> SEQ ID NO 14
<211> LENGTH: 70
<212> TYPE: DNA
<213> ORGANISM: Bacteriophage phiC31

<400> SEQUENCE: 14
aaggggttgt gaccggggtg gacacgtacg cgggtgctta cgaccgtcag tcgcgcgagc    60
gcgagaattc                                                          70

<210> SEQ ID NO 15
<211> LENGTH: 2791
<212> TYPE: DNA
<213> ORGANISM: Artificial Sequence
<220> FEATURE:
<223> OTHER INFORMATION: Region of pKSV7

<400> SEQUENCE: 15
ccaaattagc gatcttacac cattggctaa tttaacaaga atcacccaac tagggttgaa    60
tgatcaagca tggacaaatg caccagtaaa ctacaaagca aatgtatcca ttccaaacac   120
ggtgaaaaat gtgactggcg cttttgattgc acctgctact attagcgatg gcggtagtta   180
cgcagaaccg gatataacat ggaacttacc tagttataca aatgaagtaa gctataccctt   240 tagccaaccct gtcactattg gaaaaggaac gacaacattt agtggaaccg tgacgcagcc   300
acttaaggca attttttaatg ctaagtttca tgtggacggc aaagaaacaa ccaaagaagt   360
ggaagctggg aatttattga ctgaaccagc taagcccgta aaagaaggtc acacatttgt   420
tggttggttt gatgcccaaa caggcggaac taagtggaat ttcagtacgg ataaaatgcc   480
gacaaatgac atcaatttat atgcacaatt tagtattaac agctacacag caacctttga   540
gaatgacggt gtaacaacat ctcaaacagt agattatcaa ggcttgttac aagaacctac   600
accaccaaca aaagaaggtt atactttcaa aggctggtat gacgcaaaaa ctggtggtga   660
caagtgggat ttcgcaacta gcaaaatgcc tgctaaaaac atcaccttat atgcccaata   720
tagcgccaat agctatacag caacgtttga tgttgatgga aaatcaacga ctcaagcagt   780
agactatcaa ggacttctaa agaaccaaa ggcaccaacg aaagccggat atactttcaa   840
aggctggtat gacgaaaaaa cagatgggaa aaaatgggat tttgcgacgg ataaaatgcc   900
agcaaatgac attacgctgt acgctcaatt tacgaaaaat cctgtggcac caccaacaac   960 tgagggaac acaccgccta caacaaataa cggcggaat actacaccac cttccgcaaa  1020
tatacctgga agcgacacat ctaacacatc aactgggaat tcagccagca caacaagtac  1080
aatgaacgct tatgacccctt ataattcaaa agaagcttca ctccctacaa ctggcgatag  1140

```
cgataatgcg ctctaccttt tgttagggtt attagcagta ggaactgcaa tggctcttac    1200
taaaaaagca cgtgctagta aatagaagta gtgtaaagag ctagatgtgg ttttcggact    1260
atatctagct tttttatttt ttaataacta gaatcaagga gaggatagtg gtaccttggt    1320
gagctcccta cgaaaagcta caactttaaa ttcatgaaaa aagaactgat tcgctgaaaa    1380
cggatcagtt cttttttctt tagacttatt tttacaaaaa cttttcgata atttccatat    1440
tctggggtct gtctttgctt tcaagtacag aaatatcacg aacaatgcta tctaatttaa    1500
ttttttccat tcaaattcta ttttttgttg gagcagatcg tatttactcg taagaacttg    1560
ttggatattg gctccgacaa cgcagtctgg gttggttttt ggatcaacgt gaattaaatt    1620
cgtattgcct tctatactct tataaacatc aagcagtgaa atttcttctg gtggtctagc    1680
aagaatcgga tttgctttgc cagtctgcgt agtaattaaa tcagctttt ttaaattact     1740 catgattttt ctaatgttag caggatttgt ttttacgcta ccagcaataa tttcactcga    1800
taacaaattc gtatttttaa aaatttctat ataagccaaa atgtggatag catcgctaaa    1860
ttggatagag tatttcattt ttttcaatcc tttcaaattt tctccttgac ttatcttatc    1920
ataatgttta ttataaaggt gtaaattata aatgtacagc tttagtgtta aaaaatttaa    1980
aggagtggtt taaatgactt atttagtaac tggtgcaaca ggtggacttg gaggctacgc    2040
attaaattat ttgaaagagc tggttcccat gtccgatatt tatgctttag ttcgtagcga    2100
agaaaaaggt acagacttga aagcagcagg atttaatatc cgtattggtg attatagtga    2160
tgtagaatca atgaagcaag cattcgcagg catcgaccgc gtattatttg tttcaggagc    2220
acctggtaat cgccaagtag aacacgaaaa tgtggtaaat gcggcaaaag aagcaggcgt    2280
ttcttacatc gcttacacaa gtttcgcggg cgcagataaa tccacaagcg ctttagcaga    2340
agatcatttc tttaccgaaa aagtaatcga aaaatccgga atcgcgcaca ctttcttgcg    2400
taacaactgg tacttcgaaa atgaaatgcc gatgatcggt ggcgcattga gtgctggaaa    2460
atttgtatac gctgctgaaa atggaaaagt tggctgggca ttaaaacgcg aatacgcaga    2520
agtagccgca aaagctgttg cggacgctga cttcccagaa atccttgaat tatctggccc    2580
actcatgcaa ttcgtaatca tgtcatagct gttttcctgtg tgaaattgtt atccgctcac    2640
aattccacac aacatacgag ccggaagcat aaagtgtaaa gcctggggtg cctaatgagt    2700
gagctaactc acattaattg cgttgcgctc actgcccgct ttccagtcgg gaaacctgtc    2760
gtgccagctg gactaaaagg catgcaattc a                                   2791

<210> SEQ ID NO 16
<211> LENGTH: 1309
<212> TYPE: DNA
<213> ORGANISM: Listeria monocytogenes

<400> SEQUENCE: 16
ccaaattagc gatcttacac cattggctaa tttaacaaga atcacccaac tagggttgaa     60
tgatcaagca tggacaaatg caccagtaaa ctacaaagca aatgtatcca ttccaaacac    120
ggtgaaaaat gtgactggcg ctttgattgc acctgctact attagcgatg gcggtagtta    180
cgcagaaccg gatataacat ggaacttacc tagttataca aatgaagtaa gctataccct    240
tagccaacct gtcactattg gaaaaggaac gacaacattt agtggaaccg tgacgcagcc    300
acttaaggca atttttaatg ctaagtttca tgtggacggc aaagaaacaa ccaaagaagt    360
ggaagctggg aatttattga ctgaaccagc taagcccgta aaagaaggtc acacatttgt    420
tggttggttt gatgcccaaa caggcggaac taagtggaat ttcagtacgg ataaaatgcc    480
```

-continued

```
gacaaatgac atcaatttat atgcacaatt tagtattaac agctacacag caacctttga      540
gaatgacggt gtaacaacat ctcaaacagt agattatcaa ggcttgttac aagaacctac      600
accaccaaca aaagaaggtt atactttcaa aggctggtat gacgcaaaaa ctggtggtga      660
caagtgggat ttcgcaacta gcaaaatgcc tgctaaaaac atcaccttat atgcccaata      720
tagcgccaat agctatacag caacgtttga tgttgatgga aaatcaacga ctcaagcagt      780
agactatcaa ggacttctaa aagaaccaaa ggcaccaacg aaagccggat atactttcaa      840
aggctggtat gacgaaaaaa cagatgggaa aaaatgggat tttgcgacgg ataaaatgcc      900
agcaaatgac attacgctgt acgctcaatt tacgaaaaat cctgtggcac caccaacaac      960
tggagggaac acaccgccta caacaaataa cggcgggaat actacaccac cttccgcaaa     1020
tatacctgga agcgacacat ctaacacatc aactgggaat tcagccagca caacaagtac     1080
aatgaacgct tatgacccct taattcaaa agaagcttca ctccctacaa ctggcgatag      1140
cgataatgcg ctctacctt tgttagggtt attagcagta ggaactgcaa tggctcttac      1200
taaaaaagca cgtgctagta aatagaagta gtgtaaagag ctagatgtgg ttttcggact     1260
atatctagct ttttattt ttaataacta gaatcaagga gaggatagt                   1309
```

```
<210> SEQ ID NO 17
<211> LENGTH: 1466
<212> TYPE: DNA
<213> ORGANISM: Listeria monocytogenes

<400> SEQUENCE: 17
cctacgaaaa gctacaactt taaattcatg aaaaagaaac tgattcgctg aaaacggatc       60
agttcttttt tctttagact tattttttaca aaaacttttc gataatttcc atattctggg     120
gtctgtcttt gctttcaagt acagaaatat cacgaacaat gctatctaat ttaatttttt      180
ccatttcaaa ttctattttt tgttggagca gatcgtattt actcgtaaga acttgttgga     240
tattggctcc gacaacgcag tctgggttgg ttttggatc aacgtgaatt aaattcgtat       300
tgccttctat actcttataa acatcaagca gtgaaatttc ttctggtggt ctagcaagaa     360
tcggatttgc tttgccagtc tgcgtagtaa ttaaatcagc tttttttaaa ttactcatga     420
tttttctaat gttagcagga tttgttttta cgctaccagc aataatttca ctcgataaca     480
aattcgtatt tttaaaaatt tctatataag ccaaaatgtg gatagcatcg ctaaattgga     540
tagagtattt cattttttc aatccttca attttctcc ttgacttatc ttatcataat        600
gtttattata aaggtgtaaa ttataaatgt acagctttag tgttaaaaaa tttaaaggag     660
tggtttaaat gacttattta gtaactggtg caacaggtgg acttggaggc tacgcattaa     720
attatttgaa agagctggtt cccatgtccg atatttatgc tttagttcgt agcgaagaaa     780
aaggtacaga cttgaaagca gcaggattta atatccgtat tggtgattat agtgatgtag     840
aatcaatgaa gcaagcattc gcaggcatcg accgcgtatt atttgtttca ggagcacctg     900
gtaatcgcca gtagaacac gaaaatgtgg taaatgcggc aaaagaagca ggcgtttctt      960
acatcgctta cacaagtttc gcgggcgcag ataaatccac aagcgcttta gcagaagatc     1020
atttctttac cgaaaagta atcgaaaaat ccggaatcgc gcacactttc ttgcgtaaca     1080
actggtactt cgaaaatgaa atgccgatga tcggtggcgc attgagtgct ggaaaatttg     1140
tatacgctgc tgaaaatgga aaagttggct gggcattaaa acgcgaatac gcagaagtag     1200
ccgcaaaagc tgttgcggac gctgacttcc cagaaatcct tgaattatct ggcccactca     1260
tgcaattcgt aatcatgtca tagctgtttc ctgtgtgaaa ttgttatccg ctcacaattc     1320
```

| | |
|---|---|
| cacacaacat acgagccgga agcataaagt gtaaagcctg gggtgcctaa tgagtgagct | 1380 |
| aactcacatt aattgcgttg cgctcactgc ccgctttcca gtcgggaaac ctgtcgtgcc | 1440 |
| agctggacta aaaggcatgc aattca | 1466 |

```
<210> SEQ ID NO 18
<211> LENGTH: 916
<212> TYPE: DNA
<213> ORGANISM: Listeria monocytogenes
<220> FEATURE:
<221> NAME/KEY: misc_feature
<222> LOCATION: 539
<223> OTHER INFORMATION: n = A,T,C or G

<400> SEQUENCE: 18
```

| | |
|---|---|
| agaatttagt tccgcagtgg atgctcattt ttacgcaagt gaagtgtacg aatactataa | 60 |
| aaatgtccac caactagaga gtctagatgg taaaggtgga gaaattgatt cgtttgtcca | 120 |
| ttatggcttg aattgcaata atgccttttg ggatggccaa gaaattcttt atggagatgg | 180 |
| ggacaaaaag aatttcaaac cattttcatg cgccaaaact attgttggtc atgaactaac | 240 |
| gcatgcagtt atccagtatt cggcgggatt ggaatacgaa gggcaatcag gtgcgctaaa | 300 |
| cgagtcgttc gccgatgttt ttggttattt tattgcgcca aatcattggt tgattggtga | 360 |
| ggatgtctgt gtgcgtgggt cgcgagatgg gcgaataaga agcattaaag atcctgacaa | 420 |
| atataatcaa gcggctcata tgaaggatta cgaatcgctt ccaatcacag aggaaggcga | 480 |
| ctggggcgga gttcattata atagtggtat cccgaataaa gcagcctata atactatcnc | 540 |
| taaacttgga aaagaaaaaa cagaacagct ttattttcgc gccttaaagt actatttaac | 600 |
| gaaaaaatcc cagtttaccg atgcgaaaaa agcgcttcaa caagcagcga aagatttata | 660 |
| tggtgaagat gcttctaaaa aagttgctga agcttgggaa gcagttgggg ttaactgatt | 720 |
| aacaaatgtt agagaaaaat taattctcca agtgatattc ttaaaataat tcatgaatat | 780 |
| tttttcttat attagctaat taagaagata attaactgct aatccaattt ttaacggaat | 840 |
| aaattagtga aaatgaaggc cgaattttcc ttgttctaaa aaggttgtat tagcgtatca | 900 |
| cgaggaggga gtataa | 916 |

```
<210> SEQ ID NO 19
<211> LENGTH: 1043
<212> TYPE: DNA
<213> ORGANISM: Listeria monocytogenes

<400> SEQUENCE: 19
```

| | |
|---|---|
| aaacacagaa cgaaagaaaa agtgaggtga atgatatgaa attcaaaaat gtggttctag | 60 |
| gtatgtgctt gaccgcaagt gttctagtct ttccggtaac gataaaagca aatgcctgtt | 120 |
| gtgatgaaat acttacaaac accccgcagct ccgcatatat tgacagcaaa ttaccacata | 180 |
| aacttagttg gtccgcggat aacccgacaa atactgacgt aaatacgcac tattggcttt | 240 |
| ttaaacaagc ggaaaaaata ctagctaaag atgtaaatca tatgcgagct aatttaatga | 300 |
| atgaacttaa aaaattcgat aaacaaatag ctcaaggaat atatgatgcg gatcataaaa | 360 |
| atccatatta tgatactagt acatttttat ctcattttta taatcctgat agagataata | 420 |
| cttatttgcc gggttttgct aatgcgaaaa taacaggagc aaagtatttc aatcaatcgg | 480 |
| tgactgatta ccgagaaggg aaatttgaca cagcgtttta taattaggc ctagcaatcc | 540 |
| attattatac ggatattagt caacctatgc acgccaataa ttttaccgca atatcatacc | 600 |
| ctccaggcta ccactgtgca tatgaaaatt acgtagatac cattaaacac aattatcaag | 660 |

-continued

```
caacggaaga catggtagca aaaagattt  gctcagatga cgtgaaagac tggctctatg    720
aaaatgcgaa aagggcgaaa gcggactacc cgaaaatagt caatgcgaaa actaaaaaat    780
catatttagt aggaaattcc gaatggaaaa aggatacagt ggaacctact ggagctagac    840
taagagattc acagcaaact ttggcaggtt ttttagaatt ttggtctaaa aaaacaaatg    900
aataacaata tttaggaata cattcttatc cactcgttag cgggtggata tattttatgg    960
ggaggaagta agccaaatgt atataaaagg gaggttaatc ttttctttg taatgttagt    1020 aatcgcgtta tgttccgaag ggc                                            1043
```

<210> SEQ ID NO 20
<211> LENGTH: 17
<212> TYPE: PRT
<213> ORGANISM: Listeria monocytogenes

<400> SEQUENCE: 20

Lys Val Phe Lys Lys Ile Lys Asp Ala Gly Lys Trp Val Arg Asp Lys
1               5                   10                  15

Ile

<210> SEQ ID NO 21
<211> LENGTH: 5
<212> TYPE: PRT
<213> ORGANISM: Listeria monocytogenes

<400> SEQUENCE: 21

Phe Pro Pro Pro Pro
1               5

<210> SEQ ID NO 22
<211> LENGTH: 5
<212> TYPE: PRT
<213> ORGANISM: Listeria monocytogenes

<400> SEQUENCE: 22

Phe Pro Pro Ile Pro
1               5

<210> SEQ ID NO 23
<211> LENGTH: 4
<212> TYPE: PRT
<213> ORGANISM: Listeria monocytogenes

<400> SEQUENCE: 23

Lys Lys Arg Arg
1

<210> SEQ ID NO 24
<211> LENGTH: 27
<212> TYPE: PRT
<213> ORGANISM: Listeria monocytogenes

<400> SEQUENCE: 24

Met Asn Met Lys Lys Ala Thr Ile Ala Ala Thr Ala Gly Ile Ala Val
1               5                   10                  15

Thr Ala Phe Ala Ala Pro Thr Ile Ala Ser Ala
            20                  25

<210> SEQ ID NO 25
<211> LENGTH: 52
<212> TYPE: PRT
<213> ORGANISM: Listeria monocytogenes

<400> SEQUENCE: 25

| Met | Asp | Arg | Lys | Phe | Ile | Lys | Pro | Gly | Ile | Leu | Leu | Ile | Val | Ala |
|---|---|---|---|---|---|---|---|---|---|---|---|---|---|---|
| 1 | | | | 5 | | | | | 10 | | | | | 15 |

| Phe | Leu | Val | Val | Ser | Ile | Asn | Val | Gly | Ala | Glu | Thr | Gly | Gly | Ser | Arg |
|---|---|---|---|---|---|---|---|---|---|---|---|---|---|---|---|
| | | | 20 | | | | | 25 | | | | | 30 | | |

| Thr | Ala | Gln | Val | Asn | Leu | Thr | Thr | Ser | Gln | Gln | Ala | Phe | Ile | Asp | Glu |
|---|---|---|---|---|---|---|---|---|---|---|---|---|---|---|---|
| | | | 35 | | | | | 40 | | | | | 45 | | |

| Ile | Leu | Pro | Ala |
|---|---|---|---|
| | 50 | | |

<210> SEQ ID NO 26
<211> LENGTH: 588
<212> TYPE: PRT
<213> ORGANISM: Homo sapiens

<400> SEQUENCE: 26

| Arg | Thr | Leu | Ala | Gly | Glu | Thr | Gly | Gln | Glu | Ala | Ala | Pro | Leu | Asp | Gly |
|---|---|---|---|---|---|---|---|---|---|---|---|---|---|---|---|
| 1 | | | | 5 | | | | | 10 | | | | | 15 | |

| Val | Leu | Thr | Asn | Pro | Pro | Asn | Ile | Ser | Ser | Leu | Ser | Pro | Arg | Gln | Leu |
|---|---|---|---|---|---|---|---|---|---|---|---|---|---|---|---|
| | | | 20 | | | | | 25 | | | | | 30 | | |

| Leu | Gly | Phe | Pro | Cys | Ala | Glu | Val | Ser | Gly | Leu | Ser | Thr | Glu | Arg | Val |
|---|---|---|---|---|---|---|---|---|---|---|---|---|---|---|---|
| | | | 35 | | | | | 40 | | | | | 45 | | |

| Arg | Glu | Leu | Ala | Val | Ala | Leu | Ala | Gln | Lys | Asn | Val | Lys | Leu | Ser | Thr |
|---|---|---|---|---|---|---|---|---|---|---|---|---|---|---|---|
| | 50 | | | | | 55 | | | | | 60 | | | | |

| Glu | Gln | Leu | Arg | Cys | Leu | Ala | His | Arg | Leu | Ser | Glu | Pro | Pro | Glu | Asp |
|---|---|---|---|---|---|---|---|---|---|---|---|---|---|---|---|
| 65 | | | | | 70 | | | | | 75 | | | | | 80 |

| Leu | Asp | Ala | Leu | Pro | Leu | Asp | Leu | Leu | Leu | Phe | Leu | Asn | Pro | Asp | Ala |
|---|---|---|---|---|---|---|---|---|---|---|---|---|---|---|---|
| | | | | 85 | | | | | 90 | | | | | 95 | |

| Phe | Ser | Gly | Pro | Gln | Ala | Cys | Thr | Arg | Phe | Phe | Ser | Arg | Ile | Thr | Lys |
|---|---|---|---|---|---|---|---|---|---|---|---|---|---|---|---|
| | | | 100 | | | | | 105 | | | | | 110 | | |

| Ala | Asn | Val | Asp | Leu | Leu | Pro | Arg | Gly | Ala | Pro | Glu | Arg | Gln | Arg | Leu |
|---|---|---|---|---|---|---|---|---|---|---|---|---|---|---|---|
| | | | 115 | | | | | 120 | | | | | 125 | | |

| Leu | Pro | Ala | Ala | Leu | Ala | Cys | Trp | Gly | Val | Arg | Gly | Ser | Leu | Leu | Ser |
|---|---|---|---|---|---|---|---|---|---|---|---|---|---|---|---|
| | 130 | | | | | 135 | | | | | 140 | | | | |

| Glu | Ala | Asp | Val | Arg | Ala | Leu | Gly | Gly | Leu | Ala | Cys | Asp | Leu | Pro | Gly |
|---|---|---|---|---|---|---|---|---|---|---|---|---|---|---|---|
| 145 | | | | | 150 | | | | | 155 | | | | | 160 |

| Arg | Phe | Val | Ala | Glu | Ser | Ala | Glu | Val | Leu | Leu | Pro | Arg | Leu | Val | Ser |
|---|---|---|---|---|---|---|---|---|---|---|---|---|---|---|---|
| | | | | 165 | | | | | 170 | | | | | 175 | |

| Cys | Pro | Gly | Pro | Leu | Asp | Gln | Asp | Gln | Gln | Glu | Ala | Ala | Arg | Ala | Ala |
|---|---|---|---|---|---|---|---|---|---|---|---|---|---|---|---|
| | | | 180 | | | | | 185 | | | | | 190 | | |

| Leu | Gln | Gly | Gly | Gly | Pro | Pro | Tyr | Gly | Pro | Pro | Ser | Thr | Trp | Ser | Val |
|---|---|---|---|---|---|---|---|---|---|---|---|---|---|---|---|
| | | | 195 | | | | | 200 | | | | | 205 | | |

| Ser | Thr | Met | Asp | Ala | Leu | Arg | Gly | Leu | Leu | Pro | Val | Leu | Gly | Gln | Pro |
|---|---|---|---|---|---|---|---|---|---|---|---|---|---|---|---|
| | 210 | | | | | 215 | | | | | 220 | | | | |

| Ile | Ile | Arg | Ser | Ile | Pro | Gln | Gly | Ile | Val | Ala | Ala | Trp | Arg | Gln | Arg |
|---|---|---|---|---|---|---|---|---|---|---|---|---|---|---|---|
| 225 | | | | | 230 | | | | | 235 | | | | | 240 |

| Ser | Ser | Arg | Asp | Pro | Ser | Trp | Arg | Gln | Pro | Glu | Arg | Thr | Ile | Leu | Arg |
|---|---|---|---|---|---|---|---|---|---|---|---|---|---|---|---|
| | | | | 245 | | | | | 250 | | | | | 255 | |

| Pro | Arg | Phe | Arg | Arg | Glu | Val | Glu | Lys | Thr | Ala | Cys | Pro | Ser | Gly | Lys |
|---|---|---|---|---|---|---|---|---|---|---|---|---|---|---|---|
| | | | 260 | | | | | 265 | | | | | 270 | | |

| Lys | Ala | Arg | Glu | Ile | Asp | Glu | Ser | Leu | Ile | Phe | Tyr | Lys | Lys | Trp | Glu |
|---|---|---|---|---|---|---|---|---|---|---|---|---|---|---|---|
| | | | 275 | | | | | 280 | | | | | 285 | | |

| Leu | Glu | Ala | Cys | Val | Asp | Ala | Ala | Leu | Leu | Ala | Thr | Gln | Met | Asp | Arg |
|---|---|---|---|---|---|---|---|---|---|---|---|---|---|---|---|
| | 290 | | | | | 295 | | | | | 300 | | | | |

```
Val Asn Ala Ile Pro Phe Thr Tyr Glu Gln Leu Asp Val Leu Lys His
305                 310                 315                 320

Lys Leu Asp Glu Leu Tyr Pro Gln Gly Tyr Pro Glu Ser Val Ile Gln
            325                 330                 335

His Leu Gly Tyr Leu Phe Leu Lys Met Ser Pro Glu Asp Ile Arg Lys
            340                 345                 350

Trp Asn Val Thr Ser Leu Glu Thr Leu Lys Ala Leu Leu Glu Val Asn
            355                 360                 365

Lys Gly His Glu Met Ser Pro Gln Val Ala Thr Leu Ile Asp Arg Phe
370                 375                 380

Val Lys Gly Arg Gly Gln Leu Asp Lys Asp Thr Leu Asp Thr Leu Thr
385                 390                 395                 400

Ala Phe Tyr Pro Gly Tyr Leu Cys Ser Leu Ser Pro Glu Glu Leu Ser
            405                 410                 415

Ser Val Pro Pro Ser Ser Ile Trp Ala Val Arg Pro Gln Asp Leu Asp
            420                 425                 430

Thr Cys Asp Pro Arg Gln Leu Asp Val Leu Tyr Pro Lys Ala Arg Leu
            435                 440                 445

Ala Phe Gln Asn Met Asn Gly Ser Glu Tyr Phe Val Lys Ile Gln Ser
450                 455                 460

Phe Leu Gly Gly Ala Pro Thr Glu Asp Leu Lys Ala Leu Ser Gln Gln
465                 470                 475                 480

Asn Val Ser Met Asp Leu Ala Thr Phe Met Lys Leu Arg Thr Asp Ala
            485                 490                 495

Val Leu Pro Leu Thr Val Ala Glu Val Gln Lys Leu Leu Gly Pro His
            500                 505                 510

Val Glu Gly Leu Lys Ala Glu Glu Arg His Arg Pro Val Arg Asp Trp
            515                 520                 525

Ile Leu Arg Gln Arg Gln Asp Asp Leu Asp Thr Leu Gly Leu Gly Leu
            530                 535                 540

Gln Gly Gly Ile Pro Asn Gly Tyr Leu Val Leu Asp Leu Ser Val Gln
545                 550                 555                 560

Glu Ala Leu Ser Gly Thr Pro Cys Leu Leu Gly Pro Gly Pro Val Leu
            565                 570                 575

Thr Val Leu Ala Leu Leu Leu Ala Ser Thr Leu Ala
            580                 585

<210> SEQ ID NO 27
<211> LENGTH: 546
<212> TYPE: PRT
<213> ORGANISM: Homo sapiens

<400> SEQUENCE: 27

Arg Thr Leu Ala Gly Glu Thr Gly Gln Glu Ala Ala Pro Leu Asp Gly
1               5                   10                  15

Val Leu Thr Asn Pro Pro Asn Ile Ser Ser Leu Ser Pro Arg Gln Leu
            20                  25                  30

Leu Gly Phe Pro Cys Ala Glu Val Ser Gly Leu Ser Thr Glu Arg Val
            35                  40                  45

Arg Glu Leu Ala Val Ala Leu Ala Gln Lys Asn Val Lys Leu Ser Thr
        50                  55                  60

Glu Gln Leu Arg Cys Leu Ala His Arg Leu Ser Glu Pro Pro Glu Asp
65                  70                  75                  80

Leu Asp Ala Leu Pro Leu Asp Leu Leu Leu Phe Leu Asn Pro Asp Ala
                85                  90                  95
```

-continued

```
Phe Ser Gly Pro Gln Ala Cys Thr Arg Phe Phe Ser Arg Ile Thr Lys
                100                 105                 110

Ala Asn Val Asp Leu Leu Pro Arg Gly Ala Pro Glu Arg Gln Arg Leu
            115                 120                 125

Leu Pro Ala Ala Leu Ala Cys Trp Gly Val Arg Gly Ser Leu Leu Ser
        130                 135                 140

Glu Ala Asp Val Arg Ala Leu Gly Gly Leu Ala Cys Asp Leu Pro Gly
145                 150                 155                 160

Arg Phe Val Ala Glu Ser Ala Glu Val Leu Leu Pro Arg Leu Val Ser
                165                 170                 175

Cys Pro Gly Pro Leu Asp Gln Asp Gln Gln Glu Ala Ala Arg Ala Ala
            180                 185                 190

Leu Gln Gly Gly Gly Pro Pro Tyr Gly Pro Pro Ser Thr Trp Ser Val
        195                 200                 205

Ser Thr Met Asp Ala Leu Arg Gly Leu Leu Pro Val Leu Gly Gln Pro
210                 215                 220

Ile Ile Arg Ser Ile Pro Gln Gly Ile Val Ala Ala Trp Arg Gln Arg
225                 230                 235                 240

Ser Ser Arg Asp Pro Ser Trp Arg Gln Pro Glu Arg Thr Ile Leu Arg
                245                 250                 255

Pro Arg Phe Arg Arg Glu Val Glu Lys Thr Ala Cys Pro Ser Gly Lys
            260                 265                 270

Lys Ala Arg Glu Ile Asp Glu Ser Leu Ile Phe Tyr Lys Lys Trp Glu
        275                 280                 285

Leu Glu Ala Cys Val Asp Ala Ala Leu Leu Ala Thr Gln Met Asp Arg
290                 295                 300

Val Asn Ala Ile Pro Phe Thr Tyr Glu Gln Leu Asp Val Leu Lys His
305                 310                 315                 320

Lys Leu Asp Glu Leu Tyr Pro Gln Gly Tyr Pro Glu Ser Val Ile Gln
                325                 330                 335

His Leu Gly Tyr Leu Phe Leu Lys Met Ser Pro Glu Asp Ile Arg Lys
            340                 345                 350

Trp Asn Val Thr Ser Leu Glu Thr Leu Lys Ala Leu Leu Glu Val Asn
        355                 360                 365

Lys Gly His Glu Met Ser Pro Gln Val Ala Thr Leu Ile Asp Arg Phe
        370                 375                 380

Val Lys Gly Arg Gly Gln Leu Asp Lys Asp Thr Leu Asp Thr Leu Thr
385                 390                 395                 400

Ala Phe Tyr Pro Gly Tyr Leu Cys Ser Leu Ser Pro Glu Glu Leu Ser
                405                 410                 415

Ser Val Pro Pro Ser Ser Ile Trp Ala Val Arg Pro Gln Asp Leu Asp
            420                 425                 430

Thr Cys Asp Pro Arg Gln Leu Asp Val Leu Tyr Pro Lys Ala Arg Leu
        435                 440                 445

Ala Phe Gln Asn Met Asn Gly Ser Glu Tyr Phe Val Lys Ile Gln Ser
        450                 455                 460

Phe Leu Gly Gly Ala Pro Thr Glu Asp Leu Lys Ala Leu Ser Gln Gln
465                 470                 475                 480

Asn Val Ser Met Asp Leu Ala Thr Phe Met Lys Leu Arg Thr Asp Ala
                485                 490                 495

Val Leu Pro Leu Thr Val Ala Glu Val Gln Lys Leu Leu Gly Pro His
            500                 505                 510

Val Glu Gly Leu Lys Ala Glu Glu Arg His Arg Pro Val Arg Asp Trp
        515                 520                 525
```

```
Ile Leu Arg Gln Arg Gln Asp Asp Leu Asp Thr Leu Gly Leu Gly Leu
    530                 535                 540

Gln Gly
545

<210> SEQ ID NO 28
<211> LENGTH: 7071
<212> TYPE: DNA
<213> ORGANISM: Artificial Sequence
<220> FEATURE:
<223> OTHER INFORMATION: pKSV7 vector
<220> FEATURE:
<221> NAME/KEY: misc_feature
<222> LOCATION: 1769, 1859, 1871, 2717, 3473, 3482, 3494, 3560, 5445,
      6334
<223> OTHER INFORMATION: n = A,T,C or G

<400> SEQUENCE: 28
ctcgcggatt gttgatgatt acgaaaatat taagagcaca gactattaca cagaaaatca      60
agaattaaaa aaacgtagag agagtttgaa agaagtagtg aatacatgga aagaggggta     120
tcacgaaaaa agtaaagagg ttaataaatt aaagcgagag aatgatagtt tgaatgagca     180
gttgaatgta tcagagaaat tcaagatag tacagtgact ttatatcgtg ctgcgagggc     240
gaatttccct gggtttgaga aagggtttaa taggcttaaa gagaaattct ttaatgattc     300
caaattcgag cgtgtgggac agtttatgga tgttgtacag gataatgtcc agaaggtcga     360
tagaaagcgt gagaaacagc gtacagacga tttagagatg tagaggtact tttatgccga     420
gaaaactttt tgcgtgtgac agtccttaaa atatacttag agcgtaagcg aaagtagtag     480
cgacagctat taactttcgg ttgcaaagct ctaggatttt taatggacgc agcgcatcac     540
acgcaaaaag gaaattggaa taaatgcgaa atttgagatg ttaattaaag acctttttga     600
ggtctttttt tcttagattt ttggggttat ttaggggaga aaacataggg gggtactacg     660
acctcccccc taggtgtcca ttgtccattg tccaaacaaa taaataaata ttgggttttt     720
aatgttaaaa ggttgttttt tatgttaaag tgaaaaaaac agatgttggg aggtacagtg     780
atggttgtag atagaaaaga agagaaaaaa gttgctgtta ctttaagact tacacagaag     840
aaaatgagat attaaataga atccaagaaa aatataatat tagcaaatca gatgcaccgg     900
tattctaata aaaatatgy rmaggaggaa tacsgtgcat tttaacaaaa aaagatagac     960
agcactggca tgctgcctat ctatgactaa attttgttaa atgtattagc accgttatta    1020
tatcatgagc gaaaatgtaa taaagaaac tgaaaacaag aaaaattcaa gaggacgtaa    1080
ttggacattt gttttatatc cagaatcagc aaaagccgag tggttagagt atttaaaaga    1140
gttacacatt caatttgtag tgtctccatt acatgatagg gatactgata cagaagatag    1200
gatgaaaaaa gagcattatc atattctagt gatgtatgag ggtaataaat cttatgaaca    1260
gataaaaata attacagaag aattgaatgc gactattccg cagattgcag gaagtgtgaa    1320
aggtcttgtg agatatatgc ttcacatgga cgatcctaat aaatttaaat atcaaaaaga    1380
agatatgata gtttatggcg gtgtagatgt tgatgaatta ttaaagaaaa caacaacaga    1440
tagatataaa ttaattaaag aaatgattga gtttattgat gaacaaggaa tcgtagaatt    1500
taagagttta atggattatg caatgaagtt taaatttgat gattggttcc cgcttttatg    1560
tgataactcg gcgtatgtta ttcaagaata tataaaatca aatcggtata atctgaccg    1620 atagattttg aatttaagag tgtcacaaga cactcttttt tcgcaccaac gaaaactggt    1680
ttaagccgac tgcgcaaaag acataatcga ttcacaaaaa ataggcacac gaaaaacaag    1740
```

```
ttaagggatg cagtttatgc atcccttanc ttacttatta aataatttat agctattgaa    1800
aagagataag aattgttcaa gctaatattg tttaaatcgt ccattcctgc atgttttang    1860
gaawtgttaa nttgatttt tgtaatattt tctkgtatyc tttgttamcc catttcataa     1920
cgaaataatt atactttgt ttatctttgt gtgatattct tgattttttt ctacttaatc    1980
tgataagtga gctattcact ttaggtttag gatgaaaata ttctcttgga accatactta    2040
atatagaaat atcaacttct gccattaaaa gtaatgccaa tgagcgtttt gtatttaata    2100
atcttttagc aaacccgtat tccacgatta aataaatctc attagctata ctatcaaaaa    2160
caattttgcg tattatatcc gtacttatgt tataaggtat attaccatat attttatagg    2220
attggttttt aggaaattta aactgcaata tatccttgtt taaaacttgg aaattatcgt    2280
gatcttcctt caggttatga ccatctgtgc cagttcgtaa tgtctggtca actttccgac    2340
tctgagaaac ttctggaatc gctagagaat ttctggaatg ggattcagga gtggacagaa    2400
cgacacggat atatagtgga tgtgtcaaaa cgcataccat tttgaacgat gacctctaat    2460
aattgttaat catgttggtt acgtatttat taacttctcc tagtattagt aattatcatg    2520
gctgtcatgg cgcattaacg gaataaaggg tgtgcttaaa tcgggccatt ttgcgtaata    2580
agaaaaagga ttaattatga gcgaattgaa ttaataataa ggtaatagat ttacattaga    2640
aaatgaaagg ggattttatg cgtgagaatg ttacagtcta tcccggcaat agttaccctt    2700
attatywsga taagaangaa aggattttc gctacgctca atcctttaaa aaaacacaaa     2760
agaccacatt ttttaatgtg gtcttttatt cttcaactaa agcacccatt agttcaacaa    2820
acgaaaattg ataargtgg gatattttwa awataatwta tktatgttac agtaatattg     2880
acttttaaaa aaggattgat tctaatgaag aaagcagaca agtaagcctc ctaaattcac    2940
tttagataaa aatttaggag gcatatcaaa tgaactttaa taaaattgat ttagacaatt    3000
ggaagagaaa agagatattt aatcattatt tgaaccaaca aacgactttt agtataacca    3060
cagaaattga tattagtgtt ttataccgaa acataaaaca agaaggatat aaattttacc    3120
ctgcatttat tttcttagtg acaagggtga taaactcaaa tacagctttt agaactggtt    3180
acaatagcga cggagagtta ggttattggg ataagttaga gccactttat acaatttttg    3240
atggtgtatc taaaacattc tctggtattt ggactcctgt aaagaatgac ttcaaagagt    3300
tttatgattt ataccttcct gatgtagaga aatataatgg ttcggggaaa ttgtttccca    3360
aaacacctat acctgaaaat gcttttctc tttctattat tccatggact tcatttactg    3420
ggtttaactt aaatatcaat aataatagta attaccttct acccattatt acngcaggaa    3480
anttcattaa taanggtaat tcaatatatt taccgctatc tttacaggta catcattctg    3540
tttgtgatgg ttatcatgcn ggattgttta tgaactctat tcaggaattg tcagataggc    3600
ctaatgactg gctttatat atgagataat gccgactgta cttttacrg tcggttttct     3660 aacgatmcat taataggtmc gaaaaagcma cttttttksc gcttaaaacc agtcatacca    3720
ataacttaag ggtaactagc ctcgccggaa agagcgaaaa tgcctcacat ttgtgccacc    3780 taaaaggag cgatttacat atgagttatg cagtttgtag aatgcaaaaa gtgaaatcag     3840
ctgcattaat gaatcggcca acgcgcgggg agaggcggtt tgcgtattgg gcgctcttcc    3900
gcttcctcgc tcactgactc gctgcgctcg gtcgttcggc tgcggcgagc ggtatcagct    3960
cactcaaagg cggtaatacg gttatccaca gaatcagggg ataacgcagg aaagaacatg    4020
tgagcaaaag gccagcaaaa ggccaggaac cgtaaaaagg ccgcgttgct ggcgtttttc    4080
cataggctcc gcccccctga cgagcatcac aaaaatcgac gctcaagtca gaggtggcga    4140
```

```
aacccgacag gactataaag ataccaggcg tttccccctg gaagctccct cgtgcgctct   4200
cctgttccga ccctgccgct taccggatac ctgtccgcct ttctcccttc gggaagcgtg   4260
gcgctttctc atagctcacg ctgtaggtat ctcagttcgg tgtaggtcgt tcgctccaag   4320
ctgggctgtg tgcacgaacc ccccgttcag cccgaccgct gcgccttatc cggtaactat   4380
cgtcttgagt ccaacccggt aagacacgac ttatcgccac tggcagcagc cactggtaac   4440
aggattagca gagcgaggta tgtaggcggt gctacagagt tcttgaagtg gtggcctrss   4500
yacksskmyc ctagaagaac agtatttggt atctgcgctc tgctgaagcc agttaccttc   4560
ggaaaaagag ttggtagctc ttgatccggc aaamaaacca ccgctggtag cggtggtttt   4620
tttgtttgca agcagcagat tacgcgcaga aaaaaggat ctcaagaaga tcctttgatc   4680
ttttctacgg ggtctgacgc tcagtggaac gaaaactcac gttaagggat tttggtcatg   4740
agattatcaa aaaggatctt cacctagatc cttttaaatt aaaaatgaag ttttaaatca   4800
atctaaagta tatatgagta aacttggtct gacagttacc aatgcttaat cagtgaggca   4860
cctatctcag cgatctgtct atttcgttca tccatagttg cctgactccc cgtcgtgtag   4920
ataactacga tacgggaggg cttaccatct ggccccagtg ctgcaatgat accgcgagac   4980
ccacgctcac cggctccaga tttatcagca ataaccagc cagccggaag ggccgagcgc   5040
agaagtggtc ctgcaacttt atccgcctcc atccagtcta ttaattgttg ccgggaagct   5100
agagtaagta gttcgccagt taatagtttg cgcaacgttg ttgccattgc tacaggcatc   5160
gtggtgtcac gctcgtcgtt tggtatggct tcattcagct ccggttccca acgatcaagg   5220
cgagttacat gatcccccat gttgtgcaaa aaagcggtta gctccttcgg tcctccgatc   5280
gttgtcagaa gtaagttggc cgcagtgtta tcactcatgg ttatggcagc actgcataat   5340
tctcttactg tcatgccatc cgtaagatgc ttttctgtga ctggtgrkka stcwcmcmag   5400
tcattctgag aatagtgtat gcggcgaccg agttgctctt gcccnggsgt caatacggga   5460
taataccgcs ccacatagca raactttaaa agtgctcatc attggaaaac gttcttcggg   5520
gcgaaaactc tcaaggatct taccgctgtt gagatccagt tcgatgtaac ccactcgtgc   5580
acccaactga tcttcagcat cttttacttt caccagcgtt tctgggtgag caaaaacagg   5640
aaggcaaaat gccgcaaaaa agggaataag ggcgacacgg aaatgttgaa tactcatact   5700
cttcctttt caatattatt gaagcattta tcagggttat tgtctcatga gcggatacat   5760
atttgaatgt atttagaaaa ataaacaaat aggggttccg cgcacatttc cccgaaaagt   5820
gccacctgac gtctaagaaa ccattattat catgacatta acctataaaa ataggcgtat   5880
cacgaggccc tttcgtctcg cgcgtttcgg tgatgacggt gaaaacctct gacacatgca   5940
gctcccggag acgtcacag cttgtctgta agcggatgcc gggagcagac aagcccgtca   6000
gggcgcgtca gcgggtgttg gcgggtgtcg ggctggctt aactatgcgg catcagagca   6060
gattgtactg agagtgcacm atatgcggtg tgaaataccg cacagatgcg taaggagaaa   6120
ataccgcatc aggcgccatt cgccattcag gctgcgcaac tgttgggaag ggcgatcggt   6180
gcgggcctct tcgctattac gccagctggc gaaaggggga tgtgctgcaa ggcgattaag   6240
ttgggtaacg ccagggtttt yccagtcacg acgttgtaaa acgacggcca gtgccaagct   6300
tgcatgcctg caggtcgact ctagaggatc cccgggtac cgagctcgaa ttcgtaatca   6360
tgtcatagct gtttcctgtg tgaaattgtt atccgctcac aattccacac aacatacgag   6420
ccggaagcat aaagtgtaaa gcctggggtg cctaatgagt gagctaactc acattaattg   6480
cgttgcgctc actgcccgct ttccagtcgg gaaacctgtc gtgccagctg gactaaaagg   6540
```

-continued

| | |
|---|---|
| catgcaattt cataatcaaa gagagcgaaa aagtagaacg aatgatgata ttgaccatga | 6600 |
| gcgaacacgt gaaaattatg atttgaaaaa tgataaaaat attgattaca acgaacgtgt | 6660 |
| caaagaaatt attgaatcac aaaaaacagg tacaagaaaa acgaggaaag atgctgttct | 6720 |
| tgtaaatgag ttgctagtaa catctgaccg agatttttt gagcaactgg atcagtacaa | 6780 |
| gaaagatact gtatttcata acaggaact gcaagaagtt aaggatgagt tacagaaggc | 6840 |
| aaataagcag ttacagagtg aatagagca tatgaggtct acgaacccct ttgattatga | 6900 |
| aaatgagcgt acaggtttgt tctctggacg tgaagagact ggtagaaaga tattaactgc | 6960 |
| tgatgaattt gaacgcctgc aagaaacaat ctcttcgaac ggattgttga tgattacgaa | 7020 |
| atataagagc ccgactattc ccagaaatca gaattaaaaa cgtagagaga g | 7071 |

<210> SEQ ID NO 29
<211> LENGTH: 6055
<212> TYPE: DNA
<213> ORGANISM: Artificial Sequence
<220> FEATURE:
<223> OTHER INFORMATION: pINT vector

<400> SEQUENCE: 29

| | |
|---|---|
| agatctccaa aaataaacag gtggtggtat taatgaagat aaaaaaatta gcaaacggta | 60 |
| aatattgtgt tcgcctacgt ataaaagtcg atggtgaatg gaaagaaaag cgtttgacag | 120 |
| atacaagtga aacaaactta atgtataaag catctaaatt attaaaacaa gttcagcatg | 180 |
| atagtagttc tctgaaagaa tggaacttca agaattttta tacgctattc atgaaaacat | 240 |
| ttaaagatgg gaaaagtagt caatctacta ttaatttata cgatcttgct tataatcaat | 300 |
| tcgttgatta tttcgatgaa aaattaaat ttaattcgat tgatgcggtt caatatcaac | 360 |
| aatttattaa tcatttatct gtagactatg caatatccac tgtagacacc agacaccgca | 420 |
| aaattagagc gatttttaac aaggctgttc atttaggtta catgaagaaa acccccacta | 480 |
| taggggctca tataagcgga caggacgtag cgaaaaataa agcacaattt atggaaacag | 540 |
| acaaagttca tttactatta gaagaacttg caaaatttca ttctatatca cgagcagtta | 600 |
| tctttctagc tgtccagaca ggcatgaggt tcgaagaaat tattgcacta acaaagaagg | 660 |
| atattaattt cactaaacgt tcaataactg tgaataaagc ttgggattac aagtacacta | 720 |
| atacattcat tgataccaaa acaaaaaaat cacgagtgat ctatattgat aactctaccg | 780 |
| ctcaatattt acattcgtat ttaaattggc atactgaata tatgaaggaa catgctatta | 840 |
| agaatccatt tgatgttatta ttcatcactt accacaataa gccagtagac aacgcgtctt | 900 |
| gtaataaagc tttgaagaag atatgtagta caatcaattc tgaaccagtg acattacaca | 960 |
| agctacgaca tacgcataca ggcttatgtg tagaagcggg tatggatatt atttatgtag | 1020 |
| ctgataggct tggtcatgat gacattaata caacattaaa atactatagt catctaagct | 1080 |
| ctaatttaag acaacataat cagtccaaag tagatgcttt tttcacacta aaaacagatg | 1140 |
| aaaataccac aaattttacc acaaatgcca caaaacaac ggaataacct aggataactt | 1200 |
| cgtataatgt atgctatacg aagttatatg catgggtatt atacgatata aaaaaaactc | 1260 |
| caaaacattc atccgcccct taatatcaag gcttttcaac gttttagaga tttctttaca | 1320 |
| ttactatttta acgtcctgag agggattaac acacactgat ataaagccat ttaggatata | 1380 |
| tataccacaa ataataccac aaacatttta tgtaataata atattatttt attattacat | 1440 |
| tgaaatataat attcgttata aatagttttt atatcaagat gtttttctc aaggttttta | 1500 |
| taaaatgact ttaattcttt tgtttcaagt agtccagaga agatttttc aacagcgttc | 1560 |

```
ttctttccct ccacgcatgc gacgtcaata cgactcacta tagggcgaat tgggtaccgg      1620
gccccccctc gaggtcgacg gtatcgataa gcttgatatc gaattcctgc agcccggggg      1680
atccactagt tctagagcgg ccgccaccgc ggtggagctc cagcttttgt tccctttagt      1740
gagggttaat taaataactt cgtataatgt atgctatacg aagttatgcg atcgcctctc      1800
gcctgtcccc tcagttcagt aatttcctgc atttgcctgt ttccagtcgg tagatattcc      1860
acaaaacagc agggaagcag cgcttttccg ctgcataacc ctgcttcggg gtcattatag      1920
cgattttttc ggtatatcca tcctttttcg cacgatatac aggattttgc caaagggttc      1980
gtgtagactt tccttggtgt atccaacggc gtcagccggg caggataggt gaagtaggcc      2040
cacccgcgag cgggtgttcc ttcttcactg tcccttattc gcacctggcg gtgctcaacg      2100
ggaatcctgc tctgcgaggc tggccggcta ccgccggcgt aacagatgag ggcaagcggc      2160
ggagaattac aacttatatc gtatggggct gacttcaggt gctacatttg aagagataaa      2220
ttgcactgaa atctagaaat attttatctg attaataaga tgatcttctt gagatcgttt      2280
tggtctgcgc gtaatctctt gctctgaaaa cgaaaaaacc gccttgcagg gcggttttc      2340 gaaggttctc tgagctacca actctttgaa ccgaggtaac tggcttggag gagcgcagtc      2400
accaaaactt gtcctttcag tttagcctta accggcgcat gacttcaaga ctaactcctc      2460
taaatcaatt accagtggct gctgccagtg gtgcttttgc atgtctttcc gggttggact      2520
caagacgata gttaccggat aaggcgcagc ggtcggactg aacggggggt tcgtgcatac      2580
agtccagctt ggagcgaact gcctacccgg aactgagtgt caggcgtgga atgagacaaa      2640
cgcggccata acagcggaat gacaccggta aaccgaaagg caggaacagg agagcgcacg      2700
agggagccgc caggggaaaa cgcctggtat ctttatagtc ctgtcgggtt tcgccaccac      2760
tgatttgagc gtcagatttc gtgatgcttg tcagggggc ggagcctatg gaaaaacggc      2820
tttgccgcgg ccctctcact tccctgttaa gtatcttcct ggcatcttcc aggaaatctc      2880
cgccccgttc gtaagccatt tccgctcgcc gcagtcgaac gaccgagcgt agcgagtcag      2940
tgagcgagga agcggaatat atcctgtatc acatattctg ctgacgcacc ggtgcagcct      3000
tttttctcct gccacatgaa gcacttcact gacaccctca tcagtgccaa catagtaagc      3060
cagtatacac tccgctagcg ctgatgtccg gcggtgcttt tgccgttacg caccaccccg      3120
tcagtagctg aacaggaggg acagctgata gaaacagaag ccactggagc acctcaaaaa      3180
caccatcata cactaaatca gtaagttggc agcatcaccc gacgcacttt gcgccgaata      3240
aatacctgtg acgaagatc acttcgcaga ataaataaat cctggtgtcc ctgttgatac      3300
cgggaagccc tgggccaact tttggcgaaa atgagacgtt gatcggcacg taagaggttc      3360
caactttcac cataatgaaa taagatcact accggcgta ttttttgagt tatcgagatt      3420
ttcaggagct aaggaagcta aaatggagaa aaaaatcact ggatatacca ccgttgatat      3480
atcccaatgg catcgtaaag aacattttga ggcatttcag tcagttgctc aatgtaccta      3540
taaccagacc gttcagctgg atattacggc cttttttaaag accgtaaaga aaataagca      3600 caagttttat ccggccttta ttcacattct tgcccgcctg atgaatgctc atccggaatt      3660
ccgtatggca atgaaagacg gtgagctggt gatatgggat agtgttcacc cttgttacac      3720
cgttttccat gagcaaactg aaacgttttc atcgctctgg agtgaatacc acgacgattt      3780
ccggcagttt ctacacatat attcgcaaga tgtggcgtgt tacggtgaaa acctggccta      3840
tttccctaaa gggtttattg agaatatgtt tttcgtctca gccaatccct gggtgagttt      3900
caccagtttt gatttaaacg tggccaatat ggacaacttc ttcgccccg ttttcaccat      3960
```

```
gggcaaatat tatacgcaag gcgacaaggt gctgatgccg ctggcgattc aggttcatca  4020
tgccgtttgt gatggcttcc atgtcggcag aatgcttaat gaattacaac agtactgcga  4080
tgagtggcag gcggggcgt aattttttta aggcagttat tggtgccctt aaacgcctgg   4140
ttgctacgcc tgaataagtg ataataagcg gatgaatggc agaaattcga agcaaattc   4200
gacccggtcg tcggttcagg gcagggtcgt taaatagcga cgtctaagaa accattatta  4260
tcatgacatt aacctataaa aataggcgta tcacgaggcc ctttcgtctc gcgcgtttcg  4320
gtgatgacgg tgaaaacctc tgacacatgc agctcccgga gacggtcaca gcttgtctgt  4380
aagcggatgc cggagcaga caagcccgtc agggcgcgtc agcgggtgtt ggcgggtgtc   4440
ggggctggct taactatgcg gcatcagagc agattgtact gagagtgcac aatcgcatcc  4500
gattgcagta taaatttaac gatcactcat catgttcata tttatcagag ctcgtgctat  4560
aattatacta attttataag gaggaaaaaa tatgggcatt tttagtattt ttgtaatcag  4620
cacagttcat tatcaaccaa acaaaaaata agtggttata atgaatcgtt aataagcaaa  4680
attcatataa ccaaattaaa gagggttata atgaacgaga aaatataaa acacagtcaa   4740
aactttatta cttcaaaaca taatatagat aaaataatga caaatataag attaaatgaa  4800
catgataata tctttgaaat cggctcagga aaaggccatt ttacccttga attagtaaag  4860
aggtgtaatt tcgtaactgc cattgaaata gaccataaat tatgcaaaac tacagaaaat  4920
aaacttgttg atcacgataa tttccaagtt ttaaacaagg atatattgca gtttaaattt  4980
cctaaaaacc aatcctataa aatatatggt aatataccct ataacataag tacgatata   5040
atacgcaaaa ttgtttttga tagtatagct aatgagattt atttaatcgt ggaatacggg  5100
tttgctaaaa gattattaaa tacaaaacgc tcattggcat tacttttaat ggcagaagtt  5160
gatatttcta tattaagtat ggttccaaga gaatattttc atcctaaacc taaagtgaat  5220
agctcactta tcagattaag tagaaaaaaa tcaagaatat cacacaaaga taaacaaaag  5280
tataattatt tcgttatgaa atgggttaac aaagaataca agaaaatatt tacaaaaaat  5340
caatttaaca attccttaaa acatgcagga attgacgatt taaacaatat tagctttgaa  5400
caattcttat ctcttttcaa tagctataaa ttatttaata agtaagttaa gggatgcata  5460
aactgcatcc cttaacttgt ttttcgtgtg cccgatcggt gcgggcctct tcgctattac  5520
gccagctggc gaaaggggga tgtgctgcaa ggcgattaag ttgggtaacg ccagggtttt  5580
cccagtcacg acgttgtaaa acgacggcca gtgccaagct agctttcgat catcataatt  5640
ctgtctcatt atataacatc ctccatacct tctattatag aataccataa actcatctgg  5700
caattcattt cgagtcacga agaacggaaa aactgccggt ttttatatta caaatgtatt  5760
aagtttttct attaacaaaa aacaataggt tcccatagc gaaagttgtt gattaacgtt   5820
cacatcccac ttacactata aaggtttacc cagcaataca tctcaagccc taagaataca  5880
cgttcgcttt tcaactgtta cagaattatt acaaatagtt ggtatagtcc tctttagcct  5940
ttggagctat tatctcatca tttgtttttt aggtgaaaac tgggtaaact tagtattaat  6000
caatataaaa ttaattctca aatacttaat tacgtactgg gatttctga aaaaa         6055
```

<210> SEQ ID NO 30
<211> LENGTH: 5
<212> TYPE: PRT
<213> ORGANISM: Listeria monocytogenes

<400> SEQUENCE: 30

Lys Lys Arg Arg Lys
1               5

```
<210> SEQ ID NO 31
<211> LENGTH: 6
<212> TYPE: PRT
<213> ORGANISM: Listeria monocytogenes

<400> SEQUENCE: 31

Asp Glu Trp Glu Glu Glu
 1               5

<210> SEQ ID NO 32
<211> LENGTH: 12
<212> TYPE: PRT
<213> ORGANISM: Listeria monocytogenes

<400> SEQUENCE: 32

Asp Arg Leu Ala Asp Leu Arg Asp Arg Gly Thr Gly
 1               5                  10

<210> SEQ ID NO 33
<211> LENGTH: 13
<212> TYPE: PRT
<213> ORGANISM: Listeria monocytogenes

<400> SEQUENCE: 33

Ile Lys Lys Lys Arg Arg Lys Ala Ile Ala Ser Ser Asp
 1               5                  10

<210> SEQ ID NO 34
<211> LENGTH: 5
<212> TYPE: PRT
<213> ORGANISM: Listeria monocytogenes

<400> SEQUENCE: 34

Thr Asp Ser Glu Asp
 1               5

<210> SEQ ID NO 35
<211> LENGTH: 227
<212> TYPE: DNA
<213> ORGANISM: Listeria monocytogenes

<400> SEQUENCE: 35
aagcttggga agcagttggg gttaactgat taacaaatgt tagagaaaaa ttaattctcc      60
aagtgatatt cttaaaataa ttcatgaata tttttttctta tattagctaa ttaagaagat    120
aattaactgc taatccaatt tttaacggaa taaattagtg aaaatgaagg ccgaattttc    180
cttgttctaa aaaggttgta ttagcgtatc acgaggaggg agtataa                  227

<210> SEQ ID NO 36
<211> LENGTH: 1953
<212> TYPE: DNA
<213> ORGANISM: Artificial Sequence
<220> FEATURE:
<223> OTHER INFORMATION: Fusion protein coding sequence

<400> SEQUENCE: 36
gtgggattaa atagatttat gcgtgcgatg atggtagttt tcattactgc caactgcatt      60
acgattaacc ccgacataat atttgcagcg acagatagcg aagattccag tctaaacaca    120
gatgaatggg aagaagaaaa aacagaagag cagccaagcg aggtaaatac gggaccaaga    180
tacgaaactg cacgtgaagt aagttcacgt gatattgagg aactagaaaa atcgaataaa    240
gtgaaaaata cgaacaaagc agacctaata gcaatgttga aagcaaaagc agagaaaggt    300
```

```
ggatcccgta cattagcagg tgaaacaggt caagaagcag caccacttga cggtgtatta      360
acgaatccac caaatatatc aagtttaagt ccacgtcaat tattaggttt tccatgtgca      420
gaagtttcag gtttaagtac agaacgtgtc cgtgagttag cagttgcatt agcacaaaaa      480
aacgttaaat tatctacaga acagttacgt tgtttagccc atagattaag cgaaccacca      540
gaagacttag atgcacttcc tttagacctt cttttattct taaatccaga tgcattttca      600
ggaccacaag catgtacacg ttttttagt cgaattacaa aagccaatgt tgatttatta       660
cctcgtgggg ctcctgaaag acaacgttta ttacctgctg cattagcatg ctggggtgtt      720
cgcggtagct tattaagtga agccgatgtt cgtgctttag ggggtttagc atgtgattta      780
cctggtcgtt tcgttgcaga atcagcagaa gtgttattac cgagattagt ttcatgccca      840 ggaccttag  atcaagatca acaagaggca gctagagcag ctcttcaagg aggagcccca      900
ccatatggcc caccaagtac atggagtgtt tctacaatgg atgcgttaag aggtttatta      960
ccggttttag gacaaccaat tattcgtagt attccacaag gcattgtagc agcatggcgt     1020
caacgtagtt ctcgtgatcc gtcttggcga caaccagaac gtacaattct acgtccaaga    1080
tttcgtagag aagtagaaaa aacggcgtgt cctagtggca aaaaagcacg tgaaattgat    1140
gaaagtttaa ttttttataa aaaatgggaa ttagaagcat gtgtcgatgc agcattacta    1200
gctacacaaa tggatcgtgt taatgctatt ccattcacat atgaacaatt agatgtttta    1260
aagcataaat tagacgaatt atatccacaa ggttatccag aatcagttat tcaacattta    1320
ggttacttat ttttaaaaat gagtccgaaa gacatacgca aatggaatgt tacaagttta    1380
gaaacattaa aagcgctttt agaagttaac aaaggtcatg aaatgagtcc acaagttgct    1440
acgttaattg atagattcgt taaaggccgt ggtcaattag ataaagatac tttagataca    1500
ttaacagcat tttatcctgg ctacttatgc agtttatcac cagaagaatt aagttccgtt    1560
ccaccgagta gtatctgggc agttcgtccg caagatttag atacatgcga cccacgtcaa    1620
ttagatgttt tatatccaaa agcaagatta gctttccaaa atatgaacgg tagtgaatat    1680
ttcgtaaaaa ttcaatcctt tttaggtggt gcaccaactg aagatctaaa agcattaagc    1740
caacaaaatg taagtatgga tttagctacg tttatgaaat tacgtacaga tgcagttcta    1800
ccattaacag ttgcagaagt tcaaaaatta ttaggtccac acgtagaagg attaaaagca    1860
gaagaacgtc accgtccagt tcgcgattgg atttttacgtc aacgtcaaga tgatttagat    1920
acattaggtt taggtttaca aggctaagag ctc                                 1953
```

<210> SEQ ID NO 37
<211> LENGTH: 1920
<212> TYPE: DNA
<213> ORGANISM: Listeria monocytogenes

<400> SEQUENCE: 37

```
gtgggattaa atagatttat gcgtgcgatg atggtagttt tcattactgc caactgcatt       60
acgattaacc ccgacataat atttgcagcg acagatagcg aagattccag tctaaacaca      120
gatgaatggg aagaagaaaa aacagaagag cagccaagcg aggtaaatac gggaccaaga      180
tacgaaactg cacgtgaagt aagttcacgt gatattgagg aactagaaaa atcgaataaa      240
gtgaaaaata cgaacaaagc agacctaata gcaatgttga agcaaaaagc agagaaaggt      300
ccgaataaca ataataacaa cggtgagcaa acaggaaatg tggctataaa tgaagaggct      360
tcaggagtcg accgaccaac tctgcaagtg gagcgtcgtc atccaggtct gtcatcggat      420
agcgcagcgg aaattaaaaa aagaagaaaa gccatagcgt cgtcggatag tgagcttgaa      480
```

```
agccttactt atccagataa accaacaaaa gcaaataaga gaaaagtggc gaaagagtca    540
gttgtggatg cttctgaaag tgacttagat tctagcatgc agtcagcaga cgagtctaca    600
ccacaacctt taaaagcaaa tcaaaaacca ttttttcccta agtatttaa aaaaataaaa    660 gatgcgggga atgggtacg tgataaaatc gacgaaaatc ctgaagtaaa gaaagcgatt    720
gttgataaaa gtgcagggtt aattgaccaa ttattaacca aaaagaaaag tgaagaggta    780
aatgcttcgg acttcccgcc accacctacg gatgaagagt taagacttgc tttgccagag    840
acaccgatgc ttctcggttt taatgctcct actccatcgg aaccgagctc attcgaattt    900
ccgccgccac ctacggatga agagttaaga cttgctttgc cagagacgcc aatgcttctt    960
ggttttaatg ctcctgctac atcggaaccg agctcattcg aatttccacc gcctccaaca   1020
gaagatgaac tagaaattat gcgggaaaca gcaccttcgc tagattctag ttttacaagc   1080
ggggatttag ctagtttgag aagtgctatt aatcgccata gcgaaaattt ctctgatttc   1140
ccactaatcc caacagaaga agagttgaac gggagaggcg gtagaccaac atctgaagaa   1200
tttagttcgc tgaatagtgg tgattttaca gatgacgaaa acagcgagac aacagaagaa   1260
gaaattgatc gcctagctga tttaagagat agaggaacag gaaaacactc aagaaatgcg   1320
ggttttttac cattaaatcc atttattagt agccctgttc cttcattaac tccaaaggta   1380
ccgaaaataa gcgcgccggc tctgataagt gacataacta aaaaagcgcc atttaagaat   1440
ccatcacagc cattaaatgt gtttaataaa aaaactacaa cgaaaacagt gactaaaaaa   1500 ccaaccctg taaagaccgc accaaagcta gcagaacttc ctgccacaaa accacaagaa   1560
accgtactta gggaaaataa aacacccttt atagaaaaac aagcagaaac aaacaagcag   1620
tcaatcaata tgccgagcct accagtaatc caaaaagaag ctacagagag cgataaagag   1680
gaaatgaaac cacaaaccga ggaaaaaatg gtagaggaaa gcgaatcagc taataacgca   1740
aacgaaaaaa atcgttctgc tggcattgaa gaaggaaaac taattgctaa aagtgcagaa   1800
gacgaaaaag cgaaggaaga accagggaac catacgacgt taattcttgc aatgttagct   1860
attggcgtgt tctcttttagg ggcgtttatc aaaattattc aattaagaaa aaataattaa   1920
```

<210> SEQ ID NO 38
<211> LENGTH: 639
<212> TYPE: PRT
<213> ORGANISM: Listeria monocytogenes

<400> SEQUENCE: 38

```
Val Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly Pro Asn Asn Asn Asn Asn Gly Glu Gln Thr Gly
            100                 105                 110

Asn Val Ala Ile Asn Glu Glu Ala Ser Gly Val Asp Arg Pro Thr Leu
        115                 120                 125
```

-continued

Gln Val Glu Arg Arg His Pro Gly Leu Ser Ser Asp Ser Ala Ala Glu
    130                 135                 140

Ile Lys Lys Arg Arg Lys Ala Ile Ala Ser Ser Asp Ser Glu Leu Glu
145                 150                 155                 160

Ser Leu Thr Tyr Pro Asp Lys Pro Thr Lys Ala Asn Lys Arg Lys Val
                165                 170                 175

Ala Lys Glu Ser Val Val Asp Ala Ser Glu Ser Asp Leu Asp Ser Ser
            180                 185                 190

Met Gln Ser Ala Asp Glu Ser Thr Pro Gln Pro Leu Lys Ala Asn Gln
        195                 200                 205

Lys Pro Phe Phe Pro Lys Val Phe Lys Lys Ile Lys Asp Ala Gly Lys
    210                 215                 220

Trp Val Arg Asp Lys Ile Asp Glu Asn Pro Glu Val Lys Lys Ala Ile
225                 230                 235                 240

Val Asp Lys Ser Ala Gly Leu Ile Asp Gln Leu Leu Thr Lys Lys Lys
                245                 250                 255

Ser Glu Glu Val Asn Ala Ser Asp Phe Pro Pro Pro Thr Asp Glu
            260                 265                 270

Glu Leu Arg Leu Ala Leu Pro Glu Thr Pro Met Leu Leu Gly Phe Asn
        275                 280                 285

Ala Pro Thr Pro Ser Glu Pro Ser Ser Phe Glu Phe Pro Pro Pro Pro
290                 295                 300

Thr Asp Glu Glu Leu Arg Leu Ala Leu Pro Glu Thr Pro Met Leu Leu
305                 310                 315                 320

Gly Phe Asn Ala Pro Ala Thr Ser Glu Pro Ser Ser Phe Glu Phe Pro
                325                 330                 335

Pro Pro Pro Thr Glu Asp Glu Leu Glu Ile Met Arg Glu Thr Ala Pro
            340                 345                 350

Ser Leu Asp Ser Ser Phe Thr Ser Gly Asp Leu Ala Ser Leu Arg Ser
        355                 360                 365

Ala Ile Asn Arg His Ser Glu Asn Phe Ser Asp Phe Pro Leu Ile Pro
    370                 375                 380

Thr Glu Glu Glu Leu Asn Gly Arg Gly Gly Arg Pro Thr Ser Glu Glu
385                 390                 395                 400

Phe Ser Ser Leu Asn Ser Gly Asp Phe Thr Asp Glu Asn Ser Glu
                405                 410                 415

Thr Thr Glu Glu Glu Ile Asp Arg Leu Ala Asp Leu Arg Asp Arg Gly
            420                 425                 430

Thr Gly Lys His Ser Arg Asn Ala Gly Phe Leu Pro Leu Asn Pro Phe
        435                 440                 445

Ile Ser Ser Pro Val Pro Ser Leu Thr Pro Lys Val Pro Lys Ile Ser
    450                 455                 460

Ala Pro Ala Leu Ile Ser Asp Ile Thr Lys Lys Ala Pro Phe Lys Asn
465                 470                 475                 480

Pro Ser Gln Pro Leu Asn Val Phe Asn Lys Lys Thr Thr Lys Thr
                485                 490                 495

Val Thr Lys Lys Pro Thr Pro Val Lys Thr Ala Pro Lys Leu Ala Glu
            500                 505                 510

Leu Pro Ala Thr Lys Pro Gln Glu Thr Val Leu Arg Glu Asn Lys Thr
        515                 520                 525

Pro Phe Ile Glu Lys Gln Ala Glu Thr Asn Lys Gln Ser Ile Asn Met
    530                 535                 540

Pro Ser Leu Pro Val Ile Gln Lys Glu Ala Thr Glu Ser Asp Lys Glu

```
            545                 550                 555                 560
Glu Met Lys Pro Gln Thr Glu Glu Lys Met Val Glu Glu Ser Glu Ser
                565                 570                 575

Ala Asn Ala Asn Gly Lys Asn Arg Ser Ala Gly Ile Glu Glu Gly
            580                 585                 590

Lys Leu Ile Ala Lys Ser Ala Glu Asp Glu Lys Ala Lys Glu Glu Pro
            595                 600                 605

Gly Asn His Thr Thr Leu Ile Leu Ala Met Leu Ala Ile Gly Val Phe
            610                 615                 620

Ser Leu Gly Ala Phe Ile Lys Ile Ile Gln Leu Arg Lys Asn Asn
625                 630                 635

<210> SEQ ID NO 39
<211> LENGTH: 533
<212> TYPE: DNA
<213> ORGANISM: Artificial Sequence
<220> FEATURE:
<223> OTHER INFORMATION: Expression construct

<400> SEQUENCE: 39
ggtaccggga agcagttggg gttaactgat taacaaatgt tagagaaaaa ttaattctcc    60
aagtgatatt cttaaaataa ttcatgaata ttttttctta tattagctaa ttaagaagat   120
aattaactgc taatccaatt tttaacggaa taaattagtg aaaatgaagg ccgaattttc   180
cttgttctaa aaaggttgta ttagcgtatc acgaggaggg agtataagtg ggattaaata   240
gatttatgcg tgcgatgatg gtagttttca ttactgccaa ctgcattacg attaaccccg   300
acataatatt tgcagcgaca gatagcgaag attccagtct aaacacagat gaatgggaag   360
aagaaaaaac agaagagcag ccaagcgagg taaatacggg accagatac gaaactgcac    420 gtgaagtaag ttcacgtgat attgaggaac tagaaaaatc gaataaagtg aaaaatacga   480
acaaagcaga cctaatagca atgttgaaag caaaagcaga gaaaggtgga tcc          533

<210> SEQ ID NO 40
<211> LENGTH: 100
<212> TYPE: PRT
<213> ORGANISM: Artificial Sequence
<220> FEATURE:
<223> OTHER INFORMATION: ActA-N100

<400> SEQUENCE: 40

Val Gly Leu Asn Arg Phe Met Arg Ala Met Met Val Val Phe Ile Thr
  1               5                  10                  15

Ala Asn Cys Ile Thr Ile Asn Pro Asp Ile Ile Phe Ala Ala Thr Asp
             20                  25                  30

Ser Glu Asp Ser Ser Leu Asn Thr Asp Glu Trp Glu Glu Glu Lys Thr
         35                  40                  45

Glu Glu Gln Pro Ser Glu Val Asn Thr Gly Pro Arg Tyr Glu Thr Ala
     50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                 85                  90                  95

Ala Glu Lys Gly
            100

<210> SEQ ID NO 41
<211> LENGTH: 648
<212> TYPE: PRT
```

<213> ORGANISM: Artificial Sequence
<220> FEATURE:
<223> OTHER INFORMATION: Fusion protein

<400> SEQUENCE: 41

```
Val Gly Leu Asn Arg Phe Met Arg Ala Met Met Val Val Phe Ile Thr
 1               5                  10                  15
Ala Asn Cys Ile Thr Ile Asn Pro Asp Ile Ile Phe Ala Ala Thr Asp
             20                  25                  30
Ser Glu Asp Ser Ser Leu Asn Thr Asp Glu Trp Glu Glu Glu Lys Thr
         35                  40                  45
Glu Glu Gln Pro Ser Glu Val Asn Thr Gly Pro Arg Tyr Glu Thr Ala
     50                  55                  60
Arg Glu Val Ser Ser Arg Asp Ile Glu Glu Leu Glu Lys Ser Asn Lys
 65                  70                  75                  80
Val Lys Asn Thr Asn Lys Ala Asp Leu Ile Ala Met Leu Lys Ala Lys
                 85                  90                  95
Ala Glu Lys Gly Gly Ser Arg Thr Leu Ala Gly Glu Thr Gly Gln Glu
            100                 105                 110
Ala Ala Pro Leu Asp Gly Val Leu Thr Asn Pro Pro Asn Ile Ser Ser
        115                 120                 125
Leu Ser Pro Arg Gln Leu Leu Gly Phe Pro Cys Ala Glu Val Ser Gly
    130                 135                 140
Leu Ser Thr Glu Arg Val Arg Glu Leu Ala Val Ala Leu Ala Gln Lys
145                 150                 155                 160
Asn Val Lys Leu Ser Thr Glu Gln Leu Arg Cys Leu Ala His Arg Leu
                165                 170                 175
Ser Glu Pro Pro Glu Asp Leu Asp Ala Leu Pro Leu Asp Leu Leu Leu
            180                 185                 190
Phe Leu Asn Pro Asp Ala Phe Ser Gly Pro Gln Ala Cys Thr Arg Phe
        195                 200                 205
Phe Ser Arg Ile Thr Lys Ala Asn Val Asp Leu Leu Pro Arg Gly Ala
    210                 215                 220
Pro Glu Arg Gln Arg Leu Leu Pro Ala Ala Leu Ala Cys Trp Gly Val
225                 230                 235                 240
Arg Gly Ser Leu Leu Ser Glu Ala Asp Val Arg Ala Leu Gly Gly Leu
                245                 250                 255
Ala Cys Asp Leu Pro Gly Arg Phe Val Ala Glu Ser Ala Glu Val Leu
            260                 265                 270
Leu Pro Arg Leu Val Ser Cys Pro Gly Pro Leu Asp Gln Asp Gln Gln
        275                 280                 285
Glu Ala Ala Arg Ala Ala Leu Gln Gly Gly Gly Pro Pro Tyr Gly Pro
    290                 295                 300
Pro Ser Thr Trp Ser Val Ser Thr Met Asp Ala Leu Arg Gly Leu Leu
305                 310                 315                 320
Pro Val Leu Gly Gln Pro Ile Ile Arg Ser Ile Pro Gln Gly Ile Val
                325                 330                 335
Ala Ala Trp Arg Gln Arg Ser Ser Arg Asp Pro Ser Trp Arg Gln Pro
            340                 345                 350
Glu Arg Thr Ile Leu Arg Pro Arg Phe Arg Arg Glu Val Glu Lys Thr
        355                 360                 365
Ala Cys Pro Ser Gly Lys Lys Ala Arg Glu Ile Asp Glu Ser Leu Ile
    370                 375                 380
Phe Tyr Lys Lys Trp Glu Leu Glu Ala Cys Val Asp Ala Ala Leu Leu
385                 390                 395                 400
```

Ala Thr Gln Met Asp Arg Val Asn Ala Ile Pro Phe Thr Tyr Glu Gln
            405                 410                 415

Leu Asp Val Leu Lys His Lys Leu Asp Glu Leu Tyr Pro Gln Gly Tyr
            420                 425                 430

Pro Glu Ser Val Ile Gln His Leu Gly Tyr Leu Phe Leu Lys Met Ser
            435                 440                 445

Pro Glu Asp Ile Arg Lys Trp Asn Val Thr Ser Leu Glu Thr Leu Lys
            450                 455                 460

Ala Leu Leu Glu Val Asn Lys Gly His Glu Met Ser Pro Gln Val Ala
465                 470                 475                 480

Thr Leu Ile Asp Arg Phe Val Lys Gly Arg Gly Gln Leu Asp Lys Asp
                485                 490                 495

Thr Leu Asp Thr Leu Thr Ala Phe Tyr Pro Gly Tyr Leu Cys Ser Leu
            500                 505                 510

Ser Pro Glu Glu Leu Ser Ser Val Pro Pro Ser Ser Ile Trp Ala Val
            515                 520                 525

Arg Pro Gln Asp Leu Asp Thr Cys Asp Pro Arg Gln Leu Asp Val Leu
            530                 535                 540

Tyr Pro Lys Ala Arg Leu Ala Phe Gln Asn Met Asn Gly Ser Glu Tyr
545                 550                 555                 560

Phe Val Lys Ile Gln Ser Phe Leu Gly Gly Ala Pro Thr Glu Asp Leu
                565                 570                 575

Lys Ala Leu Ser Gln Gln Asn Val Ser Met Asp Leu Ala Thr Phe Met
            580                 585                 590

Lys Leu Arg Thr Asp Ala Val Leu Pro Leu Thr Val Ala Glu Val Gln
            595                 600                 605

Lys Leu Leu Gly Pro His Val Glu Gly Leu Lys Ala Glu Glu Arg His
            610                 615                 620

Arg Pro Val Arg Asp Trp Ile Leu Arg Gln Arg Gln Asp Asp Leu Asp
625                 630                 635                 640

Thr Leu Gly Leu Gly Leu Gln Gly
                645

<210> SEQ ID NO 42
<211> LENGTH: 81
<212> TYPE: DNA
<213> ORGANISM: Homo sapiens

<400> SEQUENCE: 42
gccatgacag aatataaatt agttgtagtt ggtgcagatg gtgttggtaa aagtgcatta    60
acaattcaat taattcaata a                                             81

<210> SEQ ID NO 43
<211> LENGTH: 26
<212> TYPE: PRT
<213> ORGANISM: Homo sapiens

<400> SEQUENCE: 43

Ala Met Thr Glu Tyr Lys Leu Val Val Val Gly Ala Asp Gly Val Gly
1               5                   10                  15

Lys Ser Ala Leu Thr Ile Gln Leu Ile Gln
            20                  25

<210> SEQ ID NO 44
<211> LENGTH: 2039
<212> TYPE: DNA
<213> ORGANISM: Artificial Sequence

```
<220> FEATURE:
<223> OTHER INFORMATION: Fusion protein coding sequence

<400> SEQUENCE: 44
gtgggattaa atagatttat gcgtgcgatg atggtagttt tcattactgc caactgcatt      60
acgattaacc ccgacataat atttgcagcg acagatagcg aagattccag tctaaacaca     120
gatgaatggg aagaagaaaa aacagaagag cagccaagcg aggtaaatac gggaccaaga     180
tacgaaactg cacgtgaagt aagttcacgt gatattgagg aactagaaaa atcgaataaa     240
gtgaaaaata cgaacaaagc agacctaata gcaatgttga agcaaaagc agagaaaggt      300
ggatcccgta cattagcagg tgaaacaggt caagaagcag caccacttga cggtgtatta     360
acgaatccac caaatatatc aagtttaagt ccacgtcaat tattaggttt tccatgtgca     420
gaagtttcag gtttaagtac agaacgtgtc cgtgagttag cagttgcatt agcacaaaaa     480
aacgttaaat tatctacaga acagttacgt tgtttagccc atagattaag cgaaccacca     540
gaagacttag atgcacttcc tttagacctt cttttattct taaatccaga tgcattttca     600
ggaccacaag catgtacacg ttttttttagt cgaattacaa agccaatgt tgatttatta    660
cctcgtgggg ctcctgaaag acaacgttta ttacctgctg cattagcatg ctggggtgtt     720
cgcggtagct tattaagtga agccgatgtt cgtgctttag ggggtttagc atgtgattta     780
cctggtcgtt tcgttgcaga atcagcagaa gtgttattac cgagattagt ttcatgccca     840
ggacctttag atcaagatca acaagaggca gctagagcag ctcttcaagg aggaggccca     900
ccatatggcc caccaagtac atggagtgtt tctacaatgg atgcgttaag aggtttatta     960
ccggttttag acaaccaat tattcgtagt attccacaag gcattgtagc agcatggcgt     1020
caacgtagtc tcgtgatcc gtcttggcga caaccagaac gtacaattct acgtccaaga    1080
tttcgtagag aagtagaaaa aacggcgtgt cctagtggca aaaaagcacg tgaaattgat    1140
gaaagtttaa tttttttataa aaatgggaa ttagaagcat gtgtcgatgc agcattacta    1200
gctacacaaa tggatcgtgt taatgctatt ccattcacat atgaacaatt agatgttta     1260
aagcataaat tagacgaatt atatccacaa ggttatccag aatcagttat tcaacatta     1320
ggttacttat tttttaaaaat gagtccagaa gacatacgca aatggaatgt tacaagttta    1380
gaaacattaa aagcgctttt agaagttaac aaaggtcatg aaatgagtcc acaagttgct    1440
acgttaattg atagattcgt taaaggccgt ggtcaattag ataaagatac tttagataca    1500
ttaacagcat tttatcctgg ctacttatgc agtttatcac cagaagaatt aagttccgtt    1560
ccaccgagta gtatctgggc agttcgtccg caagatttag atacatgcga cccacgtcaa    1620
ttagatgttt tatatccaaa agcaagatta gcttttccaaa atatgaacgg tagtgaatat    1680
ttcgtaaaaa ttcaatcctt tttaggtggt gcaccaactg aagatctaaa agcattaagc    1740
caacaaaatg taagtatgga tttagctacg tttatgaaat tacgtacaga tgcagttcta    1800
ccattaacag ttgcagaagt tcaaaaatta ttaggtccac acgtagaagg attaaaagca    1860
gaagaacgtc accgtccagt tcgcgattgg attttacgtc aacgtcaaga tgatttagat    1920
acattaggtt taggttaca aggcgccatg acagaatata aattagttgt agttggtgca    1980
gatggtgttg gtaaaagtgc attaacaatt caattaattc aataattaat taagagctc    2039

<210> SEQ ID NO 45
<211> LENGTH: 674
<212> TYPE: PRT
<213> ORGANISM: Artificial Sequence
<220> FEATURE:
<223> OTHER INFORMATION: Fusion protein
```

<400> SEQUENCE: 45

```
Val Gly Leu Asn Arg Phe Met Arg Ala Met Val Phe Ile Thr
 1               5                  10                  15
Ala Asn Cys Ile Thr Ile Asn Pro Asp Ile Ile Phe Ala Ala Thr Asp
             20                  25                  30
Ser Glu Asp Ser Ser Leu Asn Thr Asp Glu Trp Glu Glu Lys Thr
         35                  40                  45
Glu Glu Gln Pro Ser Glu Val Asn Thr Gly Pro Arg Tyr Glu Thr Ala
     50                  55                  60
Arg Glu Val Ser Ser Arg Asp Ile Glu Glu Leu Glu Lys Ser Asn Lys
 65                  70                  75                  80
Val Lys Asn Thr Asn Lys Ala Asp Leu Ile Ala Met Leu Lys Ala Lys
                 85                  90                  95
Ala Glu Lys Gly Gly Ser Arg Thr Leu Ala Gly Glu Thr Gly Gln Glu
            100                 105                 110
Ala Ala Pro Leu Asp Gly Val Leu Thr Asn Pro Asn Ile Ser Ser
            115                 120                 125
Leu Ser Pro Arg Gln Leu Leu Gly Phe Pro Cys Ala Glu Val Ser Gly
    130                 135                 140
Leu Ser Thr Glu Arg Val Arg Glu Leu Ala Val Ala Leu Ala Gln Lys
145                 150                 155                 160
Asn Val Lys Leu Ser Thr Glu Gln Leu Arg Cys Leu Ala His Arg Leu
                165                 170                 175
Ser Glu Pro Pro Glu Asp Leu Asp Ala Leu Pro Leu Asp Leu Leu Leu
            180                 185                 190
Phe Leu Asn Pro Asp Ala Phe Ser Gly Pro Gln Ala Cys Thr Arg Phe
            195                 200                 205
Phe Ser Arg Ile Thr Lys Ala Asn Val Asp Leu Leu Pro Arg Gly Ala
    210                 215                 220
Pro Glu Arg Gln Arg Leu Leu Pro Ala Ala Leu Ala Cys Trp Gly Val
225                 230                 235                 240
Arg Gly Ser Leu Leu Ser Glu Ala Asp Val Arg Ala Leu Gly Gly Leu
                245                 250                 255
Ala Cys Asp Leu Pro Gly Arg Phe Val Ala Glu Ser Ala Glu Val Leu
            260                 265                 270
Leu Pro Arg Leu Val Ser Cys Pro Gly Pro Leu Asp Gln Asp Gln Gln
            275                 280                 285
Glu Ala Ala Arg Ala Ala Leu Gln Gly Gly Pro Pro Tyr Gly Pro
    290                 295                 300
Pro Ser Thr Trp Ser Val Ser Thr Met Asp Ala Leu Arg Gly Leu Leu
305                 310                 315                 320
Pro Val Leu Gly Gln Pro Ile Ile Arg Ser Ile Pro Gln Gly Ile Val
                325                 330                 335
Ala Ala Trp Arg Gln Arg Ser Ser Arg Asp Pro Ser Trp Arg Gln Pro
            340                 345                 350
Glu Arg Thr Ile Leu Arg Pro Arg Phe Arg Arg Glu Val Glu Lys Thr
    355                 360                 365
Ala Cys Pro Ser Gly Lys Lys Ala Arg Glu Ile Asp Glu Ser Leu Ile
    370                 375                 380
Phe Tyr Lys Lys Trp Glu Leu Glu Ala Cys Val Asp Ala Ala Leu Leu
385                 390                 395                 400
Ala Thr Gln Met Asp Arg Val Asn Ala Ile Pro Phe Thr Tyr Glu Gln
                405                 410                 415
```

Leu Asp Val Leu Lys His Lys Leu Asp Glu Leu Tyr Pro Gln Gly Tyr
            420                 425                 430
Pro Glu Ser Val Ile Gln His Leu Gly Tyr Leu Phe Leu Lys Met Ser
            435                 440                 445
Pro Glu Asp Ile Arg Lys Trp Asn Val Thr Ser Leu Glu Thr Leu Lys
450                 455                 460
Ala Leu Leu Glu Val Asn Lys Gly His Glu Met Ser Pro Gln Val Ala
465                 470                 475                 480
Thr Leu Ile Asp Arg Phe Val Lys Gly Arg Gly Gln Leu Asp Lys Asp
            485                 490                 495
Thr Leu Asp Thr Leu Thr Ala Phe Tyr Pro Gly Tyr Leu Cys Ser Leu
            500                 505                 510
Ser Pro Glu Glu Leu Ser Ser Val Pro Pro Ser Ser Ile Trp Ala Val
            515                 520                 525
Arg Pro Gln Asp Leu Asp Thr Cys Asp Pro Arg Gln Leu Asp Val Leu
530                 535                 540
Tyr Pro Lys Ala Arg Leu Ala Phe Gln Asn Met Asn Gly Ser Glu Tyr
545                 550                 555                 560
Phe Val Lys Ile Gln Ser Phe Leu Gly Gly Ala Pro Thr Glu Asp Leu
            565                 570                 575
Lys Ala Leu Ser Gln Gln Asn Val Ser Met Asp Leu Ala Thr Phe Met
            580                 585                 590
Lys Leu Arg Thr Asp Ala Val Leu Pro Leu Thr Val Ala Glu Val Gln
            595                 600                 605
Lys Leu Leu Gly Pro His Val Glu Gly Leu Lys Ala Glu Glu Arg His
610                 615                 620
Arg Pro Val Arg Asp Trp Ile Leu Arg Gln Arg Gln Asp Asp Leu Asp
625                 630                 635                 640
Thr Leu Gly Leu Gly Leu Gln Gly Ala Met Thr Glu Tyr Lys Leu Val
            645                 650                 655
Val Val Gly Ala Asp Gly Val Gly Lys Ser Ala Leu Thr Ile Gln Leu
            660                 665                 670
Ile Gln

<210> SEQ ID NO 46
<211> LENGTH: 533
<212> TYPE: DNA
<213> ORGANISM: Artificial Sequence
<220> FEATURE:
<223> OTHER INFORMATION: Expression construct

<400> SEQUENCE: 46

```
aagcttggga agcagttggg gttaactgat taacaaatgt tagagaaaaa ttaattctcc        60
aagtgatatt cttaaaataa ttcatgaata ttttttctta tattagctaa ttaagaagat       120
aattaactgc taatccaatt tttaacggaa taaattagtg aaaatgaagg ccgaattttc       180
cttgttctaa aaaggttgta ttagcgtatc acgaggaggg agtataagtg ggattaaata       240
gatttatgcg tgcgatgatg gtagttttca ttactgccaa ctgcattacg attaaccccg       300
acataatatt tgcagcgaca gatagcgaag attccagtct aaacacagat gaatgggaag       360
aagaaaaaac agaagagcag ccaagcgagg taaatacggg accaagatac gaaactgcac       420
gtgaagtaag ttcacgtgat attgaggaac tagaaaaatc gaataaagtg aaaaatacga       480
acaaagcaga cctaatagca atgttgaaag caaaagcaga gaaaggtgga tcc             533
```

-continued

<210> SEQ ID NO 47
<211> LENGTH: 102
<212> TYPE: PRT
<213> ORGANISM: Artificial Sequence
<220> FEATURE:
<223> OTHER INFORMATION: Fusion protein

<400> SEQUENCE: 47

Val Gly Leu Asn Arg Phe Met Arg Ala Met Met Val Val Phe Ile Thr
 1               5                  10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Glu Lys Thr
            35                  40                  45

Glu Glu Gln Pro Ser Glu Val Asn Thr Gly Pro Arg Tyr Glu Thr Ala
        50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly Gly Ser
            100

<210> SEQ ID NO 48
<211> LENGTH: 1590
<212> TYPE: DNA
<213> ORGANISM: Listeria monocytogenes

<400> SEQUENCE: 48
atgaaaaaaa taatgctagt ttttattaca cttatattag ttagtctacc aattgcgcaa     60
caaactgaag caaggatgc atctgcattc aataaagaaa attcaatttc atccatggca    120
ccaccagcat ctccgcctgc aagtcctaag acgccaatcg aaaagaaaca cgcggatgaa    180
atcgataagt atatacaagg attggattac aataaaaaca atgtattagt ataccacgga    240
gatgcagtga caaatgtgcc gccaagaaaa ggttacaaag atggaaatga atatattgtt    300
gtggagaaaa agaagaaatc catcaatcaa ataatgcag acattcaagt tgtgaatgca    360
atttcgagcc taacctatcc aggtgctctc gtaaaagcga attcggaatt agtagaaaat    420
caaccagatg ttctccctgt aaaacgtgat tcattaacac tcagcattga tttgccaggt    480
atgactaatc aagacaataa aatcgttgta aaaaatgcca ctaaatcaaa cgttaacaac    540
gcagtaaata cattagtgga agatggaat gaaaaatatg ctcaagctta tccaaatgta    600
agtgcaaaaa ttgattatga tgacgaaatg gcttacagtg aatcacaatt aattgcgaaa    660
tttggtacag catttaaagc tgtaaataat agcttgaatg taaacttcgg cgcaatcagt    720
gaagggaaaa tgcaagaaga agtcattagt tttaaacaaa tttactataa cgtgaatgtt    780
aatgaaccta aagaccttc cagattttc ggcaaagctg ttactaaaga gcagttgcaa    840
gcgcttggag tgaatgcaga aaatcctcct gcatatatct caagtgtggc gtatggccgt    900
caagtttatt tgaaattatc aactaattcc catagtacta agtaaaagc tgcttttgat    960 gctgccgtaa gcggaaaatc tgtctcaggt gatgtagaac taacaaatat catcaaaaat   1020
tcttccttca aagccgtaat ttacggaggt tccgcaaaag atgaagttca atcatcgac   1080 ggcaacctcg gagacttacg cgatattttg aaaaaggcg ctacttttaa tcgagaaaca   1140
ccaggagttc ccattgctta tacaacaaac ttcctaaaag acaatgaatt agctgttatt   1200
aaaaacaact cagaatatat tgaaacaact tcaaagctt atacagatgg aaaaattaac   1260

-continued

| atcgatcact ctggaggata cgttgctcaa ttcaacattt cttgggatga agtaaattat | 1320 |
| gatcctgaag gtaacgaaat tgttcaacat aaaaactgga gcgaaaacaa taaaagcaag | 1380 |
| ctagctcatt tcacatcgtc catctatttg cctggtaacg cgagaaatat taatgtttac | 1440 |
| gctaaagaat gcactggttt agcttgggaa tggtggagaa cggtaattga tgaccggaac | 1500 |
| ttaccacttg tgaaaaatag aaatatctcc atctggggca ccacgcttta tccgaaatat | 1560 |
| agtaataaag tagataatcc aatcgaataa | 1590 |

<210> SEQ ID NO 49
<211> LENGTH: 1593
<212> TYPE: DNA
<213> ORGANISM: Artificial Sequence
<220> FEATURE:
<223> OTHER INFORMATION: Codon-optimized sequence

<400> SEQUENCE: 49

| atgaaaaaaa taatgctagt ctttattaca ttaattttag taagtctacc aattgcacaa | 60 |
| caaaccgaag ctaaagatgc atcagcgttc aacaagaaa attcaattag ttcaatggcc | 120 |
| ccaccagctt ctccaccagc atctccaaaa acaccaattg aaaaaaaaca tgcagacgaa | 180 |
| attgataaat atattcaagg tttagattac aataagaata cgttttagt ataccacggc | 240 |
| gatgcagtaa caaatgtacc tccaagaaaa ggctataaag acggaaatga atatattgtt | 300 |
| gttgaaaaaa aaagaaatc tattaatcaa aacaatgccg acatccaagt agttaacgcg | 360 |
| attagctcat tgacgtatcc aggcgcccctt gtaaaagcta actctgaatt agtggaaaat | 420 |
| caaccagacg tacttccagt caaacgtgat agtctaacct aagtattga tttaccagga | 480 |
| atgacaaatc aagataacaa aattgttgtt aaaaatgcaa ctaaatccaa tgtaaataat | 540 |
| gcagttaaca cattagtaga acgatggaac gaaaaatacg cacaggcata cccaaatgta | 600 |
| tcagctaaaa ttgattacga cgacgaaatg gcctactcag aaagtcaatt aattgctaaa | 660 |
| tttggtacag cattcaaagc agtcaataat agtttaaatg taaattttgg agcgatctct | 720 |
| gaaggaaaga tgcaggaaga agtaaatttca ttcaaacaaa tttattataa tgttaacgta | 780 |
| aatgaaccaa cccgtccttc ccgtttcttt ggcaaagcag ttactaaaga acaattacaa | 840 |
| gcactaggtg tgaatgcaga aaacccaccg gcatatattt caagcgtcgc ttacggacga | 900 |
| caagtttact taaaattatc tacaaacagt catagtacaa aagtaaaagc agcattcgat | 960 |
| gcagctgtgt caggaaaatc agttagtgga gatgtagaat taaccaatat tattaaaaat | 1020 |
| tcgagtttta agctgttat ttatggaggt tctgcaaaag atgaagtaca aattattgac | 1080 |
| ggaaacttag gcgatttacg tgacatttta aaaaaggcg caacatttaa tagagaaaca | 1140 |
| ccaggggttc caattgctta taccaactaat ttttcttaag ataatgaact tgcagtaatt | 1200 |
| aaaaacaatt cagaatacat tgaaacaact tcgaaagcat atacagacgg aaaaattaat | 1260 |
| attgatcact caggagggta cgttgcacaa tttaatatta gttgggatga agtaaactat | 1320 |
| gatccagaag gcaatgaaat tgtacaacat aaaaattggt ctgaaaataa caatctaaa | 1380 |
| ctagcacact ttaccagttc tatctattta ccaggaaatg ctcgcaatat taatgtttac | 1440 |
| gcaaaagaat gtaccggatt agcatgggaa tggtggcgca cagttattga cgaccgcaat | 1500 |
| cttcctctag taaaaacag aaacatcagc atttggggaa caacgcttta tccgaaatac | 1560 |
| agtaataaag ttgataatcc aattgaagga tcc | 1593 |

<210> SEQ ID NO 50
<211> LENGTH: 1593
<212> TYPE: DNA

<213> ORGANISM: Artificial Sequence
<220> FEATURE:
<223> OTHER INFORMATION: Codon-optimized sequence

<400> SEQUENCE: 50

```
atgaaaaaaa taatgctagt ctttattaca ttaattttag taagtctacc aattgcacaa      60
caaaccgaag ctaaagatgc atcagcgttc aacaaagaaa attcaattag ttcaatggcc     120
ccaccagctt ctccaccagc atctccaaaa acaccaattg aaaaaaaaca tgcagacgaa     180
attgataaat atattcaagg tttagattac aataagaata cgttttagt ataccacggc      240
gatgcagtaa caaatgtacc tccaagaaaa ggctataaag acggaaatga atatattgtt     300
gttgaaaaaa aaagaaatc tattaatcaa acaatgccg acatccaagt agttaacgcg       360
attagctcat tgacgtatcc aggcgccctt gtaaaagcta actctgaatt agtggaaaat     420
caaccagacg tacttccagt caaacgtgat agtctaacct aagtattga tttaccagga      480
atgcaaaatc aagataacaa aattgttgtt aaaaatgcaa ctaaatccaa tgtaaataat     540
gcagttaaca cattagtaga acgatggaac gaaaaatacg cacaggcata cccaaatgta    600
tcagctaaaa ttgattacga cgacgaaatg gcctactcag aaagtcaatt aattgctaaa    660
tttggtacag cattcaaagc agtcaataat agtttaaatg taaatttttgg agcgatctct   720
gaaggaaaga tgcaggaaga agtaatttca ttcaaacaaa tttattataa tgttaacgta    780
aatgaaccaa cccgtccttc ccgtttcttt ggcaaagcag ttactaaaga acaattacaa    840
gcactaggtg tgaatgcaga aaacccaccg gcatatattt caagcgtcgc ttacggacga    900
caagtttact taaaattatc tacaaacagt catagtacaa aagtaaaagc agcattcgat    960
gcagctgtgt caggaaaatc agttagtgga gatgtagaat taaccaatat tattaaaaat   1020
tcgagtttta agctgttat ttatggaggt tctgcaaaag atgaagtaca aattattgac    1080
ggaaacttag gcgatttacg tgacatttta aaaaaaggcg caacatttaa tagagaaaca   1140
ccaggggttc caattgctta tacaactaat tttcttaaag ataatgaact tgcagtaatt   1200
aaaaacaatt cagaatacat tgaaacaact tcgaaagcat atacagacgg aaaaattaat   1260
attgatcact caggagggta cgttgcacaa tttaatatta gttgggatga agtaaactat   1320
gatccagaag gcaatgaaat tgtacaacat aaaaaattggt ctgaaaataa caaatctaaa   1380
ctagcacact ttaccagttc tatctattta ccaggaaatg ctcgcaatat taatgtttac   1440
gcaaaagaat gtaccggatt agcatgggaa ttttttcgca cagttattga cgaccgcaat   1500
cttcctctag taaaaacag aaacatcagc atttggggaa caacgctta tccgaaatac    1560
agtaataaag ttgataatcc aattgaagga tcc                                1593
```

<210> SEQ ID NO 51
<211> LENGTH: 177
<212> TYPE: DNA
<213> ORGANISM: Listeria monocytogenes

<400> SEQUENCE: 51

```
atgaaaaaaa taatgctagt ttttattaca cttatattag ttagtctacc aattgcgcaa     60
caaactgaag caaaggatgc atctgcattc aataaagaaa attcaatttc atccatggca    120
ccaccagcat ctccgcctgc aagtcctaag acgccaatcg aaaagaaaca cgcggat       177
```

<210> SEQ ID NO 52
<211> LENGTH: 177
<212> TYPE: DNA
<213> ORGANISM: Artificial Sequence
<220> FEATURE:

<223> OTHER INFORMATION: Codon-optimized sequence

<400> SEQUENCE: 52

```
atgaaaaaaa ttatgttagt ttttattaca ttaattttag ttagtttacc aattgcacaa    60
caaacagaag caaagatgc aagtgcattt aataaagaaa atagtattag tagtatggca   120
ccaccagcaa gtccaccagc aagtccaaaa acaccaattg aaaaaaaaca tgcagat     177
```

<210> SEQ ID NO 53
<211> LENGTH: 59
<212> TYPE: PRT
<213> ORGANISM: Listeria monocytogenes

<400> SEQUENCE: 53

```
Met Lys Lys Ile Met Leu Val Phe Ile Thr Leu Ile Leu Val Ser Leu
  1               5                  10                  15

Pro Ile Ala Gln Gln Thr Glu Ala Lys Asp Ala Ser Ala Phe Asn Lys
             20                  25                  30

Glu Asn Ser Ile Ser Ser Met Ala Pro Pro Ala Ser Pro Pro Ala Ser
         35                  40                  45

Pro Lys Thr Pro Ile Glu Lys Lys His Ala Asp
     50                  55
```

<210> SEQ ID NO 54
<211> LENGTH: 1830
<212> TYPE: DNA
<213> ORGANISM: Artificial Sequence
<220> FEATURE:
<223> OTHER INFORMATION: Fusion protein coding sequence

<400> SEQUENCE: 54

```
atgaaaaaaa ttatgttagt ttttattaca ttaattttag ttagtttacc aattgcacaa    60
caaacagaag caaagatgc aagtgcattt aataaagaaa atagtattag tagtatggca   120
ccaccagcaa gtccaccagc aagtccaaaa acaccaattg aaaaaaaaca tgcagatgga   180
tcccgtacat tagcaggtga acaggtcaa gaagcagcac cacttgacgg tgtattaacg   240
aatccaccaa atatatcaag tttaagtcca cgtcaattat taggttttcc atgtgcagaa   300
gtttcaggtt taagtacaga acgtgtccgt gagttagcag ttgcattagc acaaaaaaac   360
gttaaattat ctacagaaca gttacgttgt ttagcccata gattaagcga ccaccagaa   420
gacttagatg cacttccttt agaccttctt ttattcttaa atccagatgc attttcagga   480
ccacaagcat gtacacgttt tttagtcga attacaaaag ccaatgttga tttattacct   540
cgtgggggctc ctgaaagaca acgtttatta cctgctgcat tagcatgctg gggtgttcgc   600
ggtagcttat taagtgaagc cgatgttcgt gctttagggg gttagcatg tgatttacct   660
ggtcgtttcg ttgcagaatc agcagaagtg ttattaccga gattagtttc atgcccagga   720
cctttagatc aagatcaaca agaggcagct gagcagctc tcaaggagg ggcccacca   780
tatggcccac caagtacatg gagtgttttct acaatggatg cgttaagagg tttattaccg   840
gttttaggac aaccaattat tcgtagtatt ccacaaggca ttgtagcagc atggcgtcaa   900
cgtagttctc gtgatccgtc ttggcgacaa ccagaacgta caattctacg tccaagattt   960
cgtagagaag tagaaaaaac ggcgtgtcct agtggcaaaa aagcacgtga attgatgaa   1020
agtttaattt tttataaaaa atgggaatta gaagcatgtg tcgatgcagc attactagct   1080
acacaaatgg atcgtgttaa tgctattcca ttcacatatg aacaattaga tgttttaaag   1140
cataaaattag acgaattata tccacaaggt tatccagaat cagttattca acatttaggt   1200
```

-continued

```
tacttatttt taaaaatgag tccagaagac atacgcaaat ggaatgttac aagtttagaa    1260
acattaaaag cgcttttaga agttaacaaa ggtcatgaaa tgagtccaca agttgctacg    1320
ttaattgata gattcgttaa aggccgtggt caattagata aagatacttt agatacatta    1380
acagcatttt atcctggcta cttatgcagt ttatcaccag aagaattaag ttccgttcca    1440
ccgagtagta tctgggcagt tcgtccgcaa gatttagata catgcgaccc acgtcaatta    1500
gatgttttat atccaaaagc aagattagct ttccaaaata tgaacggtag tgaatatttc    1560
gtaaaaattc aatcctttt aggtggtgca ccaactgaag atctaaaagc attaagccaa    1620
caaaatgtaa gtatggattt agctacgttt atgaaattac gtacagatgc agttctacca    1680
ttaacagttg cagaagttca aaaattatta ggtccacacg tagaaggatt aaaagcagaa    1740
gaacgtcacc gtccagttcg cgattggatt tacgtcaac gtcaagatga tttagataca    1800
ttaggtttag gtttacaagg ctaagagctc                                    1830
```

<210> SEQ ID NO 55
<211> LENGTH: 607
<212> TYPE: PRT
<213> ORGANISM: Artificial Sequence
<220> FEATURE:
<223> OTHER INFORMATION: Fusion protein

<400> SEQUENCE: 55

```
Met Lys Lys Ile Met Leu Val Phe Ile Thr Leu Ile Leu Val Ser Leu
  1               5                  10                  15

Pro Ile Ala Gln Gln Thr Glu Ala Lys Asp Ala Ser Ala Phe Asn Lys
             20                  25                  30

Glu Asn Ser Ile Ser Ser Met Ala Pro Pro Ala Ser Pro Pro Ala Ser
         35                  40                  45

Pro Lys Thr Pro Ile Glu Lys Lys His Ala Asp Gly Ser Arg Thr Leu
     50                  55                  60

Ala Gly Glu Thr Gly Gln Glu Ala Ala Pro Leu Asp Gly Val Leu Thr
 65                  70                  75                  80

Asn Pro Pro Asn Ile Ser Ser Leu Ser Pro Arg Gln Leu Leu Gly Phe
                 85                  90                  95

Pro Cys Ala Glu Val Ser Gly Leu Ser Thr Glu Arg Val Arg Glu Leu
            100                 105                 110

Ala Val Ala Leu Ala Gln Lys Asn Val Lys Leu Ser Thr Glu Gln Leu
        115                 120                 125

Arg Cys Leu Ala His Arg Leu Ser Glu Pro Pro Glu Asp Leu Asp Ala
    130                 135                 140

Leu Pro Leu Asp Leu Leu Leu Phe Leu Asn Pro Asp Ala Phe Ser Gly
145                 150                 155                 160

Pro Gln Ala Cys Thr Arg Phe Phe Ser Arg Ile Thr Lys Ala Asn Val
                165                 170                 175

Asp Leu Leu Pro Arg Gly Ala Pro Glu Arg Gln Arg Leu Leu Pro Ala
            180                 185                 190

Ala Leu Ala Cys Trp Gly Val Arg Gly Ser Leu Leu Ser Glu Ala Asp
        195                 200                 205

Val Arg Ala Leu Gly Gly Leu Ala Cys Asp Leu Pro Gly Arg Phe Val
    210                 215                 220

Ala Glu Ser Ala Glu Val Leu Leu Pro Arg Leu Val Ser Cys Pro Gly
225                 230                 235                 240

Pro Leu Asp Gln Asp Gln Gln Glu Ala Ala Arg Ala Ala Leu Gln Gly
                245                 250                 255
```

```
Gly Gly Pro Pro Tyr Gly Pro Pro Ser Thr Trp Ser Val Ser Thr Met
            260                 265                 270

Asp Ala Leu Arg Gly Leu Leu Pro Val Leu Gly Gln Pro Ile Ile Arg
        275                 280                 285

Ser Ile Pro Gln Gly Ile Val Ala Ala Trp Arg Gln Arg Ser Ser Arg
290                 295                 300

Asp Pro Ser Trp Arg Gln Pro Glu Arg Thr Ile Leu Arg Pro Arg Phe
305                 310                 315                 320

Arg Arg Glu Val Glu Lys Thr Ala Cys Pro Ser Gly Lys Lys Ala Arg
                325                 330                 335

Glu Ile Asp Glu Ser Leu Ile Phe Tyr Lys Lys Trp Glu Leu Glu Ala
            340                 345                 350

Cys Val Asp Ala Ala Leu Leu Ala Thr Gln Met Asp Arg Val Asn Ala
        355                 360                 365

Ile Pro Phe Thr Tyr Glu Gln Leu Asp Val Leu Lys His Lys Leu Asp
370                 375                 380

Glu Leu Tyr Pro Gln Gly Tyr Pro Glu Ser Val Ile Gln His Leu Gly
385                 390                 395                 400

Tyr Leu Phe Leu Lys Met Ser Pro Glu Asp Ile Arg Lys Trp Asn Val
                405                 410                 415

Thr Ser Leu Glu Thr Leu Lys Ala Leu Leu Glu Val Asn Lys Gly His
            420                 425                 430

Glu Met Ser Pro Gln Val Ala Thr Leu Ile Asp Arg Phe Val Lys Gly
        435                 440                 445

Arg Gly Gln Leu Asp Lys Asp Thr Leu Asp Thr Leu Thr Ala Phe Tyr
450                 455                 460

Pro Gly Tyr Leu Cys Ser Leu Ser Pro Glu Glu Leu Ser Ser Val Pro
465                 470                 475                 480

Pro Ser Ser Ile Trp Ala Val Arg Pro Gln Asp Leu Asp Thr Cys Asp
                485                 490                 495

Pro Arg Gln Leu Asp Val Leu Tyr Pro Lys Ala Arg Leu Ala Phe Gln
            500                 505                 510

Asn Met Asn Gly Ser Glu Tyr Phe Val Lys Ile Gln Ser Phe Leu Gly
        515                 520                 525

Gly Ala Pro Thr Glu Asp Leu Lys Ala Leu Ser Gln Gln Asn Val Ser
530                 535                 540

Met Asp Leu Ala Thr Phe Met Lys Leu Arg Thr Asp Ala Val Leu Pro
545                 550                 555                 560

Leu Thr Val Ala Glu Val Gln Lys Leu Leu Gly Pro His Val Glu Gly
                565                 570                 575

Leu Lys Ala Glu Glu Arg His Arg Pro Val Arg Asp Trp Ile Leu Arg
            580                 585                 590

Gln Arg Gln Asp Asp Leu Asp Thr Leu Gly Leu Gly Leu Gln Gly
        595                 600                 605

<210> SEQ ID NO 56
<211> LENGTH: 1830
<212> TYPE: DNA
<213> ORGANISM: Artificial Sequence
<220> FEATURE:
<223> OTHER INFORMATION: Fusion protein coding sequence

<400> SEQUENCE: 56
atgaaaaaaa taatgctagt ttttattaca cttatattag ttagtctacc aattgcgcaa      60
caaactgaag caaggatgc atctgcattc aataagaaa attcaatttc atccatggca      120
```

| | |
|---|---|
| ccaccagcat ctccgcctgc aagtcctaag acgccaatcg aaaagaaaca cgcggatgga | 180 |
| tcccgtacat tagcaggtga aacaggtcaa gaagcagcac cacttgacgg tgtattaacg | 240 |
| aatccaccaa atatatcaag tttaagtcca cgtcaattat taggttttcc atgtgcagaa | 300 |
| gtttcaggtt taagtacaga acgtgtccgt gagttagcag ttgcattagc acaaaaaaac | 360 |
| gttaaattat ctacagaaca gttacgttgt ttagcccata gattaagcga accaccagaa | 420 |
| gacttagatg cacttccttt agaccttctt ttattcttaa atccagatgc attttcagga | 480 |
| ccacaagcat gtacacgttt ttttagtcga attacaaaag ccaatgttga tttattacct | 540 |
| cgtggggctc ctgaaagaca acgttttatta cctgctgcat tagcatgctg gggtgttcgc | 600 |
| ggtagcttat taagtgaagc cgatgttcgt gctttagggg gtttagcatg tgatttacct | 660 |
| ggtcgtttcg ttgcagaatc agcagaagtg ttattaccga gattagtttc atgcccagga | 720 |
| cctttagatc aagatcaaca agaggcagct agagcagctc ttcaaggagg aggcccacca | 780 |
| tatggcccac caagtacatg gagtgtttct acaatggatg cgttaagagg tttattaccg | 840 |
| gttttaggac aaccaattat tcgtagtatt ccacaaggca ttgtagcagc atggcgtcaa | 900 |
| cgtagttctc gtgatccgtc ttggcgacaa ccagaacgta caattctacg tccaagattt | 960 |
| cgtagagaag tagaaaaaac ggcgtgtcct agtggcaaaa aagcacgtga aattgatgaa | 1020 |
| agtttaatttt tttataaaaa atgggaatta gaagcatgtg tcgatgcagc attactagct | 1080 |
| acacaaatgg atcgtgttaa tgctattcca ttcacatatg aacaattaga tgttttaaag | 1140 |
| cataaattag acgaattata tccacaaggt tatccagaat cagttattca acatttaggt | 1200 |
| tactatttt taaaaatgag tccagaagac atacgcaaat ggaatgttac aagtttagaa | 1260 |
| acattaaaag cgcttttaga agttaacaaa ggtcatgaaa tgagtccaca agttgctacg | 1320 |
| ttaattgata gattcgttaa aggccgtggt caattagata aagatacttt agatacatta | 1380 |
| acagcatttt atcctggcta cttatgcagt ttatcaccag aagaattaag ttccgttcca | 1440 |
| ccgagtagta tctgggcagt tcgtccgcaa gatttagata catgcgaccc acgtcaatta | 1500 |
| gatgttttat atccaaaagc aagattagct ttccaaaata tgaacggtag tgaatatttc | 1560 |
| gtaaaaattc aatcctttt aggtggtgca ccaactgaag atctaaaagc attaagccaa | 1620 |
| caaaatgtaa gtatggattt agctacgttt atgaaattac gtacagatgc agttctacca | 1680 |
| ttaacagttg cagaagttca aaaattatta ggtccacacg tagaaggatt aaaagcagaa | 1740 |
| gaacgtcacc gtccagttcg cgattggatt ttacgtcaac gtcaagatga tttagataca | 1800 |
| ttaggtttag gtttacaagg ctaagagctc | 1830 |

<210> SEQ ID NO 57
<211> LENGTH: 237
<212> TYPE: DNA
<213> ORGANISM: Listeria monocytogenes

<400> SEQUENCE: 57

| | |
|---|---|
| ggtacctcct ttgattagta tattcctatc ttaaagttac ttttatgtgg aggcattaac | 60 |
| atttgttaat gacgtcaaaa ggatagcaag actagaataa agctataaag caagcatata | 120 |
| atattgcgtt tcatctttag aagcgaattt cgccaatatt ataattatca aaagagaggg | 180 |
| gtggcaaacg gtatttggca ttattaggtt aaaaaatgta gaaggagagt gaaaccc | 237 |

<210> SEQ ID NO 58
<211> LENGTH: 99
<212> TYPE: DNA
<213> ORGANISM: Artificial Sequence
<220> FEATURE:

<223> OTHER INFORMATION: Codon-optimized sequence

<400> SEQUENCE: 58
atgaaaaaac gtaaagtttt aattccatta atggcattaa gtacaatttt agttagtagt    60
acaggtaatt tagaagttat tcaagcagaa gttggatcc    99

<210> SEQ ID NO 59
<211> LENGTH: 33
<212> TYPE: PRT
<213> ORGANISM: Bacillus anthracis

<400> SEQUENCE: 59

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Gly
            20                  25                  30

Ser

<210> SEQ ID NO 60
<211> LENGTH: 336
<212> TYPE: DNA
<213> ORGANISM: Artificial Sequence
<220> FEATURE:
<223> OTHER INFORMATION: Expression construct

<400> SEQUENCE: 60
ggtacctcct tgattagta tattcctatc ttaaagttac ttttatgtgg aggcattaac     60
atttgttaat gacgtcaaaa ggatagcaag actagaataa agctataaag caagcatata   120
atattgcgtt tcatctttag aagcgaattt cgccaatatt ataattatca aaagagaggg   180
gtggcaaacg gtatttggca ttattaggtt aaaaaatgta aaggagagt gaaacccatg    240 aaaaaacgta agttttaat tccattaatg gcattaagta caattttagt tagtagtaca    300
ggtaatttag aagttattca agcagaagtt ggatcc                             336

<210> SEQ ID NO 61
<211> LENGTH: 70
<212> TYPE: PRT
<213> ORGANISM: Listeria monocytogenes

<400> SEQUENCE: 61

Met Asn Met Lys Lys Ala Thr Ile Ala Ala Thr Ala Gly Ile Ala Val
1               5                   10                  15

Thr Ala Phe Ala Ala Pro Thr Ile Ala Ser Ala Ser Thr Val Val Val
            20                  25                  30

Glu Ala Gly Asp Thr Leu Trp Gly Ile Ala Gln Ser Lys Gly Thr Thr
        35                  40                  45

Val Asp Ala Ile Lys Lys Ala Asn Asn Leu Thr Thr Asp Lys Ile Val
    50                  55                  60

Pro Gly Gln Lys Leu Gln
65                  70

<210> SEQ ID NO 62
<211> LENGTH: 447
<212> TYPE: DNA
<213> ORGANISM: Artificial Sequence
<220> FEATURE:
<223> OTHER INFORMATION: Expression construct

<400> SEQUENCE: 62
ggtacctcct tgattagta tattcctatc ttaaagttac ttttatgtgg aggcattaac     60

```
atttgttaat gacgtcaaaa ggatagcaag actagaataa agctataaag caagcatata    120
atattgcgtt tcatctttag aagcgaattt cgccaatatt ataattatca aaagagaggg    180
gtggcaaacg gtatttggca ttattaggtt aaaaaatgta gaaggagagt gaaacccatg    240
aatatgaaaa aagctacgat tgcagctaca gccggcattg ccgtaacagc ttttgcagca    300
ccaactattg cctcagcctc tacagttgtt gtcgaagcag gagacacatt atggggaatc    360
gcacaatcaa aaggtacaac ggttgatgct attaaaaaag cgaataattt aacaacagat    420
aaaatcgtgc caggtcaaaa actgcag                                        447

<210> SEQ ID NO 63
<211> LENGTH: 28
<212> TYPE: DNA
<213> ORGANISM: Artificial Sequence
<220> FEATURE:
<223> OTHER INFORMATION: Primer

<400> SEQUENCE: 63
cgcctgcagg taaataatga ggttgctg                                        28

<210> SEQ ID NO 64
<211> LENGTH: 29
<212> TYPE: DNA
<213> ORGANISM: Artificial Sequence
<220> FEATURE:
<223> OTHER INFORMATION: Primer

<400> SEQUENCE: 64
cgcggatcct taattatacg cgaccgaag                                       29

<210> SEQ ID NO 65
<211> LENGTH: 1683
<212> TYPE: DNA
<213> ORGANISM: Artificial Sequence
<220> FEATURE:
<223> OTHER INFORMATION: Expression construct

<400> SEQUENCE: 65
ggtacctcct ttgattagta tattcctatc ttaaagttac ttttatgtgg aggcattaac     60
atttgttaat gacgtcaaaa ggatagcaag actagaataa agctataaag caagcatata    120
atattgcgtt tcatctttag aagcgaattt cgccaatatt ataattatca aaagagaggg    180
gtggcaaacg gtatttggca ttattaggtt aaaaaatgta gaaggagagt gaaacccatg    240
aatatgaaaa aagctacgat tgcagctaca gccggcattg ccgtaacagc ttttgcagca    300
ccaactattg cctcagcctc tacagttgtt gtcgaagcag gagacacatt atggggaatc    360
gcacaatcaa aaggtacaac ggttgatgct attaaaaaag cgaataattt aacaacagat    420
aaaatcgtgc caggtcaaaa actgcaggta aataatgagg ttgctgctgc tgaaaaaaca    480
gagaaatctg ttagcgcaac ttggttaaac gtccgtactg gcgctggtgt tgataacagt    540
attattacgt ccatcaaagg tggaacaaaa gtaactgttg aaacaaccga atctaacggc    600
tggcacaaaa ttacttacaa cgatggaaaa actggtttcg ttaacggtaa atacttaact    660
gacaaagcag taagcactcc agttgcacca acacaagaag tgaaaaaaga aactactact    720
caacaagctg cacctgttgc agaaacaaaa actgaagtaa aacaaactac acaagcaact    780
acacctgcgc ctaaagtagc agaaacgaaa gaaactccag taatagatca aaatgctact    840
acacacgctg tcaaaagcgg tgacactatt tgggctttat ccgtaaaata cggtgtttct    900
gttcaagaca ttatgtcatg gaataattta tcttcttctt ctatttatgt aggtcaaaag    960
```

```
cttgctatta acaaaactgc taacacagct actccaaaag cagaagtgaa aacggaagct    1020
ccagcagctg aaaacaagc agctccagta gttaaagaaa atactaacac aaatactgct     1080
actacagaga aaaagaaac agcaacgcaa caacaaacag cacctaaagc accaacagaa     1140
gctgcaaaac cagctcctgc accatctaca aacacaaatg ctaataaaac gaatacaaat    1200
acaaatacaa acaatactaa tacaccatct aaaaatacta atacaaactc aaatactaat    1260
acgaatacaa actcaaatac gaatgctaat caaggttctt ccaacaataa cagcaattca    1320
agtgcaagtg ctattattgc tgaagctcaa aaacaccttg aaaagctta ttcatggggt     1380 ggtaacggac caactacatt tgattgctct ggttacacta aatatgtatt tgctaaagcg    1440
ggtatctccc ttccacgtac atctggcgca caatatgcta gcactacaag aatttctgaa    1500
tctcaagcaa aacctggtga tttagtattc ttcgactatg gtagcggaat ttctcacatt    1560
ggtatttatg ttggtaatgg tcaaatgatt aacgcgcaag acaatggcgt taaatacgat    1620
aacatccacg gctctggctg gggtaaatat ctagttggct tcggtcgcgt ataataagga    1680
tcc                                                                  1683
```

<210> SEQ ID NO 66
<211> LENGTH: 29
<212> TYPE: DNA
<213> ORGANISM: Artificial Sequence
<220> FEATURE:
<223> OTHER INFORMATION: Primer

<400> SEQUENCE: 66
aaactgcagg cattgccaac tgcacgtcc                                      29

<210> SEQ ID NO 67
<211> LENGTH: 40
<212> TYPE: DNA
<213> ORGANISM: Artificial Sequence
<220> FEATURE:
<223> OTHER INFORMATION: Primer

<400> SEQUENCE: 67
aaactgcaga gctaatgtac tggctaataa taatgctaac                          40

<210> SEQ ID NO 68
<211> LENGTH: 32
<212> TYPE: DNA
<213> ORGANISM: Artificial Sequence
<220> FEATURE:
<223> OTHER INFORMATION: Primer

<400> SEQUENCE: 68
cgcctgcagc gtacattagc aggtgaaaca gg                                  32

<210> SEQ ID NO 69
<211> LENGTH: 36
<212> TYPE: DNA
<213> ORGANISM: Artificial Sequence
<220> FEATURE:
<223> OTHER INFORMATION: Primer

<400> SEQUENCE: 69
cgcctgcagg ccttgtaaac ctaaacctaa tgtatc                              36

<210> SEQ ID NO 70
<211> LENGTH: 99
<212> TYPE: DNA
<213> ORGANISM: Homo sapiens

<400> SEQUENCE: 70

| | | |
|---|---|---|
| gcattgccaa ctgcacgtcc attactaggt agttgcggta caccagcact aggttcttta | 60 |
| ttattttgt tattttctct aggttgggtt caaccaagt | 99 |

<210> SEQ ID NO 71
<211> LENGTH: 126
<212> TYPE: DNA
<213> ORGANISM: Homo sapiens

<400> SEQUENCE: 71

| | | |
|---|---|---|
| ggtattccga atggatattt agtgttagat ttatctgttc aagaagcatt aagtggtaca | 60 |
| ccgtgtttat taggtccagg tccagtttta acagtgttag cattattatt agccagtaca | 120 |
| ttagct | 126 |

<210> SEQ ID NO 72
<211> LENGTH: 1878
<212> TYPE: DNA
<213> ORGANISM: Artificial Sequence
<220> FEATURE:
<223> OTHER INFORMATION: Codon-optimized sequence

<400> SEQUENCE: 72

| | | |
|---|---|---|
| ggatccgcat tgccaactgc acgtccatta ctaggtagtt gcggtacacc agcactaggt | 60 |
| tctttattat ttttgttatt ttctctaggt tgggttcaac caagtcgtac attagcaggt | 120 |
| gaaacaggtc aagaagcagc accacttgac ggtgtattaa cgaatccacc aaatatatca | 180 |
| agtttaagtc cacgtcaatt attaggtttt ccatgtgcag aagtttcagg tttaagtaca | 240 |
| gaacgtgtcc gtgagttagc agttgcatta gcacaaaaaa acgttaaatt atctacagaa | 300 |
| cagttacgtt gtttagccca tagattaagc gaaccaccag aagacttaga tgcacttcct | 360 |
| ttagaccttc ttttattctt aaatccagat gcattttcag gaccacaagc atgtacacgt | 420 |
| tttttagtc gaattacaaa agccaatgtt gatttattac ctcgtggggc tcctgaaaga | 480 |
| caacgtttat tacctgctgc attagcatgc tggggtgttc gcggtagctt attaagtgaa | 540 |
| gccgatgttc gtgctttagg gggtttagca tgtgatttac ctggtcgttt cgttgcagaa | 600 |
| tcagcagaag tgttattacc gagattagtt tcatgcccag gacctttaga tcaagatcaa | 660 |
| caagaggcag ctagagcagc tcttcaagga ggaggcccac catatggccc accaagtaca | 720 |
| tggagtgttt ctacaatgga tgcgttaaga ggtttattac cggttttagg acaaccaatt | 780 |
| attcgtagta ttccacaagg cattgtagca gcatggcgtc aacgtagttc tcgtgatccg | 840 |
| tcttggcgac aaccagaacg tacaattcta cgtccaagat tcgtagagaa gtagaaaaa | 900 |
| acggcgtgtc ctagtggcaa aaaagcacgt gaaattgatg aaagtttaat ttttataaaa | 960 |
| aaatgggaat tagaagcatg tgtcgatgca gcattactag ctacacaaat ggatcgtgtt | 1020 |
| aatgctattc cattcacata tgaacaatta gatgttttaa agcataaatt agacgaatta | 1080 |
| tatccacaag ttatccagaa tcagttatt caacatttag ttacttatt tttaaaaatg | 1140 |
| agtccagaag acatacgcaa atggaatgtt acaagtttag aaacattaaa agcgctttta | 1200 |
| gaagttaaca aaggtcatga atgagtcca caagttgcta cgttaattga tagattcgtt | 1260 |
| aaaggccgtg gtcaattaga taagatact ttagatacat taacagcatt ttatcctggc | 1320 |
| tacttatgca gtttatcacc agaagaatta agtccgttc caccgagtag tatctgggca | 1380 |
| gttcgtccgc aagatttaga tacatgcgac ccacgtcaat tagatgtttt atatccaaaa | 1440 |
| gcaagattag ctttccaaaa tatgaacggt agtgaatatt tcgtaaaaat tcaatccttt | 1500 |

-continued

```
ttaggtggtg caccaactga agatctaaaa gcattaagcc aacaaaatgt aagtatggat   1560
ttagctacgt ttatgaaatt acgtacagat gcagttctac cattaacagt tgcagaagtt   1620
caaaaattat taggtccaca cgtagaagga ttaaaagcag aagaacgtca ccgtccagtt   1680
cgcgattgga ttttacgtca acgtcaagat gatttagata cattaggttt aggtttacaa   1740
ggcggtattc cgaatggata tttagtgtta gatttatctg ttcaagaagc attaagtggt   1800
acaccgtgtt tattaggtcc aggtccagtt ttaacagtgt tagcattatt attagccagt   1860
acattagctt aagagctc                                                 1878
```

<210> SEQ ID NO 73
<211> LENGTH: 621
<212> TYPE: PRT
<213> ORGANISM: Homo sapiens

<400> SEQUENCE: 73

```
Ala Leu Pro Thr Ala Arg Pro Leu Leu Gly Ser Cys Gly Thr Pro Ala
 1               5                  10                  15

Leu Gly Ser Leu Leu Phe Leu Leu Phe Ser Leu Gly Trp Val Gln Pro
            20                  25                  30

Ser Arg Thr Leu Ala Gly Glu Thr Gly Gln Glu Ala Ala Pro Leu Asp
        35                  40                  45

Gly Val Leu Thr Asn Pro Pro Asn Ile Ser Ser Leu Ser Pro Arg Gln
    50                  55                  60

Leu Leu Gly Phe Pro Cys Ala Glu Val Ser Gly Leu Ser Thr Glu Arg
65                  70                  75                  80

Val Arg Glu Leu Ala Val Ala Leu Ala Gln Lys Asn Val Lys Leu Ser
                85                  90                  95

Thr Glu Gln Leu Arg Cys Leu Ala His Arg Leu Ser Glu Pro Pro Glu
            100                 105                 110

Asp Leu Asp Ala Leu Pro Leu Asp Leu Leu Leu Phe Leu Asn Pro Asp
        115                 120                 125

Ala Phe Ser Gly Pro Gln Ala Cys Thr Arg Phe Phe Ser Arg Ile Thr
    130                 135                 140

Lys Ala Asn Val Asp Leu Leu Pro Arg Gly Ala Pro Glu Arg Gln Arg
145                 150                 155                 160

Leu Leu Pro Ala Ala Leu Ala Cys Trp Gly Val Arg Gly Ser Leu Leu
                165                 170                 175

Ser Glu Ala Asp Val Arg Ala Leu Gly Gly Leu Ala Cys Asp Leu Pro
            180                 185                 190

Gly Arg Phe Val Ala Glu Ser Ala Glu Val Leu Leu Pro Arg Leu Val
        195                 200                 205

Ser Cys Pro Gly Pro Leu Asp Gln Asp Gln Gln Glu Ala Ala Arg Ala
    210                 215                 220

Ala Leu Gln Gly Gly Gly Pro Pro Tyr Gly Pro Pro Ser Thr Trp Ser
225                 230                 235                 240

Val Ser Thr Met Asp Ala Leu Arg Gly Leu Leu Pro Val Leu Gly Gln
                245                 250                 255

Pro Ile Ile Arg Ser Ile Pro Gln Gly Ile Val Ala Ala Trp Arg Gln
            260                 265                 270

Arg Ser Ser Arg Asp Pro Ser Trp Arg Gln Pro Glu Arg Thr Ile Leu
        275                 280                 285

Arg Pro Arg Phe Arg Arg Glu Val Glu Lys Thr Ala Cys Pro Ser Gly
    290                 295                 300
```

```
Lys Lys Ala Arg Glu Ile Asp Glu Ser Leu Ile Phe Tyr Lys Lys Trp
305                 310                 315                 320

Glu Leu Glu Ala Cys Val Asp Ala Ala Leu Leu Ala Thr Gln Met Asp
            325                 330                 335

Arg Val Asn Ala Ile Pro Phe Thr Tyr Glu Gln Leu Asp Val Leu Lys
        340                 345                 350

His Lys Leu Asp Glu Leu Tyr Pro Gln Gly Tyr Pro Glu Ser Val Ile
    355                 360                 365

Gln His Leu Gly Tyr Leu Phe Leu Lys Met Ser Pro Glu Asp Ile Arg
370                 375                 380

Lys Trp Asn Val Thr Ser Leu Glu Thr Leu Lys Ala Leu Leu Glu Val
385                 390                 395                 400

Asn Lys Gly His Glu Met Ser Pro Gln Val Ala Thr Leu Ile Asp Arg
            405                 410                 415

Phe Val Lys Gly Arg Gly Gln Leu Asp Lys Asp Thr Leu Asp Thr Leu
        420                 425                 430

Thr Ala Phe Tyr Pro Gly Tyr Leu Cys Ser Leu Ser Pro Glu Glu Leu
    435                 440                 445

Ser Ser Val Pro Pro Ser Ser Ile Trp Ala Val Arg Pro Gln Asp Leu
450                 455                 460

Asp Thr Cys Asp Pro Arg Gln Leu Asp Val Leu Tyr Pro Lys Ala Arg
465                 470                 475                 480

Leu Ala Phe Gln Asn Met Asn Gly Ser Glu Tyr Phe Val Lys Ile Gln
            485                 490                 495

Ser Phe Leu Gly Gly Ala Pro Thr Glu Asp Leu Lys Ala Leu Ser Gln
        500                 505                 510

Gln Asn Val Ser Met Asp Leu Ala Thr Phe Met Lys Leu Arg Thr Asp
    515                 520                 525

Ala Val Leu Pro Leu Thr Val Ala Glu Val Gln Lys Leu Leu Gly Pro
530                 535                 540

His Val Glu Gly Leu Lys Ala Glu Glu Arg His Arg Pro Val Arg Asp
545                 550                 555                 560

Trp Ile Leu Arg Gln Arg Gln Asp Asp Leu Asp Thr Leu Gly Leu Gly
            565                 570                 575

Leu Gln Gly Gly Ile Pro Asn Gly Tyr Leu Val Leu Asp Leu Ser Val
        580                 585                 590

Gln Glu Ala Leu Ser Gly Thr Pro Cys Leu Leu Gly Pro Gly Pro Val
    595                 600                 605

Leu Thr Val Leu Ala Leu Leu Ala Ser Thr Leu Ala
610                 615                 620

<210> SEQ ID NO 74
<211> LENGTH: 1653
<212> TYPE: DNA
<213> ORGANISM: Artificial Sequence
<220> FEATURE:
<223> OTHER INFORMATION: Coding sequence

<400> SEQUENCE: 74
ggatcccgta cattagcagg tgaaacaggt caagaagcag caccacttga cggtgtatta      60
acgaatccac caaatatatc aagtttaagt ccacgtcaat tattaggttt tccatgtgca     120
gaagtttcag gtttaagtac agaacgtgtc cgtgagttag cagttgcatt agcacaaaaa     180
aacgttaaat tatctacaga acagttacgt tgtttagccc atagattaag cgaaccacca     240
gaagacttag atgcacttcc tttagacctt ctttttattct taaatccaga tgcatttca      300
```

```
ggaccacaag catgtacacg ttttttttagt cgaattacaa aagccaatgt tgatttatta    360
cctcgtgggg ctcctgaaag acaacgttta ttacctgctg cattagcatg ctggggtgtt    420
cgcggtagct tattaagtga agccgatgtt cgtgctttag ggggtttagc atgtgattta    480
cctggtcgtt tcgttgcaga atcagcagaa gtgttattac cgagattagt ttcatgccca    540
ggacctttag atcaagatca acaagaggca gctagagcag ctcttcaagg aggaggccca    600
ccatatggcc caccaagtac atggagtgtt tctacaatgg atgcgttaag aggtttatta    660
ccggttttag acaaccaat tattcgtagt attccacaag gcattgtagc agcatggcgt    720
caacgtagtt ctcgtgatcc gtcttggcga caaccagaac gtacaattct acgtccaaga    780
tttcgtagag aagtagaaaa aacggcgtgt cctagtggca aaaagcacg tgaaattgat     840
gaaagtttaa ttttttataa aaaatgggaa ttagaagcat gtgtcgatgc agcattacta    900
gctacacaaa tggatcgtgt taatgctatt ccattcacat atgaacaatt agatgtttta    960
aagcataaat tagacgaatt atatccacaa ggttatccag aatcagttat tcaacattta   1020
ggttacttat tttttaaaaat gagtccagaa gacatacgca aatggaatgt tacaagttta   1080
gaaacattaa aagcgctttt agaagttaac aaaggtcatg aaatgagtcc acaagttgct   1140
acgttaattg atagattcgt taaaggccgt ggtcaattag ataaagatac tttagataca   1200
ttaacagcat tttatcctgg ctacttatgc agtttatcac cagaagaatt aagttccgtt   1260
ccaccgagta gtatctgggc agttcgtccg caagatttag atacatgcga cccacgtcaa   1320
ttagatgttt tatatccaaa agcaagatta gctttccaaa atatgaacgg tagtgaatat   1380
ttcgtaaaaa ttcaatcctt tttaggtggt gcaccaactg aagatctaaa agcattaagc   1440
caacaaaatg taagtatgga tttagctacg tttatgaaat tacgtacaga tgcagttcta   1500
ccattaacag ttgcagaagt tcaaaaatta ttaggtccac acgtagaagg attaaaagca   1560
gaagaacgtc accgtccagt tcgcgattgg atttacgtc aacgtcaaga tgatttagat   1620
acattaggtt taggtttaca aggctaagag ctc                                1653
```

<210> SEQ ID NO 75
<211> LENGTH: 546
<212> TYPE: PRT
<213> ORGANISM: Homo sapiens

<400> SEQUENCE: 75

```
Arg Thr Leu Ala Gly Glu Thr Gly Gln Glu Ala Ala Pro Leu Asp Gly
 1               5                  10                  15

Val Leu Thr Asn Pro Pro Asn Ile Ser Ser Leu Ser Pro Arg Gln Leu
            20                  25                  30

Leu Gly Phe Pro Cys Ala Glu Val Ser Gly Leu Ser Thr Glu Arg Val
        35                  40                  45

Arg Glu Leu Ala Val Ala Leu Ala Gln Lys Asn Val Lys Leu Ser Thr
    50                  55                  60

Glu Gln Leu Arg Cys Leu Ala His Arg Leu Ser Pro Pro Glu Asp
 65                  70                  75                  80

Leu Asp Ala Leu Pro Leu Asp Leu Leu Leu Phe Leu Asn Pro Asp Ala
                85                  90                  95

Phe Ser Gly Pro Gln Ala Cys Thr Arg Phe Phe Ser Arg Ile Thr Lys
            100                 105                 110

Ala Asn Val Asp Leu Leu Pro Arg Gly Ala Pro Glu Arg Gln Arg Leu
        115                 120                 125

Leu Pro Ala Ala Leu Ala Cys Trp Gly Val Arg Gly Ser Leu Leu Ser
    130                 135                 140
```

```
Glu Ala Asp Val Arg Ala Leu Gly Gly Leu Ala Cys Asp Leu Pro Gly
145                 150                 155                 160
Arg Phe Val Ala Glu Ser Ala Glu Val Leu Leu Pro Arg Leu Val Ser
                165                 170                 175
Cys Pro Gly Pro Leu Asp Gln Asp Gln Gln Glu Ala Ala Arg Ala Ala
                180                 185                 190
Leu Gln Gly Gly Gly Pro Pro Tyr Gly Pro Pro Ser Thr Trp Ser Val
        195                 200                 205
Ser Thr Met Asp Ala Leu Arg Gly Leu Leu Pro Val Leu Gly Gln Pro
        210                 215                 220
Ile Ile Arg Ser Ile Pro Gln Gly Ile Val Ala Ala Trp Arg Gln Arg
225                 230                 235                 240
Ser Ser Arg Asp Pro Ser Trp Arg Gln Pro Glu Arg Thr Ile Leu Arg
                245                 250                 255
Pro Arg Phe Arg Arg Glu Val Glu Lys Thr Ala Cys Pro Ser Gly Lys
                260                 265                 270
Lys Ala Arg Glu Ile Asp Glu Ser Leu Ile Phe Tyr Lys Lys Trp Glu
            275                 280                 285
Leu Glu Ala Cys Val Asp Ala Ala Leu Leu Ala Thr Gln Met Asp Arg
        290                 295                 300
Val Asn Ala Ile Pro Phe Thr Tyr Glu Gln Leu Asp Val Leu Lys His
305                 310                 315                 320
Lys Leu Asp Glu Leu Tyr Pro Gln Gly Tyr Pro Glu Ser Val Ile Gln
                325                 330                 335
His Leu Gly Tyr Leu Phe Leu Lys Met Ser Pro Glu Asp Ile Arg Lys
                340                 345                 350
Trp Asn Val Thr Ser Leu Glu Thr Leu Lys Ala Leu Leu Glu Val Asn
            355                 360                 365
Lys Gly His Glu Met Ser Pro Gln Val Ala Thr Leu Ile Asp Arg Phe
        370                 375                 380
Val Lys Gly Arg Gly Gln Leu Asp Lys Asp Thr Leu Asp Thr Leu Thr
385                 390                 395                 400
Ala Phe Tyr Pro Gly Tyr Leu Cys Ser Leu Ser Pro Glu Glu Leu Ser
                405                 410                 415
Ser Val Pro Pro Ser Ser Ile Trp Ala Val Arg Pro Gln Asp Leu Asp
                420                 425                 430
Thr Cys Asp Pro Arg Gln Leu Asp Val Leu Tyr Pro Lys Ala Arg Leu
            435                 440                 445
Ala Phe Gln Asn Met Asn Gly Ser Glu Tyr Phe Val Lys Ile Gln Ser
        450                 455                 460
Phe Leu Gly Gly Ala Pro Thr Glu Asp Leu Lys Ala Leu Ser Gln Gln
465                 470                 475                 480
Asn Val Ser Met Asp Leu Ala Thr Phe Met Lys Leu Arg Thr Asp Ala
                485                 490                 495
Val Leu Pro Leu Thr Val Ala Glu Val Gln Lys Leu Leu Gly Pro His
                500                 505                 510
Val Glu Gly Leu Lys Ala Glu Glu Arg His Arg Pro Val Arg Asp Trp
            515                 520                 525
Ile Leu Arg Gln Arg Gln Asp Asp Leu Asp Thr Leu Gly Leu Gly Leu
        530                 535                 540
Gln Gly
545
```

<210> SEQ ID NO 76
<211> LENGTH: 3327
<212> TYPE: DNA
<213> ORGANISM: Artificial Sequence
<220> FEATURE:
<223> OTHER INFORMATION: Sub-fragment of plasmid

<400> SEQUENCE: 76

```
ggtacctcct tgattagta tattcctatc ttaaagttac ttttatgtgg aggcattaac      60
atttgttaat gacgtcaaaa ggatagcaag actagaataa agctataaag caagcatata    120
atattgcgtt tcatctttag aagcgaattt cgccaatatt ataattatca aaagagaggg    180
gtggcaaacg gtatttggca ttattaggtt aaaaaatgta aaggagagt gaaacccatg     240
aatatgaaaa aagctacgat tgcagctaca gccggcattg ccgtaacagc ttttgcagca    300
ccaactattg cctcagcctc tacagttgtt gtcgaagcag gagacacatt atggggaatc    360
gcacaatcaa aagtacaac ggttgatgct attaaaaaag cgataatttt aacaacagat     420
aaaatcgtgc caggtcaaaa actgcagcgt acattagcag gtgaaacagg tcaagaagca    480
gcaccacttg acggtgtatt aacgaatcca ccaaatatat caagtttaag tccacgtcaa    540
ttattaggtt ttccatgtgc agaagtttca ggtttaagta cagaacgtgt ccgtgagtta    600
gcagttgcat tagcacaaaa aaacgttaaa ttatctacag aacagttacg ttgtttagcc    660
catagattaa gcgaaccacc agaagactta gatgcacttc ctttagacct tcttttattc    720
ttaaatccag atgcattttc aggaccacaa gcatgtacac gtttttttag tcgaattaca    780
aaagccaatg ttgatttatt acctcgtggg gctcctgaaa gacaacgttt attacctgct    840
gcattagcat gctggggtgt tcgcggtagc ttattaagtg aagccgatgt tcgtgcttta    900
gggggtttag catgtgattt acctggtcgt ttcgttgcag aatcagcaga agtgttatta    960
ccgagattag tttcatgccc aggaccttta gatcaagatc aacaagaggc agctagagca   1020
gctcttcaag gaggagccc accatatggc ccaccaagta catggagtgt ttctacaatg   1080
gatgcgttaa gaggtttatt accggtttta ggacaaccaa ttattcgtag tattccacaa   1140
ggcattgtag cagcatggcg tcaacgtagt tctcgtgatc cgtcttggcg acaaccagaa   1200
cgtacaattc tacgtccaag atttcgtaga gaagtagaaa aaacggcgtg tcctagtggc   1260
aaaaaagcac gtgaaattga tgaaagttta atttttata aaaaatggga attagaagca   1320
tgtgtcgatg cagcattact agctacacaa atggatcgtg ttaatgctat tccattcaca   1380
tatgaacaat tagatgtttt aaagcataaa ttagacgaat tatatccaca aggttatcca   1440
gaatcagtta ttcaacattt aggttactta ttttttaaaaa tgagtccaga agacatacgc   1500
aaatggaatg ttacaagttt agaaacatta aaagcgcttt tagaagttaa caaaggtcat   1560
gaaatgagtc cacaagttgc tacgttaatt gatagattcg ttaaaggccg tggtcaatta   1620
gataaagata ctttagatac attaacagca ttttatcctg gctacttatg cagtttatca   1680
ccagaagaat aagttccgt tccaccgagt agtatctggg cagttcgtcc gcaagattta   1740
gatacatgcg acccacgtca attagatgtt ttatatccaa aagcaagatt agctttccaa   1800
aatatgaacg gtagtgaata tttcgtaaaa attcaatcct ttttaggtgg tgcaccaact   1860
gaagatctaa aagcattaag ccaacaaat gtaagtatgg atttagctac gtttatgaaa    1920
ttacgtacag atgcagttct accattaaca gttgcagaag ttcaaaaatt attaggtcca   1980
cacgtagaag gattaaaagc agaagaacgt caccgtccag ttcgcgattg gattttacgt   2040
caacgtcaag atgatttaga tacattaggt ttaggtttac aaggcctgca ggtaaataat   2100
gaggttgctg ctgctgaaaa aacagagaaa tctgttagcg caacttggtt aaacgtccgt   2160
```

```
actggcgctg gtgttgataa cagtattatt acgtccatca aaggtggaac aaaagtaact    2220
gttgaaacaa ccgaatctaa cggctggcac aaaattactt acaacgatgg aaaaactggt    2280
ttcgttaacg gtaaatactt aactgacaaa gcagtaagca ctccagttgc accaacacaa    2340
gaagtgaaaa aagaaactac tactcaacaa gctgcacctg ttgcagaaac aaaaactgaa    2400
gtaaaacaaa ctacacaagc aactacacct gcgcctaaag tagcagaaac gaaagaaact    2460
ccagtaatag atcaaaatgc tactacacac gctgtcaaaa gcggtgacac tatttgggct    2520
ttatccgtaa aatacggtgt ttctgttcaa gacattatgt catggaataa tttatcttct    2580
tcttctattt atgtaggtca aaagcttgct attaaacaaa ctgctaacac agctactcca    2640
aaagcagaag tgaaaacgga agctccagca gctgaaaaac aagcagctcc agtagttaaa    2700
gaaaatacta acacaaatac tgctactaca gagaaaaaag aaacagcaac gcaacaacaa    2760
acagcaccta agcaccaaca agaagctgca aaaccagctc ctgcaccatc tacaaacaca    2820
aatgctaata aaacgaatac aaatacaaat acaaacaata ctaatacacc atctaaaaat    2880
actaatacaa actcaaatac taatacgaat acaaactcaa atacgaatgc taatcaaggt    2940
tcttccaaca ataacagcaa ttcaagtgca agtgctatta ttgctgaagc tcaaaaacac    3000
cttggaaaag cttattcatg gggtggtaac ggaccaacta catttgattg ctctggttac    3060
actaaatatg tatttgctaa agcgggtatc tcccttccac gtacatctgg cgcacaatat    3120
gctagcacta caagaatttc tgaatctcaa gcaaaacctg gtgatttagt attcttcgac    3180
tatggtagcg gaatttctca cattggtatt tatgttggta atggtcaaat gattaacgcg    3240
caagacaatg gcgttaaata cgataacatc cacggctctg gctggggtaa atatctagtt    3300
ggcttcggtc gcgtataata aggatcc                                        3327
```

<210> SEQ ID NO 77
<211> LENGTH: 165
<212> TYPE: PRT
<213> ORGANISM: Artificial Sequence
<220> FEATURE:
<223> OTHER INFORMATION: Fusion protein

<400> SEQUENCE: 77

```
Gly Ser Ala Lys Val Leu Glu Glu Asp Glu Glu Glu Ala Leu Pro Thr
 1               5                  10                  15

Ala Arg Pro Leu Leu Gly Ser Cys Gly Thr Pro Ala Leu Gly Ser Leu
                20                  25                  30

Leu Phe Leu Leu Phe Ser Leu Gly Trp Val Gln Pro Ser Arg Thr Leu
            35                  40                  45

Ala Gly Glu Thr Gly Gln Glu Ala Ala Glu Glu Asp Glu Glu Glu Ala
        50                  55                  60

Asp Leu Val Leu Ala Lys Val Leu Met Thr Glu Tyr Lys Leu Val Val
 65                  70                  75                  80

Val Gly Ala Asp Gly Val Gly Lys Ser Ala Leu Thr Ile Gln Leu Ile
                85                  90                  95

Gln Ala Asp Leu Val Leu Ala Lys Val Leu Met Thr Glu Tyr Lys Leu
            100                 105                 110

Val Val Val Gly Ala Val Gly Val Gly Lys Ser Ala Leu Thr Ile Gln
        115                 120                 125

Leu Ile Gln Ala Asp Leu Val Leu Ala Lys Val Leu Glu Ser Ile Ile
    130                 135                 140

Asn Phe Glu Lys Leu Ala Asp Leu Val Ala Glu Gln Lys Leu Ile Ser
145                 150                 155                 160
```

```
Glu Glu Asp Leu Val
            165

<210> SEQ ID NO 78
<211> LENGTH: 139
<212> TYPE: PRT
<213> ORGANISM: Artificial Sequence
<220> FEATURE:
<223> OTHER INFORMATION: Fusion protein

<400> SEQUENCE: 78

Gly Ser Ala Lys Val Leu Glu Glu Asp Glu Glu Thr Pro Ala Leu
 1               5                  10                  15

Gly Ser Leu Leu Phe Leu Leu Phe Ser Leu Gly Trp Val Gln Pro Glu
                20                  25                  30

Glu Asp Glu Glu Ala Asp Leu Val Leu Ala Lys Val Leu Met Thr
             35                  40                  45

Glu Tyr Lys Leu Val Val Gly Ala Asp Gly Val Gly Lys Ser Ala
 50                  55                  60

Leu Thr Ile Gln Leu Ile Gln Ala Asp Leu Val Leu Ala Lys Val Leu
65                   70                  75                  80

Met Thr Glu Tyr Lys Leu Val Val Gly Ala Val Gly Val Gly Lys
                85                  90                  95

Ser Ala Leu Thr Ile Gln Leu Ile Gln Ala Asp Leu Val Leu Ala Lys
                100                 105                 110

Val Leu Glu Ser Ile Ile Asn Phe Glu Lys Leu Ala Asp Leu Val Ala
                115                 120                 125

Glu Gln Lys Leu Ile Ser Glu Glu Asp Leu Val
            130                 135

<210> SEQ ID NO 79
<211> LENGTH: 165
<212> TYPE: PRT
<213> ORGANISM: Artificial Sequence
<220> FEATURE:
<223> OTHER INFORMATION: Fusion protein

<400> SEQUENCE: 79

Gly Ser Ala Lys Val Leu Met Thr Glu Tyr Lys Leu Val Val Gly
 1               5                  10                  15

Ala Asp Gly Val Gly Lys Ser Ala Leu Thr Ile Gln Leu Ile Gln Ala
                20                  25                  30

Asp Leu Val Leu Ala Lys Val Leu Met Thr Glu Tyr Lys Leu Val Val
             35                  40                  45

Val Gly Ala Val Gly Val Gly Lys Ser Ala Leu Thr Ile Gln Leu Ile
 50                  55                  60

Gln Ala Asp Leu Val Leu Ala Lys Val Leu Glu Glu Asp Glu Glu
65                   70                  75                  80

Ala Leu Pro Thr Ala Arg Pro Leu Leu Gly Ser Cys Gly Thr Pro Ala
                85                  90                  95

Leu Gly Ser Leu Leu Phe Leu Leu Phe Ser Leu Gly Trp Val Gln Pro
                100                 105                 110

Ser Arg Thr Leu Ala Gly Glu Thr Gly Gln Glu Ala Ala Glu Glu Asp
                115                 120                 125

Glu Glu Glu Ala Asp Leu Val Leu Ala Lys Val Leu Glu Ser Ile Ile
            130                 135                 140

Asn Phe Glu Lys Leu Ala Asp Leu Val Ala Glu Gln Lys Leu Ile Ser
145                 150                 155                 160
```

```
Glu Glu Asp Leu Val
            165

<210> SEQ ID NO 80
<211> LENGTH: 139
<212> TYPE: PRT
<213> ORGANISM: Artificial Sequence
<220> FEATURE:
<223> OTHER INFORMATION: Fusion protein

<400> SEQUENCE: 80

Gly Ser Ala Lys Val Leu Met Thr Glu Tyr Lys Leu Val Val Gly
  1               5                  10                  15

Ala Asp Gly Val Gly Lys Ser Ala Leu Thr Ile Gln Leu Ile Gln Ala
                 20                  25                  30

Asp Leu Val Leu Ala Lys Val Leu Met Thr Glu Tyr Lys Leu Val Val
             35                  40                  45

Val Gly Ala Val Gly Val Gly Lys Ser Ala Leu Thr Ile Gln Leu Ile
         50                  55                  60

Gln Ala Asp Leu Val Leu Ala Lys Val Leu Glu Glu Asp Glu Glu Glu
 65                  70                  75                  80

Thr Pro Ala Leu Gly Ser Leu Leu Phe Leu Leu Phe Ser Leu Gly Trp
                 85                  90                  95

Val Gln Pro Glu Glu Asp Glu Glu Ala Asp Leu Val Leu Ala Lys
                100                 105                 110

Val Leu Glu Ser Ile Ile Asn Phe Glu Lys Leu Ala Asp Leu Val Ala
            115                 120                 125

Glu Gln Lys Leu Ile Ser Glu Glu Asp Leu Val
        130                 135

<210> SEQ ID NO 81
<211> LENGTH: 25
<212> TYPE: PRT
<213> ORGANISM: Homo sapiens

<400> SEQUENCE: 81

Met Thr Glu Tyr Lys Leu Val Val Val Gly Ala Asp Gly Val Gly Lys
  1               5                  10                  15

Ser Ala Leu Thr Ile Gln Leu Ile Gln
             20                  25

<210> SEQ ID NO 82
<211> LENGTH: 25
<212> TYPE: PRT
<213> ORGANISM: Homo sapiens

<400> SEQUENCE: 82

Met Thr Glu Tyr Lys Leu Val Val Val Gly Ala Val Gly Asp Gly Lys
  1               5                  10                  15

Ser Ala Leu Thr Ile Gln Leu Ile Gln
             20                  25

<210> SEQ ID NO 83
<211> LENGTH: 45
<212> TYPE: PRT
<213> ORGANISM: Homo sapiens

<400> SEQUENCE: 83

Ala Leu Pro Thr Ala Arg Pro Leu Leu Gly Ser Cys Gly Thr Pro Ala
  1               5                  10                  15
```

```
Leu Gly Ser Leu Leu Phe Leu Phe Ser Leu Gly Trp Val Gln Pro
         20                  25                  30

Ser Arg Thr Leu Ala Gly Glu Thr Gly Gln Glu Ala Ala
         35                  40                  45

<210> SEQ ID NO 84
<211> LENGTH: 19
<212> TYPE: PRT
<213> ORGANISM: Homo sapiens

<400> SEQUENCE: 84

Thr Pro Ala Leu Gly Ser Leu Leu Phe Leu Phe Ser Leu Gly Trp
 1               5                  10                  15

Val Gln Pro

<210> SEQ ID NO 85
<211> LENGTH: 6
<212> TYPE: PRT
<213> ORGANISM: Artificial Sequence
<220> FEATURE:
<223> OTHER INFORMATION: Spacer

<400> SEQUENCE: 85

Glu Glu Asp Glu Glu Glu
 1               5

<210> SEQ ID NO 86
<211> LENGTH: 13
<212> TYPE: PRT
<213> ORGANISM: Homo sapiens

<400> SEQUENCE: 86

Ser Glu Ala Asp Val Arg Ala Leu Gly Gly Leu Ala Cys
 1               5                  10

<210> SEQ ID NO 87
<211> LENGTH: 10
<212> TYPE: PRT
<213> ORGANISM: Phage lambda

<400> SEQUENCE: 87

Leu Thr Ala Asp Glu Tyr Leu Lys Ile Tyr
 1               5                  10

<210> SEQ ID NO 88
<211> LENGTH: 10
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 3, 7, 8
<223> OTHER INFORMATION: Xaa = Any Amino Acid

<400> SEQUENCE: 88

Leu Thr Xaa Glu Glu Val Xaa Xaa Leu Leu
 1               5                  10

<210> SEQ ID NO 89
<211> LENGTH: 5
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
```

```
<222> LOCATION: 1
<223> OTHER INFORMATION: Xaa = d or e
<220> FEATURE:
<221> NAME/KEY: VARIANT
<222> LOCATION: 2, 3, 4
<223> OTHER INFORMATION: Xaa = f, y, w, v, l, i or a
<220> FEATURE:
<221> NAME/KEY: VARIANT
<222> LOCATION: 5
<223> OTHER INFORMATION: Xaa = s or t

<400> SEQUENCE: 89

Xaa Xaa Xaa Xaa Xaa
 1               5

<210> SEQ ID NO 90
<211> LENGTH: 15
<212> TYPE: PRT
<213> ORGANISM: Phage
<220> FEATURE:
<221> NAME/KEY: VARIANT
<222> LOCATION: 2, 7, 10, 12, 13, 14
<223> OTHER INFORMATION: Xaa = Any Amino Acid

<400> SEQUENCE: 90

His Xaa Leu Arg His Ala Xaa Ala Thr Xaa Leu Xaa Xaa Xaa Gly
 1               5                  10                  15

<210> SEQ ID NO 91
<211> LENGTH: 8
<212> TYPE: PRT
<213> ORGANISM: Phage
<220> FEATURE:
<221> NAME/KEY: VARIANT
<222> LOCATION: 5
<223> OTHER INFORMATION: Xaa = Any Amino Acid

<400> SEQUENCE: 91

Thr Gly Leu Arg Xaa Thr Glu Leu
 1               5

<210> SEQ ID NO 92
<211> LENGTH: 18
<212> TYPE: PRT
<213> ORGANISM: Phage
<220> FEATURE:
<221> NAME/KEY: VARIANT
<222> LOCATION: 2, 3, 4, 8, 9, 10, 11, 12, 14, 15, 17
<223> OTHER INFORMATION: Xaa = Any Amino Acid

<400> SEQUENCE: 92

Val Xaa Xaa Xaa Leu Gly His Xaa Xaa Xaa Xaa Xaa Thr Xaa Xaa Tyr
 1               5                  10                  15

Xaa His

<210> SEQ ID NO 93
<211> LENGTH: 9
<212> TYPE: PRT
<213> ORGANISM: Artificial Sequence
<220> FEATURE:
<223> OTHER INFORMATION: Motif
<220> FEATURE:
<221> NAME/KEY: VARIANT
<222> LOCATION: 2, 7, 8
<223> OTHER INFORMATION: Xaa = Any Amino Acid

<400> SEQUENCE: 93

Tyr Xaa Arg Val Ser Thr Xaa Xaa Gln
 1               5
```

```
<210> SEQ ID NO 94
<211> LENGTH: 16
<212> TYPE: PRT
<213> ORGANISM: Artificial Sequence
<220> FEATURE:
<223> OTHER INFORMATION: Motif
<220> FEATURE:
<221> NAME/KEY: VARIANT
<222> LOCATION: 7, 8, 9, 10, 13, 14, 15
<223> OTHER INFORMATION: Xaa = Any Amino Acid

<400> SEQUENCE: 94

Val Ala Gln Ala Glu Arg Xaa Xaa Xaa Xaa Glu Arg Xaa Xaa Xaa Gly
  1               5                  10                  15

<210> SEQ ID NO 95
<211> LENGTH: 1313
<212> TYPE: DNA
<213> ORGANISM: Listeria innocua

<400> SEQUENCE: 95
aggagggctt atttatggta aaaaaagtaa aaggtaggcg ttatgagggt tctattgaac      60
aacgtagcaa aaattcatgg cgtatgcgcg tgactgtagg ctatgactac aaaggtacgc     120
cgattcgagc tgacagaacg acgcgaacaa aaaatgagag ggagcgagaa agagagttaa     180
gaaatttcat cacagaatta gagcaaaatg gatatacagc tcctgcaaga atgcacattta    240 aagcatttgt tgagaatgag tatatgccga acatgcaca aaataaccta gaagttaaaa     300
cctggacaga atactacaaa tctatagtag caagagctta cccagccttt ggcggcgttc     360
aaatggataa aataactaca cttcatatag ttaacttagt cgcaaaatta caaaagcccg     420
gcgcaagatt agatgttaaa cctacagatt cagacgaaaa gaaaaataag ccgctttcgc     480
cgcgatctat cagaaatatt tattttgcga taaattcagt atttgaaact gcggttgagt     540
ggaaagtaat cccaattaac cccgcagagg gtgtaaggct tccaaaaaca actaaaagac     600
cgcctactat ttatactcct gctgaaattg aattgttaaa tgcagctcta gtgaaagagc     660
cacttagatt gcaagtaatg atttatatag cgctgatttc aggttgtaga gaagctgaat     720
tagcagcatt agaagtaaaa cacgtgaact taatagaaga tgagctaaca ttcgaacaaa     780
cgctagttgc aaaagcagga gaaggtttac ttcttaaaga atcaactaag aatgatgtag     840
ctgggatagt ttctataccc gcttggttaa ctaatttaat agaaacatat ataagcaatg     900
aagttttaga cctaaaaact gaagggaaat gggccaatca caattttta ttcgccgaca     960 tggaaggcaa accgattagg cctgattcga tttatcagcg ttggaaacga ttttttagaaa   1020 gacacaactt gccggtgatt cgttttcatg atttgcgtca cacatctgct acactttttat  1080 tgaacaaagg tagagatata aaaattatcc aagagcggct tagacataaa tctagtgtga    1140
ccacttcaaa catttatgca catgtttttga aagatacgca caaagatgca gctagcgatt   1200
ttgagaaccc tttttaagct ttctgcccca cctctgcccc acttaataaa aaaaggcaat     1260
tttaaactaa aatttcacaa acaaaaaacc gcttaaacgc tttgtttagg cgg            1313

<210> SEQ ID NO 96
<211> LENGTH: 1203
<212> TYPE: DNA
<213> ORGANISM: Listeria innocua

<400> SEQUENCE: 96
atggtaaaaa aagtaaaagg taggcgttat gagggttcta ttgaacaacg tagcaaaaat      60
tcatggcgta tgcgcgtgac tgtaggctat gactacaaag gtacgccgat tcgagctgac     120
```

```
agaacgacgc gaacaaaaaa tgagagggag cgagaaagag agttaagaaa tttcatcaca    180
gaattagagc aaaatggata tacagctcct gcaagaatga catttaaagc atttgttgag    240
aatgagtata tgccgaaaca tgcacaaaat aacctagaag ttaaaacctg gacagaatac    300
tacaaatcta tagtagcaag agcttaccca gcctttggcg gcgttcaaat ggataaaata    360
actacacttc atatagttaa cttagtcgca aaattacaaa agcccggcgc aagattagat    420
gttaaaccta cagattcaga cgaaaagaaa aataagccgc tttcgccgcg atctatcaga    480
aatatttatt ttgcgataaa ttcagtattt gaaactgcgg ttgagtggaa agtaatccca    540
attaaccccg cagagggtgt aaggcttcca aaaacaacta aaagaccgcc tactatttat    600
actcctgctg aaattgaatt gttaaatgca gctctagtga agagccact tagattgcaa    660
gtaatgattt atatagcgct gatttcaggt tgtagagaag ctgaattagc agcattagaa    720
gtaaaacacg tgaacttaat agaagatgag ctaacattcg aacaaacgct agttgcaaaa    780
gcaggagaag gtttacttct taaagaatca actaagaatg atgtagctgg gatagtttct    840
atacccgctt ggttaactaa tttaatagaa acatatataa gcaatgaagt tttagaccta    900
aaaactgaag ggaaatgggc caatcacaaa ttttttattcg ccgacatgga aggcaaaccg    960
attaggcctg attcgattta tcagcgttgg aaacgatttt tagaaagaca caacttgccg   1020
gtgattcgtt ttcatgattt gcgtcacaca tctgctacac ttttattgaa caaaggtaga   1080
gatataaaaa ttatccaaga gcggcttaga cataaatcta gtgtgaccac ttcaaacatt   1140
tatgcacatg ttttgaaaga tacgcacaaa gatgcagcta gcgattttga gaacccttt    1200
taa                                                               1203
```

<210> SEQ ID NO 97
<211> LENGTH: 400
<212> TYPE: PRT
<213> ORGANISM: Listeria innocua

<400> SEQUENCE: 97

```
Met Val Lys Lys Val Lys Gly Arg Arg Tyr Glu Gly Ser Ile Glu Gln
  1               5                  10                  15

Arg Ser Lys Asn Ser Trp Arg Met Arg Val Thr Val Gly Tyr Asp Tyr
             20                  25                  30

Lys Gly Thr Pro Ile Arg Ala Asp Arg Thr Thr Arg Thr Lys Asn Glu
         35                  40                  45

Arg Glu Arg Glu Arg Glu Leu Arg Asn Phe Ile Thr Glu Leu Glu Gln
     50                  55                  60

Asn Gly Tyr Thr Ala Pro Ala Arg Met Thr Phe Lys Ala Phe Val Glu
 65                  70                  75                  80

Asn Glu Tyr Met Pro Lys His Ala Gln Asn Asn Leu Glu Val Lys Thr
                 85                  90                  95

Trp Thr Glu Tyr Tyr Lys Ser Ile Val Ala Arg Ala Tyr Pro Ala Phe
            100                 105                 110

Gly Gly Val Gln Met Asp Lys Ile Thr Thr Leu His Ile Val Asn Leu
        115                 120                 125

Val Ala Lys Leu Gln Lys Pro Gly Ala Arg Leu Asp Val Lys Pro Thr
    130                 135                 140

Asp Ser Asp Glu Lys Lys Asn Lys Pro Leu Ser Pro Arg Ser Ile Arg
145                 150                 155                 160

Asn Ile Tyr Phe Ala Ile Asn Ser Val Phe Glu Thr Ala Val Glu Trp
                165                 170                 175
```

Lys Val Ile Pro Ile Asn Pro Ala Glu Gly Val Arg Leu Pro Lys Thr
                180                 185                 190

Thr Lys Arg Pro Pro Thr Ile Tyr Thr Pro Ala Glu Ile Glu Leu Leu
            195                 200                 205

Asn Ala Ala Leu Val Lys Glu Pro Leu Arg Leu Gln Val Met Ile Tyr
210                 215                 220

Ile Ala Leu Ile Ser Gly Cys Arg Glu Ala Glu Leu Ala Ala Leu Glu
225                 230                 235                 240

Val Lys His Val Asn Leu Ile Glu Asp Glu Leu Thr Phe Glu Gln Thr
                245                 250                 255

Leu Val Ala Lys Ala Gly Glu Gly Leu Leu Leu Lys Glu Ser Thr Lys
            260                 265                 270

Asn Asp Val Ala Gly Ile Val Ser Ile Pro Ala Trp Leu Thr Asn Leu
        275                 280                 285

Ile Glu Thr Tyr Ile Ser Asn Glu Val Leu Asp Leu Lys Thr Glu Gly
    290                 295                 300

Lys Trp Ala Asn His Lys Phe Leu Phe Ala Asp Met Glu Gly Lys Pro
305                 310                 315                 320

Ile Arg Pro Asp Ser Ile Tyr Gln Arg Trp Lys Arg Phe Leu Glu Arg
                325                 330                 335

His Asn Leu Pro Val Ile Arg Phe His Asp Leu Arg His Thr Ser Ala
            340                 345                 350

Thr Leu Leu Leu Asn Lys Gly Arg Asp Ile Lys Ile Ile Gln Glu Arg
        355                 360                 365

Leu Arg His Lys Ser Ser Val Thr Thr Ser Asn Ile Tyr Ala His Val
    370                 375                 380

Leu Lys Asp Thr His Lys Asp Ala Ala Ser Asp Phe Glu Asn Pro Phe
385                 390                 395                 400

<210> SEQ ID NO 98
<211> LENGTH: 340
<212> TYPE: DNA
<213> ORGANISM: Listeria innocua

<400> SEQUENCE: 98
taccgaaaaa tatagccgca gcgagtggct gcggctgtgt tttatcgctg aattatggta      60
taatattttt tgtcggaata cgacaacggg ttgttagctc agttggtaga gcagctgact     120
cttaatcagc gggtcggggg ttcgaaaccc tcacaaccca taaaaacaaa cgccagtgac     180
tgttaaagtc gttggtgttt tgtcgttttt acgggcaaaa tgttaataat ttcaataata     240
agctgatttc tttttgatta tttatcgatt acatagaaaa taagtggaat ttcaaagtat     300
ctaataattt actacatgat atacaaaagg agttgtttca                           340

<210> SEQ ID NO 99
<211> LENGTH: 45
<212> TYPE: DNA
<213> ORGANISM: Listeria innocua

<400> SEQUENCE: 99
actcttaatc agcgggtcgg gggttcgaaa ccctcacaac ccata                      45

<210> SEQ ID NO 100
<211> LENGTH: 1433
<212> TYPE: DNA
<213> ORGANISM: Listeria innocua

<400> SEQUENCE: 100

-continued

```
tggaggtgag aaagttcatg actgtaggga tttatataag ggtttccact gaagaacaag      60
tgaaggaagg cttttctata tcagcacaga aagagaagtt aaaagcatat tgcacagcgc     120
aaggatggga agatttcaag ttttacgtcg atgaaggtaa atcagcaaaa gatatgcacc     180
gccctcttct acaagaaatg atttcacata taaaaaaagg acttatagac acagtcctag     240
tatataaatt ggatcgtctt actaggtccg ttgtagattt gcataattta ttaagtatat     300
ttgatgaatt taactgtgca tttaaaagcg ctactgaagt ctacgatact tcttccgcta     360
tgggcagatt ttttattaca ataataagtt cagttgctca atttgaaaga gagaatacct     420
ctgaacgagt tagctttggg atggctgaga aagtgcgtca aggagaatat attcctctcg     480
ctcccttcgg ttatactaag gggactgacg aaaactaat agtaaataaa atagaaaaag     540
aaatatttt acaagtagtt gaaatggttt caaccggtta ttctttacga caaacttgtg      600
aatatttaac aaatattggt ttgaaaacaa ggcgttcaaa tgatgtgtgg aaagtatcta     660
cattaatttg gatgttaaaa aatcctgctg tctacggagc gataaaatgg aataatgaaa     720
tatatgaaaa tacacatgag cctctaatcg ataaggcaac atttaataaa gtagccaaaa     780
tactatcaat aagaagtaaa tcaacaacaa gccgtcgtgg acacgttcat cacatttta     840
aaaatagatt aatttgtcca gcttgtggaa aaagattatc tggattaaga acaaaatata     900
taaataaaaa taaggaaact ttttataaca ataactatcg ttgtgctacc tgcaaagaac     960
atagacgtcc agcagtacag ataagcgagc aaaaaataga gaaagcattt attgattata    1020
tttcaaacta tacactcaat aaagcaaata tctcttctaa aaaattagat aataatttga    1080
gaaaacaaga aatgattcaa aaagaaatta tttcacttca aagaaaacgt gaaaagtttc    1140
agaaagcatg ggctgctgac cttatgaatg atgatgaatt ttctaaatta atgattgata    1200
caaaaatgga gattgatgct gcagaagata gaaaaaaaga atatgacgta tcattatttg    1260
tatctcctga agatattgct aaaagaaata acattcttcg tgaactaaaa ataaattgga    1320
cttcattatc tcctactgaa aaaacagatt ttataagtat gtttattgaa ggaattgaat    1380
atgtaaaaga tgatgaaaat aaagcggtta taacgaaaat aagttttta taa            1433
```

<210> SEQ ID NO 101
<211> LENGTH: 471
<212> TYPE: PRT
<213> ORGANISM: Listeria innocua

<400> SEQUENCE: 101

```
Met Thr Val Gly Ile Tyr Ile Arg Val Ser Thr Glu Glu Gln Val Lys
  1               5                  10                  15

Glu Gly Phe Ser Ile Ser Ala Gln Lys Glu Lys Leu Lys Ala Tyr Cys
                 20                  25                  30

Thr Ala Gln Gly Trp Glu Asp Phe Lys Phe Tyr Val Asp Glu Gly Lys
             35                  40                  45

Ser Ala Lys Asp Met His Arg Pro Leu Leu Gln Glu Met Ile Ser His
         50                  55                  60

Ile Lys Lys Gly Leu Ile Asp Thr Val Leu Val Tyr Lys Leu Asp Arg
 65                  70                  75                  80

Leu Thr Arg Ser Val Val Asp Leu His Asn Leu Leu Ser Ile Phe Asp
                 85                  90                  95

Glu Phe Asn Cys Ala Phe Lys Ser Ala Thr Glu Val Tyr Asp Thr Ser
                100                 105                 110

Ser Ala Met Gly Arg Phe Phe Ile Thr Ile Ser Ser Val Ala Gln
            115                 120                 125
```

```
Phe Glu Arg Glu Asn Thr Ser Glu Arg Val Ser Phe Gly Met Ala Glu
            130                 135                 140

Lys Val Arg Gln Gly Glu Tyr Ile Pro Leu Ala Pro Phe Gly Tyr Thr
145                 150                 155                 160

Lys Gly Thr Asp Gly Lys Leu Ile Val Asn Lys Ile Glu Lys Glu Ile
                165                 170                 175

Phe Leu Gln Val Val Glu Met Val Ser Thr Gly Tyr Ser Leu Arg Gln
            180                 185                 190

Thr Cys Glu Tyr Leu Thr Asn Ile Gly Leu Lys Thr Arg Arg Ser Asn
        195                 200                 205

Asp Val Trp Lys Val Ser Thr Leu Ile Trp Met Leu Lys Asn Pro Ala
    210                 215                 220

Val Tyr Gly Ala Ile Lys Trp Asn Asn Glu Ile Tyr Glu Asn Thr His
225                 230                 235                 240

Glu Pro Leu Ile Asp Lys Ala Thr Phe Asn Lys Val Ala Lys Ile Leu
                245                 250                 255

Ser Ile Arg Ser Lys Ser Thr Thr Ser Arg Arg Gly His Val His His
            260                 265                 270

Ile Phe Lys Asn Arg Leu Ile Cys Pro Ala Cys Gly Lys Arg Leu Ser
        275                 280                 285

Gly Leu Arg Thr Lys Tyr Ile Asn Lys Asn Lys Glu Thr Phe Tyr Asn
    290                 295                 300

Asn Asn Tyr Arg Cys Ala Thr Cys Lys Glu His Arg Arg Pro Ala Val
305                 310                 315                 320

Gln Ile Ser Glu Gln Lys Ile Glu Lys Ala Phe Ile Asp Tyr Ile Ser
                325                 330                 335

Asn Tyr Thr Leu Asn Lys Ala Asn Ile Ser Ser Lys Lys Leu Asp Asn
            340                 345                 350

Asn Leu Arg Lys Gln Glu Met Ile Gln Lys Glu Ile Ile Ser Leu Gln
        355                 360                 365

Arg Lys Arg Glu Lys Phe Gln Lys Ala Trp Ala Ala Asp Leu Met Asn
    370                 375                 380

Asp Asp Glu Phe Ser Lys Leu Met Ile Asp Thr Lys Met Glu Ile Asp
385                 390                 395                 400

Ala Ala Glu Asp Arg Lys Lys Glu Tyr Asp Val Ser Leu Phe Val Ser
                405                 410                 415

Pro Glu Asp Ile Ala Lys Arg Asn Asn Ile Leu Arg Glu Leu Lys Ile
            420                 425                 430

Asn Trp Thr Ser Leu Ser Pro Thr Glu Lys Thr Asp Phe Ile Ser Met
        435                 440                 445

Phe Ile Glu Gly Ile Glu Tyr Val Lys Asp Asp Glu Asn Lys Ala Val
    450                 455                 460

Ile Thr Lys Ile Ser Phe Leu
465                 470

<210> SEQ ID NO 102
<211> LENGTH: 114
<212> TYPE: DNA
<213> ORGANISM: Listeria innocua

<400> SEQUENCE: 102
taaataattg tcagtcaatc aaaagaatta tttataggtt ttttgtcaaa tatggtgatg    60
tgtacttata acccatttttt cttgcaataa aagcttgtgt tattcccccgt tcta        114

<210> SEQ ID NO 103
```

```
<211> LENGTH: 213
<212> TYPE: DNA
<213> ORGANISM: Listeria innocua

<400> SEQUENCE: 103
ttcataaaag aatttcaaat cgcacattaa aatttcactt agaataacag cattttttgtg      60 tgatagtcta acagttcctt tttcaatgtt actgtaacct gatgtgtacc tatagcccat     120
ccgtcgcgca atgaaagctt gggtgattcc tcgctgcaat cgtaattctc gaatttttgt     180
tgtattaatt cttctggtgt ctactgtttt cat                                  213

<210> SEQ ID NO 104
<211> LENGTH: 1189
<212> TYPE: DNA
<213> ORGANISM: Listeria innocua

<400> SEQUENCE: 104
aggatgaaag agaatggcaa agaacaaatg gcaacccact aaacatttag gaatttatga      60
atacatgact aaaaaaggaa agcgttatgg gatacgagtt cgttataagc aaggtaatga     120
ttatcctgaa ataataaat ctggttttga gacaattgca gctgcaaaag tttataaaaa      180
caacattgaa aatttgaaag ctaataaaaa agaatatgtt tttacaaatg aaaaattaac     240
attaaatact tggttttgctt cttacatgga aatgtttaaa agaaaaaaca aaagtaaaga   300
cacaatagcg aataaatata gtatttataa taatcactta gaaatcccct ttggtaatta     360
ctatttaact gatataagtt tagatattta cgaagacttt ttgcgcgaaa aaattaaaaa     420
tggatacgca aacaactcag tcaaagcgat gcataaatta atgaaaagca tttaaacgc      480 tgctgttaga tatgagaaac tagaaaaaaa cagacttcaa tttgctgaaa tagagcaatt    540
agaagaaaat gaagttattg agcttaaggt attagaaaca gatgagttta atgtatttat   600
atcagcttgt agagcatttt ttactaaata tgattttaca atgatttatc ttgcagtttg    660
ggggatgcgt cgcggtgaag ttatgggggt aaaacttaaa aatcttactt ttgatgatgc    720
taaacaacaa gtacgtatta cactagattc cactcgaacc cttcgtactc ccgagggaaa    780
aggtacgaaa acaccagctg gtagaagaat attactaata gacggcgaag gttatcgact    840
acttaaatat tcggtagaaa aagcggttag cattgctaaa gaccatggat ctgttttgca    900
ccaggatgat tttattttta gaaacccaac ttctaatcgt ccttgggcgg ttacgcgtat    960
gaatgattta ctacgaaaat tagaaaaaga atacgacata aagtttaccc tcatctatt    1020 acgcccataac tttaatactc aggcattatt ggctggagct aatagcaatg atttacgaaa   1080
atttattggc cacaaaaaca gtagcatgac tgatcattat tcacatgcga cagacgaggg   1140
acgagaaaaa ttaatgaata cgatgaaaga cagattgtca ggaatctag                1189

<210> SEQ ID NO 105
<211> LENGTH: 391
<212> TYPE: PRT
<213> ORGANISM: Listeria innocua

<400> SEQUENCE: 105

Met Ala Lys Asn Lys Trp Gln Pro Thr Lys His Leu Gly Ile Tyr Glu
 1               5                  10                  15

Tyr Met Thr Lys Lys Gly Lys Arg Tyr Gly Ile Arg Val Arg Tyr Lys
            20                  25                  30

Gln Gly Asn Asp Tyr Pro Glu Ile Asn Lys Ser Gly Phe Glu Thr Ile
        35                  40                  45

Ala Ala Ala Lys Val Tyr Lys Asn Asn Ile Glu Asn Leu Lys Ala Asn
```

```
                50                   55                    60
Lys Lys Glu Tyr Val Phe Thr Asn Glu Lys Leu Thr Leu Asn Thr Trp
65                   70                   75                    80

Phe Ala Ser Tyr Met Glu Met Phe Lys Lys Asn Lys Ser Lys Asp
                85                    90                    95

Thr Ile Ala Asn Lys Tyr Ser Ile Tyr Asn Asn His Leu Glu Ile Pro
               100                   105                   110

Phe Gly Asn Tyr Tyr Leu Thr Asp Ile Ser Leu Asp Ile Tyr Glu Asp
               115                   120                   125

Phe Leu Arg Glu Lys Ile Lys Asn Gly Tyr Ala Asn Asn Ser Val Lys
    130                  135                   140

Ala Met His Lys Leu Met Lys Ser Ile Leu Asn Ala Ala Val Arg Tyr
145                   150                  155                  160

Glu Lys Leu Glu Lys Asn Arg Leu Gln Phe Ala Glu Ile Glu Gln Leu
                 165                  170                  175

Glu Glu Asn Glu Val Ile Glu Leu Lys Val Leu Glu Thr Asp Glu Phe
                180                  185                  190

Asn Val Phe Ile Ser Ala Cys Arg Ala Phe Phe Thr Lys Tyr Asp Phe
                195                  200                  205

Thr Met Ile Tyr Leu Ala Val Trp Gly Met Arg Arg Gly Glu Val Met
    210                  215                  220

Gly Val Lys Leu Lys Asn Leu Thr Phe Asp Asp Ala Lys Gln Gln Val
225                  230                  235                  240

Arg Ile Thr Leu Asp Ser Thr Arg Thr Leu Arg Thr Pro Glu Gly Lys
                245                  250                  255

Gly Thr Lys Thr Pro Ala Gly Arg Arg Ile Leu Leu Ile Asp Gly Glu
                260                  265                  270

Gly Tyr Arg Leu Leu Lys Tyr Ser Val Glu Lys Ala Val Ser Ile Ala
    275                  280                  285

Lys Asp His Gly Ser Val Leu His Gln Asp Asp Phe Ile Phe Arg Asn
    290                  295                  300

Pro Thr Ser Asn Arg Pro Trp Ala Val Thr Arg Met Asn Asp Leu Leu
305                  310                  315                  320

Arg Lys Leu Glu Lys Glu Tyr Asp Ile Lys Val Tyr Pro His Leu Leu
                325                  330                  335

Arg His Asn Phe Asn Thr Gln Ala Leu Leu Ala Gly Ala Asn Ser Asn
                340                  345                  350

Asp Leu Arg Lys Phe Ile Gly His Lys Asn Ser Ser Met Thr Asp His
    355                  360                  365

Tyr Ser His Ala Thr Asp Glu Gly Arg Glu Lys Leu Met Asn Thr Met
370                  375                  380

Lys Asp Arg Leu Ser Gly Ile
385                  390

<210> SEQ ID NO 106
<211> LENGTH: 160
<212> TYPE: DNA
<213> ORGANISM: Listeria innocua

<400> SEQUENCE: 106
aaaattgtgg gataaaaatt aaatataaaa atatcccaca aaaaatccca caatagtttg      60
atattgtatg atattcaaat gaaatcaaaa aataaaaac cccgtatttc ctaagaaaat     120
acggggtttt gatatcatat aaaatcaatt aaaaattgac                          160
```

<210> SEQ ID NO 107
<211> LENGTH: 574
<212> TYPE: DNA
<213> ORGANISM: Listeria innocua

<400> SEQUENCE: 107

```
tcttgttgcc tccttttttgt aatcaatagt tgcaatgcaa gagtatcata aaaaagcgat      60
gtataaccaa aaatgtaatg aaatgtccga ttcttgtcgt gaacgactag aaaatggagc     120
ttatttagag atattcttac acaacgtgag tatcattaag ttttttggtc ataagataat     180
actcattatg agttactatt cacattttaa acattcctgt ttctatttat cacaaaaaat     240
acatatcaat ccaagatatg cgttatttca cttatgaata ttccttattt atttaattat     300
ttatcagttt tatttattac taggtgaata atatagtata attattcacc tacgacagac     360
gagacacgag aaaaattaat gaatacgatg aaagacagat tgtcaggaat ctagaaaatt     420
gtgggataaa aattaaatat aaaaatatcc cacaaaaaat cccacaataa tttgatattg     480
tatgatattc aaatgaaatc aaaaaaatca aaaccccgca tttcctaaga aaatacgggg     540
ttttgatatc atataaaatc gatttaaaat ggac                                 574
```

<210> SEQ ID NO 108
<211> LENGTH: 1152
<212> TYPE: DNA
<213> ORGANISM: Listeria innocua

<400> SEQUENCE: 108

```
atgaaaataa aaaaaatgaa aaatggtaaa tatactgttc gtttgcgtat taaagttgat      60
ggagagtgga agaaaaaacg tttgacagat acaagtgaaa caaatttgat gtacaaagca     120
tcaaaattat taaaacaagt tgaacatgat agtaattcac taaagaatg gaatttcaaa      180
gaattctatt cgctatttat gaaaactttc aaagaaaata aagtagtca atcaacaatt      240
aacttgtatg acttagctta taatcagttc gttaattatt tcgacgaaaa aataaagtta     300
aattcaattg acgctgttca atatcagcaa tttattaatc atttagcatt agattacgct     360
gtcgctacta tagataccag acaccgcaaa attagagcga ttttcaataa agccgtccat     420
ttaggttaca tgaaaaaaaa ccctgctctg gcgctcaca taagcggtca tgatatagca     480
aaaacaaaag cgcaatattt agaaacagat aaagtacatc tattattaga agagcttgca     540
aaacttcatt ctatatcaag agcagttatt tttttagcag ttcaaacagg aatgcgattt     600
gaagaaatta ttgcactgac aaaaaaagat attaattttta ctaaacgttc tatatcagtg     660
aataaggcat gggattataa atacactaac acgtttacgg acactaaaac aaaaaagtca     720
cgagtaatct atattgataa ttcaactgtt caatatttac agtcttacct tgcttggcat     780
gctgattata tgaaagagca tgcaattgaa atccggtga tgttgttatt cattacttat      840
cacaataaac ctgttgacaa cgcttcatgt aacaaagcac tgaagaaaat atgtactaca     900
attaattctg aaacagtaac attacacaag cttcgacaca cgcacacagg tctatgtgta     960
gaggctggta tggatattat ttatgtagct gacaggcttg gtcatgatga tattaataca    1020
acattaaaat attatagtca tctgagttct aatttacgac aacaaaaatca atctaaagta    1080
gatgcttttt tcacactaaa aacagatgaa ataccacaa aatttgccac aaatgccaca     1140
aaaacaacgg aa                                                        1152
```

<210> SEQ ID NO 109
<211> LENGTH: 384
<212> TYPE: PRT
<213> ORGANISM: Listeria innocua

```
<400> SEQUENCE: 109

Met Lys Ile Lys Lys Met Lys Asn Gly Lys Tyr Thr Val Arg Leu Arg
  1               5                  10                  15

Ile Lys Val Asp Gly Glu Trp Lys Glu Lys Arg Leu Thr Asp Thr Ser
             20                  25                  30

Glu Thr Asn Leu Met Tyr Lys Ala Ser Lys Leu Leu Lys Gln Val Glu
         35                  40                  45

His Asp Ser Asn Ser Leu Lys Glu Trp Asn Phe Lys Glu Phe Tyr Ser
     50                  55                  60

Leu Phe Met Lys Thr Phe Lys Glu Asn Lys Ser Ser Gln Ser Thr Ile
 65                  70                  75                  80

Asn Leu Tyr Asp Leu Ala Tyr Asn Gln Phe Val Asn Tyr Phe Asp Glu
                 85                  90                  95

Lys Ile Lys Leu Asn Ser Ile Asp Ala Val Gln Tyr Gln Gln Phe Ile
            100                 105                 110

Asn His Leu Ala Leu Asp Tyr Ala Val Ala Thr Ile Asp Thr Arg His
        115                 120                 125

Arg Lys Ile Arg Ala Ile Phe Asn Lys Ala Val His Leu Gly Tyr Met
130                 135                 140

Lys Lys Asn Pro Ala Leu Gly Ala His Ile Ser Gly His Asp Ile Ala
145                 150                 155                 160

Lys Thr Lys Ala Gln Tyr Leu Glu Thr Asp Lys Val His Leu Leu Leu
                165                 170                 175

Glu Glu Leu Ala Lys Leu His Ser Ile Ser Arg Ala Val Ile Phe Leu
            180                 185                 190

Ala Val Gln Thr Gly Met Arg Phe Glu Glu Ile Ile Ala Leu Thr Lys
        195                 200                 205

Lys Asp Ile Asn Phe Thr Lys Arg Ser Ile Ser Val Asn Lys Ala Trp
210                 215                 220

Asp Tyr Lys Tyr Thr Asn Thr Phe Thr Asp Thr Lys Thr Lys Lys Ser
225                 230                 235                 240

Arg Val Ile Tyr Ile Asp Asn Ser Thr Val Gln Tyr Leu Gln Ser Tyr
                245                 250                 255

Leu Ala Trp His Ala Asp Tyr Met Lys Glu His Ala Ile Glu Asn Pro
            260                 265                 270

Val Met Leu Leu Phe Ile Thr Tyr His Asn Lys Pro Val Asp Asn Ala
        275                 280                 285

Ser Cys Asn Lys Ala Leu Lys Lys Ile Cys Thr Thr Ile Asn Ser Glu
290                 295                 300

Thr Val Thr Leu His Lys Leu Arg His Thr His Thr Gly Leu Cys Val
305                 310                 315                 320

Glu Ala Gly Met Asp Ile Ile Tyr Val Ala Asp Arg Leu Gly His Asp
                325                 330                 335

Asp Ile Asn Thr Thr Leu Lys Tyr Tyr Ser His Leu Ser Ser Asn Leu
            340                 345                 350

Arg Gln Gln Asn Gln Ser Lys Val Asp Ala Phe Phe Thr Leu Lys Thr
        355                 360                 365

Asp Glu Asn Thr Thr Lys Phe Ala Thr Asn Ala Thr Lys Thr Thr Glu
370                 375                 380

<210> SEQ ID NO 110
<211> LENGTH: 299
<212> TYPE: DNA
<213> ORGANISM: Listeria innocua
```

<400> SEQUENCE: 110

```
taaaacgggt attgcaaggt ataaaaaaat ctctaaaaca ttcgtttatc ctttaatatc    60
aaggatttcc aacgttttag agatttcttt acatcactac ttaatgccct cggagggaat   120
cgaaccccca ttttaagaac cggaatctta cgtgctatcc gttgcaccac gagggcttta   180
tgtacaaaga aaatgtttac cgtacgaata ataattatag cgaaattcgt atgtttttac   240
aagctttatt ttgaatgaag aagccagcgc atcctgagat ttgctggctt caatagtta    299
```

<210> SEQ ID NO 111
<211> LENGTH: 15
<212> TYPE: DNA
<213> ORGANISM: Listeria innocua

<400> SEQUENCE: 111

```
atgccctcgg aggga                                                    15
```

<210> SEQ ID NO 112
<211> LENGTH: 253
<212> TYPE: DNA
<213> ORGANISM: Listeria monocytogenes

<400> SEQUENCE: 112

```
taaaatgaaa aacatcttta caacatggct tttgccagat gtgggatgtt ttttagtat    60
gccctcggag ggaatcgaac ccccatttta agaaccggaa tcttacgtgc tatccgttgc   120
accacgaggg ctatatgtag ccagaaatg cttaccgtac gaataataat tatagcgaaa   180
ttcgtagtgt tttacaagtt ttattttaaa tgaagaagcc agcgcctcca agatttgct   240
ggctcaagta tta                                                     253
```

<210> SEQ ID NO 113
<211> LENGTH: 1161
<212> TYPE: DNA
<213> ORGANISM: Listeria monocytogenes

<400> SEQUENCE: 113

```
atggctagct atgtaaattt aggaaataat aaatatgagc taagagtttc aaagggatat    60
gatgcacgtg aaaacaaat acgcaaaaca aaaaacgtca cagttaaaac agtaaaagcg   120
ttaaaactag aactttctaa ttttgaagct tatgtctatt caagcgatta cacagaaata   180
aaagatatgc gatttattga ctttgtggaa aaatggcgct taaattacgc aaaaagagaa   240
ctaaaaggta atactattga taagtataac ctctttctcg aaaactggat tataccttat   300
tttgagagga agaaaataag taaaattaca actatgcagt tgctcgacta ctttcatgaa   360
gttcaaaaaa aaggagttgg tccaagcgct ttagagggac atcatcgagt tataagaagt   420
ttatttaaat atgctacctt gtggggaatt actgaaacag acgtatcttt atcagtgaaa   480
aaacctacct ataaagtgcc agaaaaaaat atttataata gacgagaaat agaagtgtta   540
atagatcgca ttaagatatt acaaaaatat caacaagtaa tgattaaatt agcgctatac   600
tgcggtctta acgtggcga agttatcggt ttaacaacta agatatgaa ttacaataaa   660
aatacaatta acgtttatag agcggttata aagagtgcta gcgaaggtat aaaactagat   720
gaaactaaaa ataagcgaaa aagaattgtc cccgctcccg ctggactgat gcaagaaatt   780
aagaacttg caaagaaaaa gcaaaaaaac aaagataaat aggtttgtt gtggaaagga   840
acaaagatt tagatgggaa aactgttgta ttaatttca gtcatgacga cggcaccccc   900
tttacccccg cttctgtcac tagaatgttt aatcgatttt tagagaaaga agaaaataac   960
```

```
gatcttacta aaatatcatt tcatgatttg cgtcattctg ctgcaagctt ccttctcgaa    1020
caaggtatta atgtaaaagt cattcaaaac attttaggac attcagacat taaagttaca    1080
ttaaatacgt atgcacatat cactgaagat ggttactcag aagcagcaaa aacttttgat    1140
aatttctata aatctagtaa a                                              1161
```

<210> SEQ ID NO 114
<211> LENGTH: 387
<212> TYPE: PRT
<213> ORGANISM: Listeria monocytogenes

<400> SEQUENCE: 114

```
Met Ala Ser Tyr Val Asn Leu Gly Asn Asn Lys Tyr Glu Leu Arg Val
 1               5                  10                  15

Ser Lys Gly Tyr Asp Ala Arg Gly Lys Gln Ile Arg Lys Thr Lys Asn
                20                  25                  30

Val Thr Val Lys Thr Val Lys Ala Leu Lys Leu Glu Leu Ser Asn Phe
            35                  40                  45

Glu Ala Tyr Val Tyr Ser Ser Asp Tyr Thr Glu Ile Lys Asp Met Arg
        50                  55                  60

Phe Ile Asp Phe Val Glu Lys Trp Arg Leu Asn Tyr Ala Lys Arg Glu
65                  70                  75                  80

Leu Lys Gly Asn Thr Ile Asp Lys Tyr Asn Leu Phe Leu Glu Asn Trp
                85                  90                  95

Ile Ile Pro Tyr Phe Glu Arg Lys Lys Ile Ser Lys Ile Thr Thr Met
            100                 105                 110

Gln Leu Leu Asp Tyr Phe His Glu Val Gln Lys Lys Gly Val Gly Pro
        115                 120                 125

Ser Ala Leu Glu Gly His His Arg Val Ile Arg Ser Leu Phe Lys Tyr
    130                 135                 140

Ala Thr Leu Trp Gly Ile Thr Glu Thr Asp Val Ser Leu Ser Val Lys
145                 150                 155                 160

Lys Pro Thr Tyr Lys Val Pro Glu Lys Asn Ile Tyr Asn Arg Arg Glu
                165                 170                 175

Ile Glu Val Leu Ile Asp Arg Ile Lys Ile Leu Gln Lys Tyr Gln Gln
            180                 185                 190

Val Met Ile Lys Leu Ala Leu Tyr Cys Gly Leu Arg Arg Gly Glu Val
        195                 200                 205

Ile Gly Leu Thr Thr Lys Asp Met Asn Tyr Asn Lys Asn Thr Ile Asn
    210                 215                 220

Val Tyr Arg Ala Val Ile Lys Ser Ala Ser Glu Gly Ile Lys Leu Asp
225                 230                 235                 240

Glu Thr Lys Asn Lys Arg Lys Arg Ile Val Pro Ala Pro Ala Gly Leu
                245                 250                 255

Met Gln Glu Ile Lys Glu Leu Ala Lys Glu Lys Gln Lys Asn Lys Asp
            260                 265                 270

Lys Leu Gly Leu Leu Trp Lys Gly Thr Lys Asp Leu Asp Gly Lys Thr
        275                 280                 285

Val Val Leu Ile Phe Ser His Asp Asp Gly Thr Pro Phe Thr Pro Ala
    290                 295                 300

Ser Val Thr Arg Met Phe Asn Arg Phe Leu Glu Lys Glu Asn Asn
305                 310                 315                 320

Asp Leu Thr Lys Ile Ser Phe Asp Leu Arg His Ser Ala Ala Ser
                325                 330                 335
```

```
Phe Leu Leu Glu Gln Gly Ile Asn Val Lys Val Ile Gln Asn Ile Leu
                340                 345                 350
Gly His Ser Asp Ile Lys Val Thr Leu Asn Thr Tyr Ala His Ile Thr
            355                 360                 365
Glu Asp Gly Tyr Ser Glu Ala Ala Lys Thr Phe Asp Asn Phe Tyr Lys
        370                 375                 380
Ser Ser Lys
385

<210> SEQ ID NO 115
<211> LENGTH: 841
<212> TYPE: DNA
<213> ORGANISM: Listeria monocytogenes

<400> SEQUENCE: 115
taaggtgtcg aataaggtgt tttgctattt ttaggcaaat aaaaaaagct tcgcatatta      60
gcgaaacacc tacagcacca acgttttata ttaagccact tgtcggattt gaaccgacga     120 cccccttcctt accatggaag tgctctacca actgagctaa agcggcagca agcctttca     180 aataaaaaaa tggctccaca ggcaggactc gaacctgcga ccgatcggtt aacagccgat     240
tgctctacca actgagctac tgtggaataa taaattgccc ggcagcgacc tactctcgca     300 ggggaagcc cccaactacc attggcgcag agaagcttaa ctaccgtgtt cgggatggga     360
acgggtgtga ccttctcgcc ataactacca gacaatattg agttgttgaa agattgctct     420
ctcaaaacta gagaagaaag tgttcagtta ggtaacttcg tttcattttt tggttaagtc     480
ctcgatcgat tagtatttgt ccgctccatg tatcgctaca cttccactcc aaacctatct     540
acctgatcat ctttcaggga tcttactttc cgaagaaatg ggaaatctca tcttgagggg     600
ggcttcacgc ttagatgctt tcagcgttta tccctgccac acatagctac ccagcgatgc     660
tcctggcgga caactggta caccagcggt gtgtccatcc cggtcctctc gtactaagga     720
cagctcctct caaatttcct gcgcccgcga cggatagga ccgaactgtc tcacgacgtt     780
ctgaacccag ctcgcgtgcc gctttaatgg gcgaacagcc caacccttgg gaccgactac     840
a                                                                    841

<210> SEQ ID NO 116
<211> LENGTH: 399
<212> TYPE: DNA
<213> ORGANISM: Listeria monocytogenes

<400> SEQUENCE: 116
aaaaacaccc cacccgttct gttattatac ccatagtata atcgatttat actacctatt      60
caagatatcc ataataaata tcattattct tttaaacaat aaaaaaagcc tcgcatacta     120
gcgaaacata caaattatcc atatattatt taagccactt gtcggatttg aaccgacgac     180
cccttcctta ccatggaagt gctctaccaa ctgagctaaa gcggcagcaa agcctttcaa     240
ataaaaaaat ggctccacag gcaggactcg aacctgcgac cgatcggtta acagccgatt     300
gctctaccaa ctgagctact gtggaataat aaattgcccg gcagcgacct actctcgcag     360
ggggaagccc ccaactacca ttggcgcaga gaagcttaa                            399

<210> SEQ ID NO 117
<211> LENGTH: 399
<212> TYPE: DNA
<213> ORGANISM: Listeria monocytogenes

<400> SEQUENCE: 117
```

```
aaaaacaccc cacccgttct gttattatac ccatagtata atcgatttat actacctatt        60
caagatatcc ataataaata tcattattct tttaaacaat aaaaaaagcc tcgcatacta       120
gcgaaacata caaattatcc atatattatt taagccactt gtcggatttg aaccgacgac       180
cccttcctta ccatggaagt gctctaccaa ctgagctaaa gcggcagcaa agcctttcaa       240
ataaaaaaat ggctccacag gcaggactcg aacctgcgac cgatcggtta acagccgatt       300
gctctaccaa ctgagctact gtggaataat aaattgcccg gcagcgacct actctcgcag       360
ggggaagccc ccaactacca ttggcgcaga gaagcttaa                              399

<210> SEQ ID NO 118
<211> LENGTH: 399
<212> TYPE: DNA
<213> ORGANISM: Listeria monocytogenes

<400> SEQUENCE: 118
aaaaacaccc cacccgttct gttattatac ccatagtata atcgatttat actacctatt        60
caagatatcc ataataaata tcattattct tttaaacaat aaaaaaagcc tcgcatacta       120
gcgaaacata caaattatcc atatattatt taagccactt gtcggatttg aaccgacgac       180
cccttcctta ccatggaagt gctctaccaa ctgagctaaa gcggcagcaa agcctttcaa       240
ataaaaaaat ggctccacag gcaggactcg aacctgcgac cgatcggtta acagccgatt       300
gctctaccaa ctgagctact gtggaataat aaattgcccg gcagcgacct actctcgcag       360
ggggaagccc ccaactacca ttggcgcaga gaagcttaa                              399

<210> SEQ ID NO 119
<211> LENGTH: 384
<212> TYPE: PRT
<213> ORGANISM: Bacteriophage PSA

<400> SEQUENCE: 119

Met Lys Ile Lys Lys Leu Ala Asn Gly Lys Tyr Cys Val Arg Leu Arg
 1               5                  10                  15

Ile Lys Val Asp Gly Glu Trp Lys Glu Lys Arg Leu Thr Asp Thr Ser
            20                  25                  30

Glu Thr Asn Leu Met Tyr Lys Ala Ser Lys Leu Leu Lys Gln Val Gln
        35                  40                  45

His Asp Ser Ser Ser Leu Lys Glu Trp Asn Phe Lys Glu Phe Tyr Thr
    50                  55                  60

Leu Phe Met Lys Thr Phe Lys Asp Gly Lys Ser Ser Gln Ser Thr Ile
65                  70                  75                  80

Asn Leu Tyr Asp Leu Ala Tyr Asn Gln Phe Val Asp Tyr Phe Asp Glu
                85                  90                  95

Lys Ile Lys Leu Asn Ser Ile Asp Ala Val Gln Tyr Gln Gln Phe Ile
            100                 105                 110

Asn His Leu Ser Val Asp Tyr Ala Ile Ser Thr Val Asp Thr Arg His
        115                 120                 125

Arg Lys Ile Arg Ala Ile Phe Asn Lys Ala Val His Leu Gly Tyr Met
    130                 135                 140

Lys Lys Asn Pro Thr Ile Gly Ala His Ile Ser Gly Gln Asp Val Ala
145                 150                 155                 160

Lys Asn Lys Ala Gln Phe Met Glu Thr Asp Lys Val His Leu Leu Leu
                165                 170                 175

Glu Glu Leu Ala Lys Phe His Ser Ile Ser Arg Ala Val Ile Phe Leu
            180                 185                 190
```

```
Ala Val Gln Thr Gly Met Arg Phe Glu Glu Ile Ile Ala Leu Thr Lys
        195                 200                 205

Lys Asp Ile Asn Phe Thr Lys Arg Ser Ile Thr Val Asn Lys Ala Trp
    210                 215                 220

Asp Tyr Lys Tyr Thr Asn Thr Phe Ile Asp Thr Lys Thr Lys Lys Ser
225                 230                 235                 240

Arg Val Ile Tyr Ile Asp Asn Ser Thr Ala Gln Tyr Leu His Ser Tyr
                245                 250                 255

Leu Asn Trp His Thr Asp Tyr Met Lys Glu His Ala Ile Lys Asn Pro
                260                 265                 270

Leu Met Leu Leu Phe Ile Thr Tyr His Asn Lys Pro Val Asp Asn Ala
            275                 280                 285

Ser Cys Asn Lys Ala Leu Lys Lys Ile Cys Ser Thr Ile Asn Ser Glu
        290                 295                 300

Pro Val Thr Leu His Lys Leu Arg His Thr His Thr Gly Leu Cys Val
305                 310                 315                 320

Glu Ala Gly Met Asp Ile Ile Tyr Val Ala Asp Arg Leu Gly His Asp
                325                 330                 335

Asp Ile Asn Thr Thr Leu Lys Tyr Tyr Ser His Leu Ser Ser Asn Leu
                340                 345                 350

Arg Gln His Asn Gln Ser Lys Val Asp Ala Phe Phe Thr Leu Lys Thr
            355                 360                 365

Asp Glu Asn Thr Thr Asn Phe Thr Asn Ala Thr Lys Thr Thr Glu
        370                 375                 380

<210> SEQ ID NO 120
<211> LENGTH: 387
<212> TYPE: PRT
<213> ORGANISM: Listeria monocytogenes

<400> SEQUENCE: 120

Met Ala Ser Tyr Val Asn Leu Gly Asn Asn Lys Tyr Glu Leu Arg Val
1               5                   10                  15

Ser Lys Gly Tyr Asp Ala Arg Gly Lys Gln Ile Arg Lys Thr Lys Asn
            20                  25                  30

Val Thr Val Lys Thr Val Lys Ala Leu Lys Leu Glu Leu Ser Asn Phe
        35                  40                  45

Glu Ala Tyr Val Tyr Ser Ser Asp Tyr Thr Glu Ile Lys Asp Met Arg
    50                  55                  60

Phe Ile Asp Phe Val Glu Lys Trp Arg Leu Asn Tyr Ala Lys Arg Glu
65                  70                  75                  80

Leu Lys Gly Asn Thr Ile Asp Lys Tyr Asn Leu Phe Leu Glu Asn Trp
                85                  90                  95

Ile Ile Pro Tyr Phe Glu Arg Lys Lys Ile Ser Lys Ile Thr Thr Met
                100                 105                 110

Gln Leu Leu Asp Tyr Phe His Glu Val Gln Lys Lys Gly Val Gly Pro
            115                 120                 125

Ser Ala Leu Glu Gly His His Arg Val Ile Arg Ser Leu Phe Lys Tyr
        130                 135                 140

Ala Thr Leu Trp Gly Ile Thr Glu Thr Asp Val Ser Leu Ser Val Lys
145                 150                 155                 160

Lys Pro Thr Tyr Lys Val Pro Glu Lys Asn Ile Tyr Asn Arg Arg Glu
                165                 170                 175

Ile Glu Val Leu Ile Asp Arg Ile Lys Ile Leu Gln Lys Tyr Gln Gln
                180                 185                 190
```

```
Val Met Ile Lys Leu Ala Leu Tyr Cys Gly Leu Arg Arg Gly Glu Val
        195                 200                 205

Ile Gly Leu Thr Thr Lys Asp Met Asn Tyr Asn Lys Asn Thr Ile Asn
    210                 215                 220

Val Tyr Arg Ala Val Ile Lys Ser Ala Ser Glu Gly Ile Lys Leu Asp
225                 230                 235                 240

Glu Thr Lys Asn Lys Arg Lys Arg Ile Val Pro Ala Pro Ala Gly Leu
                245                 250                 255

Met Gln Glu Ile Lys Glu Leu Ala Lys Glu Lys Gln Lys Asn Lys Asp
            260                 265                 270

Lys Leu Gly Leu Leu Trp Lys Gly Thr Lys Asp Leu Asp Gly Lys Thr
        275                 280                 285

Val Val Leu Ile Phe Ser His Asp Asp Gly Thr Pro Phe Thr Pro Ala
    290                 295                 300

Ser Val Thr Arg Met Phe Asn Arg Phe Leu Glu Lys Glu Asn Asn
305                 310                 315                 320

Asp Leu Thr Lys Ile Ser Phe His Asp Leu Arg His Ser Ala Ala Ser
                325                 330                 335

Phe Leu Leu Glu Gln Gly Ile Asn Val Lys Val Ile Gln Asn Ile Leu
            340                 345                 350

Gly His Ser Asp Ile Lys Val Thr Leu Asn Thr Tyr Ala His Ile Thr
        355                 360                 365

Glu Asp Gly Tyr Ser Glu Ala Ala Lys Thr Phe Asp Asn Phe Tyr Lys
    370                 375                 380

Ser Ser Lys
385

<210> SEQ ID NO 121
<211> LENGTH: 17
<212> TYPE: DNA
<213> ORGANISM: Artificial Sequence
<220> FEATURE:
<223> OTHER INFORMATION: Insertion site on pKSV7

<400> SEQUENCE: 121
ggtaccttgg tgagctc                                                    17

<210> SEQ ID NO 122
<211> LENGTH: 300
<212> TYPE: DNA
<213> ORGANISM: Listeria monocytogenes

<400> SEQUENCE: 122
gtgggattaa atagatttat gcgtgcgatg atggtagttt tcattactgc caactgcatt    60
acgattaacc ccgacataat atttgcagcg acagatagcg aagattccag tctaaacaca   120
gatgaatggg aagaagaaaa aacagaagag cagccaagcg aggtaaatac gggaccaaga   180
tacgaaactg cacgtgaagt aagttcacgt gatattgagg aactagaaaa atcgaataaa   240
gtgaaaaata cgaacaaagc agacctaata gcaatgttga agcaaaagc agagaaaggt   300

<210> SEQ ID NO 123
<211> LENGTH: 8
<212> TYPE: PRT
<213> ORGANISM: Listeria monocytogenes

<400> SEQUENCE: 123

Asp Lys Ser Ala Gly Leu Ile Asp
  1               5
```

```
<210> SEQ ID NO 124
<211> LENGTH: 6
<212> TYPE: PRT
<213> ORGANISM: Listeria monocytogenes

<400> SEQUENCE: 124

Leu Lys Glu Lys Ala Glu
1               5

<210> SEQ ID NO 125
<211> LENGTH: 29
<212> TYPE: PRT
<213> ORGANISM: Listeria monocytogenes

<400> SEQUENCE: 125

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala
            20                  25

<210> SEQ ID NO 126
<211> LENGTH: 5
<212> TYPE: PRT
<213> ORGANISM: Listeria monocytogenes

<400> SEQUENCE: 126

Thr Glu Ala Lys Asp
1               5

<210> SEQ ID NO 127
<211> LENGTH: 5
<212> TYPE: PRT
<213> ORGANISM: Lactococcus lactis

<400> SEQUENCE: 127

Val Tyr Ala Asp Thr
1               5

<210> SEQ ID NO 128
<211> LENGTH: 5
<212> TYPE: PRT
<213> ORGANISM: Bacillus anthracis

<400> SEQUENCE: 128

Ile Gln Ala Glu Val
1               5

<210> SEQ ID NO 129
<211> LENGTH: 5
<212> TYPE: PRT
<213> ORGANISM: Listeria monocytogenes

<400> SEQUENCE: 129

Ala Ser Ala Ser Thr
1               5

<210> SEQ ID NO 130
<211> LENGTH: 5
<212> TYPE: PRT
<213> ORGANISM: Listeria monocytogenes

<400> SEQUENCE: 130

Val Gly Ala Phe Gly
1               5
```

```
<210> SEQ ID NO 131
<211> LENGTH: 5
<212> TYPE: PRT
<213> ORGANISM: Bacillus anthracis

<400> SEQUENCE: 131

Ala Phe Ala Glu Asp
 1               5

<210> SEQ ID NO 132
<211> LENGTH: 5
<212> TYPE: PRT
<213> ORGANISM: Staphylococcus aureus

<400> SEQUENCE: 132

Val Gln Ala Ala Glu
 1               5

<210> SEQ ID NO 133
<211> LENGTH: 5
<212> TYPE: PRT
<213> ORGANISM: Listeria monocytogenes

<400> SEQUENCE: 133

Asp Lys Ala Leu Thr
 1               5

<210> SEQ ID NO 134
<211> LENGTH: 5
<212> TYPE: PRT
<213> ORGANISM: Bacillus subtillis

<400> SEQUENCE: 134

Val Gly Ala Phe Gly
 1               5

<210> SEQ ID NO 135
<211> LENGTH: 7
<212> TYPE: PRT
<213> ORGANISM: Listeria monocytogenes
<220> FEATURE:
<221> NAME/KEY: VARIANT
<222> LOCATION: 1
<223> OTHER INFORMATION: Xaa = e or d
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 7
<223> OTHER INFORMATION: Xaa = d or e

<400> SEQUENCE: 135

Xaa Phe Pro Pro Pro Xaa Xaa
 1               5

<210> SEQ ID NO 136
<211> LENGTH: 3552
<212> TYPE: DNA
<213> ORGANISM: Artificial Sequence
<220> FEATURE:
<223> OTHER INFORMATION: Sub-fragment of plasmid

<400> SEQUENCE: 136
ggtacctcct tgattagta tattcctatc ttaaagttac ttttatgtgg aggcattaac      60
atttgttaat gacgtcaaaa ggatagcaag actagaataa agctataaag caagcatata    120
```

```
atattgcgtt tcatctttag aagcgaattt cgccaatatt ataattatca aaagagaggg    180
gtggcaaacg gtatttggca ttattaggtt aaaaaatgta aaggagagt gaaacccatg    240 aatatgaaaa aagctacgat tgcagctaca gccggcattg ccgtaacagc ttttgcagca    300
ccaactattg cctcagcctc tacagttgtt gtcgaagcag gagacacatt atggggaatc    360
gcacaatcaa aaggtacaac ggttgatgct attaaaaaag cgataatttt aacaacagat    420
aaaatcgtgc caggtcaaaa actgcaggca ttgccaactg cacgtccatt actaggtagt    480
tgcggtacac cagcactagg ttctttatta tttttgttat tttctctagg ttgggttcaa    540
ccaagtcgta cattagcagg tgaaacaggt caagaagcag caccacttga cggtgtatta    600
acgaatccac caaatatatc aagtttaagt ccacgtcaat tattaggttt tccatgtgca    660
gaagtttcag gtttaagtac agaacgtgtc cgtgagttag cagttgcatt agcacaaaaa    720
aacgttaaat tatctacaga acagttacgt tgtttagccc atagattaag cgaaccacca    780
gaagacttag atgcacttcc tttagacctt cttttattct taaatccaga tgcattttca    840
ggaccacaag catgtacacg tttttttagt cgaattacaa aagccaatgt tgatttatta    900
cctcgtgggg ctcctgaaag acaacgttta ttacctgctg cattagcatg ctggggtgtt    960
cgcggtagct tattaagtga agccgatgtt cgtgctttag ggggtttagc atgtgattta    1020
cctggtcgtt tcgttgcaga atcagcagaa gtgttattac cgagattagt ttcatgccca    1080
ggacctttag atcaagatca acaagaggca gctagagcag ctcttcaagg aggaggccca    1140
ccatatggcc caccagtac atggagtgtt tctacaatgg atgcgttaag aggtttatta    1200
ccggttttag gacaaccaat tattcgtagt attccacaag gcattgtagc agcatggcgt    1260
caacgtagtt ctcgtgatcc gtcttggcga caaccagaac gtacaattct acgtccaaga    1320
tttcgtagag aagtagaaaa aacggcgtgt cctagtggca aaaaagcacg tgaaattgat    1380
gaaagtttaa ttttttataa aaatgggaa ttagaagcat gtgtcgatgc agcattacta    1440
gctacacaaa tggatcgtgt taatgctatt ccattcacat atgaacaatt agatgtttta    1500
aagcataaat tagacgaatt atatccacaa ggttatccag aatcagttat tcaacattta    1560
ggttacttat tttaaaaat gagtccagaa gacatacgca aatggaatgt tacaagttta    1620
gaaacattaa aagcgctttt agaagttaac aaaggtcatg aaatgagtcc acaagttgct    1680
acgttaattg atagattcgt taaaggccgt ggtcaattag ataaagatac tttagataca    1740
ttaacagcat tttatcctgg ctacttatgc agtttatcac cagaagaatt aagttccgtt    1800
ccaccgagta gtatctgggc agttcgtccg caagatttag atacatgcga cccacgtcaa    1860
ttagatgttt tatatccaaa agcaagatta gctttccaaa atatgaacgg tagtgaatat    1920
ttcgtaaaaa ttcaatcctt tttaggtggt gcaccaactg aagatctaaa agcattaagc    1980
caacaaaatg taagtatgga tttagctacg tttatgaaat tacgtacaga tgcagttcta    2040
ccattaacag ttgcagaagt tcaaaaatta ttaggtccac acgtagaagg attaaaagca    2100
gaagaacgtc accgtccagt tcgcgattgg attttacgtc aacgtcaaga tgatttagat    2160
acattaggtt taggtttaca aggcggtatt ccgaatggat atttagtgtt agatttatct    2220
gttcaagaag cattaagtgg tacaccgtgt ttattaggtc caggtccagt tttaacagtg    2280
ttagcattat tattagccag tacattagct ctgcaggtaa ataatgaggt tgctgctgct    2340
gaaaaaacag agaaatctgt tagcgcaact tggttaaacg tccgtactgg cgctggtgtt    2400
gataacagta ttattacgtc catcaaaggt ggaacaaaag taactgttga aacaaccgaa    2460
tctaacggct ggcacaaaat tacttacaac gatggaaaaa ctggtttcgt taacggtaaa    2520
```

```
tacttaactg acaaagcagt aagcactcca gttgcaccaa cacaagaagt gaaaaaagaa    2580
actactactc aacaagctgc acctgttgca gaaacaaaaa ctgaagtaaa acaaactaca    2640
caagcaacta cacctgcgcc taaagtagca gaaacgaaag aaactccagt aatagatcaa    2700
aatgctacta cacacgctgt caaaagcggt gacactattt gggctttatc cgtaaaatac    2760
ggtgtttctg ttcaagacat tatgtcatgg aataatttat cttcttcttc tatttatgta    2820
ggtcaaaagc ttgctattaa acaaactgct aacacagcta ctccaaaagc agaagtgaaa    2880
acggaagctc cagcagctga aaacaagca gctccagtag ttaagaaaa tactaacaca     2940 aatactgcta ctacagagaa aaagaaaca gcaacgcaac aacaaacagc acctaaagca    3000
ccaacagaag ctgcaaaacc agctcctgca ccatctacaa acacaaatgc taataaaacg    3060
aatacaaata caaatacaaa caatactaat acaccatcta aaaatactaa tacaaactca    3120
aatactaata cgaatacaaa ctcaaatacg aatgctaatc aaggttcttc caacaataac    3180
agcaattcaa gtgcaagtgc tattattgct gaagctcaaa acaccttgg aaaagcttat     3240 tcatggggtg gtaacggacc aactacattt gattgctctg ttacactaa atatgtattt      3300 gctaaagcgg gtatctccct tccacgtaca tctggcgcac aatatgctag cactacaaga    3360
atttctgaat ctcaagcaaa acctggtgat ttagtattct tcgactatgg tagcggaatt    3420
tctcacattg gtatttatgt tggtaatggt caaatgatta cgcgcaaga caatggcgtt    3480 aaatacgata acatccacgg ctctggctgg ggtaaatatc tagttggctt cggtcgcgta    3540
taataaggat cc                                                         3552

<210> SEQ ID NO 137
<211> LENGTH: 4
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 3
<223> OTHER INFORMATION: Xaa = g, a, s, or t

<400> SEQUENCE: 137

Leu Leu Xaa His
 1

<210> SEQ ID NO 138
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 1
<223> OTHER INFORMATION: Xaa = d or e
<220> FEATURE:
<221> NAME/KEY: VARIANT
<222> LOCATION: 2, 3, 4, 5
<223> OTHER INFORMATION: Xaa = f, y, w, v, l, i or a
<220> FEATURE:
<221> NAME/KEY: VARIANT
<222> LOCATION: 6
<223> OTHER INFORMATION: Xaa = s or t

<400> SEQUENCE: 138

Xaa Xaa Xaa Xaa Xaa Xaa
 1               5
```

```
<210> SEQ ID NO 139
<211> LENGTH: 7
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 1
<223> OTHER INFORMATION: Xaa = d or e
<220> FEATURE:
<221> NAME/KEY: VARIANT
<222> LOCATION: 2, 3, 4, 5, 6,
<223> OTHER INFORMATION: Xaa = f, y, w, v, l, i or a
<220> FEATURE:
<221> NAME/KEY: VARIANT
<222> LOCATION: 7
<223> OTHER INFORMATION: Xaa = s or t

<400> SEQUENCE: 139

Xaa Xaa Xaa Xaa Xaa Xaa Xaa
 1               5

<210> SEQ ID NO 140
<211> LENGTH: 8
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 1
<223> OTHER INFORMATION: Xaa = d or e
<220> FEATURE:
<221> NAME/KEY: VARIANT
<222> LOCATION: 2, 3, 4, 5, 6, 7
<223> OTHER INFORMATION: Xaa = f, y, w, v, l, i or a
<220> FEATURE:
<221> NAME/KEY: VARIANT
<222> LOCATION: 8
<223> OTHER INFORMATION: Xaa = s or t

<400> SEQUENCE: 140

Xaa Xaa Xaa Xaa Xaa Xaa Xaa Xaa
 1               5

<210> SEQ ID NO 141
<211> LENGTH: 8
<212> TYPE: PRT
<213> ORGANISM: Artificial Sequence
<220> FEATURE:
<223> OTHER INFORMATION: Motif

<400> SEQUENCE: 141

Val Leu Val Leu Asp Arg Leu Arg
 1               5
```

What is claimed is:

1. A polynucleotide comprising:
   (a) a promoter; and
   (b) a nucleic acid sequence operably linked to the promoter, wherein the nucleic acid sequence encodes a fusion protein comprising:
   (i) a modified ActA comprising more than the first 59 contiguous amino acid residues of SEQ ID NO: 38, and less than the 380 contiguous amino acid residues of SEQ ID NO: 38, wherein the first amino acid residue of SEQ ID NO: 38 is valine, or the first amino acid residue of SEQ ID NO: 38 is substituted with methionine; and
   (ii) a heterologous antigen.

2. The polynucleotide of claim 1, wherein the promoter is an actA promoter.

3. The polynucleotide of claim 1, wherein the modified ActA comprises less than the first 265 contiguous amino acid residues of SEQ ID NO: 38, wherein the first amino acid residue of SEQ ID NO: 38 is substituted with methionine.

4. The polynucleotide of claim 1, wherein the modified ActA comprises at least the first 85 contiguous amino acids of SEQ ID NO: 38 and less than the first 125 contiguous amino acids of SEQ ID NO: 38, wherein the first amino acid residue of SEQ ID NO: 38 is substituted with methionine.

5. The polynucleotide of claim 4, wherein the modified ActA consists of amino acids 1-100 of SEQ ID NO: 38, wherein the first amino acid residue of SEQ ID NO: 38 is substituted with methionine.

6. The polynucleotide of claim 5, wherein the promoter is an actA promoter.

7. The polynucleotide of claim 1, wherein the heterologous antigen is non-Listerial.

8. The polynucleotide of claim 1, wherein the heterologous antigen is from a cancer cell, tumor, or infectious agent.

9. A plasmid comprising the polynucleotide of claim 1.

10. A *Listeria* bacterium comprising the polynucleotide of claim 1.

11. The *Listeria* bacterium of claim 10, which is *Listeria monocytogenes*.

12. The *Listeria* bacterium of claim 11 which is attenuated for cell-to-cell spread or entry into nonphagocytic cells.

13. The *Listeria* bacterium of claim 12 which is an actA deletion mutant or an actA insertion mutant.

14. The *Listeria* bacterium of claim 13, wherein the promoter is an actA promoter.

15. The *Listeria* bacterium of claim 10, wherein the *Listeria* bacterium comprises the polynucleotide in its genome.

16. The *Listeria* bacterium of claim 15, wherein the polynucleotide has been integrated into a virulence gene in the genome, wherein the integration of the polynucleotide:
    (a) disrupts expression of the virulence gene; or
    (b) disrupts a coding sequence of the virulence gene.

17. The *Listeria* bacterium of claim 16, wherein the virulence gene is actA or inlB.

18. The *Listeria* bacterium of claim 15, wherein the nucleic acid sequence encoding the fusion protein has been integrated into a virulence gene in the genome, wherein the integration of the nucleic acid sequence:
    (a) disrupts expression of the virulence gene; or
    (b) disrupts a coding sequence of the virulence gene.

19. A vaccine comprising the *Listeria* bacterium of claim 10.

20. A *Listeria* bacterium comprising a genome, wherein the genome comprises a polynucleotide comprising a nucleic acid sequence encoding a heterologous antigen that has been integrated into a virulence gene in the genome, wherein integration of the polynucleotide
    (a) disrupts expression of the virulence gene; or
    (b) disrupts a coding sequence of the virulence gene.

21. The *Listeria* bacterium of claim 20, wherein none of the virulence gene has been deleted.

22. The *Listeria* bacterium of claim 20, wherein the virulence gene is actA or inlB.

23. The *Listeria* bacterium of claim 20, which is *Listeria monocytogenes*.

24. The *Listeria* bacterium of claim 20, wherein the heterologous antigen is from a cancer cell, tumor, or infectious agent.

25. The *Listeria* bacterium of claim 20, further comprising:
    a second nucleic acid sequence encoding a second heterologous antigen that has been integrated into a second virulence gene.

26. The *Listeria* bacterium of claim 20, wherein the nucleic acid sequence encodes a fusion protein comprising the heterologous antigen and a modified ActA comprising more than the first 59 contiguous amino acid residues of SEQ ID NO: 38, and less than the 380 contiguous amino acid residues of SEQ ID NO: 38, wherein the first amino acid residue of SEQ ID NO: 38 is valine, or the first amino acid residue of SEQ ID NO: 38 is substituted with methionine.

27. A method of producing a *Listeria* bacterium for use in a vaccine, comprising:
    integrating a polynucleotide into a virulence gene in the genome of the *Listeria* bacterium, wherein the polynucleotide comprises a nucleic acid sequence encoding a heterologous antigen and wherein the integration of the polynucleotide
    (a) disrupts expression of the virulence gene; or
    (b) disrupts a coding sequence of the virulence gene.

28. The method of claim 27, wherein the polynucleotide is integrated into the virulence gene by homologous recombination.

29. The method of claim 27, wherein all or part of the virulence gene is deleted during integration of the polynucleotide into the virulence gene.

30. The method of claim 27, wherein the virulence gene is actA or inlB.

31. A polynucleotide comprising a first nucleic acid sequence encoding actA-N100 (SEQ ID NO: 40), wherein the first amino acid residue of SEQ ID NO: 40 is valine, or the first amino acid residue of SEQ ID NO: 40 is substituted with methionine, operably linked and in frame with, a second nucleic acid sequence encoding a heterologous antigen.

32. A *Listeria* bacterium comprising the polynucleotide of claim 31.

33. The *Listeria* bacterium of claim 32, wherein the polynucleotide is genomic.

34. The *Listeria* bacterium of claim 32, wherein the polynucleotide is integrated into actA or inlB.

35. The *Listeria* bacterium of claim 32, wherein the polynucleotide is plasmid-based.

36. The *Listeria* bacterium of claim 32 which is *Listeria monocytogenes*.

37. The *Listeria* bacterium of claim 32, wherein the heterologous antigen is from a cancer cell, tumor, or infectious agent.

38. The *Listeria* bacterium of claim 32, wherein the heterologous antigen is immunologically cross-reactive with, or shares at least one epitope with, the cancer, tumor, or infectious agent.

39. The *Listeria* bacterium of claim 32, wherein the polynucleotide is operably linked to an actA promoter.

40. A vaccine comprising the *Listeria* bacterium of claim 32.

41. A polynucleotide comprising a first nucleic acid sequence encoding a modified ActA, wherein the modified ActA comprises:
    a. amino acids 1-59 of SEQ ID NO: 38, wherein the first amino acid residue of SEQ ID NO: 38 is valine, or the first amino acid residue of SEQ ID NO: 38 is substituted with methionine; and
    b. an inactivating mutation in, deletion of, or truncation prior to, at least one domain for ActA-mediated regulation of the host cell cytoskeleton,
    wherein the first nucleic acid sequence is operably linked and in frame with a second nucleic acid sequence encoding a heterologous antigen.

42. The polynucleotide of claim 41, wherein the domain is a cofilin homology region having an amino acid sequence set forth as KKRR (SEQ ID NO:23).

43. The polynucleotide of claim 41, wherein the domain is a phospholipid core binding domain having an amino acid sequence set forth as KVFKKIKDAGKWVRDKI (SEQ ID NO:20).

44. The polynucleotide of claim 41, wherein the at least one domain comprises four proline-rich domains having amino acid sequences set forth as FPPPP (SEQ ID NO: 21), FPPPP (SEQ ID NO: 21), FPPPP (SEQ ID NO: 21) and FPPIP (SEQ ID NO: 22) of ActA.

45. A *Listeria* bacterium containing the polynucleotide of claim 41.

46. The *Listeria* bacterium of claim 45, wherein the polynucleotide is genomic.

47. The *Listeria* bacterium of claim 45, wherein the polynucleotide is not genomic.

48. The *Listeria* bacterium of claim 45, wherein the polynucleotide is operably linked with one or more of:
   a. actA promoter; or
   b. a bacterial promoter that is not actA promoter.

49. The *Listeria* bacterium of claim 45 that is *Listeria monocytogenes*.

50. A vaccine comprising the *Listeria* bacterium of claim 49.

51. A plasmid comprising a first nucleic acid sequence encoding a phage integrase, a second nucleic acid sequence encoding a phage attachment site (attPP' site), and a third nucleic acid sequence encoding a heterologous antigen or regulatory nucleic acid sequence, wherein:
   a. each of the nucleic acid sequences is from *L. innocua* 0071;
   b. each of the nucleic acid sequences is from *L. innocua* 1765;
   c. each of the nucleic acid sequences is from *L. innocua* 2601;
   d. each of the nucleic acid sequences is from *L. monocytogenes* f6854__2703; or
   e. the first nucleic acid sequence encodes a phiC31 integrase,
   wherein the plasmid is useful for mediating site-specific integration of the nucleic acid sequence encoding the heterologous antigen at a bacterial attachment site (attBB' site) in a bacterial genome that is compatible with the attPP' site of the plasmid.

52. A method of modifying a bacterial genome, comprising transfecting a bacterium with the plasmid of claim 51, and allowing integrase-catalyzed integration of the third nucleic acid sequence into the bacterial genome under conditions suitable for integration.

53. A plasmid comprising:
   a. a first nucleic acid sequence encoding a first region of homology to a bacterial genome,
   b. a second nucleic acid sequence encoding a second region of homology to the bacterial genome, and
   c. a third nucleic acid sequence comprising a bacterial attachment site (attBB'), wherein the third nucleic acid sequence is flanked by the first and second nucleic acid sequences, wherein the first nucleic acid sequence and second nucleic acid sequence are operably linked with each other and able to mediate homologous integration of the third nucleic acid sequence into the bacterial genome.

54. A bacterium modified by integration of the plasmid of claim 53.

55. A bacterial genome comprising a polynucleotide containing two operably linked heterologous recombinase binding sites flanking a first nucleic acid sequence, wherein the two sites are:
   a. two lox sites; or
   b. two Frt sites,
   the nucleic acid sequence flanked by the two lox sites is excisable by Cre recombinase, and the nucleic acid sequence flanked by the two Frt sites is excisable by FLP recombinase.

56. A method of excising the first nucleic acid sequence of claim 55 from the bacterial genome, comprising contacting the genome with Cre recombinase or FLP recombinase, and allowing the recombinase to catalyze excision of the first nucleic acid sequence, under conditions allowing or facilitating excision, wherein:
   a. the first nucleic acid sequence is flanked by lox sites and the recombinase is Cre recombinase; or
   b. the first nucleic acid sequence is flanked by Frt sites and the recombinase is FLP recombinase.

57. The *Listeria* bacterium of claim 18, wherein the virulence gene is a prfA-dependent gene.

58. The *Listeria* bacterium of claim 18, wherein the virulence gene is not a prfA-dependent gene.

59. The plasmid of claim 51, further comprising a first promoter operably linked with the first nucleic acid sequence, and a second promoter operably linked with the third nucleic acid sequence.

60. The *Listeria* bacterium of claim 54, wherein the integration is in a region of the genome that is necessary for mediating growth or spread.

61. The *Listeria* bacterium of claim 54, wherein the integration is in a region of the genome that is not necessary for mediating growth or spread.

62. The *Listeria* bacterium of claim 55, wherein each lox site is a loxP site.

63. The polynucleotide of claim 1, wherein the first amino acid residue of SEQ ID NO: 38 is valine.

64. The polynucleotide of claim 63, wherein the modified ActA comprises less than the first 265 contiguous amino acid residues of SEQ ID NO: 38.

65. The polynucleotide of claim 63, wherein the modified ActA comprises at least the first 85 contiguous amino acids of SEQ ID NO: 38 and less than the first 125 contiguous amino acids of SEQ ID NO: 38.

66. The polynucleotide of claim 65, wherein the modified ActA consists of amino acids 1-100 of SEQ ID NO: 38.

67. The polynucleotide of claim 66, wherein the promoter is an actA promoter.

68. The polynucleotide of claim 1, wherein the first amino acid residue of SEQ ID NO: 38 is substituted with methionine.

69. The *Listeria* bacterium of claim 26, wherein the first amino acid residue of SEQ ID NO: 38 is valine.

70. The *Listeria* bacterium of claim 26, wherein the first amino acid residue of SEQ ID NO: 38 is substituted with methionine.

71. The polynucleotide of claim 31, wherein the first amino acid residue of SEQ ID NO: 40 is valine.

72. The polynucleotide of claim 31, wherein the first amino acid residue of SEQ ID NO: 40 is substituted with methionine.

73. The polynucleotide of claim 41, wherein the first amino acid residue of SEQ ID NO: 38 is valine.

74. The polynucleotide of claim 41, wherein the first amino acid residue of SEQ ID NO: 38 is substituted with methionine.

75. The polynucleotide of claim 73, comprising an inactivating mutation in at least one domain for actA-mediated regulation of the host cell cytoskeleton.

76. The polynucleotide of claim 73, comprising a deletion of at least one domain for actA-mediated regulation of the host cell cytoskeleton.

77. The polynucleotide of claim 73, comprising a truncation prior to, at least one domain for actA-mediated regulation of the host cell cytoskeleton.

78. The polynucleotide of claim 74, comprising an inactivating mutation in at least one domain for actA-mediated regulation of the host cell cytoskeleton.

79. The polynucleotide of claim 74, comprising a deletion of at least one domain for actA-mediated regulation of the host cell cytoskeleton.

80. The polynucleotide of claim 74, comprising a truncation prior to, at least one domain for actA-mediated regulation of the host cell cytoskeleton.

81. A polynucleotide comprising:
(a) a promoter; and
(b) a nucleic acid sequence operably linked to the promoter, wherein the nucleic acid sequence encodes a fusion protein comprising:
(i) a modified ActA comprising at least the first 59 contiguous amino acids of SEQ ID NO: 38, and less than the 380 contiguous amino acids of SEQ ID NO: 38, wherein the first amino acid residue of SEQ ID NO: 38 is valine, or the first amino acid residue of SEQ ID NO: 38 is substituted with methionine; and
(ii) a heterologous antigen.

82. The polynucleotide of claim 81, wherein the promoter is an actA promoter.

83. The polynucleotide of claim 81, wherein the first amino acid residue of SEQ ID NO: 38 is valine.

84. The polynucleotide of claim 81, wherein the first amino acid residue of SEQ ID NO: 38 is substituted with methionine.

* * * * *

(12) EX PARTE REEXAMINATION CERTIFICATE (9356th)
United States Patent
Dubensky, Jr. et al.

(10) Number: US 7,935,804 C1
(45) Certificate Issued: Oct. 8, 2012

(54) ENGINEERED LISTERIA AND METHODS OF USE THEREOF

(75) Inventors: Thomas W. Dubensky, Jr., Piedmont, CA (US); Justin Skoble, Berkeley, CA (US); Peter M. Lauer, Berkeley, CA (US); David N. Cook, Lafayette, CA (US)

(73) Assignee: Aduro Biotech, Berkeley, CA (US)

Reexamination Request:
No. 90/011,863, Aug. 17, 2011

Reexamination Certificate for:
Patent No.: 7,935,804
Issued: May 3, 2011
Appl. No.: 11/395,197
Filed: Mar. 30, 2006

Related U.S. Application Data

(60) Provisional application No. 60/784,576, filed on Mar. 21, 2006, provisional application No. 60/778,471, filed on Mar. 1, 2006.

(51) Int. Cl.
*C07H 21/02* (2006.01)
*C07H 21/04* (2006.01)
*A61K 39/02* (2006.01)

(52) U.S. Cl. ..... 536/23.7; 424/93.2; 424/9.2; 424/190.1; 424/234.1; 530/300; 530/350; 536/24.3; 536/23.1; 536/24.32

(58) Field of Classification Search .................. None
See application file for complete search history.

(56) References Cited

To view the complete listing of prior art documents cited during the proceeding for Reexamination Control Number 90/011,863, please refer to the USPTO's public Patent Application Information Retrieval (PAIR) system under the Display References tab.

*Primary Examiner* — Bruce Campell

(57) ABSTRACT

The invention provides a bacterium containing a polynucleotide comprising a nucleic acid encoding a heterologous antigen, as well as fusion protein partners. Also provided are vectors for mediating site-specific recombination and vectors comprising removable antibiotic resistance genes.

US 7,935,804 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 6, 14, 22, 30, 39, 48, 51-56, 59-62, 67 and 81-84 are cancelled.

Claims 1, 3-5, 20, 26, 27, 31, 41 and 64-66 are determined to be patentable as amended.

Claims 7-13, 15-19, 21, 23-25, 28, 29, 32-38, 40, 42-47, 49, 50, 57, 58, 63 and 68-80, dependent on an amended claim, are determined to be patentable.

1. A polynucleotide comprising:
   (a) [a] *an* actA promoter; and
   (b) a nucleic acid sequence operably linked to the promoter, wherein the nucleic acid sequence encodes a fusion protein comprising:
      (i) a [modified] *truncated* ActA [comprising] *59 to 379 residues in length, which residues comprise* more than the first 59 contiguous amino acid residues of SEQ ID NO: 38, and less than the 380 contiguous amino acid residues of SEQ ID NO: 38, wherein the first amino acid residue of SEQ ID NO: 38 is valine, or the first amino acid residue of SEQ ID NO: 38 is substituted with methionine; and
      (ii) a heterologous antigen.

3. The polynucleotide of claim 1, wherein the [modified] *truncated* ActA comprises less than the first 265 contiguous amino acid residues of SEQ ID NO: 38, wherein the first amino acid residue of SEQ ID NO: 38 is substituted with methionine.

4. The polynucleotide of claim 1, wherein the [modified] *truncated* ActA comprises at least the first 85 contiguous amino acids of SEQ ID NO: 38 and less than the first 125 contiguous amino acids of SEQ ID NO: 38, wherein the first amino acid residue of SEQ ID NO: 38 is substituted with methionine.

5. The polynucleotide of claim 4, wherein the [modified] *truncated* ActA consists of amino acids 1-100 of SEQ ID NO: 38, wherein the first amino acid residue of SEQ ID NO: 38 is substituted with methionine.

20. A Listeria bacterium comprising a genome, wherein the genome comprises a polynucleotide comprising a nucleic acid sequence encoding a heterologous antigen that has been integrated into a virulence gene in the genome *selected from the group consisting of actA and inlB*, wherein integration of the polynucleotide (a) disrupts expression of the virulence gene; or
   (b) disrupts a coding sequence of the virulence gene.

26. The Listeria bacterium of claim 20, wherein the nucleic acid sequence encodes a fusion protein comprising the heterologous antigen and a [modified] *truncated* ActA [comprising] *59 to 379 residues in length, which residues comprise* more than the first 59 contiguous amino acid residues of SEQ ID NO: 38, and less than the 380 contiguous amino acid residues of SEQ ID NO: 38, wherein the first amino acid residue of SEQ ID NO: 38 is valine, or the first amino acid residue of SEQ ID NO: 38 is substituted with methionine.

27. A method of producing a Listeria bacterium for use in a vaccine, comprising:
   integrating a polynucleotide into a virulence gene *selected from the group consisting of actA and inlB* in the genome of the Listeria bacterium, wherein the polynucleotide comprises a nucleic acid sequence encoding a heterologous antigen and wherein the integration of the polynucleotide
      (a) disrupts expression of the virulence gene; or
      (b) disrupts a coding sequence of the virulence gene.

31. A polynucleotide comprising:
   (*a*) *an* actA *promoter; and*
   (*b*) *a nucleic acid sequence operably linked to the promoter, wherein the nucleic acid sequence encodes a fusion protein comprising:*
      a first nucleic acid sequence encoding [actA] *ActA*-N100 (SEQ ID NO: 40), wherein the first amino acid residue of SEQ ID NO: 40 is valine, or the first amino acid residue of SEQ ID NO: 40 is substituted with methionine, operably linked and in frame with, a second nucleic acid sequence encoding a heterologous antigen.

41. A polynucleotide comprising a first nucleic acid sequence encoding a [modified] *truncated* ActA, wherein the [modified] *truncated* ActA comprises:
   a. amino acids 1-59 of SEQ ID NO: 38, wherein the first amino acid residue of SEQ ID NO: 38 is valine, or the first amino acid residue of SEQ ID NO: 38 is substituted with methionine; and
   b. [an inactivating mutation in, deletion of, or] *a* truncation prior to[,] at least one domain for ActA-mediated regulation of the host cell cytoskeleton,
   wherein the first nucleic acid sequence is operably linked and in frame with a second nucleic acid sequence encoding a heterologous antigen, *and wherein the polynucleotide is operably linked to an actA promoter*.

64. The polynucleotide of claim 63, wherein the [modified] *truncated* ActA comprises less than the first 265 contiguous amino acid residues of SEQ ID NO: 38.

65. The polynucleotide of claim 63, wherein the [modified] *truncated* ActA comprises at least the first 85 contiguous amino acids of SEQ ID NO: 38 and less than the first 125 contiguous amino acids of SEQ ID NO: 38.

66. The polynucleotide of claim 65, wherein the [modified] *truncated* ActA consists of amino acids 1-100 of SEQ ID NO: 38.

* * * * *